(12) United States Patent
Raeppel et al.

(10) Patent No.: US 8,906,852 B2
(45) Date of Patent: Dec. 9, 2014

(54) INHIBITORS OF PROTEIN TYROSINE KINASE ACTIVITY

(75) Inventors: Stéphane Raeppel, St. Lazare (CA); Franck Raeppel, Montreal (CA); Stephen William Claridge, Montreal (CA); Lijie Zhan, Montreal (CA); Frédéric Gaudette, Sherbrooke (CA); Michael Mannion, Montreal (CA); Norifumi Sato, Himeji (JP); Yohei Yuki, Tokyo (JP); Masashi Kishida, Ako (JP); Arkadii Vaisburg, Kirkland (CA)

(73) Assignee: MethylGene Inc., Montreal (CA)

( * ) Notice: Subject to any disclaimer, the term of this patent is extended or adjusted under 35 U.S.C. 154(b) by 489 days.

(21) Appl. No.: 13/082,923

(22) Filed: Apr. 8, 2011

(65) Prior Publication Data

US 2011/0257100 A1 Oct. 20, 2011

Related U.S. Application Data

(60) Provisional application No. 61/324,803, filed on Apr. 16, 2010.

(51) Int. Cl.
| | | |
|---|---|---|
| A61K 38/00 | (2006.01) |
| C07K 14/47 | (2006.01) |
| A61P 35/00 | (2006.01) |
| C07K 14/515 | (2006.01) |
| A61P 9/10 | (2006.01) |
| A61P 27/02 | (2006.01) |
| A61K 38/05 | (2006.01) |
| A01N 57/00 | (2006.01) |
| A61K 31/675 | (2006.01) |
| A61K 31/535 | (2006.01) |
| A61K 31/497 | (2006.01) |
| A01N 43/42 | (2006.01) |
| A61K 31/44 | (2006.01) |
| C07F 9/06 | (2006.01) |
| C07F 9/28 | (2006.01) |
| C07D 513/02 | (2006.01) |
| C07D 495/04 | (2006.01) |
| C07F 9/6561 | (2006.01) |
| C07D 519/00 | (2006.01) |

(52) U.S. Cl.
CPC ............ C07D 495/04 (2013.01); C07F 9/6561 (2013.01); A61K 38/005 (2013.01); C07D 519/00 (2013.01)
USPC ......... 514/7.5; 514/13.3; 514/19.2; 514/20.8; 514/21.91; 514/81; 514/228.8; 514/230.8; 514/233.8; 514/253.04; 514/301; 546/23; 546/114; 544/96; 544/121; 544/127; 544/362; 540/467; 540/575; 435/184

(58) Field of Classification Search
None
See application file for complete search history.

(56) References Cited

U.S. PATENT DOCUMENTS

| | | | |
|---|---|---|---|
| 8,455,484 B2 * | 6/2013 | Raeppel et al. | ............ 514/233.8 |
| 2007/0004675 A1 | 1/2007 | Saavedra et al. | |
| 2013/0096088 A1 * | 4/2013 | Raeppel et al. | ................. 514/81 |
| 2013/0165477 A1 * | 6/2013 | Claridge et al. | ............... 514/301 |

FOREIGN PATENT DOCUMENTS

| | | |
|---|---|---|
| WO | WO 2009/026717 | 3/2009 |
| WO | WO 2009/026720 | 3/2009 |
| WO | WO 2009026717 A1 * | 3/2009 |
| WO | WO 2009/109035 | 9/2009 |
| WO | WO 2009109035 A1 * | 9/2009 |

* cited by examiner

*Primary Examiner* — Maury Audet
*Assistant Examiner* — Zachary J Miknis
(74) *Attorney, Agent, or Firm* — Wood, Phillips, Katz, Clark & Mortimer

(57) ABSTRACT

This invention relates to compounds that inhibit protein tyrosine kinase activity. In particular the invention relates to compounds that inhibit the protein tyrosine kinase activity of growth factor receptors, resulting in the inhibition of receptor signaling, for example, the inhibition of VEGF receptor signaling. The invention also provides compounds, compositions and methods for treating cell proliferative diseases and conditions and ophthalmic diseases, disorders and conditions.

17 Claims, No Drawings

INHIBITORS OF PROTEIN TYROSINE KINASE ACTIVITY

RELATED APPLICATION

This application claims the benefit of U.S. Provisional Application Ser. No. 61/324,803, filed Apr. 16, 2010. The entire teachings of the above-referenced application are incorporated herein by reference.

FIELD OF THE INVENTION

This invention relates to compounds that inhibit protein tyrosine kinase activity. In particular the invention relates to compounds that inhibit the protein tyrosine kinase activity of growth factor receptors, resulting in the inhibition of receptor signaling, for example, the inhibition of VEGF receptor signaling and HGF receptor signaling. More particularly, the invention relates to compounds, compositions and methods for the inhibition of VEGF receptor signaling.

SUMMARY OF THE RELATED ART

Tyrosine kinases may be classified as growth factor receptor (e.g. EGFR, PDGFR, FGFR and erbB2) or non-receptor (e.g. c-src and bcr-abl) kinases. The receptor type tyrosine kinases make up about 20 different subfamilies. The non-receptor type tyrosine kinases make up numerous subfamilies. These tyrosine kinases have diverse biological activity. Receptor tyrosine kinases are large enzymes that span the cell membrane and possess an extracellular binding domain for growth factors, a transmembrane domain, and an intracellular portion that functions as a kinase to phosphorylate a specific tyrosine residue in proteins and hence to influence cell proliferation. Aberrant or inappropriate protein kinase activity can contribute to the rise of disease states associated with such aberrant kinase activity.

Angiogenesis is an important component of certain normal physiological processes such as embryogenesis and wound healing, but aberrant angiogenesis contributes to some pathological disorders and in particular to tumor growth. VEGF-A (vascular endothelial growth factor A) is a key factor promoting neovascularization (angiogenesis) of tumors. VEGF induces endothelial cell proliferation and migration by signaling through two high affinity receptors, the fms-like tyrosine kinase receptor, Flt-1, and the kinase insert domain-containing receptor, KDR. These signaling responses are critically dependent upon receptor dimerization and activation of intrinsic receptor tyrosine kinase (RTK) activity. The binding of VEGF as a disulfide-linked homodimer stimulates receptor dimerization and activation of the RTK domain. The kinase autophosphorylates cytoplasmic receptor tyrosine residues, which then serve as binding sites for molecules involved in the propagation of a signaling cascade. Although multiple pathways are likely to be elucidated for both receptors, KDR signaling is most extensively studied, with a mitogenic response suggested to involve ERK-1 and ERK-2 mitogen-activated protein kinases.

Disruption of VEGF receptor signaling is a highly attractive therapeutic target in cancer, as angiogenesis is a prerequisite for all solid tumor growth, and that the mature endothelium remains relatively quiescent (with the exception of the female reproductive system and wound healing). A number of experimental approaches to inhibiting VEGF signaling have been examined, including use of neutralizing antibodies, receptor antagonists, soluble receptors, antisense constructs and dominant-negative strategies.

Despite the attractiveness of anti-angiogenic therapy by VEGF inhibition alone, several issues may limit this approach. VEGF expression levels can themselves be elevated by numerous diverse stimuli and perhaps most importantly, the hypoxic state of tumors resulting from VEGFr inhibition, can lead to the induction of factors that themselves promote tumor invasion and metastasis thus, potentially undermining the impact of VEGF inhibitors as cancer therapeutics.

The HGF (hepatocyte growth factor) and the HGF receptor, c-met, are implicated in the ability of tumor cells to undermine the activity of VEGF inhibition. HGF derived from either stromal fibroblasts surrounding tumor cells or expressed from the tumor itself has been suggested to play a critical role in tumor angiogenesis, invasion and metastasis. For example, invasive growth of certain cancer cells is drastically enhanced by tumor-stromal interactions involving the HGF/c-Met (HGF receptor) pathway. HGF, which was originally identified as a potent mitogen for hepatocytes is primarily secreted from stromal cells, and the secreted HGF can promote motility and invasion of various cancer cells that express c-Met in a paracrine manner. Binding of HGF to c-Met leads to receptor phosphorylation and activation of Ras/mitogen-activated protein kinase (MAPK) signaling pathway, thereby enhancing malignant behaviors of cancer cells. Moreover, stimulation of the HGF/c-met pathway itself can lead to the induction of VEGF expression, itself contributing directly to angiogenic activity.

Thus, anti-tumor anti-angiogenic strategies or approaches that target VEGF/VEGFr signaling or HGF/c-met signaling may represent improved cancer therapeutics.

Tyrosine kinases also contribute to the pathology of ophthalmic diseases, disorders and conditions, such as age-related macular degeneration (AMD) and diabetic retinopathy (DR). Blindness from such diseases has been linked to anomalies in retinal neovascularization. The formation of new blood vessels is regulated by growth factors such as VEGF and HGF that activate receptor tyrosine kinases resulting in the initiation of signaling pathways leading to plasma leakage into the macula, causing vision loss. Kinases are thus attractive targets for the treatment of eye diseases involving neovascularization.

Thus, there is a need to develop a strategy for controlling neovascularization of the eye and to develop a strategy for the treatment of ocular diseases.

Here we describe small molecules that are potent inhibitors of protein tyrosine kinase activity.

BRIEF SUMMARY OF THE INVENTION

The present invention provides new compounds and methods for treating a disease responsive to inhibition of kinase activity, for example a disease responsive to inhibition of protein tyrosine kinase activity, for example a disease responsive to inhibition of protein tyrosine kinase activity of growth factor receptors, for example a disease responsive to inhibition of receptor type tyrosine kinase signaling, or for example, a disease responsive to inhibition of VEGF receptor signaling. In some embodiments the disease is a cell proliferative disease. In other embodiments, the disease is an ophthalmic disease. The compounds of the invention are inhibitors of kinase activity, such as protein tyrosine kinase activity, for example protein tyrosine kinase activity of growth factor receptors, or for example receptor type tyrosine kinase signaling.

In a first aspect, the invention provides compounds of Formula (I) that are useful as kinase inhibitors:

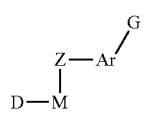
(I)

and N-oxides, hydrates, solvates, tautomers, pharmaceutically acceptable salts, prodrugs and complexes thereof, and racemic and scalemic mixtures, diastereomers and enantiomers thereof, wherein D, M, Z, Ar and G are as defined herein. Because compounds of the present invention are useful as kinase inhibitors they are, therefore, useful research tools for the study of the role of kinases in both normal and disease states. In some embodiments, the invention provides compounds that are useful as inhibitors of VEGF receptor signaling and, therefore, are useful research tools for the study of the role of VEGF in both normal and disease states.

In a second aspect, the invention provides compositions comprising a compound according to the present invention and a pharmaceutically acceptable carrier, excipient or diluent. For example, the invention provides compositions comprising a compound that is an inhibitor of VEGF receptor signaling, or a pharmaceutically acceptable salt thereof, and a pharmaceutically acceptable carrier, excipient, or diluent.

In a third aspect, the invention provides a method of inhibiting kinase activity, for example protein tyrosine kinase, for example tyrosine kinase activity of a growth factor receptor, the method comprising contacting the kinase with a compound according to the present invention, or with a composition according to the present invention. In some embodiments of this aspect, the invention provides a method of inhibiting receptor type tyrosine kinase signaling, for example inhibiting VEGF receptor signaling. Inhibition can be in a cell or a multicellular organism. If in a cell, the method according to this aspect of the invention comprises contacting the cell with a compound according to the present invention, or with a composition according to the present invention. If in a multicellular organism, the method according to this aspect of the invention comprises administering to the organism a compound according to the present invention, or a composition according to the present invention. In some embodiments the organism is a mammal, for example a primate, for example a human.

In a fourth aspect, the invention provides a method of inhibiting angiogenesis, the method comprising administering to a patient in need thereof a therapeutically effective amount of a compound according to the present invention, or a therapeutically effective amount of a composition according to the present invention. In some embodiments of this aspect, the angiogenesis to be inhibited is involved in tumor growth. In some other embodiments the angiogenesis to be inhibited is retinal angiogenesis. In some embodiments of this aspect, the patient is a mammal, for example a primate, for example a human.

In a fifth aspect, the invention provides a method of treating a disease responsive to inhibition of kinase activity, for example a disease responsive to inhibition of protein tyrosine kinase activity, for example a disease responsive to inhibition of protein tyrosine kinase activity of growth factor receptors. In some embodiments of this aspect, the invention provides a method of treating a disease responsive to inhibition of receptor type tyrosine kinase signaling, for example a disease responsive to inhibition of VEGF receptor signaling, the method comprising administering to an organism in need thereof a therapeutically effective amount of a compound according to the present invention, or a composition according to the present invention. In some embodiments of this aspect, the organism is a mammal, for example a primate, for example a human.

In a sixth aspect, the invention provides a method of treating a cell proliferative disease, the method comprising administering to a patient in need thereof a therapeutically effective amount of a compound according to the present invention, or a therapeutically effective amount of a composition according to the present invention. In some embodiments of this aspect, the cell proliferative disease is cancer. In some embodiments, the patient is a mammal, for example a primate, for example a human.

In a seventh aspect, the invention provides a method of treating an ophthalmic disease, disorder or condition, the method comprising administering to a patient in need thereof a therapeutically effective amount of a compound according to the present invention, or a therapeutically effective amount of a composition according to the present invention. In some embodiments of this aspect, the disease is caused by choroidal angiogenesis. In some embodiments of this aspect, the patient is a mammal, for example a primate, for example a human.

In an eighth aspect, the invention provides for the use of a compound according to the present invention for or in the manufacture of a medicament to inhibit kinase activity, for example to inhibit protein tyrosine kinase activity, for example to inhibit protein tyrosine kinase activity of growth factor receptors. In some embodiments of this aspect, the invention provides for the use of a compound according to the present invention for or in the manufacture of a medicament to inhibit receptor type tyrosine kinase signaling, for example to inhibit VEGF receptor signaling. In some embodiments of this aspect, the invention provides for the use of a compound according to the present invention for or in the manufacture of a medicament to treat a disease responsive to inhibition of kinase activity. In some embodiments of this aspect, the disease is responsive to inhibition of protein tyrosine kinase activity, for example inhibition of protein tyrosine kinase activity of growth factor receptors. In some embodiments of this aspect, the disease is responsive to inhibition of receptor type tyrosine kinase signaling, for example VEGF receptor signaling. In some embodiments of this aspect, the disease is a cell proliferative disease, for example cancer. In some embodiments of this aspect, the disease is an ophthalmic disease, disorder or condition. In some embodiments of this aspect, the ophthalmic disease, disorder or condition is caused by choroidal angiogenesis. In some embodiments of this aspect, the disease is age-related macular degeneration, diabetic retinopathy or retinal edema.

In a ninth aspect, the invention provides for the use of a compound according to the present invention, or a composition thereof, to inhibit kinase activity, for example to inhibit receptor type tyrosine kinase activity, for example to inhibit protein tyrosine kinase activity of growth factor receptors. In some embodiments of this aspect, the invention provides for the use of a compound according to the present invention, or a composition thereof, to inhibit receptor type tyrosine kinase signaling, for example to inhibit VEGF receptor signaling.

In a tenth aspect, the invention provides for the use of a compound according to the present invention, or a composition thereof, to treat a disease responsive to inhibition of kinase activity, for example a disease responsive to inhibition of protein tyrosine kinase activity, for example a disease responsive to inhibition or protein tyrosine kinase activity of growth factor receptors. In some embodiments of this aspect, the invention provides for the use of a compound according to the present invention, or a composition thereof, to treat a disease responsive to inhibition of receptor type tyrosine kinase signaling, for example a disease responsive to inhibition of VEGF receptor signaling. In some embodiments of this aspect, the disease is a cell proliferative disease, for example cancer. In some embodiments of this aspect, the disease is an ophthalmic disease, disorder or condition. In some embodiments of this aspect, the ophthalmic disease, disorder or condition is caused by choroidal angiogenesis.

The foregoing merely summarizes some aspects of the invention and is not intended to be limiting in nature. These aspects and other aspects and embodiments are described more fully below.

DETAILED DESCRIPTION

The invention provides compounds, compositions and methods for inhibiting kinase activity, for example protein tyrosine kinase activity, for example receptor protein kinase activity, for example the VEGF receptor KDR. The invention also provides compounds, compositions and methods for inhibiting angiogenesis, treating a disease responsive to inhibition of kinase activity, treating cell proliferative diseases and conditions and treating ophthalmic diseases, disorders and conditions. The patent and scientific literature referred to herein reflects knowledge that is available to those with skill in the art. The issued patents, published patent applications, and references that are cited herein are hereby incorporated by reference to the same extent as if each was specifically and individually indicated to be incorporated by reference. In the case of inconsistencies, the present disclosure will prevail.

For purposes of the present invention, the following definitions will be used (unless expressly stated otherwise):

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which a divalent moiety is required and is stated as being "aryl," those skilled in the art will understand that the term "aryl" refers to the corresponding divalent moiety, arylene. All atoms are understood to have their normal number of valences for bond formation (i.e., 4 for carbon, 3 for nitrogen, 2 for oxygen, and 2, 4, or 6 for sulfur, depending on the oxidation state of the S). On occasion a moiety may be defined, for example, as $(A)_a$-B—, wherein a is 0 or 1. In such instances, when a is 0 the moiety is B— and when a is 1 the moiety is A-B—.

For simplicity, reference to a "$C_n$-$C_m$" heterocyclyl or "$C_n$-$C_m$" heteroaryl means a heterocyclyl or heteroaryl having from "n" to "m" annular atoms, where "n" and "m" are integers. Thus, for example, a $C_5$-$C_6$ heterocyclyl is a 5- or 6-membered ring having at least one heteroatom, and includes pyrrolidinyl ($C_5$) and piperazinyl and piperidinyl ($C_6$); $C_6$ heteroaryl includes, for example, pyridyl and pyrimidyl.

The term "hydrocarbyl" refers to a straight, branched, or cyclic alkyl, alkenyl, or alkynyl, each as defined herein. A "$C_0$" hydrocarbyl is used to refer to a covalent bond. Thus, "$C_0$-$C_3$ hydrocarbyl" includes a covalent bond, methyl, ethyl, ethenyl, ethynyl, propyl, propenyl, propynyl, and cyclopropyl.

The term "alkyl" is intended to mean a straight chain or branched aliphatic group having from 1 to 12 carbon atoms, alternatively 1-8 carbon atoms, and alternatively 1-6 carbon atoms. In some embodiments, the alkyl group has 1-4 carbon atoms. In some embodiments, the alkyl groups have from 2 to 12 carbon atoms, alternatively 2-8 carbon atoms and alternatively 2-6 carbon atoms. In some embodiments, the alkyl group has 2-4 carbon atoms. Examples of alkyl groups include, without limitation, methyl, ethyl, propyl, isopropyl, butyl, isobutyl, sec-butyl, tert-butyl, pentyl, hexyl and the like. A "$C_0$" alkyl (as in "$C_0$-$C_3$ alkyl") is a covalent bond.

The term "alkenyl" is intended to mean an unsaturated straight chain or branched aliphatic group with one or more carbon-carbon double bonds, having from 2 to 12 carbon atoms, alternatively 2-8 carbon atoms, and alternatively 2-6 carbon atoms. In some embodiments, the alkenyl group has 2-4 carbon atoms. Examples alkenyl groups include, without limitation, ethenyl, propenyl, butenyl, pentenyl, and hexenyl.

The term "alkynyl" is intended to mean an unsaturated straight chain or branched aliphatic group with one or more carbon-carbon triple bonds, having from 2 to 12 carbon atoms, alternatively 2-8 carbon atoms, and alternatively 2-6 carbon atoms. In some embodiments, the alkynyl group has 2-4 carbon atoms. Examples of alkynyl groups include, without limitation, ethynyl, propynyl, butynyl, pentynyl, and hexynyl.

The terms "alkylene," "alkenylene," or "alkynylene" as used herein are intended to mean an alkyl, alkenyl, or alkynyl group, respectively, as defined hereinabove, that is positioned between and serves to connect two other chemical groups. Examples of alkylene groups include, without limitation, methylene, ethylene, propylene, and butylene. Examples of alkenylene groups include, without limitation, ethenylene, propenylene, and butenylene. Examples of alkynylene groups include, without limitation, ethynylene, propynylene, and butynylene.

The term "carbocycle" as employed herein is intended to mean a cycloalkyl or aryl moiety.

The term "cycloalkyl" is intended to mean a saturated, partially unsaturated or unsaturated mono-, bi-, tri- or polycyclic hydrocarbon group having about 3 to 15 carbons, alternatively having 3 to 12 carbons, alternatively 3 to 8 carbons, alternatively 3 to 6 carbons, and alternatively 5 or 6 carbons. In some embodiments, the cycloalkyl group is fused to an aryl, heteroaryl or heterocyclic group. Examples of cycloalkyl groups include, without limitation, cyclopenten-2-enone, cyclopenten-2-enol, cyclohex-2-enone, cyclohex-2-enol, cyclopropyl, cyclobutyl, cyclobutenyl, cyclopentyl, cyclopentenyl, cyclohexyl, cyclohexenyl, cycloheptyl, cyclooctyl, etc.

The term "heteroalkyl" is intended to mean a saturated, partially unsaturated or unsaturated, straight chain or branched aliphatic group, wherein one or more carbon atoms in the group are independently replaced by a heteroatom selected from the group consisting of O, S, and N.

The term "aryl" is intended to mean a mono-, bi-, tri- or polycyclic aromatic moiety, comprising one to three aromatic rings. In some embodiments the aryl is a $C_6$-$C_{14}$ aromatic moiety, alternatively the aryl group is a $C_6$-$C_{10}$ aryl group, alternatively a $C_6$ aryl group. Examples of aryl groups include, without limitation, phenyl, naphthyl, anthracenyl, and fluorenyl.

The terms "aralkyl" or "arylalkyl" are intended to mean a group comprising an aryl group covalently linked to an alkyl group. If an aralkyl group is described as "optionally substituted", it is intended that either or both of the aryl and alkyl moieties may independently be optionally substituted or unsubstituted. In some embodiments, the aralkyl group is $(C_1$-$C_6)$alk$(C_6$-$C_{10})$aryl, including, without limitation, benzyl, phenethyl, and naphthylmethyl. For simplicity, when written as "arylalkyl" this term, and terms related thereto, is intended to indicate the order of groups in a compound as "aryl-alkyl". Similarly, "alkyl-aryl" is intended to indicate the order of the groups in a compound as "alkyl-aryl".

The terms "heterocyclyl", "heterocyclic" or "heterocycle" are intended to mean a group which is a mono-, bi-, or polycyclic structure having from about 3 to about 14 atoms, alternatively 3 to 8 atoms, alternatively 4 to 7 atoms, alternatively 5 or 6 atoms wherein one or more atoms, for example 1 or 2 atoms, are independently selected from the group consisting of N, O, and S, the remaining ring-constituting atoms being carbon atoms. The ring structure may be saturated, unsaturated or partially unsaturated. In some embodiments, the heterocyclic group is non-aromatic, in which case the group is also known as a heterocycloalkyl. In some embodiments the heterocyclyl is a spiro-heterocyclyl, such as 2,7-diazaspiro[4.4]nonane, 2,8-diazaspiro[5.5]undecane, 2,8-diazaspiro[4.5]decane, 2,7-diazaspiro[3.5]nonane, 2,6-diazaspiro[3.4]octane, 2-oxa-7-azaspiro[4.4]nonane, 2-oxa-8-azaspiro[5.5]undecane, 8-oxa-2-azaspiro[4.5]decane, 7-oxa-2-azaspiro[3.5]nonane, 6-oxa-2-azaspiro[3.4]octane, 1-oxa-7-azaspiro[4.4]nonane, 2-oxa-8-azaspiro[5.5]undecane, 2-oxa-8-azaspiro[4.5]decane, 2-oxa-7-azaspiro[3.5]nonane and 2-oxa-6-azaspiro[3.4]octane. In a bicyclic or polycyclic structure, one or more rings may be aromatic; for example, one ring of a bicyclic heterocycle or one or two rings of a tricyclic heterocycle may be aromatic, as in indan and 9,10-dihydro anthracene. Examples of heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, morpholine, thienyl, pyridyl, imidazolyl, isoxazolyl, pyrazolyl, piperazino, piperidyl, piperidino, morpholinyl, homopiperazinyl, homopiperazino, thiomorpholinyl, thiomorpholino, tetrahydropyrrolyl, and azepanyl. In some embodiments, the heterocyclic group is fused to an aryl, heteroaryl, or cycloalkyl group. Examples of such fused heterocycles include, without limitation, tetrahydroquinoline and dihydrobenzofuran. Specifically excluded from the scope of this term are compounds where an annular O or S atom is adjacent to another O or S atom.

In some embodiments, the heterocyclic group is a heteroaryl group. As used herein, the term "heteroaryl" is intended to mean a mono-, bi-, tri- or polycyclic group having 5 to 14 ring atoms, alternatively 5, 6, 9, or 10 ring atoms; having for example 6, 10, or 14 pi electrons shared in a cyclic array; and having, in addition to carbon atoms, between one or more heteroatoms independently selected from the group consisting of N, O, and S. For example, a heteroaryl group includes, without limitation, pyrimidinyl, pyridinyl, benzimidazolyl, benzothiazolyl, benzofuranyl and indolinyl. Other examples of heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, and isoxazolyl.

The terms "arylene," "heteroarylene," or "heterocyclylene" are intended to mean an aryl, heteroaryl, or heterocyclyl group, respectively, as defined hereinabove, that is positioned between and serves to connect two other chemical groups.

Examples of heterocyclyls and heteroaryls include, but are not limited to, azepinyl, azetidinyl, acridinyl, azocinyl, benzidolyl, benzimidazolyl, benzofuranyl, benzofurazanyl, benzofuryl, benzothiofuranyl, benzothiophenyl, benzoxazolyl, benzothiazolyl, benzothienyl, benztriazolyl, benztetrazolyl, benzisoxazolyl, benzisothiazolyl, benzimidazolinyl, benzoxazolyl, benzoxadiazolyl, benzopyranyl, carbazolyl, 4aH-carbazolyl, carbolinyl, chromanyl, chromenyl, cinnolinyl, coumarinyl, decahydroquinolinyl, 1,3-dioxolane, 2H,6H-1,5,2-dithiazinyl, dihydrofuro[2,3-b]tetrahydrofuran, dihydroisoindolyl, dihydroquinazolinyl (such as 3,4-dihydro-4-oxo-quinazolinyl), furanyl, furopyridinyl (such as furo[2,3-c]pyridinyl, furo[3,2-b]pyridinyl or furo[2,3-b]pyridinyl), furyl, furazanyl, hexahydrodiazepinyl, imidazolidinyl, imidazolinyl, imidazolyl, indazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolidinyl, isothiazolyl, isoxazolinyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxetanyl, 2-oxoazepinyl, 2-oxopiperazinyl, 2-oxopiperidinyl, 2-oxopyrrolodinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolopyridyl, 2H-pyrrolyl, pyrrolyl, quinazolinyl, quinolinyl, 4H-quinolizinyl, quinoxalinyl, quinuclidinyl, tetrahydro-1,1-dioxothienyl, tetrahydrofuranyl, tetrahydrofuryl, tetrahydroisoquinolinyl, tetrahydroquinolinyl, tetrahydropyranyl, tetrazolyl, thiazolidinyl, 6H-1,2,5-thiadiazinyl, thiadiazolyl (e.g., 1,2,3-thiadiazolyl, 1,2,4-thiadiazolyl, 1,2,5-thiadiazolyl, 1,3,4-thiadiazolyl), thiamorpholinyl, thiamorpholinyl sulfoxide, thiamorpholuiyl sulfone, thianthrenyl, thiazolyl, thienyl, thienothiazolyl, thienooxazolyl, thienoimidazolyl, thiophenyl, triazinyl, triazinylazepinyl, triazolyl (e.g., 1,2,3-triazolyl, 1,2,4-triazolyl, 1,2,5-triazolyl, 1,3,4-triazolyl), and xanthenyl.

The term "azolyl" as employed herein is intended to mean a five-membered saturated or unsaturated heterocyclic group containing two or more hetero-atoms, as ring atoms, selected from the group consisting of nitrogen, sulfur and oxygen, wherein at least one of the hetero-atoms is a nitrogen atom. Examples of azolyl groups include, but are not limited to, optionally substituted imidazolyl, oxazolyl, thiazolyl, pyrazolyl, isoxazolyl, isothiazolyl, 1,3,4-thiadiazolyl, 1,2,4-thiadiazolyl, 1,2,4-oxadiazolyl, and 1,3,4-oxadiazolyl.

As employed herein, and unless stated otherwise, when a moiety (e.g., alkyl, heteroalkyl, cycloalkyl, aryl, heteroaryl, heterocyclyl, etc.) is described as "optionally substituted" it is meant that the group optionally has from one to four, alternatively from one to three, alternatively one or two, independently selected non-hydrogen substituents. Suitable substituents include, without limitation, halo, hydroxy, oxo (e.g., an annular —CH— substituted with oxo is —C(O)—) nitro, halohydrocarbyl, hydrocarbyl, alkyl, cycloalkyl, heterocyclyl, aryl, heteroaryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups.

Examples of substituents, which are themselves not further substituted (unless expressly stated otherwise) are:
(a) halo, cyano, oxo, carboxy, formyl, nitro, amino, amidino, guanidino,
(b) $C_1$-$C_5$alkyl or alkenyl or arylalkyl imino, carbamoyl, azido, carboxamido, mercapto, hydroxy, hydroxyalkyl, alkylaryl, arylalkyl, $C_1$-$C_8$alkyl, $C_2$-$C_8$alkenyl, $C_1$-$C_8$alkoxy, $C_1$-$C_8$alkyamino, $C_1$-$C_8$alkoxycarbonyl, aryloxycarbonyl, $C_2$-$C_8$acyl, $C_2$-$C_8$acylamino, $C_1$-$C_8$alkylthio, arylalkylthio, arylthio, $C_1$-$C_8$alkylsulfinyl, arylalkylsulfinyl, arylsulfinyl, $C_1$-$C_8$alkylsulfonyl, arylalkylsulfonyl, arylsulfonyl, $C_0$-$C_6$N-alkyl carbamoyl, $C_2$-$C_{15}$N,N-dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$heterocycle, $C_5$-$C_{15}$heteroaryl or any of these rings fused or spiro-fused to a cycloalkyl, heterocyclyl, or aryl, wherein each of the foregoing is further optionally substituted with one more moieties listed in (a), above; and (c) —$(CR^{32}R^{33})_s$—$NR^{30}R^{31}$, wherein s is from 0 (in which case the nitrogen is directly bonded to the moiety that is substituted) to 6, $R^{32}$ and $R^{33}$ are each independently hydrogen, halo, hydroxyl or $C_1$-$C_4$alkyl, and $R^{30}$ and $R^{31}$ are each independently hydrogen, cyano, oxo, hydroxyl, $C_1$-$C_8$alkyl, $C_1$-$C_8$heteroalkyl, $C_2$-$C_8$alkenyl, carboxamido, $C_1$-$C_3$alkyl-carboxamido, carboxamido-$C_1$-$C_3$alkyl, amidino, $C_2$-$C_8$hydroxyalkyl, $C_1$-$C_3$alkylaryl, aryl-$C_1$-$C_3$alkyl, $C_1$-$C_3$alkylheteroaryl, heteroaryl-$C_1$-$C_3$alkyl, $C_1$-$C_3$alkylheterocyclyl, heterocyclyl-$C_1$-$C_3$alkyl $C_1$-$C_3$alkylcycloalkyl, cycloalkyl-$C_1$-$C_3$alkyl, $C_2$-$C_8$alkoxy, $C_2$-$C_8$alkoxy-$C_1$-$C_4$alkyl, $C_1$-$C_8$alkoxycarbonyl, aryloxycarbonyl, aryl-$C_1$-$C_3$alkoxycarbonyl, heteroaryloxycarbonyl, heteroaryl-$C_1$-$C_3$alkoxycarbonyl, $C_1$-$C_8$acyl, $C_0$-$C_8$alkyl-carbonyl, aryl-$C_0$-$C_8$alkyl-carbonyl, heteroaryl-$C_0$-$C_8$alkyl-carbonyl, cycloalkyl-$C_0$-$C_8$alkyl-carbonyl, $C_0$-$C_8$alkyl-NH-carbonyl, aryl-$C_0$-$C_8$alkyl-NH-carbonyl, heteroaryl-$C_0$-$C_8$alkyl-NH-carbonyl, cycloalkyl-$C_0$-$C_8$alkyl-NH-carbonyl, $C_0$-$C_8$alkyl-O-carbonyl, aryl-$C_0$-$C_8$alkyl-O-carbonyl, heteroaryl-$C_0$-$C_8$alkyl-O-carbonyl, cycloalkyl-$C_0$-$C_8$alkyl-O-carbonyl, $C_1$-$C_8$alkylsulfonyl, arylalkylsulfonyl, arylsulfonyl, heteroarylalkylsulfonyl, heteroarylsulfonyl, $C_1$-$C_8$alkyl-NH-sulfonyl, arylalkyl-NH-sulfonyl, aryl-NH-sulfonyl, heteroarylalkyl-NH-sulfonyl, heteroaryl-NH-sulfonyl aroyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, or protecting group, wherein each of the foregoing is further optionally substituted with one more moieties listed in (a), above; or $R^{30}$ and $R^{31}$ taken together with the N to which they are attached form a heterocyclyl or heteroaryl, each of which is optionally substituted with from 1 to 3 substituents selected from the group consisting of (a) above, a protecting group, and ($X^{30}$—$Y^{31}$—), wherein said heterocyclyl may also be bridged (forming a bicyclic moiety with a methylene, ethylene or propylene bridge); wherein $X^{30}$ is selected from the group consisting of $C_1$-$C_8$alkyl, $C_2$-$C_8$alkenyl-, $C_2$-$C_8$alkynyl-, —$C_0$-$C_3$alkyl-$C_2$-$C_8$alkenyl-$C_0$-$C_3$alkyl, $C_0$-$C_3$alkyl-$C_2$-$C_8$alkynyl-$C_0$-$C_3$alkyl, $C_0$-$C_3$alkyl-O—$C_0$-$C_3$alkyl-, HO—$C_0$-$C_3$alkyl-, $C_0$-$C_3$alkyl-N($R^{30}$)—$C_0$-$C_3$alkyl-, N($R^{30}$)($R^{31}$)—$C_0$-$C_3$alkyl-, N($R^{30}$)($R^{31}$)—$C_0$-$C_3$alkenyl-, N($R^{30}$)($R^{31}$)—$C_0$-$C_3$alkynyl-, (N($R^{30}$)($R^{31}$))$_2$—C=N—, $C_0$-$C_3$alkyl-S(O)$_{0-2}$—$C_0$-$C_3$alkyl-, $CF_3$—$C_0$-$C_3$alkyl-, $C_1$-$C_8$heteroalkyl, aryl, cycloalkyl, heterocyclyl, heteroaryl, cycloalkyl-$C_1$-$C_3$alkyl-, heterocyclyl-$C_1$-$C_3$alkyl-, heteroaryl-$C_1$-$C_3$alkyl-, N($R^{30}$)($R^{31}$)-heterocyclyl-$C_1$-$C_3$alkyl-, wherein the aryl, cycloalkyl, heteroaryl and heterocyclyl are optionally substituted with from 1 to 3 substituents from (a); and $Y^{31}$ is selected from the group consisting of a direct bond, —O—, —N($R^{30}$)—, —C(O)—, —O—C(O)—, —C(O)—O—, —N($R^{30}$)—C(O)—, —C(O)—N($R^{30}$)—, —N($R^{30}$)—C(S)—, —C(S)—N($R^{30}$)—, —N($R^{30}$)—C(O)—N($R^{31}$)—, —N($R^{30}$)—C(N$R^{30}$)—N($R^{31}$)—, —N($R^{30}$)—C(N$R^{31}$)—, —C(N$R^{31}$)—N($R^{30}$) —, —N($R^{30}$)—C(S)—N($R^{31}$)—, —N($R^{30}$)—C(O)—O—, —O—C(O)—N($R^{31}$)—, —N($R^{30}$)—C(S)—O—, —O—C(S)—N($R^{31}$)—, —S(O)$_{0-2}$—, —SO$_2$N($R^{31}$)—, —N($R^{31}$)—SO$_2$— and —N($R^{30}$)—SO$_2$N($R^{31}$)—.

A moiety that is substituted is one in which one or more (for example one to four, alternatively from one to three and alternatively one or two), hydrogens have been independently replaced with another chemical substituent. As a non-limiting example, substituted phenyls include 2-fluorophenyl, 3,4-dichlorophenyl, 3-chloro-4-fluoro-phenyl, 2-fluoro-3-propylphenyl. As another non-limiting example, substituted n-octyls include 2,4-dimethyl-5-ethyl-octyl and 3-cyclopentyl-octyl. Included within this definition are methylenes (—CH$_2$—) substituted with oxygen to form carbonyl (—CO—).

When there are two optional substituents bonded to adjacent atoms of a ring structure, such as for example a phenyl, thiophenyl, or pyridinyl, the substituents, together with the atoms to which they are bonded, optionally form a 5- or 6-membered cycloalkyl or heterocycle having 1, 2, or 3 annular heteroatoms.

In some embodiments, a hydrocarbyl, heteroalkyl, heterocyclic and/or aryl group is unsubstituted.

In some embodiments, a hydrocarbyl, heteroalkyl, heterocyclic and/or aryl group is substituted with from 1 to 3 independently selected substituents.

Examples of substituents on alkyl groups include, but are not limited to, hydroxyl, halogen (e.g., a single halogen substituent or multiple halo substituents; in the latter case, groups such as $CF_3$ or an alkyl group bearing $Cl_3$), oxo, cyano, nitro, alkyl, cycloalkyl, alkenyl, cycloalkenyl, alkynyl, heterocycle, aryl, —OR$^a$, —SR$^a$, —S(=O)R$^e$, —S(=O)$_2$R$^e$, —P(=O)$_2$R$^e$, —S(=O)$_2$OR$^e$, —P(=O)$_2$OR$^e$, —NR$^b$R$^c$, —NR$^b$S(=O)$_2$R$^c$, —NR$^b$P(=O)$_2$R$^c$, —S(=O)$_2$NR$^b$R$^c$, —P(=O)$_2$NR$^b$R$^c$, —C(=O)OR$^e$, —C(=O)R$^a$, —C(=O)NR$^b$R$^c$, —OC(=O)R$^a$, —OC(=O)NR$^b$R$^c$, —NR$^b$C(=O)OR$^e$, —NR$^d$C(=O)NR$^b$R$^c$, —NR$^d$S(=O)$_2$NR$^b$R$^c$, —NR$^d$P(=O)$_2$NR$^b$R$^c$, —NR$^b$C(=O)R$^a$ or —NR$^b$P(=O)$_2$R$^e$, wherein R$^a$ is hydrogen, alkyl, cycloalkyl, alkenyl, cycloalkenyl, alkynyl, heterocycle or aryl; R$^b$, R$^c$ and R$^d$ are independently hydrogen, alkyl, cycloalkyl, heterocycle or aryl, or said R$^b$ and R$^c$ together with the N to which they are bonded optionally form a heterocycle; and R$^e$ is alkyl, cycloalkyl, alkenyl, cycloalkenyl, alkynyl, heterocycle or aryl. In the aforementioned exemplary substituents, groups such as alkyl, cycloalkyl, alkenyl, alkynyl, cycloalkenyl, heterocycle and aryl can themselves be optionally substituted.

Examples of substituents on alkenyl and alkynyl groups include, but are not limited to, alkyl or substituted alkyl, as well as those groups recited as examples of alkyl substituents.

Examples of substituents on cycloalkyl groups include, but are not limited to, nitro, cyano, alkyl or substituted alkyl, as well as those groups recited above as examples of alkyl substituents. Other examples of substituents include, but are not limited to, spiro-attached or fused cyclic substituents, for example, spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

Examples of substituents on cycloalkenyl groups include, but are not limited to, nitro, cyano, alkyl or substituted alkyl, as well as those groups recited as examples of alkyl substituents. Other examples of substituents include, but are not limited to, spiro-attached or fused cyclic substituents, for examples spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

Examples of substituents on aryl groups include, but are not limited to, nitro, cycloalkyl or substituted cycloalkyl, cycloalkenyl or substituted cycloalkenyl, cyano, alkyl or substituted alkyl, as well as those groups recited above as examples of alkyl substituents. Other examples of substituents include, but are not limited to, fused cyclic groups, such as fused cycloalkyl, fused cycloalkenyl, fused heterocycle, or fused aryl, where the aforementioned cycloalkyl, cycloalkenyl, heterocycle and aryl substituents can themselves be optionally substituted. Still other examples of substituents on aryl groups (phenyl, as a non-limiting example) include, but are not limited to, haloalkyl and those groups recited as examples of alkyl substituents.

Examples of substituents on heterocyclic groups include, but are not limited to, cycloalkyl, substituted cycloalkyl, cycloalkenyl, substituted cycloalkenyl, nitro, oxo (i.e., =O), cyano, alkyl, substituted alkyl, as well as those groups recited as examples of alkyl substituents. Other examples of substituents on heterocyclic groups include, but are not limited to, spiro-attached or fused cyclic substituents at any available point or points of attachment, for example spiro-attached cycloalkyl, spiro-attached cycloalkenyl, spiro-attached heterocycle (excluding heteroaryl), fused cycloalkyl, fused cycloalkenyl, fused heterocycle and fused aryl, where the aforementioned cycloalkyl, cycloalkenyl, heterocycle and aryl substituents can themselves be optionally substituted.

In some embodiments, a heterocyclic group is substituted on carbon, nitrogen and/or sulfur at one or more positions. Examples of substituents on nitrogen include, but are not limited to alkyl, aryl, aralkyl, alkylcarbonyl, alkylsulfonyl, arylcarbonyl, arylsulfonyl, alkoxycarbonyl, or aralkoxycarbonyl. Examples of substituents on sulfur include, but are not limited to, oxo and $C_{1-6}$alkyl. In some embodiments, nitrogen and sulfur heteroatoms may independently be optionally oxidized and nitrogen heteroatoms may independently be optionally quaternized.

In some embodiments, substituents on ring groups, such as aryl, heteroaryl, cycloalkyl and heterocyclyl, include halogen, alkoxy and/or alkyl.

In some embodiments, substituents on alkyl groups include halogen and/or hydroxy.

A "halohydrocarbyl" as employed herein is a hydrocarbyl moiety, in which from one to all hydrogens have been replaced with halo.

The term "halogen" or "halo" as employed herein refers to chlorine, bromine, fluorine, or iodine. As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., NH$_2$—CO—). The nitrogen atom of an acylamino or carbamoyl substituent is additionally optionally substituted. The term "sulfonamido" refers to a sulfonamide substituent attached by either the sulfur or the nitrogen atom. The term "amino" is meant to include NH$_2$, alkylamino, dialkylamino (wherein each alkyl may be the same or different), arylamino, and cyclic amino groups. The term "ureido" as employed herein refers to a substituted or unsubstituted urea moiety.

The term "radical" as used herein means a chemical moiety comprising one or more unpaired electrons.

Where optional substituents are chosen from "one or more" groups it is to be understood that this definition includes all substituents being chosen from within one of the specified groups or from within the combination of all of the specified groups.

In addition, substituents on cyclic moieties (i.e., cycloalkyl, heterocyclyl, aryl, heteroaryl) include 5- to 6-membered mono- and 9- to 14-membered bi-cyclic moieties fused to the parent cyclic moiety to form a bi- or tri-cyclic fused ring system. Substituents on cyclic moieties also include 5- to 6-membered mono- and 9- to 14-membered bi-cyclic moieties attached to the parent cyclic moiety by a covalent bond to form a bi- or tri-cyclic bi-ring system. For example, an optionally substituted phenyl includes, but is not limited to, the following:

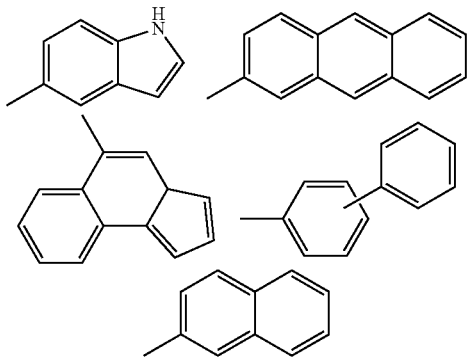

An "unsubstituted" moiety (e.g., unsubstituted cycloalkyl, unsubstituted heteroaryl, etc.) means a moiety as defined above that does not have any optional substituents.

A saturated, partially unsaturated or unsaturated three- to eight-membered carbocyclic ring is for example a four- to seven-membered, alternatively a five- or six-membered, saturated or unsaturated carbocyclic ring. Examples of saturated or unsaturated three- to eight-membered carbocyclic rings include phenyl, cyclopropyl, cyclobutyl, cyclopentyl, cyclohexyl, and cycloheptyl.

A saturated or unsaturated carbocyclic and heterocyclic group may condense with another saturated or heterocyclic group to form a bicyclic group, for example a saturated or unsaturated nine- to twelve-membered bicyclic carbocyclic or heterocyclic group. Bicyclic groups include naphthyl, quinolyl, 1,2,3,4-tetrahydroquinolyl, 1,4-benzoxanyl, indanyl, indolyl, and 1,2,3,4-tetrahydronaphthyl.

When a carbocyclic or heterocyclic group is substituted by two $C_1$-$C_6$alkyl groups, the two alkyl groups may combine together to form an alkylene chain, for example a $C_1$-$C_3$alkylene chain. Carbocyclic or heterocyclic groups having this crosslinked structure include bicyclo[2.2.2]octanyl and norbornanyl.

The terms "kinase inhibitor" and "inhibitor of kinase activity", and the like, are used to identify a compound which is capable of interacting with a kinase and inhibiting its enzymatic activity.

The term "inhibiting kinase enzymatic activity" and the like is used to mean reducing the ability of a kinase to transfer a phosphate group from a donor molecule, such as ATP, to a specific target molecule (substrate). For example, the inhibition of kinase activity may be at least about 10%. In some embodiments of the invention, such reduction of kinase activity is at least about 25%, alternatively at least about 50%, alternatively at least about 75%, and alternatively at least about 90%. In other embodiments, kinase activity is reduced by at least 95% and alternatively by at least 99%. The $IC_{50}$ value is the concentration of kinase inhibitor which reduces the activity of a kinase to 50% of the uninhibited enzyme.

The terms "inhibitor of VEGF receptor signaling" is used to identify a compound having a structure as defined herein, which is capable of interacting with a VEGF receptor and inhibiting the activity of the VEGF receptor. In some embodiments, such reduction of activity is at least about 50%, alternatively at least about 75%, and alternatively at least about 90%. In some embodiments, activity is reduced by at least 95% and alternatively by at least 99%.

The term "inhibiting effective amount" is meant to denote a dosage sufficient to cause inhibition of kinase activity. The amount of a compound of the invention which constitutes an "inhibiting effective amount" will vary depending on the compound, the kinase, and the like. The inhibiting effective amount can be determined routinely by one of ordinary skill in the art. The kinase may be in a cell, which in turn may be in a multicellular organism. The multicellular organism may be, for example, a plant, a fungus or an animal, for example a mammal and for example a human. The fungus may be infecting a plant or a mammal, for example a human, and could therefore be located in and/or on the plant or mammal.

In an exemplary embodiment, such inhibition is specific, i.e., the kinase inhibitor reduces the ability of a kinase to transfer a phosphate group from a donor molecule, such as ATP, to a specific target molecule (substrate) at a concentration that is lower than the concentration of the inhibitor that is required to produce another, unrelated biological effect. For example, the concentration of the inhibitor required for kinase inhibitory activity is at least 2-fold lower, alternatively at least 5-fold lower, alternatively at least 10-fold lower, and alternatively at least 20-fold lower than the concentration required to produce an unrelated biological effect.

Thus, the invention provides a method for inhibiting kinase enzymatic activity, comprising contacting the kinase with an inhibiting effective amount of a compound or composition according to the invention. In some embodiments, the kinase is in an organism. Thus, the invention provides a method for inhibiting kinase enzymatic activity in an organism, comprising administering to the organism an inhibiting effective amount of a compound or composition according to the invention. In some embodiments, the organism is a mammal, for example a domesticated mammal. In some embodiments, the organism is a human.

The term "therapeutically effective amount" as employed herein is an amount of a compound of the invention, that when administered to a patient, elicits the desired therapeutic effect. The therapeutic effect is dependent upon the disease being treated and the results desired. As such, the therapeutic effect can be treatment of a disease-state. Further, the therapeutic effect can be inhibition of kinase activity. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art.

In some embodiments, the therapeutic effect is inhibition of angiogenesis. The phrase "inhibition of angiogenesis" is used to denote an ability of a compound according to the present invention to retard the growth of blood vessels, such as blood vessels contacted with the inhibitor as compared to blood vessels not contacted. In some embodiments, angiogenesis is tumor angiogenesis. The phrase "tumor angiogenesis" is intended to mean the proliferation of blood vessels that penetrate into or otherwise contact a cancerous growth, such as a tumor. In some embodiments, angiogenesis is abnormal blood vessel formation in the eye.

In an exemplary embodiment, angiogenesis is retarded by at least 25% as compared to angiogenesis of non-contacted blood vessels, alternatively at least 50%, alternatively at least 75%, alternatively at least 90%, alternatively at least 95%, and alternatively, at least 99%. Alternatively, angiogenesis is inhibited by 100% (i.e., the blood vessels do not increase in size or number). In some embodiments, the phrase "inhibition of angiogenesis" includes regression in the number or size of blood vessels, as compared to non-contacted blood vessels. Thus, a compound according to the invention that inhibits angiogenesis may induce blood vessel growth retardation, blood vessel growth arrest, or induce regression of blood vessel growth.

Thus, the invention provides a method for inhibiting angiogenesis in an animal, comprising administering to an animal in need of such treatment a therapeutically effective amount of a compound or composition of the invention. In some embodiments, the animal is a mammal, for example a domesticated mammal. In some embodiments, the animal is a human.

In some embodiments, the therapeutic effect is treatment of an ophthalmic disease, disorder or condition. The phrase "treatment of an ophthalmic disease, disorder or condition" is intended to mean the ability of a compound according to the present invention to treat (a) a disease disorder or condition caused by choroidal angiogenesis, including, without limitation, age-related macular degeneration, or (b) diabetic retinopathy or retinal edema. In some embodiments the phrase "treatment of an ophthalmic disease, disorder or condition" is intended to mean the ability of a compound according to the present invention to treat an exudative and/or inflammatory ophthalmic disease, disorder or condition, a disorder related to impaired retinal vessel permeability and/or integrity, a disorder related to retinal microvessel rupture leading to focal hemorrhage, a disease of the back of the eye, a retinal disease, or a disease of the front of the eye, or other ophthalmic disease, disorder or condition.

In some embodiments, the ophthalmic disease, disorder or condition includes but is not limited to Age Related Macular Degeneration (ARMD), exudative macular degeneration (also known as "wet" or neovascular age-related macular degeneration (wet-AMD), macular oedema, aged disciform macular degeneration, cystoid macular oedema, palpebral oedema, retinal oedema, diabetic retinopathy, Acute Macular Neuroretinopathy, Central Serous Chorioretinopathy, chorioretinopathy, Choroidal Neovascularization, neovascular maculopathy, neovascular glaucoma, obstructive arterial and venous retinopathies (e.g. Retinal Venous Occlusion or Retinal Arterial Occlusion), Central Retinal Vein Occlusion, Disseminated Intravascular Coagulopathy, Branch Retinal Vein Occlusion, Hypertensive Fundus Changes, Ocular Ischemic Syndrome, Retinal Arterial Microaneurysms, Coat's Disease, Parafoveal Telangiectasis, Hemi-Retinal Vein Occlusion, Papillophlebitis, Central Retinal Artery Occlusion, Branch Retinal Artery Occlusion, Carotid Artery Disease(CAD), Frosted Branch Angitis, Sickle Cell Retinopathy and other Hemoglobinopathies, Angioid Streaks, macular oedema occurring as a result of aetiologies such as disease (e.g. Diabetic Macular Oedema), eye injury or eye surgery, retinal ischemia or degeneration produced for example by injury, trauma or tumours, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, Thygeson keratitis, progressive Mooren's ulcer, an ocular inflammatory disease caused by bacterial or viral infection or by an ophthalmic operation, an ocular inflammatory disease caused by a physical injury to the eye, and a symptom caused by an ocular inflammatory disease including itching, flare, oedema and ulcer, erythema, erythema exsudativum multiforme, erythema nodosum, erythema annulare, scleroedema, dermatitis, angioneurotic oedema, laryngeal oedema, glottic oedema, subglottic laryngitis, bronchitis, rhinitis, pharyngitis, sinusitis, laryngitis or otitis media.

In some embodiments, the ophthalmic disease, disorder or condition is (a) a disease disorder or condition caused by choroidal angiogenesis, including, without limitation, age-related macular degeneration, or (b) diabetic retinopathy or retinal edema.

In some embodiments, the ophthalmic disease, disorder or condition includes but is not limited to age-related macular degeneration, diabetic retinopathy, retinal edema, retinal vein occlusion, neovascular glaucoma, retinopathy of prematurity, pigmentary retinal degeneration, uveitis, corneal neovascularization or proliferative vitreoretinopathy.

In some embodiments, the ophthalmic disease, disorder or condition is age-related macular degeneration, diabetic retinopathy or retinal edema.

Thus, the invention provides a method for treating an ophthalmic disease, disorder or condition in an animal, comprising administering to an animal in need of such treatment a therapeutically effective amount of a compound or composition of the invention. In some embodiments, the animal is a mammal, for example a domesticated mammal. In some embodiments, the animal is a human.

In some embodiments, the therapeutic effect is inhibition of retinal neovascularization. The phrase "inhibition of retinal neovascularization" is intended to mean the ability of a compound according to the present invention to retard the growth of blood vessels in the eye, for example new blood vessels originating from retinal veins, for example, to retard the growth of new blood vessels originating from retinal veins and extending along the inner (vitreal) surface of the retina.

In an exemplary embodiment, retinal neovascularization is retarded by at least 25% as compared to retinal neovascularization of non-contacted blood vessels, alternatively at least 50%, alternatively at least 75%, alternatively at least 90%, alternatively at least 95%, and alternatively, at least 99%. Alternatively, retinal neovascularization is inhibited by 100% (i.e., the blood vessels do not increase in size or number). In some embodiments, the phrase "inhibition of retinal neovascularization" includes regression in the number or size of blood vessels, as compared to non-contacted blood vessels. Thus, a compound according to the invention that inhibits retinal neovascularization may induce blood vessel growth retardation, blood vessel growth arrest, or induce regression of blood vessel growth.

Thus, the invention provides a method for inhibiting retinal neovascularization in an animal, comprising administering to an animal in need of such treatment a therapeutically effective amount of a compound or composition of the invention. In some embodiments, the animal is a mammal, for example a domesticated mammal. In some embodiments, the animal is a human.

In some embodiments, the therapeutic effect is inhibition of cell proliferation. The phrase "inhibition of cell proliferation" is used to denote an ability of a compound according to the present invention to retard the growth of cells contacted with the inhibitor as compared to cells not contacted. An assessment of cell proliferation can be made by counting contacted and non-contacted cells using a Coulter Cell Counter (Coulter, Miami, Fla.) or a hemacytometer. Where the cells are in a solid growth (e.g., a solid tumor or organ), such an assessment of cell proliferation can be made by measuring the growth with calipers or comparing the size of the growth of contacted cells with non-contacted cells.

In an exemplary embodiment, growth of cells contacted with the inhibitor is retarded by at least 25% as compared to growth of non-contacted cells, alternatively at least 50%, alternatively at least 75%, alternatively at least 90%, alternatively at least 95%, and alternatively, at least 99%. Alternatively, cell proliferation is inhibited by 100% (i.e., the contacted cells do not increase in number). In some embodiments, the phrase "inhibition of cell proliferation" includes a reduction in the number or size of contacted cells, as compared to non-contacted cells. Thus, a compound according to the invention that inhibits cell proliferation in a contacted cell may induce the contacted cell to undergo growth retardation, to undergo growth arrest, to undergo programmed cell death (i.e., to apoptose), or to undergo necrotic cell death.

In some embodiments, the contacted cell is a neoplastic cell. The term "neoplastic cell" is used to denote a cell that shows aberrant cell growth. In some embodiments, the aberrant cell growth of a neoplastic cell is increased cell growth. A neoplastic cell may be a hyperplastic cell, a cell that shows a lack of contact inhibition of growth in vitro, a benign tumor cell that is incapable of metastasis in vivo, or a cancer cell that is capable of metastasis in vivo and that may recur after attempted removal. The term "tumorigenesis" is used to denote the induction of cell proliferation that leads to the development of a neoplastic growth.

In some embodiments, the contacted cell is in an animal. Thus, the invention provides a method for treating a cell proliferative disease or condition in an animal, comprising administering to an animal in need of such treatment a therapeutically effective amount of a compound or composition of the invention. In some embodiments, the animal is a mammal, for example a domesticated mammal. In some embodiments, the animal is a human.

The term "cell proliferative disease or condition" is meant to refer to any condition characterized by aberrant cell growth, such as abnormally increased cellular proliferation. Examples of such cell proliferative diseases or conditions amenable to inhibition and treatment include, but are not limited to, cancer. Examples of particular types of cancer include, but are not limited to, breast cancer, lung cancer, colon cancer, rectal cancer, bladder cancer, prostate cancer, leukemia and renal cancer. In some embodiments, the invention provides a method for inhibiting neoplastic cell proliferation in an animal comprising administering to an animal having at least one neoplastic cell present in its body a therapeutically effective amount of a compound of the invention or a composition thereof.

The term "patient" as employed herein for the purposes of the present invention includes humans and other animals, for example mammals, and other organisms. Thus the compounds, compositions and methods of the present invention are applicable to both human therapy and veterinary applications. In some embodiments the patient is a mammal, for example a human.

The terms "treating", "treatment", or the like, as used herein cover the treatment of a disease-state in an organism, and includes at least one of: (i) preventing the disease-state from occurring, in particular, when such animal is predisposed to the disease-state but has not yet been diagnosed as having it; (ii) inhibiting the disease-state, i.e., partially or completely arresting its development; (iii) relieving the disease-state, i.e., causing regression of symptoms of the disease-state, or ameliorating a symptom of the disease; and (iv) reversal or regression of the disease-state, such as eliminating or curing of the disease, in some embodiments of the present invention the organism is an animal, for example a mammal, for example a primate, for example a human. As is known in the art, adjustments for systemic versus localized delivery, age, body weight, general health, sex, diet, time of administration, drug interaction, the severity of the condition, etc., may be necessary, and will be ascertainable with routine experimentation by one of ordinary skill in the art. In some embodiments, the terms "treating", "treatment", or the like, as used herein cover the treatment of a disease-state in an organism and includes at least one of (ii), (iii) and (iv) above.

Administration for non-ophthalmic diseases, disorders or conditions may be by any route, including, without limitation, parenteral, oral, sublingual, transdermal, topical, intranasal, intratracheal, or intrarectal. In some embodiments, compounds of the invention are administered intravenously in a hospital setting. In some embodiments, administration may be by the oral route.

Examples of routes of administration for ophthalmic diseases, disorders and conditions include but are not limited to, systemic, periocular, retrobulbar, intracanalicular, intravitral injection, topical (for example, eye drops), subconjunctival injection, subtenon, transcleral, intracameral, subretinal, electroporation, and sustained-release implant. Other routes of administration, other injection sites or other forms of administration for ophthalmic situations will be known or contemplated by one skilled in the art and are intended to be within the scope of the present invention.

In some embodiments of the present invention, routes of administration for ophthalmic diseases, disorders and conditions include topical, subconjunctival injection, intravitreal injection, or other ocular routes, systemically, or other methods known to one skilled in the art to a patient following ocular surgery.

In some other embodiments of the present invention, routes of administration for ophthalmic diseases, disorders and conditions include topical, intravitreal, transcleral, periocular, conjunctival, subtenon, intracameral, subretinal, subconjunctival, retrobulbar, or intracanalicular.

In some embodiments of the present invention, routes of administration for ophthalmic diseases, disorders and conditions include topical administration (for example, eye drops), systemic administration (for example, oral or intravenous), subconjunctival injection, periocular injection, intravitreal injection, and surgical implant for local delivery.

In some embodiments of the present invention, routes of administration for ophthalmic diseases, disorders and conditions include intravitreal injection, periocular injection, and sustained-release implant for local delivery.

In some embodiments of the present invention, an intraocular injection may be into the vitreous (intravitreal), under the conjunctiva (subconjunctival), behind the eye (retrobulbar), into the sclera, under the Capsule of Tenon (sub-Tenon), or may be in a depot form.

In some embodiments of the present invention, administration is local, including without limitation, topical, intravitreal, periorbital, intraocular, and other local administration to the eye, the ocular and/or periocular tissues and spaces, including without limitation, via a delivery device.

The compounds of the present invention form salts which are also within the scope of this invention.

The term "salt(s)", as employed herein, denotes acidic and/or basic salts formed with inorganic and/or organic acids and bases. In addition, when a compound of the present invention contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic (exhibiting minimal or no undesired toxicological effects), physiologically acceptable) salts are preferred, although other salts are also useful, e.g., in isolation or purification steps which may be employed during preparation. Salts of the compounds of the invention may be formed, for example, by reacting a compound of the present invention with an amount of acid or base, such as an equivalent amount, in a medium such as one in which the salts precipitates or in an aqueous medium followed by lyophilization.

The compounds of the present invention which contain a basic moiety, such as but not limited to an amine or a pyridine or imidazole ring, may form salts with a variety of organic and inorganic acids. Examples of acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfanotes (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The compounds of the present invention which contain an acidic moiety, such as but not limited to a carboxylic acid, may form salts with a variety of organic and inorganic bases. Examples of basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl and butyl chlorides, bromides and iodides), dialkyl sulfates (e.g. dimethyl, diethyl, dibuty and diamyl sulfates), long chain halides (e.g. decyl, lauryl, myristyl and stearyl chlorides, bromides and iodides), aralkyl halides (e.g. benzyl and phenethyl bromides), and others.

As used herein, the term "pharmaceutically acceptable salts" is intended to mean salts that retain the desired biological activity of the above-identified compounds and exhibit minimal or no undesired toxicological effects. Examples of such salts include, but are not limited to, salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acid, naphthalenedisulfonic acid, methanesulfonic acid, p-toluenesulfonic acid and polygalacturonic acid. Other salts include pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sultanate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

Another aspect of the invention provides compositions comprising a compound according to the present invention. For example, in some embodiments of the invention, a composition comprises a compound, or an N-oxide, hydrate, solvate, pharmaceutically acceptable salt, complex or prodrug of a compound according to the present invention present in at least about 30% enantiomeric or diastereomeric excess. In some embodiments of the invention, the compound, N-oxide, hydrate, solvate, pharmaceutically acceptable salt, complex or prodrug is present in at least about 50%, at least about 80%, or even at least about 90% enantiomeric or diastereomeric excess. In some embodiments of the invention, the compound, N-oxide, hydrate, solvate, pharmaceutically acceptable salt, complex or prodrug is present in at least about 95%, alternatively at least about 98% and alternatively at least about 99% enantiomeric or diastereomeric excess. In other embodiments of the invention, a compound, N-oxide, hydrate, solvate, pharmaceutically acceptable salt, complex or prodrug is present as a substantially racemic mixture.

Some compounds of the invention may have chiral centers and/or geometric isomeric centers (E- and Z-isomers), and it is to be understood that the invention encompasses all such optical, enantiomeric, diastereoisomeric and geometric isomers. The invention also comprises all tautomeric forms of the compounds disclosed herein. Where compounds of the invention include chiral centers, the invention encompasses the enantiomerically and/or diasteromerically pure isomers of such compounds, the enantiomerically and/or diastereomerically enriched mixtures of such compounds, and the racemic and scalemic mixtures of such compounds. For example, a composition may include a mixture of enantiomers or diastereomers of a compound of Formula (I) in at least about 30% diastereomeric or enantiomeric excess. In some embodiments of the invention, the compound is present in at least about 50% enantiomeric or diastereomeric excess, in at least about 80% enantiomeric or diastereomeric excess, or even in at least about 90% enantiomeric or diastereomeric excess. In some embodiments of the invention, the compound is present in at least about 95%, alternatively in at least about 98% enantiomeric or diastereomeric excess, and alternatively in at least about 99% enantiomeric or diastereomeric excess.

The chiral centers of the present invention may have the S or R configuration. The racemic forms can be resolved by physical methods, such as, for example, fractional crystallization, separation or crystallization of diastereomeric derivates or separation by chiral column chromatography. The individual optical isomers can be obtained either starting from chiral precursors/intermediates or from the racemates by any suitable method, including without limitation, conventional methods, such as, for example, salt formation with an optically active acid followed by crystallization.

The present invention also includes prodrugs of compounds of the invention. The term "prodrug" is intended to represent a compound covalently bonded to a carrier, which prodrug is capable of releasing the active ingredient when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of the invention include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of the present invention), amides (e.g., trifluoroacetylamino, acetylamino, and the like), and the like.

The compounds of the invention may be administered, for example, as is or as a prodrug, for example in the form of an in vivo hydrolyzable ester or in vivo hydrolyzable amide. An in vivo hydrolyzable ester of a compound of the invention containing a carboxy or hydroxy group is, for example, a pharmaceutically acceptable ester which is hydrolyzed in the human or animal body to produce the parent acid or alcohol. Suitable pharmaceutically acceptable esters for carboxy include $C_1$-$C_6$alkoxymethyl esters (e.g., methoxymethyl), $C_1$-$C_6$alkanoyloxymethyl esters (e.g., for example pivaloyloxymethyl), phthalidyl esters, $C_3$-$C_8$cycloalkoxycarbonyloxy-$C_1$-$C_6$alkyl esters (e.g., 1-cyclohexylcarbonyloxyethyl); 1,3-dioxolen-2-onylmethyl esters (e.g., 5-methyl-1,3-dioxolen-2-onylmethyl; and $C_1$-$C_6$alkoxycarbonyloxyethyl esters (e.g., 1-methoxycarbonyloxyethyl) and may be formed at any appropriate carboxy group in the compounds of this invention.

An in vivo hydrolyzable ester of a compound of the invention containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolyzable ester forming groups for hydroxy include alkanoyl, benzoyl, phenylacetyl and substituted benzoyl and phenylacetyl, alkoxycarbonyl (to give alkyl carbonate esters), dialkylcarbamoyl and N—(N,N-dialkylaminoethyl)-N-alkylcarbamoyl (to give carbamates), N,N-dialkylaminoacetyl and carboxyacetyl. Examples of substituents on benzoyl include morpholino and piperazino linked from a ring nitrogen atom via a methylene group to the 3- or 4-position of the benzoyl ring. A suitable value for an in vivo hydrolyzable amide of a compound of the invention containing a carboxy group is, for example, a N—$C_1$-$C_6$alkyl or N,N-di-$C_1$-$C_6$alkyl amide such as N-methyl, N-ethyl, N-propyl, N,N-dimethyl, N-ethyl-N-methyl or N,N-diethyl amide.

Upon administration to a subject, the prodrug undergoes chemical conversion by metabolic or chemical processes to yield a compound of the present invention.

The present invention is also directed to solvates and hydrates of the compounds of the present invention. The term "solvate" refers to a molecular complex of a compound with one or more solvent molecules in a stoichiometric or non-stoichiometric amount. A molecular complex of a compound or moiety of a compound and a solvent can be stabilized by non-covalent intra-molecular forces such as, for example, electrostatic forces, van der Waals forces, or hydrogen bonds. Those skilled in the art of organic chemistry will appreciate that many organic compounds can form such complexes with solvents in which they are obtained, prepared or synthesized, or from which they are precipitated or crystallized. The term "hydrate" refers to a complex in which the one or more solvent molecules are water and includes monohydrates, hemi-hydrates, dihydrates, hexahydrates, and the like. The meaning of the words "solvate" and "hydrate" are well known to those skilled in the art. Techniques for the preparation of solvates are well established in the art (see, for example, Brittain, Polymorphism in Pharmaceutical solids. Marcel Dekker, New York, 1999; Hilfiker, Polymorphism in the Pharmaceutical Industry, Wiley, Weinheim, Germany, 2006).

In some embodiments of this aspect, the solvent is an inorganic solvent (for example, water). In some embodiments of this aspect, the solvent is an organic solvent (such as, but not limited to, alcohols, such as, without limitation, methanol, ethanol, isopropanol, and the like, acetic acid, ketones, esters, and the like). In certain embodiments, the solvent is one commonly used in the pharmaceutical art, is known to be innocuous to a recipient to which such solvate is administered (for example, water, ethanol, and the like) and in preferred embodiments, does not interfere with the biological activity of the solute.

Throughout the specification, embodiments of one or more chemical substituents are identified. Also encompassed are combinations of various embodiments. For example, the invention describes some embodiments of D in the compounds and describes some embodiments of group G. Thus, as an example, also contemplated as within the scope of the invention are compounds in which examples of D are as described and in which examples of group G are as described.

Compounds

According to one aspect, the invention is directed to compounds having the Formula (I):

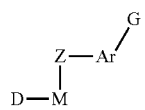
(I)

including N-oxides, hydrates, solvates, tautomers, pharmaceutically acceptable salts, prodrugs and complexes thereof, and racemic and scalemic mixtures, diastereomers and enantiomers thereof, wherein, D is selected from the group consisting of an aromatic, heteroaromatic, cycloalkyl or heterocyclic ring system, $C_1$-$C_6$alkyl-heterocyclyl-C(O)—, $C_1$-$C_6$alkyl-heterocyclyl-$C_1$-$C_6$alkyl-N($R^6$)—C(O)—, ($R^6$)($R^6$)N—C(O)—O-heterocyclyl-C(O)—, heterocyclyl-C(O)—, PivO-heterocyclyl-C(O)—, $C_1$-$C_6$alkyl-O—C(O)-heterocyclyl-C(O)—, $C_1$-$C_6$alkyl-C(O)—N($R^6$)-heterocyclyl-C(O)—, ($C_1$-$C_6$alkyl)(Box)N-heterocyclyl-C(O)—, HO-heterocyclyl-C(O)—, HO—C(O)-heterocyclyl-C(O)—, $C_1$-$C_6$alkyl-C(O)—O-heterocyclyl-C(O)—, ($R^6$)($R^6$)N—$C_1$-$C_6$alkyl-N($R^6$)—C(O)-heterocyclyl-C(O)—, $C_1$-$C_6$alkyl-heterocyclyl-C(O)-heterocyclyl-C(O)— and ($R^6$)($R^6$)N-heterocyclyl-C(O)—, wherein each of the aromatic, heteroaromatic, cycloalkyl and heterocyclic groups is optionally substituted with 1 or more independently selected $R^{38}$;

M is an optionally substituted fused heterocyclic moiety;

Z is selected from the group consisting of —O—, —S(O)$_{0-2}$— and —NR$^5$—, wherein R$^5$ is selected from the group consisting of H, optionally substituted $C_1$-$C_5$alkyl, an optionally substituted ($C_1$-$C_5$)acyl and $C_1$-$C_6$ alkyl-O—C(O), wherein $C_1$-$C_6$ alkyl is optionally substituted;

Ar is a group of the formula C,

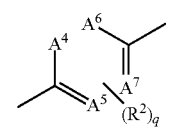
C wherein, $A^4$, $A^5$, $A^6$ and $A^7$ are independently selected from the group consisting of N and —CH—, with the proviso that no more than two of $A^4$, $A^5$, $A^6$ and $A^7$ can be N, wherein Ar is optionally substituted; and G is a group B-L-T, wherein B is selected from the group consisting of a covalent bond, —N($R^{13}$)—, —N(SO$_2$R$^{13}$)—, —O—, —S(O)$_{0-2}$ and —C(=O)—;

L is selected from the group consisting of a covalent bond, —C(=S)N(R$^{13}$)—, —C(=NR$^{14}$)N(R$^{13}$)—, —SO$_2$N(R$^{13}$)—, —SO$_2$—, —C(=O)N(R$^{13}$)—, —N(R$^{13}$)—, —N(R$^{13}$)C$_{1-2}$alkyl-C(=O)—, —C(=O)C$_{0-1}$alkyl-C(=O)N(R$^{13}$)—, —C$_{0-4}$alkylene, —C(=O)C$_{0-1}$alkyl-C(=O)OR$^3$—, —C(=NR$^{14}$)—C$_{0-1}$alkyl-C(=O)—, —C(=O)—, —C(=O)C$_{0-1}$ alkyl-C(=O)— and an optionally substituted four to six-membered heterocyclyl containing between one and three annular heteroatoms including at least one nitrogen, wherein the alkyl and alkylene are optionally substituted; and T is selected from the group consisting of —H, —R$^{13}$, —C$_{0-4}$alkyl, —C$_{0-4}$alkyl-Q, —N(R$^{13}$)C$_{0-4}$alkyl-Q, —SO$_2$C$_{0-4}$alkyl-Q, —C(=O)C$_{0-4}$alkyl-Q, —C$_{0-4}$alkyl-N(R$^{13}$)Q and —C(=O)N(R$^{13}$)—C$_{0-4}$alkyl-Q, wherein each C$_{0-4}$alkyl is optionally substituted;

wherein

R$^{38}$ is selected from the group consisting of C$_2$-C$_6$alkynyl-heterocyclyl, H(O)C— and C$_1$-C$_6$alkyl-C(O)—O—C$_1$-C$_6$alkyl-C(O)—, R$^{37}$O—C$_1$-C$_6$alkyl-C(O)-heterocyclyl-C$_1$-C$_6$alkyl-, R$^{37}$O—(CH$_2$)$_{1-6}$N(A)-(CH$_2$)$_{1-4}$—, C$_1$-C$_6$alkyl-S(O)$_2$—(CH$_2$)$_2$—N(A)-CH$_2$—, R$^{37}$O—(CH$_2$)$_j$—[(CH$_2$)$_i$O]$_x$—(CH$_2$)$_{i1}$—N(A)-(CH$_2$)$_{j1}$—, R$^{37}$O—C(O)—C$_1$-C$_6$alkyl-heterocyclyl-CH$_2$—, R$^{37}$O—(CH$_2$)$_j$—[(CH$_2$)$_i$O]$_x$—(CH$_2$)$_{i1}$—N(R$^{39}$)—C(O)—, R$^{37}$—O—C(O)—C$_1$-C$_6$alkyl-heterocyclyl-C(O)—, HOOC—C$_1$-C$_6$alkyl-N(A)-CH$_2$—, (HOOC)(NR$^9$R$^{10}$)—C$_1$-C$_6$alkyl-N(A)-CH$_2$—, R$^{37}$O—C(O)—C$_1$-C$_6$alkyl-C(O)—, (R$^9$)(R$^{10}$)N—C$_1$-C$_6$alkyl-C(O)-heterocyclyl-CH$_2$—, cycloalkyl-N(R$^{39}$)—C(O)—O—C$_1$-C$_6$alkyl-, R$^{37}$—O—C$_1$-C$_6$alkyl-O—C$_1$-C$_6$alkyl-C(O)—, (R$^9$)(R$^{10}$)N—C(O)—C$_1$-C$_6$alkyl-heterocyclyl-CH$_2$—, (R$^9$)(R$^{10}$)N—C$_1$-C$_6$alkyl-C(O)—O—C$_1$-C$_6$alkyl-heterocyclyl-CH$_2$—, NC—C$_1$-C$_6$alkyl-heterocyclyl-CH$_2$—, F$_3$C—C$_1$-C$_6$alkyl-heterocyclyl-CH$_2$—, C$_1$-C$_6$alkyl-C(O)—O—C$_1$-C$_6$alkyl-C(O)-(5 to 10-membered heterocyclyl)-C$_1$-C$_6$alkyl-, (optionally substituted 8- to 10-membered fused heterocyclyl)-C$_1$-C$_6$alkyl-, F-heterocyclyl-$C_1$-$C_6$alkyl-,
heteroaryl-$C_1$-$C_6$alkyl-heterocyclyl-$C_1$-$C_6$alkyl-,
$R^{37}$—$C_1$-$C_6$alkyl-O—$C_1$-$C_6$alkyl-heterocyclyl-$C_1$-$C_6$alkyl-,
$R^{37}$O—$C_1$-$C_6$alkyl-O-heterocyclyl-$C_1$-$C_6$alkyl-,
$R^{37}$O—C(O)—$C_1$-$C_6$alkyl-heterocyclyl-$C_1$-$C_6$alkyl-,
heterocyclyl-$C_1$-$C_6$alkyl-O-aryl-N($R^6$)—$C_1$-$C_6$alkyl-,
(heteroaryl substituted with one or more $C_1$-$C_6$alkyl)-N($R^6$)—$C_1$-$C_6$alkyl-,
($C_1$-$C_6$alkyl)$_2$N—$C_1$-$C_6$alkyl-aryl-N($R^6$)—$C_1$-$C_6$alkyl-,
($C_1$-$C_6$alkyl)$_2$N—$C_1$-$C_6$alkyl-C(O)-aryl-N($R^6$)—$C_1$-$C_6$alkyl-,
heterocyclyl-$C_1$-$C_6$alkyl-O-aryl-N($R^6$)—$C_1$-$C_6$alkyl-,
($R^6$)$_2$N-heterocyclyl-$C_1$-$C_6$alkyl-,
$C_1$-$C_6$alkyl-C(O)—N($R^6$)-heterocyclyl-$C_1$-$C_6$alkyl-,
$C_1$-$C_6$alkylC(O)—O—$C_1$-$C_6$alkyl-C(O)—N($R^6$)-heterocyclyl-$C_1$-$C_6$alkyl-,
$R^{37}$O—$C_1$-$C_6$alkyl-C(O)—N($R^6$)-heterocyclyl-$C_1$-$C_6$alkyl-,
heteroaryl-$C_1$-$C_6$alkyl-C(O)—N($R^6$)-heterocyclyl-$C_1$-$C_6$alkyl-,
$C_1$-$C_6$alkyl-S(O)$_2$—N($R^6$)-heterocyclyl-$C_1$-$C_6$alkyl-,
$C_1$-$C_6$alkyl-O—C(O)—N($R^6$)-heterocyclyl-$C_1$-$C_6$alkyl-,
$C_1$-$C_6$alkyl-N($R^6$)—C(O)—N($R^6$)-heterocyclyl-$C_1$-$C_6$alkyl-,
$C_1$-$C_6$alkyl-heterocyclyl-C(O)—N($R^6$)-heterocyclyl-$C_1$-$C_6$alkyl-,
$R^{37}$O—$C_1$-$C_6$alkyl-N($R^6$)—C(O)—N($R^6$)-heterocyclyl-$C_1$-$C_6$alkyl-,
(heterocyclyl optionally substituted with one or more $C_1$-$C_6$alkyl)-$C_1$-$C_6$alkyl-,
($C_1$-$C_6$alkyl)$_2$N—$C_1$-$C_6$alkyl-,
$C_1$-$C_6$alkyl-heterocyclyl-C(O)—$C_1$-$C_6$alkyl-,
heterocyclyl-C(O)—$C_1$-$C_6$alkyl-,
$C_1$-$C_6$alkyl—O—C(O)—$C_1$-$C_6$alkyl-,
$C_1$-$C_6$alkyl-O—C(O)—$C_1$-$C_6$alkyl-heteroaryl-N($R^6$)—C(O)—$C_1$-$C_6$alkyl-,
($C_1$-$C_6$alkyl)$_2$N-heterocyclyl-C(O)—$C_1$-$C_6$alkyl-,
heteroaryl-$C_1$-$C_6$alkyl-N($R^6$)—C(O)—$C_1$-$C_6$alkyl-,
(Boc)(H)N-heterocyclyl-C(O)—$C_1$-$C_6$alkyl-,
$C_1$-$C_6$alkyl-O—C(O)-heterocyclyl-C(O)—$C_1$-$C_6$alkyl-,
Boc-heterocyclyl-$C_1$-$C_6$alkyl-,
Ac—O—$C_1$-$C_6$alkyl-C(O)-heterocyclyl-C(O)—$C_1$-$C_6$alkyl-,
$R^{37}$O—$C_1$-$C_6$alkyl-C(O)-heterocyclyl-C(O)—$C_1$-$C_6$alkyl-,
(Boc)(H)N—$C_1$-$C_6$alkyl-C(O)-heterocyclyl-C(O)—$C_1$-$C_6$alkyl-,
NH$_2$—$C_1$-$C_6$alkyl-C(O)-heterocyclyl-C(O)—$C_1$-$C_6$alkyl-,
($C_1$-$C_6$alkyl)(H)N—C(O)-heterocyclyl-C(O)—$C_1$-$C_6$alkyl-,
NH$_2$-heterocyclyl-C(O)—$C_1$-$C_6$alkyl-,
$R^{37}$O—$C_1$-$C_6$alkyl-O—$C_1$-$C_6$alkyl-heterocyclyl-C(O)—,
$C_1$-$C_6$alkyl-O—C(O)—N($R^6$)-heterocyclyl-C(O)—,
($R^6$)($R^6$)N-heterocyclyl-C(O)—,
($R^6$)($R^6$)N-heterocyclyl-$C_1$-$C_6$alkyl-,
heterocyclyl-O—$C_1$-$C_6$alkyl-,
$C_1$-$C_6$alkyl-N($R^6$)—C(O)—N($R^6$)-heterocyclyl-C(O)—,
($R^6$)($R^6$)N—C(O)-heterocyclyl-O—$C_1$-$C_6$alkyl-,
$C_2$-$C_6$alkenyl-C(O)—N($R^6$)-heterocyclyl-$C_1$-$C_6$alkyl-,
$R^{37}$O—$C_1$-$C_6$alkyl-C(O)-heterocyclyl-O—$C_1$-$C_6$alkyl-,
$R^{37O}$—$C_1$-$C_6$alkyl-N($R^6$)-heterocycyl-$C_1$-$C_6$alkyl-,
$R^{37}$O—(CH$_2$)$_j$—[(CH$_2$)$_i$O]$_x$—$C_1$-$C_6$alkyl-N($R^6$)-heterocyclyl-$C_1$-$C_6$alkyl-,
halo-$C_1$-$C_6$alkyl-heterocyclyl-$C_1$-$C_6$alkyl-,
halo-$C_1$-$C_6$alkyl-N($R^6$)-heterocyclyl-$C_1$-$C_6$alkyl-,
$R^{37}$O—C(O)—$C_1$-$C_6$alkyl-N($R^6$)-heterocyclyl-$C_1$-$C_6$alkyl-,
$R^{37}$—O—C(O)—$C_1$-$C_6$alkyl-N($R^6$)—C(O)—N($R^6$)-heterocyclyl-$C_1$-$C_6$alkyl-,
($C_1$-$C_6$alkyl)(H)N—C(O)-heterocyclyl-N[$C_1$-$C_6$alkyl-C(O)—OH]—$C_1$-$C_6$alkyl-,
$C_1$-$C_6$alkyl-O—C(O)-heterocyclyl-$C_1$-$C_6$alkyl-,
HO—C(O)-heterocyclyl-$C_1$-$C_6$alkyl-,
$C_1$-$C_6$alkyl-heterocyclyl-C(O)-heterocyclyl-$C_1$-$C_6$alkyl-,
$R^{37}$O—$C_1$-$C_6$alkyl-N($R^6$)—C(O)-heterocyclyl-$C_1$-$C_6$alkyl-,
($R^6$)($R^6$)N—$C_1$-$C_6$alkyl-N($R^6$)—CO-heterocyclyl-$C_1$-$C_6$alkyl-,
($C_1$-$C_6$alkyl)($C_1$-$C_6$alkyl)N-heterocyclyl-$C_1$-$C_6$alkyl-,
$R^{37}$O—$C_1$-$C_6$alkyl-C(O)-[($C_1$-$C_6$alkyl)($C_1$-$C_6$alkyl)heterocyclyl]-$C_1$-$C_6$alkyl-,
$C_2$-$C_6$alkenyl-C(O)-[($C_1$-$C_6$alkyl)($C_1$-$C_6$alkyl)heterocyclyl]-$C_1$-$C_6$alkyl-,
$R^{37}$—O—$C_1$-$C_6$alkyl-[($C_1$-$C_6$alkyl)($C_1$-$C_6$alkyl)heterocyclyl]-$C_1$-$C_6$alkyl-,
$C_1$-$C_6$alkyl-O—$C_1$-$C_6$alkyl-NR($R^6$)—$C_1$-$C_6$alkyl-,
$C_1$-$C_6$alkyl-O—$C_1$-$C_6$alkyl-N[C(O)—NH—$C_1$-$C_6$alkyl]-$C_1$-$C_6$alkyl-,
$C_1$-$C_6$alkyl-O—$C_1$-$C_6$alkyl-N[C(O)—$C_1$-$C_6$alkyl]-$C_1$-$C_6$alkyl-,
$C_1$-$C_6$alkyl-O—$C_1$-$C_6$alkyl-[C(O)—$C_1$-$C_6$alkyl-OH]—$C_1$-$C_6$alkyl-,
$R^{37}$O—C(O)—$C_1$-$C_6$alkyl-C(O)-heterocyclyl-$C_1$-$C_6$alkyl-,
$R^{37}$O—C(O)—$C_1$-$C_6$alkyl-heterocyclyl-$C_1$-$C_6$alkyl-,
spiro-heterocyclyl-$C_1$-$C_6$alkyl-,
$R^{37}$O—$C_1$-$C_6$alkyl-C(O)-spiro-heterocyclyl-$C_1$-$C_6$alkyl-,
$R^{37}$O—$C_1$-$C_6$alkyl-C(O)-heterocyclyl-$C_1$-$C_6$alkyl-,
$C_1$-$C_6$alkyl-heterocyclyl-$C_1$-$C_6$alkyl-,
$C_1$-$C_6$alkyl-C(O)—O—$C_1$-$C_6$alkyl-C(O)-heterocyclyl-$C_1$-$C_6$alkyl-,
heterocyclyl-$C_1$-$C_6$alkyl-C(O)-heterocyclyl-$C_1$-$C_6$alkyl-,
($R^6$)($R^6$)N—$C_1$-$C_6$alkyl-C(O)-heterocyclyl-$C_1$-$C_6$alkyl-,
heterocyclyl-C(O)-heterocyclyl-$C_1$-$C_6$alkyl-,
($R^6$)($R^6$)N—$C_2$-$C_6$alkenyl-C(O)-heterocyclyl-$C_1$-$C_6$alkyl-,
heterocyclyl-$C_2$-$C_6$alkenyl-C(O)-heterocyclyl-$C_1$-$C_6$alkyl-,
($R^6$)($R^6$)N—$C_1$-$C_6$alkyl-N($R^6$)—$C_1$-$C_6$alkyl-C(O)-heterocyclyl-$C_1$-$C_6$alkyl-, heterocyclyl-C(O)—,
($R^6$)($R^6$)N—C(O)-heterocyclyl-$C_1$-$C_6$alkyl-,
$R^{37}$O—C(O)—$C_1$-$C_6$alkyl-N(R)—C(O)-heterocyclyl-$C_1$-$C_6$alkyl-,
$C_2$-$C_6$alkenyl-C(O)—O—$C_1$-$C_6$alkyl-N($R^6$)—C(O)-heterocyclyl-$C_1$-$C_6$alkyl-,
($R^6$)($R^6$)N—C(O)-heterocyclyl-C(O)—,
$R^{37}$O—$C_1$-$C_6$alkyl-N($R^6$)—C(O)-heterocyclyl-$C_1$-$C_6$alkyl-,
$R^{37}$O—$C_1$-$C_6$alkyl-heterocyclyl-$C_1$-$C_6$alkyl-(heterocyclyl)-,
$R^{37}$O—C(O)—$C_1$-$C_6$alkyl-heterocyclyl-C(O)—,
$R^{37}$O—$C_1$-$C_6$alkyl-heterocyclyl-C(O)—,
$R^{37}$O—$C_1$-$C_6$alkyl-C(O)-heterocyclyl-C(O)—,
$C_1$-$C_6$alkyl-O—C(O)—N($R^6$)—$C_1$-$C_6$alkyl-C(O)—O—$C_1$-$C_6$alkyl-C(O)-heterocyclyl-$C_1$-$C_6$alkyl-,
$R^{37}$O—(CH$_2$)$_n$[(CH$_2$)$_i$O]$_x$—$C_1$-$C_6$alkyl-N($R^6$)—C(O)-heterocyclyl-$C_1$-$C_6$alkyl-,
HO-heterocyclyl-$C_1$-$C_6$alkyl-,
$R^{37}$O-cycloalkyl-C(O)-heterocyclyl-$C_1$-$C_6$alkyl- and
$R^{37}$O—(CH$_2$)$_n$[(CH$_2$)$_i$O]$_x$—$C_1$-$C_6$alkyl-C(O)—N($R^6$)-heterocyclyl-$C_1$-$C_6$alkyl;
A is selected from the group consisting of —C(O)—$C_1$-$C_6$alkyl-N($R^{39}$)—C(O)—$C_1$-$C_6$alkyl-N($R^9$)($R^{10}$)—C(O)—N($R^{39}$)—$C_1$-$C_6$alkyl, —C(=N$R^{37}$)—$C_1$-$C_6$alkyl, —C(O)—(CH$_2$)$_n$—S(O)$_2$—$C_1$-$C_6$alkyl, —C(O)—N($R^{39}$)-cycloalkyl, —C(O)—N($R^9$)($R^{10}$), ($R^{37}$O)($R^{37a}$O)P(O)O—$C_1$-$C_6$alkyl-C(O)—, —C(=N$R^{37}$)—H and —$C_1$-$C_6$alkyl-CF$_3$;
each $R^6$ is independently H or $C_1$-$C_6$alkyl;

$R^{37}$ is selected from the group consisting of H, $C_1$-$C_6$alkyl and $C_3$-$C_{10}$cycloalkyl;

$R^{37a}$ is selected from the group consisting of H, $C_1$-$C_6$alkyl and $C_3$-$C_{10}$cycloalkyl;

j is an integer ranging from 0 to 4, alternatively 0 to 2;

i is 2 or 3;

x is an integer ranging from 0 to 6, alternatively 2 or 3;

i1 is 2 or 3;

j1 is an integer ranging from 0 to 4, alternatively 1 or 2;

n is an integer ranging from 0 to 4;

$R^{39}$ is selected from the group consisting of H, —OH, $C_1$-$C_6$ alkyl, $C_3$-$C_{10}$ cycloalkyl, —$(CH_2)_{n2}(C_6$-$C_{10}$ aryl), —$(CH_2)_{n2}(C_5$-$C_{10}$ heteroaryl), —$(CH_2)_{n2}$(5-10 membered heterocyclyl), —$(CH_2)_{n2}$—O—$(CH_2)_{i2}OR^{37}$ and —$(CH_2)_{n2}OR^{37}$, wherein the alkyl, aryl, heteroaryl and heterocyclyl moieties of the foregoing $R^{39}$ groups are optionally substituted;

$R^9$ is selected from the group consisting of H, —OH, $C_1$-$C_6$ alkyl, $C_3$-$C_{10}$ cycloalkyl, —$(CH_2)_{n3}(C_6$-$C_{10}$ aryl), —$(CH_2)_{n3}(C_5$-$C_{10}$ heteroaryl), —$(CH_2)_{n3}$(5-10 membered heterocyclyl), —$(CH_2)_{n3}O(CH_2)_{i3}OR^{37}$ and —$(CH_2)_{n3}OR^{37}$, wherein the alkyl, aryl, heteroaryl and heterocyclyl moieties of the foregoing $R^9$ groups are optionally substituted;

$R^{10}$ is selected from the group consisting of H, —OH, $C_1$-$C_6$ alkyl, $C_3$-$C_{10}$ cycloalkyl, —$(CH_2)_{n4}(C_6$-$C_{10}$ aryl), —$(CH_2)_{n4}(C_5$-$C_{10}$ heteroaryl), —$(CH_2)_{n4}$(5-10 membered heterocyclyl), —$(CH_2)_{n4}O(CH_2)_{i4}OR^{37}$ and —$(CH_2)_{n4}OR^{37}$, wherein the alkyl, aryl, heteroaryl and heterocyclyl moieties of the foregoing $R^{10}$ groups are optionally substituted;

n2 is an integer ranging from 0 to 6;

i2 is an integer ranging from 2 to 6;

n3 is an integer ranging from 0 to 6;

i3 is an integer ranging from 2 to 6;

n4 is an integer ranging from 0 to 6;

i4 is an integer ranging from 2 to 6;

$R^2$ at each occurrence is independently selected from the group consisting of —H, halogen, trihalomethyl, —CN, —$NO_2$, —$NH_2$, —$OR^3$, —$NR^3R^4$, —$S(O)_{0-2}R^3$, —$S(O)_2NR^3R^3$, —$C(O)OR^3$, —$C(O)NR^3R^3$, —$N(R^3)SO_2R^3$, —$N(R^3)C(O)R^3$, —$N(R^3)CO_2R^3$, —$C(O)R^3$, $C_1$-$C_4$ alkoxy, $C_1$-$C_4$ alkylthio, —$O(CH_2)_n$aryl, —$O(CH_2)_n$heteroaryl, —$(CH_2)_{0-5}$(aryl), —$(CH_2)_{0-5}$(heteroaryl), $C_1$-$C_6$ alkyl, $C_2$-$C_6$ alkenyl, $C_2$-$C_6$ alkynyl, —$CH_2(CH_2)_{0-4}$-$T^2$, wherein $T^2$ is selected from the group consisting of —OH, —OMe, —OEt, —$NH_2$, —NHMe, —$NMe_2$, —NHEt and —$NEt_2$, and wherein the aryl, heteroaryl, $C_1$-$C_6$ alkyl, $C_2$-$C_6$ alkenyl, and $C_2$-$C_6$ alkynyl are optionally substituted; and q is an integer from 0 to 4;

$R^{13}$ is selected from the group consisting of —H, —CN, —$NO_2$, —$NH_2$, —$OR^3$, —$NR^3R^4$, —$S(O)_{0-2}R^3$, —$S(O)_2NR^3R^3$, —$C(O)OR^3$, —$C(O)NR^3R^3$, —$N(R^3)SO_2R^3$, —$N(R^3)C(O)R^3$, —$N(R^3)CO_2R^3$, —$C(O)R^3$, —$C(O)SR^3$, $C_1$-$C_4$ alkoxy, $C_1$-$C_4$ alkylthio, —$O(CH_2)_{n5}$aryl, —$O(CH_2)_{n5}$heteroaryl, —$(CH_2)_{n5}$(aryl), —$(CH_2)_{n5}$(heteroaryl), $C_1$-$C_6$ alkyl, $C_2$-$C_6$ alkenyl, $C_2$-$C_6$ alkynyl, —$CH_2(CH_2)_{0-4}$-$T^2$, an optionally substituted $C_{1-4}$ alkylcarbonyl, and a saturated or unsaturated three- to seven-membered cycloalkyl or heterocyclic group, wherein $T^2$ is selected from the group consisting of —OH, —OMe, —OEt, —NHMe, —$NMe_2$, —NHEt and —$NEt_2$, and wherein the aryl, heteroaryl, $C_1$-$C_6$ alkyl, $C_2$-$C_6$ alkenyl, and $C_2$-$C_6$ alkynyl are optionally substituted;

two $R^{13}$, together with the atom or atoms to which they are attached, can combine to form a heteroalicyclic optionally substituted with between one and four of $R^{60}$, wherein the heteroalicyclic can have up to four annular heteroatoms, and the heteroalicyclic can have an aryl or heteroaryl fused thereto, in which case the aryl or heteroaryl is optionally substituted with an additional one to four of $R^{60}$;

n5 is an integer ranging from 0 to 6

$R^{60}$ is selected from the group consisting of —H, halogen, trihalomethyl, —CN, —$NO_2$, —$NH_2$, —$OR^3$, —$NR^3R^4$, —$S(O)_{0-2}R^3$, —$SO_2NR^3R^3$, —$CO_2R^3$, —$C(O)NR^3$, $R^3$, —$N(R^3)SO_2R^3$, —$N(R^3)C(O)R^3$, —$N(R^3)CO_2R^3$, —$C(O)R^3$, an optionally substituted ($C_1$-$C_6$)alkyl, an optionally substituted aryl, an optionally substituted heteroarylalkyl and an optionally substituted arylalkyl;

two $R^{60}$, when attached to a non-aromatic carbon, can be oxo;

each $R^3$ is independently selected from the group consisting of —H and $R^4$;

$R^4$ is selected from the group consisting of a ($C_1$-$C_6$)alkyl, an aryl, a lower arylalkyl, a heterocyclyl and a lower heterocyclyl-alkyl, each of which is optionally substituted, or $R^3$ and $R^4$, taken together with a common nitrogen to which they are attached, form an optionally substituted five- to seven-membered heterocyclyl, the optionally substituted five- to seven-membered heterocyclyl optionally containing at least one additional annular heteroatom selected from the group consisting of N, O, S and P;

$R^{14}$ is selected from the group —H, —$NO_2$, —$NH_2$, —$N(R^3)R^4$, —CN, —$OR^3$, an optionally substituted ($C_1$-$C_6$)alkyl, an optionally substituted heteroalicyclyl-alkyl, an optionally substituted aryl, an optionally substituted arylalkyl and an optionally substituted heteroalicyclic, Q is a three- to ten-membered ring system, optionally substituted with zero, one or more of $R^{20}$;

$R^{20}$ is selected from the group consisting of —H, halogen, trihalomethyl, —CN, —$NO_2$, —$NH_2$, —$OR^3$, —$OCF_3$, —$NR^3R^4$, —$S(O)_2NR^3R^3$, —$C(O)OR^3$, —$C(O)NR^3R^3$, —$N(R^3)SO_2R^3$, —$N(R^3)C(O)R^3$, —$N(R^3)C(O)OR^3$, —$C(O)R^3$, —$C(O)SR^3$, $C_1$-$C_4$ alkoxy, $C_1$-$C_4$ alkylthio, —$O(CH_2)_{n6}$aryl, —$O(CH_2)_{n6}$heteroaryl, —$(CH_2)_{n6}$(aryl), —$(CH_2)_{n6}$(heteroaryl), $C_1$-$C_6$ alkyl, $C_2$-$C_6$ alkenyl, $C_2$-$C_6$ alkynyl, —$CH_2(CH_2)_{0-4}$-$T^2$, an optionally substituted. $C_{1-4}$ alkylcarbonyl, $C_{1-4}$ alkoxy, an amino optionally substituted by $C_{1-4}$ alkyl optionally substituted by $C_{1-4}$ alkoxy, —$(CH_2)_{n6}P(=O)(C_1$-$C_6$alkyl$)_2$, a saturated or unsaturated three- to seven-membered cycloalkyl or heterocyclic group, —$SiMe_3$ and —$SbF_5$; and n6 is an integer ranging from 0 to 6.

In some embodiments of the first aspect, the compounds have the Formula (I), wherein D is -aryl or -heteroaryl each of which is substituted with 1 or more $R^{38}$.

In some embodiments of the first aspect, the compounds have the Formula (I), wherein D is selected from the group consisting of

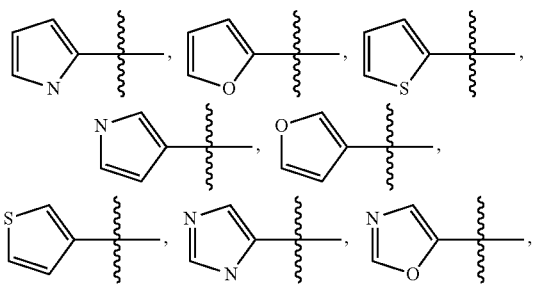

-continued

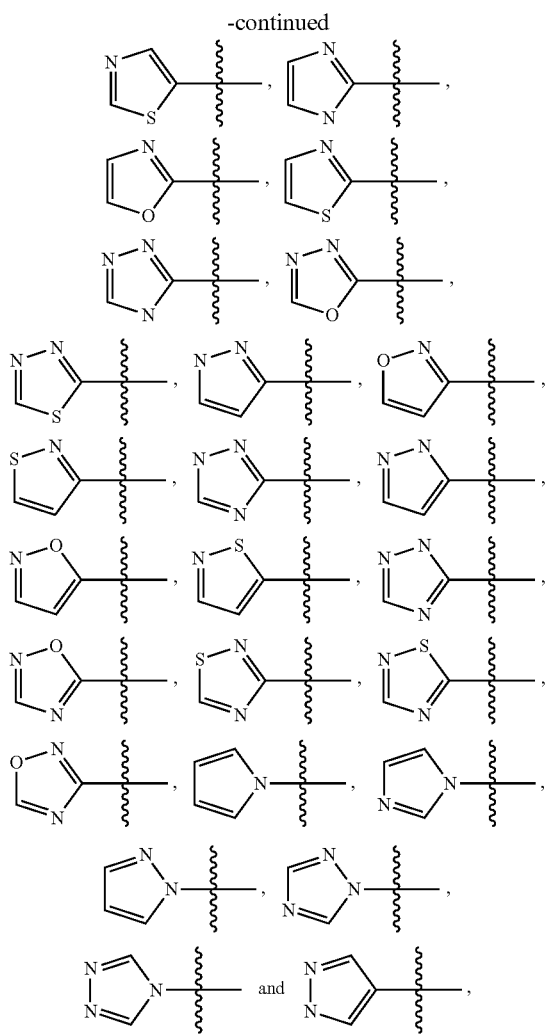

wherein the members of said group are substituted by 1 or more $R^{38}$.

In some embodiments of the first aspect, the compounds have the Formula (I), wherein D is selected from the group consisting of

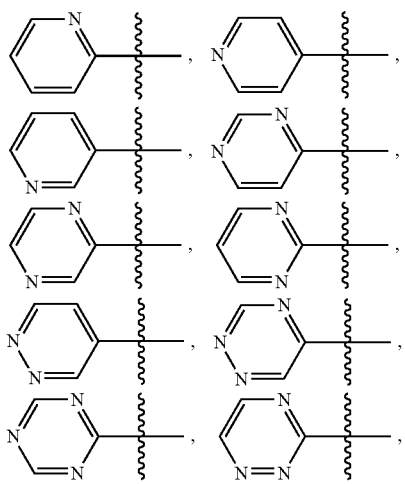

-continued

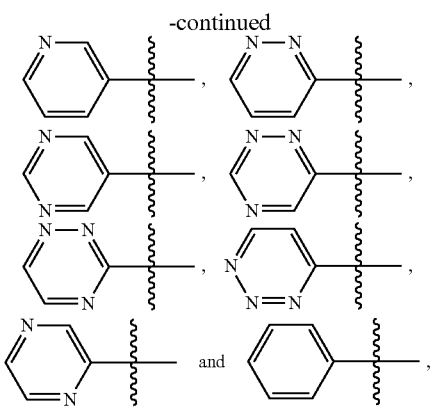

wherein the members of said group are substituted with 1 or more $R^{38}$.

In some embodiments of the first aspect, the compounds have the Formula (I), wherein D is selected from the group consisting of phenyl, pyridine, imidazole, pyrazole and tetrahydropyridine substituted with one $R^{38}$, wherein when D is imidazole said imidazole is further optionally substituted with one $C_1$-$C_6$alkyl.

In some embodiments of the first aspect, the compounds have the Formula (I), wherein D is phenyl or pyridine substituted with one $R^{38}$.

In some embodiments of the first aspect, the compounds have the Formula (I), wherein D is pyridine substituted with one $R^{38}$.

In some embodiments of the first aspect, the compounds have the Formula (I), wherein D is pyridine substituted with one $R^{38}$, wherein $R^{38}$ is selected from the group consisting of $R^{37}O$—$(CH_2)_{1-6}$—$N(A)$-$(CH_2)_{1-4}$—, $R^{37}O$—$(CH_2)_j$—$[(CH_2)_iO]_x$—$(CH_2)_{i1}$—$N(A)$-$(CH_2)_{j1}$—, $R^{37}O$—$C(O)$—$C_0$-$C_6$alkyl-heterocyclyl-$CH_2$—, $R^{37}O$—$(CH_2)_j$—$[(CH_2)_iO]_x$—$(CH_2)_{i1}$—$N(R^{39})$—$C(O)$—, $R^{37}$—$O$—$C(O)$—$C_1$-$C_6$alkyl-heterocyclyl-$C(O)$—, $C_0$-$C_6$alkyl-heterocyclyl-$C_0$-$C_6$alkyl-heterocyclyl-$C(O)$—, $(R^9)(R^{10})N$—$C_1$-$C_6$alkyl-$C(O)$-heterocyclyl-$CH_2$—, $(R^9)(R^{10})N$—$C(O)$—$C_1$-$C_6$alkyl-heterocyclyl-$CH_2$—, $(R^9)(R^{10})N$—$C_1$-$C_6$alkyl-$C(O)$—$O$—$C_1$-$C_6$alkyl-heterocyclyl-$CH_2$—, $NC$—$C_1$-$C_6$alkyl-heterocyclyl-$CH_2$—, $F_3C$—$C_1$-$C_6$alkyl-heterocyclyl-$CH_2$— and $N(R^9)(R^{10})N$—$C_1$-$C_6$alkyl-$C(O)$—$O$—$C_1$-$C_6$alkyl-$C(O)$-heterocyclyl-$CH_2$—.

In some embodiments of the first aspect, the compounds have the Formula (I), wherein D is pyridine substituted with one $R^{38}$, wherein $R^{38}$ is selected from the group consisting of $R^{37}O$—$(CH_2)_{1-6}$—$N(A)$-$(CH_2)_{1-4}$—, $R^{37}O$—$(CH_2H(CH_2)_j$—$[(CH_2)_iO]_x$—$(CH_2)_{i1}$—$N(A)$-$(CH_2)_{j1}$—, $R^{37}O$—$C(O)$—$C_0$-$C_6$alkyl-heterocyclyl-$CH_2$—, $R^{37}O$—$(CH_2)_j$—$[(CH_2)_iO]_x$—$(CH_2)_{i1}$—$N(R^{39})$—$C(O)$—, $R^{37}$—$O$—$C(O)$—$C_1$-$C_6$alkyl-heterocyclyl-$C(O)$—, $(R^9)(R^{10})N$—$C_1$-$C_6$alkyl-$C(O)$-heterocyclyl-$CH_2$—, $(R^9)(R^{10})N$—$C(O)$—$C_1$-$C_6$alkyl-heterocyclyl-$CH_2$—, $(R^9)(R^{10})N$—$C_1$-$C_6$alkyl-$C(O)$—$O$—$C_1$-$C_6$alkyl-heterocyclyl-$CH_2$—, $NC$—$C_1$-$C_6$alkyl-heterocyclyl-$CH_2$—, $F_3C$—$C_1$-$C_6$alkyl-heterocyclyl-$CH_2$— and $N(R^9)(R^{10})N$—$C_1$-$C_6$alkyl-$C(O)$—$O$—$C_1$-$C_6$alkyl-$C(O)$-heterocyclyl-$CH_2$—.

In some embodiments of the first aspect, the compounds have the Formula (I), wherein D is pyridine substituted with one $R^{38}$, wherein $R^{38}$ is $R^{37}O$—$(CH_2)_{1-6}$—$N(A)$-$(CH_2)_{1-4}$— or $R^{37}O$—$(CH_2)_j$—$[(CH_2)_iO]_x$—$(CH_2)_{i1}$—$N(A)$-$(CH_2)_{j1}$—, and A is selected from the group consisting of —$C(O)$—$C_1$-$C_6$alkyl-$N(R^{39})$—$C(O)$—$C_1$-$C_6$alkyl-$N(R^9)(R^{10})$, —$C(O)$—$N(R^{39})$—$C_1$-$C_6$alkyl, —$C(=NR^{37})$—$C_1$-$C_6$alkyl, —C(O)—(CH$_2$)$_n$—S(O)$_2$—C$_1$-C$_6$alkyl, —C(O)—N(R$^9$)(R$^{10}$) and (R$^{37}$O)(R$^{37a}$O)P(O)O—C$_1$-C$_6$alkyl-C(O)—.

In some embodiments of the first aspect, the compounds have the Formula (I), wherein D is pyridine substituted with one R$^{38}$, wherein R$^{38}$ is R$^{37}$O—(CH$_2$)$_{1-6}$—N(A)-(CH$_2$)$_{1-4}$—, alternatively R$^{37}$O—(CH$_2$)$_2$—N(A)-(CH$_2$)—, alternatively R$^{37}$O—(CH$_2$)$_2$—N(A)-(CH$_2$)$_2$—.

In some embodiments of the first aspect, the compounds have the Formula (I), wherein D is pyridine substituted with one R$^{38}$, wherein R$^{38}$ is R$^{37}$O—(CH$_2$)$_{1-6}$—N(A)-(CH$_2$)$_{1-4}$—, and A is selected from the group consisting of —C(O)—C$_1$-C$_6$alkyl-N(R$^{39}$)—C(O)—C$_1$-C$_6$alkyl-N(R$^9$)(R$^{10}$), —C(O)—N(R$^{39}$)—C$_1$-C$_6$alkyl, —C(=NR$^{37}$)—C$_1$-C$_6$alkyl, —C(O)—(CH$_2$)$_n$—S(O)$_2$—C$_1$-C$_6$alkyl, —C(O)—)N(R$^9$)(R$^{10}$) and (R$^{37}$O)(R$^{37a}$O)P(O)O—C$_1$-C$_6$alkyl-C(O)—.

In some embodiments of the first aspect, the compounds have the Formula (I), wherein D is pyridine substituted with one R$^{38}$, wherein R$^{38}$ is R$^{37}$O—(CH$_2$)$_2$—N(A)-(CH$_2$)—, and A is selected from the group consisting of —C(O)—C$_1$-C$_6$alkyl-N(R$^{39}$)—C(O)—C$_1$-C$_6$alkyl-N(R$^9$)(R$^{10}$), —C(O)—N(R$^{39}$)—C$_1$-C$_6$alkyl, —C(=NR$^{37}$)—C$_1$-C$_6$alkyl, —C(O)—(CH$_2$)$_n$—S(O)$_2$—C$_1$-C$_6$alkyl, —C(O)—N(R$^9$)(R$^{10}$) and (R$^{37}$O)(R$^{37a}$O)P(O)O—C$_1$-C$_6$alkyl-C(O)—.

In some embodiments of the first aspect, the compounds have the Formula (I), wherein D is pyridine substituted with one R$^{38}$, wherein R$^{38}$ is R$^{37}$O—(CH$_2$)$_2$—N(A)-(CH$_2$)$_2$—, and A is —C(O)—N(R$^{39}$)—C$_1$-C$_6$alkyl.

In some embodiments of the first aspect, the compounds have the Formula (I), wherein D is pyridine substituted with one R$^{38}$, wherein R$^{38}$ is R$^{37}$O—(CH$_2$)$_2$—N(A)-(CH$_2$)—, and A is —C(O)—N(R$^{39}$)—C$_1$-C$_6$alkyl.

In some embodiments of the first aspect, the compounds have the Formula (I), wherein D is pyridine substituted with one R$^{38}$, wherein R$^{38}$ is R$^{37}$O—(CH$_2$)$_2$—N(A)-(CH$_2$)—, and A is —C(O)—H.

In some embodiments of the first aspect, the compounds have the Formula (I), wherein D is pyridine substituted with one R$^{38}$, wherein R$^{38}$ is R$^{37}$O—(CH$_2$)$_j$—[(CH$_2$)$_i$O]$_x$—(CH$_2$)$_{i1}$—N(A)-(CH$_2$)$_{j1}$—.

In some embodiments of the first aspect, the compounds have the Formula (I), wherein D is pyridine substituted with one R$^{38}$, wherein R$^{38}$ is R$^{37}$O—(CH$_2$)$_j$—[(CH$_2$)$_i$O]$_x$—(CH$_2$)$_{i1}$—N(A)-(CH$_2$)$_{j1}$—, and A is —C(O)—N(R$^{39}$)—C$_1$-C$_6$alkyl, In some embodiments of the first aspect, the compounds have the Formula (I), wherein D is pyridine substituted with one R$^{38}$, wherein R$^{38}$ is R$^{37}$O—C(O)—C$_0$-C$_6$alkyl-heterocyclyl-CH$_2$—.

In some embodiments of the first aspect, the compounds have the Formula (I), wherein D is pyridine substituted with one R$^{38}$, wherein R$^{38}$ is R$^{37}$O—(CH$_2$)$_j$—[(CH$_2$)$_i$O]$_x$—(CH$_2$)$_{i1}$—N(R$^{39}$)—C(O)—.

In some embodiments of the first aspect, the compounds have the Formula (I), wherein D is pyridine substituted with one R$^{38}$, wherein R$^{38}$ is R$^{37}$—O—C(O)—C$_1$-C$_6$alkyl-heterocyclyl-C(O)—.

In some embodiments of the first aspect, the compounds have the Formula (I), wherein D is pyridine substituted with one R$^{38}$, wherein R$^{38}$ is C$_0$-C$_6$alkyl-heterocyclyl-C$_0$-C$_6$alkyl-heterocyclyl-C(O)—.

In some embodiments of the first aspect, the compounds have the Formula (I), wherein D is pyridine substituted with one R$^{38}$, wherein R$^{38}$ is (R$^9$)(R$^{10}$)N—C$_1$-C$_6$alkyl-C(O)-heterocyclyl-CH$_2$—.

In some embodiments of the first aspect, the compounds have the Formula (I), wherein D is pyridine substituted with one R$^{38}$, wherein R$^{38}$ is (R$^9$)(R$^{10}$)N—C(O)—C$_1$-C$_6$alkyl-heterocyclyl-CH$_2$—.

In some embodiments of the first aspect, the compounds have the Formula (I), wherein D is pyridine substituted with one R$^{38}$, wherein R$^{38}$ is (R$^9$)(R$^{10}$)N—C(O)—C$_1$-C$_6$alkyl-C(O)—O—C$_1$-C$_6$alkyl-heterocyclyl-CH$_2$—.

In some embodiments of the first aspect, the compounds have the Formula (I), wherein D is pyridine substituted with one R$^{38}$, wherein R$^{38}$ is NC—C$_1$-C$_6$alkyl-heterocyclyl-CH$_2$—.

In some embodiments of the first aspect, the compounds have the Formula (I), wherein D is pyridine substituted with one R$^{38}$, wherein R$^{38}$ is F$_3$C—C$_1$-C$_6$alkyl-heterocyclyl-CH$_2$—.

In some embodiments of the first aspect, the compounds have the Formula (I), wherein D is pyridine substituted with one R$^{38}$, wherein R$^{38}$ is)N(R$^9$)(R$^{10}$)N—C$_1$-C$_6$alkyl-C(O)—O—C$_1$-C$_6$alkyl-C(O)-heterocyclyl-CH$_2$—.

In some embodiments of the first aspect, the compounds have the Formula (I), wherein D is pyridine substituted with one R$^{38}$, wherein R$^{38}$ is (optionally substituted 8- to 10-membered fused heterocyclyl)-C$_1$-C$_6$alkyl-.

In some embodiments of the first aspect, the compounds have the Formula (I), wherein D is pyridine substituted with one R$^{38}$, wherein R$^{38}$ is (optionally substituted 8- to 10-membered fused heterocyclyl)-C$_1$-C$_6$alkyl-, wherein the optional substituent is selected from the group consisting of H, halo, —N(R$^9$)(R$^{10}$) nitro, —OH, oxo, C$_1$-C$_6$alkyl, —C(O)—C$_1$-C$_6$alkyl-OH, Ac, cycloalkyl, heterocyclyl, aryl, heteroaryl, —S(O)$_{0-2}$—C$_1$-C$_6$alkyl, —S(O)$_{0-2}$-cycloalkyl, —S(O)$_{0-2}$-heterocyclyl, —S(O)$_{0-2}$-aryl, —S(O)$_{0-2}$-heteroaryl, —C(O)H, —C(O)—C$_1$-C$_6$alkyl, —C(O)—N(R$^9$)(R$^{10}$), —C$_1$-C$_6$alkyl-OH, —C$_1$-C$_6$alkyl-C(O)—OH and —C$_1$-C$_6$alkyl-C(O)—N(R$^9$)(R$^{10}$), wherein the alkyl, cycloalkyl, heterocyclyl, aryl and heteroaryl groups are themselves optionally substituted, for example with halo or —C$_1$-C$_6$alkyl.

In some embodiments of the first aspect, the compounds have the Formula I, wherein D is imidazole substituted with one R$^{38}$ and one C$_1$-C$_6$alkyl.

In some embodiments of the first aspect, the compounds have the Formula I, wherein D is imidazole substituted with one R$^{38}$ and one C$_1$-C$_6$alkyl, wherein R$^{38}$ is R$^{37}$O—(CH$_2$)$_{1-6}$—N(A)-(CH$_2$)$_{1-4}$—.

In some embodiments of the first aspect, the compounds have the Formula I, wherein D is imidazole substituted with one R$^{38}$ and one C$_1$-C$_6$alkyl, wherein R$^{38}$ is R$^{37}$O—(CH$_2$)$_{1-6}$—N(A)-(CH$_2$)$_{1-4}$—, and A is —C(O)—N(R$^{39}$)—C$_1$-C$_6$alkyl or —C(O)—N(R$^{39}$)-cycloalkyl.

In some embodiments of the first aspect, the compounds have the Formula I, wherein D is imidazole substituted with one R$^{38}$ and one C$_1$-C$_6$alkyl, wherein R$^{38}$ is R$^{37}$O—(CH$_2$)$_2$—N(A)-(CH$_2$)—, and A is —C(O)—N(R$^{39}$)—C$_1$-C$_6$alkyl or —C(O)—N(R$^{39}$)-cycloalkyl.

In some embodiments of the first aspect, the compounds have the Formula I, wherein D is imidazole substituted with one R$^{38}$ and one C$_1$-C$_6$alkyl, wherein R$^{38}$ is R$^{37}$O—(CH$_2$)$_2$—N(A)-(CH$_2$)—, and A is —C(O)—N(R$^{39}$)—C$_1$-C$_6$alkyl.

In some embodiments of the first aspect, the compounds have the Formula I, wherein D is imidazole substituted with one R$^{38}$, wherein R$^{38}$ is C$_1$-C$_6$alkyl-C(O)—O—C$_1$-C$_6$alkyl-C(O)-(5 to 10-membered heterocyclyl)-C$_1$-C$_6$alkyl-.

In some embodiments of the first aspect, the compounds have the Formula (I), wherein D is phenyl substituted with one R$^{38}$.

In some embodiments of the first aspect, the compounds have the Formula (I), wherein D is phenyl substituted with one $R^{38}$, wherein $R^{38}$ is $R^{37}O$—$(CH_2)_{1-6}$—N(A)-$(CH_2)_{1-4}$—.

In some embodiments of the first aspect, the compounds have the Formula (I), wherein D is phenyl substituted with one $R^{38}$, wherein $R^{38}$ is $R^{37}O$—$(CH_2)_{1-6}$—N(A)-$(CH_2)_{1-4}$—, and A is —C(O)—N($R^{39}$)—$C_1$-$C_6$alkyl or —C(O)—N($R^{39}$)-cycloalkyl.

In some embodiments of the first aspect, the compounds have the Formula (I), wherein D is phenyl substituted with one $R^{38}$, wherein $R^{38}$ is $R^{37}O$—$(CH_2)_2$—N(A)-$(CH_2)$—, and A is —C(O)—N($R^{39}$)—$C_1$-$C_6$alkyl or —C(O)—N($R^{39}$)-cycloalkyl.

In some embodiments of the first aspect, the compounds have the Formula (I), wherein D is tetrahydropyridine substituted with one $R^{38}$.

In some embodiments of the first aspect, the compounds have the Formula (I), wherein D is tetrahydropyridine substituted with one $R^{38}$, wherein $R^{38}$ is $R^{37}O$—C(O)—$C_1$-$C_6$alkyl-C(O)— or $R^{37}$—O—$C_1$-$C_6$alkyl-O—$C_1$-$C_6$alkyl-C(O)—.

In some embodiments of the first aspect, the compounds have the Formula (I), wherein D is tetrahydropyridine substituted with one $R^{38}$, wherein $R^{38}$ is $R^{37}O$—C(O)—$C_1$-$C_6$alkyl-C(O)—.

In some embodiments of the first aspect, the compounds have the Formula (I), wherein D is tetrahydropyridine substituted with one $R^{38}$, wherein $R^{38}$ is $R^{37}$—O—$C_1$-$C_6$alkyl-O—$C_1$-$C_6$alkyl-C(O)—.

In some embodiments of the first aspect, the compounds have the Formula (I), wherein D is pyrazole substituted with one $R^{38}$.

In some embodiments of the first aspect, the compounds have the Formula (I), wherein D is pyrazole substituted with one $R^{38}$, wherein the $R^{38}$ is cycloalkyl-N($R^{39}$)—C(O)—O—$C_1$-$C_6$alkyl- or $R^{37}O$—$(CH_2)_{1-6}$—N(A)-$(CH_2)_{1-4}$—.

In some embodiments of the first aspect, the compounds have the Formula (I), wherein D is pyrazole substituted with one $R^{38}$, wherein $R^{38}$ is cycloalkyl-N($R^{39}$)—C(O)—O—$C_1$-$C_6$alkyl- or $R^{37}O$—$(CH_2)_{1-6}$—N(A)-$(CH_2)_{1-4}$—, and A is —C(O)—N($R^{39}$)—$C_1$-$C_6$alkyl.

In some embodiments of the first aspect, the compounds have the Formula (I), wherein D is pyrazole substituted with one $R^{38}$, wherein the $R^{38}$ is cycloalkyl-N($R^{39}$)—C(O)—O—$C_1$-$C_6$alkyl-.

In some embodiments of the first aspect, the compounds have the Formula (I), wherein D is pyrazole substituted with one $R^{38}$, wherein the $R^{38}$ is $R^{37}O$—$(CH_2)_{1-6}$—N(A)-$(CH_2)_{1-4}$—.

In some embodiments of the first aspect, the compounds have the Formula (I), wherein D is pyrazole substituted with one $R^{38}$, wherein the $R^{38}$ is $R^{37}O$—$(CH_2)_{1-6}$—N(A)-$(CH_2)_{1-4}$—, and A is —C(O)—N($R^{39}$)—$C_1$-$C_6$alkyl.

In some embodiments of the first aspect, the compounds have the Formula (I), wherein D is pyrazole substituted with one $R^{38}$, wherein the $R^{38}$ is $R^{37}O$—$(CH_2)_2$—N(A)-$(CH_2)_2$—, and A is —C(O)—N($R^{39}$)—$C_1$-$C_6$alkyl.

In some embodiments of the first aspect, the compounds have the Formula (I), wherein $R^{38}$ is $R^{37}O$—$(CH_2)_{1-6}$—N(A)-$(CH_2)_{1-4}$—, alternatively $R^{37}O$—$(CH_2)_2$—N(A)-$(CH_2)_{1-2}$—, MeO—$(CH_2)_2$—N(A)-$CH_2$— or MeO—$(CH_2)_2$—N(A)-$(CH_2)_2$—.

In some embodiments of the first aspect, the compounds have the Formula (I), wherein $R^{38}$ is $C_1$-$C_6$alkyl-$S(O)_2$—$(CH_2)_2$—N(A)-$CH_2$—, alternatively $CH_3$—$S(O)_2$—$(CH_2)_2$—N(A)-$CH_2$—.

In some embodiments of the first aspect, the compounds have the Formula (I), wherein $R^{38}$ is $R^{37}O$—$(CH_2)_j$—$[(CH_2)_iO]_x$—$(CH_2)_{i1}$—N(A)-$(CH_2)_{j1}$—, alternatively $CH_3$—O—$[CH_2$—$CH_2$—O]_3$—$(CH_2)_2$—N(A)-$CH_2$—.

In some embodiments of the first aspect, the compounds have the Formula (I), wherein $R^{38}$ is $R^{37}O$—C(O)—$C_0$-$C_6$alkyl-heterocyclyl-$CH_2$—, alternatively $R^{37}O$—C(O)—$C_1$-$C_6$alkyl-heterocyclyl-$CH_2$—, alternatively HO—C(O)—$(CH_2)_2$-piperazine-$CH_2$—, EtO—C(O)-piperidine-$CH_2$—, EtO—C(O)—$CH_2$-piperidine-$CH_2$—, EtO—C(O)—$CH_2$-piperazine-$CH_2$—, HO—C(O)-piperidine-$CH_2$—, HO—C(O)—$CH_2$-piperidine-$CH_2$—HO—C(O)—$CH_2$-piperazine-$CH_2$—, $(CH_3)_3C$—O—C(O)-piperazine-$CH_2$— or HO—C(O)-pyrrolidine-$CH_2$—.

In some embodiments of the first aspect, the compounds have the Formula (I), wherein $R^{38}$ is $R^{37}O$—$(CH_2)_j$—$[(CH_2)_iO]_x$—$(CH_2)_{i1}$—N($R^{39}$)—C(O)—, alternatively $CH_3$—O—$[CH_2$—$CH_2$—O]_3$—$(CH_2)_2$—N(A)-C(O)—.

In some embodiments of the first aspect, the compounds have the Formula (I), wherein $R^{38}$ is $R^{37}$—O—C(O)—$C_1$-$C_6$alkyl-heterocyclyl-C(O)—, alternatively $CH_3$—$CH_2$—O—C(O)—$(CH_2)_2$-piperazine-C(O)— or HO—C(O)—$(CH_2)_2$-piperazine-C(O)—.

In some embodiments of the first aspect, the compounds have the Formula (I), wherein $R^{38}$ is HOOC—$C_1$-$C_6$alkyl-N(A)-$CH_2$—, alternatively HOOC—$(CH_2)_3$—N(A)-$CH_2$—.

In some embodiments of the first aspect, the compounds have the Formula (I), wherein $R^{38}$ is (HOOC)($NR^9R^{10}$)—$C_1$-$C_6$alkyl-N(A)-$CH_2$—, alternatively (HOOC)($NH_2$)CH—$(CH_2)_4$—N(A)-$CH_2$—.

In some embodiments of the first aspect, the compounds have the Formula (I), wherein $R^{38}$ is $R^{37}O$—C(O)—$C_1$-$C_6$alkyl-C(O)—, alternatively HO—C(O)—$(CH_2)_2$—C(O)—.

In some embodiments of the first aspect, the compounds have the Formula (I), wherein $R^{38}$ is $R^9)(R^{10})N$—$C_1$-$C_6$alkyl-C(O)-heterocyclyl-$CH_2$—, alternatively

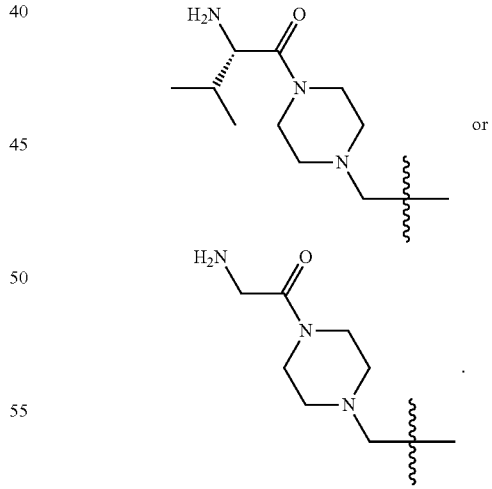

In some embodiments of the first aspect, the compounds have the Formula (I), wherein $R^{38}$ is cycloalkyl-N($R^{39}$)—C(O)—O—$C_1$-$C_6$alkyl-, alternatively $C_3$cycloalkyl-NH—C(O)—O—$(CH_2)_2$—.

In some embodiments of the first aspect, the compounds have the Formula (I), wherein $R^{38}$ is $R^{37}$—O—$C_1$-$C_6$alkyl-O—$C_1$-$C_6$alkyl-C(O)—, alternatively MeO—$(CH_2)_2$—O—$CH_2$—C(O)—.

In some embodiments of the first aspect, the compounds have the Formula (I), wherein $R^{38}$ is $(R^9)(R^{10})N-C(O)-C_1-C_6$alkyl-heterocyclyl-$CH_2$—, alternatively

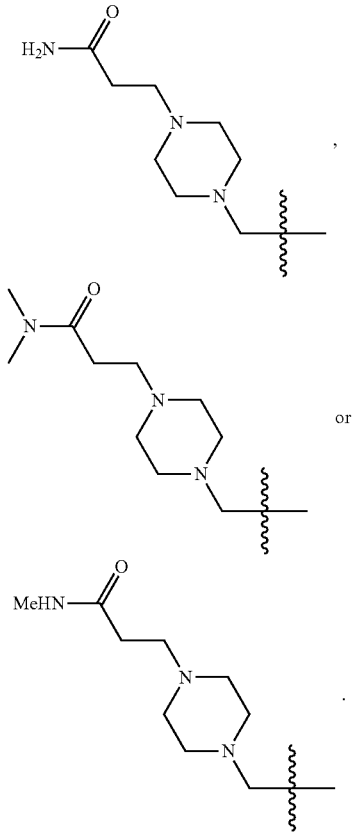

In some embodiments of the first aspect, the compounds have the Formula (I), wherein $R^{38}$ is $(R^9)(R^{10})N-C_1-C_6$alkyl-C(O)—O—$C_1$-$C_6$alkyl-heterocyclyl-$CH_2$—, alternatively

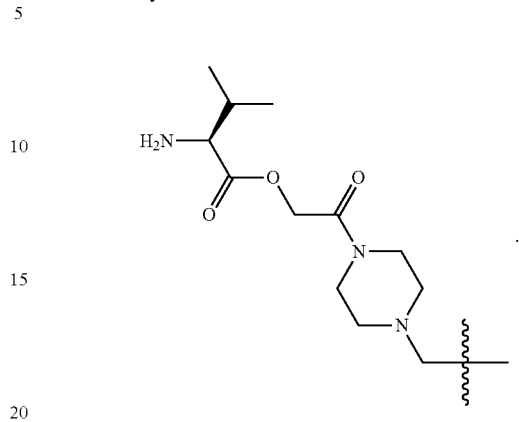

In some embodiments of the first aspect, the compounds have the Formula (I), wherein $R^{38}$ is $C_1$-$C_6$alkyl-C(O)—O—$C_1$-$C_6$alkyl-C(O)-(5 to 10-membered heterocyclyl)-$C_1$-$C_6$alkyl-.

In some embodiments of the first aspect, the compounds have the Formula (I), wherein $R^{38}$ is $C_1$-$C_6$alkyl-C(O)—O—$C_1$-$C_6$alkyl-C(O)-(5 to 10-membered heterocyclyl)-$C_1$-$C_6$alkyl-, wherein the heterocyclyl is a 6-membered heterocyclyl.

In some embodiments of the first aspect, the compounds have the Formula (I), wherein $R^{38}$ is $C_1$-$C_6$alkyl-C(O)—O—$C_1$-$C_6$alkyl-C(O)-(5 to 10-membered heterocyclyl)-$C_1$-$C_6$alkyl-, which is

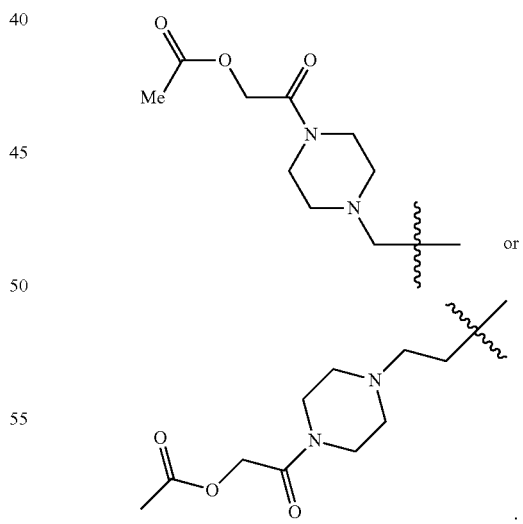

In some embodiments of the first aspect, the compounds have the Formula (I), wherein $R^{38}$ is $(R^9)(R^{10})N-C_1$-$C_6$alkyl-C(O)—O—$C_1$-$C_6$alkyl-heterocyclyl-$CH_2$—, alternatively

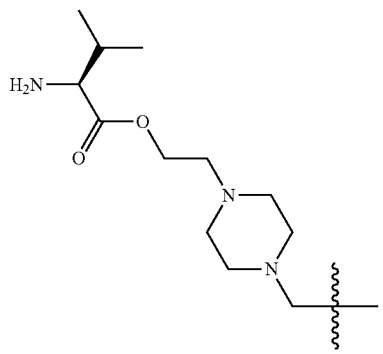

In some embodiments of the first aspect, the compounds have the Formula (I), wherein $R^{38}$ is NC—$C_1$-$C_6$alkyl-heterocyclyl-$CH_2$—, alternatively NC—$(CH_2)_2$-piperazine-$CH_2$—.

In some embodiments of the first aspect, the compounds have the Formula (I), wherein $R^{38}$ is $F_3C$—$C_1$-$C_6$alkyl-heterocyclyl-$CH_2$—, alternatively $F_3C$—$CH_2$-piperazine-$CH_2$—.

In some embodiments of the first aspect, the compounds have the Formula (I), wherein $R^{38}$ is (optionally substituted 8- to 10-membered fused heterocyclyl)-$C_1$-$C_6$alkyl-.

In some embodiments of the first aspect, the compounds have the Formula (I), wherein $R^{38}$ is (optionally substituted 8- to 10-membered fused heterocyclyl)-$C_1$-$C_6$alkyl, which is

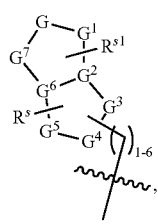

wherein

G is selected from the group consisting of $CH_2$, O, NH, S, SO and $SO_2$;

$G^1$ is selected from the group consisting of $CH_2$, O, NH, S, SO and $SO_2$;

$G^2$ is CH or N;

$G^3$ is selected from the group consisting of $CH_2$, O, NH, S, SO and $SO_2$;

$G^4$ is selected from the group consisting of $CH_2$, O, NH, S, SO and $SO_2$;

$G^5$ is selected from the group consisting of $CH_2$, O, NH, S, SO and $SO_2$;

$G^6$ is CH or N;

$G^7$ is selected from the group consisting of $CH_2$, O, NH, S, SO and $SO_2$;

$R^s$ is an optional substituent; and $R^{s1}$ is an optional substituent, provided that two O atoms are not adjacent to each other.

In some embodiments of the first aspect, the compounds have the Formula (I), wherein $R^{38}$ is (optionally substituted 8- to 10-membered fused heterocyclyl)-$C_1$-$C_6$alkyl, selected from the group consisting of

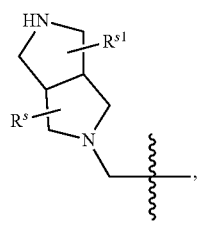
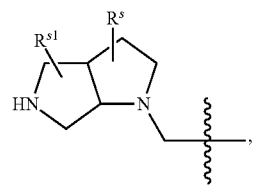
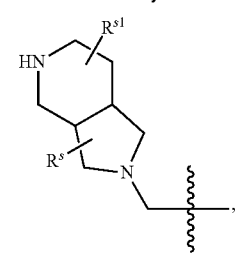
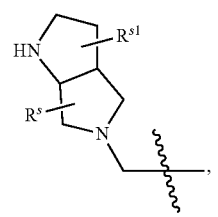
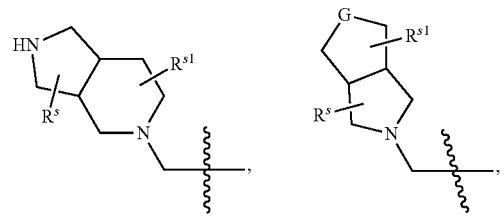

In some embodiments of the first aspect, the compounds have the Formula (I), wherein $R^{38}$ is (optionally substituted 8- to 10-membered fused heterocyclyl)-$C_1$-$C_6$alkyl, selected from the group consisting of

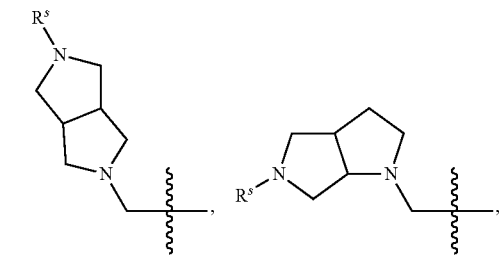
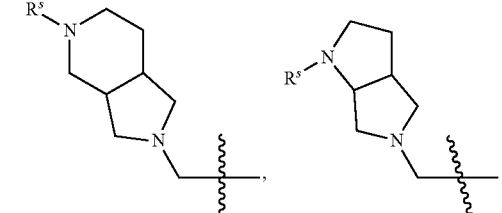
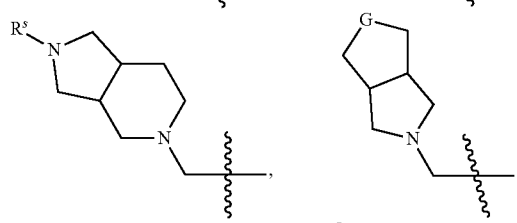
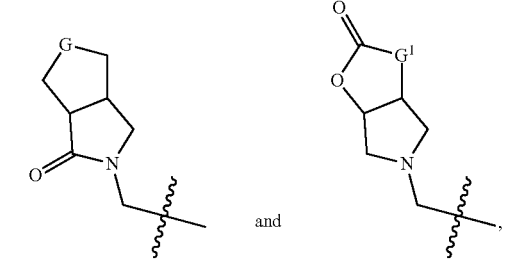

and

wherein G is selected from the group consisting of $CH_2$, O, NH, S, SO and $SO_2$; $G^1$ is selected from the group consisting of $CH_2$, O, NH, S, SO and $SO_2$; and $R^s$ is an optional substituent.

In some embodiments of the first aspect, the compounds have the Formula (I), wherein $R^s$ is selected from the group consisting of H, halo, —N($R^9$)($R^{10}$), nitro, —OH, oxo, $C_1$-$C_6$alkyl, —C(O)—$C_1$-$C_6$alkyl-OH, Ac, cycloalkyl, heterocyclyl, aryl, heteroaryl, —S(O)$_{0-2}$—$C_1$-$C_6$alkyl, —S(O)$_{0-2}$-cycloalkyl, —S(O)$_{0-2}$-heterocyclyl, —S(O)$_{0-2}$-aryl, —S(O)$_{0-2}$-heteroaryl, —C(O)H, —C(O)—$C_1$-$C_6$alkyl, —C(O)—N(R⁹)(R¹⁰), —C₁-C₆alkyl-OH, —C₁-C₆alkyl-C(O)—OH, —C₁-C₆alkyl-C(O)—N(R⁹)(R¹⁰), wherein the alkyl, cycloalkyl, heterocyclyl, aryl and heteroaryl groups are themselves optionally substituted, for example with halo or —C₁-C₆alkyl.

In some embodiments of the first aspect, the compounds have the Formula (I), wherein R$^{s1}$ is selected from the group consisting of H, halo, —N(R⁹)(R¹⁰), nitro, —OH, oxo, C₁-C₆alkyl, —C(O)—C₁-C₆alkyl-OH, Ac, cycloalkyl, heterocyclyl, aryl, heteroaryl, —S(O)₀₋₂—C₁-C₆alkyl, —S(O)₀₋₂-cycloalkyl, —S(O)₀₋₂-heterocyclyl, —S(O)₀₋₂-aryl, —S(O)₀₋₂-heteroaryl, —C(O)H, —C(O)—C₁-C₆alkyl, —C(O)—N(R⁹)(R¹⁰), —C₁-C₆alkyl-OH, —C₁-C₆alkyl-C(O)—OH, —C₁-C₆alkyl-C(O)—N(R⁹)(R¹⁰), wherein the alkyl, cycloalkyl, heterocyclyl, aryl and heteroaryl groups are themselves optionally substituted, for example with halo or —C₁-C₆alkyl.

In some embodiments of the first aspect, the compounds have the Formula (I), wherein R³⁸ is (optionally substituted 8- to 10-membered fused heterocyclyl)-C₁-C₆alkyl-, wherein the optional substituent is selected from the group consisting of H, halo —N(R⁹)(R¹⁰), nitro, —OH, oxo, C₁-C₆alkyl, —C(O)—C₁-C₆alkyl-OH, Ac, cycloalkyl, heterocyclyl, aryl, heteroaryl, —S(O)₀₋₂—C₁-C₆alkyl, —S(O)₀₋₂-cycloalkyl, —S(O)₀₋₂-heterocyclyl, —S(O)₀₋₂-aryl, —S(O)₀₋₂-heteroaryl, —C(O)H, —C(O)—C₁-C₆alkyl, —C(O)—N(R⁹)(R¹⁰), —C₁-C₆alkyl-OH, —C₁-C₆alkyl-C(O)—OH and —C₁-C₆alkyl-C(O)—N(R⁹)(R¹⁰), wherein the alkyl, cycloalkyl, heterocyclyl, aryl and heteroaryl groups are themselves optionally substituted, for example with halo or —C₁-C₆alkyl.

In some embodiments of the first aspect, the compounds have the Formula (I), wherein A is —C(O)—C₁-C₆alkyl-N(R³⁹)—C(O)—C₁-C₆alkyl-N(R⁹)(R¹⁰), alternatively —C(O)—CH₂—NH—C(O)—CH(NH₂)—CH(CH₃)₂, —C(O)—CH₂—NH—C(O)—CH₂—NH₂ or —C(O)—CH[CH(CH₃)₂]—NH—C(O)—CH₂—NH₂).

In some embodiments of the first aspect, the compounds have the Formula (I), wherein A is —C(O)—N(R³⁹)—C₁-C₆alkyl, alternatively —C(O)—NH—CH₂—CH₃, —C(O)—NH—CH₃, —C(O)—NH—CH(CH₃)₂, —C(O)—NH—CH(CH₃)₂ or —C(O)—N(CH₃)₂.

In some embodiments of the first aspect, the compounds have the Formula (I), wherein A is —C(=NR³⁷)—C₁-C₆alkyl, alternatively —C(=NH)H.

In some embodiments of the first aspect, the compounds have the Formula (I), wherein A is —C(O)—(CH₂)ₙ—S(O)₂—C₁-C₆alkyl, alternatively —C(O)—CH₂—S(O)₂-Me.

In some embodiments of the first aspect, the compounds have the Formula (I), wherein A is —C(O)—N(R³⁹)-cycloalkyl, alternatively —C(O)—NH-cyclopentyl or —C(O)—NH—C₃cycloalkyl.

In some embodiments of the first aspect, the compounds have the Formula (I), wherein A is —C(O)—N(R⁹)(R¹⁰), alternatively —C(O)—NH₂.

In some embodiments of the first aspect, the compounds have the Formula (I), wherein A is (R³⁷O)(R³⁷ᵃO)P(O)O—C₁-C₆alkyl-C(O)—, alternatively (HO)₂P(O)O—CH₂—C(O)—.

In some embodiments of the first aspect, the compounds have the Formula (I), wherein M is a structure selected from the group consisting of

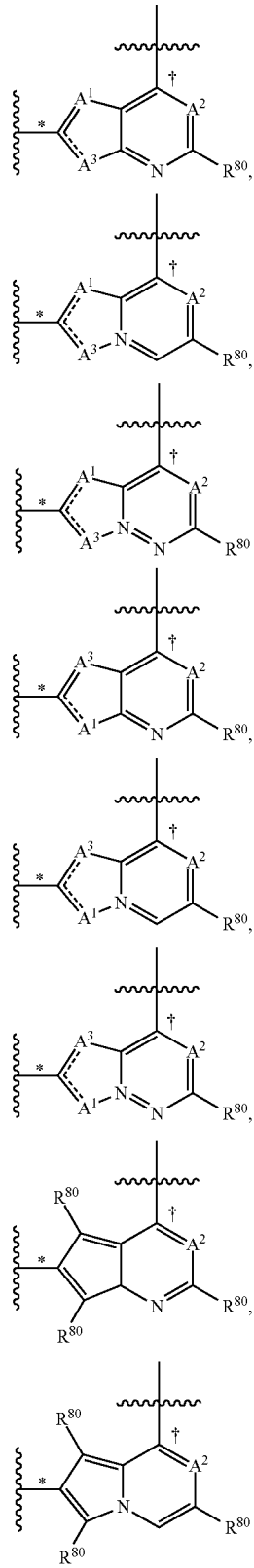

-continued

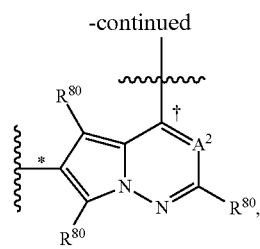

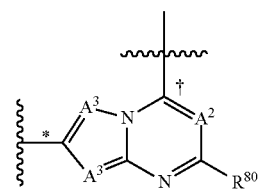

wherein

* represents the point of attachment to D;

† represents the point of attachment to Z;

A¹ is selected from the group consisting of CH, —O—, —S—; —N(H)—, —N($C_1$-$C_6$ alkyl)-, —N—(Y-aryl)-, —N—OMe, —$NCH_2$OMe and N-Bn;

Y is a bond or —$(C(R^x)(H))_t$—, wherein t is an integer from 1 to 6; and $R^x$ at each occurrence is independently selected from the group consisting of H and $C_1$-$C_6$ alkyl, wherein the $C_1$-$C_6$ alkyl is optionally substituted;

A² is selected from the group consisting of N and CR, wherein R is selected from the group consisting of —H, halogen, —CN, $C_1$-$C_6$ alkyl, $C_2$-$C_6$ alkenyl, $C_2$-$C_6$ alkynyl, —COOH and —C(O)Oalkyl, wherein the $C_1$-$C_6$ alkyl, $C_2$-$C_6$ alkenyl, $C_2$-$C_6$ alkynyl and —C(O)Oalkyl are optionally substituted;

each A³ is independently selected from the group consisting of CH and N;

each $R^{80}$ is independently selected from the group consisting of H, halogen, $NO_2$, cyano, $OR^{83}$, $N(R^{83})_2$, $CO_2R^{83}$, C(O)N($R^{83})_2$, $SO_2R^{83}$, $SO_2N(R^{83})_2$, $NR^{83}SO_2R^{83}$, $NR^{83}$C(O)$R^{83}$, $NR^{83}CO_2R^{83}$, —CO($CH_2)_lR^{83}$, —CONH($CH_2)_lR^{83}$, alkylaminoalkyl, alkylaminoalkynyl, $C_1$-$C_6$alkyl, substituted $C_1$-$C_6$alkyl, $C_3$-$C_7$cycloalkyl, substituted $C_3$-$C_7$cycloalkyl, alkenyl, substituted alkenyl, alkynyl, substituted alkynyl, hydroxyalkyl, aryl, substituted aryl, heteroaryl, substituted heteroaryl, arylalkyl, substituted arylalkyl, heterocycloalkyl, and substituted heterocycloalkyl; and each $R^{83}$ is independently selected from the group consisting of H, alkyl, substituted alkyl, cycloalkyl, substituted cycloalkyl, aryl, substituted aryl, arylalkyl, substituted arylalkyl, heteroaryl, substituted heteroaryl, heterocycloalkyl, and substituted heterocycloalkyl; or two $R^{83}$ taken together with the N atom to which they are attached form a heterocyclic ring.

In some embodiments of the first aspect, the compounds have the Formula (I), wherein M is a structure selected from the group consisting of

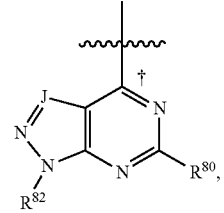

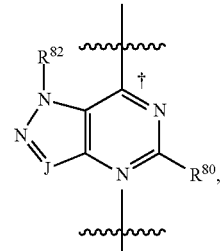

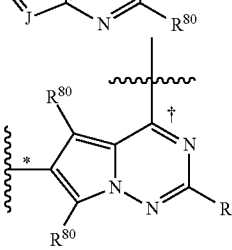

wherein

J is $CR^{80}$ or N;

$R^{82}$ is selected from the group consisting of H, $C_1$-$C_6$alkyl or substituted $C_1$-$C_6$alkyl, —Y-(aryl), —Y-(heteroaryl), -alkoxy and —$CH_2$OMe;

wherein *, †, $R^{80}$ and Y are as defined above.

In some embodiments of the first aspect, the compounds have the Formula (I), wherein M is a structure selected from the group consisting of

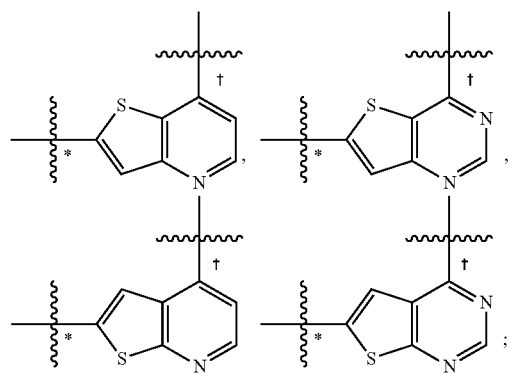

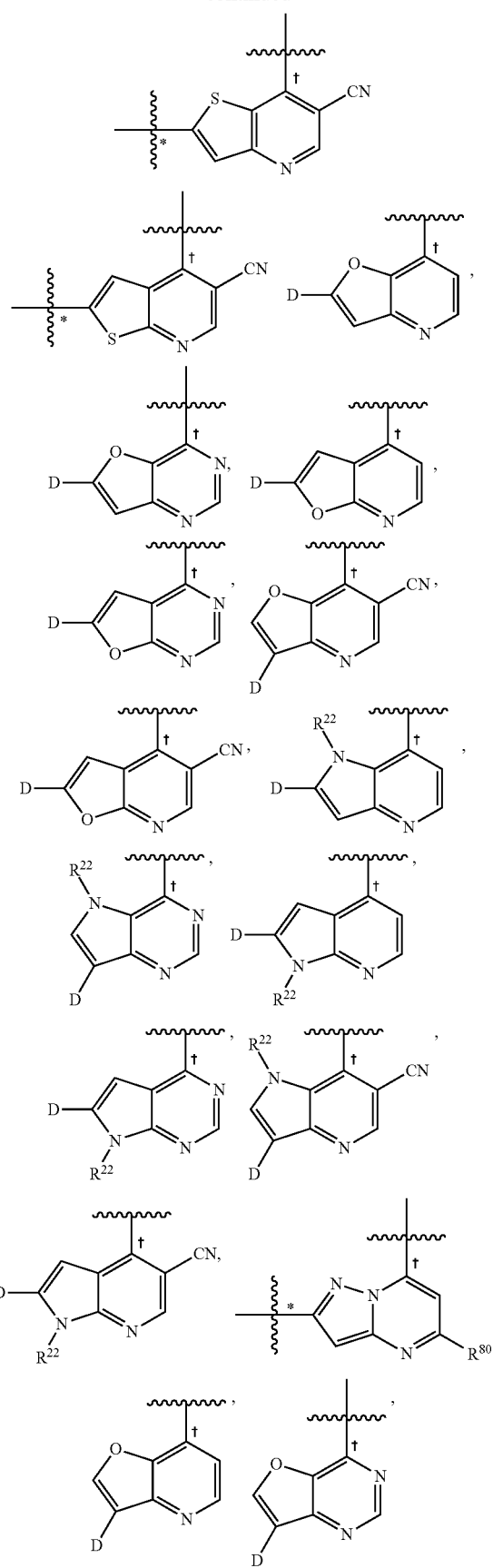
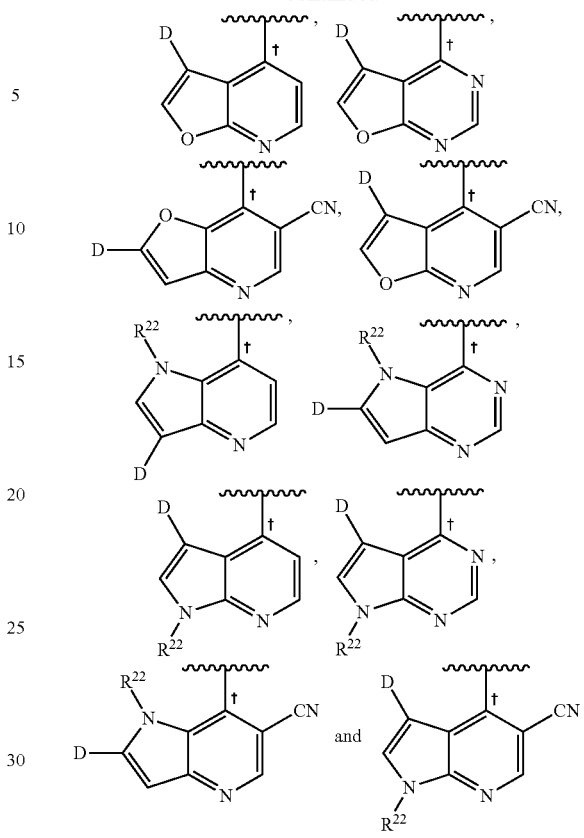

wherein
† is as defined above; and
$R^{22}$ is selected from the group consisting of —H, —$C_1$-$C_6$alkyl, —Y-aryl, alkoxy, —$CH_2$—O-Me and —Bn.

In some embodiments of the first aspect, the compounds have the Formula (I), wherein M is

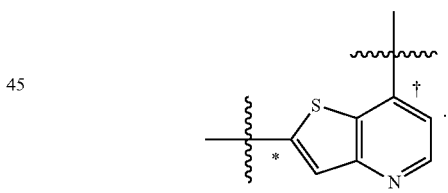

In some embodiments of the first aspect, the compounds have the Formula (I), wherein Z is O.

In some embodiments of the first aspect, the compounds have the Formula (I), wherein Ar is selected from the group consisting of phenyl, pyrazine, pyridazine, pryimidine and pyridine, wherein each of said phenyl, pyrazine, pyridazine, pryimidine and pyridine are optionally substituted with between zero and four $R^2$.

In some embodiments of the first aspect, the compound have the Formula (I), wherein Ar is phenyl, optionally substituted with between zero and four $R^2$.

In some embodiments of the first aspect, the compounds have the Formula (I), wherein Ar is phenyl, substituted with between zero and four halo.

In some embodiments of the first aspect, the compounds have the Formula (I), wherein G is selected from the group consisting of

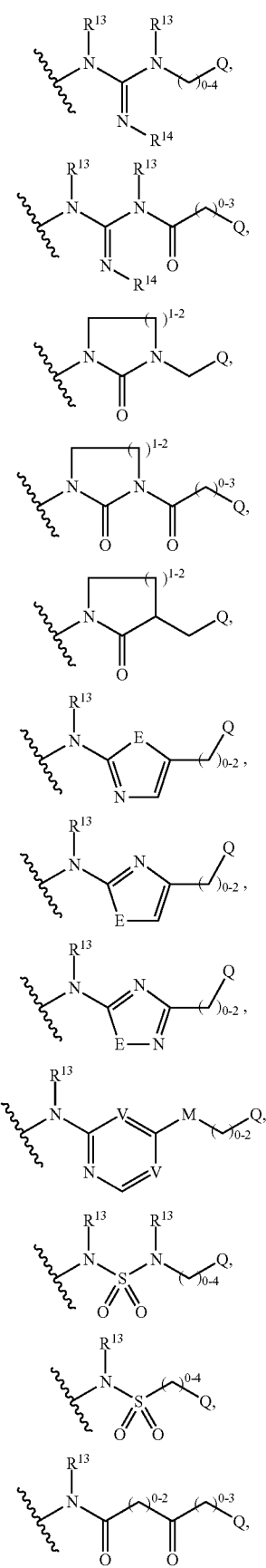
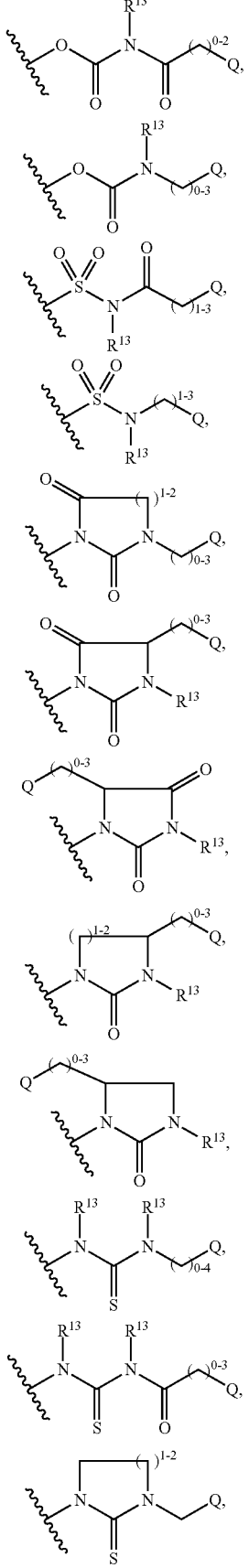

-continued
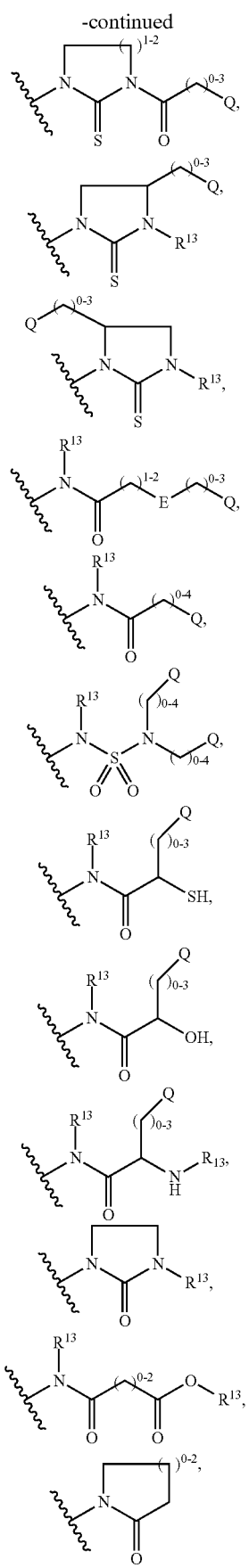
-continued
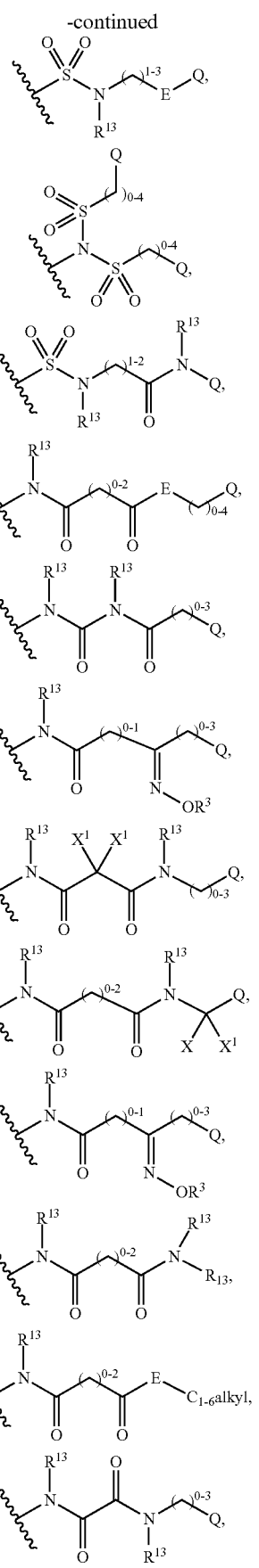

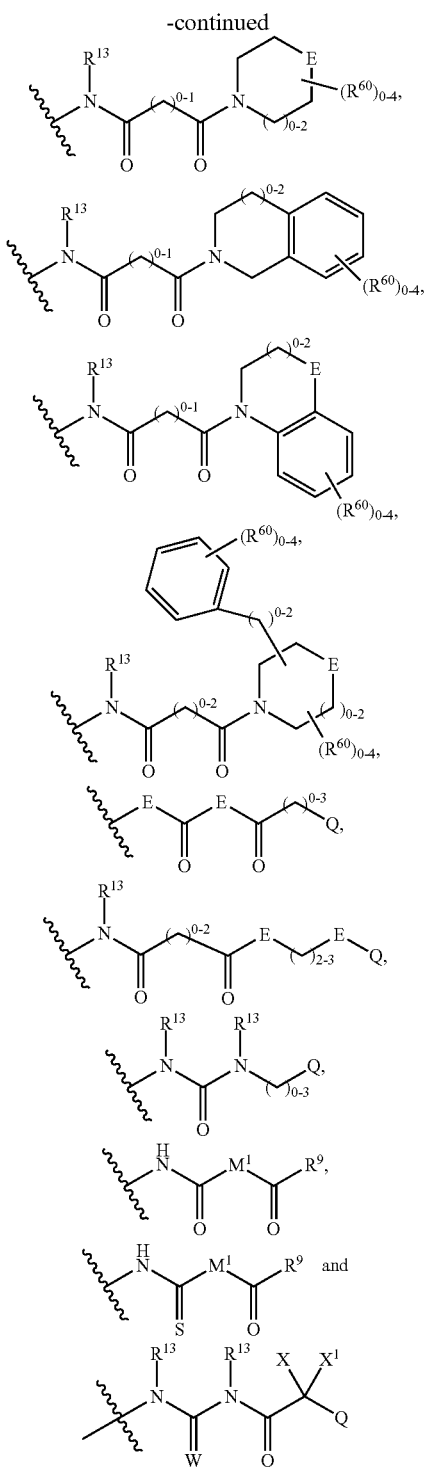

wherein $R^{13}$, $R^{14}$, Q, $R^3$ and $R^4$ are as defined above;

W is S, O or NH;

any methylene group is independently optionally substituted with $R^{25}$, wherein $R^{25}$ is selected from the group consisting of halogen, trihalomethyl, —CN, —NO$_2$, —NH$_2$, —OR$^3$, —NR$^3$R$^4$, —S(O)$_{0-2}$R$^3$, —SO$_2$NR$^3$R$^3$, —CO$_2$R$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, an optionally substituted aryl, an optionally substituted arylalkyl, an optionally substituted heteroarylalkyl, and an optionally substituted (C$_1$-C$_6$)alkyl, two $R^{25}$, together with the carbon or carbons to which they are attached, can combine to form a three- to seven-membered alicyclic or heteroalicyclic, and two $R^{25}$, on a single carbon can be oxo;

$R^9$ is selected from the group consisting of a C$_{1-6}$ alkyl on which one or more hydrogen atoms are optionally substituted by —R$^{21}$, -T$^1$-R$^{15}$, or —NR$^{16}$R$^{17}$, a —N(R$^{18}$)(R$^{19}$) moiety and a saturated or unsaturated three- to eight-membered carbocyclic or heterocyclic group which is optionally substituted by a C$_{1-6}$ alkyl, a C$_{1-6}$ alkoxy, a halogen atom, nitro, a trifluoromethyl, a C$_{1-6}$ alkoxy carbonyl, cyano, a cyano C$_{1-6}$ alkyl, a C$_{1-6}$ alkylthio, a phenoxy, an acetyl, or a saturated or unsaturated five- or six-membered heterocyclyl ring wherein, when the three- to eight-membered carbocyclic or heterocyclic group is substituted by two C$_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group, wherein $T^1$ is selected from the group consisting of —O—, —S— and —NH—;

$R^{21}$ represents a saturated or unsaturated three- to eight-membered carbocyclic or heterocyclic group;

$R^{15}$, $R^{16}$, and $R^{17}$, which may be the same or different, represent a C$_{1-6}$ alkyl or a saturated or unsaturated three- to eight-membered carbocyclic or heterocyclic group; wherein the three- to eight-membered carbocyclic or heterocyclic group represented by $R^{21}$, $R^{15}$, $R^{16}$, and $R^{17}$ is optionally substituted by a C$_{1-6}$ alkyl, a C$_{1-6}$ alkoxy, a halogen atom, nitro, a trifluoromethyl, a C$_{1-6}$ alkoxy carbonyl, a cyano, a cyano C$_{1-6}$ alkyl, a C$_{1-6}$ alkylthio, a phenoxy, an acetyl, or a saturated or unsaturated five- or six-membered heterocyclyl ring; and wherein when the three- to eight-membered carbocyclic or heterocyclic group is substituted by two C$_{1-6}$ alkyl groups, the two alkyl groups may combine together to form an alkylene chain; and wherein the three- to eight-membered carbocyclic or heterocyclic group may be a bicyclic group condensed with another saturated or unsaturated three- to eight-membered carbocyclic or heterocyclic group; and $R^{18}$ and $R^{19}$, which may be the same or different, represent (1) a hydrogen atom, (2) a C$_{1-6}$ alkyl which is optionally substituted by a C$_{1-6}$ alkoxy, a C$_{1-6}$ alkylthio, or a saturated or unsaturated three- to eight-membered carbocyclic or heterocyclic group in which the three- to eight-membered carbocyclic or heterocyclic group is optionally substituted by a C$_{1-6}$ alkyl, a C$_{1-6}$ alkoxy, a halogen atom, nitro, a trifluoromethyl, a C$_{1-6}$ alkoxy carbonyl, cyano, a cyano C$_{1-6}$ alkyl, a C$_{1-6}$ alkylthio, a phenoxy, an acetyl, or a saturated or unsaturated five- or six-membered heterocyclyl ring and wherein when the three- to eight-membered carbocyclic or heterocyclic group is substituted by two C$_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group, or (3) a saturated or unsaturated three- to eight-membered carbocyclic or heterocyclic group which is optionally substituted by a C$_{1-6}$ alkyl, a C$_{1-6}$ alkoxy, a halogen atom, nitro, a trifluoromethyl, a C$_{1-6}$ alkoxy carbonyl, cyano, a cyano C$_{1-6}$ alkyl, a C$_{1-6}$ alkylthio, a phenoxy, an acetyl, or a saturated or unsaturated five- or six-membered heterocyclyl ring and in which, when the three to eight-membered carbocyclic or heterocyclic group is substituted by two $C_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group;

X and $X^1$ are each independently selected from the group consisting of —H, halogen, cyano, nitro, $C_1$-$C_6$ alkyl, or X and $X^1$ together with the atom to which they are attached form a $C_3$-$C_4$ cycloalkyl;

E is selected from the group consisting of —O—, —N($R^{13}$)—, —CH$_2$— and —S(O)$_{0-2}$—;

M is selected from the group consisting of —O—, —N($R^{13}$)—, —CH$_2$— and —C(=O)N($R^{13}$);

$M^1$ represents —C($R^{26}$)($R^{27}$)—, wherein $R^{26}$ and $R^{27}$ are independently selected from the group consisting of a hydrogen atom, a $C_{1-4}$ alkyl, a $C_{1-4}$ alkoxy and —N($R^{12}$), wherein $R^{12}$ is a hydrogen atom or a $C_{1-4}$ alkyl; and each V is independently selected from the group consisting of =N— and =C(H)—.

In some embodiments of the first aspect, the compounds have the Formula (I), wherein G is selected from the group consisting of

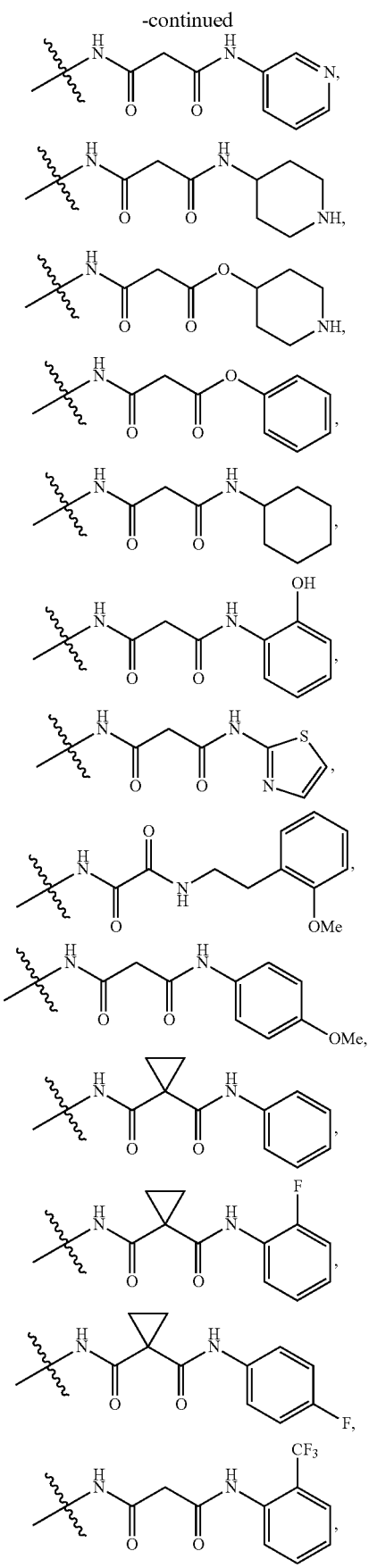

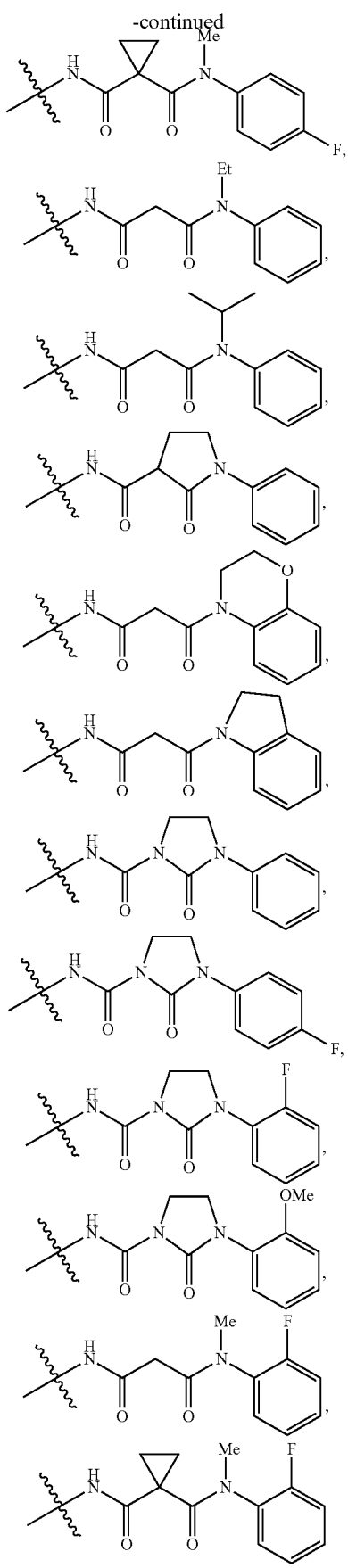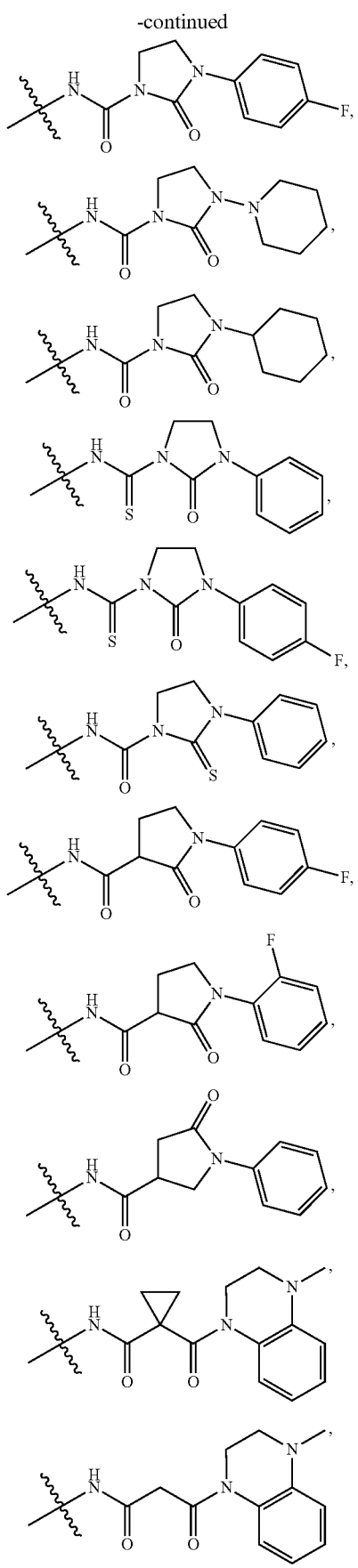

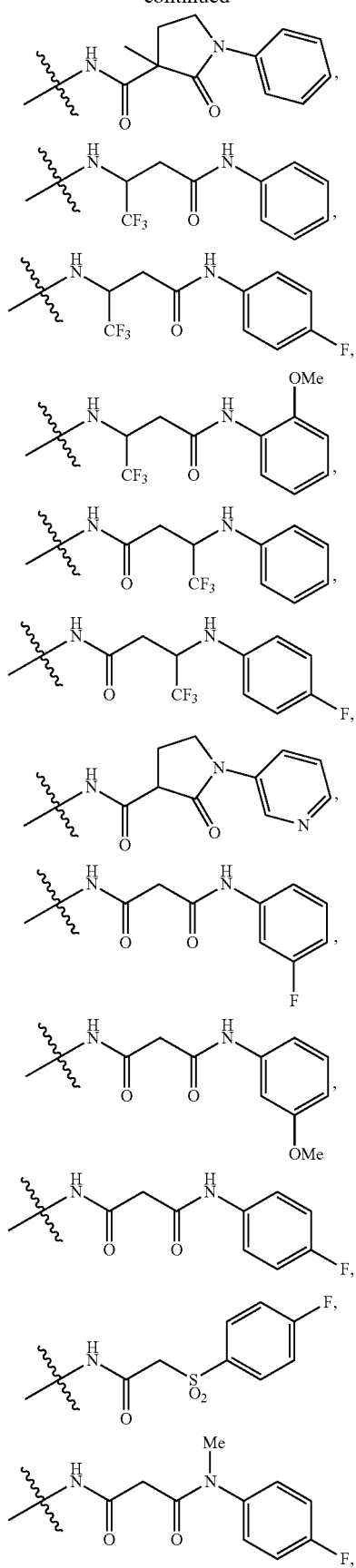
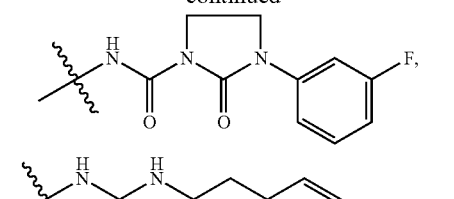
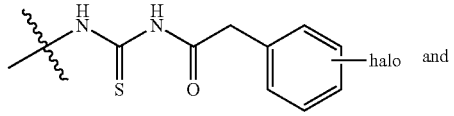
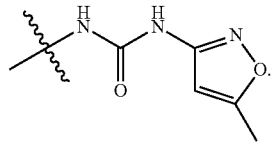
In some embodiments of the first aspect, the compounds have the Formula (I), wherein G is selected from the group consisting of
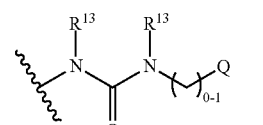
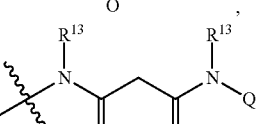
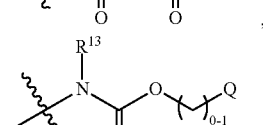
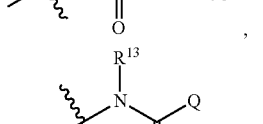
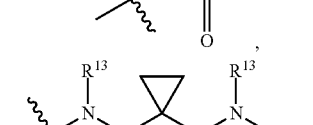
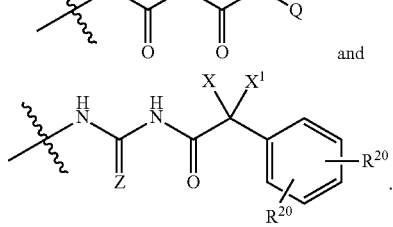
In some embodiments of the first aspect, the compounds have the Formula (I), wherein G is selected from the group consisting of
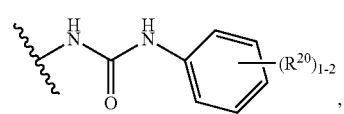

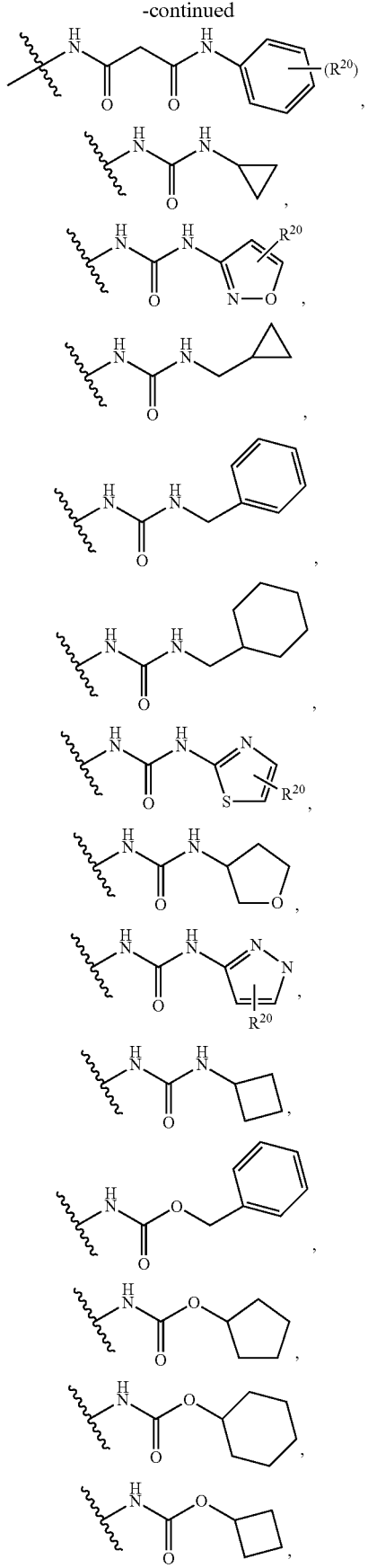
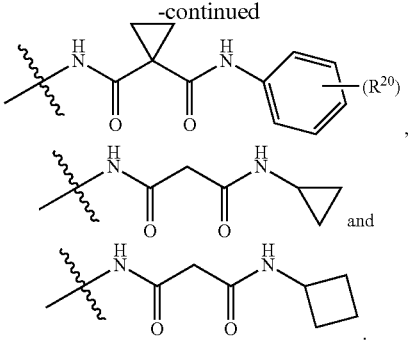
In some embodiments of the first aspect, the compounds have the Formula (I), wherein G is selected from the group consisting of
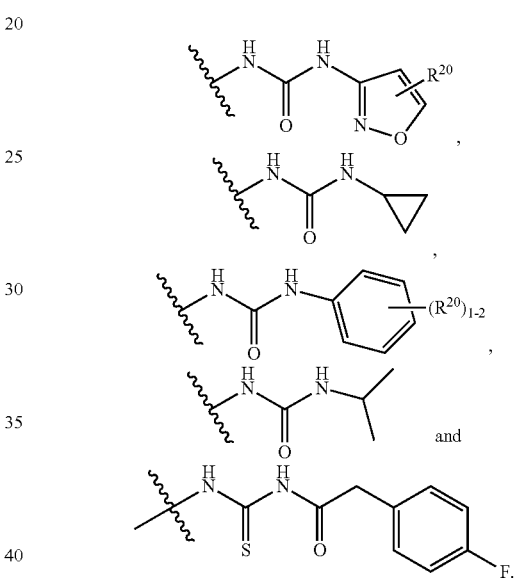
In some embodiments of the first aspect, the compounds have the Formula (I), wherein G is selected from the group consisting of
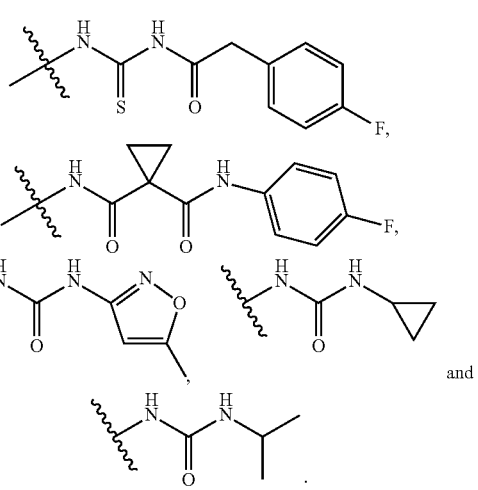

In some embodiments of the first aspect, the compounds have the Formula (I), wherein G is

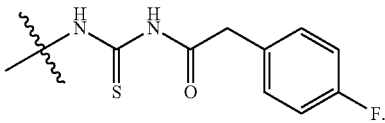 [SMILES: *NC(=S)NC(=O)Cc1ccc(F)cc1]

In some embodiments of the first aspect, the compounds have the Formula (I), wherein G is

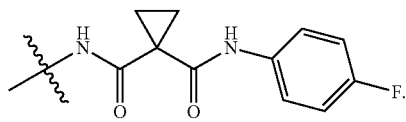 [SMILES: *NC(=O)C1(C(=O)Nc2ccc(F)cc2)CC1]

In some embodiments of the first aspect, the compounds have the Formula (I), wherein G is

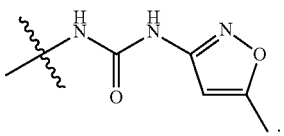 [SMILES: *NC(=O)Nc1cc(C)on1]

In some embodiments of the first aspect, the compounds have the Formula (I), wherein G is

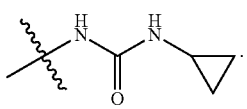 [SMILES: *NC(=O)NC1CC1]

In some embodiments of the first aspect, the compounds have the Formula (I), wherein G is

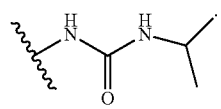

In some embodiments of the first aspect, the compounds have the Formula (I), wherein Q is selected from the group consisting of

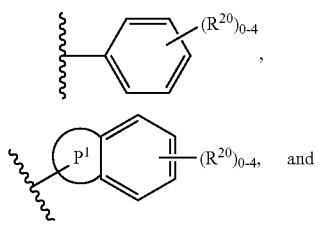

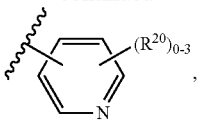

wherein $P^1$ is a five- to seven-membered ring, including the two shared carbon atoms of the aromatic ring to which $P^1$ is fused, and wherein $P^1$ optionally contains between one and three heteroatoms.

In some embodiments of the first aspect, the compounds have the Formula (I), wherein Q is selected from the group consisting of phenyl, napthyl, 1,2,3,4-tetrahydronaphthyl, indanyl, benzodioxanyl, benzofuranyl, phenazinyl, phenothiazinyl, phenoxazinyl, tetrahydroisoquinolyl, pyrrolyl, pyrazolyl, pyrazolidinyl, imidazolyl, imidazolinyl, imidazolidinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, thiazolyl, thiazolinyl, thiazolidinyl, isothiazolyl, isothiazolidinyl, indolyl, isoindolyl, indolinyl, isoindolinyl, octahydroindolyl, octahydroisoindolyl, quinolyl, isoquinolyl, benzimidazolyl, thiadiazolyl, benzopyranyl, benzothiazolyl, benzoxazolyl, furyl, thienyl, benzothieliyl, and oxadiazolyl; each optionally substituted with between one and four of $R^{20}$.

In some embodiments of the first aspect, the compounds have the Formula (I), wherein Q is phenyl or $C_3$cycloalkyl.

In some embodiments of the first aspect, the compounds have the Formula (I), wherein Q is phenyl substituted with one or two independently selected $R^{20}$.

In some embodiments of the first aspect, the compounds have the Formula (I), wherein Q is phenyl substituted with one $R^{20}$, wherein the $R^{20}$ is selected from the group consisting of —P(O)(Me)$_2$, —CH$_3$, F, —CF$_3$, —S(O)$_2$CH$_3$, Cl, —OCF$_3$, —OMe, Br, —S(O)$_2$—NH$_2$, —COOCH$_3$, —C(O)NH(CH$_3$) and —C(O)N(CH$_3$)(CH$_3$).

In some embodiments of the first aspect, the compounds have the Formula (I), wherein Q is $C_3$cycloalkyl.

In some embodiments of the first aspect, the compounds of have the Formula (Ia),

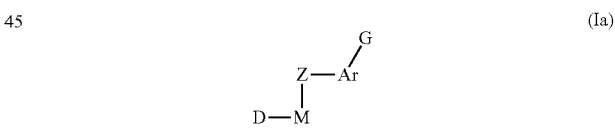

wherein D, M, Z, Ar and G are as defined in Formula (I), except that $R^{38}$ is selected from the group consisting of $(R^{23})(R^{24})(O)$P—C$_1$-C$_6$alkyl-heterocyclyl-C$_1$-C$_6$alkyl-, (optionally substituted 7- or 8-membered heterocyclyl)-C$_1$-C$_6$alkyl-, (optionally substituted 8- to 10-membered fused heterocyclyl)-C$_1$-C$_6$alkyl-, (optionally substituted spiro-heterocyclyl)-C$_1$-C$_6$alkyl-, (optionally substituted bridged bicyclic ring system)-C$_1$-C$_6$alkyl-, (substituted piperazine)-C$_1$-C$_6$alkyl-, $(R^9)(R^{10})$N—C$_1$-C$_6$alkyl-C(O)—O—C$_1$-C$_6$alkyl-C(O)-(5 to 10-membered heterocyclyl)-C$_1$-C$_6$alkyl-, C$_1$-C$_6$alkyl-S(O)$_{0-2}$—C$_1$-C$_6$alkyl-(5 to 10-membered heterocyclyl)-C$_1$-C$_6$alkyl-, $(R^{23})(R^{24})$P(O)O—C$_1$-C$_6$alkyl-C(O)-(5 to 10-membered heterocyclyl)-C$_1$-C$_6$alkyl-, $R^{37}$S(O)$_{0-2}$-aryl-C(O)—O—C$_1$-C$_6$alkyl-C(O)-(5 to 10-membered heterocyclyl)-C$_1$-C$_6$alkyl-, $R^{37}$O—C$_1$-C$_6$alkyl-piperazine-C$_1$-C$_6$alkyl-, $R^{37}$O—C(O)—C$_1$-C$_6$alkyl-(5 to 10-membered heterocyclyl)-C$_1$-C$_6$alkyl)(R$^9$)(R$^{10}$)N—C$_1$-C$_6$alkyl-piperazine-C$_1$-C$_6$alkyl-, R$^{37a}$O—C(O)—C$_1$-C$_6$alkyl-N(R$^{37}$)—C(O)—C$_1$-C$_6$alkyl-(5 to 10-membered heterocyclyl)-C$_1$-C$_6$alkyl-, R$^{11}$—C$_1$-C$_6$alkyl-C(O)-piperazine-C$_1$-C$_6$alkyl-, C$_0$-C$_6$alkyl-(5 or 6-membered heterocyclyl)-C$_1$-C$_6$alkyl-piperazine-C$_1$-C$_6$alkyl-, (5-10-membered optionally substituted heterocyclyl)-C$_1$-C$_6$alkyl-O-(oxo substituted 5 to 10-membered heterocyclyl)-C$_1$-C$_6$alkyl-, (5-10-membered optionally substituted heterocyclyl)-C$_1$-C$_6$alkyl-N(R$^1$)-(oxo substituted 5 to 10-membered heterocyclyl)-C$_1$-C$_6$alkyl-, (5-10-membered optionally substituted heterocyclyl)-C$_1$-C$_6$alkyl-S(O)$_{0-2}$-(oxo substituted 5 to 10-membered heterocyclyl)-C$_1$-C$_6$alkyl-, (R$^{23}$)(R$^{24}$)P(O)—C$_1$-C$_6$alkyl-C(O)—, (R$^{23}$)(R$^{24}$)(O)P—C$_1$-C$_6$alkyl-N(R$^{37}$)—C$_1$-C$_6$alkyl-, (R$^9$)(R$^{10}$)N—C(H)(R$^{28}$)—, R$^{29}$O—C(O)—C(H)(C(O)—OR$^{29a}$)—O—C$_1$-C$_6$alkyl-(5 to 10-membered heterocyclyl)-C$_1$-C$_6$alkyl-, R$^{29}$O—C(O)—C(H)(C(O)—OR$^{29a}$)—O—C$_1$-C$_6$alkyl-C(O)-(5 to 10-membered heterocyclyl)-C$_1$-C$_6$alkyl- and (substituted piperidine)-C$_1$-C$_6$alkyl-;
wherein
R$^1$ is H or C$_1$-C$_6$alkyl;
R$^{11}$ is —OH, —O—C$_1$-C$_6$alkyl, optionally substituted 5 to 10-membered heterocyclyl, or —O-(amino acid);
R$^{23}$ is selected from the group consisting of H, —OH, C$_1$-C$_6$alkyl, C$_1$-C$_6$alkoxy, aryl, —O-aryl, cycloalkyl, —O-cycloalkyl, heteroaryl, —O-heteroaryl, 5 to 10-membered heterocyclyl, —O-(5 to 10-membered heterocyclyl), —C$_1$-C$_6$alkyl-aryl, —O—C$_1$-C$_6$alkyl-aryl, —C$_1$-C$_6$alkyl-heteroaryl, —O—C$_1$-C$_6$alkyl-heteroaryl, —C$_1$-C$_6$alkyl-cycloalkyl, —O—C$_1$-C$_6$alkyl-cycloalkyl, —C$_1$-C$_6$alkyl-(5 to 10-membered heterocyclyl) and —O—C$_1$-C$_6$alkyl-(5 to 10-membered heterocyclyl);
R$^{24}$ is selected from the group consisting of H, —OH, C$_1$-C$_6$alkyl, C$_1$-C$_6$alkoxy, aryl, —O-aryl, cycloalkyl, —O-cycloalkyl, heteroaryl, —O-heteroaryl, 5 to 10-membered heterocyclyl, —O-(5 to 10-membered heterocyclyl), —C$_1$-C$_6$alkyl-aryl, —O—C$_1$-C$_6$alkyl-aryl, —C$_1$-C$_6$alkyl-heteroaryl, —O—C$_1$-C$_6$alkyl-heteroaryl, —C$_1$-C$_6$alkyl-cycloalkyl, —O—C$_1$-C$_6$alkyl-cycloalkyl, —C$_1$-C$_6$alkyl-(5 to 10-membered heterocyclyl) and —O—C$_1$-C$_6$alkyl-(5 to 10-membered heterocyclyl);
R$^{28}$ is selected from the group consisting of H, —CF$_3$, —CHF$_2$, —CH$_2$F, CN, optionally substituted C$_1$-C$_6$alkyl and C$_3$-C$_6$cycloalkyl;
R$^{29}$ is selected from the group consisting of H, C$_1$-C$_6$alkyl and a cation; and
R$^{29a}$ is selected from the group consisting of H, C$_1$-C$_6$alkyl and a cation.

In some embodiments of the first aspect, the compounds have the Formula (Ia), wherein R$^{38}$ is (R$^{23}$)(R$^{24}$)(O)P—C$_1$-C$_6$alkyl-heterocyclyl-C$_1$-C$_6$alkyl-.

In some embodiments of the first aspect, the compounds have the Formula (Ia), wherein R$^{38}$ is (R$^{23}$)(R$^{24}$)(O)P—C$_1$-C$_6$alkyl-heterocyclyl-C$_1$-C$_6$alkyl-, wherein the heterocyclyl is a six-membered heterocyclyl.

In some embodiments of the first aspect, the compounds have the Formula (Ia), wherein R$^{38}$ is (R$^{23}$)(R$^{24}$)(O)P—C$_1$-C$_6$alkyl-heterocyclyl-C$_1$-C$_6$alkyl-, wherein the heterocyclyl is selected from the group consisting of tetrahydrofuranyl, tetrahydrothiophenyl, pyrrolidine, tetrahydropyranyl, tetrahydrothiopyranyl, piperidinyl, dioxanyl, oxathianyl, morpholinyl, dithianyl, piperazinyl, azathianyl, oxepanyl, thiepaneyl, azepanyl, dioxepanyl, oxathiepanyl, oxaazepanyl, dithiepanyl, thieazepanyl and diazepanyl.

In some embodiments of the first aspect, the compounds have the Formula (Ia), wherein R$^{38}$ is (R$^{23}$)(R$^{24}$)(O)P—C$_1$-C$_6$alkyl-heterocyclyl-C$_1$-C$_6$alkyl-, wherein the heterocyclyl is selected from the group consisting of piperidinyl, morpholinyl and piperazinyl.

In some embodiments of the first aspect, the compounds have the Formula (Ia), wherein R$^{38}$ is (optionally substituted 7- or 8-membered heterocyclyl)-C$_1$-C$_6$alkyl-.

In some embodiments of the first aspect, the compounds have the Formula (Ia), wherein R$^{38}$ is (optionally substituted 7-membered heterocyclyl)-C$_1$-C$_6$alkyl-.

In some embodiments of the first aspect, the compounds have the Formula (Ia), wherein R$^{38}$ is (optionally substituted 7-membered heterocyclyl)-C$_1$-C$_6$alkyl-, wherein the heterocyclyl has one or two N atoms.

In some embodiments of the first aspect, the compounds have the Formula (Ia), wherein R$^{38}$ is (optionally substituted 8-membered heterocyclyl)-C$_1$-C$_6$alkyl-.

In some embodiments of the first aspect, the compounds have the Formula (Ia), wherein R$^{38}$ is (optionally substituted 8-membered heterocyclyl)-C$_1$-C$_6$alkyl-, wherein the heterocyclyl has one or two N atoms.

In some embodiments of the first aspect, the compounds have the Formula (Ia), wherein R$^{38}$ is (optionally substituted 8- to 10-membered fused heterocyclyl)-C$_1$-C$_6$alkyl.

In some embodiments of the first aspect, the compounds have the Formula (Ia), wherein R$^{38}$ is (optionally substituted 8- to 10-membered fused heterocyclyl)-C$_1$-C$_6$alkyl, which is

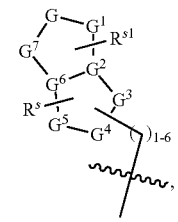

wherein
G is selected from the group consisting of CH$_2$, O, NH, S, SO and SO$_2$;
G$^1$ is selected from the group consisting of CH$_2$, O, NH, S, SO and SO$_2$;
G$^2$ is CH or N;
G$^3$ is selected from the group consisting of CH$_2$, O, NH, S, SO and SO$_2$;
G$^4$ is selected from the group consisting of CH$_2$, O, NH, S, SO and SO$_2$;
G$^5$ is selected from the group consisting of CH$_2$, O, NH, S, SO and SO$_2$;
G$^6$ is CH or N;
G$^7$ is selected from the group consisting of CH$_2$, O, NH, S, SO and SO$_2$;
R$^s$ is an optional substituent; and
R$^{s1}$ is an optional substituent,
provided that two O atoms are not adjacent to each other.

In some embodiments of the first aspect, the compounds have the Formula (Ia), wherein R$^{38}$ is (optionally substituted 8- to 10-membered fused heterocyclyl)-C$_1$-C$_6$alkyl, selected from the group consisting of

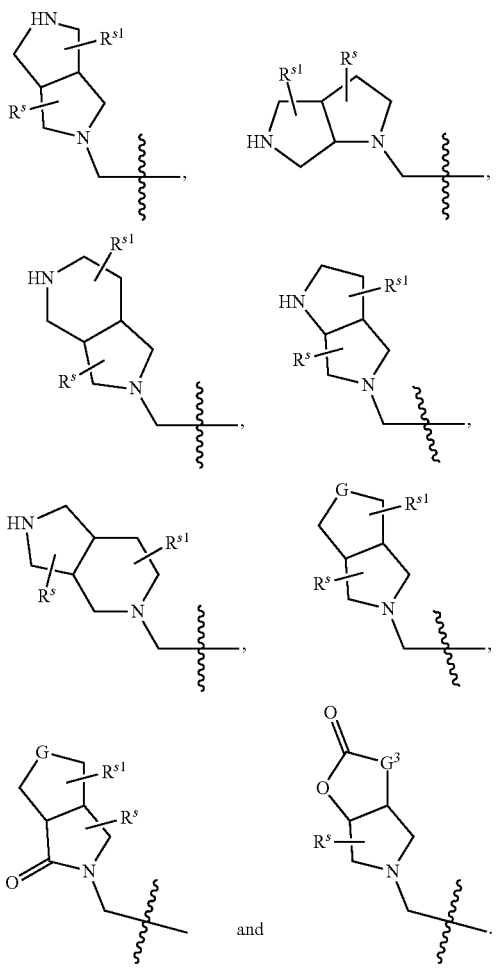

In some embodiments of the first aspect, the compounds have the Formula (Ia), wherein $R^{38}$ is (optionally substituted 8- to 10-membered fused heterocyclyl)-$C_1$-$C_6$alkyl, selected from the group consisting of

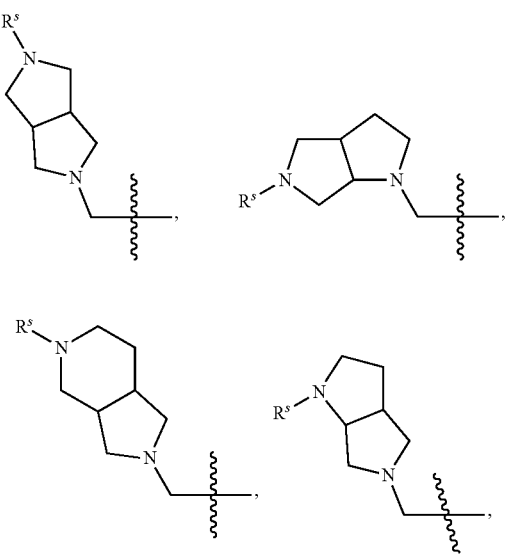

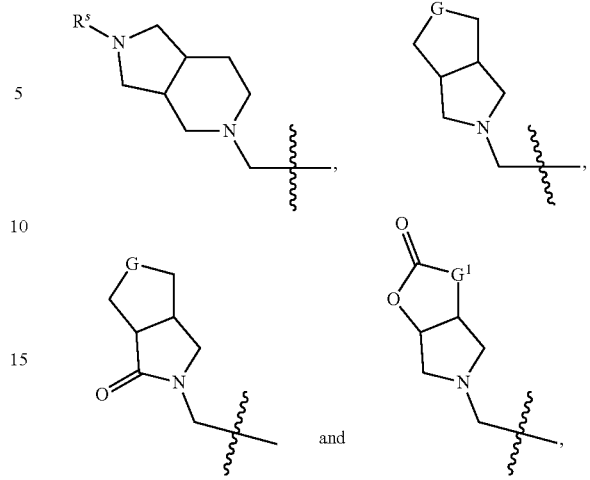

wherein G is selected from the group consisting of $CH_2$, O, NH, S, SO and $SO_2$, $G^1$ is selected from the group consisting of $CH_2$, O, NH, S, SO and $SO_2$; and $R^s$ is an optional substituent.

In some embodiments of the first aspect, the compounds have the Formula (Ia), wherein $R^{38}$ is (optionally substituted spiro-heterocyclyl)-$C_1$-$C_6$alkyl-.

In some embodiments of the first aspect, the compounds have the Formula (Ia), wherein $R^{38}$ is (optionally substituted spiro-heterocyclyl)-$C_1$-$C_6$alkyl-, wherein the optionally substituted spiro-heterocyclyl is selected from the group consisting of optionally substituted [4-4] spiro-heterocyclyl, optionally substituted [4-5] spiro-heterocyclyl, optionally substituted [4-6] spiro-heterocyclyl, optionally substituted [5-4] spiro-heterocyclyl, optionally substituted [5-5] spiro-heterocyclyl, optionally substituted [5-6] spiro-heterocyclyl, optionally substituted [6-4] spiro-heterocyclyl, optionally substituted [6-5] spiro-heterocyclyl and optionally substituted [6-6] spiro-heterocyclyl.

In some embodiments of the first aspect, the compounds have the Formula (Ia), wherein $R^{38}$ is (optionally substituted spiro-heterocyclyl)-$C_1$-$C_6$alkyl-, wherein the optionally substituted spiro-heterocyclyl is selected from the group consisting of optionally substituted [4-4] spiro-heterocyclyl, optionally substituted [4-5] spiro-heterocyclyl, optionally substituted [4-6] spiro-heterocyclyl, optionally substituted [5-4] spiro-heterocyclyl, optionally substituted [5-5] spiro-heterocyclyl, optionally substituted [5-6] spiro-heterocyclyl, optionally substituted [6-4] spiro-heterocyclyl, optionally substituted [6-5] spiro-heterocyclyl and optionally substituted [6-6] spiro-heterocyclyl, and wherein the optional substituent is a fused cycloalkyl, heterocyclyl, aryl or heteroaryl ring.

In some embodiments of the first aspect, the compounds have the Formula (Ia), wherein $R^{38}$ is (optionally substituted spiro-heterocyclyl)-$C_1$-$C_6$alkyl-, wherein the spiro-heterocyclyl is optionally substituted with one or more substituents selected from the group consisting of H, halo, —N($R^9$)($R^{10}$), nitro, —OH, oxo, $C_1$-$C_6$alkyl, —C(O)—$C_1$-$C_6$alkyl-OH, Ac, cycloalkyl, heterocyclyl, aryl, heteroaryl, —S(O)$_{0-2}$—$C_1$-$C_6$alkyl, —S(O)$_{0-2}$-cycloalkyl, —S(O)$_{0-2}$-heterocyclyl, —S(O)$_{0-2}$-aryl, —S(O)$_{0-2}$-heteroaryl, —C(O)H, —C(O)—$C_1$-$C_6$alkyl, —C(O)—N($R^9$)($R^{10}$), —$C_1$-$C_6$alkyl-OH, —$C_1$-$C_6$alkyl-C(O)—OH, —$C_1$-$C_6$alkyl-C(O)—N($R^9$)($R^{10}$), wherein the alkyl, cycloalkyl, heterocyclyl, aryl and heteroaryl groups are themselves optionally substituted, for example with halo or —$C_1$-$C_6$alkyl In some embodiments of the first aspect, the compounds have the Formula (Ia), wherein $R^{38}$ is (optionally substituted spiro-heterocyclyl)-$C_1$-$C_6$alkyl-, wherein the optionally substituted spiro-heterocyclyl is selected from the group consisting of

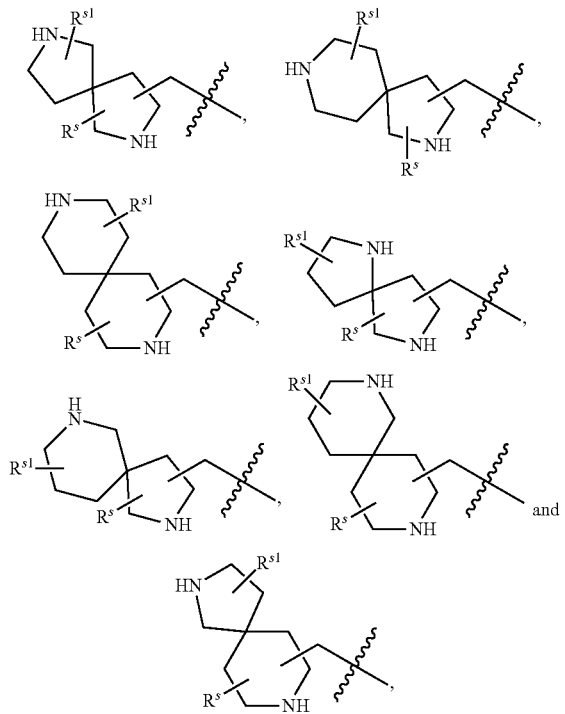

wherein $R^s$ and $R^{s1}$ are optional substituents.

In some embodiments of the first aspect, the compounds have the Formula (Ia), wherein $R^{38}$ is (optionally substituted spiro-heterocyclyl)-$C_1$-$C_6$alkyl-, wherein the optionally substituted spiro-heterocyclyl is selected from the group consisting of

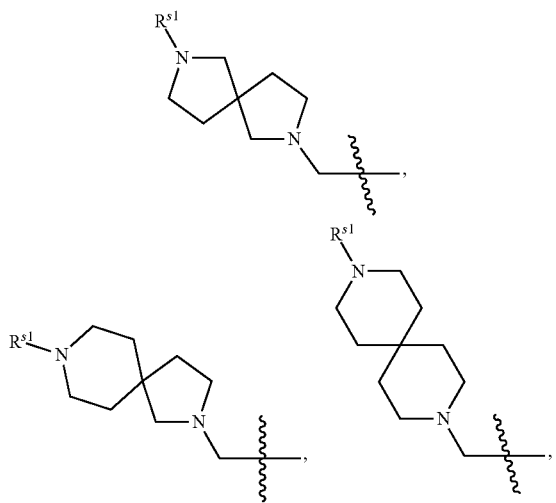

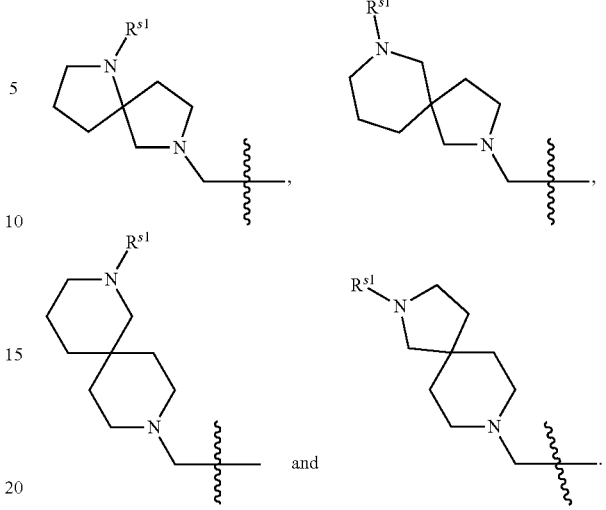

In some embodiments of the first aspect, the compounds have the Formula (Ia), wherein $R^s$ is selected from the group consisting of H, halo, —N($R^9$)($R^{10}$), nitro, —OH, oxo, $C_1$-$C_6$alkyl, —C(O)—$C_1$-$C_6$alkyl-OH, Ac, cycloalkyl, heterocyclyl, aryl, heteroaryl, —S(O)$_{0-2}$—$C_1$-$C_6$alkyl, —S(O)$_{0-2}$-cycloalkyl, —S(O)$_{0-2}$-heterocyclyl, —S(O)$_{0-2}$-aryl, —S(O)$_{0-2}$-heteroaryl, —C(O)H, —C(O)—$C_1$-$C_6$alkyl, —C(O)—N($R^9$)($R^{10}$), —$C_1$-$C_6$alkyl-OH, —$C_1$-$C_6$alkyl-C(O)—OH, —$C_1$-$C_6$alkyl-C(O)—N($R^9$)($R^{10}$), wherein the alkyl, cycloalkyl, heterocyclyl, aryl and heteroaryl groups are themselves optionally substituted, for example with halo or —$C_1$-$C_6$alkyl.

In some embodiments of the first aspect, the compounds have the Formula (Ia), wherein $R^{s1}$ is selected from the group consisting of H, halo, —N($R^9$)($R^{10}$), nitro, —OH, oxo, $C_1$-$C_6$alkyl, —C(O)—$C_1$-$C_6$alkyl-OH, Ac, cycloalkyl, heterocyclyl, aryl, heteroaryl, —S(O)$_{0-2}$—$C_1$-$C_6$alkyl, —S(O)$_{0-2}$-cycloalkyl, —S(O)$_{0-2}$-heterocyclyl, —S(O)$_{0-2}$-aryl, —S(O)$_{0-2}$-heteroaryl, —C(O)H, —C(O)—$C_1$-$C_6$alkyl, —C(O)—N($R^9$)($R^{10}$), —$C_1$-$C_6$alkyl-OH, —$C_1$-$C_6$alkyl-C(O)—OH, —$C_1$-$C_6$alkyl-C(O)—N($R^9$)($R^{10}$), wherein the alkyl, cycloalkyl, heterocyclyl, aryl and heteroaryl groups are themselves optionally substituted, for example with halo or —$C_1$-$C_6$alkyl.

In some embodiments of the first aspect, the compounds have the Formula (Ia), wherein $R^{38}$ is (optionally substituted bridged bicyclic ring system)-$C_1$-$C_6$alkyl-.

In some embodiments of the first aspect, the compounds have the Formula (Ia), wherein $R^{38}$ is (optionally substituted bridged bicyclic ring system)-$C_1$-$C_6$alkyl-, wherein the bridged bicyclic ring system is selected from the group consisting of [1.1.0], [2.2.0], [2.2.1], [2.2.2], [3.2.0], [3.2.1], [3.2.2], [3.3.0], [3.3.1], [3.3.2], [4.2.0], [4.2.1], [4.3.0], [4.3.1], [4.3.2], [4.4.0], [4.4.1], [4.4.2] bridged bicyclic ring systems.

In some embodiments of the first aspect, the compounds have the Formula (Ia), wherein $R^{38}$ is (optionally substituted bridged bicyclic ring system)-$C_1$-$C_6$alkyl-, wherein the bridged bicyclic ring system is a bridged bicyclic amine.

In some embodiments of the first aspect, the compounds have the Formula (Ia), wherein $R^{38}$ is (optionally substituted bridged bicyclic ring system)-$C_1$-$C_6$alkyl- selected from the group consisting of

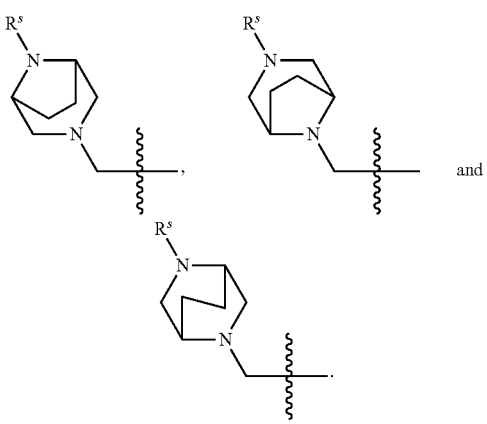

In some embodiments of the first aspect, the compounds have the Formula (Ia), wherein $R^{38}$ is (substituted piperazine)-$C_1$-$C_6$alkyl-.

In some embodiments of the first aspect, the compounds have the Formula (Ia), wherein $R^{38}$ is (substituted piperazine)-$C_1$-$C_6$alkyl- selected from group consisting of

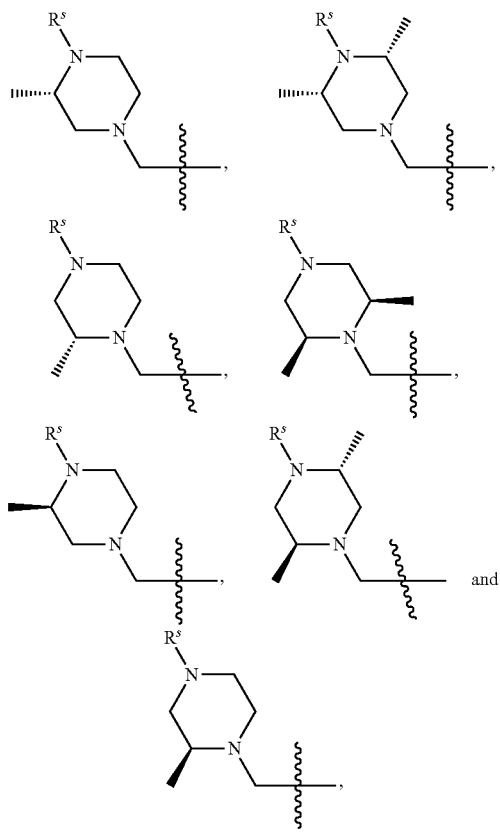

wherein $R^s$ is an optional substituent.

In some embodiments of the first aspect, the compounds have the Formula (Ia), wherein $R^{38}$ is $(R^9)(R^{10})N$—$C_1$-$C_6$alkyl-C(O)—O—$C_1$-$C_6$alkyl-C(O)-(5 to 10-membered heterocyclyl)-$C_1$-$C_6$alkyl-.

In some embodiments of the first aspect, the compounds have the Formula (Ia), wherein $R^{38}$ is $(R^9)(R^{10})N$—$C_1$-$C_6$alkyl-C(O)—O—$C_1$-$C_6$alkyl-C(O)-(5 to 10-membered heterocyclyl)-$C_1$-$C_6$alkyl-, wherein the 5 to 10-membered heterocyclyl is a 6-membered heterocyclyl.

In some embodiments of the first aspect, the compounds have the Formula (Ia), wherein $R^{38}$ is $(R^9)(R^{10})N$—$C_1$-$C_6$alkyl-C(O)—O—$C_1$-$C_6$alkyl-C(O)-(5 to 10-membered heterocyclyl)-$C_1$-$C_6$alkyl-, which is

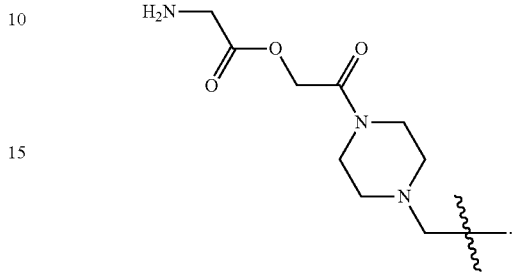

In some embodiments of the first aspect, the compounds have the Formula (Ia), wherein $R^{38}$ is $C_1$-$C_6$alkyl-$S(O)_{0-2}$—$C_1$-$C_6$alkyl-(5 to 10-membered heterocyclyl)-$C_1$-$C_6$alkyl-.

In some embodiments of the first aspect, the compounds have the Formula (Ia), wherein $R^{38}$ is $C_1$-$C_6$alkyl-$S(O)_{0-2}$—$C_1$-$C_6$alkyl-(5 to 10-membered heterocyclyl)-$C_1$-$C_6$alkyl-, wherein the 5 to 10-membered heterocyclyl is a 6-membered heterocyclyl.

In some embodiments of the first aspect, the compounds have the Formula (Ia), wherein $R^{38}$ is $C_1$-$C_6$alkyl-$S(O)_{0-2}$—$C_1$-$C_6$alkyl-(5 to 10-membered heterocyclyl)-$C_1$-$C_6$alkyl-, which is

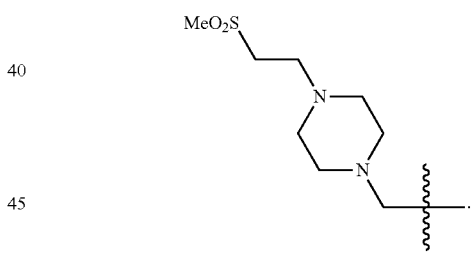

In some embodiments of the first aspect, the compounds have the Formula (Ia), wherein $R^{38}$ is $(R^{23})(R^{24})P(O)O$—$C_1$-$C_6$alkyl-C(O)-(5 to 10-membered heterocyclyl)-$C_1$-$C_6$alkyl-.

In some embodiments of the first aspect, the compounds have the Formula (Ia), wherein $R^{38}$ is $(R^{23})(R^{24})P(O)O$—$C_1$-$C_6$alkyl-C(O)-(5 to 10-membered heterocyclyl)-$C_1$-$C_6$alkyl-, wherein the 5 to 10-membered heterocyclyl is a 6-membered heterocyclyl.

In some embodiments of the first aspect, the compounds have the Formula (Ia), wherein $R^{38}$ is $(R^{23})(R^{24})P(O)O$—$C_1$-$C_6$alkyl-C(O)-(5 to 10-membered heterocyclyl)-$C_1$-$C_6$alkyl-, wherein the 5 to 10-membered heterocyclyl is a 6-membered heterocyclyl and each of $R^{37}$ and $R^{37a}$ are H.

In some embodiments of the first aspect, the compounds have the Formula (Ia), wherein $R^{38}$ is $(R^{23})(R^{24})P(O)O$—$C_1$-$C_6$alkyl-C(O)-(5 to 10-membered heterocyclyl)-$C_1$-$C_6$alkyl-, which is

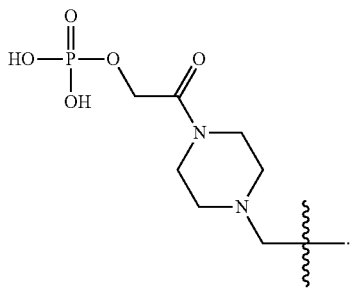

In some embodiments of the first aspect, the compounds have the Formula (Ia), wherein $R^{38}$ is $R^{37}S(O)_{0-2}$-aryl-C(O)—O—$C_1$-$C_6$alkyl-C(O)-(5 to 10-membered heterocyclyl)-$C_1$-$C_6$alkyl-.

In some embodiments of the first aspect, the compounds have the Formula (Ia), wherein $R^{38}$ is $R^{37}S(O)_{0-2}$-aryl-C(O)—O—$C_1$-$C_6$alkyl-C(O)-(5 to 10-membered heterocyclyl)-$C_1$-$C_6$alkyl-, wherein the 5 to 10-membered heterocyclyl is a 6-membered heterocyclyl.

In some embodiments of the first aspect, the compounds have the Formula (Ia), wherein $R^{38}$ is $R^{37}S(O)_{0-2}$-aryl-C(O)—O—$C_1$-$C_6$alkyl-C(O)-(5 to 10-membered heterocyclyl)-$C_1$-$C_6$alkyl-, which is

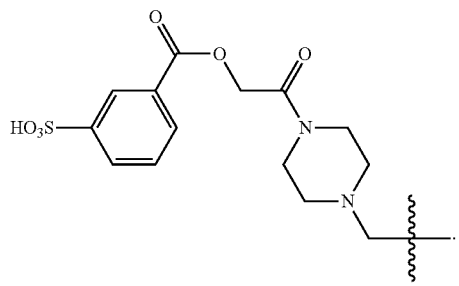

In some embodiments of the first aspect, the compounds have the Formula (Ia), wherein $R^{38}$ is $R^{37}$O—$C_1$-$C_6$alkyl-piperazine-$C_1$-$C_6$alkyl-.

In some embodiments of the first aspect, the compounds have the Formula (Ia), wherein $R^{38}$ is $R^{37}$O—$C_1$-$C_6$alkyl-piperazine-$C_1$-$C_6$alkyl-, wherein D is

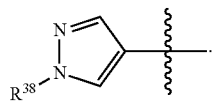

In some embodiments of the first aspect, the compounds have the Formula (Ia), wherein $R^{38}$ is $R^{37}$O—$C_1$-$C_6$alkyl-piperazine-$C_1$-$C_6$alkyl-, which is

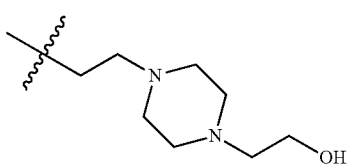 or

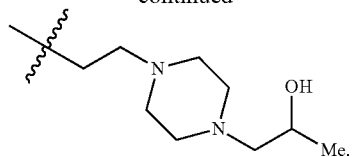

In some embodiments of the first aspect, the compounds have the Formula (Ia), wherein $R^{38}$ is $R^{37}$O—C(O)—$C_1$-$C_6$alkyl-(5 to 10-membered heterocyclyl)-$C_1$-$C_6$alkyl-.

In some embodiments of the first aspect, the compounds have the Formula (Ia), wherein $R^{38}$ is $R^{37}$O—C(O)—$C_1$-$C_6$alkyl-(5 to 10-membered heterocyclyl)-$C_1$-$C_6$alkyl-, wherein the 5 to 10-membered heterocyclyl is a six-membered heterocyclyl.

In some embodiments of the first aspect, the compounds have the Formula (Ia), wherein $R^{38}$ is $R^{37}$O—C(O)—$C_1$-$C_6$alkyl-(5 to 10-membered heterocyclyl)-$C_1$-$C_6$alkyl-, wherein D is

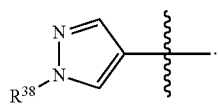

In some embodiments of the first aspect, the compounds have the Formula (Ia), wherein $R^{38}$ is $R^{37}$O—C(O)—$C_1$-$C_6$alkyl-(5 to 10-membered heterocyclyl)-$C_1$-$C_6$alkyl-, wherein the 5 to 10-membered heterocyclyl is a six-membered heterocyclyl and wherein D is

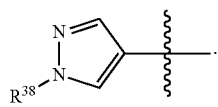

In some embodiments of the first aspect, the compounds have the Formula (Ia), wherein $R^{38}$ is $R^{37}$O—C(O)—$C_1$-$C_6$alkyl-(5 to 10-membered heterocyclyl)-$C_1$-$C_6$alkyl-, which is

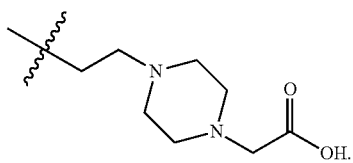 [SMILES: *CCN1CCN(CC(=O)O)CC1]

In some embodiments of the first aspect, the compounds have the Formula (Ia), wherein $R^{38}$ is $(R^9)(R^{10})$N—$C_1$-$C_6$alkyl-piperazine-$C_1$-$C_6$alkyl-.

In some embodiments of the first aspect, the compounds have the Formula (Ia), wherein $R^{38}$ is $(R^9)(R^{10})$N—$C_1$-$C_6$alkyl-piperazine-$C_1$-$C_6$alkyl-, wherein D is

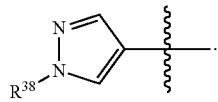

In some embodiments of the first aspect, the compounds have the Formula (Ia), wherein $R^{38}$ is $(R^9)(R^{10})N$—$C_1$-$C_6$alkyl-piperazine-$C_1$-$C_6$alkyl-, wherein $R^9$ and $R^{10}$ are independently H or $C_1$-$C_4$alkyl.

In some embodiments of the first aspect, the compounds have the Formula (Ia), wherein $R^{38}$ is $(R^9)(R^{10})N$—$C_1$-$C_6$alkyl-piperazine-$C_1$-$C_6$alkyl-, wherein $R^9$ and $R^{10}$ are independently H or $C_1$-$C_4$alkyl, and D is

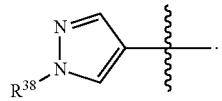

In some embodiments of the first aspect, the compounds have the Formula (Ia), wherein $R^{38}$ is $(R^9)(R^{10})N$—$C_1$-$C_6$alkyl-piperazine-$C_1$-$C_6$alkyl-, which is

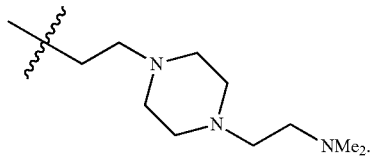 [SMILES: *CCN1CCN(CCN(C)C)CC1]

In some embodiments of the first aspect, the compounds have the Formula (Ia), wherein $R^{38}$ is $R^{37a}O$—$C(O)$—$C_1$-$C_6$alkyl-$N(R^{37})$—$C(O)$—$C_1$-$C_6$alkyl-(5 to 10-membered heterocyclyl)-$C_1$-$C_6$alkyl-.

In some embodiments of the first aspect, the compounds have the Formula (Ia), wherein $R^{38}$ is $R^{37a}O$—$C(O)$—$C_1$-$C_6$alkyl-$N(R^{37})$—$C(O)$—$C_1$-$C_6$alkyl-(5 to 10-membered heterocyclyl)-$C_1$-$C_6$alkyl-, wherein the 5 to 10-membered heterocyclyl is a six-membered heterocyclyl.

In some embodiments of the first aspect, the compounds have the Formula (Ia), wherein $R^{38}$ is $R^{37a}O$—$C(O)$—$C_1$-$C_6$alkyl-$N(R^{37})$—$C(O)$—$C_1$-$C_6$alkyl-(5 to 10-membered heterocyclyl)-$C_1$-$C_6$alkyl-, and D is

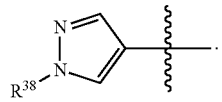

In some embodiments of the first aspect, the compounds have the Formula (Ia), wherein $R^{38}$ is $R^{37a}O$—$C(O)$—$C_1$-$C_6$alkyl-$N(R^{37})$—$C(O)$—$C_1$-$C_6$alkyl-(5 to 10-membered heterocyclyl)-$C_1$-$C_6$alkyl-, wherein the 5 to 10-membered heterocyclyl is a six-membered heterocyclyl, and D is

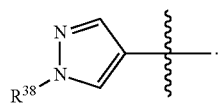

In some embodiments of the first aspect, the compounds have the Formula (Ia), wherein $R^{38}$ is $R^{37a}O$—$C(O)$—$C_1$-$C_6$alkyl-$N(R^{37})$—$C(O)$—$C_1$-$C_6$alkyl-(5 to 10-membered heterocyclyl)-$C_1$-$C_6$alkyl-, which is

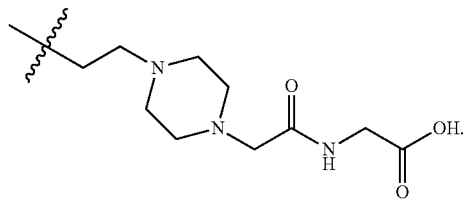 [SMILES: *CCN1CCN(CC(=O)NCC(=O)O)CC1]

In some embodiments of the first aspect, the compounds have the Formula (Ia), wherein $R^{38}$ is $R^{11}$—$C_1$-$C_6$alkyl-C(O)-piperazine-$C_1$-$C_6$alkyl-.

In some embodiments of the first aspect, the compounds have the Formula (Ia), wherein $R^{38}$ is $R^{11}$—$C_1$-$C_6$alkyl-C(O)-piperazine-$C_1$-$C_6$alkyl- and D is

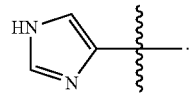

In some embodiments of the first aspect, the compounds have the Formula (Ia), wherein $R^{38}$ is $R^{11}$—$C_1$-$C_6$alkyl-C(O)-piperazine-$C_1$-$C_6$alkyl-, wherein $R^{11}$ is —O-(amino acid).

In some embodiments of the first aspect, the compounds have the Formula (Ia), wherein $R^{38}$ is $R^{11}$—$C_1$-$C_6$alkyl-C(O)-piperazine-$C_1$-$C_6$alkyl-, wherein $R^{11}$ is —O-(amino acid) and D is

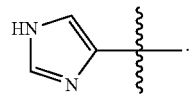

In some embodiments of the first aspect, the compounds have the Formula (Ia), wherein $R^{38}$ is $C_0$-$C_6$alkyl-(5 or 6-membered heterocyclyl)-$C_1$-$C_6$alkyl-piperazine-$C_1$-$C_6$alkyl-.

In some embodiments of the first aspect, the compounds have the Formula (Ia), wherein $R^{38}$ is $C_0$-$C_6$alkyl-(5 or 6-membered heterocyclyl)-$C_1$-$C_6$alkyl-piperazine-$C_1$-$C_6$alkyl-, wherein D is

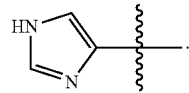

In some embodiments of the first aspect, the compounds have the Formula (Ia), wherein $R^{38}$ is (5-10-membered optionally substituted heterocycle)-$C_1$-$C_6$alkyl-O-(oxo substituted 5 to 10-membered heterocycle)-$C_1$-$C_6$alkyl-.

In some embodiments of the first aspect, the compounds have the Formula (Ia), wherein $R^{38}$ is (5-10-membered optionally substituted heterocycle)-$C_1$-$C_6$alkyl-O-(oxo substituted 5 to 10-membered heterocycle)-$C_1$-$C_6$alkyl-, wherein the 5-10-membered optionally substituted heterocycle is a 6-membered heterocycle, optionally substituted with $C_1$-$C_6$alkyl.

In some embodiments of the first aspect, the compounds have the Formula (Ia), wherein $R^{38}$ is (5-10-membered optionally substituted heterocycle)-$C_1$-$C_6$alkyl-O-(oxo substituted 5 to 10-membered heterocycle)-$C_1$-$C_6$alkyl-, wherein the oxo substituted 5 to 10-membered heterocycle is a 5-membered heterocycle, for example

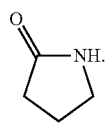

In some embodiments of the first aspect, the compounds have the Formula (Ia), wherein $R^{38}$ is (5-10-membered optionally substituted heterocycle)-$C_1$-$C_6$alkyl-O-(oxo substituted 5 to 10-membered heterocycle)-$C_1$-$C_6$alkyl-, wherein the 5-10-membered optionally substituted heterocycle is a 6-membered heterocycle, optionally substituted with $C_1$-$C_6$alkyl and the oxo substituted 5 to 10-membered heterocycle is a 5-membered heterocycle, for example

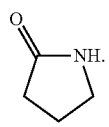

In some embodiments of the first aspect, the compounds have the Formula (Ia), wherein $R^{38}$ is (5-10-membered optionally substituted heterocycle)-$C_1$-$C_6$alkyl-O-(oxo substituted 5 to 10-membered heterocycle)-$C_1$-$C_6$alkyl-, selected from the group consisting of

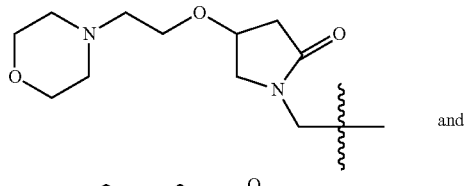

and

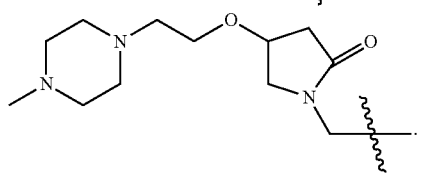

In some embodiments of the first aspect, the compounds have the Formula (Ia), wherein $R^{38}$ is (5-10-membered optionally substituted heterocycle)-$C_1$-$C_6$alkyl-N($R^1$)-(oxo substituted 5 to 10-membered heterocycle)-$C_1$-$C_6$alkyl-.

In some embodiments of the first aspect, the compounds have the Formula (Ia), wherein $R^{38}$ is (5-10-membered optionally substituted heterocycle)-$C_1$-$C_6$alkyl-N($R^1$)-(oxo substituted 5 to 10-membered heterocycle)-$C_1$-$C_6$alkyl-, wherein 5-10-membered optionally substituted heterocycle is a 6-membered heterocycle, optionally substituted with $C_1$-$C_6$alkyl.

In some embodiments of the first aspect, the compounds have the Formula (Ia), wherein $R^{38}$ is (5-10-membered optionally substituted heterocycle)-$C_1$-$C_6$alkyl-N($R^1$)-(oxo substituted 5 to 10-membered heterocycle)-$C_1$-$C_6$alkyl-, wherein the oxo substituted 5 to 10-membered heterocycle is a 5-membered heterocycle, for example

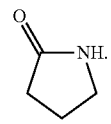

In some embodiments of the first aspect, the compounds have the Formula (Ia), wherein $R^{38}$ is (5-10-membered optionally substituted heterocycle)-$C_1$-$C_6$alkyl-N($R^1$)-(oxo substituted 5 to 10-membered heterocycle)-$C_1$-$C_6$alkyl-, wherein 5-10-membered optionally substituted heterocycle is a 6-membered heterocycle, optionally substituted with $C_1$-$C_6$alkyl and the oxo substituted 5 to 10-membered heterocycle is a 5-membered heterocycle, for example

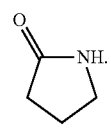

In some embodiments of the first aspect, the compounds have the Formula (Ia), wherein $R^{38}$ is (5-10-membered optionally substituted heterocycle)-$C_1$-$C_6$alkyl-N($R^1$)-(oxo substituted 5 to 10-membered heterocycle)-$C_1$-$C_6$alkyl-, wherein 5-10-membered optionally substituted heterocycle is a 6-membered heterocycle, optionally substituted with $C_1$-$C_6$alkyl and the oxo substituted 5 to 10-membered heterocycle is a 5-membered heterocycle, for example

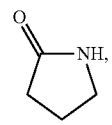

selected from the group consisting of

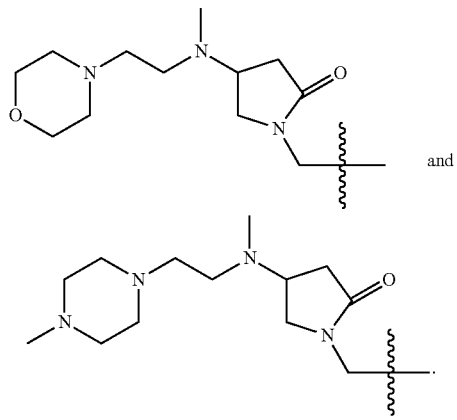

In some embodiments of the first aspect, the compounds have the Formula (1a), wherein $R^{38}$ is (5-10-membered optionally substituted heterocycle)-$C_1$-$C_6$alkyl-S(O)$_{0-2}$-(oxo substituted 5 to 10-membered heterocycle)-$C_1$-$C_6$alkyl-.

In some embodiments of the first aspect, the compounds have the Formula (1a), wherein $R^{38}$ is $(R^{23})(R^{23})$P(O)—$C_1$-$C_6$alkyl-C(O)—.

In some embodiments of the first aspect, the compounds have the Formula (1a), wherein $R^{38}$ is $(R^{23})(R^{24})(O)P$—$C_1$-$C_6$alkyl-N($R^{37}$)—$C_1$-$C_6$alkyl-.

In some embodiments of the first aspect, the compounds have the Formula (1a), wherein $R^{38}$ is $(R^9)(R^{10})N$—$C(H)(R^{28})$—.

In some embodiments of the first aspect, the compounds have the Formula (1a), wherein $R^{38}$ is $R^{29}O$—$C(O)$—$C(H)(C(O)$—$OR^{29})$—$O$—$C_1$-$C_6$alkyl-(5 to 10-membered heterocyclyl)-$C_1$-$C_6$alkyl-.

In some embodiments of the first aspect, the compounds have the Formula (1a), wherein $R^{38}$ is $R^{29}O$—$C(O)$—$C(H)(C(O)$—$OR^{29a})$—$O$—$C_1$-$C_6$alkyl-(5 to 10-membered heterocyclyl)-$C_1$-$C_6$alkyl-, wherein the heterocyclyl is selected from the group consisting of tetrahydrofuranyl, tetrahydrothiophenyl, pyrrolidine, tetrahydropyranyl, tetrahydrothiopyranyl, piperidinyl, dioxanyl, oxathianyl, morpholinyl, dithianyl, piperazinyl, azathianyl, oxepanyl, theipaneyl, azepanyl, dioxepanyl, oxatheipanyl, oxaazepanyl, dithiepanyl, thieazepanyl and diazepanyl.

In some embodiments of the first aspect, the compounds have the Formula (1a), wherein $R^{38}$ is $R^{29}O$—$C(O)$—$C(H)(C(O)$—$OR^{29a})$—$O$—$C_1$-$C_6$alkyl-(5 to 10-membered heterocyclyl)-$C_1$-$C_6$alkyl-, wherein the heterocyclyl is selected from the group consisting of piperidinyl, morpholinyl and piperazinyl.

In some embodiments of the first aspect, the compounds have the Formula (1a), wherein $R^{38}$ is $R^{29}O$—$C(O)$—$C(H)(C(O)$—$OR^{29a})$—$O$—$C_1$-$C_6$alkyl-C(O)-(5 to 10-membered heterocyclyl)-$C_1$-$C_6$alkyl-.

In some embodiments of the first aspect, the compounds have the Formula (1a), wherein $R^{38}$ is $R^{29}O$—$C(O)$—$C(H)(C(O)$—$OR^{29a})$—$O$—$C_1$-$C_6$alkyl-C(O)-(5 to 10-membered heterocyclyl)-$C_1$-$C_6$alkyl-, wherein the heterocyclyl is selected from the group consisting of tetrahydrofuranyl, tetrahydrothiophenyl, pyrrolidine, tetrahydropyranyl, tetrahydrothiopyranyl, piperidinyl, dioxanyl, oxathianyl, morpholinyl, dithianyl, piperazinyl, azathianyl, oxepanyl, theipaneyl, azepanyl, dioxepanyl, oxatheipanyl, oxaazepanyl, dithiepanyl, thieazepanyl and diazepanyl.

In some embodiments of the first aspect, the compounds have the Formula (Ia), wherein $R^{38}$ is $R^{29}O$—$C(O)$—$C(H)(C(O)$—$OR^{29a})$—$O$—$C_1$-$C_6$alkyl-C(O)-(5 to 10-membered heterocyclyl)-$C_1$-$C_6$alkyl-, wherein the heterocyclyl is selected from the group consisting of piperidinyl, morpholinyl and piperazinyl.

In some embodiments of the first aspect, the compounds have the Formula (Ia), wherein $R^{23}$ is selected from the group consisting of H, $C_1$-$C_6$alkyl, aryl, cycloalkyl, heteroaryl, 5 to 10-membered heterocyclyl, —$C_1$-$C_6$alkyl-aryl, —$C_1$-$C_6$alkyl-heteroaryl, —$C_1$-$C_6$alkyl-cycloalkyl and —$C_1$-$C_6$alkyl-(5 to 10-membered heterocyclyl).

In some embodiments of the first aspect, the compounds have the Formula (1a), wherein $R^{23}$ is selected from the group consisting of —OH, $C_1$-$C_6$alkoxy, —O-aryl, —O-cycloalkyl, —O-heteroaryl, —O-(5 to 10-membered heterocyclyl), —O—$C_1$-$C_6$alkyl-aryl, —O—$C_1$-$C_6$alkyl-heteroaryl, —O—$C_1$-$C_6$alkyl-cycloalkyl and —O—$C_1$-$C_6$alkyl-(5 to 10-membered heterocyclyl).

In some embodiments of the first aspect, the compounds have the Formula (1a), wherein $R^{24}$ is selected from the group consisting of H, $C_1$-$C_6$alkyl, aryl, cycloalkyl, heteroaryl, 5 to 10-membered heterocyclyl, —$C_1$-$C_6$alkyl-aryl, —$C_1$-$C_6$alkyl-heteroaryl, —$C_1$-$C_6$alkyl-cycloalkyl and —$C_1$-$C_6$alkyl-(5 to 10-membered heterocyclyl).

In some embodiments of the first aspect, the compounds have the Formula (1a), wherein $R^{24}$ is selected from the group consisting of —OH, $C_1$-$C_6$alkoxy, —O-aryl, —O-cycloalkyl, —O-heteroaryl, —O-(5 to 10-membered heterocyclyl), —O—$C_1$-$C_6$alkyl-aryl, —O—$C_1$-$C_6$alkyl-heteroaryl, —O—$C_1$-$C_6$alkyl-cycloalkyl and —O—$C_1$-$C_6$alkyl-(5 to 10-membered heterocyclyl).

In some embodiments of the first aspect, the compounds have the Formula (a), wherein $R^{28}$ is selected from the group consisting of —$CF_3$, —$CHF_2$, —$CH_2F$, CN, optionally substituted $C_1$-$C_6$alkyl and $C_3$-$C_6$cycloalkyl.

In some embodiments of the first aspect, the compounds have the Formula (a), wherein $R^{28}$ is selected from the group consisting of —$CF_3$, —$CHF_2$, —$CH_2F$ and CN.

In some embodiments of the first aspect, the compounds have the Formula (1a), wherein $R^{29}$ is H or $C_1$-$C_6$alkyl.

In some embodiments of the first aspect, the compounds have the Formula (1a), wherein $R^{29a}$ is H or $C_1$-$C_6$alkyl.

In some embodiments of the first aspect, the compounds have the Formula (1a), wherein $R^{29}$ is a cation, for example a pharmaceutically acceptable cation, for example a cation selected from the group consisting of $Li^+$, $Na^+$, $K^+$, $Mg^{2+}/2$ and $Ca^{2+}/2$.

In some embodiments of the first aspect, the compounds have the Formula (1a), wherein $R^{29}$ is Na+ or K+.

In some embodiments of the first aspect, the compounds have the Formula (1a), wherein $R^{29a}$ is a cation, for example a pharmaceutically acceptable cation, for example a cation selected from the group consisting of $Li^+$, $Na^+$, $K^+$, $Mg^{2+}/2$ and $Ca^{2+}/2$.

In some embodiments of the first aspect, the compounds have the Formula (1a), wherein $R^{29a}$ is Na+ or K+.

In some embodiments of the first aspect, compounds of the present invention have the formulas Formula (II) and Formula (III):

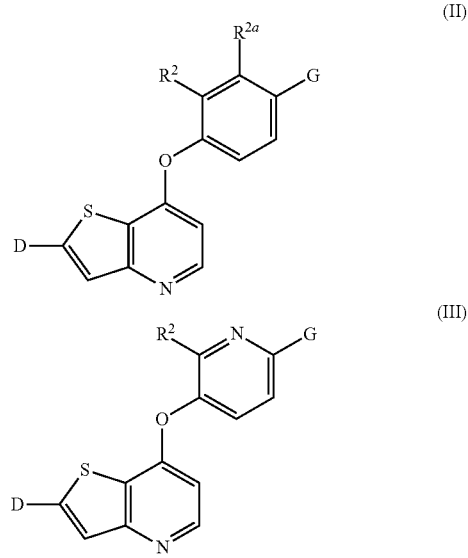

including N-oxides, hydrates, solvates, tautomers, pharmaceutically acceptable salts, prodrugs and complexes thereof, and racemic and scalemic mixtures, diastereomers and enantiomers thereof, wherein, D is selected from the group consisting of pyridine, phenyl, imidazole, pyrazole, and tetrahydropyridine, wherein the pyridine, phenyl, imidazole, pyrazole and tetrahydropyridine are substituted with one $R^{38}$, or D is unsubstituted tetrahydropyridine;

$R^{38}$ is selected from the group consisting of $R^{37}O$—$(CH_7)_{1-6}$—$N(A)$-$(CH_2)_{1-4}$—, (oxo substituted heterocyclyl)-$C_1$-$C_2$alkyl- (wherein the oxo substituted heterocyclyl is further optionally substituted with a substituent selected from the group consisting of —$N(R^9)(R^{10})$, $C_1$-$C_6$alkyl, —$N(R^{37})(Ac)$, and —OH), $R^{37}O$—$(CH_2)_n$—O—$(CH_2)_{n1}C(O)$—$N(R^{40})$—$CH_2$—, $C_1$-$C_6$alkyl-heterocyclyl-$(CH_2)_{1-2}$—, (heterocyclyl)-C(O)— (wherein the heterocyclyl is optionally substituted with $C_1$-$C_6$alkyl), $C_1$-$C_6$alkyl-S(O)$_2$—$(CH_2)_2$—N(A)-$CH_2$—, $C_0$-$C_6$alkyl-heterocyclyl-$(CH_2)_{1-3}$—, HO-heterocyclyl-$CH_2$—, $(R^9)(R^{10})$N-heterocyclyl-$CH_2$—, $(R^9)(R^{10})$N—$C_0$-$C_6$alkyl-heterocyclyl-C(O)—, $(C_1$-$C_6$alkyl)-C(O)-heterocyclyl-$CH_2$—, $R^{37}O$—$C_1$-$C_6$alkyl-heterocyclyl-$CH_2$—, $R^{37}O$—$C_1$-$C_6$alkyl-C(O)-heterocyclyl-$(CH_2)_{1-6}$—, $C_0$-$C_6$alkyl-heterocyclyl-$C_1$-$C_6$alkyl-$N(R^{39})$—C(O)—, $R^{37}O$—$(CH_2)_j$—$[(CH_2)_iO]_x$—$(CH_2)_{i1}$—N(A)-$(CH_2)_{j1}$—, $R^{37}O$—C(O)—$C_0$-$C_6$alkyl-heterocyclyl-$CH_2$—, $R^{37}O$—$(CH_2)_j$—$[(CH_2)_iO]_x$—$(CH_2)_{i1}$—$N(R^{39})$—C(O)—, $R^{37}$—O—C(O)—$C_1$-$C_6$alkyl-heterocyclyl-C(O)—, HOOC—$C_1$-$C_6$alkyl-N(A)-$CH_2$—, (HOOC)($NR^9R^{10}$)—$C_1$-$C_6$alkyl-N(A)-$CH_2$—, $R^{37}$—O—C(O)-heterocyclyl-C(O)—, $C_0$-$C_6$alkyl-heterocyclyl-$C_0$-$C_6$alkyl-heterocyclyl-C(O)—, $R^{37}O$—C(O)—$C_1$-$C_6$alkyl-C(O)—, $(R^9)(R^{10})$N—$C_1$-$C_6$alkyl-C(O)-heterocyclyl-$CH_2$—, cycloalkyl-$N(R^{39})$—C(O)—O—$C_1$-$C_6$alkyl-, $R^{37}$—O—$C_1$-$C_6$alkyl-O—$C_1$-$C_6$alkyl-C(O)—, $C_1$-$C_6$alkyl-SO$_2$—, $(R^9)(R^{10})$N—C(O)—$C_1$-$C_6$alkyl-heterocyclyl-$CH_2$—, $(R^9)(R^{10})$N—$C_1$-$C_6$alkyl-C(O)—O—$C_1$-$C_6$alkyl-heterocyclyl-$CH_2$—, $R^{37}O$—$C_1$-$C_6$alkyl-heterocyclyl-$CH_2$—, (HO— substituted $C_1$-$C_6$alkyl-$N(R^{39})$—C(O)—, NC—$C_1$-$C_6$alkyl-heterocyclyl-$CH_2$—, heterocyclyl-$C_1$-$C_6$alkyl-heterocyclyl-$CH_2$—, $F_3C$—$C_1$-$C_6$alkyl-heterocyclyl-$CH_2$—, $C_1$-$C_6$alkyl-S(O)$_2$-heterocyclyl-$CH_2$—, heteroaryl-$C_1$-$C_6$alkyl-heterocyclyl-$CH_2$—, $R^{37}O$—$C_1$-$C_6$alkyl-, $(R^9)(R^{10})$N—$C_1$-$C_6$alkyl-C(O)—O—$C_1$-$C_6$alkyl-C(O)-heterocyclyl-$CH_2$—, $C_1$-$C_6$alkyl-C(O)—O—$C_1$-$C_6$alkyl-C(O)-(5 to 10-membered heterocyclyl)-$C_1$-$C_6$alkyl-, (optionally substituted 8- to 10-membered fused heterocyclyl)-$C_1$-$C_6$alkyl-, (di-fluoro substituted heterocyclyl)-$C_1$-$C_6$alkyl-, $C_0$-$C_6$alkyl-(5 or 6-membered heterocyclyl)-$C_1$-$C_6$alkyl-piperazine-$C_1$-$C_6$alkyl-, H(O)C— and $C_1$-$C_6$alkyl-C(O)—O—$C_1$-$C_6$alkyl-C(O)—, $R^{37}O$—$C_1$-$C_6$alkyl-C(O)-heterocyclyl-$C_1$-$C_6$alkyl-;
wherein when D is imidazole, the imidazole is further optionally substituted with $C_1$-$C_6$alkyl;
$R^{37}$ is 1-1, $C_1$-$C_6$alkyl;
$R^{37a}$ is H, $C_1$-$C_6$alkyl;
A is H, Ac, —C(O)—$CH_2$—OMe, —C(O)—$CH(NH_2)$—C$(CH_3)_3$, —C(O)—$C_1$-$C_6$alkyl-$N(R^{39})$—C(O)—$C_1$-$C_6$alkyl-$N(R^9)(R^{10})$, —C(O)—$N(R^{39})$—$C_1$-$C_6$alkyl, —C(O)—H, —C(O)—$C_1$-$C_6$alkyl, —$C_1$-$C_6$alkyl-O—$C_1$-$C_6$alkyl, —C(O)—$C_1$-$C_6$alkyl-OH, —C(O)—$(CH_2)_n$—S(O)$_2$—$C_1$-$C_6$alkyl, —C(O)—$N(R^{39})$-cycloalkyl, —C(O)—$N(R^9)(R^{10})$, $(R^{23})(R^{24})$P(O)O—$C_1$-$C_6$alkyl-C(O)—, $C_1$-$C_6$alkyl and —C(O)—$C_1$-$C_6$alkyl-$N(R^{39})$—C(O)—$C_1$-$C_6$alkyl-$N(R^9)$—C(O)—OBn;
j is an integer ranging from 0 to 4, alternatively 0 to 2;
i is 2 or 3:
x is an integer ranging from 0 to 6, alternatively 2 or 3;
i1 is 2 or 3;
j1 is an integer ranging from 0 to 4, alternatively 1 or 2;
n is an integer ranging from 0 to 4;
n1 is an integer ranging from 0 to 4;
$R^{39}$ is H, $C_1$-$C_6$alkyl,
$R^{40}$ is $C_1$-$C_6$alkyl-$OR^{41}$;
$R^{41}$ is H, $C_1$-$C_6$alkyl;
$R^9$ is H, $C_1$-$C_6$alkyl;
$R^{10}$ is H, $C_1$-$C_6$alkyl;
$R^{23}$ is selected from the group consisting of —OH, $C_1$-$C_6$alkoxy, —O-aryl, —O-cycloalkyl, —O-heteroaryl and —O-(5 to 10-membered heterocyclyl);
$R^{24}$ is selected from the group consisting of —OH, $C_1$-$C_6$alkoxy, —O-aryl, —O-cycloalkyl, —O-heteroaryl, —O-(5 to 10-membered heterocyclyl);
$R^2$ is H or F;
$R^{2a}$ is H, F, Cl;
G is selected from the group consisting of

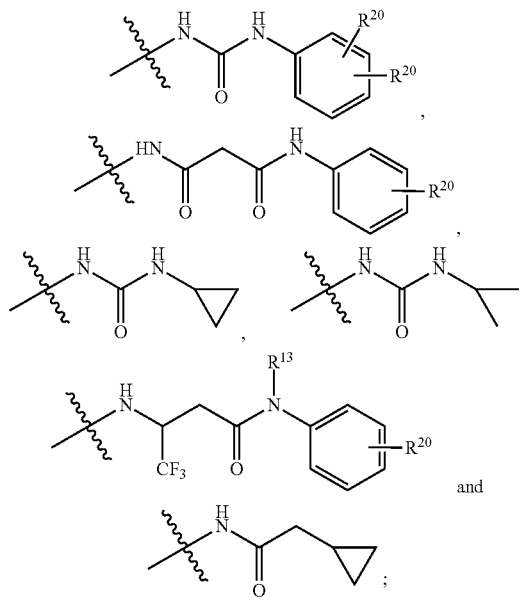

$R^{13}$ is H or $C_1$-$C_6$alkyl; and
each $R^{20}$ is independently selected from the group consisting of H, halo, —PO($C_1$-$C_6$alkyl)$_2$, —S(O)$_2$—$C_1$-$C_6$alkyl) and —C(O)—$NH_2$.

In some embodiments of the first aspect, the compounds have the Formula (II).

In some embodiments of the first aspect, the compounds have the Formula (II), wherein D is pyridine substituted with one $R^{38}$.

In some embodiments of the first aspect, the compounds have the Formula (II), wherein D is pyridine substituted with one $R^{38}$, wherein $R^{38}$ is selected from the group consisting of $R^{37}O$—$(CH_2)_{1-6}$—N(A)-$(CH_2)_{1-4}$—, $R^{37}O$—$(CH_2)_j$—$[(CH_2)_iO]_x$—$(CH_2)_{i1}$—N(A)-$(CH_2)_{j1}$—, $R^{37}O$—C(O)—$C_0$-$C_6$alkyl-heterocyclyl-$CH_2$—, $R^{37}O$—$(CH_2)_j$—$[(CH_2)_iO]_x$—$(CH_2)_{i1}$—$N(R^{39})$—C(O)—, $R^{37}$—O—C(O)—$C_1$-$C_6$alkyl-heterocyclyl-C(O)—, $C_0$-$C_6$alkyl-heterocyclyl-$C_0$-$C_6$alkyl-heterocyclyl-C(O)—, $(R^9)(R^{10})$N—$C_1$-$C_6$alkyl-C(O)-heterocyclyl-$CH_2$—, $(R^9)(R^{10})$N—C(O)—$C_1$-$C_6$alkyl-heterocyclyl-$CH_2$—, $(R^9)(R^{10})$N—$C_1$-$C_6$alkyl-C(O)—O—$C_1$-$C_6$alkyl-heterocyclyl-$CH_2$—, NC—$C_1$-$C_6$alkyl-heterocyclyl-$CH_2$—, $F_3C$—$C_1$-$C_6$alkyl-heterocyclyl-$CH_2$— and $N(R^9)(R^{10})$N—$C_1$-$C_6$alkyl-C(O)—O—$C_1$-$C_6$alkyl-C(O)-heterocyclyl-$CH_2$—.

In some embodiments of the first aspect, the compounds have the Formula (II), wherein D is pyridine substituted with one $R^{38}$, wherein $R^{38}$ is selected from the group consisting of $R^{37}O$—$(CH_2)_{1-6}$—N(A)-$(CH_2)_{1-4}$—, $R^{37}O$—$(CH_2)_j$—$[(CH_2)_iO]_x$($CH_2)_{i1}$—N(A)-$(CH_2)_{j1}$—, $R^{37}O$—C(O)—$C_0$-

C₆alkyl-heterocyclyl-CH₂—, R³⁷O—(CH₂)ⱼ—[CH₂)ᵢO]ₓ—(CH₂)ᵢ₁—N(R³⁹)—C(O)—, R³⁷—O—C(O)—C₁-C₆alkyl-heterocyclyl-C(O)—, (R⁹)(R¹⁰)N—C₁-C₆alkyl-C(O)-heterocyclyl-CH₂—, (R⁹)(R¹⁰)N—C(O)—C₁-C₆alkyl-heterocyclyl-CH₂—, (R⁹)(R¹⁰)N—C₁-C₆alkyl-C(O)—O—C₁-C₆alkyl-heterocyclyl-CH₂—, NC—C₁-C₆alkyl-heterocyclyl-CH₂—, F₃C—C₁-C₆alkyl-heterocyclyl-CH₂— and N(R⁹)(R¹⁰)N—C₁-C₆alkyl-C(O)—O—C₁-C₆alkyl-C(O)-heterocyclyl-CH₂—.

In some embodiments of the first aspect, the compounds have the Formula (II), wherein D is pyridine substituted with one R³⁸, wherein R³⁸ is R³⁷O—(CH₂)₁₋₆—N(A)-(CH₂)₁₋₄— or R³⁷O—(CH₂)ⱼ—[(CH₂)ᵢO]ₓ—(CH₂)ᵢ₁—N(A)-CH₂)ⱼ₁—, and A is selected from the group consisting of —C(O)—C₁-C₆alkyl-N(R³⁹)—C(O)—C₁-C₆alkyl-N(R⁹)(R¹⁰)—C(O)—N(R³⁹)—C₁-C₆alkyl, —C(=NR³⁷)—C₁-C₆alkyl, —C(O)—(CH₂)ₙ—S(O)₂—C₁-C₆alkyl, —C(O)—N(R⁹)(R¹⁰) and (R²³)(R²⁴)P(O)O—C₁-C₆alkyl-C(O)—.

In some embodiments of the first aspect, the compounds have the Formula (II), wherein D is pyridine substituted with one R³⁸, wherein R³⁸ is R³⁷O—(CH₂)₁₋₆—N(A)-(CH₂)₁₋₄—, alternatively R³⁷O—(CH₂)₂—N(A)-(CH₂)₂—, alternatively R³⁷O—(CH₂)₂—N(A)-(CH₂)₂—.

In some embodiments of the first aspect, the compounds have the Formula (II), wherein D is pyridine substituted with one R³⁸, wherein R³⁸ is R³⁷O—(CH₂)₁₋₆—N(A)-(CH₂)₁₋₄—, and A is selected from the group consisting of —C(O)—C₁-C₆alkyl-N(R³⁹)—C(O)—C₁-C₆alkyl-N(R⁹)(R¹⁰), —C(O)—N(R³⁹)—C₁-C₆alkyl, —C(=NR³⁷)—C₁-C₆alkyl, —C(O)—(CH₂)ₙ—S(O)₂—C₁-C₆alkyl, —C(O)—N(R⁹)(R¹⁰) and (R²³)(R²⁴)P(O)O—C₁-C₆alkyl-C(O)—.

In some embodiments of the first aspect, the compounds have the Formula (II), wherein D is pyridine substituted with one R³⁸, wherein R³⁸ is R³⁷O—(CH₂)₂—N(A)-(CH₂)₂—, and A is selected from the group consisting of —C(O)—C₁-C₆alkyl-N(R³⁹)—C(O)—C₁-C₆alkyl-N(R⁹)(R¹⁰) C(O)—N(R³⁹)—C₁-C₆alkyl, —C(=NR³⁷)—C₁-C₆alkyl, —C(O)—(CH₂)ₙ—S(O)₂—C₁-C₆alkyl, —C(O)—N(R⁹)(R¹⁰) and (R²³)(R²⁴)P(O)O—C₁-C₆alkyl-C(O)—.

In some embodiments of the first aspect, the compounds have the Formula (II), wherein D is pyridine substituted with one R³⁸, wherein R³⁸ is R³⁷O—(CH₂)₂—N(A)-(CH₂)₂—, and A is —C(O)—N(R³⁹)—C₁-C₆alkyl.

In some embodiments of the first aspect, the compounds have the Formula (II), wherein D is pyridine substituted with one R³⁸, wherein R³⁸ is R³⁷O—(CH₂)₂—N(A)-(CH₂)₂—, and A is —C(O)—N(R³⁹)—C₁-C₆alkyl.

In some embodiments of the first aspect, the compounds have the Formula (II), wherein D is pyridine substituted with one R³⁸, wherein R³⁸ is R³⁷O—(CH₂)₂—N(A)-(CH₂)₂—, and A is —C(O)—H.

In some embodiments of the first aspect, the compounds have the Formula (II), wherein D is pyridine substituted with one R³⁸, wherein R³⁸ is (oxo substituted heterocyclyl)-C₁-C₂alkyl-; in some embodiments of the first aspect, the compounds have the Formula (II), wherein R³⁸-D- is

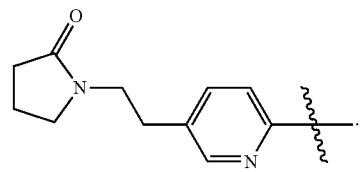

In some embodiments of the first aspect, the compounds have the Formula (II), wherein D is pyridine substituted with one R³⁸, wherein R³⁸ is C₀-C₆alkyl-heterocyclyl-(CH₂)₁₋₃—.

In some embodiments of the first aspect, the compounds have the Formula (II), wherein D is pyridine substituted with one R³⁸, wherein R³⁸ is C₀-C₆alkyl-(7-membered heterocyclyl)-CH₂—. In some embodiments, the C₀-C₆alkyl-heterocyclyl-(CH₂)₁₋₃— is CH₃-(7-membered heterocyclyl)-CH₂—, for example C₀-C₆alkyl-(1,4-diazepanyl)-CH₂—, for example CH₃-(1,4-diazepanyl)-CH₂—.

In some embodiments of the first aspect, the compounds have the Formula (II), wherein D is pyridine substituted with one R³⁸, wherein R³⁸ is R³⁷O—(CH₂)ⱼ—[CH₂)ᵢO]ₓ—(CH₂)ᵢ₁—N(A)-(CH₂)ⱼ₁—.

In some embodiments of the first aspect, the compounds have the Formula (II), wherein D is pyridine substituted with one R³⁸, wherein R³⁸ is R³⁷O—(CH₂)ⱼ—[(CH₂)ᵢO]ₓ—(CH₂)ᵢ₁—N(A)-(CH₂)ⱼ₁—, and A is —C(O)—N(R³⁹)—C₁-C₆alkyl, In some embodiments of the first aspect, the compounds have the Formula (II), wherein D is pyridine substituted with one R³⁸, wherein R³⁸ is R³⁷O—C(O)—C₀-C₆alkyl-heterocyclyl-CH₂—.

In some embodiments of the first aspect, the compounds have the Formula (II), wherein D is pyridine substituted with one R³⁸, wherein R³⁸ is R³⁷O—(CH₂)ⱼ—[(CH₂)ᵢO]ₓ—(CH₂)ᵢ₁—N(R³⁹)—C(O)—.

In some embodiments of the first aspect, the compounds have the Formula (II), wherein D is pyridine substituted with one R³⁸, wherein R³⁸ is R³⁷—O—C(O)—C₁-C₆alkyl-heterocyclyl-C(O)—.

In some embodiments of the first aspect, the compounds have the Formula (II), wherein D is pyridine substituted with one R³⁸, wherein R³⁸ is C₀-C₆alkyl-heterocyclyl-C₀-C₆alkyl-heterocyclyl-C(O)—.

In some embodiments of the first aspect, the compounds have the Formula (II), wherein D is pyridine substituted with one R³⁸, wherein R³⁸ is (R⁹)(R¹⁰)N—C₁-C₆alkyl-C(O)-heterocyclyl—CH₂—.

In some embodiments of the first aspect, the compounds have the Formula (II), wherein D is pyridine substituted with one R³⁸, wherein R³⁸ is (R⁹)(R¹⁰)N—C(O)—C₁-C₆alkyl-heterocyclyl-CH₂—.

In some embodiments of the first aspect, the compounds have the Formula (II), wherein D is pyridine substituted with one R³⁸, wherein R³⁸ is (R⁹)(R¹⁰)N—C₁-C₆alkyl-C(O)—O—C₁-C₆alkyl-heterocyclyl-CH₂—.

In some embodiments of the first aspect, the compounds have the Formula (II), wherein D is pyridine substituted with one R³⁸, wherein R³⁸ is NC—C₁-C₆alkyl-heterocyclyl-CH₂—.

In some embodiments of the first aspect, the compounds have the Formula (II), wherein D is pyridine substituted with one R³⁸, wherein R³⁸ is F₃C—C₁-C₆alkyl-heterocyclyl-CH₂—.

In some embodiments of the first aspect, the compounds have the Formula (II), wherein D is pyridine substituted with one R³⁸, wherein R³⁸ is)N(R⁹)(R¹⁰)N—C₁-C₆alkyl-C(O)—O—C₁-C₆alkyl-C(O)-heterocyclyl-CH₂—.

In some embodiments of the first aspect, the compounds have the Formula (II), wherein D is pyridine substituted with one R³⁸, wherein R³⁸ is C₁-C₆alkyl-C(O)—O—C₁-C₆alkyl-C(O)-(5 to 10-membered heterocyclyl)-C₁-C₆alkyl-.

In some embodiments of the first aspect, the compounds have the Formula (II) or Formula (III), wherein the phenyl ring of group G is substituted with one R²⁰, which is —PO ($C_1$-$C_6$alkyl)$_2$, said $R^{20}$ being ortho to the point of attachment of the nitrogen atom attached to the phenyl ring.

In some embodiments of the first aspect, the compounds have the Formula (II), wherein D is pyridine substituted with one $R^{38}$, and wherein the phenyl ring of group G is substituted with one $R^{20}$, which is —PO($C_1$-$C_6$alkyl)$_2$, said $R^{20}$ being ortho to the point of attachment of the nitrogen atom attached to the phenyl ring.

In some embodiments of the first aspect, the compounds have the Formula (II), wherein D is pyridine substituted with one $R^{38}$, wherein $R^{38}$ is $R^{37}$O—(CH$_2$)$_{1-6}$—N(A)-(CH$_2$)$_{1-4}$—, and wherein the phenyl ring of group G is substituted with one $R^{20}$, which is —PO($C_1$-$C_6$alkyl)$_2$, said $R^{20}$ being ortho to the point of attachment of the nitrogen atom attached to the phenyl ring.

In some embodiments of the first aspect, the compounds have the Formula (II), wherein D is pyridine substituted with one $R^{38}$, wherein $R^{38}$ is (optionally substituted 8- to 10-membered fused heterocyclyl)-$C_1$-$C_6$alkyl-.

In some embodiments of the first aspect, the compounds have the Formula (II), wherein D is pyridine substituted with one $R^{38}$, wherein $R^{38}$ is (optionally substituted 8- to 10-membered fused heterocyclyl)-$C_1$-$C_6$alkyl-, wherein the optional substituent is selected from the group consisting of H, halo, —N($R^9$)($R^{10}$), nitro, —OH, oxo, $C_1$-$C_6$alkyl, —C(O)—$C_1$-$C_6$alkyl-OH, Ac, cycloalkyl, heterocyclyl, aryl, heteroaryl, —S(O)$_{0-2}$—$C_1$-$C_6$alkyl, —S(O)$_{0-2}$-cycloalkyl, —S(O)$_{0-2}$-heterocyclyl, —S(O)$_{0-2}$-aryl, —S(O)$_{0-2}$-heteroaryl, —C(O)H, —C(O)—$C_1$-$C_6$alkyl, —C(O)—N($R^9$)($R^{10}$), $C_1$-$C_6$alkyl-OH, —$C_1$-$C_6$alkyl-C(O)—OH and —$C_1$-$C_6$alkyl-C(O)—N($R^9$)($R^{10}$), wherein the alkyl, cycloalkyl, heterocyclyl, aryl and heteroaryl groups are themselves optionally substituted, for example with halo or —$C_1$-$C_6$alkyl.

In some embodiments of the first aspect, the compounds have the Formula (II), wherein D is pyridine substituted with one $R^{38}$, wherein $R^{38}$ is (di-fluoro substituted heterocyclyl)-$C_1$-$C_6$alkyl-.

In some embodiments of the first aspect, the compounds have the Formula (II), wherein D is pyridine substituted with one $R^{38}$, wherein $R^{38}$ is $C_0$-$C_6$alkyl-(5 or 6-membered heterocyclyl)-$C_1$-$C_6$alkyl-piperazine-$C_1$-$C_6$alkyl-.

In some embodiments of the first aspect, the compounds have the Formula (II), wherein D is pyridine substituted with one $R^{38}$, wherein $R^{38}$ is $R^{37}$O—$C_1$-$C_6$alkyl-C(O)-heterocyclyl-CH$_2$—

In some embodiments of the first aspect, the compounds have the Formula (II), wherein D is imidazole substituted with one $R^{38}$ and one $C_1$-$C_6$alkyl (for example, —CH$_3$).

In some embodiments of the first aspect, the compounds have the Formula (II), wherein D is imidazole substituted with one $R^{38}$ and one $C_1$-$C_6$alkyl, wherein $R^{38}$ is $R^{37}$O—(CH$_2$)$_{1-6}$—N(A)-(CH$_2$)$_{1-4}$—.

In some embodiments of the first aspect, the compounds have the Formula (II), wherein D is imidazole substituted with one $R^{38}$ and one $C_1$-$C_6$alkyl, wherein $R^{38}$ is $R^{37}$O—CH$_2$)$_{1-6}$—N(A)-(CH$_2$)$_{1-4}$—, and A is —C(O)—N($R^{39}$)—$C_1$-$C_6$alkyl or —C(O)—N($R^{39}$)-cycloalkyl.

In some embodiments of the first aspect, the compounds have the Formula (II), wherein D is imidazole substituted with one $R^{38}$ and one $C_1$-$C_6$alkyl, wherein $R^{38}$ is $R^{37}$O—(CH$_2$)$_2$—N(A)-(CH$_2$)—, and A is —C(O)—N($R^{39}$)—$C_1$-$C_6$alkyl or —C(O)—N($R^{39}$)-cycloalkyl.

In some embodiments of the first aspect, the compounds have the Formula (II), wherein D is imidazole substituted with one $R^{38}$ and one $C_1$-$C_6$alkyl, wherein $R^{38}$ is $R^{37}$O—(CH$_2$)$_2$—N(A)-(CH$_2$)—, and A is —C(O)—N($R^{39}$)—$C_1$-$C_6$alkyl.

In some embodiments of the first aspect, the compounds have the Formula (II), wherein D is imidazole substituted with one $R^{38}$, wherein $R^{38}$ is $C_0$-$C_6$alkyl-heterocyclyl-(CH$_2$)$_{1-3}$—, for example, piperazine-(CH$_2$)$_2$—.

In some embodiments of the first aspect, the compounds have the Formula (II), wherein D is imidazole substituted with one $R^{38}$, wherein $R^{38}$ is $C_1$-$C_6$alkyl-C(O)—O—$C_1$-$C_6$alkyl-C(O)-(5 to 10-membered heterocyclyl)-$C_1$-$C_6$alkyl-.

In some embodiments of the first aspect, the compounds have the Formula (II), wherein D is imidazole substituted with one $R^{38}$, wherein $R^{38}$ is $C_1$-$C_6$alkyl-C(O)—O—$C_1$-$C_6$alkyl-C(O)-(5 to 10-membered heterocyclyl)-$C_1$-$C_6$alkyl- wherein the heterocyclyl is a 6-membered heterocyclyl.

In some embodiments of the first aspect, the compounds have the Formula (II), wherein $R^{38}$ is $C_1$-$C_6$alkyl-C(O)—O—$C_1$-$C_6$alkyl-C(O)-(5 to 10-membered heterocyclyl)-$C_1$-$C_6$alkyl-, which is

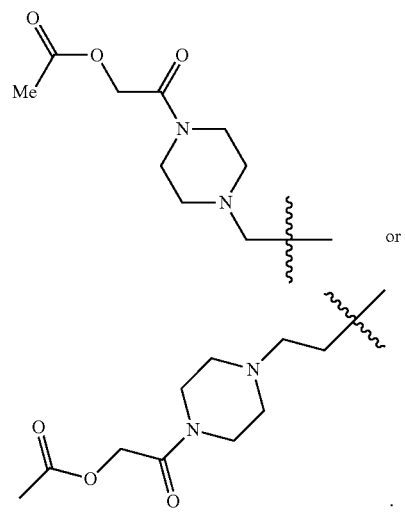

In some embodiments of the first aspect, the compounds have the Formula (II), wherein D is imidazole substituted with one $R^{38}$, wherein $R^{38}$ is $R^{37}$O—$C_1$-$C_6$alkyl-C(O)-heterocyclyl-(CH$_2$)$_{1-6}$—, for example, HO—$C_1$-$C_6$alkyl-C(O)-heterocyclyl-(CH$_2$)$_{1-2}$—.

In some embodiments of the first aspect, the compounds have the Formula (II), wherein D is imidazole substituted with one $R^{38}$, wherein $R^{38}$ is $R^{37}$O—$C_1$-$C_6$alkyl-C(O)-heterocyclyl-(CH$_2$)$_{1-6}$—, wherein the heterocyclyl is a 5- or 6-membered heterocyclyl.

In some embodiments of the first aspect, the compounds have the Formula (II), wherein D is imidazole substituted with one $R^{38}$, wherein $R^{38}$ is $R^{37}$O—$C_1$-$C_6$alkyl-C(O)-heterocyclyl-(CH$_2$)$_{1-6}$—, wherein the heterocyclyl is a 5- or 6-membered heterocyclyl, $R^{37}$ is H and the —(CH$_2$)$_{1-6}$— is —(CH$_2$)$_{1-2}$—.

In some embodiments of the first aspect, the compounds have the Formula (II), wherein D is phenyl substituted with one $R^{38}$.

In some embodiments of the first aspect, the compounds have the Formula (II), wherein D is phenyl substituted with one $R^{38}$, wherein $R^{38}$ is $R^{37}$O—(CH$_2$)$_{1-6}$—N(A)-(CH$_2$)$_{1-4}$—.

In some embodiments of the first aspect, the compounds have the Formula (II), wherein D is phenyl substituted with one $R^{38}$, wherein $R^{38}$ is $R^{37}O$—$(CH_2)_{1-6}$—N(A)-$(CH_2)_{1-4}$—, and A is —C(O)—N($R^{39}$)—$C_1$-$C_6$alkyl or —C(O)—N($R^{39}$)-cycloalkyl.

In some embodiments of the first aspect, the compounds have the Formula (II), wherein D is phenyl substituted with one $R^{38}$, wherein $R^{38}$ is $R^{37}O$—$(CH_2)_2$—N(A)-$(CH_2)$—, and A is —C(O)—N($R^{39}$)—$C_1$-$C_6$alkyl or —C(O)—N($R^{39}$)-cycloalkyl.

In some embodiments of the first aspect, the compounds have the Formula (II), wherein D is tetrahydropyridine substituted with one $R^{38}$.

In some embodiments of the first aspect, the compounds have the Formula (II), wherein D is tetrahydropyridine substituted with one $R^{38}$, wherein $R^{38}$ is $R^{37}O$—C(O)—$C_1$-$C_6$alkyl-C(O)— or $R^{37}$—O—$C_1$-$C_6$alkyl-O—$C_1$-$C_6$alkyl-C(O)—.

In some embodiments of the first aspect, the compounds have the Formula (II), wherein D is tetrahydropyridine substituted with one $R^{38}$, wherein $R^{38}$ is $R^{37}O$—C(O)—$C_1$-$C_6$alkyl-C(O)—.

In some embodiments of the first aspect, the compounds have the Formula (II), wherein D is tetrahydropyridine substituted with one $R^{38}$, wherein $R^{38}$ is $R^{37}$—O—$C_1$-$C_6$alkyl-O—$C_1$-$C_6$alkyl-C(O)—.

In some embodiments of the first aspect, the compounds have the Formula (II), wherein D is pyrazole substituted with one $R^{38}$.

In some embodiments of the first aspect, the compounds have the Formula (II), wherein D is pyrazole substituted with one $R^{38}$, wherein the $R^{38}$ is cycloalkyl-N($R^{39}$)—C(O)—O—$C_1$-$C_6$alkyl- or $R^{37}O$—$(CH_2)_{1-6}$—N(A)-$(CH_2)_{1-4}$—.

In some embodiments of the first aspect, the compounds have the Formula (II), wherein D is pyrazole substituted with one $R^{38}$, wherein $R^{38}$ is cycloalkyl-N($R^{39}$)—C(O)—O—$C_1$-$C_6$alkyl- or $R^{37}O$—$(CH_2)_{1-6}$—N(A)-$(CH_2)_{1-4}$—, and A is —C(O)—N($R^{39}$)—$C_1$-$C_6$alkyl.

In some embodiments of the first aspect, the compounds have the Formula (II), wherein D is pyrazole substituted with one $R^{38}$, wherein the $R^{38}$ is cycloalkyl-N($R^{39}$)—C(O)—O—$C_1$-$C_6$alkyl-.

In some embodiments of the first aspect, the compounds have the Formula (II), wherein D is pyrazole substituted with one $R^{38}$, wherein the $R^{38}$ is $R^{37}O$—$(CH_2)_{1-6}$—N(A)-$(CH_2)_{1-4}$—.

In some embodiments of the first aspect, the compounds have the Formula (II), wherein D is pyrazole substituted with one $R^{38}$, wherein the $R^{38}$ is $R^{37}O$—$(CH_2)_{1-6}$—N(A)-$(CH_2)_{1-4}$—, and A is —C(O)—N($R^{39}$)—$C_1$-$C_6$alkyl.

In some embodiments of the first aspect, the compounds have the Formula (II), wherein D is pyrazole substituted with one $R^{38}$, wherein the $R^{38}$ is $R^{37}O$—$(CH_2)_2$—N(A)-$(CH_2)_2$—, and A is —C(O)—N($R^{39}$)—$C_1$-$C_6$alkyl.

In some embodiments of the first aspect, the compounds have the Formula (III).

In some embodiments of the first aspect, the compounds have the Formula (III), wherein D is pyridine, substituted with one $R^{38}$.

In some embodiments of the first aspect, the compounds have the Formula (III), wherein D is pyridine substituted with one $R^{38}$, wherein $R^{38}$ is $R^{37}O$—$(CH_2)_{1-6}$—N(A)-$(CH_2)_{1-4}$—, alternatively $R^{37}O$—$(CH_2)_2$—N(A)-$(CH_2)$—.

In some embodiments of the first aspect, the compounds have the Formula (III), wherein D is pyridine substituted with one $R^{38}$, wherein $R^{38}$ is $R^{37}O$—$(CH_2)_{1-6}$—N(A)-$(CH_2)_{1-4}$—, and A is —C(O)—N($R^{39}$)—$C_1$-$C_6$alkyl.

In some embodiments of the first aspect, the compounds have the Formula (III), wherein D is pyridine substituted with one $R^{38}$, wherein $R^{38}$ is $R^{37}O$—$(CH_2)_2$—N(A)-$(CH_2)$—, and A is —C(O)—N($R^{39}$)—$C_1$-$C_6$alkyl.

In some embodiments of the first aspect, the compounds have the Formula (II) or Formula (III), wherein D is further selected from the group heterocycle-C≡C—, alternatively morpholine-C≡C—.

In some embodiments of the first aspect, the compounds have the Formula (II) or Formula (III), wherein $R^{38}$ is selected from the group consisting of $R^{37}O$—$(CH_2)_{1-6}$—N(A)-$(CH_2)_{1-4}$—, $(C_1$-$C_6$alkyl-S(O)$_2$—$(CH_2)_2$—N(A)-$CH_2$—, $R^{37}O$—$(CH_2)_j$—$[(CH_2)_iO]_x$—$(CH_2)_{i1}$—N(A)-$(CH_2)_{j1}$—, $R^{37}O$—C(O)—$C_0$-$C_6$alkyl-heterocyclyl-$CH_2$—, $R^{37}O$—$(CH_2)_j$—$[(CH_2)_iO]_x$—$(CH_2)_{i1}$—N($R^{39}$)—C(O)—, $R^{37}$—O—C(O)—$C_1$-$C_6$alkyl-heterocyclyl-C(O)—, HOOC—$C_1$-$C_6$alkyl-N(A)-$CH_2$—, (HOOC)(NR$^9$R$^{10}$)—$C_1$-$C_6$alkyl-N(A)-$CH_2$—, $R^{37}O$—C(O)—$C_1$-$C_6$alkyl-C(O)—, (R$^9$)(R$^{10}$)N—$C_1$-$C_6$alkyl-C(O)-heterocyclyl-$CH_2$—, cycloalkyl-N(R$^{39}$)—C(O)—O—$C_1$-$C_6$alkyl-, $R^{37}$—O—$C_1$-$C_6$alkyl-O—$C_1$-$C_6$alkyl-C(O)—, (R$^9$)(R$^{10}$)N—C(O)—$C_1$-$C_6$alkyl-heterocyclyl-$CH_2$—, (R$^9$)(R$^{10}$)N—$C_1$-$C_6$alkyl-C(O)—O—$C_1$-$C_6$alkyl-heterocyclyl-$CH_2$—, NC—$C_1$-$C_6$alkyl-heterocyclyl-$CH_2$—, $F_3$C—$C_1$-$C_6$alkyl-heterocyclyl-$CH_2$— and (R$^9$)(R$^{10}$)N—$C_1$-$C_6$alkyl-C(O)—O—$C_1$-$C_6$alkyl-C(O)-heterocyclyl-$CH_2$—.

In some embodiments of the first aspect, the compounds have the Formula (II) or Formula (III), wherein $R^{38}$ is (oxo substituted heterocyclyl)-$C_1$-$C_2$alkyl-, wherein the oxo substituted heterocyclyl is further optionally substituted with a substituent selected from the group consisting of —N(R$^9$)(R$^{10}$), $C_1$-$C_6$alkyl, —N(R$^{37}$)(Ac), and —OH. Alternatively $R^{38}$ is

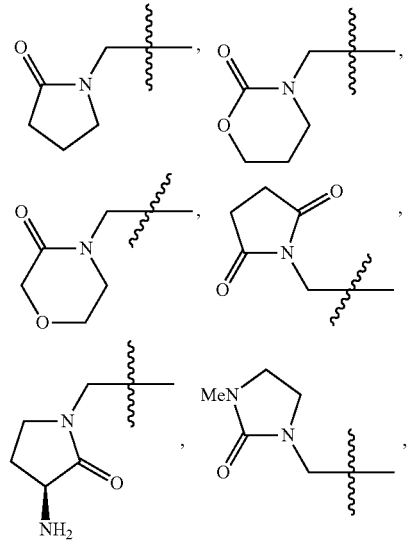

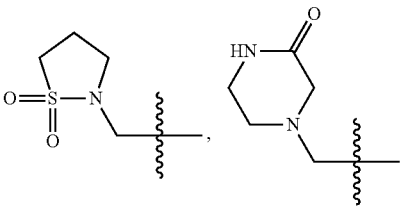

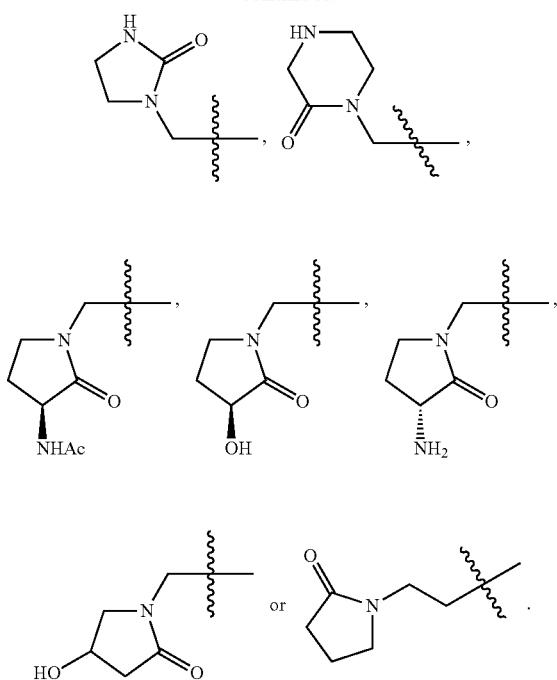

In some embodiments of the first aspect, the compounds have the Formula (II) or Formula (III), wherein $R^{38}$ is (oxo substituted heterocyclyl)-$C_1$-$C_2$alkyl-, wherein the oxo substituted heterocyclyl is further optionally substituted with a substituent selected from the group consisting of —N($R^9$)($R^{10}$), $C_1$-$C_6$alkyl, —N($R^{37}$)(Ac), and —OH. Alternatively $R^{38}$ is

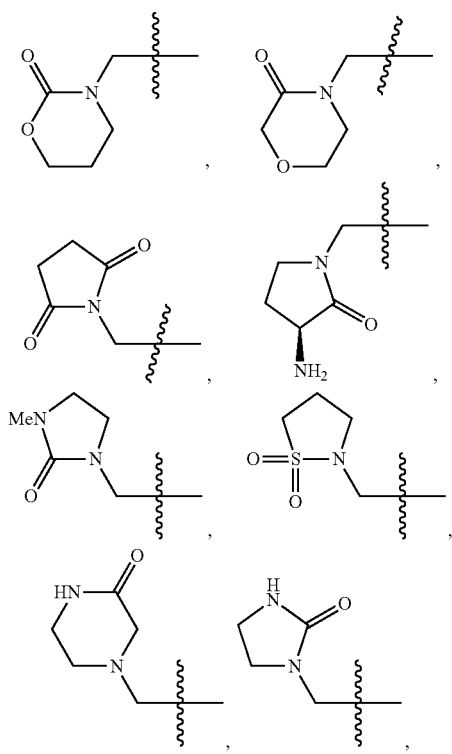

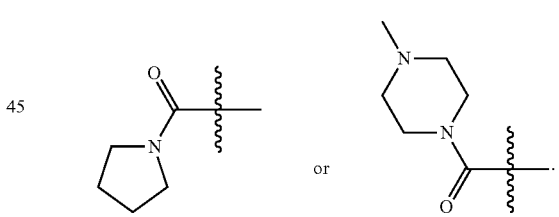

In some embodiments of the first aspect, the compounds have the Formula (II) or Formula (III), wherein $R^{38}$ is (oxo substituted heterocyclyl)-$C_1$-$C_2$alkyl-, wherein the oxo substituted heterocyclyl is further substituted with a substituent selected from the group consisting of —N($R^9$)($R^{10}$), $C_1$-$C_6$alkyl, —N($R^{37}$)(Ac), and —OH.

In some embodiments of the first aspect, the compounds have the Formula (II) or Formula (III), wherein $R^{38}$ is $C_1$-$C_6$alkyl-heterocyclyl-(CH$_2$)$_{1-2}$—, alternatively $C_1$-$C_6$alkyl-piperazine-CH$_2$— or CH$_3$-piperazine-(CH$_2$)$_2$—).

In some embodiments of the first aspect, the compounds have the Formula (II) or Formula (III), wherein $R^{38}$ is (heterocyclyl)-C(O)—, wherein the heterocyclyl is optionally substituted with $C_1$-$C_6$alkyl. Alternatively $R^{38}$ is

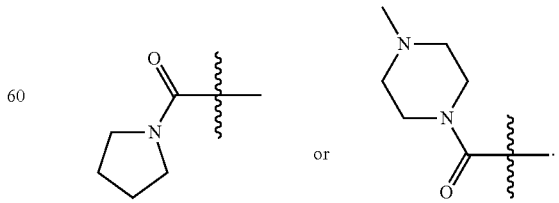

In some embodiments of the first aspect, the compounds have the Formula (II) or Formula (III), wherein $R^{38}$ is (heterocyclyl)-C(O)—, wherein the heterocyclyl is substituted with $C_1$-$C_6$alkyl. Alternatively $R^{38}$ is In some embodiments of the first aspect, the compounds have the Formula (II) or Formula (III), wherein $R^{38}$ is $C_0$-$C_6$alkyl-heterocyclyl-$(CH_2)_{1-3}$—, alternatively heterocyclyl-$(CH_2)$—, piperazine-$CH_2$—,

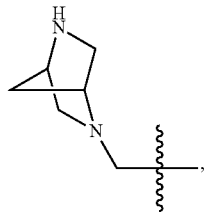

morpholine-$CH_2$—, morpholine-$(CH_2)_2$—, $CH_3$-piperazine-$(CH_2)_2$—, morpholine-$(CH_2)_3$— or piperazine-$(CH_2)_2$—.

In some embodiments of the first aspect, the compounds have the Formula (II) or Formula (III), wherein $R^{38}$ is HO-heterocyclyl-$CH_2$—, alternatively HO-pyrrolidine-$CH_2$—.

In some embodiments of the first aspect, the compounds have the Formula (II) or Formula (III), wherein $R^{38}$ is $(R^9)(R^{10})$N-heterocyclyl-$CH_2$—, alternatively $NH_2$-pyrrolidine-$CH_2$—

In some embodiments of the first aspect, the compounds have the Formula (II) or Formula (III), wherein $R^{38}$ is $(R^9)(R^{10})$N—$C_0$-$C_6$alkyl-heterocyclyl-C(O)—, alternatively $N(CH_3)_2$-pyrrolidine-C(O)— or $(CH(CH_3)_2)_2$N—$(CH_2)_2$-piperazine-C(O)—.

In some embodiments of the first aspect, the compounds have the Formula (II) or Formula (III), wherein $R^{38}$ is ($C_1$-$C_6$alkyl)-C(O)-heterocyclyl-$CH_2$—, alternatively $CH_3$—C(O)-piperazine-$CH_2$—).

In some embodiments of the first aspect, the compounds have the Formula (II) or Formula (III), wherein $R^{38}$ is $R^{37}$O—$C_1$-$C_6$alkyl-heterocyclyl-$CH_2$—, for example, HO—$C_1$-$C_6$alkyl-heterocyclyl-$CH_2$—, alternatively HO—$(CH_2)_2$-piperazine-$CH_2$—.

In some embodiments of the first aspect, the compounds have the Formula (II) or Formula (III), wherein $R^{38}$ is HO—$C_1$-$C_6$alkyl-C(O)-heterocyclyl-$CH_2$—, alternatively HO—$(CH_2)$—C(O)-piperazine-$CH_2$—.

In some embodiments of the first aspect, the compounds have the Formula (II) or Formula (III), wherein $R^{38}$ is $C_0$-$C_6$alkyl-heterocyclyl-$C_1$-$C_6$alkyl-$N(R^{39})$—C(O)—, alternatively morpholine-$(CH_2)_2$—NH—C(O)—, morpholine-$(CH_2)_3$—NH—C(O)— or $CH_3$-piperazine-$(CH_2)_2$—NH—C(O)—.

In some embodiments of the first aspect, the compounds have the Formula (II) or Formula (III), wherein $R^{38}$ is $R^{37}$—O—C(O)-heterocyclyl-C(O)—, alternatively EtO—C(O)-piperidine-C(O)—, BuO—C(O)-morpholine-C(O)—, HO—C(O)-piperidine-C(O)— or HO—C(O)-morpholine-C(O)—.

In some embodiments of the first aspect, the compounds have the Formula (II) or Formula (III), wherein $R^{38}$ is $C_0$-$C_6$alkyl-heterocyclyl-$C_0$-$C_6$alkyl-heterocyclyl-C(O)—, alternatively $C_0$-$C_6$alkyl-heterocyclyl-$C_1$-$C_6$alkyl-heterocyclyl-C(O)—, morpholine-$(CH_2)_2$-piperazine-C(O)—, $CH_3$-piperidine-$CH_2$-piperazine-C(O)— or $CH_3$-piperazine-piperidine-C(O)—.

In some embodiments of the first aspect, the compounds have the Formula (II) or Formula (III), wherein $R^{38}$ is $CH_3$-piperazine-piperidine-C(O)—.

In some embodiments of the first aspect, the compounds have the Formula (II) or Formula (III), wherein $R^{38}$ is $C_1$-$C_6$alkyl-$SO_2$—, alternatively Me-$S(O)_2$—.

In some embodiments of the first aspect, the compounds have the Formula (II) or Formula (III), wherein $R^{38}$ is $R^{37}$O—$C_1$-$C_6$alkyl-heterocyclyl-$CH_2$—, alternatively MeO—$(CH_2)_2$-piperazine-$CH_2$—.

In some embodiments of the first aspect, the compounds have the Formula (II) or Formula (III), wherein $R^{38}$ is (HO—substituted $C_1$-$C_6$alkyl-$N(R^{39})$—C(O)—, alternatively HO—$CH_2$—$[CH(OH)]_4$—$CH_2$—N(Me)—C(O)—.

In some embodiments of the first aspect, the compounds have the Formula (II) or Formula (III), wherein $R^{38}$ is heterocyclyl-$C_1$-$C_6$alkyl-heterocyclyl-$CH_2$—, alternatively morpholine-$(CH_2)_2$-piperazine-$CH_2$—.

In some embodiments of the first aspect, the compounds have the Formula (II) or Formula (III), wherein $R^{38}$ is $C_1$-$C_6$alkyl-$S(O)_2$-heterocyclyl-$CH_2$—, alternatively Me-$S(O)_2$-piperazine-$CH_2$—.

In some embodiments of the first aspect, the compounds have the Formula (II) or Formula (III), wherein $R^{38}$ is heteroaryl-$C_1$-$C_6$alkyl-heterocyclyl-$CH_2$—, imidazole-$(CH_2)_2$-piperazine-$CH_2$—.

In some embodiments of the first aspect, the compounds have the Formula (II) or Formula (III), wherein $R^{38}$ is $R^{37}$O—$C_1$-$C_6$alkyl-, alternatively HO—$(CH_2)_4$—.

In some embodiments of the first aspect, the compounds have the Formula (II) or Formula (III), wherein $R^{38}$ is $R^{37}$O—$(CH_2)_{1-6}$—N(A)-$(CH_2)_{1-4}$—, alternatively $R^{37}$O—$(CH_2)_2$—N(A)-$(CH_2)_{1-2}$—, MeO—$(CH_2)_2$—N(A)-$CH_2$— or MeO—$(CH_2)_2$—N(A)-$(CH_2)_2$—.

In some embodiments of the first aspect, the compounds have the Formula (II) or Formula (III), wherein $R^{38}$ is $C_1$-$C_6$alkyl-$S(O)_2$—$(CH_2)_2$—N(A)-$CH_2$—, alternatively $CH_3$—$S(O)_2$—$(CH_2)_2$—N(A)-$CH_2$—.

In some embodiments of the first aspect, the compounds have the Formula (II) or Formula (III), wherein $R^{38}$ is $R^{37}$O—$(CH_2)_j$—$[(CH_2)_iO]_x$—$(CH_2)^{i1}$—N(A)-$(CH_2)_{j1}$—, alternatively $CH_3$—O—$[CH_2$—$CH_2$—$O]_3$—$(CH_2)_2$—N(A)-$CH_2$—.

In some embodiments of the first aspect, the compounds have the Formula (II) or Formula (III), wherein $R^{38}$ is $R^{37}$O—C(O)—$C_0$-$C_6$alkyl-heterocyclyl-$CH_2$—, alternatively $R^{37}$O—C(O)—$C_1$-$C_6$alkyl-heterocyclyl-$CH_2$—, alternatively HO—C(O)—$(CH_2)_2$-piperazine-$CH_2$—, EtO—C(O)-piperidine-$CH_2$—, EtO—C(O)—$CH_2$-piperidine-$CH_2$—, EtO—C(O)—$CH_2$-piperazine-$CH_2$—, HO—C(O)-piperidine-$CH_2$—, HO—C(O)—$CH_2$-piperidine-$CH_2$—HO—C(O)—$CH_2$-piperazine-$CH_2$—, $(CH_3)_3$C—O—C(O)-piperazine-$CH_2$— or HO—C(O)-pyrrolidine-$CH_2$—.

In some embodiments of the first aspect, the compounds have the Formula (II) or Formula (III), wherein $R^{38}$ is $R^{37}$O—$(CH_2)_j$—$[(CH_2)_iO]_x$—$(CH_2)_{i1}$—$N(R^{39})$—C(O)—, alternatively $CH_3$—O—$[CH_2$—$CH_2$—$O]_3$—$(CH_2)_2$—N(A)-C(O)—.

In some embodiments of the first aspect, the compounds have the Formula (II) or Formula (III), wherein $R^{38}$ is $R^{37}$—O—C(O)—$C_1$-$C_6$alkyl-heterocyclyl-C(O)—, alternatively $CH_3$—$CH_2$—O—C(O)—$(CH_2)_2$-piperazine-C(O)— or HO—C(O)—$(CH_2)_2$-piperazine-C(O)—.

In some embodiments of the first aspect, the compounds have the Formula (II) or Formula (III), wherein $R^{38}$ is HOOC—$C_1$-$C_6$alkyl-N(A)-$CH_2$—, alternatively HOOC—$(CH_2)_3$—N(A)-$CH_2$—.

In some embodiments of the first aspect, the compounds have the Formula (II) or Formula (III), wherein $R^{38}$ is (HOOC)($NR^9R^{10}$)—$C_1$-$C_6$alkyl-N(A)-$CH_2$—, alternatively (HOOC)($NH_2$)CH—$(CH_2)_4$—N(A)-$CH_2$—.

In some embodiments of the first aspect, the compounds have the Formula (II) or Formula (III), wherein $R^{38}$ is $R^{37}O$—C(O)—$C_1$-$C_6$alkyl-C(O)—, alternatively HO—C(O)—$(CH_2)_2$—C(O)—.

In some embodiments of the first aspect, the compounds have the Formula (II) or Formula (III), wherein $R^{38}$ is $(R^9)(R^{10})N$—$C_1$-$C_6$alkyl-C(O)-heterocyclyl-$CH_2$—, alternatively

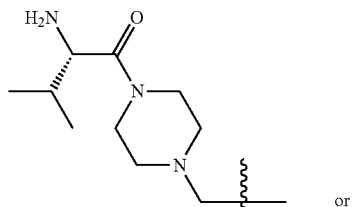

or

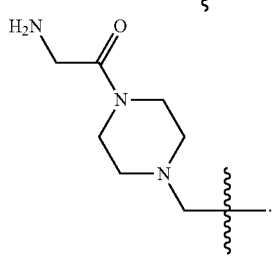

In some embodiments of the first aspect, the compounds have the Formula (II) or Formula (III), wherein $R^{38}$ is cycloalkyl-N($R^{39}$)—C(O)—O—$C_1$-$C_6$alkyl-, alternatively $C_3$cycloalkyl-NH—C(O)—O—$(CH_2)_2$—.

In some embodiments of the first aspect, the compounds have the Formula (II) or Formula (III), wherein $R^{38}$ is $R^{37}$—O—$C_1$-$C_6$alkyl-O—$C_1$-$C_6$alkyl-C(O)—, alternatively MeO—$(CH_2)_2$—O—$CH_2$—C(O)—.

In some embodiments of the first aspect, the compounds have the Formula (II) or Formula (III), wherein $R^{38}$ is $(R^9)(R^{10})N$—C(O)—$C_1$-$C_6$alkyl-heterocyclyl-$CH_2$—, alternatively

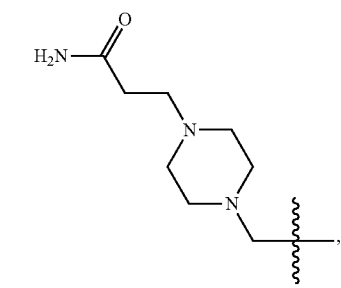

or

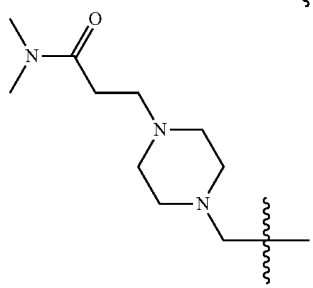

-continued

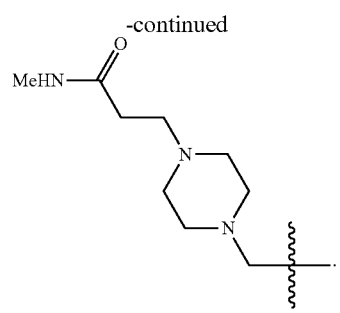

In some embodiments of the first aspect, the compounds have the Formula (II) or Formula (III), wherein $R^{38}$ is $(R^9)(R^{10})N$—$C_1$-$C_6$alkyl-C(O)—O—$C_1$-$C_6$alkyl-heterocyclyl-$CH_2$—, alternatively

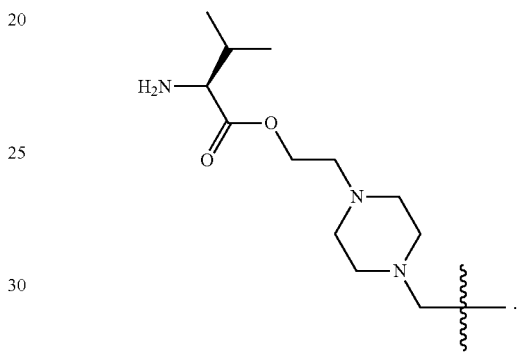

In some embodiments of the first aspect, the compounds have the Formula (II) or Formula (III), wherein $R^{38}$ is NC—$C_1$-$C_6$alkyl-heterocyclyl-$CH_2$—, alternatively NC—$(CH_2)_2$-piperazine-$CH_2$—.

In some embodiments of the first aspect, the compounds have the Formula (H) or Formula (III), wherein $R^{38}$ is $F_3C$—$C_1$-$C_6$alkyl-heterocyclyl-$CH_2$—, alternatively $F_3C$—$CH_2$-piperazine-$CH_2$—.

In some embodiments of the first aspect, the compounds have the Formula (II) or Formula (III), wherein $R^{38}$ is $(R^9)(R^{10})N$—$C_1$-$C_6$alkyl-C(O)—O—$C_1$-$C_6$alkyl-C(O)-heterocyclyl-$CH_2$—, alternatively

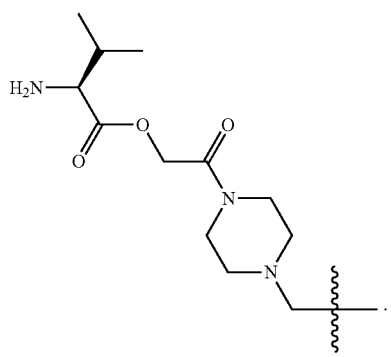 [SMILES: *CN1CCN(C(=O)COC(=O)[C@@H](N)C(C)C)CC1]

In some embodiments of the first aspect, the compounds have the Formula (II) or Formula (III), wherein $R^{38}$ is (optionally substituted 8- to 10-membered fused heterocyclyl)-$C_1$-$C_6$alkyl-.

In some embodiments of the first aspect, the compounds have the Formula (II) or Formula (III), wherein $R^{38}$ is (optionally substituted 8-membered fused heterocyclyl)-$C_1$-$C_6$alkyl, which is

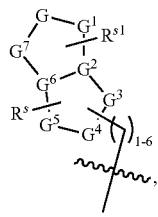

wherein

G is selected from the group consisting of $CH_2$, O, NH, S, SO and $SO_2$;

$G^1$ is selected from the group consisting of $CH_2$, O, NH, S, SO and $SO_2$;

$G^2$ is CH or N;

$G^3$ is selected from the group consisting of $CH_2$, O, NH, S, SO and $SO_2$;

$G^4$ is selected from the group consisting of $CH_2$, O, NH, S, SO and $SO_2$;

$G^5$ is selected from the group consisting of $CH_2$, O, NH, S, SO and $SO_2$;

$G^6$ is CH or N;

$G^7$ is selected from the group consisting of $CH_2$, O, NH, S, SO and $SO_2$;

$R^s$ is an optional substituent; and $R^{s1}$ is an optional substituent, provided that two O atoms are not adjacent to each other.

In some embodiments of the first aspect, the compounds have the Formula (II) or Formula (III), wherein $R^{38}$ is (optionally substituted 8- to 10-membered fused heterocyclyl)-$C_1$-$C_6$alkyl, selected from the group consisting of

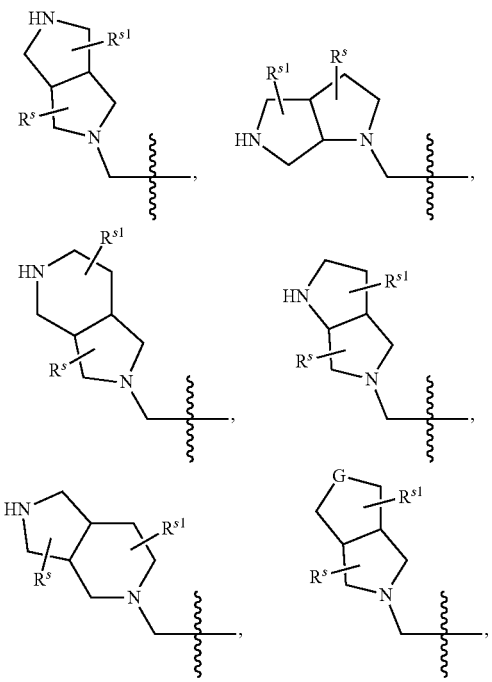

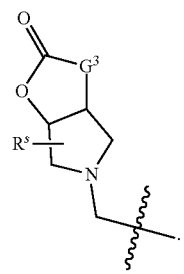

In some embodiments of the first aspect, the compounds have the Formula (II) or Formula (III), wherein $R^{38}$ is (optionally substituted 8- to 10-membered fused heterocyclyl)-$C_1$-$C_6$alkyl, selected from the group consisting of

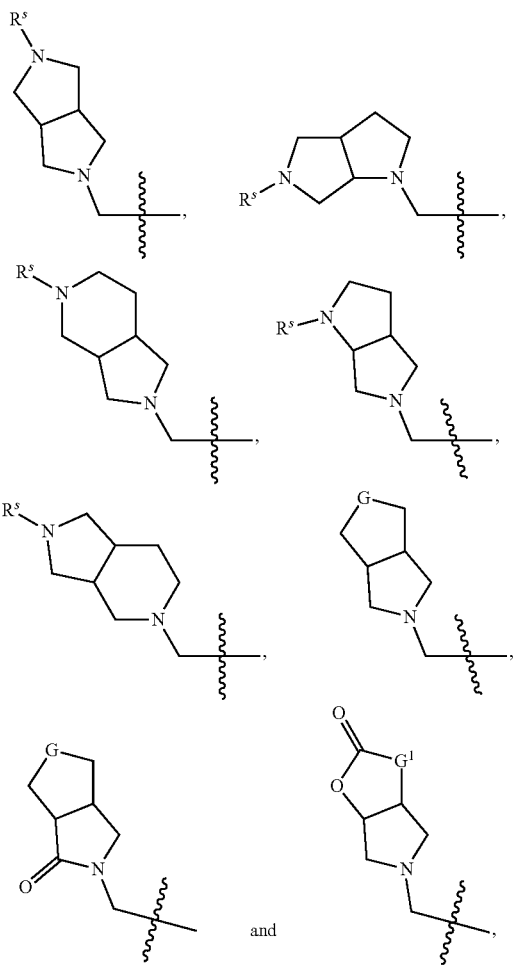

and wherein G is selected from the group consisting of $CH_2$, O, NH, S, SO and $SO_2$; $G^1$ is selected from the group consisting of $CH_2$, O, NH, S, SO and $SO_2$; and $R^s$ is an optional substituent.

In some embodiments of the first aspect, the compounds have the Formula (II) or Formula (III), wherein $R^s$ is selected from the group consisting of H, halo, —N($R^9$)($R^{10}$), nitro, —OH, oxo, $C_1$-$C_6$alkyl, —C(O)—$C_1$-$C_6$alkyl-OH, Ac, cycloalkyl, heterocyclyl, aryl, heteroaryl, —S(O)$_{0-2}$—$C_1$-$C_6$alkyl, —S(O)$_{0-2}$-cycloalkyl, —S(O)$_{0-2}$-heterocyclyl, —S(O)$_{0-2}$-aryl, —S(O)$_{0-2}$-heteroaryl, —C(O)H, —C(O)—

$C_1$-$C_6$alkyl, —C(O)—N($R^9$)($R^{10}$), —$C_1$-$C_6$alkyl-OH, —$C_1$-$C_6$alkyl-C(O)—OH, —$C_1$-$C_6$alkyl-C(O)—N($R^9$)($R^{10}$), wherein the alkyl, cycloalkyl, heterocyclyl, aryl and heteroaryl groups are themselves optionally substituted, for example with halo or —$C_1$-$C_6$alkyl.

In some embodiments of the first aspect, the compounds have the Formula (II) or Formula (III), wherein $R^{s1}$ is selected from the group consisting of H, halo, —N($R^9$)($R^{10}$), nitro, —OH, oxo, $C_1$-$C_6$alkyl, —C(O)—$C_1$-$C_6$alkyl-OH, Ac, cycloalkyl, heterocyclyl, aryl, heteroaryl, —S(O)$_{0-2}$—$C_1$-$C_6$alkyl, —S(O)$_{0-2}$-cycloalkyl, —S(O)$_{0-2}$-heterocyclyl, —S(O)$_{0-2}$-aryl, —S(O)$_{0-2}$-heteroaryl, —C(O)H, —C(O)—N($R^9$)($R^{10}$), —$C_1$-$C_6$alkyl-OH, —$C_1$-$C_6$alkyl-C(O)—OH, —$C_1$-$C_6$alkyl-C(O)—N($R^9$)($R^{10}$), wherein the alkyl, cycloalkyl, heterocyclyl, aryl and heteroaryl groups are themselves optionally substituted, for example with halo or —$C_1$-$C_6$alkyl.

In some embodiments of the first aspect, the compounds have the Formula (II) or Formula (III), wherein $R^{38}$ is (optionally substituted 8- to 10-membered fused heterocyclyl)-$C_1$-$C_6$alkyl-, wherein the optional substituent is selected from the group consisting of H, halo, —N($R^9$)($R^{10}$), nitro, —OH, oxo, $C_1$-$C_6$alkyl, —C(O)—$C_1$-$C_6$alkyl-OH, Ac, cycloalkyl, heterocyclyl, aryl, heteroaryl, —S(O)$_{0-2}$—$C_1$-$C_6$alkyl, —S(O)$_{0-2}$-cycloalkyl, —S(O)$_{0-2}$-heterocyclyl, —S(O)$_{0-2}$-aryl, —S(O)$_{0-2}$-heteroaryl, —C(O)H, —C(O)—$C_1$-$C_6$alkyl, —C(O)—N($R^9$)($R^{10}$)—$C_1$-$C_6$alkyl-OH, —$C_1$-$C_6$alkyl-C(O)—OH and —$C_1$-$C_6$alkyl-C(O)—N($R^9$)($R^{10}$), wherein the alkyl, cycloalkyl, heterocyclyl, aryl and heteroaryl groups are themselves optionally substituted, for example with halo or —$C_1$-$C_6$alkyl.

In some embodiments of the first aspect, the compounds have the Formula (II) or Formula (III), wherein $R^{38}$ is (difluoro substituted heterocyclyl)-$C_1$-$C_6$alkyl-.

In some embodiments of the first aspect, the compounds have the Formula (II) or Formula (III), wherein $R^{38}$ is (difluoro substituted heterocyclyl)-$C_1$-$C_6$alkyl-, wherein the two fluoro substituents are substituents on the same carbon atom.

In some embodiments of the first aspect, the compounds have the Formula (II) or Formula (III), wherein $R^{38}$ is $C_0$-$C_6$alkyl-(5 or 6-membered heterocyclyl)-$C_1$-$C_6$alkyl-piperazine-$C_1$-$C_6$alkyl-.

In some embodiments of the first aspect, the compounds have the Formula (II) or Formula (III), wherein $R^{38}$ is $R^{37}$O—$C_1$-$C_6$alkyl-C(O)-heterocyclyl-(CH$_2$)$_{1-6}$—, for example, HO—$C_1$-$C_6$alkyl-C(O)-heterocyclyl-(CH$_2$)$_{1-2}$—.

In some embodiments of the first aspect, the compounds have the Formula (II) or Formula (III), wherein $R^{38}$ is $R^{37}$O—$C_1$-$C_6$alkyl-C(O)-heterocyclyl-(CH$_2$)$_{1-6}$—, wherein the heterocyclyl is a 5- or 6-membered heterocyclyl.

In some embodiments of the first aspect, the compounds have the Formula (II) or Formula (III), wherein $R^{38}$ is $R^{37}$O—$C_1$-$C_6$alkyl-C(O)-heterocyclyl-(CH$_2$)$_{1-6}$—, wherein the heterocyclyl is a 5- or 6-membered heterocyclyl, $R^{37}$ is H and the —(CH$_2$)$_{1-6}$— is —(CH$_2$)$_{1-2}$—.

In some embodiments of the first aspect, the compounds have the Formula (II) or Formula (III), wherein $R^{38}$ is $R^{37}$O—$C_1$-$C_6$alkyl-C(O)-heterocyclyl-CH$_2$—, for example, HO—$C_1$-$C_6$alkyl-C(O)-heterocyclyl-CH$_2$—.

In some embodiments of the first aspect, the compounds have the Formula (II) or Formula (III), wherein A is selected from the group consisting of —C(O)—$C_1$-$C_6$alkyl-N($R^{39}$)—C(O)—$C_1$-$C_6$alkyl-N($R^9$)($R^{10}$)—C(O)—N($R^{39}$)—$C_1$-$C_6$alkyl, —C(=N$R^{37}$)—$C_1$-$C_6$alkyl, —C(O)—(CH$_2$)$_n$—S(O)$_2$—$C_1$-$C_6$alkyl, —C(O)—N($R^{39}$)-cycloalkyl and —C(O)—N($R^9$)($R^{10}$), ($R^{23}$)($R^{24}$)P(O)O—$C_1$-$C_6$alkyl-C(O)—.

In some embodiments of the first aspect, the compounds have the Formula (II) or Formula (III), wherein A is H.

In some embodiments of the first aspect, the compounds have the Formula (II) or Formula (III), wherein A is not H.

In some embodiments of the first aspect, the compounds have the Formula (II) or Formula (III), wherein A is Ac.

In some embodiments of the first aspect, the compounds have the Formula (II) or Formula (III), wherein A is —C(O)—CH$_2$—OMe.

In some embodiments of the first aspect, the compounds have the Formula (II) or Formula (III), wherein A is —C(O)—CH(NH$_2$)—C(CH$_3$)$_3$.

In some embodiments of the first aspect, the compounds have the Formula (II) or Formula (III), wherein A is —C(O)—H, —C(O)—$C_1$-$C_6$alkyl, alternatively —C(O)—CH$_3$, —C(O)—CH$_2$—CH$_3$.

In some embodiments of the first aspect, the compounds have the Formula (II) or Formula (III), wherein A is —$C_1$-$C_6$alkyl-O—$C_1$-$C_6$alkyl, alternatively —(CH$_2$)$_2$—OMe).

In some embodiments of the first aspect, the compounds have the Formula (II) or Formula (III), wherein A is —C(O)—$C_1$-$C_6$alkyl-OH.

In some embodiments of the first aspect, the compounds have the Formula (II) or Formula (III), wherein A is —C(O)—$C_1$-$C_6$alkyl-N($R^{39}$)—C(O)—$C_1$-$C_6$alkyl-N($R^9$)($R^{10}$), alternatively —C(O)—CH$_2$—NH—C(O)—CH(NH$_2$)—CH(CH$_3$)$_2$, —C(O)—CH$_2$—NH—C(O)—CH$_2$—NH$_2$ or —C(O)—CH[CH(CH$_3$)$_2$]—NH—C(O)—CH$_2$—NH$_2$).

In some embodiments of the first aspect, the compounds have the Formula (II) or Formula (III), wherein A is —C(O)—N($R^{39}$)—$C_1$-$C_6$alkyl, alternatively —C(O)—NH—CH$_2$—CH$_3$, —C(O)—NH—CH$_3$, —C(O)—NH—CH(CH$_3$)$_2$, —C(O)—NH—CH(CH$_3$)$_2$ or —C(O)—N(CH$_3$)$_2$.

In some embodiments of the first aspect, the compounds have the Formula (II) or Formula (III), wherein A is —C(=N$R^{37}$)—$C_1$-$C_6$alkyl, alternatively —C(=NH)H.

In some embodiments of the first aspect, the compounds have the Formula (II) or Formula (III), wherein A is —C(O)—(CH$_2$)$_n$—S(O)$_2$—$C_1$-$C_6$alkyl, alternatively —C(O)—CH$_2$—S(O)$_2$-Me.

In some embodiments of the first aspect, the compounds have the Formula (II) or Formula (III), wherein A is —C(O)—N($R^{39}$)-cycloalkyl, alternatively —C(O)—NH-cyclopentyl or —C(O)—NH—$C_3$cycloalkyl.

In some embodiments of the first aspect, the compounds have the Formula (II) or Formula (III), wherein A is —C(O)—N($R^9$)($R^{10}$), alternatively —C(O)—NH$_2$.

In some embodiments of the first aspect, the compounds have the Formula (II) or Formula (III), wherein A is ($R^{23}$)($R^{24}$)P(O)O—$C_1$-$C_6$alkyl-C(O)—, alternatively (HO)$_2$P(O)O—CH$_2$—C(O)—.

In some embodiments of the first aspect, the compounds have the Formula (II) or Formula (III), wherein A is $C_1$-$C_6$alkyl.

In some embodiments of the first aspect, the compounds have the Formula (II) or Formula (III), wherein A is not $C_1$-$C_6$alkyl.

In some embodiments of the first aspect, the compounds have the Formula (II) or Formula (III), wherein $R^{13}$ is H.

In some embodiments of the first aspect, the compounds have the Formula (II) or Formula (III), wherein each $R^{20}$ is independently H or halo (for example, Br, Cl or F, alternatively F).

In some embodiments of the first aspect, the compounds have the Formula (II) or Formula (III), wherein G includes a single $R^{20}$ substituent.

In some embodiments of the first aspect, the compounds have the Formula (II) or Formula (III), wherein G includes a single $R^{20}$ substituent selected from the group consisting of —PO($C_1$-$C_6$alkyl)$_2$ (for example, —PO(Me)$_2$), —S(O)$_2$—$C_1$-$C_6$alkyl) (for example, —S(O)$_2$Me) and —C(O)—NH$_2$.

In some embodiments of the first aspect, the compounds have the Formula (II) or Formula (III), wherein $R^{38}$ is selected from the group consisting of $R^{37}O$—$(CH_2)_{1-6}$—N(A)-$(CH_2)_{1-4}$—, ($C_1$-$C_6$alkyl-S(O)$_2$—$(CH_2)_2$—N(A)-CH$_2$—, $R^{37}O$—$(CH_2)_j$—[$(CH_2)_iO]_x$—$(CH_2)_{i1}$—N(A)-$(CH_2)_{j1}$—, $R^{37}O$—C(O)—$C_0$-$C_6$alkyl-heterocyclyl-CH$_2$—, $R^{37}O$—$(CH_2)_j$—[$(CH_2)_iO]_x$—$(CH_2)_{i1}$—N($R^{39}$)—C(O)—, $R^{37}$—O—C(O)—$C_1$-$C_6$alkyl-heterocyclyl-C(O)—, HOOC—$C_1$-$C_6$alkyl-N(A)-CH$_2$—, (HOOC)(NR$^9$R$^{10}$)—$C_1$-$C_6$alkyl-N(A)-CH$_2$—, $R^{37}O$—C(O)—$C_1$-$C_6$alkyl-C(O)—, ($R^9$)($R^{10}$)N—$C_1$-$C_6$alkyl-C(O)-heterocyclyl-CH$_2$—, cycloalkyl-N($R^{39}$)—C(O)—O—$C_1$-$C_6$alkyl-, $R^{37}$—O—$C_1$-$C_6$alkyl-O—$C_1$-$C_6$alkyl-C(O)—, ($R^9$)($R^{10}$)N—C(O)—$C_1$-$C_6$alkyl-heterocyclyl-CH$_2$—, ($R^9$)($R^{10}$)N—$C_1$-$C_6$alkyl-C(O)—O—$C_1$-$C_6$alkyl-heterocyclyl-CH$_2$—, NC—$C_1$-$C_6$alkyl-heterocyclyl-CH$_2$—, $F_3$C—$C_1$-$C_6$alkyl-heterocyclyl-CH$_2$— and ($R^9$)($R^{10}$)N—$C_1$-$C_6$alkyl-C(O)—O—$C_1$-$C_6$alkyl-C(O)-heterocyclyl-CH$_2$—; and A is selected from the group consisting of —C(O)—$C_1$-$C_6$alkyl-N($R^{39}$)—C(O)—$C_1$-$C_6$alkyl-, N($R^9$)($R^{10}$), —C(O)—N($R^{39}$)—$C_1$-$C_6$alkyl, —C(=N$R^{37}$)—$C_1$-$C_6$alkyl, —C(O)—(CH$_2$)$_n$—S(O)$_2$—$C_1$-$C_6$alkyl, —C(O)—N($R^{39}$)-cycloalkyl, —C(O)—N($R^9$)($R^{10}$) and ($R^{23}$)($R^{24}$)P(O)O—$C_1$-$C_6$alkyl-C(O)—.

In some embodiments of the first aspect, the compounds have the Formula (IV):

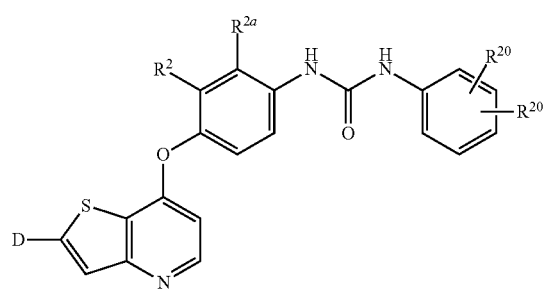

(IV)

including N-oxides, hydrates, solvates, tautomers, pharmaceutically acceptable salts, prodrugs and complexes thereof, and racemic and scalemic mixtures, diastereomers and enantiomers thereof, wherein, D is selected from the group consisting of pyridine, phenyl, imidazole and heterocycle-C≡C— (for example, morpholine-C≡C—), wherein said pyridine, phenyl and imidazole are each substituted with one $R^{38}$;

$R^{38}$ is selected from the group consisting of $R^{37}O$—(CH$_2$)$_2$—N(A)-CH$_2$— (for example, $R^{37}O$—(CH$_2$)$_2$—N(A)-CH$_2$—), (oxo substituted heterocyclyl)-$C_1$-$C_6$alkyl- (for example

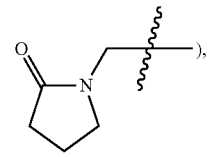

and (heterocyclyl)-C(O)— (for example,

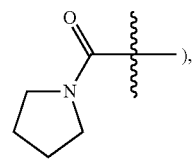

wherein when D is imidazole, the imidazole is further optionally substituted with $C_1$-$C_6$alkyl (for example, —CH$_3$);
$R^{37}$ is H or $C_1$-$C_6$alkyl;
A is H or Ac;
$R^2$ is F;
$R^{2a}$ is H; and
each $R^{20}$ is independently selected from the group consisting of H, —PO($C_1$-$C_6$alkyl)$_2$ (for example, —PO(Me)$_2$), —S(O)$_2$—$C_1$-$C_6$alkyl) (for example, —S(O)$_2$Me) and —C(O)—NH$_2$.

In some embodiments of the first aspect, the compounds have the Formula (IV), wherein one $R^{20}$ is H and the other $R^{20}$ is —PO($C_1$-$C_6$alkyl)$_2$, said —PO($C_1$-$C_6$alkyl)$_2$ being ortho to the point of attachment of the nitrogen atom attached to the phenyl ring of group G.

In some embodiments of the first aspect, the compounds have the Formula (VI):

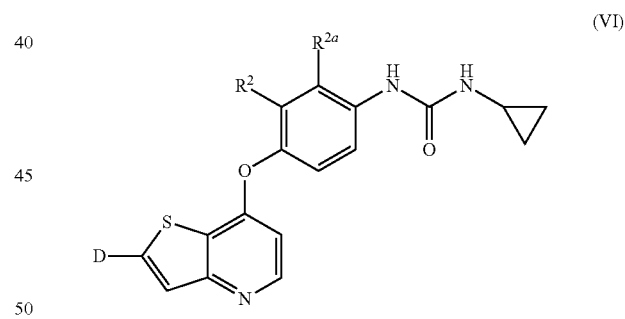

(VI)

including N-oxides, hydrates, solvates, tautomers, pharmaceutically acceptable salts, prodrugs and complexes thereof, and racemic and scalemic mixtures, diastereomers and enantiomers thereof, wherein, D is selected from the group consisting of pyridine, phenyl, imidazole, pyrazole and tetrahydropyridine, each substituted with one $R^{38}$, or D is unsubstituted tetrahydropyridine;

$R^{38}$ is selected from the group consisting of $R^{37}O$—(CH$_2$)$_2$—N(A)-(CH$_2$)$_{1-2}$—, $R^{37}O$—(CH$_2$)$_n$—O—(CH$_2$)$_{n1}$C(O)—N($R^{40}$)—CH$_2$—, $C_1$-$C_6$alkyl-heterocyclyl-(CH$_2$)$_{1-2}$—, (oxo substituted heterocyclyl)-$C_1$-$C_6$alkyl- (wherein the oxo substituted heterocyclyl is further optionally substituted with a substituent selected from the group consisting of —N($R^9$)($R^{10}$), $C_1$-$C_6$alkyl, —N($R^{37}$)(Ac), —OH and (heterocyclyl)-C(O)—, wherein the heterocyclyl is optionally substituted with $C_1$-$C_6$alkyl), $C_1$-$C_6$alkyl-S(O)$_2$—(CH$_2$)$_2$—N(A)-CH$_2$—, $C_0$-$C_6$alkyl-heterocyclyl-(CH$_2$)$_{1-3}$—, HO-heterocyclyl-CH$_2$—, (R$^9$)(R$^{10}$)N-heterocyclyl-CH$_2$—, (C$_1$-$C_6$alkyl)-C(O)-heterocyclyl-CH$_2$—, R$^{37}$O—C$_1$-$C_6$alkyl-heterocyclyl-CH$_2$—, R$^{37}$O—C$_1$-$C_6$alkyl-C(O)-heterocyclyl-(CH)$_{1-6}$—, C$_0$-$C_6$alkyl-heterocyclyl-C$_1$-$C_6$alkyl-N(R$^{39}$)—C(O)—, R$^{37}$O—(CH$_2$)$_j$[(CH$_2$)$_i$O]$_x$—(CH$_2$)$_{i1}$—N(A)-(CH$_2$)$_{j1}$—, R$^{37}$O—C(O)—C$_0$-$C_6$alkyl-heterocyclyl-CH$_2$—, (R$^9$)(R$^{10}$)N-heterocyclyl-C(O)—, R$^{37}$O—(CH$_2$)$_j$—[(CH$_2$)$_i$O]$_x$—(CH$_2$)$_{i1}$—N(R$^{39}$)—C(O)—, R$_{37}$—O—C(O)—C$_1$-$C_6$alkyl-heterocyclyl-C(O)—, HOOC—C$_1$-$C_6$alkyl-N(A)-CH$_2$—, (HOOC)(NR$^9$R$^{10}$)—C$_1$-$C_6$alkyl-N(A)-CH$_2$—, R$^{37}$—O—C(O)-heterocyclyl-C(O)—, (R$^9$)(R$^{10}$)N—C$_0$-$C_6$alkyl-heterocyclyl-C(O)—, C$_0$-$C_6$alkyl-heterocyclyl-C$_0$-$C_6$alkyl-heterocyclyl-C(O)—, R$^{37}$O—C(O)—C$_1$-$C_6$alkyl-C(O)—, (R$^9$)(R$^{10}$)N—C$_1$-$C_6$alkyl-C(O)-heterocyclyl-CH$_2$—, cycloalkyl-N(R$^{39}$)—C(O)—O—C$_1$-$C_6$alkyl-, R$^{37}$—O—C$_1$-$C_6$alkyl-O—C$_1$-$C_6$alkyl-C(O)—, C$_1$-$C_6$alkyl-SO$_2$—, (R$^9$)(R$^{10}$)N—C(O)—C$_1$-$C_6$alkyl-heterocyclyl-CH$_2$—, (R$^9$)(R$^{10}$)N—C$_6$alkyl-C(O)—O—C$_1$-$C_6$alkyl-heterocyclyl-CH$_2$—, R$^{37}$O—C$_1$-$C_6$alkyl-heterocyclyl-CH$_2$—, (HO— substituted C$_1$-$C_6$alkyl)-N(R$^{39}$)—C(O)—, NC—C$_1$-$C_6$alkyl-heterocyclyl-CH$_2$—, heterocyclyl-C$_1$-$C_6$alkyl-heterocyclyl-CH$_2$—, F$_3$C—C$_1$-$C_6$alkyl-heterocyclyl-CH$_2$—, C$_1$-$C_6$alkyl-S(O)$_2$-heterocyclyl-CH$_2$—, heteroaryl-C$_1$-$C_6$alkyl-heterocyclyl-CH$_2$—, R$^{37}$O—C$_1$-$C_6$alkyl-, N(R$^9$)(R$^{10}$)N—C$_1$-$C_6$alkyl-C(O)—O—C$_1$-$C_6$alkyl-C(O)-heterocyclyl-CH$_2$—, C$_1$-$C_6$alkyl-C(O)—O—C$_1$-$C_6$alkyl-C(O)-(5 to 10-membered heterocyclyl)-C$_1$-$C_6$alkyl-, (optionally substituted 8- to 10-membered fused heterocyclyl)-C$_1$-$C_6$alkyl- and (di-fluoro substituted heterocyclyl)-C$_1$-$C_6$alkyl-;

wherein when D is imidazole, the imidazole is further optionally substituted with $C_1$-$C_6$alkyl;

$R^{37}$ is 1-1, $C_1$-$C_6$alkyl;

$R^{37a}$ is H, $C_1$-$C_6$alkyl;

A is H, Ac, —C(O)—CH$_2$—OMe, —C(O)—CH(NH$_2$)—C(CH$_3$)$_3$, —C(O)—(CH$_2$)$_n$—N(R$^{39}$)—C(O)—C$_1$-$C_6$alkyl-N(R$^9$)(R$^{10}$)—C(O)—N(R$^{39}$)—C$_1$-$C_6$alkyl, —C(O)—H, —C(O)—C$_1$-$C_6$alkyl, —C$_1$-$C_6$alkyl-O—C$_1$-$C_6$alkyl, —C(O)—C$_1$-$C_6$alkyl-OH, —C(O)—C$_1$-$C_6$alkyl-N(R$^{39}$)—C(O)—C$_1$-$C_6$alkyl-N(R$^9$)(R$^{10}$), —C(=NH)—H, —C(O)—(CH$_2$)$_n$—S(O)$_2$—C$_1$-$C_6$alkyl, —C(O)—N(R$^{39}$)-cycloalkyl, —C(O)—N(R$^9$)(R$^{10}$), (R$^{23}$)(R$^{24}$)P(O)O—C$_1$-$C_6$alkyl-C(O)— and C$_1$-$C_6$alkyl, j is an integer ranging from 0 to 4, alternatively 0 to 2;
i is 2 or 3;
x is an integer ranging from 0 to 6, alternatively 2 or 3;
i1 is 2 or 3;
j1 is an integer ranging from 0 to 4, alternatively 1 or 2;
n is an integer ranging from 0 to 4;
n1 is an integer ranging from 0 to 4;
$R^{39}$ is H or $C_1$-$C_6$alkyl;
$R^{40}$ is —$C_1$-$C_6$alkyl-OR$^{41}$;
$R^{41}$ is H or $C_1$-$C_6$alkyl;
$R^9$ is H or $C_1$-$C_6$alkyl;
$R^{10}$ is H or $C_1$-$C_6$alkyl;
$R^{23}$ is selected from the group consisting of —OH, $C_1$-$C_6$alkoxy, —O-cycloalkyl, —O-heteroaryl and —O-(5 to 10-membered heterocyclyl);
$R^{24}$ is selected from the group consisting of —OH, $C_1$-$C_6$alkoxy, —O-cycloalkyl, —O-heteroaryl, —O-(5 to 10-membered heterocyclyl);
$R^2$ is H or F; and
$R^{2a}$ is H, F or Cl.

In some embodiments of the first aspect, the compounds have the Formula (VI), wherein D is pyridine substituted with one $R^{38}$.

In some embodiments of the first aspect, the compounds have the Formula (VI), wherein D is phenyl substituted with one $R^{38}$.

In some embodiments of the first aspect, the compounds have the Formula (VI), wherein D is imidazole substituted with one $R^{38}$, and further optionally substituted with $C_1$-$C_6$alkyl (for example —CH$_3$).

In some embodiments of the first aspect, the compounds have the Formula (VI), wherein D is pyrazole substituted with one $R^{38}$.

In some embodiments of the first aspect, the compounds have the Formula (VI), wherein D is tetrahydropyridine substituted with one $R^{38}$, or D is unsubstituted tetrahydropyridine.

In some embodiments of the first aspect, the compounds have the Formula (VI), wherein $R^{38}$ is selected from the group consisting of R$^{37}$O—C(O)—C$_0$-$C_6$alkyl-heterocyclyl-CH$_2$—, R$^{37}$O—(CH$_2$)$_j$—[(CH$_2$)$_i$O]$_x$—(CH$_2$)$_{i1}$—N(R$^{39}$)—C(O)—, R$_{37}$—O—C(O)—C$_1$-$C_6$alkyl-heterocyclyl-C(O)—, R$^{37}$O—C(O)—C$_1$-$C_6$alkyl-C(O)—, (R$^9$)(R$^{10}$)N—C$_1$-$C_6$alkyl-C(O)-heterocyclyl-CH$_2$—, cycloalkyl-N(R$^{39}$)—C(O)—O—C$_1$-$C_6$alkyl-, R$^{37}$—O—C$_1$-$C_6$alkyl-O—C$_1$-$C_6$alkyl-C(O)—, (R$^9$)(R$^{10}$)N—C(O)—C$_1$-$C_6$alkyl-heterocyclyl-CH$_2$—, (R$^9$)(R$^{10}$)N—C$_1$-$C_6$alkyl-C(O)—O—C$_1$-$C_6$alkyl-heterocyclyl —CH$_2$—, NC—C$_1$-$C_6$alkyl-heterocyclyl-CH$_2$—, F$_3$C—C$_1$-$C_6$alkyl-heterocyclyl-CH$_2$— and N(R$^9$)(R$^{10}$)N—C$_1$-$C_6$alkyl-C(O)—O—C$_1$-$C_6$alkyl-C(O)-heterocyclyl-CH$_2$—.

In some embodiments of the first aspect, the compounds have the Formula (VI), wherein $R^{38}$ is R$^{37}$O—(CH$_2$)$_2$—N(A)-(CH$_2$)$_{1-2}$—, for example, MeO—(CH$_2$)$_2$—N(A)-CH$_2$— or MeO—(CH$_2$)$_2$—N(A)-(CH$_2$)$_2$—.

In some embodiments of the first aspect, the compounds have the Formula (VI), wherein $R^{38}$ is R$^{37}$O—(CH$_2$)$_6$—O—(CH$_2$)$_{n1}$C(O)—N(R$^{40}$)—CH$_2$—.

In some embodiments of the first aspect, the compounds have the Formula (VI), wherein $R^{38}$ is $C_1$-$C_6$alkyl-heterocyclyl-(CH$_2$)$_{1-2}$—, for example, $C_1$-$C_6$alkyl-piperazine-CH$_2$— or CH$_3$-piperazine-(CH$_2$)$_2$—.

In some embodiments of the first aspect, the compounds have the Formula (VI), wherein D is pyridine substituted with one $R^{38}$, wherein $R^{38}$ is $C_1$-$C_6$alkyl-heterocyclyl-(CH$_2$)$_{1-2}$—.

In some embodiments of the first aspect, the compounds have the Formula (VI), wherein D is pyridine substituted with one $R^{38}$, wherein $R^{38}$ is $C_1$-$C_6$alkyl-(7-membered heterocyclyl)-CH$_2$—. In some embodiments, the $C_1$-$C_6$alkyl-heterocyclyl-(CH$_2$)$_{1-2}$— is CH$_3$-(7-membered heterocyclyl)-CH$_2$—, for example $C_1$-$C_6$alkyl-(1,4-diazepanyl)-CH$_2$—, for example CH$_3$-(1,4-diazepanyl)-CH$_2$—.

In some embodiments of the first aspect, the compounds have the Formula (VI), wherein D is pyridine substituted with one $R^{38}$, wherein $R^{38}$ is (optionally substituted 8- to 10-membered fused heterocyclyl)-C$_1$-$C_6$alkyl-.

In some embodiments of the first aspect, the compounds have the Formula (VI), wherein D is pyridine substituted with one $R^{38}$, wherein $R^{38}$ is (optionally substituted 8- to 10-membered fused heterocyclyl)-C$_1$-$C_6$alkyl-, wherein the optional substituent is selected from the group consisting of H, halo, —N(R$^9$)(R$^{10}$), nitro, —OH, oxo, $C_1$-$C_6$alkyl, —C(O)—C$_1$-$C_6$alkyl-OH, Ac, cycloalkyl, heterocyclyl, aryl, heteroaryl, —S(O)$_{0-2}$—C$_1$-$C_6$alkyl, —S(O)$_{0-2}$-cycloalkyl, —S(O)$_{0-2}$-heterocyclyl, —S(O)$_{0-2}$-aryl, —S(O)$_{0-2}$-heteroaryl, —C(O)H, —C(O)—C$_1$-$C_6$alkyl, —C(O)—N(R$^9$)(R$^{10}$), —C$_1$-$C_6$alkyl-OH, —C$_1$-$C_6$alkyl-C(O)—OH and —C$_1$-$C_6$alkyl-C (O)—N($R^9$)($R^{10}$), wherein the alkyl, cycloalkyl, heterocyclyl, aryl and heteroaryl groups are themselves optionally substituted, for example with halo or —$C_1$-$C_6$alkyl.

In some embodiments of the first aspect, the compounds have the Formula (VI), wherein D is pyridine substituted with one $R^{38}$ wherein $R^{38}$ is (di-fluoro substituted heterocyclyl)-$C_1$-$C_6$alkyl-.

In some embodiments of the first aspect, the compounds have the Formula (VI), wherein D is pyridine substituted with one $R^{38}$ wherein $R^{38}$ is (di-fluoro substituted heterocyclyl)-$C_1$-$C_6$alkyl-, wherein the two fluoro substituents are substituents on the same carbon atom.

In some embodiments of the first aspect, the compounds have the Formula (VI), wherein D is pyridine substituted with one $R^{38}$ wherein $R^{38}$ is $R^{37}$O—$C_1$-$C_6$alkyl-C(O)-heterocyclyl-CH$_2$—, for example, HO—$C_1$-$C_6$alkyl-C(O)-heterocyclyl-CH$_2$—.

In some embodiments of the first aspect, the compounds have the Formula (VI), wherein $R^{38}$ is (oxo substituted heterocyclyl)-$C_1$-$C_6$alkyl-, wherein the oxo substituted heterocyclyl is further optionally substituted with a substituent selected from the group consisting of —N($R^9$)($R^{10}$), $C_1$-$C_6$alkyl, —N($R^{37}$)(Ac) and —OH. For example, $R^{38}$ is selected from the group consisting of

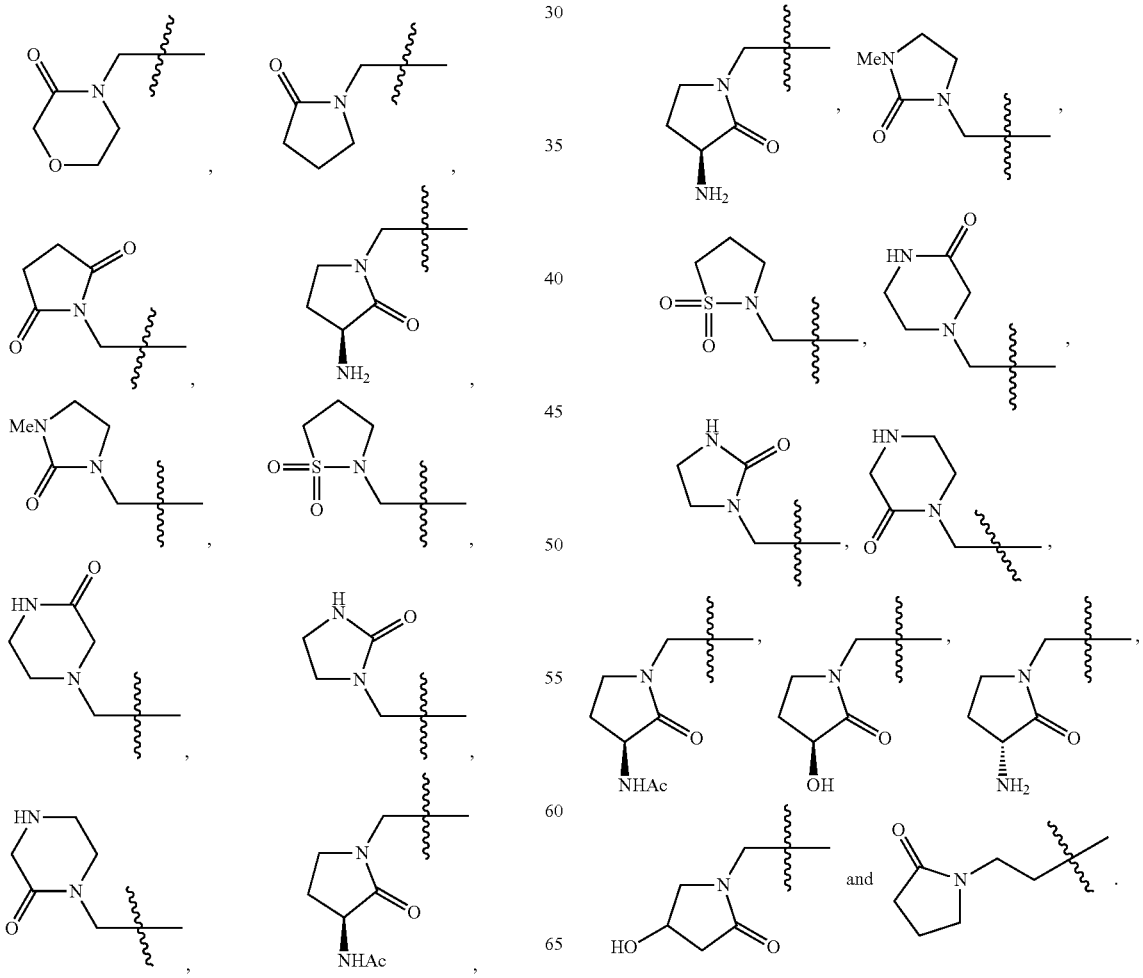

In some embodiments of the first aspect, the compounds have the Formula (VI), wherein $R^{38}$ is selected from the group consisting of In some embodiments of the first aspect, the compounds have the Formula (VI), wherein $R^{38}$ is (heterocyclyl)-C(O)—, wherein the heterocyclyl is optionally substituted with $C_1$-$C_6$alkyl, for example

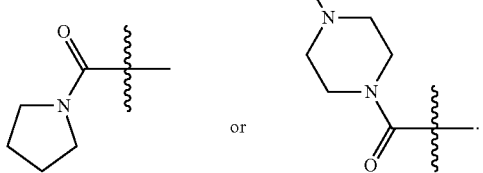

In some embodiments of the first aspect, the compounds have the Formula (VI), wherein $R^{38}$ is $C_1$-$C_6$alkyl-S(O)$_2$—(CH$_2$)$_2$—N(A)-CH$_2$—, for example CH$_3$—S(O)$_2$—(CH$_2$)$_2$—N(A)-CH$_2$—.

In some embodiments of the first aspect, the compounds have the Formula (VI), wherein $R^{38}$ is $C_0$-$C_6$alkyl-heterocyclyl-(CH$_2$)$_{1-3}$—, for example heterocyclyl-(CH$_2$)—, piperazine-CH$_2$—,

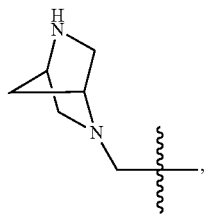

morpholine-CH$_2$—, morpholine-(CH$_2$)$_2$—, CH$_3$-piperazine-(CH$_2$)$_2$—, morpholine-(CH$_2$)$_3$— or piperazine-(CH$_2$)$_2$—.

In some embodiments of the first aspect, the compounds have the Formula (VI), wherein $R^{38}$ is HO-heterocyclyl-CH$_2$—, for example HO-pyrrolidine-CH$_2$—.

In some embodiments of the first aspect, the compounds have the Formula (VI), wherein $R^{38}$ is $(R^9)(R^{10})$N-heterocyclyl-CH$_2$—, for example NH$_2$-pyrrolidine-CH$_2$—.

In some embodiments of the first aspect, the compounds have the Formula (VI), wherein $R^{38}$ is ($C_1$-$C_6$alkyl)-C(O)-heterocyclyl-CH$_2$—, for example CH$_3$—C(O)-piperazine-CH$_2$—.

In some embodiments of the first aspect, the compounds have the Formula (VI), wherein $R^{38}$ is $R^{37}$O—$C_1$-$C_6$alkyl-heterocyclyl-CH$_2$—, for example HO—$C_1$-$C_6$alkyl-heterocyclyl-CH$_2$—, for example HO—(CH$_2$)$_2$-piperazine-CH$_2$—.

In some embodiments of the first aspect, the compounds have the Formula (VI), wherein $R^{38}$ is HO—$C_1$-$C_6$alkyl-C(O)-heterocyclyl-CH$_2$—, for example HO—(CH$_2$)—C(O)-piperazine-CH$_2$—.

In some embodiments of the first aspect, the compounds have the Formula (VI), wherein $R^{38}$ is $C_0$-$C_6$alkyl-heterocyclyl-$C_1$-$C_6$alkyl-N($R^{39}$)—C(O)—, for example, morpholine-(CH$_2$)$_2$—NH—C(O)—, morpholine-(CH$_2$)$_3$—NH—C(O)— or CH$_3$-piperazine-(CH$_2$)$_2$—NH—C(O)—.

In some embodiments of the first aspect, the compounds have the Formula (VI), wherein $R^{38}$ is $R^{37}$O—(CH$_2$)$_j$—[(CH$_2$)$_i$O]$_x$—(CH$_2$)$_{i1}$—N(A)-(CH$_2$)$_{j1}$—, for example, CH$_3$—O—[CH$_2$—CH$_2$—O]$_3$—(CH$_2$)$_2$—N(A)-CH$_2$—.

In some embodiments of the first aspect, the compounds have the Formula (VI), wherein $R^{38}$ is $R^{37}$O—C(O)—$C_0$-$C_6$alkyl-heterocyclyl-CH$_2$—, for example, $R^{37}$O—C(O)—$C_1$-$C_6$alkyl-heterocyclyl-CH$_2$—, HO—C(O)—(CH$_2$)$_2$-piperazine-CH$_2$—, EtO—C(O)-piperidine-CH$_2$—, EtO—C(O)—CH$_2$-piperidine-CH$_2$—, EtO—C(O)—CH$_2$-piperazine-CH$_2$—, HO—C(O)-piperidine-CH$_2$—, HO—C(O)—CH$_2$-piperidine-CH$_2$—, HO—C(O)—CH$_2$-piperazine-CH$_2$—, (CH$_3$)$_3$C—O—C(O)-piperazine-CH$_2$—, or HO—C(O)-pyrrolidine-CH$_2$—.

In some embodiments of the first aspect, the compounds have the Formula (VI), wherein $R^{38}$ is $(R^9)(R^{10})$N-heterocyclyl-C(O)—, for example, N(CH$_3$)$_2$-pyrrolidine-C(O)—.

In some embodiments of the first aspect, the compounds have the Formula (VI), wherein $R^{38}$ is $R^{37}$O—(CH$_2$)$_j$—[(CH$_2$)$_i$O]$_x$—(CH$_2$)$_{i1}$—N($R^{39}$)—C(O)—, for example, CH$_3$—O—[CH$_2$—CH$_2$—O]$_3$—(CH$_2$)$_2$—N(A)-C(O)—.

In some embodiments of the first aspect, the compounds have the Formula (VI), wherein $R^{38}$ is $R_{37}$—O—C(O)—$C_1$-$C_6$alkyl-heterocyclyl-C(O)—, for example, CH$_3$—CH$_2$—O—C(O)—(CH$_2$)$_2$-piperazine-C(O)— or HO—C(O)—(CH$_2$)$_2$-piperazine-C(O)—.

In some embodiments of the first aspect, the compounds have the Formula (VI), wherein $R^{38}$ is HOOC—$C_1$-$C_6$alkyl-N(A)-CH$_2$—, for example, HOOC—(CH$_2$)$_3$—N(A)-CH$_2$—.

In some embodiments of the first aspect, the compounds have the Formula (VI), wherein $R^{38}$ is (HOOC)(NR$^9$R$^{10}$)—$C_1$-$C_6$alkyl-N(A)-CH$_2$—, for example, (HOOC)(NH$_2$)—CH—(CH$_2$)$_4$—N(A)-CH$_2$—.

In some embodiments of the first aspect, the compounds have the Formula (VI), wherein $R^{38}$ is $R^{37}$—O—C(O)-heterocyclyl-C(O)—, for example, EtO—C(O)-piperidine-C(O)—, BuO—C(O)-morpholine-C(O)—, HO—C(O)-piperidine-C(O)— or HO—C(O)-morpholine-C(O)—.

In some embodiments of the first aspect, the compounds have the Formula (VI), wherein $R^3$ is $(R^9)(R^{10})$N—$C_0$-$C_6$alkyl-heterocyclyl-C(O)—, for example, N(CH$_3$)$_2$-pyrrolidine-C(O)—, (CH(CH$_3$)$_2$)$_2$N—(CH$_2$)$_2$-piperazine-C(O)—.

In some embodiments of the first aspect, the compounds have the Formula (VI), wherein $R^{38}$ is $C_0$-$C_6$alkyl-heterocyclyl-$C_0$-$C_6$alkyl-heterocyclyl-C(O)—, for example, $C_0$-$C_6$alkyl-heterocyclyl-$C_1$-$C_6$alkyl-heterocyclyl-C(O)—, morpholine-(CH$_2$)$_2$-piperazine-C(O)—, CH$_3$-piperidine-CH$_2$-piperazine-C(O)— or CH$_3$-piperazine-piperidine-C(O)—.

In some embodiments of the first aspect, the compounds have the Formula (VI), wherein $R^{38}$ is $R^{37}$O—C(O)—$C_1$-$C_6$alkyl-C(O)—, for example, HO—C(O)—(CH$_2$)$_2$—C(O)—.

In some embodiments of the first aspect, the compounds have the Formula (VI), wherein $R^{38}$ is $(R^9)(R^{10})$N—$C_1$-$C_6$alkyl-C(O)-heterocyclyl-CH$_2$—, for example,

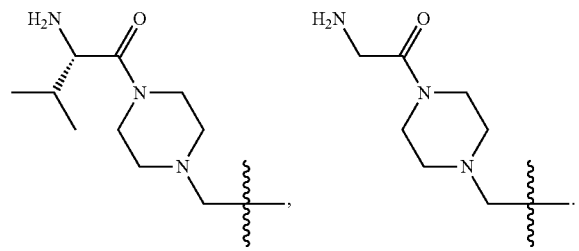

In some embodiments of the first aspect, the compounds have the Formula (VI), wherein $R^{38}$ is cycloalkyl-N($R^{39}$)—C(O)—O—$C_1$-$C_6$alkyl-, for example, $C_3$cycloalkyl-NH—C(O)—O—(CH$_2$)$_2$.

In some embodiments of the first aspect, the compounds have the Formula (VI), wherein $R^{38}$ is $R^{37}$—O—$C_1$-$C_6$alkyl-O—$C_1$-$C_6$alkyl-C(O)—, for example, MeO—$(CH_2)_2$—O—$CH_2$—C(O)—.

In some embodiments of the first aspect, the compounds have the Formula (VI), wherein $R^{38}$ is $C_1$-$C_6$alkyl-$SO_2$—, for example, Me-$S(O)_2$—.

In some embodiments of the first aspect, the compounds have the Formula (VI), wherein $R^{38}$ is $(R^9)(R^{10})$N—C(O)—$C_1$-$C_6$alkyl-heterocyclyl-$CH_2$—, for example,

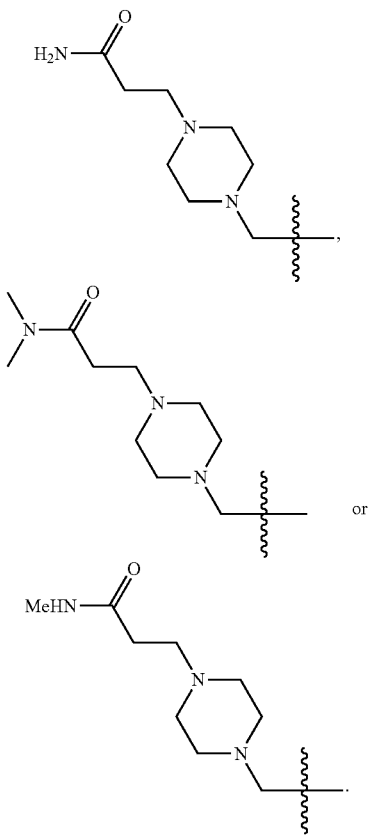

In some embodiments of the first aspect, the compounds have the Formula (VI), wherein $R^{38}$ is $(R^9)(R^{10})$N—$C_1$-$C_6$alkyl-C(O)—O—$C_1$-$C_6$alkyl-heterocyclyl-$CH_2$—, for example,

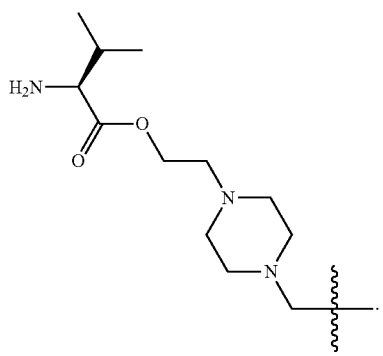

In some embodiments of the first aspect, the compounds have the Formula (VI), wherein $R^{38}$ is $R^{37}$O—$C_1$-$C_6$alkyl-heterocyclyl-$CH_2$—, for example, MeO—$(CH_2)_2$-piperazine-$CH_2$—.

In some embodiments of the first aspect, the compounds have the Formula (VI), wherein $R^{38}$ is (HO— substituted $C_1$-$C_6$alkyl)-N($R^{39}$)—C(O)—, for example, HO—$CH_2$—[CH(OH)]$_4$—$CH_2$—N(Me)—C(O)—.

In some embodiments of the first aspect, the compounds have the Formula (VI), wherein $R^{38}$ is NC—$C_1$-$C_6$alkyl-heterocyclyl-$CH_2$—, for example, NC—$(CH_2)_2$-piperazine-$CH_2$—.

In some embodiments of the first aspect, the compounds have the Formula (VI), wherein $R^{38}$ is heterocyclyl-$C_1$-$C_6$alkyl-heterocyclyl-$CH_2$—, for example, morpholine-$(CH_2)_2$-piperazine-$CH_2$—.

In some embodiments of the first aspect, the compounds have the Formula (VI), wherein $R^{38}$ is $F_3$C—$C_1$-$C_6$alkyl-heterocyclyl-$CH_2$—, for example, $F_3$C—$CH_2$-piperazine-$CH_2$—.

In some embodiments of the first aspect, the compounds have the Formula (VI), wherein $R^{38}$ is $C_1$-$C_6$alkyl-$S(O)_2$-heterocyclyl-$CH_2$—, for example, Me-$S(O)_2$-piperazine-$CH_2$—.

In some embodiments of the first aspect, the compounds have the Formula (VI), wherein $R^{38}$ is heteroaryl-$C_1$-$C_6$alkyl-heterocyclyl-$CH_2$—, for example, imidazole-$(CH_2)_2$-piperazine-$CH_2$—.

In some embodiments of the first aspect, the compounds have the Formula (VI), wherein $R^{38}$ is $R^{37}$O—$C_1$-$C_6$alkyl-, for example, HO—$(CH_2)_4$—.

In some embodiments of the first aspect, the compounds have the Formula (VI), wherein $R^{38}$ is $N(R^9)(R^{10})$N—$C_1$-$C_6$alkyl-C(O)—O—$C_1$-$C_6$alkyl-C(O)-heterocyclyl-$CH_2$—, for example,

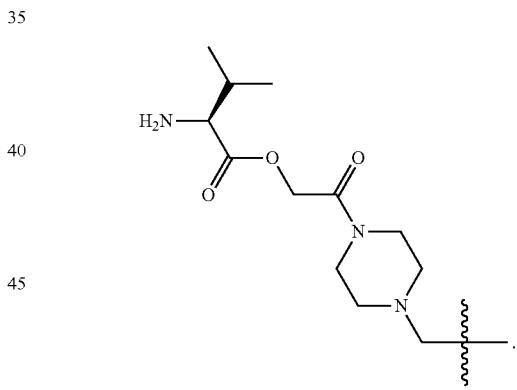

In some embodiments of the first aspect, the compounds have the Formula (VI), wherein $R^{38}$ is $C_1$-$C_6$alkyl-C(O)—O—$C_1$-$C_6$alkyl-C(O)-(5 to 10-membered heterocyclyl)-$C_1$-$C_6$alkyl-.

In some embodiments of the first aspect, the compounds have the Formula (VI), wherein $R^{38}$ is $C_1$-$C_6$alkyl-C(O)—O—$C_1$-$C_6$alkyl-C(O)-(5 to 10-membered heterocyclyl)-$C_1$-$C_6$alkyl-.

In some embodiments of the first aspect, the compounds have the Formula (VI), wherein $R^{38}$ is $C_1$-$C_6$alkyl-C(O)—O—$C_1$-$C_6$alkyl-C(O)-(5 to 10-membered heterocyclyl)-$C_1$-$C_6$alkyl- wherein the heterocyclyl is a 6-membered heterocyclyl.

In some embodiments of the first aspect, the compounds have the Formula (VI), wherein $R^{38}$ is $C_1$-$C_6$alkyl-C(O)—O—$C_1$-$C_6$alkyl-C(O)-(5 to 10-membered heterocyclyl)-$C_1$-$C_6$alkyl-, which is

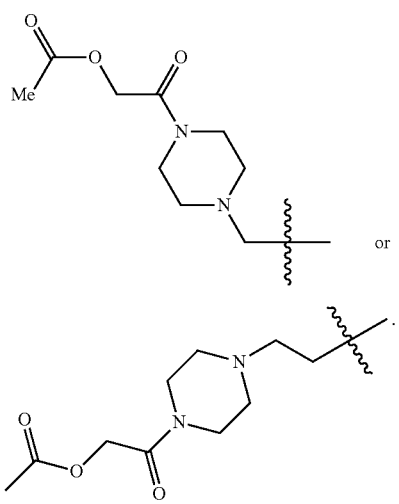

or

In some embodiments of the first aspect, the compounds have the Formula (VI), wherein $R^{38}$ is (optionally substituted 8- to 10-membered fused heterocyclyl)-$C_1$-$C_6$alkyl-.

In some embodiments of the first aspect, the compounds have the Formula (VI), wherein $R^{38}$ is (optionally substituted 8-membered fused heterocyclyl)-$C_1$-$C_6$alkyl-, which is

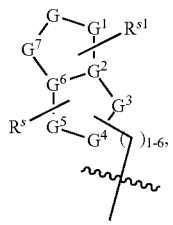

wherein

G is selected from the group consisting of $CH_2$, O, NH, S, SO and $SO_2$;

$G^1$ is selected from the group consisting of $CH_2$, O, NH, S, SO and $SO_2$;

$G^2$ is CH or N;

$G^3$ is selected from the group consisting of $CH_2$, O, NH, S, SO and $SO_2$;

$G^4$ is selected from the group consisting of $CH_2$, O, NH, S, SO and $SO_2$;

$G^5$ is selected from the group consisting of $CH_2$, O, NH, S, SO and $SO_2$;

$G^6$ is CH or N;

$G^7$ is selected from the group consisting of $CH_2$, O, NH, S, SO and $SO_2$;

$R^s$ is an optional substituent; and $R^{s1}$ is an optional substituent, provided that two O atoms are not adjacent to each other.

In some embodiments of the first aspect, the compounds have the Formula (VI), wherein $R^{38}$ is (optionally substituted 8- to 10-membered fused heterocyclyl)-$C_1$-$C_6$alkyl, selected from the group consisting of

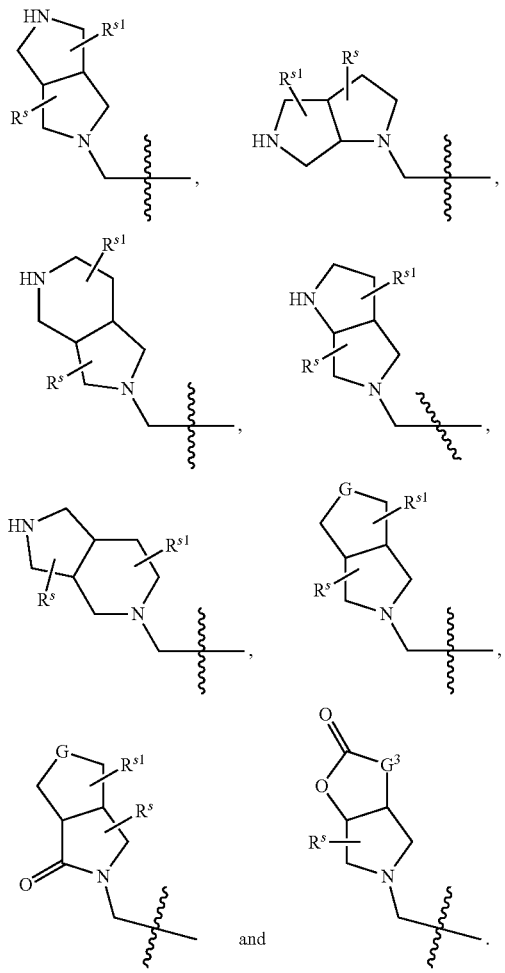

and

In some embodiments of the first aspect, the compounds have the Formula (VI), wherein $R^{38}$ is (optionally substituted 8- to 10-membered fused heterocyclyl)-$C_1$-$C_6$alkyl, selected from the group consisting of

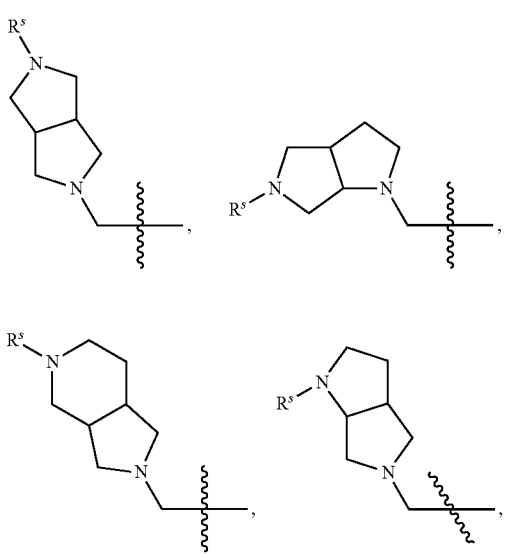

-continued

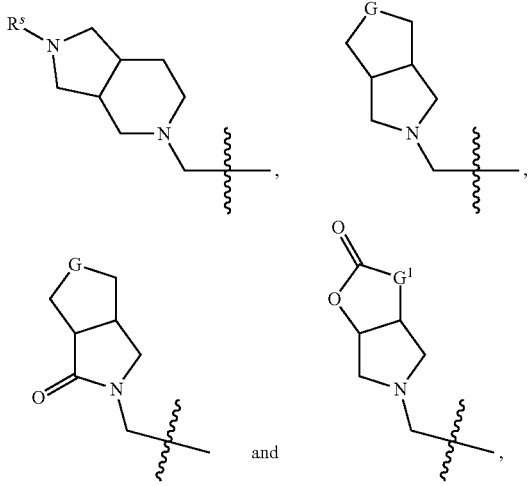

wherein G is selected from the group consisting of $CH_2$, O, NH, S, SO and $SO_2$; $G^1$ is selected from the group consisting of $CH_2$, O, NH, S, SO and $SO_2$; and $R^s$ is an optional substituent.

In some embodiments of the first aspect, the compounds have the Formula (VI), wherein
$R^s$ is selected from the group consisting of H, halo, —$N(R^9)(R^{10})$, nitro, —OH, oxo, $C_1$-$C_6$alkyl, —C(O)—$C_1$-$C_6$alkyl-OH, Ac, cycloalkyl, heterocyclyl, aryl, heteroaryl, —$S(O)_{0-2}$—$C_1$-$C_6$alkyl, —$S(O)_{0-2}$-cycloalkyl, —$S(O)_{0-2}$-heterocyclyl, —$S(O)_{0-2}$-aryl, —$S(O)_{0-2}$-heteroaryl, —C(O)H, —C(O)—$C_1$-$C_6$alkyl, —C(O)—$N(R^9)(R^{10})$, —$C_1$-$C_6$alkyl-OH, —$C_1$-$C_6$alkyl-C(O)—OH, —$C_1$-$C_6$alkyl-C(O)—$N(R^9)(10$, wherein the alkyl, cycloalkyl, heterocyclyl, aryl and heteroaryl groups are themselves optionally substituted, for example with halo or —$C_1$-$C_6$alkyl.

In some embodiments of the first aspect, the compounds have the Formula (VI), wherein $R^{s1}$ is selected from the group consisting of H, halo, —$N(R^9)(R^{10})$, nitro, —OH, oxo, $C_1$-$C_6$alkyl, —C(O)—$C_1$-$C_6$alkyl-OH, Ac, cycloalkyl, heterocyclyl, aryl, heteroaryl —$S(O)_{0-2}$—$C_1$-$C_6$alkyl, —$S(O)_{0-2}$-cycloalkyl, —$S(O)_{0-2}$-heterocyclyl, —$S(O)_{0-2}$-aryl, —$S(O)_{0-2}$-heteroaryl, —C(O)H, —C(O)—$C_1$-$C_6$alkyl, —C(O)—$N(R^9)(R^{10})$, —$C_1$-$C_6$alkyl-OH, —$C_1$-$C_6$alkyl-C(O)—OH, —$C_1$-$C_6$alkyl-C(O)—$N(R^9)(R^{10})$, wherein the alkyl, cycloalkyl, heterocyclyl, aryl and heteroaryl groups are themselves optionally substituted, for example with halo or —$C_1$-$C_6$alkyl.

In some embodiments of the first aspect, the compounds have the Formula (VI), wherein $R^{38}$ is (optionally substituted 8- to 10-membered fused heterocyclyl)-$C_1$-$C_6$alkyl-, wherein the optional substituent is selected from the group consisting of H, halo, —$N(R^9)(R^{10})$, nitro, —OH, oxo, —C(O)—$C_1$-$C_6$alkyl-OH, Ac, cycloalkyl, heterocyclyl, aryl, heteroaryl, —$S(O)_{0-2}$—$C_1$-$C_6$alkyl, —$S(O)_{0-2}$-cycloalkyl, —$S(O)_{0-2}$-heterocyclyl, —$S(O)_{0-2}$-aryl, —$S(O)_{0-2}$-heteroaryl, —C(O)H, —C(O)—$C_1$-$C_6$alkyl, —C(O)—$N(R^9)(R^{10})$, $C_1$-$C_6$alkyl-OH, —$C_1$-$C_6$alkyl-C(O)—OH and —$C_1$-$C_6$alkyl-C(O)—$N(R^9)(R^{10})$, wherein the alkyl, cycloalkyl, heterocyclyl, aryl and heteroaryl groups are themselves optionally substituted, for example with halo or —$C_1$-$C_6$alkyl.

In some embodiments of the first aspect, the compounds have the Formula (VI), wherein $R^{38}$ is (di-fluoro substituted heterocyclyl)-$C_1$-$C_6$alkyl-.

In some embodiments of the first aspect, the compounds have the Formula (VI), wherein $R^{38}$ is (di-fluoro substituted heterocyclyl)-$C_1$-$C_6$alkyl-, wherein the two fluoro substituents are substituents on the same carbon atom.

In some embodiments of the first aspect, the compounds have the Formula (VI), wherein $R^{38}$ is $R^{37}$O—$C_1$-$C_6$alkyl-C(O)-heterocyclyl-$CH_2$—, for example, HO—$C_1$-$C_6$alkyl-C(O)-heterocyclyl-$CH_2$—.

In some embodiments of the first aspect, the compounds have the Formula (VI), wherein $R^{38}$ is $R^{37}$O—$C_1$-$C_6$alkyl-C(O)-heterocyclyl-$(CH_2)_{1-6}$—, for example, HO—$C_1$-$C_6$alkyl-C(O)-heterocyclyl-$(CH_2)_{1-2}$—.

In some embodiments of the first aspect, the compounds have the Formula (VI), wherein $R^{38}$ is $R^{37}$O—$C_1$-$C_6$alkyl-C(O)-heterocyclyl-$(CH_2)_{1-6}$—, wherein the heterocyclyl is a 5- or 6-membered heterocyclyl.

In some embodiments of the first aspect, the compounds have the Formula (VI), wherein $R^{38}$ is $R^{37}$O—$C_1$-$C_6$alkyl-C(O)-heterocyclyl-$(CH_2)_{1-6}$—, wherein the heterocyclyl is a 5- or 6-membered heterocyclyl, $R^{37}$ is H and the —$(CH_2)_{1-6}$— is —$(CH_2)_{1-2}$—.

In some embodiments of the first aspect, the compounds have the Formula (VI), wherein A is selected from the group consisting of —C(O)—$(CH_2)_n$—$N(R^{39})$—C(O)—$C_1$-$C_6$alkyl-$N(R^9)(R^{10})$—C(O)—$N(R^{39})$—$C_1$-$C_6$alkyl —C(O)—$C_1$-$C_6$alkyl-$N(R^{39})$—C(O)—$C_1$-$C_6$alkyl-$N(R^9)(R^{10})$—C(=NH)—H, —C(O)—$(CH_2)_n$—$S(O)_2$—$C_1$-$C_6$alkyl —C(O)—$N(R^{39})$-cycloalkyl —C(O)—$N(R^9)(R^{10})$ and $(R^{23})(R^{24})$P(O)O—$C_1$-$C_6$alkyl —C(O)—.

In some embodiments of the first aspect, the compounds have the Formula (VI), wherein A is H.

In some embodiments of the first aspect, the compounds have the Formula (VI), wherein A is not H.

In some embodiments of the first aspect, the compounds have the Formula (VI), wherein A is Ac.

In some embodiments of the first aspect, the compounds have the Formula (VI), wherein A is —C(O)—$CH_2$—OMe.

In some embodiments of the first aspect, the compounds have the Formula (VI), wherein A is —C(O)—$CH(NH_2)$—$C(CH_3)_3$.

In some embodiments of the first aspect, the compounds have the Formula (VI), wherein A is —C(O)—$(CH_2)$—$N(R^{39})$—C(O)—$C_1$-$C_6$alkyl-$N(R^9)(R^{10})$, for example, —C(O)—$CH_2$—NH—C(O)—$CH(NH_2)$—$CH(CH_3)_2$.

In some embodiments of the first aspect, the compounds have the Formula (VI), wherein A is —C(O)—$N(R^{39})$—$C_1$-$C_6$alkyl, for example, —C(O)—NH—$CH_2$—$CH_3$, —C(O)—NH—$CH_3$, —C(O)—NH—$CH(CH_3)_2$ or —C(O)—$N(CH_3)_2$.

In some embodiments of the first aspect, the compounds have the Formula (VI), wherein A is —C(O)—H.

In some embodiments of the first aspect, the compounds have the Formula (VI), wherein A is —C(O)—$C_1$-$C_6$alkyl, for example, —C(O)—$CH_3$ or —C(O)—$CH_2$—$CH_3$.

In some embodiments of the first aspect, the compounds have the Formula (VI), wherein A is —$C_1$-$C_6$alkyl-O—$C_1$-$C_6$alkyl, for example, —$(CH_2)_2$—OMe.

In some embodiments of the first aspect, the compounds have the Formula (VI), wherein A is —C(O)—$C_1$-$C_6$alkyl-OH.

In some embodiments of the first aspect, the compounds have the Formula (VI), wherein A is —C(O)—$C_1$-$C_6$alkyl-$N(R^{39})$—C(O)—$C_1$-$C_6$alkyl-$N(R^9)(R^{10})$, for example, —C(O)—$CH_2$—NH—C(O)—$CH_2$—$NH_2$ or —C(O)—CH[CH($CH_3)_2$]—NH—C(O)—$CH_2$—$NH_2$.

In some embodiments of the first aspect, the compounds have the Formula (VI), wherein A is —C(=NH)—H.

In some embodiments of the first aspect, the compounds have the Formula (VI), wherein A is —C(O)—(CH$_2$)$_n$—S(O)$_2$—C$_1$-C$_6$alkyl, for example, —C(O)—CH$_2$—S)$_2$-Me.

In some embodiments of the first aspect, the compounds have the Formula (VI), wherein A is —C(O)—N(R$^{39}$)-cycloalkyl, for example, —C(O)—NH-cyclopentyl or —C(O)—NH—C$_3$cycloalkyl.

In some embodiments of the first aspect, the compounds have the Formula (VI), wherein A is —C(O)—N(R$^9$)(R$^{10}$), for example, —C(O)—NH$_2$.

In some embodiments of the first aspect, the compounds have the Formula (VI), wherein A is (R$^{23}$)(R$^{24}$)P(O)O—C$_1$-C$_6$alkyl-C(O)—, for example, (HO)$_2$P(O)O—CH$_2$—C(O)—.

In some embodiments of the first aspect, the compounds have the Formula (VI), wherein A is C$_1$-C$_6$alkyl.

In some embodiments of the first aspect, the compounds have the Formula (VI), wherein A is not C$_1$-C$_6$alkyl.

In some embodiments of the first aspect, the present invention is directed to compounds having the Formula (VI) wherein D is pyridine, substituted with R$^{38}$.

In some embodiments of the first aspect, the present invention is directed to compounds having the Formula (VI), wherein D is pyridine substituted with R$^{38}$, and R$^{38}$ is R$^{37}$O—(CH$_2$)$_2$—N(A)-(CH$_2$)$_{1-2}$—.

In some embodiments of the first aspect, the present invention is directed to compounds having the Formula (VI), wherein D is pyridine substituted with R$^{38}$, R$^{38}$ is R$^{37}$O—(CH$_2$)$_2$—N(A)-(CH$_2$)$_{1-2}$— and A is selected from the group consisting of —C(O)—(CH$_2$)$_n$—N(R$^{39}$)—C(O)—C$_1$-C$_6$alkyl-N(R$^9$)(R$^{10}$).

In some embodiments of the first aspect, the compounds have the Formula (VI), wherein D is pyridine substituted with one R$^{38}$, wherein R$^{38}$ is (oxo substituted heterocyclyl)-C$_1$-C$_2$alkyl-; in some embodiments of the first aspect, the compounds have the Formula (VI), wherein R$^{38}$-D- is

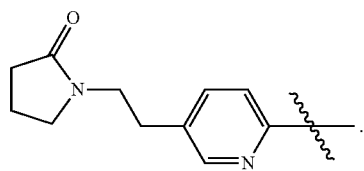 [SMILES: *c1ccc(CCN2CCCC2=O)cn1]

In some embodiments of the first aspect, the compounds have the Formula (VI), wherein D is imidazole substituted with one R$^{38}$, wherein R$^{38}$ is C$_1$-C$_6$alkyl-C(O)—O—C$_1$-C$_6$alkyl-C(O)-(5 to 10-membered heterocyclyl)-C$_1$-C$_6$alkyl-.

In some embodiments of the first aspect, the compounds have the Formula (VI), wherein D is imidazole substituted with one R$^{38}$, wherein R$^{38}$ is C$_1$-C$_6$alkyl-C(O)—O—C$_1$-C$_6$alkyl-C(O)-(5 to 10-membered heterocyclyl)-C$_1$-C$_6$alkyl- wherein the heterocyclyl is a 6-membered heterocyclyl.

In some embodiments of the first aspect, the compounds have the Formula (VI), wherein D is imidazole substituted with one R$^{38}$, wherein R$^{38}$ is C$_1$-C$_6$alkyl-C(O)—O—C$_1$-C$_6$alkyl-C(O)-(5 to 10-membered heterocyclyl)-C$_1$-C$_6$alkyl-, which is

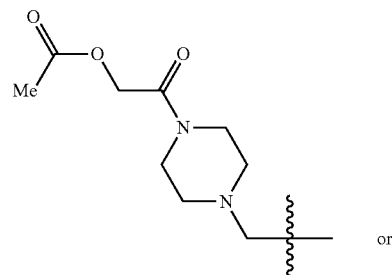

or

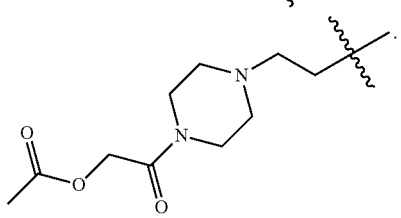

In some embodiments of the first aspect, the compounds have the Formula (VI), wherein D is imidazole substituted with one R$^{38}$, wherein R$^{38}$ is R$^{37}$O—C$_1$-C$_6$alkyl-C(O)-heterocyclyl-CH$_2$—, for example, HO—C$_1$-C$_6$alkyl-C(O)-heterocyclyl-CH$_2$—.

In some embodiments of the first aspect, the compounds have the Formula (VI), wherein D is imidazole substituted with one R$^{38}$, wherein R$^{38}$ is R$^{37}$O—C$_1$-C$_6$alkyl-C(O)-heterocyclyl-(CH$_7$)$_{1-6}$—, for example, HO—C$_1$-C$_6$alkyl-C(O)-heterocyclyl-(CH$_2$)$_{1-2}$—.

In some embodiments of the first aspect, the compounds have the Formula (VI), wherein D is imidazole substituted with one R$^{38}$, wherein R$^{38}$ is R$^{37}$O—C$_1$-C$_6$alkyl-C(O)-heterocyclyl-(CH$_2$)$_{1-6}$—, wherein the heterocyclyl is a 5- or 6-membered heterocyclyl.

In some embodiments of the first aspect, the compounds have the Formula (VI), wherein D is imidazole substituted with one R$^{38}$, wherein R$^{38}$ is R$^{37}$O—C$_1$-C$_6$alkyl-C(O)-heterocyclyl-(CH$_2$)$_{1-6}$—, wherein the heterocyclyl is a 5- or 6-membered heterocyclyl, R$^{37}$ is H and the —(CH$_2$)$_{1-6}$— is —(CH$_2$)$_{1-2}$—.

In some embodiments of the first aspect, the compounds have the Formula (VII)

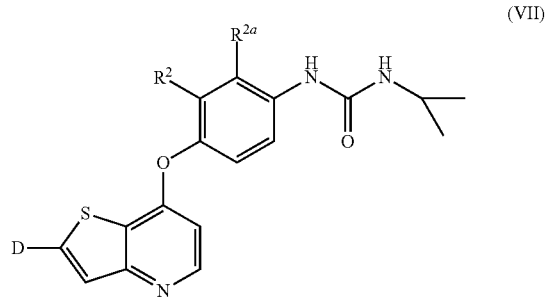

including N-oxides, hydrates, solvates, tautomers, pharmaceutically acceptable salts, prodrugs and complexes thereof, and racemic and scalemic mixtures, diastereomers and enantiomers thereof, wherein, D is pyridine or imidazole, wherein the pyridine and imidazole are substituted with one R$^{38}$;

R$^{38}$ is selected from the group consisting of (oxo substituted heterocyclyl)-C$_1$-C$_6$alkyl-, (heterocyclyl)-C(O)—, C$_1$-C$_6$alkyl, R$^{37}$O—(CH$_2$)$_2$—N(A)-CH$_2$—, heterocyclyl-C$_1$-C$_6$alkyl-N(R$^{39}$)—C(O)—, heterocyclyl-CH$_2$—;

wherein when D is imidazole, the imidazole is further optionally substituted with C$_1$-C$_6$alkyl (for example, —CH$_3$);

$R^{37}$ is H or $C_1$-$C_6$alkyl;
A is —C(O)—N($R^{39}$)—$C_1$-$C_6$alkyl or —C(O)—$C_1$-$C_6$alkyl;
$R^{39}$ is H or $C_1$-$C_6$alkyl;
$R^2$ is F; and
$R^{2a}$ is H.

In some embodiments of the first aspect, the compounds have the Formula (VII), wherein $R^{38}$ is (oxo substituted heterocyclyl)-$C_1$-$C_6$alkyl-, for example,

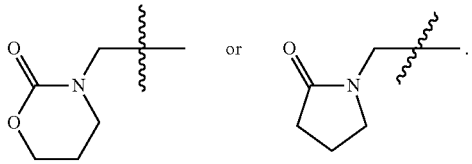

In some embodiments of the first aspect, the compounds have the Formula (VII), wherein $R^{38}$ is (heterocyclyl)-C(O)—, for example,

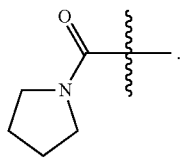 [SMILES: *C(=O)N1CCCC1]

In some embodiments of the first aspect, the compounds have the Formula (VII), wherein $R^{38}$ is $C_1$-$C_6$alkyl.

In some embodiments of the first aspect, the compounds have the Formula (VII), wherein $R^{38}$ is not $C_1$-$C_6$alkyl.

In some embodiments of the first aspect, the compounds have the Formula (VII), wherein $R^{38}$ is $R^{37}$O—($CH_2$)$_2$—N(A)-$CH_2$—, for example, MeO—($CH_2$)$_2$—N(A)-$CH_2$—.

In some embodiments of the first aspect, the compounds have the Formula (VII), wherein $R^{38}$ is heterocyclyl-$C_1$-$C_6$alkyl-N($R^{39}$)—C(O)—, for example morpholine-($CH_2$)$_2$—NH—C(O)—.

In some embodiments of the first aspect, the compounds have the Formula (VII), wherein $R^{38}$ is heterocyclyl-$CH_2$—, for example, preferably morpholine-$CH_2$—.

In some embodiments of the first aspect, the compounds have the Formula (VII), wherein A is —C(O)—N($R^{39}$)—$C_1$-$C_6$alkyl, for example, —C(O)—NH—CH($CH_3$)$_2$ or —C(O)—NH—$CH_2$—$CH_3$.

In some embodiments of the first aspect, the compounds have the Formula (VII), wherein A is —C(O)—$C_1$-$C_6$alkyl, for example, —C(O)—$CH_3$.

In some embodiments of the first aspect, the compounds have the Formula (VIII)

(VIII)

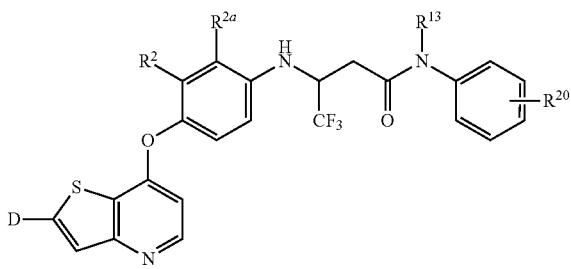

including N-oxides, hydrates, solvates, tautomers, pharmaceutically acceptable salts, prodrugs and complexes thereof, and racemic and scalemic mixtures, diastereomers and enantiomers thereof, wherein,
D is pyridine substituted with one $R^{38}$;
$R^{38}$ is $R^{37}$O—($CH_2$)$_2$—N(A)-$CH_2$—, for example, MeO—($CH_2$)$_2$—N(A)-$CH_2$—;
A is H or —C(O)—$C_1$-$C_6$alkyl, for example —C(O)—$CH_3$;
$R^{13}$ is H or $C_1$-$C_6$alkyl;
$R^{37}$ is $C_1$-$C_6$alkyl;
$R^2$ is F;
$R^{2a}$ is H; and
$R^{20}$ is H or F.

In some embodiments of the first aspect, the compounds have the Formula (IX):

(IX)

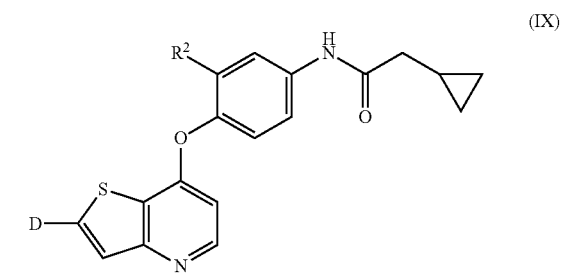

including N-oxides, hydrates, solvates, tautomers, pharmaceutically acceptable salts, prodrugs and complexes thereof, and racemic and scalemic mixtures, diastereomers and enantiomers thereof, wherein,
D is pyridine substituted with one $R^{38}$;
$R^{38}$ is $R^{37}$O—($CH_2$)$_2$—N(A)-$CH_2$—, for example, MeO—($CH_2$)$_2$—N(A)-$CH_2$—;
A is H or —C(O)—$C_1$-$C_6$alkyl;
$R^{37}$ is H or $C_1$-$C_6$alkyl; and
$R^2$ is F.

In some embodiments of the first aspect, the compounds have the Formula (X):

(X)

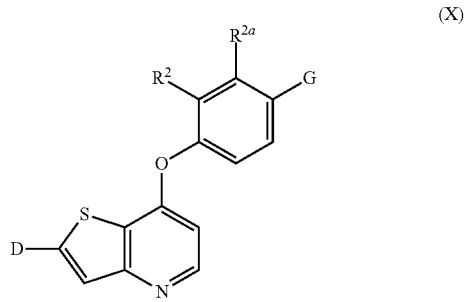

including N-oxides, hydrates, solvates, tautomers, pharmaceutically acceptable salts, prodrugs and complexes thereof, and racemic and scalemic mixtures, diastereomers and enantiomers thereof, wherein,
D is pyridine, substituted with $R^{38}$;
$R^{38}$ is $R^{37}$O—($CH_2$)$_{1-6}$—N(A)-($CH_2$)$_{1-4}$—, $R^{37}$O—($CH_2$)$_j$—[($CH_2$)$_i$O]$_x$—($CH_2$)$_{i1}$—N(A)-($CH_2$)$_{j1}$—, $R^{37}$O—C(O)—$C_0$-$C_6$alkyl-heterocyclyl-$CH_2$—, $R^{37}$O—($CH_2$)$_j$—[($CH_2$)$_i$O]$_x$—($CH_2$)$_{i1}$—N($R^{39}$)—C(O)—, $R^{37}$—O—C(O)—$C_1$-$C_6$alkyl-heterocyclyl-C(O)—, ($R^9$)($R^{10}$)N—$C_1$-$C_6$alkyl-C(O)-heterocyclyl-$CH_2$—, ($R^9$)($R^{10}$)N—

C(O)—C$_1$-C$_6$alkyl-heterocyclyl-CH$_2$—, (R$^9$)(R$^{10}$)N—C$_1$-C$_6$alkyl-C(O)—O—C$_1$-C$_6$alkyl-heterocyclyl-CH$_2$—, F$_3$C—C$_1$-C$_6$alkyl-heterocyclyl-CH$_2$—, N(R$^9$)(R$^{10}$)N—C$_1$-C$_6$alkyl-C(O)—O—C$_1$-C$_6$alkyl-C(O)-heterocyclyl-CH$_2$— and C$_1$-C$_6$alkyl-C(O)—O—C$_1$-C$_6$alkyl-C(O)-(5 to 10-membered heterocyclyl)-C$_1$-C$_6$alkyl-;

R$^{37}$ is H or C$_1$-C$_6$alkyl;

A is selected from the group consisting of —C(O)—C$_1$-C$_6$alkyl-N(R$^{39}$)—C(O)—C$_1$-C$_6$alkyl-N(R$^9$)(R$^{10}$), —C(O)—N(R$^{39}$)—C$_1$-C$_6$alkyl, —C(=NR$^{37}$)—C$_1$-C$_6$alkyl, —C(O)—(CH$_2$)$_n$—S(O)$_2$—C$_1$-C$_6$alkyl, —C(O)—N(R$^9$)(R$^{10}$) and (R$^{23}$)(R$^{24}$)P(O)O—C$_1$-C$_6$alkyl-C(O)—;

n is an integer ranging from 0 to 4;

R$^{39}$ is H or C$_1$-C$_6$alkyl;

R$^9$ is H or C$_1$-C$_6$alkyl;

R$^{10}$ is H or C$_1$-C$_6$alkyl;

R$^2$ is F;

R$^{2a}$ is 14 or F;

R$^{23}$ is selected from the group consisting of —OH, C$_1$-C$_6$alkoxy, —O-aryl, —O-cycloalkyl, —O-heteroaryl and —O-(5 to 10-membered heterocyclyl);

R$^{24}$ is selected from the group consisting of —OH, C$_1$-C$_6$alkoxy, —O-aryl, —O-cycloalkyl, —O-heteroaryl, —O-(5 to 10-membered heterocyclyl);

j is an integer ranging from 0 to 4, alternatively 0 to 2;

i is 2 or 3;

x is an integer ranging from 0 to 6, alternatively 2 or 3;

i1 is 2 or 3;

j1 is an integer ranging from 0 to 4, alternatively 1 or 2; and

G is

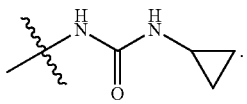 [SMILES: *NC(=O)NC1CC1]

In some embodiments of the compounds of Formula (X), R$^{38}$ further includes C$_0$-C$_6$alkyl-heterocyclyl-C$_0$-C$_6$alkyl-heterocyclyl-C(O)—, alternatively —C(O)-piperidine-piperazine-CH$_3$.

In some embodiments of the first aspect, the compounds have the Formula (X), wherein R$^{38}$ is R$^{37}$O—(CH$_2$)$_{1-6}$—N(A)-(CH$_2$)$_{1-4}$—, alternatively R$^{37}$O—(CH$_2$)$_2$—N(A)-(CH$_2$)$_{1-2}$—, MeO—(CH$_2$)$_2$—N(A)-CH$_2$— or MeO—(CH$_2$)$_2$—N(A)-(CH$_2$)$_2$—.

In some embodiments of the first aspect, the compounds have the Formula (X), wherein R$^{38}$ is R$^{37}$O—(CH$_2$)$_j$—[(CH$_2$)$_i$O]$_x$—(CH$_2$)$_{i1}$—N(A)-(CH$_2$)$_{j1}$—, alternatively CH$_3$—O—[CH$_2$—CH$_2$—O]$_3$—(CH$_2$)$_2$—N(A)-CH$_2$—.

In some embodiments of the first aspect, the compounds have the Formula (X), wherein R$^{38}$ is R$^{37}$O—C(O)—C$_0$-C$_6$alkyl-heterocyclyl-CH$_2$—, alternatively R$^{37}$O—C(O)—C$_1$-C$_6$alkyl-heterocyclyl-CH$_2$—, alternatively HO—C(O)—(CH$_2$)$_2$-piperazine-CH$_2$—, EtO—C(O)-piperidine-CH$_2$—, EtO—C(O)—CH$_2$-piperidine-CH$_2$—, EtO—C(O)—CH$_2$-piperazine-CH$_2$—, HO—C(O)-piperidine-CH$_2$—, HO—C(O)—CH$_2$-piperidine-CH$_2$—HO—C(O)—CH$_2$-piperazine-CH$_2$—, (CH$_3$)$_3$C—O—C(O)-piperazine-CH$_2$— or HO—C(O)-pyrrolidine-CH$_2$—.

In some embodiments of the first aspect, the compounds have the Formula (X), wherein R$^{38}$ is R$^{37}$O—(CH$_2$)$_j$—[(CH$_2$)$_i$O]$_x$—(CH$_2$)$_{i1}$—N(R$^{39}$)—C(O)—, alternatively CH$_3$—O—[CH$_2$—CH$_2$—O]$_3$—(CH$_2$)$_2$—N(A)-C(O)—.

In some embodiments of the first aspect, the compounds have the Formula (X), wherein R$^{38}$ is R$^{37}$—O—C(O)—C$_1$-C$_6$alkyl-heterocyclyl-C(O)—, alternatively CH$_3$—CH$_2$—O—C(O)—(CH$_2$)$_2$-piperazine-C(O)— or HO—C(O)—(CH$_2$)-2-piperazine-C(O)—.

In some embodiments of the first aspect, the compounds have the Formula (X), wherein R$^{38}$, wherein R$^{38}$ is (R$^9$)(R$^{10}$)N—C$_1$-C$_6$alkyl-C(O)-heterocyclyl-CH$_2$—.

In some embodiments of the first aspect, the compounds have the Formula (X), wherein R$^{38}$ is (R$^9$)(R$^{10}$)N—C(O)—C$_1$-C$_6$alkyl-heterocyclyl-CH$_2$—, alternatively

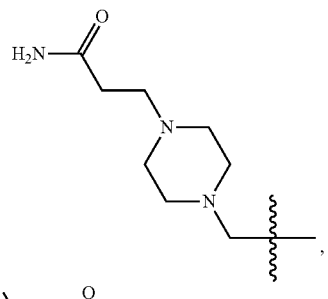

,

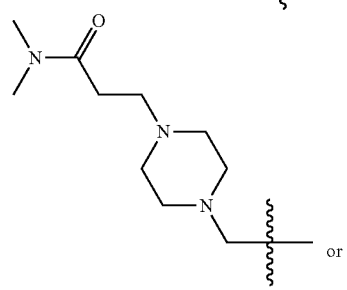

or

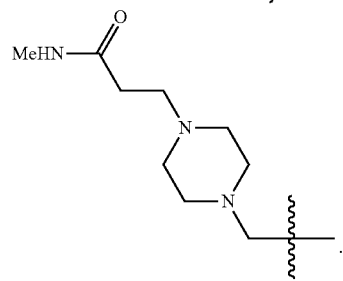

.

In some embodiments of the first aspect, the compounds have the Formula (X), wherein R$^{38}$ is (R$^9$)(R$^{10}$)N—C$_1$-C$_6$alkyl-C(O)—O—C$_1$-C$_6$alkyl-heterocyclyl-CH$_2$—, alternatively

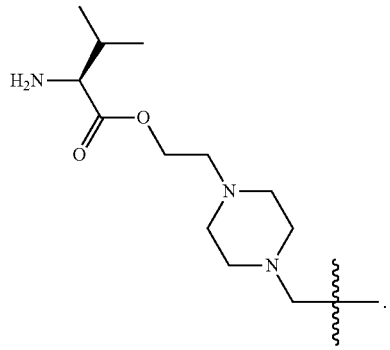 [SMILES: *CN1CCN(CCOC(=O)[C@@H](N)C(C)C)CC1]

.

In some embodiments of the first aspect, the compounds have the Formula (X), wherein $R^{38}$ is $F_3C-C_1-C_6$alkyl-heterocyclyl-$CH_2-$, alternatively $F_3C-CH_2$-piperazine-$CH_2-$.

In some embodiments of the first aspect, the compounds have the Formula (X), wherein $R^{38}$ is $(R^9)(R^{10})N-C_1-C_6$alkyl-C(O)—O—$C_1$-$C_6$alkyl-C(O)-heterocyclyl-$CH_2-$, alternatively

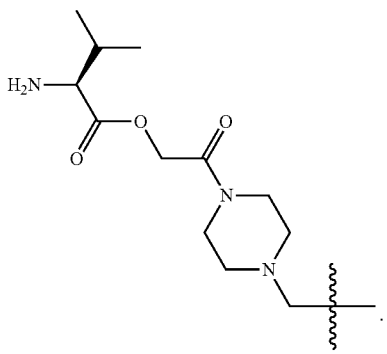 [SMILES: *CN1CCN(C(=O)COC(=O)[C@@H](N)C(C)C)CC1]

In some embodiments of the first aspect, the compounds have the Formula (X), wherein $R^{38}$ is $C_1$-$C_6$alkyl-C(O)—O—$C_1$-$C_6$alkyl-C(O)-(5 to 10-membered heterocyclyl)-$C_1$-$C_6$alkyl-, for example

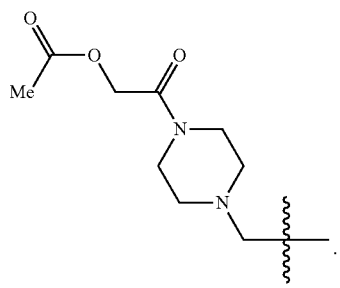 [SMILES: *CN1CCN(C(=O)COC(C)=O)CC1]

In some embodiments of the first aspect, the compounds have the Formula (X), wherein A is —C(O)—$C_1$-$C_6$alkyl-N($R^{39}$)—C(O)—$C_1$-$C_6$alkyl-N($R^9$)($R^{10}$), alternatively —C(O)—$CH_2$—NH—C(O)—CH($NH_2$)—CH($CH_3$)$_2$, —C(O)—$CH_2$—NH—C(O)—$CH_2$—$NH_2$ or —C(O)—CH[CH($CH_3$)$_2$]—NH—C(O)—$CH_2$—$NH_2$).

In some embodiments of the first aspect, the compounds have the Formula (X), wherein A is —C(O)—N($R^{39}$)—$C_1$-$C_6$alkyl, alternatively —C(O)—NH—$CH_2$—$CH_3$, —C(O)—NH—$CH_3$, —C(O)—NH—CH($CH_3$)$_2$, —C(O)—NH—CH($CH_3$)$_2$ or —C(O)—N($CH_3$)$_2$.

In some embodiments of the first aspect, the compounds have the Formula (X), wherein A is —C(=N$R^{37}$)—$C_1$-$C_6$alkyl, alternatively —C(=NH)H.

In some embodiments of the first aspect, the compounds have the Formula (X), wherein A is —C(O)—($CH_2$), —S(O)$_2$—$C_1$-$C_6$alkyl, alternatively —C(O)—$CH_2$—S(O)$_2$-Me.

In some embodiments of the first aspect, the compounds have the Formula (X), wherein A is —C(O)—N($R^9$)($R^{10}$), alternatively —C(O)—$NH_2$.

In some embodiments of the first aspect, the compounds have the Formula (X), wherein A is $(R^{23})(R^{24})$P(O)O—$C_1$-$C_6$alkyl-C(O)—, alternatively $(HO)_2$P(O)O—$CH_2$—C(O)—.

In some embodiments of the first aspect, the compounds have the Formula (XI):

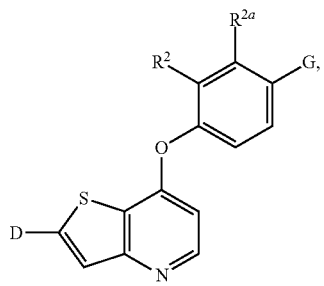

(XI)

including N-oxides, hydrates, solvates, tautomers, pharmaceutically acceptable salts, prodrugs and complexes thereof, and racemic and scalemic mixtures, diastereomers and enantiomers thereof, wherein,
wherein
D is imidazole substituted with one $R^{38}$ and further substituted with $C_1$-$C_6$alkyl;
$R^{38}$ is $R^{37}O-(CH_2)_{1-6}-N(A)-(CH_2)_{1-4}-$;
$R^{37}$ is H or $C_1$-$C_6$alkyl;
A is —C(O)—N($R^{39}$)—$C_1$-$C_6$alkyl,
$R^{39}$ is $F_1$ or $C_1$-$C_6$alkyl;
$R^2$ is F;
$R^{2a}$ is H; and
G is

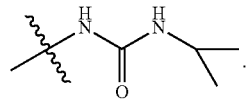 [SMILES: *NC(=O)NC(C)C]

In some embodiments of the first aspect, the compounds have the Formula (XI), wherein $R^{38}$ is selected from the group consisting of $R^{37}O-(CH_2)_2-N(A)-(CH_2)_{1-2}-$, MeO—$(CH_2)_2-N(A)-CH_2-$ and MeO—$(CH_2)_2-N(A)-(CH_2)_2-$.

In some embodiments of the first aspect, the compounds of have the Formula (XII):

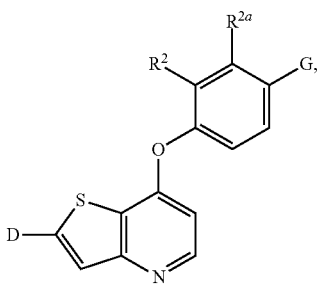

(XII)

wherein
including N-oxides, hydrates, solvates, tautomers, pharmaceutically acceptable salts, prodrugs and complexes thereof, and racemic and scalemic mixtures, diastereomers and enantiomers thereof, wherein,
D is phenyl, substituted with $R^{38}$;
$R^{38}$ is $R^{37}O-(CH_2)_{1-6}-N(A)-(CH_2)_{1-4}-$;

$R^{37}$ is H or $C_1$-$C_6$alkyl;
A is —C(O)—N($R^{39}$)—$C_1$-$C_6$alkyl, —C(O)—N($R^{39}$)-cycloalkyl
$R^{39}$ is H or $C_1$-$C_6$alkyl;
$R^2$ is F;
$R^{2a}$ is H; and
G is

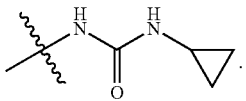

In some embodiments of the first aspect, the compounds have the Formula (XII), wherein $R^{38}$ is selected from the group consisting of $R^{37}O$—$(CH_2)_2$—N(A)-$(CH_2)_{1-2}$—, MeO—$(CH_2)_2$—N(A)-$CH_2$— and MeO—$(CH_2)_2$—N(A)-$(CH_2)_2$—.

In some embodiments of the first aspect, the compounds have the Formula (XII), wherein A is selected from the group consisting of —C(O)—N($R^{39}$)—$C_{3-6}$cycloalkyl, —C(O)—N($R^{39}$)—$C_3$cycloalkyl, —C(O)—N($R^{39}$)—$C_4$cycloalkyl, —C(O)—N($R^{39}$)—$C_5$cycloalkyl and —C(O)—N($R^{39}$)—$C_6$cycloalkyl.

In some embodiments of the first aspect, the compounds have the formula (XIII):

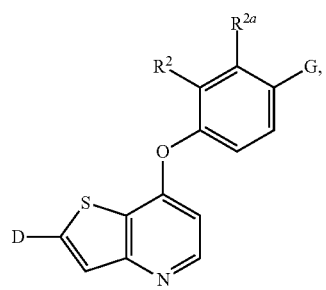

including N-oxides, hydrates, solvates, tautomers, pharmaceutically acceptable salts, prodrugs and complexes thereof, and racemic and scalemic mixtures, diastereomers and enantiomers thereof, wherein,
D is imidazole substituted with one $R^{38}$ and further substituted with $C_1$-$C_6$alkyl;
$R^{38}$ is $R^{37}O$—$(CH_2)_{1-6}$—N(A)-$(CH_2)_{1-4}$—;
$R^{37}$ is H or $C_1$-$C_6$alkyl;
A is —C(O)—N($R^{39}$)—$C_1$-$C_6$alkyl,
$R^{39}$ is H or $C^1$-$C^6$alkyl;
$R^2$ is F;
$R^{2a}$ is H; and
G is

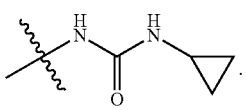 [SMILES: *NC(=O)NC1CC1]

In some embodiments of the first aspect, the compounds have the Formula (XIII), wherein $R^{38}$ is selected from the group consisting of $R^{37}O$—$(CH_2)_2$—N(A)-$(CH_2)_{1-2}$—, MeO—$(CH_2)_2$—N(A)-$CH_2$— and MeO—$(CH_2)_2$—N(A)-$(CH_2)_2$—.

In some embodiments of the first aspect, the compounds have the Formula (XIV):

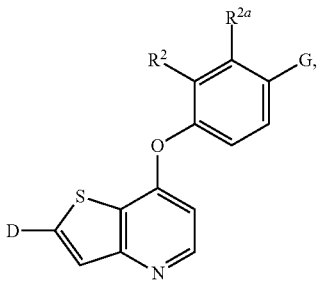

including N-oxides, hydrates, solvates, tautomers, pharmaceutically acceptable salts, prodrugs and complexes thereof, and racemic and scalemic mixtures, diastereomers and enantiomers thereof, wherein,
D is tetrahydropyridine substituted with $R^{38}$;
$R^{38}$ is $R^{37}O$—C(O)—$C_1$-$C_6$alkyl-C(O)—, $R^{37}$—O—$C_1$-$C_6$alkyl-O—$C_1$-$C_6$alkyl-C(O)—;
$R^{37}$ is H or $C_1$-$C_6$alkyl;
$R^2$ is F;
$R^{2a}$ is H; and
G is

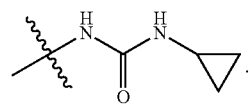 [SMILES: *NC(=O)NC1CC1]

In some embodiments of the first aspect, the compounds have the Formula (XIV), wherein $R^{38}$ is HO—C(O)—$(CH_2)_2$—C(O)—.

In some embodiments of the first aspect, the compounds have the Formula (XIV), wherein $R^{38}$ is $R^{37}$—O—$C_1$-$C_6$alkyl-O—$C_1$-$C_6$alkyl-C(O)—, alternatively MeO—$(CH_2)_2$—O—$CH_2$—C(O)—.

In some embodiments of the first aspect, the compounds have the Formula (XV):

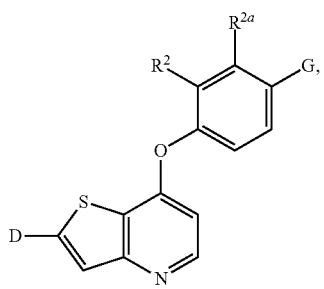

including N-oxides, hydrates, solvates, tautomers, pharmaceutically acceptable salts, prodrugs and complexes thereof, and racemic and scalemic mixtures, diastereomers and enantiomers thereof, wherein,
D is pyrazole, substituted with $R^{38}$;
$R^{38}$ is cycloalkyl-N($R^{39}$)—C(O)—O—$C_1$-$C_6$alkyl-, $R^{37}O$—$(CH_2)_{1-6}$—N(A)-$(CH_2)_{1-4}$—;
A is —C(O)—N($R^{39}$)—$C_1$-$C_6$alkyl, $R^{39}$ is H or $C_1$-$C_6$alkyl;
$R^2$ is F;
$R^{2a}$ is H; and
G is

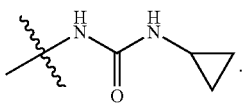 [SMILES: *NC(=O)NC1CC1]

In some embodiments of the first aspect, the compounds have the Formula (XV), wherein $R^{38}$ is cycloalkyl-N($R^{39}$)—C(O)—O—$C_1$-$C_6$alkyl-, alternatively $C_3$cycloalkyl-NH—C(O)—O—$(CH_2)_2$—.

In some embodiments of the first aspect, the compounds have the Formula (XV), wherein $R^{38}$ is $R^{37}$O—$(CH_2)_{1-6}$—N(A)-$(CH_2)_{1-4}$—, for example, selected from the group consisting of $R^{37}$O—$(CH_2)_2$—N(A)-$(CH_2)_{1-2}$—, MeO—$(CH_2)_2$—N(A)-$CH_2$— and MeO—$(CH_2)_2$—N(A)-$(CH_2)_2$—.

In some embodiments of the first aspect, the compounds have the Formula (XVI):

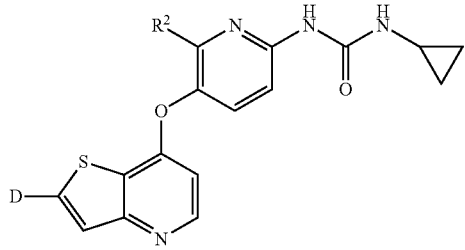

(XVI)

including N-oxides, hydrates, solvates, tautomers, pharmaceutically acceptable salts, prodrugs and complexes thereof, and racemic and scalemic mixtures, diastereomers and enantiomers thereof, wherein,
D is pyridine substituted with one $R^{38}$;
$R^{38}$ is $R^{37}$O—$(CH_2)_2$—N(A)-$CH_2$;
A is selected from the group consisting of H, —C(O)—$C_1$-$C_6$alkyl, —C(O)—N($R^{39}$)—$C_1$-$C_6$alkyl, and —C(O)—$C_1$-$C_6$alkyl-OH;
$R^{37}$ is H, $C_1$-$C_6$alkyl;
$R^{39}$ is H, $C_1$-$C_6$alkyl; and
$R^2$ is H.

In some embodiments of the first aspect, the compounds have the Formula (XVI),
wherein $R^{38}$ is MeO—$(CH_2)_2$—N(A)-$CH_2$—.

In some embodiments of the first aspect, the compounds have the Formula (XVI),
wherein A is —C(O)—$C_1$-$C_6$alkyl, for example, —C(O)—$CH_3$).

In some embodiments of the first aspect, the compounds have the Formula (XVI), wherein A is —C(O)—N($R^{39}$)—$C_1$-$C_6$alkyl, for example, —C(O)—NH—$CH_2$—$CH_3$.

In some embodiments of the first aspect, the compounds have the Formula (XVI), wherein A is —C(O)—$C_1$-$C_6$alkyl-OH, for example, —C(O)—$CH_2$—OH.

In some embodiments of the first aspect, the compounds have the Formula (XVII):

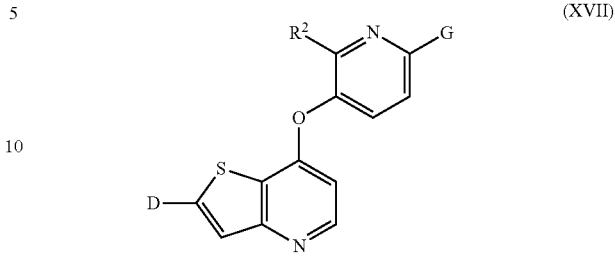

(XVII)

including N-oxides, hydrates, solvates, tautomers, pharmaceutically acceptable salts, prodrugs and complexes thereof, and racemic and scalemic mixtures, diastereomers and enantiomers thereof, wherein.
D is pyridine, substituted with $R^{38}$;
$R^{38}$ is $R^{37}$O—$(CH_2)_{1-6}$—N(A)-$(CH_2)_{1-4}$—,
$R^{37}$ is H or $C_1$-$C_6$alkyl;
A is —C(O)—N($R^{39}$)—$C_1$-$C_6$alkyl,
$R^{39}$ is H or $C_1$-$C_6$alkyl;
$R^2$ is H; and
G is

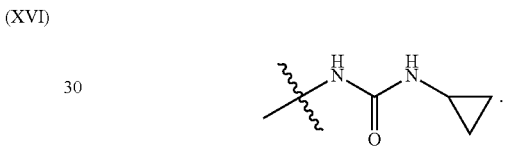

In some embodiments of the first aspect, the compounds have the Formula (XXVII), wherein $R^{38}$ is selected from the group consisting of $R^{37}$O—$(CH_2)_2$—N(A)-$(CH_2)_{1-2}$—, MeO—$(CH_2)_2$—N(A)-$CH_2$— and MeO—$(CH_2)_2$—N(A)-$(CH_2)_2$—.

In some embodiments of the first aspect, the compounds have the Formula (XVIII):

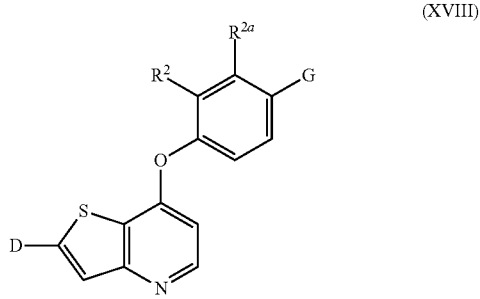

(XVIII)

including N-oxides, hydrates, solvates, tautomers, pharmaceutically acceptable salts, prodrugs and complexes thereof, and racemic and scalemic mixtures, diastereomers and enantiomers thereof, wherein,
D is pyridine or imidazole, each substituted with $R^{38}$, and wherein the imidazole is further substituted with —$C_1$-$C_6$alkyl, for example —$CH_3$;
$R^{38}$ is $R^{37}$O—$(CH_2)_{1-6}$—N(A)-$(CH_2)_{1-4}$— or $R^{37}$O—$C_1$-$C_6$alkyl-C(O)-heterocyclyl-$CH_2$—;
$R^{37}$ is H or $C_1$-$C_6$alkyl;
A is —C(O)—N($R^{39}$)—$C_1$-$C_6$alkyl, —C(O)—H,
$R^{39}$ is H or $C_1$-$C_6$alkyl;

$R^2$ is H or F;
$R^{2a}$ is H or F; and
G is

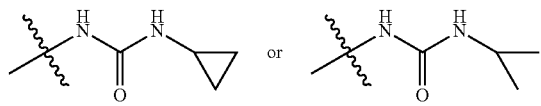 or

In some embodiments of the first aspect, the compounds have the Formula (XVIII), wherein D is pyridine substituted with one $R^{38}$, wherein $R^{38}$ is $R^{37}O$—$(CH_2)_{1-6}$—N(A)-$(CH_2)_{1-4}$—, alternatively $R^{37}O$—$(CH_2)_2$—N(A)-$(CH_2)$—.

In some embodiments of the first aspect, the compounds have the Formula (XVIII), wherein D is pyridine substituted with one $R^{38}$, wherein $R^{38}$ is $R^{37}O$—$(CH_2)_{1-6}$—N(A)-$(CH_2)_{1-4}$—, and A is —C(O)—N($R^{39}$)—$C_1$-$C_6$alkyl.

In some embodiments of the first aspect, the compounds have the Formula (XVIII), wherein D is pyridine substituted with one $R^{38}$, wherein $R^{38}$ is HO—$(CH_2)_2$—N(A)-$(CH_2)$—, and A is —C(O)—N($R^{39}$)—$C_1$-$C_6$alkyl, In some embodiments of the first aspect, the compounds have the Formula (XVIII), wherein D is pyridine substituted with one $R^{38}$, wherein $R^{38}$ is HO—$(CH_2)_2$—N(A)-$(CH_2)$—, A is —C(O)—N($R^{39}$)—$C_1$-$C_6$alkyl and G is

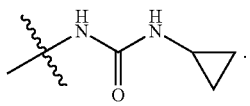 [SMILES: *NC(=O)NC1CC1]

In some embodiments of the first aspect, the compounds have the Formula (XVIII), wherein D is pyridine substituted with one $R^{38}$, wherein $R^{38}$ is $R^{37}O$—$(CH_2)_{1-6}$—N(A)-$(CH_2)_{1-4}$—, and A is —C(O)—H.

In some embodiments of the first aspect, the compounds have the Formula (XVIII), wherein D is pyridine substituted with one $R^{38}$, wherein $R^{38}$ is HO—$(CH_2)_2$—N(A)-$(CH_2)$—, and A is —C(O)—H.

In some embodiments of the first aspect, the compounds have the Formula (XVIII), wherein D is pyridine substituted with one $R^{38}$, wherein $R^{38}$ is HO—$(CH_2)_2$—N(A)-$(CH_2)$—, A is —C(O)—H and G is

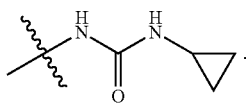 [SMILES: *NC(=O)NC1CC1]

In some embodiments of the first aspect, the compounds have the Formula (XVIII), wherein D is imidazole substituted with one $R^{38}$ and further substituted with one —$CH_3$, wherein $R^{38}$ is $R^{37}O$—$(CH_2)_{1-6}$—N(A)-$(CH_2)_{1-4}$—, alternatively $R^{37}O$—$(CH_2)_2$—N(A)-$(CH_2)$—.

In some embodiments of the first aspect, the compounds have the Formula (XVIII), wherein D is imidazole substituted with one $R^{38}$ and further substituted with —$CH_3$, wherein $R^{38}$ is $R^{37}O$—$(CH_2)_{1-6}$—N(A)-$(CH_2)_{1-4}$—, and A is —C(O)—N($R^{39}$)—$C_1$-$C_6$alkyl.

In some embodiments of the first aspect, the compounds have the Formula (XVIII), wherein D is imidazole substituted with one $R^{38}$ and further substituted with —$CH_3$, wherein $R^{38}$ is HO—$(CH_2)_2$—N(A)-$(CH_2)$—, and A is —C(O)—N($R^{39}$)—$C_1$-$C_6$alkyl.

In some embodiments of the first aspect, the compounds have the Formula (XVIII), wherein D is imidazole substituted with one $R^{38}$ and further substituted with —$CH_3$, wherein $R^{38}$ is HO—$(CH_2)_2$—N(A)-$(CH_2)$—, A is —C(O)—N($R^{39}$)—$C_1$-$C_6$alkyl and G is

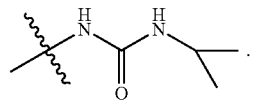 [SMILES: *NC(=O)NC(C)C]

In some embodiments of the first aspect, the compounds have the Formula (XVIII), wherein D is pyridine substituted with one $R^{38}$, wherein $R^{38}$ is $R^{37}O$—$C_1$-$C_6$alkyl-heterocyclyl-$CH_2$—.

In some embodiments of the first aspect, the compounds have the Formula (XVIII), wherein D is pyridine substituted with one $R^{38}$, wherein $R^{38}$ is HO—$C_1$-$C_6$alkyl-C(O)-heterocyclyl-$CH_2$—, for example, HO—$CH_2$—C(O)-piperazine-$CH_2$—.

In some embodiments of the first aspect, the compounds have the Formula (XVIII), wherein D is pyridine substituted with one $R^{38}$, wherein $R^{38}$ is HO—$C_1$-$C_6$alkyl-C(O)-heterocyclyl-$CH_2$—, for example, HO—$CH_2$—C(O)-piperazine-$CH_2$—, and G is

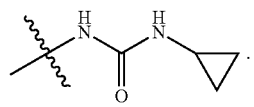 [SMILES: *NC(=O)NC1CC1]

In some embodiments of the first aspect, the compounds have the Formula (XIX):

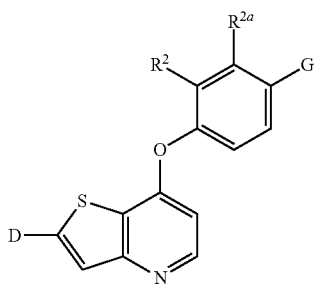

(XIX)

including N-oxides, hydrates, solvates, tautomers, pharmaceutically acceptable salts, prodrugs and complexes thereof, and racemic and scalemic mixtures, diastereomers and enantiomers thereof, wherein;
D is pyridine substituted with one $R^{38}$;
$R^{38}$ is $R^{37}O$—$(CH_2)_2$—N(A)-$(CH_2)_2$—;
$R^{37}$ is $C_1$-$C_6$alkyl;
A is H or $C_1$-$C_6$alkyl,
$R^2$ is F;
$R^{2a}$ is H; and
G is

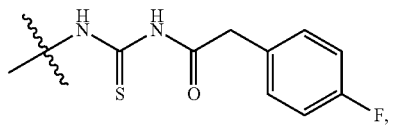

-continued

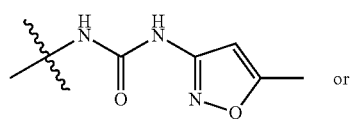 or

In some embodiments of the first aspect, the compounds have the Formula (XIX), wherein A is H.

In some embodiments of the first aspect, the compounds have the Formula (XIX), wherein $R^{37}$ is —CH$_3$.

In some embodiments of the first aspect, G is

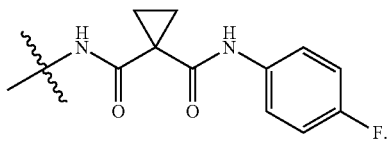

In some embodiments of the first aspect,

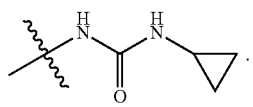 [SMILES: *NC(=O)NC1CC1] is 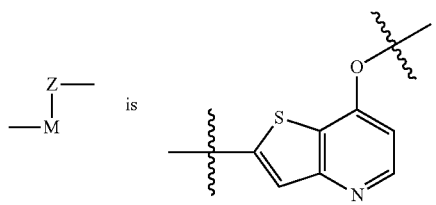.

In some embodiments of the first aspect, Ar is

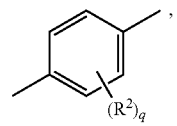, wherein Ar is optionally substituted.

In some embodiments of the first aspect, D is pyridinyl, imidazolyl or triazolyl, each of which is substituted with one $R^{38}$.

In some embodiments of the first aspect, $R^{38}$ is selected from the group consisting of $R^{37}$O—C(O)—C$_1$-C$_6$alkyl-heterocyclyl-C$_1$-C$_6$alkyl-, C$_1$-C$_6$alkyl-heterocyclyl-C(O)-heterocyclyl-C$_1$-C$_6$alkyl-, $R^{37}$O—C$_1$-C$_6$alkyl-N($R^6$)—C(O)-heterocyclyl-C$_1$-C$_6$alkyl-, ($R^6$)($R^6$)N—C$_1$-C$_6$alkyl-N($R^6$)—C(O)-heterocyclyl-C$_1$-C$_6$alkyl-, $R^{37}$O—C$_1$-C$_6$alkyl-C(O)-heterocyclyl-C$_1$-C$_6$alkyl-, $R^{37}$O—C$_1$-C$_6$alkyl-heterocyclyl-C$_1$-C$_6$alkyl- and $R^{37}$O—(CH$_2$)$_j$—[(CH$_2$)$_i$O]$_x$—C$_1$-C$_6$alkyl-N($R^6$)—C(O)-heterocyclyl-C$_1$-C$_6$alkyl-, wherein each of said alkyl and heterocyclyl is optionally substituted.

In some embodiments of the first aspect, D is pyridinyl substituted with one $R^{38}$.

In some embodiments of the first aspect, when $R^{38}$ is attached to D by a C$_1$-C$_6$ alkyl, the C$_1$-C$_6$ alkyl is —CH$_2$—.

In some embodiments of the first aspect, D is selected from the group consisting of C$_1$-C$_6$alkyl-heterocyclyl-C(O)—, C$_1$-C$_6$alkyl-heterocyclyl-C$_1$-C$_6$alkyl —N($R^6$)—C(O)—, ($R^6$)($R^6$)N—C(O)—O-heterocyclyl-C(O)—, heterocyclyl-C(O)—, PivO-heterocyclyl-C(O)—, C$_1$-C$_6$alkyl-O—C(O)-heterocyclyl-C(O)—, C$_1$-C$_6$alkyl-C(O)—N($R^6$)-heterocyclyl-C(O)—, (C$_1$-C$_6$alkyl)(Box)N-heterocyclyl-C(O)—, HO-heterocyclyl-C(O)—, HO—C(O)-heterocyclyl-C(O)—, C$_1$-C$_6$alkyl-C(O)—O-heterocyclyl-C(O)—, ($R^6$)($R^6$)N—C$_1$-C$_6$alkyl —N($R^6$)—C(O)-heterocyclyl-C(O)—, C$_1$-C$_6$alkyl-heterocyclyl-C(O)-heterocyclyl-C(O)— and ($R^6$)($R^6$)N-heterocyclyl-C(O)—, wherein said each of said alkyl and heterocyclyl is optionally substituted.

In some embodiments of the first aspect, $R^6$ is H.

In some embodiments of the first aspect, the compound is selected from the group consisting of:

In some embodiments of the first aspect, the compounds are selected from the group consisting of

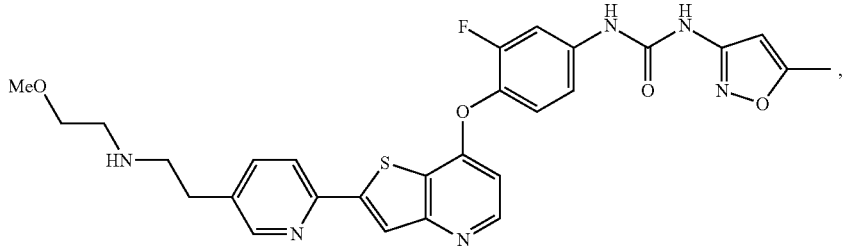 [SMILES: COCCNCCc1ccc(-c2cc3nccc(Oc4ccc(NC(=O)Nc5cc(C)on5)cc4F)c3s2)nc1],

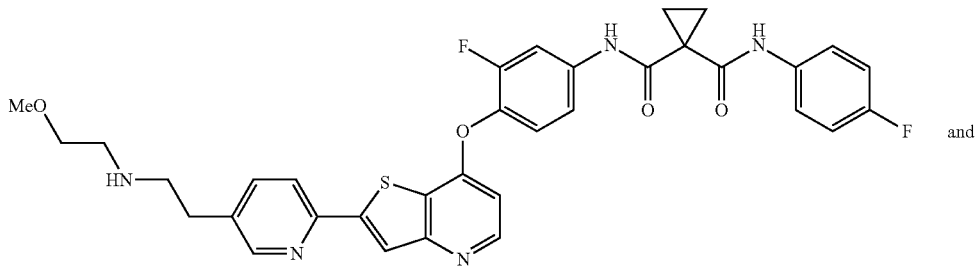 and

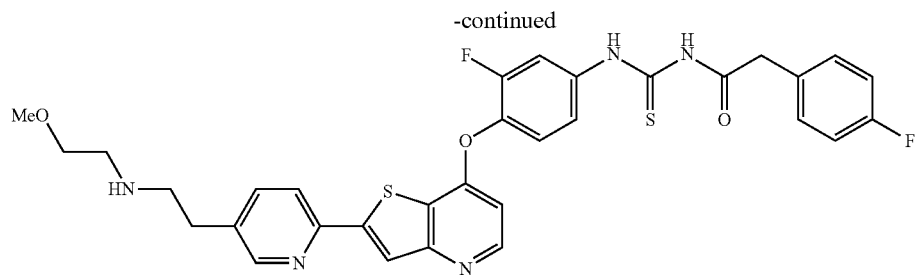

including N-oxides, hydrates, solvates, tautomers, pharmaceutically acceptable salts, prodrugs and complexes thereof, and racemic and scalemic mixtures, diastereomers and enantiomers thereof.

In one embodiment of the first aspect, the compound is

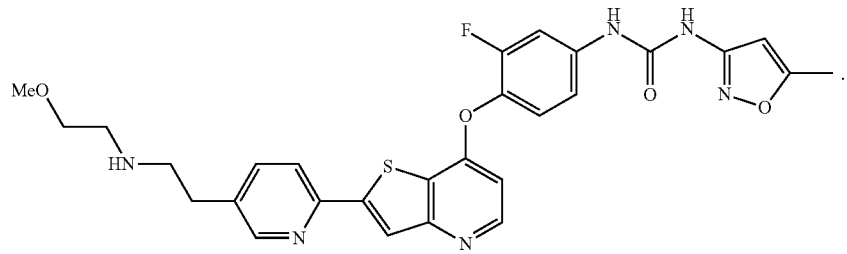

In one embodiment of the first aspect, the compound is

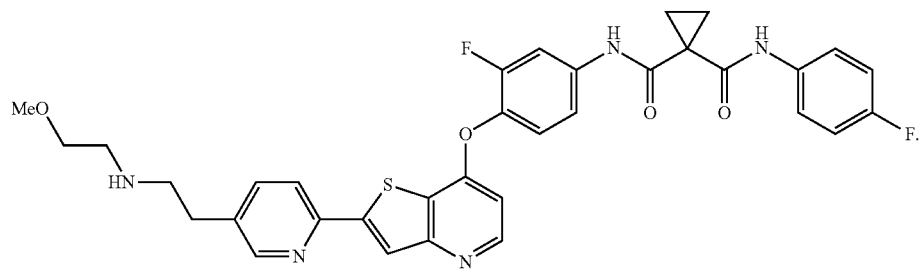 [SMILES: COCCNCCc1ccc(-c2cc3nccc(Oc4ccc(NC(=O)C5(C(=O)Nc6ccc(F)cc6)CC5)cc4F)c3s2)nc1]

In one embodiment of the first aspect, the compound is

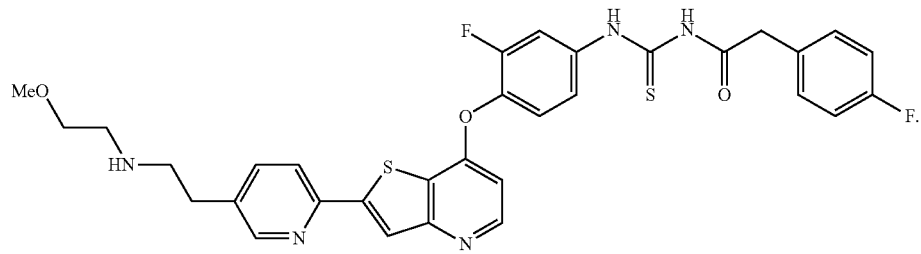 [SMILES: COCCNCCc1ccc(-c2cc3nccc(Oc4ccc(NC(=S)NC(=O)Cc5ccc(F)cc5)cc4F)c3s2)nc1]

Compounds of above formulas may generally be prepared according to the following Schemes. Tautomers and solvates (e.g., hydrates) of the compounds of above formulas are also within the scope of the present invention. Methods of solvation are generally known in the art. Accordingly, the compounds of the present invention may be in the free, hydrate or salt form, and may be obtained by methods exemplified by the following schemes below.

The following examples and preparations describe the manner and process of making and using the invention and are illustrative rather than limiting. It should be understood that there may be other embodiments which fall within the spirit and scope of the invention as defined by the claims appended hereto.

Compounds according to the invention include but are not limited to those described in the examples below. Compounds were named using Chemdraw Ultra (versions 10.0, 10.0.4 or version 8.0.3), which are available through Cambridgesoft (www.Cambridgesoft.com, 100 Cambridge Park Drive, Cambridge, Mass. 02140, or were derived therefrom.

The data presented herein demonstrate the inhibitory effects of the kinase inhibitors of the invention. These data lead one to reasonably expect that the compounds of the invention are useful not only for inhibition of kinase activity, protein tyrosine kinase activity, or embodiments thereof, such as, VEGF receptor signaling, but also as therapeutic agents for the treatment of proliferative diseases, including cancer and tumor growth and ophthalmic diseases, disorders and conditions.

Synthetic Schemes and Experimental Procedures

The compounds of the invention can be prepared according to the reaction schemes or the examples illustrated below utilizing methods known to one of ordinary skill in the art. These schemes serve to exemplify some procedures that can be used to make the compounds of the invention. One skilled in the art will recognize that other general synthetic procedures may be used. The compounds of the invention can be prepared from starting components that are commercially available. Any kind of substitutions can be made to the starting components to obtain the compounds of the invention according to procedures that are well known to those skilled in the art.

All reagents and solvents were obtained from commercial sources and used as received. $^1$H-NMR spectra were recorded on Mercury Plus Varian 400 MHz instrument in the solvents indicated. Low resolution mass-spectra (LRMS) were acquired on Agilent MSD instrument. Analytical HPLC was performed on Agilent 1100 instrument using Zorbax 3 µm, XDB-C8, 2.1×50 mm column; eluting with methanol/water containing 0.1% formic acid, with a gradients-95% methanol in 15 minutes. Automated column chromatography was performed on Biotage SP1 or Biotage SP4 instruments using Biotage® SNAP, SiliaSep™ or SiliaFlash® cartridges. Flash column chromatography was performed using silica gel (SiliaFlash F60, 40-63 µM, pore size 60 Å, SiliCycle®). Preparative column chromatography was performed on Gilson 215 instrument using Phenomenex Luna 15 µM, C18(2) 100A, 250×21 mm column eluting with a mixture methanol/water containing 0.05% of formic acid, with a gradient 0-95% methanol in up to 60 minutes.

PARTICULAR EXAMPLES

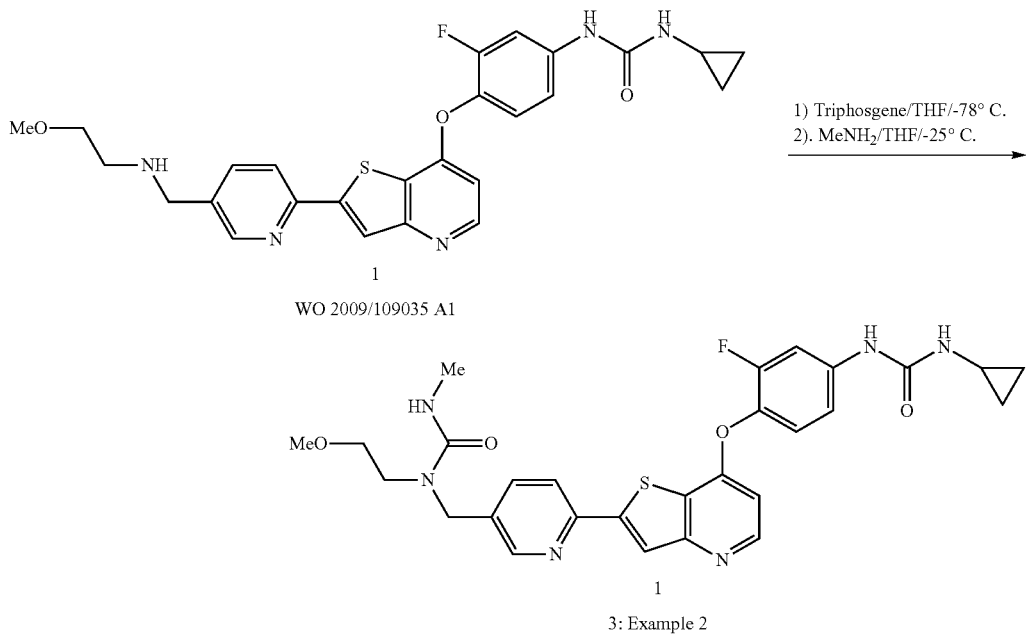

Example 2

N-[3-((6-(7-(4-(3-cyclopropylureido)-2-fluorophenoxy)thieno[3,2-b]pyridin-2-yl)pyridin-3-yl)methyl)]-N-(1-methyl)-N-[3-(2-methoxyethyl)]urea To a stirred solution of 1 (150 mg, 0.296 mmol) in THF (9 mL) at −78° C. under nitrogen was added dropwise a solution of triphosgene (50 mg, 0.17 mmol) in THF (1 mL). The reaction mixture was allowed to warm to −25° C. over 1 h, and a solution of methylamine in THF (0.6 mL, 2.0 M) was slowly added. The reaction mixture was allowed to warm-up to RT over 1.5 h and stirred at RT for 30 min. The reaction mixture was cooled down to −20° C. and a solution of triphosgene (120 mg, 0.40 mmol) in THF (2 mL) was slowly added. After 1 h of stirring between −20 and −10° C., a solution of methylamine in THF (1 mL, 2.0 M) was added. The reaction mixture was allowed to warm-up to RT over 1.5 h and stirred at RT overnight and then partitioned between AcOEt and water. The organic layer was collected and successively washed with 1N NaOH and brine, dried over anhydrous magnesium sulfate, filtered and concentrated. The residue was purified by Biotage (SNAP 25 g cartridge; MeOH/DCM: 0/100 to 10/90 over 20 CV, then 10/90 over 5 CV), to afford the title compound 3 (35 mg, 0.06 mmol, 25% yield) as a white fluffy solid. $^1$H NMR (400 MHz, DMSO-$d_6$) δ (ppm): 8.74 (s, 1H), 8.52 (d, J=5.3 Hz, 1H), 8.48 (d, J=1.6 Hz, 1H), 8.31 (s, 1H), 8.23 (d, J=8.2 Hz, 1H), 7.78-7.69 (m, 2H), 7.38 (t, J=9.1 Hz, 1H), 7.23-7.17 (m, 1H), 6.64 (dd, J=5.4, 0.9 Hz, 1H), 6.62-6.58 (m, 1H), 6.38 (q, J=4.4 Hz, 1H), 4.53 (s, 2H), 3.44-3.36 (m, 4H), 3.22 (s, 3H), 2.60 (d, J=4.3 Hz, 3H), 2.58-2.52 (m, 1H), 0.72-0.58 (m, 2H), 0.50-0.36 (m, 2H). MS (m/z): 565.2 (M+H).

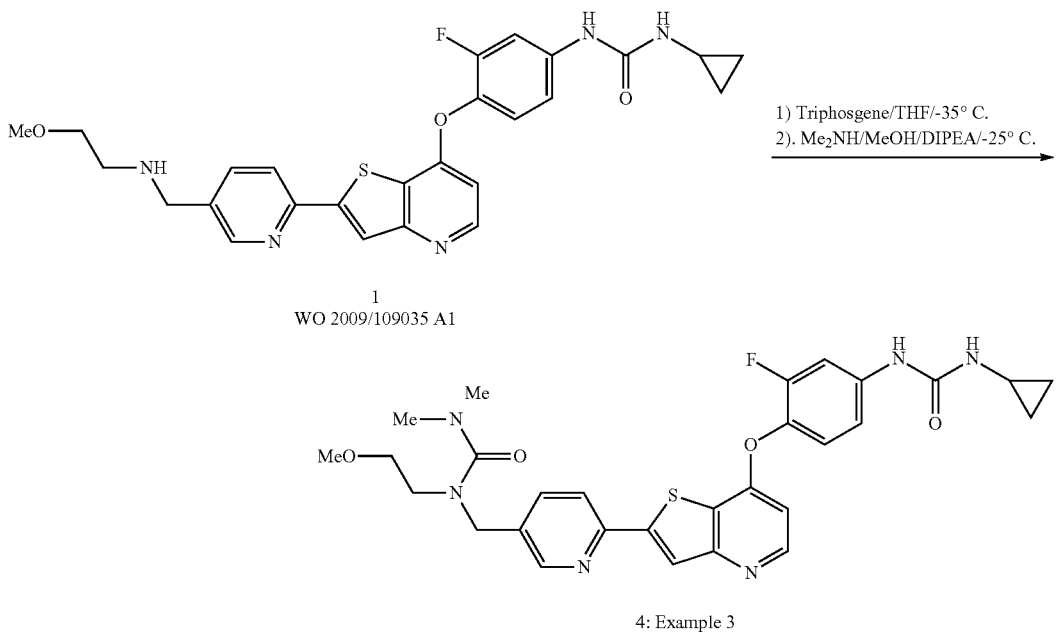

Scheme 3

1: WO 2009/109035 A1

4: Example 3

Example 3

N-[3-((6-(7-(4-(3-cyclopropylureido)-2-fluorophenoxy)thieno[3,2-b]pyridin-2-yl)pyridin-3-yl)methyl)]-N-(1,1-dimethyl)-N-[3-(2-methoxyethyl)]urea To a stirred suspension of 1 (200 mg, 0.394 mmol) in THF (25 mL) at −35° C. under nitrogen was added dropwise a solution of triphosgene (222 mg, 0.75 mmol) in THF (5 mL). The reaction mixture (suspension) was allowed to warm to −10° C. over 1.5 h, and a solution of dimethylamine in MeOH (1.87 mL, 2.0 M) was slowly added. The reaction mixture was allowed to warm to RT over 1.5 h and DIPEA (300 µL, 1.72 mmol) was added. The reaction mixture was stirred at RT for 3.5 days then partitioned between AcOEt and a saturated aqueous solution of ammonium chloride. The organic layer was successively washed with a saturated aqueous solution of ammonium chloride, a saturated aqueous solution of sodium bicarbonate, water and brine, dried over anhydrous magnesium sulfate, filtered and concentrated. The residue was purified by Biotage (SNAP 25 g cartridge; MeOH/DCM: 0/100 to 10/90 over 20 CV), to afford the title compound 4 (32 mg, 0.055 mmol, 14% yield) as an ivory solid. $^1$H NMR (400 MHz, DMSO-$d_6$) δ (ppm): 8.72 (s, 1H), 8.54 (d, J=1.4 Hz, 1H), 8.52 (d, J=5.3 Hz, 1H), 8.32 (s, 1H), 8.24 (d, J=8.2 Hz, 1H), 7.82 (dd, J=8.2, 2.2 Hz, 1H), 7.73 (dd, J=13.5, 2.5 Hz, 1H), 7.38 (t, J=9.1 Hz, 1H), 7.20 (bd, J=9.0 Hz, 1H), 6.64 (dd, J=5.4, 0.9 Hz, 1H), 6.58 (bd, J=2.5 Hz, 1H), 4.40 (s, 2H), 3.49 (t, J=5.7 Hz, 2H), 3.25 (t, J=5.7 Hz, 2H), 3.23 (s, 3H), 2.77 (s, 6H), 2.59-2.51 (m, 1H), 0.69-0.62 (m, 2H), 0.46-0.40 (m, 2H). MS (m/z): 579.6 (M+H).

Scheme 4

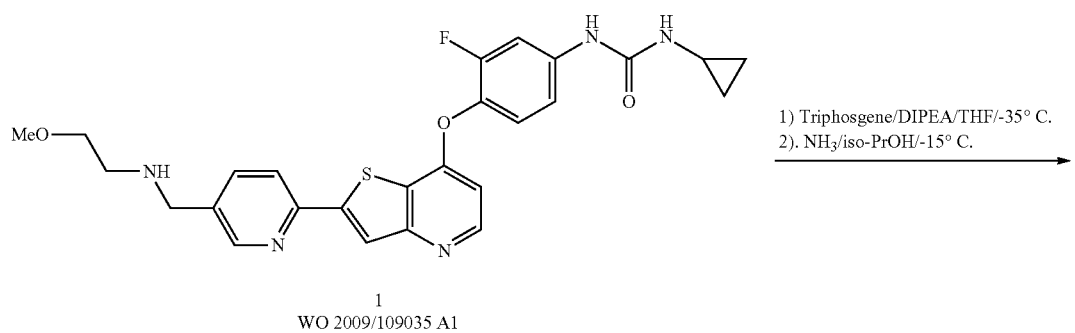

1
WO 2009/109035 A1

1) Triphosgene/DIPEA/THF/-35° C.
2). NH₃/iso-PrOH/-15° C.

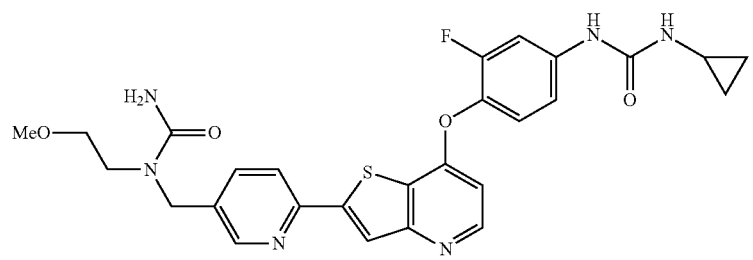

5: Example 4

Example 4

N-[3-((6-(7-(4-(3-cyclopropylureido)-2-fluorophenoxy)thieno[3,2-b]pyridin-2-yl)pyridin-3-yl)methyl)]-N-[3-(2-methoxyethyl)]urea To a stirred suspension of 1 (200 mg, 0.394 mmol) and DIPEA (200 μL, 1.12 mmol) in THF (28 mL) at −35° C. under nitrogen was added dropwise a solution of triphosgene (133 mg, 0.45 mmol) in THF (2 mL). The reaction mixture was stirred from −35° C. to −15° C. over 30 min, and a solution of ammonia in i-PrOH (1.87 mL, 2.0 M) was slowly added at −25° C. The reaction mixture was allowed to warm-up to RT over 1.5 h and 28% ammonium hydroxide solution in water (3 mL) was added. The reaction mixture was then stirred at RT overnight, partitioned between AcOEt and water. The organic layer was successively washed with water and brine, dried over anhydrous magnesium sulfate, filtered and concentrated. The residue was purified by Biotage (SNAP 25 g cartridge; MeOH/DCM: 0/100 to 10/90 over 20 CV, then 10/90 over 5 CV), to afford the title compound 5 (151 mg, 0.27 mmol, 73% yield) as an off-white solid. ¹H NMR (400 MHz, DMSO-d₆) δ (ppm): 8.72 (s, 1H), 8.52 (d, J=5.5 Hz, 1H), 8.49 (d, J=1.6 Hz, 1H), 8.31 (s, 1H), 8.24 (d, J=8.2 Hz, 1H), 7.79-7.69 (m, 2H), 7.38 (t, J=9.0 Hz, 1H), 7.20 (dd, J=8.9, 1.3 Hz, 1H), 6.64 (d, J=5.3 Hz, 1H), 6.58 (bd, J=2.5 Hz, 1H), 6.02 (s, 2H), 4.52 (s, 2H), 3.45-3.36 (m, 4H), 3.23 (s, 3H), 2.59-2.52 (m, 1H), 0.72-0.58 (m, 2H), 0.50-0.36 (m, 2H). MS (m/z): 551.5 (M+H).

Scheme 6

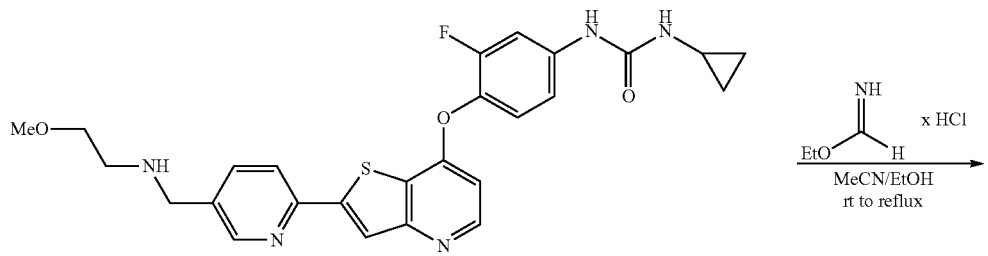

1
WO 2009/109035 A1

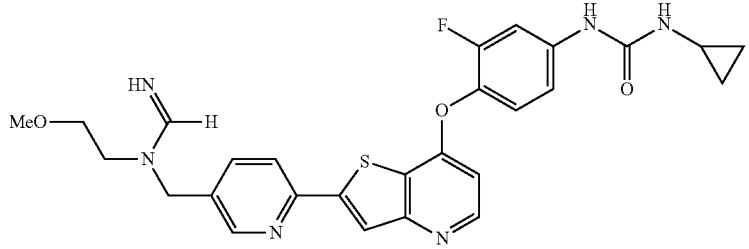

7: Example 6

Example 6

N-((6-(7-(4-(3-cyclopropylureido)-2-fluorophenoxy)thieno[3,2-b]pyridin-2-yl)pyridin-3-yl)methyl)-N-(2-methoxyethyl)formimidamide

A suspension of 1 (150 mg, 0.296 mmol) and ethylformimidate hydrochloride (130 mg, 1.18 mmol) in MeCN/EtOH (10 mL/5 mL) was heated to reflux overnight. More ethylformimidate hydrochloride (130 mg, 1.18 mmol), MeCN (20 mL) and EtOH (10 mL) were added, and the reaction mixture was heated to reflux overnight then cooled to RT. Finally the reaction mixture was concentrated and partitioned between AcOEt and water. The aqueous layer was concentrated (the desired compound is water-soluble at pH around 4-5). The residue was purified by Gilson (Phenomenex. Luna, 15µ, C18(2) 100A, 250×50.00 mm, 15 µm, 0.05% of formic acid in both MeOH/water:20/80 to 95/5 over 60 min, flow=30 mL/min), to afford the title compound 7 (30 mg, 0.056 mmol, 23% yield) as a yellow-mustard solid. $^1$H NMR (400 MHz, DMSO-$d_6$) δ (ppm): mixture of isomers and/or rotamers, 9.62-9.48 (m, ~0.5H), 8.70-8.56 (m, ~0.5H), 8.53 (d, J=5.5 Hz, 1H), 8.45-8.25 (m, 4H), 8.15-7.80 (m, ~2H), 7.75 (dd, J=13.7, 2.3 Hz, 1H), 7.36 (t, J=9.1 Hz, 1H), 7.36-7.30 (m, ~1H), 7.24 (bd, J=10.2 Hz, 1H), 6.67 (d, J=5.3 Hz, 1H), 4H are masked by water's peak, 3.24 (s, 3H), 2.60-2.50 (m, 1H), 0.66-0.58 (m, 2H), 0.44-0.38 (m, 2H). MS (m/z): 535.6 (M+H).

Scheme 7

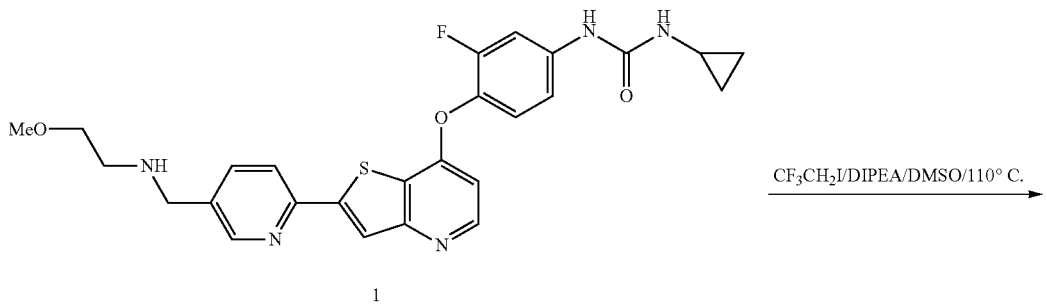

1
WO 2009/109035 A1

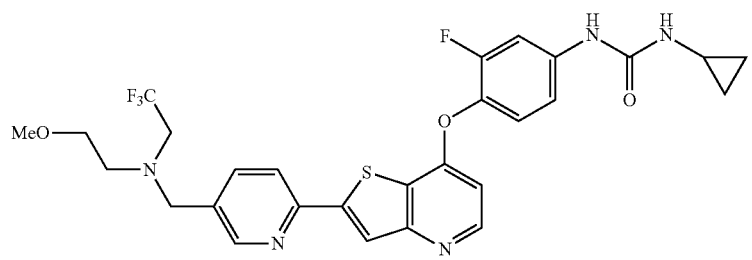

8: Example 7

Example 7

1-cyclopropyl-3-(3-fluoro-4-(2-(5-(((2-methoxy-ethyl)(2,2,2-trifluoroethyl)amino)-methyl)pyridin-2-yl)thieno [3,2-b]pyridin-7-yloxy)phenyl)urea A solution of 1 (150 mg, 0.296 mmol), DIPEA (0.3 mL, 1.72 mmol) and 2-iodo-1,1,1-trifluoroethane (2 mL, 20.29 mmol) in DMSO (4 mL) was stirred at 110° C. overnight, then cooled to RT. The reaction mixture was partitioned between AcOEt and water. The organic layer was washed with a saturated aqueous solution of ammonium chloride, a saturated aqueous solution of sodium bicarbonate, dried over anhydrous magnesium sulfate, filtered and concentrated. The residue was purified three times by Biotage (SNAP 12 g cartridge; MeOH/DCM: 00/100 to 10/90 over 20 CV, then 10/90 over 5 CV) and then by Gilson (Phenomenex, Luna 15µ. C18(2) 100A, 250×50.00 mm, 15 µm, 0.05% formic acid in both MeOH/water:60/40 to 95/5 over 60 min, flow=30 mL/min), to afford the title compound δ (2.6 mg, 0.004 mmol, 2% yield) as a colorless sticky film. $^1$H NMR (400 MHz, MeCN-d$_3$) δ (ppm): 8.55 (d, J=1.4 Hz, 1H), 8.48 (d, J=5.5 Hz, 1H), 8.06 (s, 1H), 8.02 (d, J=8.2 Hz, 1H), 7.87 (dd, J=8.2, 2.2 Hz, 1H), 7.72 (dd, J=13.6, 2.3 Hz, 1H), 7.51 (bs, 1H), 7.26 (t, J=8.5 Hz, 1H), 7.21 (dd, J=9.1, 2.3 Hz, 1H), 6.62 (dd, J=5.4, 0.9 Hz, 1H), 5.51 (bs, 1H), 3.93 (s, 2H), 3.48 (t, J=5.6 Hz, 2H), 3.36 (q, J=9.8 Hz, 2H), 3.27 (s, 3H), 2.85 (t, J=5.5 Hz, 2H), 1.79-1.75 (m, 1H), 0.77-0.69 (m, 2H), 0.56-0.49 (m, 2H). MS (m/z): 590.6 (M+H).

Example 8

1-cyclopropyl-3-(3-fluoro-4-(2-(5-((2-hydroxyethylamino)methyl)pyridin-2-yl)-thieno[3,2-b]pyridin-7-yloxy)phenyl)urea To a solution of 1 (400 mg, 0.788 mmol) in anhydrous DCM under nitrogen was slowly added BBr$_3$ in DCM (6.3 mL, 1.0 M) at −50° C. The reaction mixture was allowed to warm to RT over 5 h. The reaction mixture was then quenched by addition of methanol and concentrated. The residue was dissolved in a mixture of methanol/1N HCl/DMSO and purified twice by Gilson (Phenomenex, Luna, 15µ, C18(2) 100A, 250×50.00 mm, 15 µm, 0.05% of formic acid in both MeOH/water:20/80 to 95/5 over 60 min, flow=30 mL/min), then (Phenomenex, Luna, 15µ, C18(2) 100A, 250×50.00 mm, 15 µm, 0.05% of formic acid in both MeOH/water:20/80 to 70/30 over 60 min, flow=30 mL/min), to afford the title compound 9 (53 mg, 0.107 mmol, 15% yield, formate salt) as an off-white solid. $^1$H NMR (400 MHz, DMSO-d$_6$) δ (ppm): 9.12 (s, 1H), 8.60 (d, J=1.4 Hz, 1H), 8.52 (d, J=5.5 Hz, 1H), 8.32 (s, 1H), 8.30-8.21 (m, 2H), 7.92 (dd, J=8.1, 2.1 Hz, 1H), 7.74 (dd, J=13.6, 2.4 Hz, 1H), 7.37 (t, J=9.1 Hz, 1H), 7.22 (dd, J=9.1, 1.5 Hz, 1H), 6.94 (bd, J=2.9 Hz, 1H), 6.64 (d, J=5.5 Hz, 1H), 3.83 (s, 2H), 3.50 (t, J=5.7 Hz, 2H), 2.62 (t, J=5.7 Hz, 2H), 2.59-2.51 (m, 1H), 0.67-0.60 (m, 2H), 0.45-0.39 (m, 2H), one N<u>H</u> and one O<u>H</u> are missing. MS (m/z): 494.6 (M+H).

Compound 10 (example 9) was prepared in one step by reacting N-((6-(7-(4-(3-cyclopropylureido)-2-fluorophenoxy)thieno[3,2-b]pyridin-2-yl)pyridin-3-yl)methyl)-N-(2-methoxyethyl)acetamide with BBr$_3$ reagent similarly to compound 9 (example 8, scheme 8).

Scheme 8

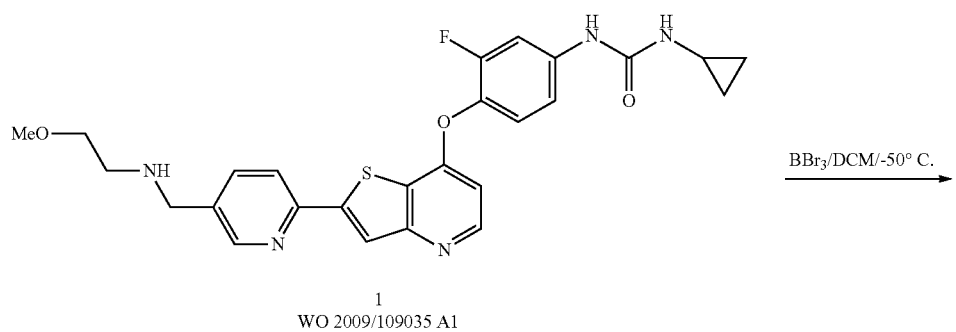

1
WO 2009/109035 A1

BBr$_3$/DCM/−50° C.

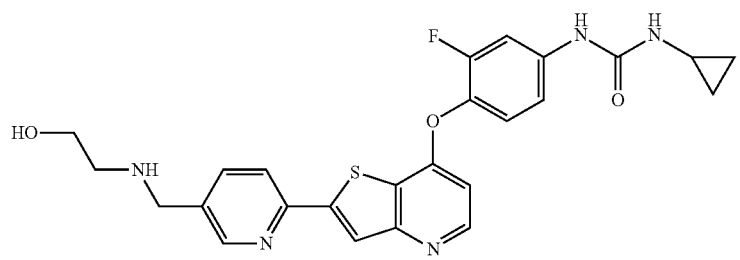

9: Example 8

TABLE 1
Characterization of compound 10 (example 9)
| Cpd | Ex. | Structure | Characterization |
|---|---|---|---|
| 10 | 9 | 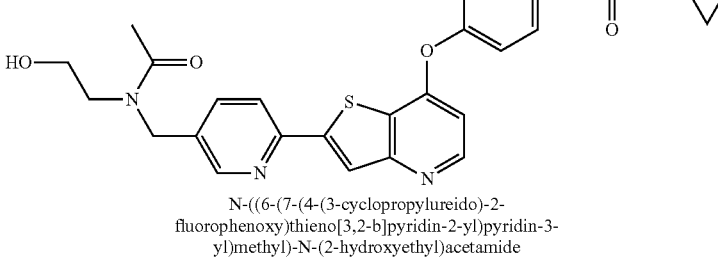<br>N-((6-(7-(4-(3-cyclopropylureido)-2-fluorophenoxy)thieno[3,2-b]pyridin-2-yl)pyridin-3-yl)methyl)-N-(2-hydroxyethyl)acetamide | $^1$H NMR (400 MHz, DMSO-$d_6$) δ (ppm): mixture of rotamers, 9.22 (s, 1H), 8.56-8.46 (m, 2H), 8.36 and 8.32 (2s, 1H), 8.29 and 8.22 (2d, J = 8.0 Hz, 1H), 7.83-7.70 (m, 2H), 7.37 (t, J = 8.8 Hz, 1H), 7.22 (d, J = 9.2 Hz, 1H), 7.07-7.02 (m, 1H), 6.67-6.62 (m, 1H), 4.90 (s, 1H), 4.72 and 4.59 (2s, 2H), 3.59-3.45 (m, 2H), 3.38 (t, J = 5.6 Hz, 2H), 2.59-2.50 (m, 1H), 2.14 and 2.06 (2s, 3H), 0.67-0.61 (m, 2H), 0.45-0.40 (m, 2H). MS (m/z): 536.6 (M + H). |
Scheme 9
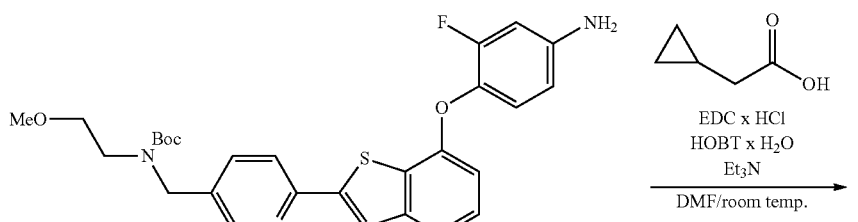
11
WO 2009/109035 A1
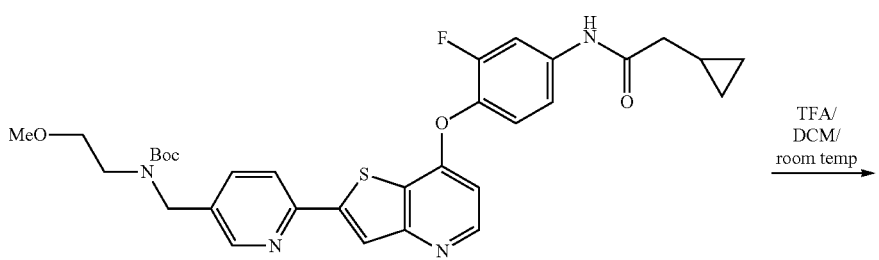
12
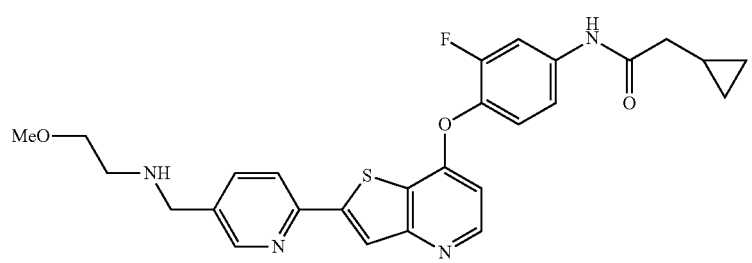
13: Example 10

Example 10

2-cyclopropyl-N-(3-fluoro-4-(2-(5-((2-methoxyethylamino)methyl)pyridin-2-yl)-thieno[3,2-b]pyridin-7-yloxy)phenyl)acetamide

Step 1. tert-butyl (6-(7-(4-(2-cyclopropylacetamido)-2-fluorophenoxy)thieno[3,2-b]-pyridin-2-yl)pyridin-3-yl)methyl(2-methoxyethyl)carbamate (12)

To a stirred solution of tert-butyl (6-(7-(4-amino-2-fluorophenoxy)thieno[3,2-b]pyridin-2-yl)pyridin-3-yl)methyl(2-methoxyethyl)carbamate (11, 500 mg, 0.95 mmol), cyclopropylacetic acid (115 mg, 1.149 mmol) and triethylamine (400 µL, 2.86 mmol) in DMF (10 mL) under nitrogen were added HOBT hydrate (161 mg, 1.05 mmol) and EDC hydrochloride (457 mg, 2.38 mmol) reagents, and the reaction mixture was stirred at RT overnight. More cyclopropylacetic acid (115 mg, 1.149 mmol) and EDC hydrochloride (500 mg, 2.61 mmol) were added, and the reaction mixture was stirred at RT overnight. The reaction mixture was then quenched by addition of water and extracted with AcOEt. The organic layer was successively washed with water (×2), a saturated aqueous solution of sodium bicarbonate, a saturated aqueous solution of ammonium chloride and brine, dried over anhydrous magnesium sulfate, filtered and concentrated. The residue was purified twice by Biotage (SiliaFlash 40 g cartridge; MeOH/DCM: 0/100 to 10/90 over 20 CV and SiliaFlash 40 g; MeOH/DCM: 0/100 to 5/95 over 20 CV, then 5/95 to 10/90 over 10 CV), to afford the title compound 12 as pale yellow sticky solid. The material was used in the next step without any further purification. MS (m/z): 607.7 (M+H).

Step 2. 2-cyclopropyl-N-(3-fluoro-4-(2-(5-((2-methoxyethylamino)methyl)pyridin-2-yl)-thieno[3,2-b]pyridin-7-yloxy)phenyl)acetamide (13)

A solution of 12 (0.94 mmol) and TFA (10 mL) in DCM (50 mL) was stirred at RT for 3 h. The TFA was removed by co-evaporation with DCM and MeOH, the residue was diluted with water, and the pH was adjusted to 12-13 with 4N NaOH. The resultant suspension was sonicated for 10 min. The solid was collected by filtration, rinsed with water, and air-dried and purified by Biotage (SiliaSep 25 g cartridge; 2% of ammonium hydroxide in MeOH/DCM: 1/99 to 10/90 over 20 CV, then 10/90 to 20/80 over 10 CV) to provide a material that was triturated with methanol to afford the title compound 13 (245 mg, 0.48 mmol, 50% over 2 steps) as a white fluffy solid. $^1$H NMR (400 MHz, DMSO-$d_6$) δ (ppm): 10.20 (s, 1H), 8.57 (bd, J=1.6 Hz, 1H), 8.52 (d, J=5.3 Hz, 1H), 8.32 (s, 1H), 8.23 (d, J=8.0 Hz, 1H), 7.94-7.86 (m, 2H), 7.47 (t, 8.7 Hz, 1H), 7.42 (dd, J=9.1, 2.2 Hz, 1H), 6.67 (d, J=5.3 Hz, 1H), 3.78 (s, 2H), 3.41 (t, J=5.7 Hz, 2H), 3.24 (s, 3H), 2.65 (t, J=5.7 Hz, 2H), 2.37-2.28 (m, 1H), 2.25 (d, J=7.0 Hz, 2H), 1.14-1.02 (m, 1H), 0.57-0.43 (m, 2H), 0.28-0.15 (m, 2H). MS (m/z): 507.5 (M+H).

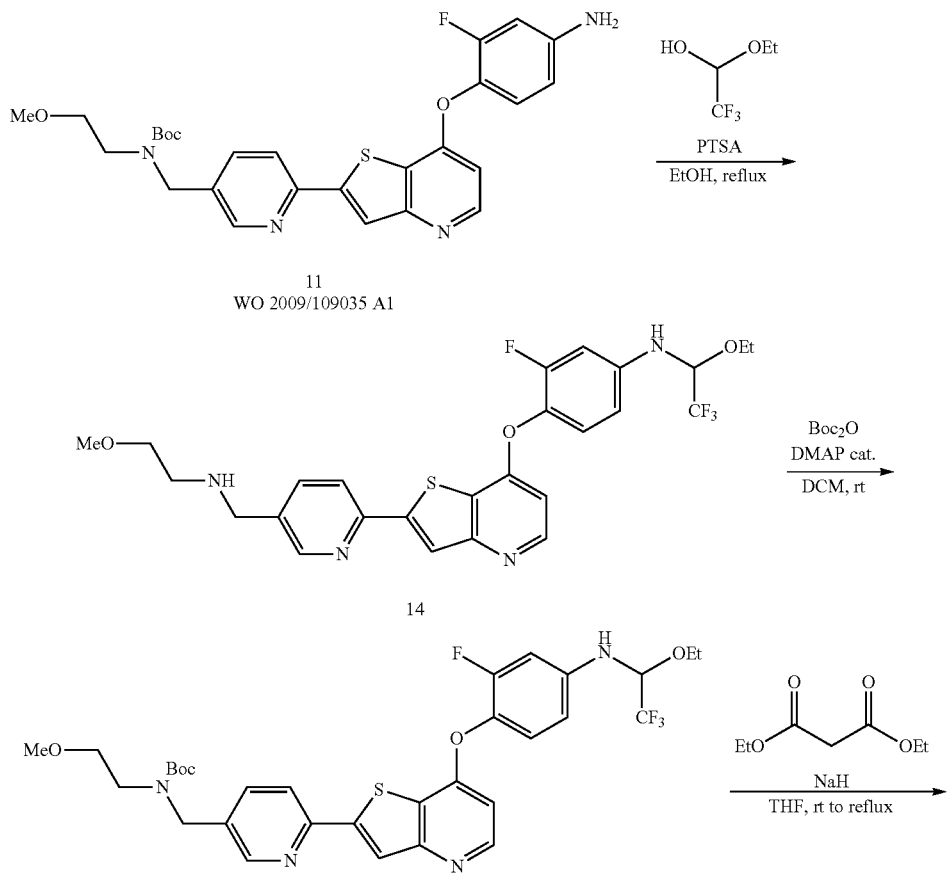

Scheme 10

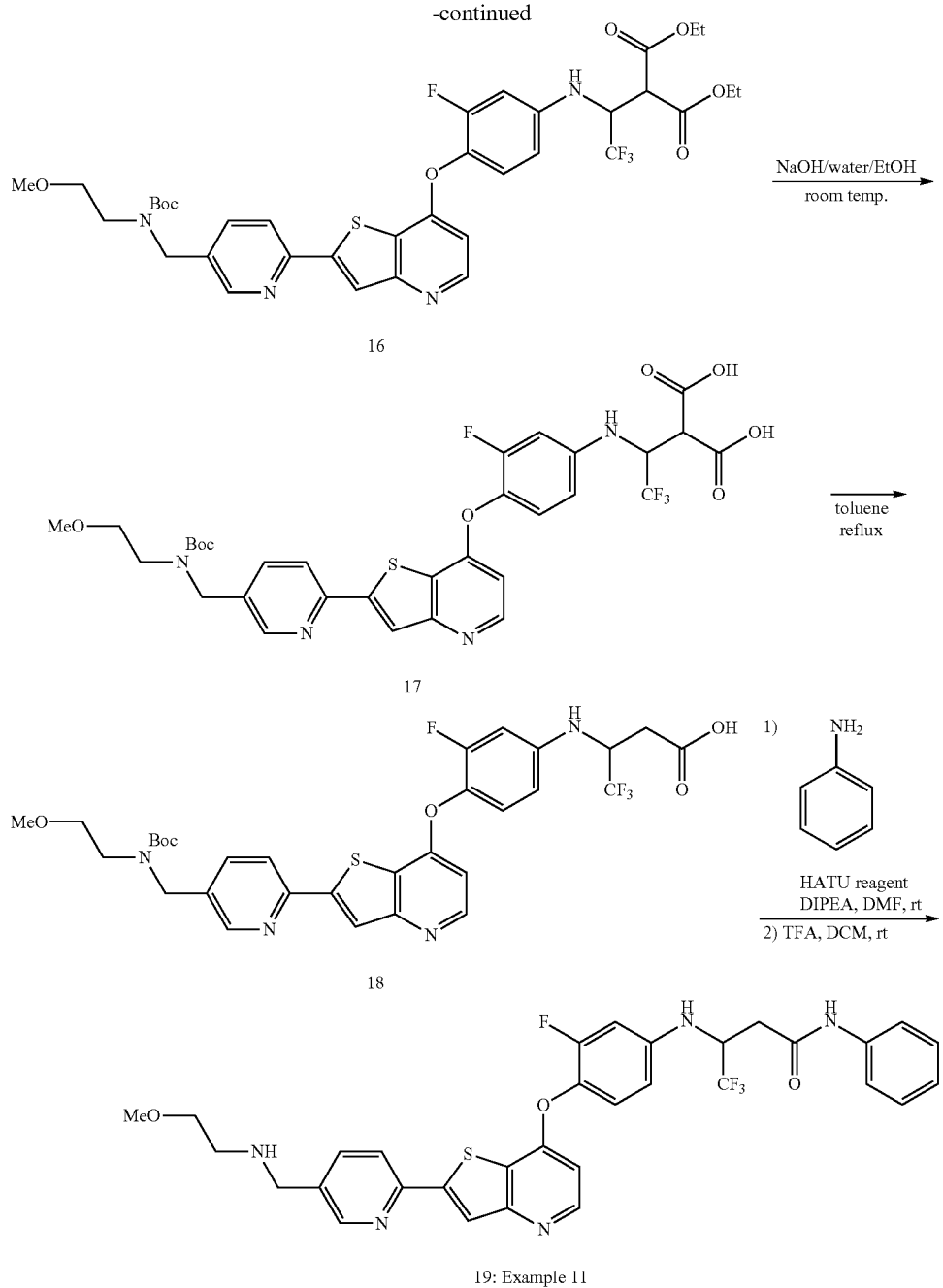

Example 11

4,4,4-trifluoro-3-(3-fluoro-4-(2-(5-((2-methoxyethylamino)methyl)pyridin-2-yl)thieno[3,2-b]pyridin-7-yloxy)phenylamino)-N-phenylbutanamide (19)

Step 1. N-(1-ethoxy-2,2,2-trifluoroethyl)-3-fluoro-4-(2-(5-((2-methoxyethylamino)-methyl)pyridin-2-yl)thieno[3,2-b]pyridin-7-yloxy)aniline (14)

A solution of 11 (2 g, 3.62 mmol), PTSA monohydrate (0.76 g, 3.98 mmol) and trifluoroacetaldehyde ethyl hemiacetal (2.38 mL, 18.11 mmol) in EtOH (50 mL) was heated to reflux overnight. More trifluoroacetaldehyde ethyl hemiacetal (1.2 mL, 9.13 mmol) was added and the reaction mixture was heated to reflux overnight. Once again, more trifluoroacetaldehyde ethyl hemiacetal (2 mL, 15.22 mmol) were added and the reaction mixture was heated to reflux overnight. Finally, another portion of trifluoroacetaldehyde ethyl hemiacetal (2 mL, 15.22 mmol) and PTSA monohydrate (0.76 g, 3.98 mmol) were added and the reaction mixture was heated to reflux for 5 days. The reaction mixture was concentrated and partitioned between AcOEt and water. The organic layer was successively washed with a saturated aqueous solution of sodium bicarbonate and brine, dried over anhydrous magnesium sulfate, filtered and concentrated. The residue was purified by Biotage (SNAP 100 g cartridge; MeOH/DCM: 0/100 to 10/90 over 20 CV), to afford the title compound 14 (1.519 g, 2.76 mmol, 76% yield) as a pale orange sticky solid. $^1$H NMR (400 MHz, DMSO-$d_6$) δ (ppm): 8.56 (d, J=1.4 Hz, 1H), 8.50 (d, J=5.5 Hz, 1H), 8.30 (s, 1H), 8.22 (d, J=8.0 Hz, 1H), 7.89 (dd, J=8.0, 2.2 Hz, 1H), 7.31 (t, J=9.1 Hz, 1H), 7.11-7.02 (m, 2H), 6.87 (dd, J=9.0, 1.8 Hz, 1H), 6.62 (dd, J=5.3, 0.8 Hz, 1H), 5.73-5.64 (m, 1H), 3.78 (s, 2H), 3.77-3.59 (m, 2H), 3.41 (t, J=5.7 Hz, 2H), 3.24 (s, 3H), 2.65 (t, J=5.7 Hz, 2H), 1.15 (t, J=7.0 Hz, 31-1), one NH proton is missing. MS (m/z): 551.6 (M+H).

Step 2. tert-butyl (6-(7-(4-(1-ethoxy-2,2,2-trifluoro-ethylamino)-2-fluorophenoxy)-thieno[3,2-b]pyridin-2-yl)pyridin-3-yl)methyl(2-methoxyethyl carbamate (15)

To a solution of 14 (1.354 g, 2.46 mmol) and DMAP (10% mol) in DCM (45 mL) was added a solution of Boc$_2$O (0.751 g, 3.44 mmol) in DCM (5 mL). The reaction mixture was stirred at RT overnight. The reaction mixture was then concentrated and partitioned between AcOEt and water. The organic layer was successively washed with a saturated aqueous solution of ammonium chloride, a saturated aqueous solution of sodium bicarbonate and brine, dried over anhydrous magnesium sulfate, filtered and concentrated. The residue was purified by Biotage (Snap 50 g, HP-Sil; MeOH/DCM: 0/100 to 10/90 over 20 CV). The desired fractions were collected, concentrated and dried under high vacuum to afford the title compound 15 (1.484 g, 2.28 mmol, 93% yield) as a colorless sticky foam. MS (m/z): 651.7 (M+H).

Step 3. diethyl 2-(1-(4-(2-(5-((tert-butoxycarbonyl(2-methoxyethyl)amino)methyl)-pyridin-2-yl)thieno[3,2-b]pyridin-7-yloxy)-3-fluorophenylamino)-2,2,2-trifluoroethyl)-malonate (16)

To a solution of 15 (1.484 g, 2.28 mmol) and diethyl malonate (0.415 mL, 2.74 mmol) in anhydrous THF (25 mL) under nitrogen was added NaH (274 mg, 6.84 mmol, 60% dispersion in mineral oil) and the reaction mixture was heated to reflux for 2 h, then cooled to RT. The reaction mixture was then quenched with a saturated aqueous solution of ammonium chloride and extracted with AcOEt. The organic layer was washed with a saturated aqueous solution of ammonium chloride (×2) and brine, dried over anhydrous magnesium sulfate, filtered and concentrated. The residue was purified by Biotage (SNAP 50 g cartridge, MeOH/DCM: 0/100 to 10/90 over 20 CV), to afford the title compound 16 (1.794 g, 2.346 mmol, 103% yield, crude) as a pale yellow sticky oil. MS (m/z): 765.6 (M+H).

Step 4. 2-(1-(4-(2-(5-((tert-butoxycarbonyl(2-methoxyethyl)amino)methyl)pyridin-2-yl)thieno[3,2-b]pyridin-7-yloxy)-3-fluorophenylamino)-2,2,2-trifluoroethyl)malonic acid (17)

A solution of 16 (1.794 g, 2.346 mmol) in a mixture of EtOH/1N NaOH (25 mL/11.7 mL) was stirred at RT overnight. The reaction mixture was then concentrated, diluted with water and the pH was adjusted to 3-4 by addition of 1N HCl. The resulting suspension was stirred for 30 min, and the solid was collected by filtration, rinsed with water, air-dried and dried under high vacuum to afford the title compound 17 (1.217 g; mixed with the acid 18) as a pale yellow fluffy solid. MS (m/z): 665.5 and 709.5 (M+H).

Step 5. 3-(4-(2-(5-((tert-butoxycarbonyl(2-methoxyethyl)amino)methyl)pyridin-2-yl)thieno[3,2-b]pyridin-7-yloxy)-3-fluorophenylamino)-4,4,4-trifluorobutanoic acid (18)

A solution of 17 (1.21 g, mixture of 17 and 18) in toluene (50 mL) was heated to reflux for 1 h then cooled to RT. The reaction mixture was then concentrated, re-dissolved in MeOH, and concentrated again. The residue was triturated with a mixture of AcOEt/hexanes. The resulting suspension (gel) was collected by filtration, rinsed with hexanes, air-dried and dried under high vacuum to afford the title compound 18 (1.157 g, 1.74 mmol, quant, yield) as an off-white solid. MS (m/z): 665.6 (M+H).

Step 6. 4,4,4-trifluoro-3-(3-fluoro-4-(2-(5-((2-methoxyethylamino)methyl)pyridin-2-yl)thieno[3,2-b]pyridin-7-yloxy)phenylamino)-N-phenylbutanamided (19)

To a solution of 18 (200 mg, 0.30 mmol), aniline (42 mg, 0.45 mmol) and DIPEA (158 µl, 0.90 mmol) in DMF (4 mL) under nitrogen was added HATU reagent (229 mg, 0.60 mmol). The reaction mixture was stirred at RT overnight. The reaction mixture was then quenched by addition of a saturated aqueous solution of ammonium chloride, and extracted with AcOEt. The organic layer was successively washed with a saturated aqueous solution of ammonium chloride, a saturated aqueous solution of sodium bicarbonate, water and brine, dried over anhydrous magnesium sulfate, filtered and concentrated. The residue was purified by Biotage (SNAP 25 g cartridge; MeOH/DCM: 0/100 to 10/90 over 20 CV), to afford the title compound 19 as a colorless sticky oil. MS (m/z): 740.8 (M+H).

A solution of this material (0.3 mmol) and TFA (5 mL) in DCM (25 mL) was stirred at RT for 3 hr. The reaction mixture was concentrated, diluted with a minimum of MeOH, and co-precipitated by addition of water. The pH was adjusted to 11-12 with 1N NaOH, and the suspension was stirred for 30 min. The solid was collected by filtration, rinsed with water, air-dried and dried under high vacuum to afford the title compound 19 (161 mg, 0.25 mmol, 84% yield over 2 steps) as an ivory solid. $^1$H NMR (400 MHz, DMSO-$d_6$) δ (ppm): 10.13 (s, 1H), 8.56 (d, J=1.4 Hz, 1H), 8.48 (d, J=5.3 Hz, 1H), 8.30 (s, 1H), 8.22 (d, J=8.0 Hz, 1H), 7.89 (dd, J=8.2, 2.2 Hz, 1H), 7.57 (bd, J=7.4 Hz, 2H), 7.34-7.27 (m, 2H), 7.24 (t, J=9.1 Hz, 1H), 7.05 (bt, J=7.4 Hz, 1H), 6.87 (dd, J=13.5, 2.7 Hz, 1H), 6.69 (dd, J=8.6, 2.2 Hz, 1H), 6.60 (d, J=9.4 Hz, 1H), 6.55 (d, J=4.7 Hz, 1H), 4.86-4.75 (m, 1H), 3.78 (s, 2H), 3.41 (t, J=5.7 Hz, 2H), 3.24 (s, 3H), 2.92 (dd, J=15.3, 3.7 Hz, 1H), 2.77 (dd, J=15.4, 9.5 Hz, 1H), 2.65 (t, J=5.7 Hz, 2H), 2.34-2.22 (m, 1H). MS (m/z): 640.5 (M+H).

Compounds 20-21 (examples 12-13) were prepared in two steps from acid 18 and the corresponding amines similarly to compound 19 (example 11, scheme 10).

TABLE 2

Characterization of compounds 20 and 21 (examples 12 and 13)

| Cpd | Ex. | Structure | Characterization |
|---|---|---|---|
| 20 | 12 | 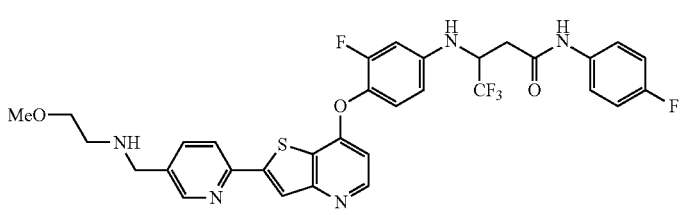 [SMILES: COCCNCc1ccc(-c2cc3nccc(Oc4ccc(NC(CC(=O)Nc5ccc(F)cc5)C(F)(F)F)cc4F)c3s2)nc1]<br>4,4,4-trifluoro-3-(3-fluoro-4-(2-(5-((2-methoxyethylamino)methy)pyridin-2-yl)thieno[3,2-b]pyridin-7-yloxy)phenylamino)-N-(4-fluorophenyl)butanamide | $^1$H NMR (400 MHz, DMSO-d$_6$) δ (ppm): 10.18 (s, 1H), 8.56 (d, J = 1.8 Hz, 1H), 8.48 (d, J = 5.3 Hz, 1H), 8.30 (s, 1H), 8.22 (d, J = 8.2 Hz, 1H), 7.89 (dd, J = 8.2, 2.2 Hz, 1H), 7.62-7.54 (m, 2H), 7.24 (t, J = 9.2 Hz, 1H), 7.19-7.11 (m, 2H), 6.87 (dd, J = 13.5, 2.5 Hz, 1H), 6.68 (dd, J = 8.9, 2.1 Hz, 1H), 6.58 (d, J = 9.4 Hz, 1H), 6.54 (d, J = 5.3 Hz, 1H), 4.86-4.74 (m, 1H), 3.78 (s, 2H), 3.41 (t, J = 5.7 Hz, 2H), 3.24 (s, 3H), 2.92 (dd, J = 15.7, 3.7 Hz, 1H), 2.75 (dd, J = 15.7, 9.6 Hz, 1H), 2.65 (t, J = 5.7 Hz, 2H), one N$\underline{H}$ is missing. MS (m/z): 658.5 (M + 1). |
| 21 | 13 | 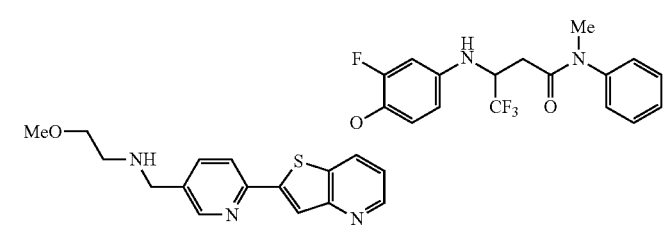<br>4,4,4-trifluoro-3-(3-fluoro-4-(2-(5-((2-methoxyethylamino)methyl)pyridin-2-yl)thieno[3,2-b]pyridin-7-yloxy)phenylamino)-N-methyl-N-phenylbutanamide | $^1$H NMR (400 MHz, DMSO)-d$_6$) δ (ppm): 8.57 (d, J = 1.4 Hz, 1H), 8.50 (d, J = 5.5 Hz, 1H), 8.30 (s, 1H), 8.22 (d, J = 8.0 Hz, 1H), 7.89 (dd, J = 8.1, 2.1 Hz, 1H), 7.52 (bt, J = 7.5 Hz, 2H), 7.46-7.36 (m, 3H), 7.24 (t, J = 9.2 Hz, 1H), 6.81 (dd, J = 13.5, 2.5 Hz, 1H), 6.63 (dd, J = 9.0, 1.8 Hz, 1H), 6.59 (d, J = 5.3 Hz, 1H), 6.46 (bd, J = 9.2 Hz, 1H), 4.81-4.66 (m, 1H), 3.78 (s, 2H), 3.41 (t, J = 5.7 Hz, 2H), 3.24 (s, 3H), 3.19 (s, 3H), 2.65 (t, J = 5.7 Hz, 2H), 2.62-2.55 (m, 1H), 2.43 (bdd, J = 16.0, 8.6 Hz, 1H), one N$\underline{H}$ is missing. MS (m/z): 654.5 (M + 1). |

Scheme 11

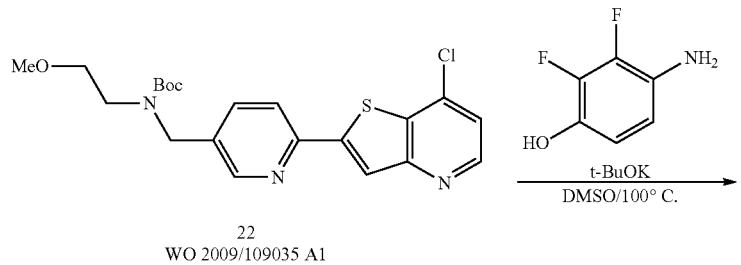

22
WO 2009/109035 A1

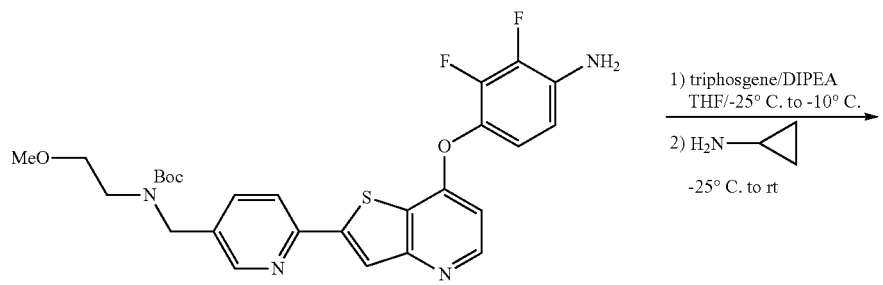

23

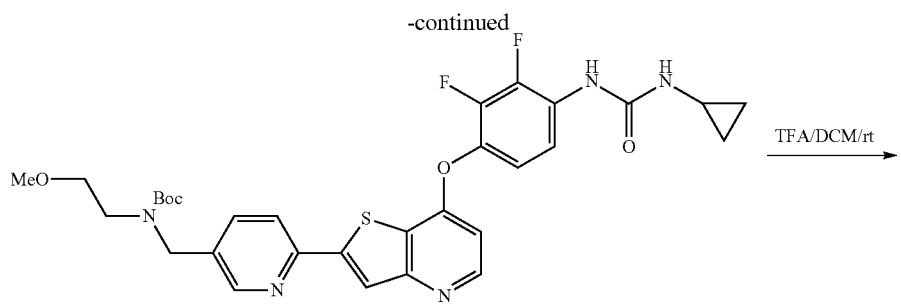

24

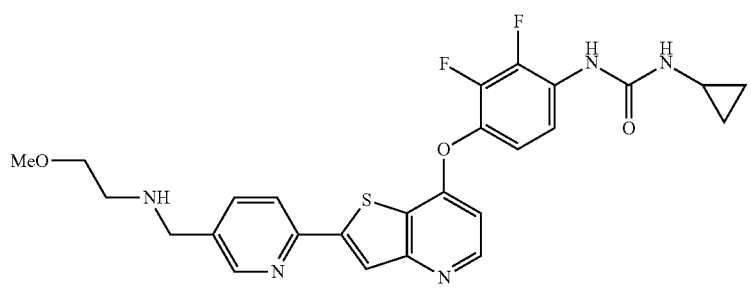

25: Example 14

Example 14

1-cyclopropyl-3-(2,3-difluoro-4-(2-(5-((2-methoxyethylamino)methyl)pyridin-2-yl)thieno[3,2-b]pyridin-7-yloxy)phenyl)urea (25)

Step 1. tert-butyl (6-(7-(4-amino-2,3-difluorophenoxy)thieno[3,2-b]pyridin-2-yl)pyridin-3-yl)methyl (2-methoxyethyl)carbamate (23)

To a stirred solution of 4-amino-2,3-difluorophenol (1.471 g, 10.14 mmol) in DMSO (11.5 mL) at RT under nitrogen was added potassium tart-butoxide (1.345 g, 11.98 mmol). After 30 min, tert-butyl (6-(7-chlorothieno[3,2-b]pyridin-2-yl)pyridin-3-yl)methyl(2-methoxyethyl)carbamate (22, 4.0 g, 9.22 mmol) was added and the reaction mixture was heated at 100° C. for 2.5 h, then cooled to RT. The reaction mixture was poured into water (90 mL) and stirred for 30 min. A saturated aqueous solution of sodium chloride was added and the mixture was stirred at RT for 3 days. The solid was collected by filtration, rinsed with water, air-dried and dried under high vacuum. The crude product was purified by Biotage (40+M cartridge; AcOEt/hexanes:50/50 over 3 CV, 50/50 to 100% AcOEt over 6 CV, then 100% AcOEt over 8 CV), to provide a material that upon trituration with diethyl ether afforded title compound 23 (1.94 g, 3.58 mmol, 38% yield) as an off-white solid. MS (m/z): 543.3 (M+H).

Step 2. tert-butyl (6-(7-(4-(3-cyclopropylureido)-2,3-difluorophenoxy)thieno[3,2-b]-pyridin-2-yl)pyridin-3-yl)methyl(2-methoxyethyl)carbamate (24)

To a stirred solution of aniline 23 (500 mg, 0.92 mmol) and DIPEA (0.8 mL, 4.61 mmol) in THF (18 mL) at −25° C. under nitrogen was added dropwise a solution of triphosgene (273 mg, 0.920 mmol) in THF (2 mL). The reaction mixture was stirred at −25° C. and cyclopropylamine (0.32 mL, 4.61 mmol) was slowly added. The reaction mixture was allowed to warm to RT over 1.5 h and stirred at RT overnight. The reaction mixture was then partitioned between AcOEt and water. The organic layer was successively washed with a saturated aqueous solution of ammonium chloride, 1N NaOH and brine, dried over anhydrous magnesium sulfate, filtered and concentrated to afford the title compound 24 as an off-white solid. The crude material was used in the next step without any further purification. MS (m/z): 626.6 (M+H).

Step 3. 1-cyclopropyl-3-(2,3-difluoro-4-(2-(5-((2-methoxyethylamino)methyl)pyridin-2-yl)thieno[3,2-b]pyridin-7-yloxy)phenyl)urea (25)

A solution of intermediate 24 (0.92 mmol) and TFA (10 mL) in DCM (50 mL) was stirred at RT for 3 h. The reaction mixture was concentrated, diluted with a minimum of MeOH and water was added. The pH was adjusted to ca pH12 with 4N NaOH. The fine suspension was sonicated for 15 min, collected by filtration, rinsed with water and dried under high vacuum to afford the title compound 25 (578 mg, 0.9 mmol, 98% yield, TFA salt) as a pale ivory solid. $^1$H NMR (400 MHz, DMSO-d$_6$) δ (ppm): 8.78-8.61 (m, 1H), 8.57 (d, J=1.6 Hz, 1H), 8.53 (d, J=5.5 Hz, 1H), 8.33 (s, 1H), 8.23 (d, J=8.2 Hz, 1H), 8.02 (t, J=7.8 Hz, 1H), 7.90 (dd, J=8.1, 2.1 Hz, 1H), 7.28 (td, J=9.0, 2.1 Hz, 1H), 7.16-7.01 (m, 1H), 6.75 (d, J=5.3 Hz, 1H), 3.78 (d, J=6.1 Hz, 2H), 3.41 (t, J=5.7 Hz, 2H), 3.24 (s, 3H), 2.65 (q, J=6.0 Hz, 2H), 2.61-2.53 (m, 1H), 2.30-2.21 (m, 1H), 0.72-0.58 (m, 2H), 0.49-0.36 (m, 2H). MS (m/z): 526.6 (M+H).

Scheme 12

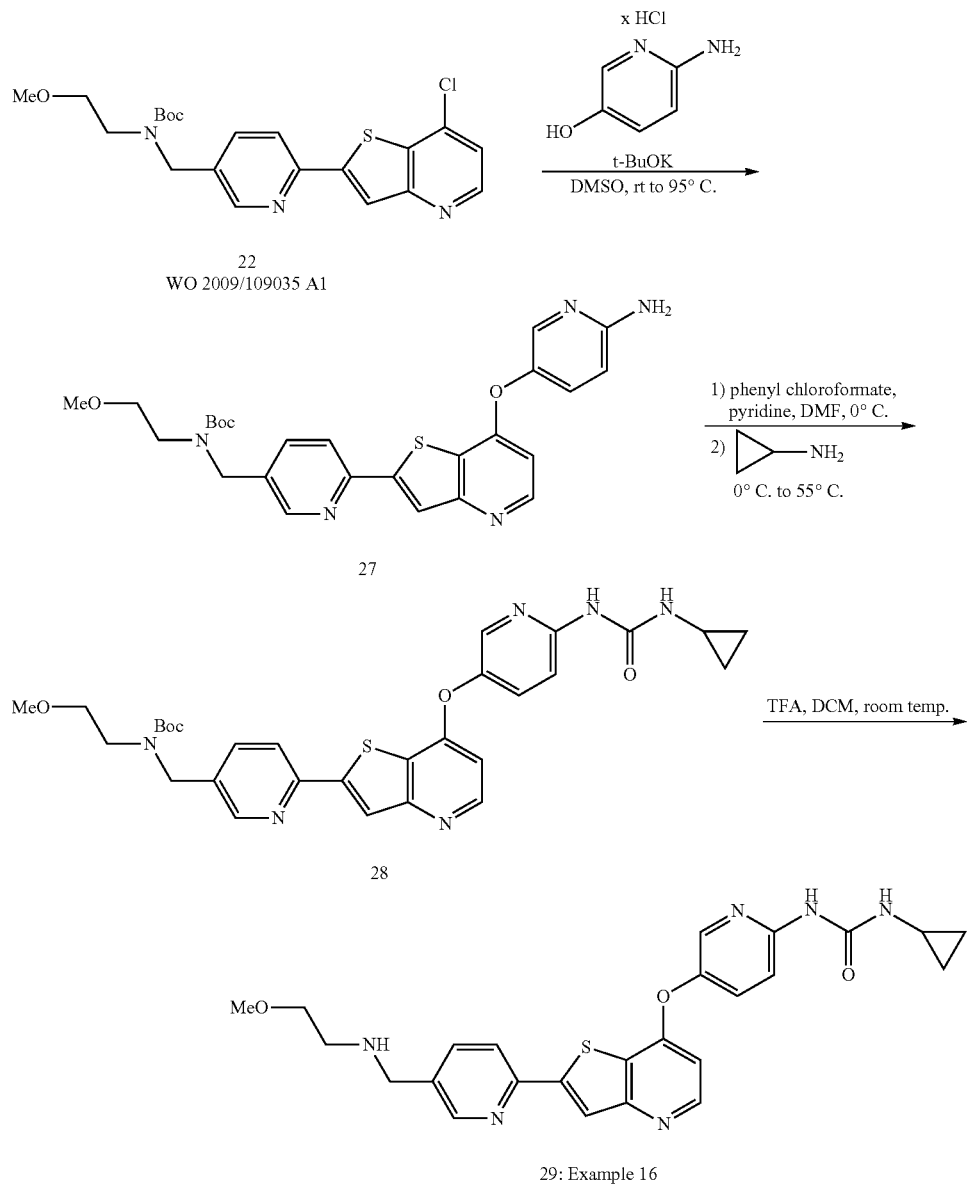

Example 16

1-cyclopropyl-3-(5-(2-(5-((2-methoxyethylamino)methyl)pyridin-2-yl)thieno[3,2-b]-pyridin-7-yloxy)pyridin-2-yl)urea (29)

Step 1. tert-butyl (6-(7-(6-aminopyridin-3-yloxy)thieno[3,2-b]pyridin-2-yl)pyridin-3-yl)methyl(2-methoxyethyl)carbamate (27)

A stirred suspension of 22 (1.0 g, 2.3 mmol), 2-amino-5-hydroxypyridine hydrochloride (405 mg, 2.77 mmol) and potassium tert-butoxide (817 mg, 6.91 mmol) in DMSO (20 mL) under nitrogen was heated to 95° C. for 1 hr then cooled to RT. The reaction mixture was then partitioned between water and AcOEt. The organic layer was successively washed with water, 0.1 N NaOH, a saturated aqueous solution of sodium bicarbonate, a saturated aqueous solution of ammonium chloride and brine, dried over anhydrous magnesium sulfate, filtered and concentrated. The residue was purified twice by Biotage (SNAP 50 g cartridge; MeOH/DCM: 0/100 to 10/90 over 20 CV and Silia Flash 80 g; MeOH/DCM: 0/100 to 10/90 over 20 CV), to afford the title compound 27 (634 mg, 1.249 mmol, 54% yield) as pale yellow sticky oil. MS (m/z): 508.6 (M+H).

Step 2. tert-butyl (6-(7-(6-(3-cyclopropylureido)pyridin-3-yloxy)thieno[3,2-b]pyridin-2-yl)pyridin-3-yl)methyl(2-methoxyethyl)carbamate (28)

To a stirred solution of aniline 27 (634 mg, 1.249 mmol) and pyridine (303 μL, 3.746 mmol) in DMF (15 mL) at 0° C. under nitrogen was added dropwise phenyl chloroformate (415 μL, 3.308 mmol). The reaction mixture was stirred at 0°

C. for 2 hrs and cyclopropylamine (433 μL, 6.250 mmol) was slowly added. The reaction mixture was allowed to warm-up to RT over 30 min and was heated at 55° C. for 5 hr then cooled to RT. The reaction mixture was partitioned between AcOEt and a saturated aqueous solution of sodium bicarbonate. The organic layer was successively washed with a saturated aqueous solution of sodium bicarbonate, 1N NaOH, a saturated aqueous solution of ammonium chloride and brine, dried over anhydrous magnesium sulfate, filtered and concentrated. The residue was purified by Biotage (SiliaFlash 40 g cartridge; MeOH/DCM: 0/100 to 10/90 over 20 CV). The desired fractions were collected, concentrated and dried under high vacuum to afford the title compound 28 (754 mg, 1.27 mmol, quant. yield) as a pale yellow sticky oil. MS (m/z): 591.6 (M+H).

Step 3. 1-cyclopropyl-3-(5-(2-(5-((2-methoxyethylamino)methyl)pyridin-2-yl)thieno[3,2-b]-pyridin-7-yloxy)pyridin-2-yl)urea (29)

A solution of 28 (754 mg, 1.27 mmol) and TFA (5 mL) in DCM (25 mL) was stirred at RT for 5.5 hr. The TFA was removed by co-evaporation with DCM, dissolved in a minimum of methanol, diluted with water, and the pH was adjusted to around 13 with 1N NaOH. The resulting sticky suspension was extracted with DCM in the presence of traces of methanol. The combined organic layer was dried over anhydrous magnesium sulfate, filtered, and concentrated. The residue was purified by Biotage (SiliaSep 40 g cartridge; 2% of ammonium hydroxide in MeOH/DCM: 1/99 to 10/90 over 20 CV) to produce a material that upon trituration with MeOH afforded the title compound 29 (360 mg, 0.734 mmol, 67% yield over 2 steps) as a white fluffy solid. $^1$H NMR (400 MHz, DMSO-d$_6$) δ (ppm): 9.23 (bs, 1H), 8.56 (d, J=1.6 Hz, 1H), 8.51 (d, J=5.5 Hz, 1H), 8.31 (s, 1H), 8.27-8.20 (m, 2H), 7.89 (dd, J=8.2, 2.2 Hz, 1H), 7.79-7.72 (m, 2H), 7.66 (bd, J=9.0 Hz, 1H), 6.69 (d, J=5.5 Hz, 1H), 3.78 (s, 2H), 3.41 (t, J=5.9 Hz, 2H), 3.24 (s, 3H), 2.68-2.57 (m, 3H), 0.74-0.60 (m, 2H), 0.52-0.39 (m, 2H), one NH is missing. MS (m/z): 491.6 (M±H).

Scheme 13

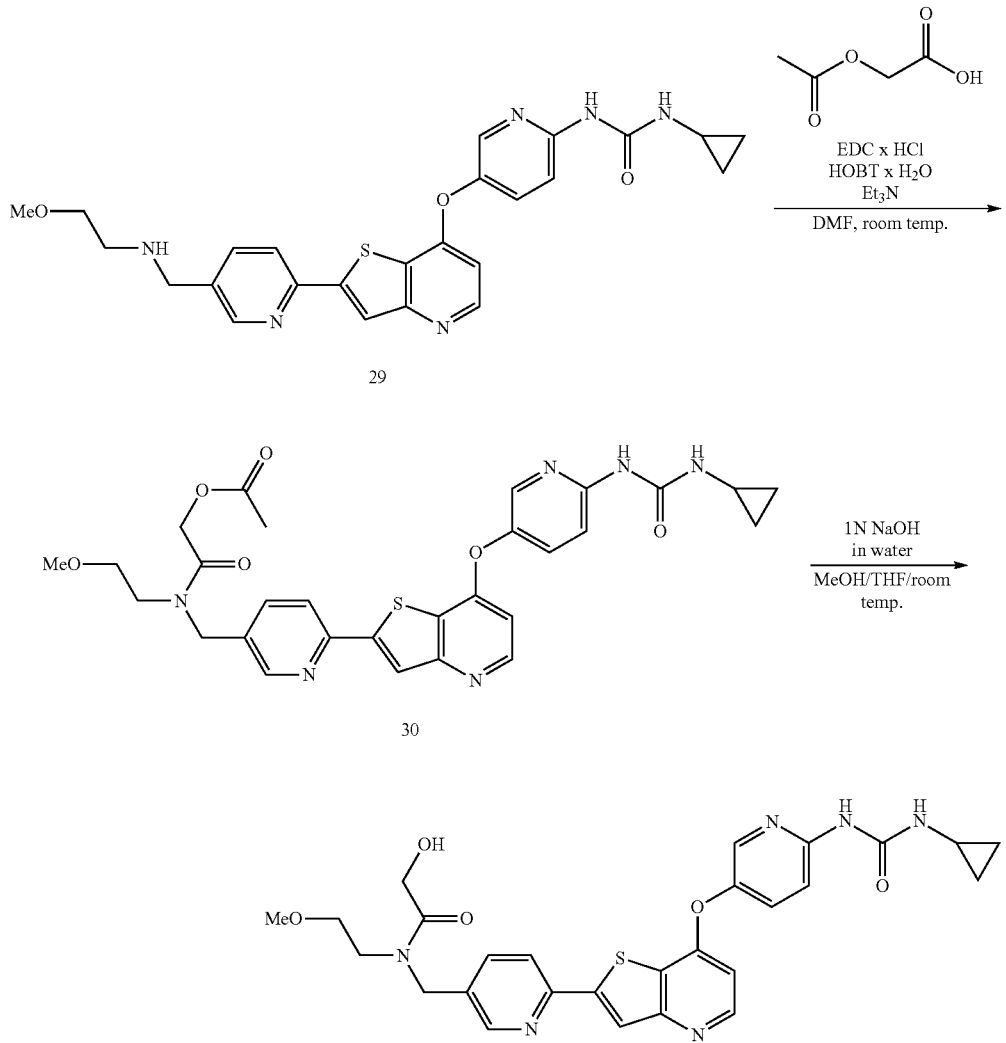

29

30

31: Example 17

Example 17

N-((6-(7-(6-(3-cyclopropylureido)pyridin-3-yloxy)thieno[3,2-b]pyridin-2-yl)pyridin-3-yl)methyl)-2-hydroxy-N-(2-methoxyethyl)acetamide (31)

Step 1. 2-(((6-(7-(6-(3-cyclopropylureido)pyridin-3-yloxy)thieno[3,2-b]pyridin-2-yl)pyridin-3-yl)methyl)(2-methoxyethyl)amino)-2-oxoethyl acetate (30)

To a stirred solution of compound 29 (108 mg. 0.22 mmol), acetoxyacetic acid (73 mg, 0.62 mmol) and triethylamine (114 μL, 0.82 mmol) in DMF (3 mL) under nitrogen were added EDC hydrochloride (118 mg, 0.62 mmol) and HOBT monohydrate (39 mg, 0.25 mmol) reagents, and the reaction mixture was stirred at RT overnight. The reaction was then quenched by addition of water and extracted with AcOEt. The organic phase was successively washed with water, a saturated aqueous solution of sodium bicarbonate, a saturated aqueous solution of ammonium chloride and brine, dried over anhydrous magnesium sulfate, filtered and concentrated. The crude 30 was used in the next step without any further purification. MS (m/z): 591.7 (M+H).

Step 2. N-((6-(7-(6-(3-cyclopropylureido)pyridin-3-yloxy)thieno[3,2-b]pyridin-2-yl)pyridin-3-yl)methyl)-2-hydroxy-N-(2-methoxyethyl)acetamide (31)

To a stirred solution of 30 (from the previous step) in MeOH/THF (15/5 mL) was added 1N NaOH (2.6 mL). The reaction mixture was stirred at RT overnight, concentrated and diluted with water. The resultant suspension was shaken for 15 min. The solid was collected by filtration, rinsed with water and air-dried. The residue was purified by Biotage (SiliaSep 25 g cartridge; MeOH/DCM: 0/100 to 10/90 over 20 CV) to produce a material that upon trituration with methanol afforded the title compound 31 (79 mg, 0.144 mmol, 72% over 2 steps) as a white fluffy solid. $^1$H NMR (400 MHz, DMSO-$d_6$) δ (ppm): mixture of rotamers, 9.23 (bs, 1H), 8.56-8.49 (m, 2H), 8.38-8.20 (m, 3H), 7.84-7.70 (m, 3H), 7.66 (bd, J=9.0 Hz, 1H), 6.73-6.67 (m, 1H), 4.82-4.57 (m, 3H), 4.23 and 4.13 (2d, J=6.0 Hz, 2H), 3.52-3.39 (m, 4H), 3.23-3.21 (2s, 3H), 2.65-2.57 (m, 1H), 0.74-0.60 (m, 2H), 0.53-0.37 (m, 2H). MS (m/z): 549.6 (M+H).

Scheme 14

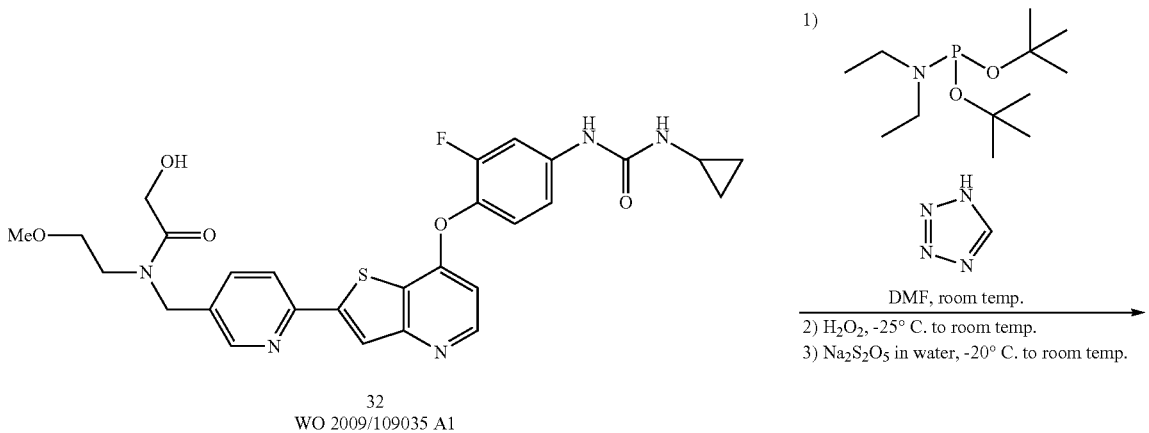

32
WO 2009/109035 A1

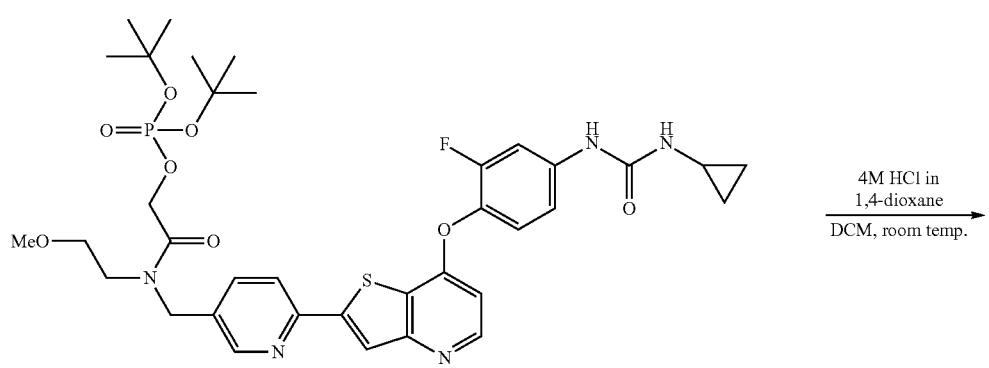

33

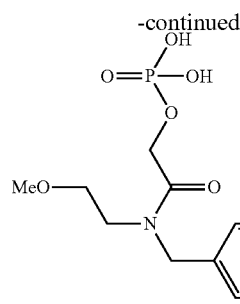

34: Example 18

Example 18

2-(((6-(7-(4-(3-cyclopropylureido)-2-fluorophenoxy)thieno[3,2-b]pyridin-2-yl)pyridin-3-yl)methyl)(2-methoxyethyl)amino)-2-oxoethyl dihydrogen phosphate (34)

Step 1. di-tert-butyl 2-(((6-(7-(4-(3-cyclopropylureido)-2-fluorophenoxy)thieno[3,2-b]-pyridin-2-yl)pyridin-3-yl)methyl)(2-methoxyethyl)amino)-2-oxoethyl phosphate (33)

To a stirred suspension of compound 32 (200 mg, 0.35 mmol) and tetrazole (74 mg, 1.06 mmol) in DMF (3 mL) under argon was added (t-BuO)$_2$PNEt$_2$ (750 µL, 2.70 mmol)) in three portions over 5 hr. The reaction mixture was stirred at RT for 2 days, cooled-down to −25° C. and hydrogen peroxide (0.217 mL, 3.54 mmol, 50% in water) was slowly added. The reaction mixture was allowed to warm to RT over 1 h, and stirred at RT for 45 min. The reaction mixture was then cooled down again to −20° C. and an aqueous solution of sodium metabisulfite (1.5 g in 10 mL of water) was slowly added. The reaction mixture was allowed to warm to RT over 1 h, and partitioned between water and AcOEt. The organic layer was successively washed with water, a saturated aqueous solution of sodium bicarbonate, a saturated aqueous solution of ammonium chloride and brine, dried over anhydrous magnesium sulfate, filtered and concentrated. The residue was purified by Biotage (SiliaSep 25 g cartridge; MeOH/DCM: 0/100 to 10/90 over 20 CV), to afford the title compound 33 as a sticky oil which was used in the next step without any further purification. MS (m/z): 646.5, 702.5, 758.7 (M+H).

Step 2. 2-(((6-(7-(4-(3-cyclopropylureido)-2-fluorophenoxy)thieno[3,2-b]pyridin-2-yl)pyridin-3-yl)methyl)(2-methoxyethyl)amino)-2-oxoethyl dihydrogen phosphate (34)

To a stirred solution of 33 from the previous step in DCM (15 mL) was added a solution of 4M HCl in 1,4-dioxane (0.44 mL, 1.75 mmol). The reaction mixture (suspension) was stirred at RT for 1 h. The solid was collected by filtration, rinsed with DCM and dried under high vacuum. The residue was suspended in MeOH, concentrated and triturated with a minimum of methanol/water to afford the title compound 34 (136 mg, 0.21 mmol, 60% over 3 steps) as an off-white fluffy solid. $^1$H NMR (400 MHz, DMSO-d$_6$) δ (ppm): mixture of rotamers, 8.71 (s, 1H), 8.58-8.48 (m, 2H), 8.37 and 8.33 (2 s, 1H), 8.29 and 8.24 (2d, J=8.2 Hz, 1H), 7.86-7.77 (m, 1H), 7.73 (dd, J=13.6, 2.4 Hz, 1H), 7.38 (t, J=9.1 Hz, 1H), 7.20 (bd, J=9.0 Hz, 1H), 6.64 (d, J=5.3 Hz, 1H), 6.57 (d, J=2.5 Hz, 1H), 4.74-4.50 (m, 4H), 3.47 (bs, 4H), 3.24 and 3.21 (2s, 3H), 2.59-2.51 (m, 1H), 0.73-0.58 (m, 2H), 0.50-0.36 (m, 2H). MS (m/z): 646.7 (M+H).

Compounds 35-38 (examples 19-22) were prepared in one step by reacting the corresponding secondary amine precursors 25 (scheme 11), 179 (scheme 43), 29 (scheme 12) and 288 (scheme 64) with ethyl isocyanate.

TABLE 3

Characterization of compounds 35-38 (examples 19-22)

| Cpd | Ex. | Structure | Characterization |
|---|---|---|---|
| 35 | 19 | 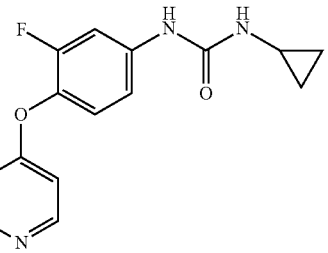<br>N-[3-((6-(7-(4-(3-cyclopropylureido)-2,3-difluorophenoxy)thieno[3,2-b]pyridin-2-yl)pyridin-3-yl)methyl)]-N-(1-ethyl)-N-(2-methoxyethyl)urea | $^1$H NMR (400 MHz. DMSO-d$_6$ δ (ppm): 8.53 (d, J = 5.5 Hz, 1H), 8.51-8.46 (m, 2H), 8.33 (s, 1H), 8.25 (d, J = 8.2 Hz, 1H), 8.03 (bt, J = 7.8 Hz, 1H), 7.75 (dd. J = 8.2, 2.2 Hz, 1H), 7.28 (td, J = 8.9, 2.1 Hz, 1H), 6.88 (bd, J = 2.9 Hz, 1H), 6.75 (dd, J = 5.5. 0.6 Hz, 1H), 6.44 (t, J = 5.4 Hz, 1H), 4.53 (s, 2H). 3.44-3.35 (m, 4H), 3.23 (s, 3H), 3.12-3.04 (m, 2H), 2.61-2.53 (m. 1H), 1.02 (t, J = 7.1 Hz, 3H), 0.73-0.59 (m, 2H), 0.49-0.35 (m, 2H). MS (m/z): 597.6 (M + H). |

TABLE 3-continued

Characterization of compounds 35-38 (examples 19-22)

| Cpd | Ex. | Structure | Characterization |
|---|---|---|---|
| 36 | 20 | N-[3-((6-(7-(4-(3-cyclopropylureido)-2-fluorophenoxy)-thieno[3,2-b]-pyridin-2-yl)pyridin-3-yl)methyl)]-N-(1-ethyl)-N-[3-(2,5,8,11-tetraoxatridecan-13-yl)]urea | $^1$H NMR (400 MHz, DMSO-$d_6$) δ (ppm): 8.76 (s, 1H), 8.52 (d, J = 5.5 Hz, 1H), 8.49 (d, J = 2.0 Hz, 1H), 8.31 (s, 1H), 8.23 (d, J = 8.2 Hz, 1H), 7.79-7.69 (m, 2H), 7.38 (t, J = 9.0 Hz, 1H), 7.20 (dd, J = 8.8, 1.4 Hz, 1H), 6.64 (d, J = 5.5 Hz, 1H), 6.61 (bd, J = 2.5 Hz, 1H), 6.44 (t, J = 5.4 Hz, 1H), 4.54 (s, 2H), 3.56-3.35 (m, 16H), 3.21 (s, 3H), 3.12-3.04 (m, 2H), 2.59-2.51 (m, 1H), 1.03 (t, J = 7.1 Hz, 3H), 0.72-0.58 (m, 2H), 0.49-0.36 (m, 2H). MS (m/z): 711.7 (M + H). |
| 37 | 21 | N-[3((6-(7-(6-(3-cyclopropylureido)-pyridin-3-yloxy)thieno[3,2-b]-pyridin-2-yl)pyridin-3-yl)methyl)]-N-(1-ethyl)-N-[3-(2-methoxyethyl)]urea | $^1$H NMR (400 MHz, DMSO-$d_6$) δ (ppm): 9.23 (bs, 1H), 8.52 (d, J = 5.5 Hz, 1H), 8.48 (d, J = 1.8 Hz, 1H), 8.31 (s, 1H), 8.27-8.21 (m, 2H), 7.78-7.72 (m, 3H), 7.66 (bd, J = 9.0 Hz, 1H), 6.69 (d, J = 5.3 Hz, 1H), 6.44 (t, J = 5.4 Hz, 1H), 4.53 (s, 2H), 3.44-3.35 (m, 4H), 3.23 (s, 3H), 3.12-3.03 (m, 2H), 2.65-2.57 (m, 1H), 1.02 (t, J = 7.1 Hz, 3H), 0.74-0.60 (m, 2H), 0.51-0.38 (m, 2H). MS (m/z): 562.6 (M + H). |
| 38 | 22 | N-[3-(2-(6-(7-(4-(3-cyclopropylureido)-2-fluorophenoxy)-thieno[3,2-b]-pyridin-2-yl)pyridin-3-yl)ethyl)]-N-(1-ethyl)-N-[3-(2-methoxyethyl)]urea | $^1$H NMR (400 MHz, DMSO-$d_6$) δ (ppm): 8.75 (s, 1H). 8.51 (d, J = 5.5 Hz, 1H), 8.49 (bd, J = 1.6 Hz, 1H), 8.31 (s, 1H), 8.21 (d., J = 8.2 Hz, 1H), 7.81 (dd, J = 8.1, 2.1 Hz, 1H), 7.73 (dd, J = 13.6, 2.4 Hz, 1H), 7.38 (t, J = 9.1 Hz, 1H), 7.20 (bd, J = 9.2 Hz, 1H), 6.63 (bd, J = 5.4 Hz, 1H), 6.61 (bd, J = 2.7 Hz, 1H), 6.25 (t, J = 5.6 Hz, 1H), 3.45 (t, J = 7.4 Hz, 2H), 3.37 (t, J = 4.7 Hz, 2H), 3.31 (t, J = 4.9 Hz, 2H), 3.24 (s, 3H), 3.07-2.98 (m, 2H), 2.83 (t, J = 7.4 Hz, 2H), 2.59-2.51 (m, 1H), 0.97 (t, J = 7.1 Hz, 3H), 0.72-0.58 (m, 2H), 0.49-0.36 (m, 2H). MS (m/z): 593.6 (M + H). |

Compounds 39-44 (examples 23-28) were prepared in one step by reacting the corresponding amine precursor 20 (table 2), 29 (scheme 12), 288 (scheme 64), 13 (scheme 9), 98 (scheme 25) and 108 (scheme 28), with acetic anhydride.

TABLE 4

Characterization of compounds 39-44 (examples 23-28)

| Cpd | Ex. | Structure | Characterization |
|---|---|---|---|
| 39 | 23 | 4,4,4-trifluoro-3-(3-fluoro-4-(2-(5-((N-methoxyethyl)acetamido)methyl)pyridin-2-yl)thieno[3,2-b]-pyridin-7-yloxy)-phenylamino)-N-(4-fluorophenyl)butanamide | $^1$H NMR (400 MHz, DMSO-$d_6$) δ (ppm): mixture of rotamers, 10.29 (s, 1H), 8.55-8.46 (m, 2H), 8.34 and 8.31 (2s, 1H), 8.28 and 8.22 (2d, J = 8.2 Hz, 1H), 7.82-7.74 (m, 1H), 7.63-7.54 (m, 2H), 7.23 (t, J = 9.1 Hz, 1H), 7.19-7.10 (m, 2H), 6.87 (dd, J = 13.5, 2.5 Hz, 1H), 6.73-6.61 (m, 2H), 6.57-6.51 (m, 1H), 4.86-4.73 (m, 1H), 4.71 and 4.59 (2s, 2H), 3.54-3.40 (m, 4H), 3.24 and 3.21 (2s, 3H), 2.90 (dd, J = 15.4, 3.6 Hz, 1H), 2.76 (dd, J = 15.5, 9.7 Hz, 1H), 2.13 and 2.05 (2s, 3H). MS (m/z): 700.6 (M + H). |

TABLE 4-continued

Characterization of compounds 39-44 (examples 23-28)

| Cpd | Ex. | Structure | Characterization |
|---|---|---|---|
| 40 | 24 | 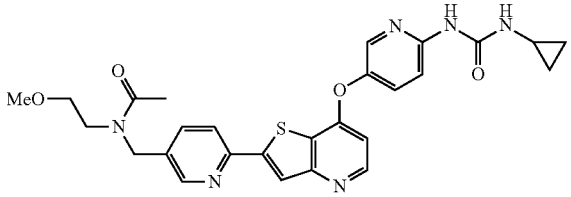 [SMILES: COCCN(Cc1ccc(-c2cc3nccc(Oc4ccc(NC(=O)NC5CC5)nc4)c3s2)nc1)C(C)=O]<br>N-((6-(7-(6-(3-cyclopropylureido)-pyridin-3-yloxy)thieno[3,2-b]-pyridirin-2-yl)pyridin-3-yl)methyl)-N-(2-methoxyethyl)-acetamide | $^1$H NMR (400 MHz, DMSO-d$_6$) δ (ppm): mixture of rotamers, 9.24 (bs, 1H), 8.60-8.48 (m, 2H), 8.38-8.14 (m, 3H), 7.89-7.62 (m, 4H), 6.73-6.67 (m, 1H). 4.73-4.54 (m, 2H), 3.54-3.37 (m, 4H), 3.26-3.18 (m, 3H), 2.65-2.57 (m, 1H), 2.12 and 2.05 (2s, 3H), 0.74-0.60 (m, 2H), 0.52-0.39 (m, 2H). MS (m/z): 533.6 (M + H). |
| 41 | 25 | 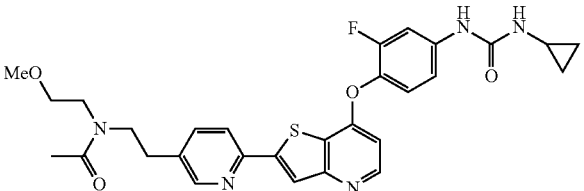<br>N-(2-(6-(7-(4-(3-cyclopropylureido)-2-fluorophcnoxy)-thieno[3,2-b]-pyridin-2-yl)pyridin-3-yl)ethyl)-N-(2-methoxyethyl)-acetamide | $^1$H NMR (400 MHz, DMSO-d$_6$) δ (ppm): mixture of rotamers, 8.75 (s, 1H), 8.58-8.47 (m, 2H), 8.33 and 8.31 (2s, 1H), 8.23 and 8.20 (2d, J = 8.1 Hz, 1H), 7.86 and 7.81 (2dd, J = 8.1, 2.1 Hz, 1H), 7.73 (dd, J = 13.6, 2.4 Hz, 1H), 7.38 (t, J = 9.0 Hz. 1H), 7.20 (bd, J = 10.2 Hz, 1H), 6.64 (d, J = 5.5 Hz, 1H), 6.61 (bd, J = 2.3 Hz, 1H), 3.57 (t, J = 7.4 Hz, 1H), 3.52 (t, J = 7.4 Hz, 1H), 3.47-3.40 (m, 4H), 3.26 and 3.25 (2s, 3H), 2.92 (t, J = 7.4 Hz, 1H), 2.84 (t, J = 7.3 Hz, 1H), 2.59-2.51 (m, 1H), 2.00 and 1.91 (2s, 3H), 0.72-0.58 (m, 2H), 0.49-0.36 (m, 2H). MS (m/z): 564.6 (M + H). |
| 42 | 26 | 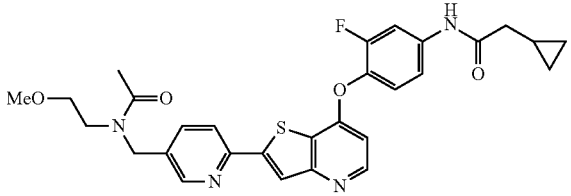 [SMILES: COCCN(Cc1ccc(-c2cc3nccc(Oc4ccc(NC(=O)CC5CC5)cc4F)c3s2)nc1)C(C)=O]<br>2-cyclopropyl-N-(3-fluoro-4-(2-(5-((N-(2-methoxyethyl)-acetamido)methyl)pyridin-2-yl)thieno[3,2-b]-pyridin-7-yloxy)phenyl)-acetamide | $^1$H NMR (400 MHz, DMSO-d$_6$) δ (ppm): mixture of rotamers, 10.20 (s, 1H), 8.55-8.48 (m, 2H), 8.37 and 8.33 (2s, 1H), 8.29 and 8.23 (2d, J = 8.1 Hz, 1H), 7.90 (dd, J = 13.2, 2.2 Hz, 1H), 7.82-7.75 (m, 1H), 7.47 (t, J = 8.8 Hz, 1H), 7.42 (dd, J = 8.9, 2.2 Hz, 1H), 6.70-6.65 (m, 1H), 4.71 and 4.59 (2s, 2H), 3.54-3.40 (m, 4H), 3.24 and 3.21 (2s, 3H), 2.25 (d, J = 7.0 Hz, 2H), 2.13 and 2.05 (2s, 3H), 1.13-1.02 (m, 1H), 0.57-0.43 (m, 2H), 0.28-0.15 (m, 2H). MS (m/z): 549.6 (M + H). |
| 43 | 27 | 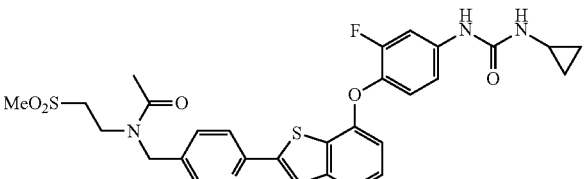<br>N-((6-(7-(4-(3-cyclopropylureido)-2-fluorophenoxy)thieno[3,2-b]pyridin-2-yi)pyridin-3-yl)methyl)-N-(2-(methylsulfonyl)ethyl)acetamide | $^1$H NMR (400 MHz, DMSO-d$_6$) δ (ppm): mixture of rotamers, 8.80 (s, 1H), 8.58-8.50 (m, 2H), 8.39-8.33 (m, 1H), 8.32-8.23 (m, 1H), 7.86-7.77 (m, 1H), 7.76-7.70 (m, 1H), 7.38 (t, J = 8.8 Hz, 1H), 7.21 (d, J = 8.8 Hz, 1H), 6.68-6.63 (m, 2H), 4.72 and 4.60 (2s, 2H), 3.75-3.52 (m, 3H), 3.40-3.30 (m, 1H), 3.04 and 3.01 (2s, 3H), 2.59-2.50 (m, 1H), 2.19 and 2.09 (2s, 3H), 0.68-0.62 (m, 2H), 0.45-0.40 (m, 2H). MS (m/z): 598.5 (M + H). |
| 44 | 28 | 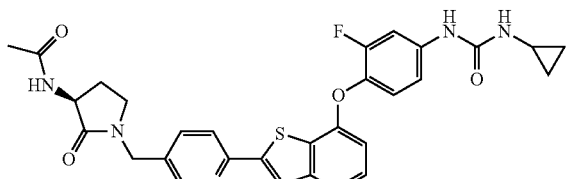<br>(S)-N-(1-((6-(7-(4-(3-cyclopropylureido)-2-fluorophenoxy)thieno[3,2-b]pyridin-2-yl)pyridin-3-yl)methyl)-2-oxopyrrolidin-3-yl)acetamide | $^1$H NMR (400 MHz, DMSO-d$_6$) δ (ppm): 8.75 (s, 1H), 8.55 (d, J = 1.6 Hz, 1H), 8.52 (d, J = 5.6 Hz, 1H), 8.36 (s, 1H), 8.30-8.25 (m, 2H), 7.84 (dd, J = 8.0, 2.0 Hz, 1H), 7.73 (dd, J = 13.6, 2.4 Hz, 1H), 7.38 (t, J = 9.2 Hz, 1H), 7.23-7.18 (m, 1H), 6.65 (d, J = 5.2 Hz, 1H), 6.60 (d, J = 2.4 Hz, 1H), 4.62-4.35 (m, 3H), 3.30-3.23 (m, 2H), 2.59-2.52 (m, 1H), 2.34-2.24 (m, 1H), 1.86 (s, 3H), 1.84-1.74 (m, 1H), 0.68-0.62 (m, 2H), 0.46-0.40 (m, 2H). MS (m/z): 575.5 (M + H). |

Compounds 45-46 (examples 29-30) were prepared in two steps from the corresponding secondary amine precursor 179 (scheme 43) and 288 (scheme 64), and acetoxyacetic acid similarly to compound 31 (example 17, scheme 13).

TABLE 5

Characterization of compounds 45-46 (examples 29-30)

| Cpd | Ex. | Structure | Characterization |
|---|---|---|---|
| 45 | 29 | N-((6-(7-(4-(3-cyclopropylureido)-2-fluorophenoxy)-thieno[3,2-b]-pyridin-2-yl)pyridin-3-yl)methyl])-2-hydroxy-N-(2,5,8,11-tetraoxatridecan-13-yl)acetamide | $^1$H NMR (400 MHz, DMSO-$d_6$) δ (ppm): mixture of rotamers, 8.73 (s, 1H), 8.57-8.49 (m, 2H), 8.38-8.20 (m, 2H)S 7.85-7.76 (m, 1H), 7.73 (dd, J = 13.6, 2.4 Hz, 1H), 7.38 (t, J = 9.1 Hz, 1H), 7.20 (bd, J = 9.5 Hz, 1H), 6.67-6.62 (m, 1H), 6.59 (d, J = 2.5 Hz, 1H), 4.81-4.57 (m, 3H), 4.24 and 4.15 (2d, J = 5.7 Hz, 2H), 3.58-3.37 (m, 16H), 3.22-3.19 (m, 3H), 2.59-2.51 (m, 1H), 0.72-0.58 (m, 2H), 0.49-0.36 (m, 2H). MS (m/z): 698.6 (M + H). |
| 46 | 30 | N-(2-(6-(7-(4-(3-cyclopropylureido)-2-fluorophenoxy)thieno[3,2-b]pyridin-2-yl)pyridin-3-yl)ethyl)-2-hydroxy-N-(2-methoxyethyl)-acetamide | $^1$H NMR (400 MHz, DMSO-$d_6$) δ (ppm): mixture of rotamers, 8.71 (s, 1H), 8.58-8.48 (m, 2H), 8.33 and 8.31 (2s, 1H), 8.22 (t, J = 8.5 Hz, 1H), 7.87 and 7.82 (2dd, J = 8.2, 2.0 Hz, 1H), 7.73 (dd, J = 13.5, 2.3 Hz, 1H), 7.38 (t, J = 9.1 Hz, 1H), 7.20 (bd, J = 9.0 Hz, 1H), 6.64 (d, J = 5.3 Hz, 1H), 6.58 (bd, J = 2.3 Hz, 1H), 4.49 and 4.43 (2t, J = 5.5 Hz, 1H), 4.10 and 4.02 (2d, J = 5.5 Hz, 2H), 3.62-3.40 (m, 5H), one CH$_2$ is masked by water's peak, 3.26 and 3.25 (2s, 3H), 2.96-2.83 (m, 2H), 2.59-2.51 (m, 1H), 0.72-0.58 (m, 2H), 0.50-0.36 (m, 2H). MS (m/z): 580.6 (M + H). |

Scheme 15

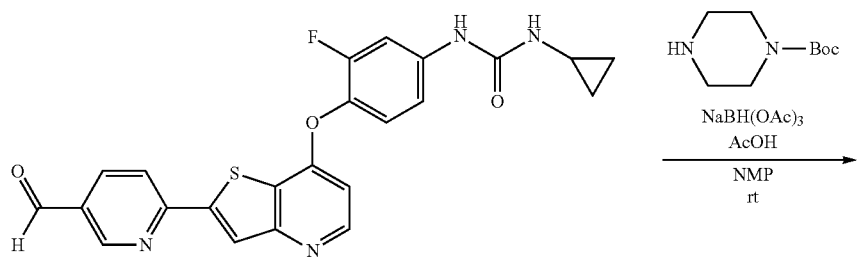

47
WO 2009/109035 A1

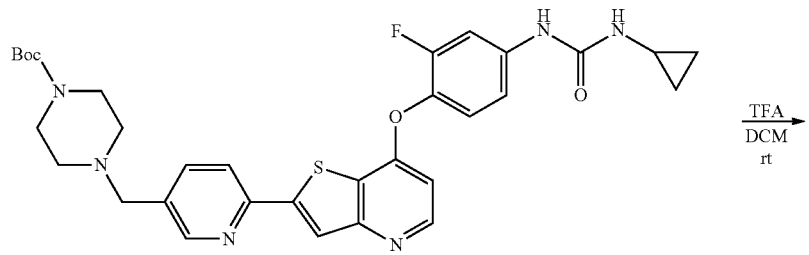

48: Example 31

-continued

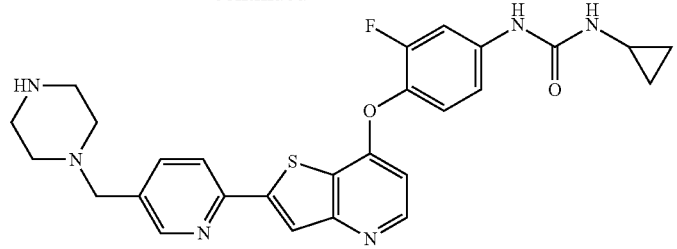

49: Example 32

Examples 31 and 32 tert-butyl 4-((6-(7-(4-(3-cyclopropylureido)-2-fluorophenoxy)thieno[3,2-b]-pyridin-2-yl)pyridin-3-yl)methyl)piperazine-1-carboxylate (48) and 1-cyclopropyl-3-(3-fluoro-4-(2-(5-(piperazin-1-ylmethyl)pyridin-2-yl)thieno[3,2-b]-pyridin-7-yloxy)phenyl)urea (49)

Step 1. tert-butyl 4-((6-(7-(4-(3-cyclopropylureido)-2-fluorophenoxy)thieno[3,2-b]-pyridin-2-yl)pyridin-3-yl)methyl)piperazine-1-carboxylate (48)

A suspension of 1-cyclopropyl-3-(3-fluoro-4-(2-(5-formylpyridin-2-yl)thieno[3,2-b]pyridin-7-yloxy)phenyl)urea (47, 3 g, 5.90 mmol, acetate salt), 1-boc-piperazine (1.65 g, 8.85 mmol) and acetic acid (675 µL, 11.80 mmol) in NMP (50 mL) at RT under nitrogen was sonicated for 3 h in order to obtain a solution, then NaBH(OAc)$_3$ (3.95 g, 17.70 mmol) was added. The reaction mixture was stirred at RT for 3 days then quenched by addition of water. The pH was adjusted to 12-13 with 4N NaOH and the suspension was stirred and sonicated for 1 h. The solid was collected by filtration, rinsed with water and air-dried. The residue was purified twice by Biotage (SNAP 50 g KP-Sil cartridge; MeOH/DCM: 1/99 to 10/90 over 20 CV). The desired fractions were collected, concentrated, and co-precipitated with AcOEt with traces of methanol/hexanes to afford the title compound 48 (1.511 g, 2.44 mmol, 41% yield) as a white fluffy solid. $^1$H NMR (400 MHz, DMSO-d$_6$) δ (ppm): 8.71 (s, 1H), 8.56 (bd, J=2.0 Hz, 1H), 8.52 (d, J=5.5 Hz, 1H), 8.33 (s, 1H), 8.25 (d, J=8.2 Hz, 1H), 7.87 (dd, J=8.1, 2.1 Hz, 1H), 7.73 (dd, J=13.6, 2.4 Hz, 1H), 7.38 (t, J=9.1 Hz, 1H), 7.20 (bdd, J=8.8, 1.2 Hz, 1H), 6.65 (d, J=5.3 Hz, 1H), 6.57 (bd, J=2.5 Hz, 1H), 3.57 (s, 2H), 4H are hidden by water's peak, 2.59-2.51 (m, 1H), 2.42-2.27 (m, 4H), 1.39 (s, 9H), 0.72-0.58 (m, 2H), 0.50-0.36 (m, 2H). MS (m/z): 619.4 (M+H).

Step 2. 1-cyclopropyl-3-(3-fluoro-4-(2-(5-(piperazin-1-ylmethyl)pyridin-2-yl)thieno[3,2-b]-pyridin-7-yloxy)phenyl)urea (49)

A solution of 48 (1.456 g, 2.35 mmol) and TFA (15 mL) in DCM (50 mL) was stirred at RT for 5 hr. The TFA was removed by co-evaporation with DCM, the residue was diluted with water, and the pH was adjusted to ~12-13 with 1N NaOH. The resultant suspension was sonicated for 15 min. The solid was collected by filtration, rinsed with water and dried under high vacuum to afford the title compound 49 (1.227 g, traces of TEA) as an off-white fluffy solid. $^1$H NMR (400 MHz. DMSO-d$_6$) δ (ppm): 8.76 (bs, 1H), 8.54 (d, J=1.4 Hz, 1H), 8.52 (d, J=5.5 Hz, 1H), 8.32 (s, 1H), 8.24 (d, J=8.2 Hz, 1H), 7.85 (dd, J=8.1, 2.1 Hz, 1H), 7.73 (dd, J=13.5, 2.3 Hz, 1H), 7.38 (t, J=9.1 Hz, 1H), 7.20 (bd, J=10.2 Hz, 1H), 6.64 (d, J=5.5 Hz, 1H), 6.62 (bs, 1H), 3.58-3.48 (m, 2H), 2.73-2.64 (m, 4H), 2.59-2.52 (m, 1H), 2.38-2.25 (m, 4H), 0.69-0.62 (m, 2H), 0.46-0.40 (m, 2H), one NH is missing. MS (m/z): 519.6 (M+H).

Compounds 50-60 (examples 33-43) were prepared in one step by reductive amination of compound 47 with an appropriate amine similarly to compound 48 (example 31, scheme 15).

TABLE 6

Characterization of compounds 50-60 (examples 33-43)

| Cpd | Ex. | Structure | Characterization |
|---|---|---|---|
| 50 | 33 | 1-(4-(2-(5-((bis(2-methoxyethyl)amino)methyl)pyridin-2-yl)thieno[3,2-b]-pyridin-7-yloxy)-3-fluorophenyl)-3-cyclopropylurea | $^1$H NMR (400 MHz, MeOH-d$_4$) δ (ppm): 8.65 (d, J = 1.6 Hz, 1H), 8.49 (d, J = 5.5 Hz, 1H), 8.14-8.08 (m, 2H), 8.00 (dd, J = 8.2, 2.2 Hz, 1H), 7.69 (dd, J = 13.1, 2.5 Hz, 1H), 7.52 (t, J = 8.8 Hz, 1H), 7.25-7.20 (m, 1H), 6.66 (dd, J = 5.7, 1.0 Hz, 1H), 4.04-3.97 (br s, 2H), 3.61 (t, J = 5.5 Hz, 4H), 3.38 (s, 6H), 2.98-2.90 (m, 4H), 2.67-2.60 (m, 1H), 0.83-0.77 (m, 2H), 0.59-0.54 (m, 2H). MS (m/z): 566.6 (M + H). |

TABLE 6-continued

Characterization of compounds 50-60 (examples 33-43)

| Cpd | Ex. | Structure | Characterization |
|---|---|---|---|
| 50-A | 33-A | 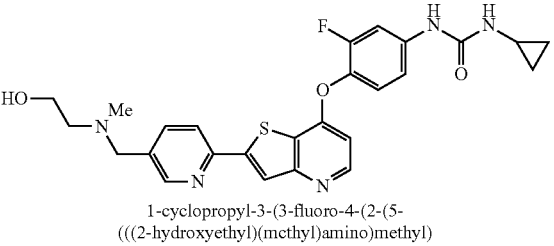<br>1-cyclopropyl-3-(3-fluoro-4-(2-(5-(((2-hydroxyethyl)(methyl)amino)methyl)pyridin-2-yl)thieno[3,2-b]pyridin-7-yloxy)phenyl)urea | $^1$H NMR (400 MHz, DMSO-d$_6$) δ (ppm): 8.79 (s, 1H), 8.56 (s, 1H), 8.51 (d, J = 5.48 Hz, 1H), 8.32 (s, 1H), 8.23 (d, J = 8.021 Hz, 1H), 7.88 (m, 1H), 7.73 (m, 1H), 7.37 (t, J = 9.0 Hz, 1H), 7.20 (s, 1H), 6.63 (m, 2H), 4.45 (t, J = 5.48 Hz, 1H), 3.59 (sm, 2H), 3.52 (q, J = 6.065 Hz, 2H), 2.55 (m, 1H), 2.45 (t, J = 6.26 Hz, 2H), 2.19 (s, 3H), 0.644 (m, 2H), 0.429 (m, 2H) MS (m/z) 508.503 (M + H). |
| 51 | 34 | 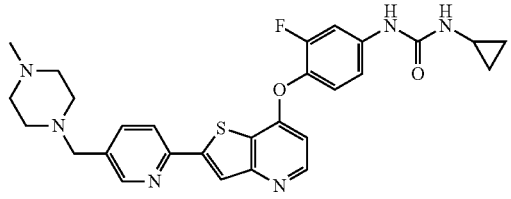 [SMILES: CN1CCN(Cc2ccc(-c3cc4nccc(Oc5ccc(NC(=O)NC6CC6)cc5F)c4s3)nc2)CC1]<br>1-cyclopropyl-3-(3-fluoro-4-(2-(5-((4-methylpiperazin-1-yl)methyl)pyridin-2-yl)thieno[3,2-b]-pyridin-7-yloxy)phenyl)urea | $^1$H NMR (400 MHz, MeOH-d$_4$) δ (ppm): 8.60 (d, J = 1.8 Hz, 1H); 8.49 (d, J = 5.3 Hz, 1H), 8.14-8.08 (m, 2H), 7.93 (dd, J = 8.0, 2.2 Hz, 1H), 7.70 (dd, J = 13.1,2.9 Hz, 1H), 7.33 (t, J = 8.8 Hz, 1H), 7.25-7.20 (m, 1H), 6.66 (dd, J = 5.7, 1.0 Hz, 1H), 3.67 (s, 2H). 2.85-2.37 (m, 9H), 2.32 (s, 3H), 0.83-0.77 (m, 2H), 0.59-0.54 (m, 2H). MS (m/z): 533.6 (M + H). |
| 52 | 35 | 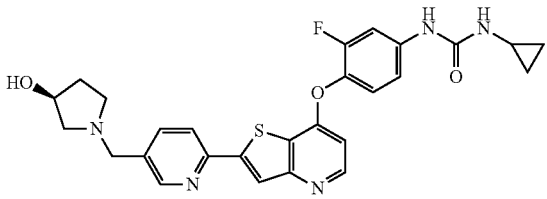 [SMILES: O=C(Nc1ccc(Oc2ccnc3cc(-c4ccc(CN5CC[C@H](O)C5)cn4)sc23)c(F)c1)NC1CC1]<br>(S)-1-cyclopropyl-3-(3-fluoro-4-(2-(5-((3-hydroxypyrrolidin-1-yl)methyl)pyridin-2-yl)thieno[3,2-b]-pyridin-7-yloxy)phenyl)urea | $^1$H NMR (400 MHz, DMSO-d$_6$) δ (ppm): 8.77-8.69 (m, 1H), 8.56 (d, J = 1.6 Hz, 1H), 8.52 (d, J = 5.5 Hz, 1H), 8.32 (s, 1H), 8.24 (d, J = 8.2 Hz, 1H), 7.86 (dd, J = 8.1, 2.1 Hz, 1H), 7.73 (dd, J = 13.5, 2.3 Hz, 1H), 7.38 (t, J = 9.0 Hz, 1H), 7.20 (bd, J = 8.9 Hz, 1H), 6.64 (dd, J = 5.4, 0.7 Hz, 1H), 6.62-6.54 (m, 1H), 4.72 (d, J = 4.7 Hz, 1H), 4.25-4.16 (m, 1H), 3.67 (d, J = 13.5 Hz, 1H), 3.61 (d, J = 13.5 Hz, 1H), 2.69 (dd, J = 9.6, 6.3 Hz, 1H), 2.61 (q, J = 7.6 Hz, 1H), 2.58-2.51 (m, 1H), 2.47-2.39 (m, 1H), 2.34 (dd, J = 9.6, 3.5 Hz, 1H), 2.01 (hex, J = 6.5 Hz, 1H), 1.60-1.51 (m, 1H), 0.72-0.58 (m, 2H), 0.50-0.36 (m, 2H). MS (m/z): 520.5 (M + H). |
| 53 | 36 | 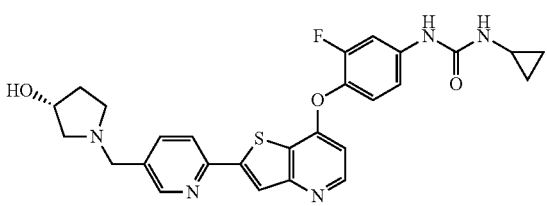 [SMILES: O=C(Nc1ccc(Oc2ccnc3cc(-c4ccc(CN5CC[C@@H](O)C5)cn4)sc23)c(F)c1)NC1CC1]<br>(R)-1-cyclopropyl-3-(3-fluoro-4-(2-(5-((3-hydroxypyrrolidin-1-yl)methyl)pyridin-2-yl)thieno[3,2-b]-pyridin-7-yloxy)phenyl)urea | $^1$H NMR (400 MHz, DMSO-d$_6$) δ (ppm): 8.71 (s, 1H), 8.56 (d, J = 1.8 Hz, 1H), 8.52 (d, J = 5.5 Hz, 1H), 8.32 (s, 1H), 8.24 (d, J = 8.0 Hz, 1H), 7.86 (dd, J = 8.2, 2.0 Hz, 1H), 7.73 (dd, J = 13.6, 2.4 Hz, 1H), 7.38 (t, J = 9.1 Hz, 1H), 7.20 (bd, J = 8.6 Hz, 1H), 6.64 (d, J = 5.5 Hz, 1H), 6.57 (bd, J = 2.3 Hz, 1H), 4.73 (bd, J = 4.5 Hz, 1H), 4.25-4.16 (m, 1H), 3.68 (d, J = 13.3 Hz, 1H), 3.62 (d, J = 12.9 Hz, 1H), 2.75-2.52 (m, 3H), 2.48-2.30 (m, 2H), 2.00 (hex, J = 7.0 Hz, 1H), 1.61-1.51 (m, 1H), 0.72-0.58 (m, 2H), 0.50-0.36 (m, 2H). MS (m/z): 520.5 (M + H). |
| 54 | 37 | 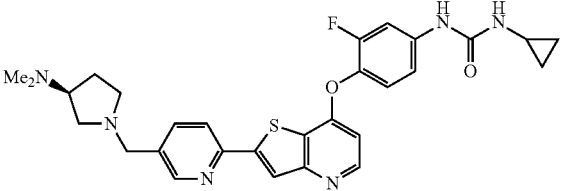 [SMILES: CN(C)[C@H]1CCN(Cc2ccc(-c3cc4nccc(Oc5ccc(NC(=O)NC6CC6)cc5F)c4s3)nc2)C1]<br>(S)-1-cyclopropyl-3-(4-(2-(5-((3-(dimethylamino)pyrrolidin-1-yl)methyl)pyridin-2-yl)thieno[3,2-b]pyridin-7-yloxy)-3-fluorophenyl)urea | $^1$H NMR (400 MHz, DMSO-d$_6$) δ (ppm): 8.70 (s, 1H), 8.59 (d, J = 1.8 Hz, 1H), 8.55 (d, J = 5.5 Hz, 1H), 8.36 (s, 1H), 8.27 (d, J = 8.0 Hz, 1H), 7.89 (dd, J = 8.0, 1.9 Hz, 1H), 7.42 (t, J = 9.0 Hz, 1H), 7.25-7.23 (m, 1H), 6.68 (d, J = 5.3 Hz, 1H), 6.62 (d, J = 2.6 Hz, 1H), 3.71(d, J = 3.5 Hz, 1H), 3.62 (d, J = 3.5 Hz, 1H), 2.75-2.70 (m, 2H), 2.66-2.57 (m, 2H), 2.52-2.47 (m, 1H), 2.35-2.33 (m, 1H), 2.13-2.11 (m, 6H). 1.92-1.87 (m, 1H), 1.67-1.62 (m, 1H), 0.71-0.67 (m, 2H), 0.48-0.45 (m, 2H). MS (m/z): 547.6 (M + H). |

TABLE 6-continued

Characterization of compounds 50-60 (examples 33-43)

| Cpd | Ex. | Structure | Characterization |
|---|---|---|---|
| 54-A | 37-A | 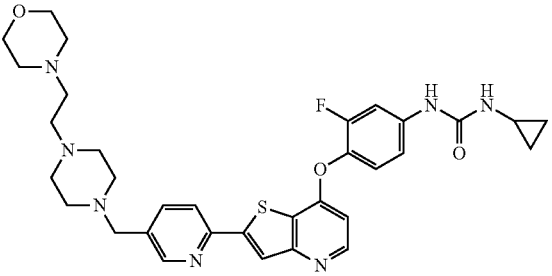 [SMILES: O=C(Nc1ccc(Oc2ccnc3cc(-c4ccc(CN5CCN(CCN6CCOCC6)CC5)cn4)sc23)c(F)c1)NC1CC1]<br>1-cyclopropyl-3-(3-fluoro-4-(2-(5-((4-(2-morpholinoethyl)piperazin-1-yl)methyl)pyridin-2-yl)thieno[3,2-b]pyridin-7-yloxy)phenyl)urea | $^1$H NMR (400 MHz, DMSO-d$_6$) δ (ppm): 8.83 (s, 1H), 8.58-8.55 (m, 2H), 8.36 (s, 1H), 8.28 (d, 1H, J = 8.2 Hz), 8.19 (s, 1H), 7.89 (dd, 1H, J1 = 1.9 Hz, J2 = 8.2 Hz), 7.77 (dd, 1H, J1 = 2.3 Hz, J2 = 13.5 Hz), 7.41 (t, 1H, J = 9.0 Hz), 7.25-7.22 (m, 1H), 6.69-6.67 (m, 1H), 3.59-3.57 (m, 6H), 2.62-2.57 (m, 1H), 2.54-2.42 (m, 16H), 0.71-0.66 (m, 2H), 0.48-0.44 (m, 2H). MS (m/z): 632.7 (M + H) |
| 54-B | 37-B | 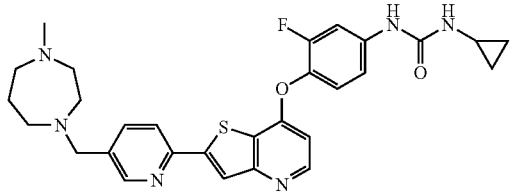 [SMILES: CN1CCCN(Cc2ccc(-c3cc4nccc(Oc5ccc(NC(=O)NC6CC6)cc5F)c4s3)nc2)CC1]<br>1-cyclopropyl-3-(3-fluoro-4-(2-(5-((4-methyl-1,4-diazepan-1-yl)methyl)pyridin-2-yl)thieno[3,2-b]pyridin-7-yloxy)phenyl)urea | $^1$H NMR (400 MHz, DMSO-d$_6$) δ (ppm): 8.79 (s, 1H), 8.56 (bd, J = 1.4 Hz, 1H), 8.52 (d, J = 5.5 Hz, 1H), 8.32 (s, 1H), 8.23 (d, J = 8.2 Hz, 1H), 7.87 (dd, J = 8.2, 2.2 Hz, 1H), 7.73 (dd, J = 13.6, 2.4 Hz, 1H), 7.38 (t, J = 9.1 Hz, 1H), 7.21 (dd, J = 8.9, 1.5 Hz, 1H), 6.68-6.61 (m, 2H), 3.68 (s, 2H), 2.70-2.61 (m, 4H), 2.59-2.50 (m, 5H), 2.24 (s, 3H), 1.77-1.67 (m, 2H), 0.72-0.58 (m, 2H), 0.49-0.36 (m, 2H). MS (m/z): 547.6 (M + H) |
| 54-C | 37-C | 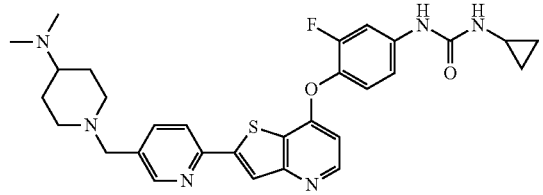 [SMILES: CN(C)C1CCN(Cc2ccc(-c3cc4nccc(Oc5ccc(NC(=O)NC6CC6)cc5F)c4s3)nc2)CC1]<br>1-cyclopropyl-3-(4-(2-(5-((4-(dimethylamino)piperidin-1-yl)methyl)pyridin-2-yl)thieno[3,2-b]pyridin-7-yloxy)-3-fluorophenyl)urea | $^1$H NMR (400 MHz, DMSO-d$_6$) δ (ppm): 9.25 (s, 1H), 8.58-8.54 (m, 2H), 8.36 (s, 1H), 8.32 (s, 1H), 8.27 (d, 1H, J = 8.0 Hz), 7.89 (dd, 1H, J1 = 6.1 Hz, J2 = 1.9 Hz), 7.78 (dd, 1H, J1 = 2.5 Hz, J2 = 13.7 Hz), 7.40 (t, 1H, J = 9.0 Hz), 7.27-7.24 (m, 1H), 7.07 (d, 1H, J = 1.9 Hz), 6.69 (d, 1H, J = 5.5 Hz), 3.57 (s, 2H), 2.90-2.87 (m, 2H), 2.60-2.58 (m, 1H), 2.26 (s, 6H), 2.22-2.20 (m, 1H), 2.03-1.98 (m, 2H), 1.79-1.76 (m, 2H), 1.49-1.44 (m, 2H), 0.69-0.65 (m, 2H), 0.48-0.44 (m, 2H) (formate salt). MS (m/z): 561.7 (M + H) |
| 54-D | 37-D | 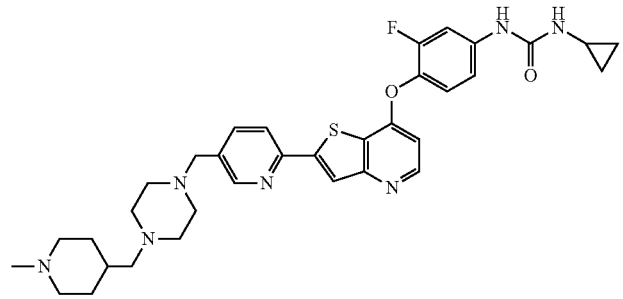 [SMILES: CN1CCC(CN2CCN(Cc3ccc(-c4cc5nccc(Oc6ccc(NC(=O)NC7CC7)cc6F)c5s4)nc3)CC2)CC1]<br>1-cyclopropyl-3-(3-fluoro-4-(2-(5-((4-((1-methylpiperidin-4-yl)methyl)piperazin-1-yl)methyl)pyridin-2-yl)thieno[3,2-b]pyridin-7-yloxy)phenyl)urea | $^1$H NMR (400 MHz, CD$_3$OD) δ (ppm): 8.56-8.54 (m, 1H), 8.45 (d, 1H, J = 5.5 Hz), 8.08-8.06 (m, 2H), 7.89 (dd, 1H, J1 = 2.2 Hz, J2 = 8.3 Hz), 7.66 (dd, 1H, J1 = 2.3 Hz, 2 = 12.9 Hz) 7.29 (m, 1H, J = 8.8 Hz), 7.20-7.18 (m, 1H), 6.63 (dd,1H, J1 = 1.0 Hz, J2 = 5.5 Hz), 3.61 (s, 2H), 2.86-2.83 (m, 2H), 2.62-2.54 (m, 8H), 2.24 (s, 3h), 2.21-2.20 (D, 2H, J = 7.0 Hz), 1.99 (t, 2H, J = 10.4 Hz), 1.77-1.74 (m, 2H), 1.60-1.48 (m, 1H), 1.27-1.15 (m, 2H), 0.78-0.73 (m, 2H), 0.54-0.53 (m, 2H). MS (m/z): 630.6 (M + H) |
| 54-E | 37-E | 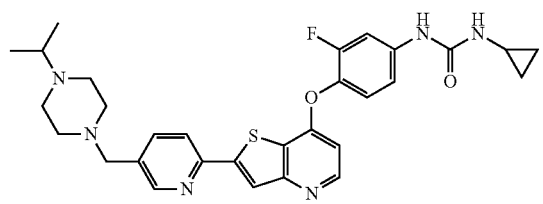<br>1-cyclopropyl-3-(3-fluoro-4-(2-(5-((4-isopropylpiperazin-1-yl)methyl)pyridin-2-yl)thieno[3,2-b]pyridin-7-yloxy)phenyl)urea | $^1$H NMR (400 MHz, DMSO-d$_6$) δ (ppm): 8.71 (s, 1H), 8.54 (bd, J = 1.6 Hz, 1H), 8.52 (d, J = 5.5 Hz, 1H), 8.32 (s, 1H), 8.24 (d, J = 8.2 Hz, 1H), 7.85 (dd, J = 8.1, 2.1 Hz, 1H), 7.73 (dd, J = 13.6, 2.4 Hz, 1H), 7.38 (t, J = 9.0 Hz, 1H), 7.20 (bd, J = 10.2 Hz, 1H), 6.64 (d, J = 5.3 Hz, 1H), 6.57 (bd, J = 2.3 Hz, 1H), 3.53 (s, 2H), 2.65-2.51 (m, 2H), 2.49-2.32 (m, 8H), 0.95 (d, J = 6.7 Hz, 6H), 0.71-0.58 (m, 2H), 0.50-0.38 (m, 2H). MS (m/z): 561.5 (M + H). |

TABLE 6-continued

Characterization of compounds 50-60 (examples 33-43)

| Cpd | Ex. | Structure | Characterization |
|---|---|---|---|
| 54-F | 37-F | 1-cyclopropyl-3-(3-fluoro-4-(2-(5-((4-(methylsulfonyl)piperazin-1-yl)methyl)pyridin-2-yl)thieno[3,2-b]pyridin-7-yloxy)phenyl)urea | $^1$H NMR (400 MHz. DMSO-d$_6$) δ (ppm): 8.72 (s, 1H), 8.57 (bd, J = 1.4 Hz, 1H), 8.52 (d, J = 5.5 Hz, 1H), 8.34 (s, 1H), 8.26 (d, J = 8.0 Hz, 1H), 7.88 (dd, J = 8.1, 2.2 Hz, 1H), 7.73 (dd, J = 13.6, 2.4 Hz, 1H), 7.38 (t, J = 9.1 Hz, 1H), 7.20 (bd, J = 9.2 Hz, 1H), 6.65 (d, J = 5.3 Hz, 1H), 6.59 (bd, J = 2.5 Hz, 1H), 3.62 (s, 2H), 3.16-3.10 (m, 4H), 2.88 (s, 3H), 2.57-2.52 (m, 1H), 4H are hidden by waters peak, 0.72-0.58 (m, 2H), 0.50-0.36 (m, 2H). MS (m/z): 567.2 (M + H). |
| 54-G | 37-G | 1-(4-(2-(5-((4-(2-(1H-imidazol-1-yl)ethyl)piperazin-1-yl)methyl)pyridin-2-yl)thieno[3,2-b]pyridin-7-yloxy)-3-fluorophenyl)-3-cyclopropylurea | $^1$H NMR (400 MHz, DMSO-d$_6$) δ (ppm): 8.72 (s, 1H), 8.54 (bd, J = 1.4 Hz, 1H), 8.52 (d, J = 5.5 Hz, 1H), 8.32 (s, 1H), 8.24 (d, J = 8.2 Hz, 1H), 7.85 (dd, J = 8.1, 2.1 Hz, 1H), 7.73 (dd, J = 13.6, 2.4 Hz, 1H), 7.61 (bs, 1H), 7.38 (t, J = 9.1 Hz, 1H), 7.20 (dd, J = 8.9, 1.3 Hz, 1H), 7.17 (bs, 1H), 6.85 (bs, 1H), 6.64 (dd. J = 5.4, 0.7 Hz, 1H), 6.58 (bd, J = 2.5 Hz, 1H), 4.05 (t, J = 6.4 Hz, 2H), 3.54 (s, 2H), 2.60 (t, J = 6.5 Hz, 2H), 2.58-2.54 (m, 1H), 2.50-2.30 (m, 8H), 0.72-0.58 (m, 2H), 0.49-0.37 (m, 2H). MS (m/z): 613.5 (M + H). |
| 55 | 38 | 1-cyclopropyl-3-(3-fluoro-4-(2-(5-((4-(2-hydroxyethyl)piperazin-1-yl)methyl)pyridin-2-yl)thieno[3,2-b]-pyridin-7-yloxy)phenyl)urea | $^1$H NMR (400 MHz, DMSO-d$_6$) δ (ppm): 8.72 (s, 1H), 8.54 (d, J = 1.6 Hz, 1H), 8.52 (d, J = 5.3 Hz, 1H), 8.33 (s, 1H), 8.24 (d, J = 8.0 Hz, 1H), 7.85 (dd, J = 8.2, 2.2 Hz, 1H), 7.73 (dd, J = 13.5, 2.3 Hz, 1H), 7.38 (t, J = 9.1 Hz, 1H), 7.20 (bd, J = 9.0 Hz, 1H), 6.64 (dd, J = 5.4, 0.7 Hz, 1H), 6.57 (bd, J = 2.5 Hz, 1H), 4.48-4.30 (m, 1H), 3.54 (s, 2H), 3.48 (q, J = 6.0 Hz, 2H), 2.59-2.51 (m, 1H), 2.48-2.30 (m, 8H), one CH$_2$ is hidden, 0.72-0.58 (m, 2H), 0.49-0.36 (m, 2H). MS (m/z): 563.6 (M + H). |
| 56 | 39 | 1-cyclopropy]-3-(3-fluoro-4-(2-(5-((4-(2-methoxyethyl)piperazin-1-yl)methyl)pyridin-2-yl)thieno[3,2-b]-pyridin-7-yloxy)phenyl)urea | $^1$H NMR (400 MHz, DMSO-d$_6$) δ (ppm): 8.72 (s, 1H), 8.54 (bd, J = 1.6 Hz, 1H), 8.52 (d, J = 5.3 Hz, 1H), 8.32 (s, 1H), 8.24 (d, J = 8.0 Hz, 1H), 7.85 (dd, 7 = 8.2, 2.0 Hz, 1H), 7.73 (dd, J = 13.6, 2.4 Hz, 1H), 7.38 (t, J = 9.0 Hz, 1H), 7.20 (bd, J = 9.0 Hz, 1H), 6.64 (d, J = 5.5 Hz, 1H), 6.57 (bd, J = 2.5 Hz, 1H), 3.54 (s, 2H), 3.41 (t, J = 5.9 Hz, 2H), 3.22 (s, 3H), 2.59-2.51 (m, 1H), 2.49-2.30 (m, 10H), 0.72-0.58 (m, 2H), 0.50-0.37 (m, 2H). MS (m/z): 577.6 (M + H). |
| 57 | 40 | 1-(4-(2-(5-((4-(2-cyanoethyl)piperazin-1-yl)methyl)pyridin-2-yl)thieno[3,2-b]-pyridin-7-yloxy)-3-fluorophenyl)-3-cyclopropylurea | $^1$H NMR (400 MHz, DMSO-d$_6$) δ (ppm): 8.72 (s, 1H), 8.54 (bd, J = 1.6 Hz, 1H), 8.52 (d, J = 5.5 Hz, 1H), 8.33 (s, 1H), 8.24 (d, J = 8.0 Hz, 1H), 7.85 (dd, J = 8.1, 2.1 Hz, 1H), 7.73 (dd, J = 13.6, 2.4 Hz, 1H), 7.38 (t, J = 9.1 Hz, 1H), 7.20 (dd, J = 9.0, 1.4 Hz, 1H), 6.64 (dd, J = 5.5, 0.8 Hz, 1H), 6.58 (bd, J = 2.5 Hz, 1H), 3.56 (s, 2H), 2.66 (bt, J = 6.5 Hz, 2H), 2.59-2.35 (m, 11H), 0.72-0.58 (m, 2H), 0.50-0.37 (m, 2H). MS (m/z): 572.7 (M + H). |

TABLE 6-continued

Characterization of compounds 50-60 (examples 33-43)

| Cpd | Ex. | Structure | Characterization |
|---|---|---|---|
| 58 | 41 | 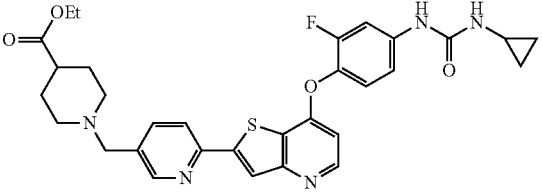 [SMILES: CCOC(=O)C1CCN(Cc2ccc(-c3cc4nccc(Oc5ccc(NC(=O)NC6CC6)cc5F)c4s3)nc2)CC1] ethyl 1-((6-(7-(4-(3-cyclopropylureido)-2-fluorophenoxy)-thieno[3,2-b]pyridin-2-yl)pyridin-3-yl)methyl)piperidine-4-carboxylate | $^1$H NMR (400 MHz, DMSO-$d_6$) δ (ppm): 8.71 (s, 1H), 8.54 (d, J = 1.4 Hz, 1H), 8.52 (d, J = 5.5 Hz, 1H), 8.33 (s, 1H), 8.24 (d, J = 8.0 Hz, 1H), 7.86 (dd, J = 8.2, 2.2 Hz, 1H), 7.73 (dd, J = 13.6, 2.4 Hz, 1H), 7.38 (t, J = 9.1 Hz, 1H), 7.20 (bd, J = 9.0 Hz, 1H), 6.65 (d, J = 5.5 Hz, 1H), 6.58 (bd, 2.7 Hz, 1H), 4.05 (q, J = 7.1 Hz, 2H), 3.54 (s, 2H), 2.82-2.72 (m, 2H), 2.59-2.51 (m, 1H), 2.35-2.25 (m, 2H), 2.10-2.00 (m, 2H), 1.84-1.76 (m, 2H), 1.64-1.51 (m, 2H), 1.17 (t, J = 7.1 Hz, 3H), 0.72-0.58 (m, 2H), 0.49-0.37 (m, 2H). MS (m/z): 590.6 (M + H). |
| 59 | 42 | 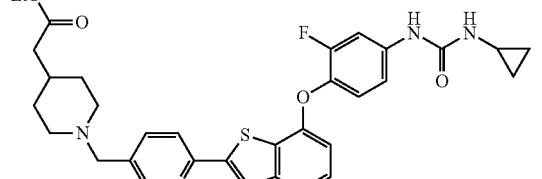 ethyl 2-(1-((6-(7-(4-(3-cyclopropylureido)-2-fluorophenoxy)-thieno[3,2-b]pyridin-2-yl)pyridin-3-yl)methyl)piperidin-4-yl)acetate | $^1$H NMR (400 MHz, DMSO-$d_6$) δ (ppm): 8.71 (s, 1H), 8.53 (d, J = 1.6 Hz, 1H), 8.52 (d, J = 5.3 Hz, 1H), 8.32 (s, 1H), 8.24 (d, J = 8.2 Hz, 1H), 7.84 (dd, J = 8.1, 2.1 Hz, 1H), 7.73 (dd, J = 13.6, 2.4 Hz, 1H), 7.38 (t, J = 9.0 Hz, 1H), 7.20 (bd, J = 8.8 Hz, 1H), 6.64 (d, J = 5.5 Hz, 1H), 6.58 (bd, J = 2.5 Hz, 1H), 4.04 (q, J = 7.1 Hz, 2H), 3.52 (s, 2H), 2.84-2.75 (m, 2H), 2.59-2.51 (m, 1H), 2.22 (d, J = 6.7 Hz, 2H), 1.97 (bt, J = 10.8 Hz, 2H), 1.73-1.56 (m, 3H), 1.28-1.17 (m, 2H), 1.16 (t, J = 7.1 Hz, 3H), 0.72-0.58 (m, 2H), 0.50-0.36 (m, 2H). MS (m/z): 604.6 (M + H). |
| 60 | 43 | 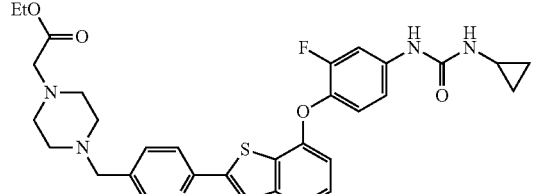 ethyl 2-(4-((6-(7-(4-(3-cyclopropylureido)-2-fluorophenoxy)-thieno[3,2-b]pyridin-2-yl)pyridin-3-yl)methyl)piperazin-1-yl)acetate | $^1$H NMR (400 MHz, DMSO-$d_6$) δ (ppm): 8.72 (s, 1H), 8.54 (d, J = 1.4 Hz, 1H), 8.52 (d, J = 5.5 Hz, 1H), 8.33 (s, 1H), 8.24 (d, J = 8.0 Hz, 1H), 7.85 (dd, J = 8.1, 2.0 Hz, 1H), 7.73 (dd, J = 13.5, 2.5 Hz, 1H), 7.38 (t, J = 9.1 Hz, 1H), 7.20 (bd, J = 10.3 Hz, 1H), 6.64 (d, J = 5.3 Hz, 1H), 6.58 (bd, J = 2.3 Hz, 1H), 4.07 (q, J = 7.1 Hz, 2H), 3.55 (s, 2H), 3.19 (s, 2H), 2.59-2.51 (m, 1H), 2.47-2.35 (m, 4H), 1.18 (t, J = 7.1 Hz, 3H), 0.72-0.58 (m, 2H), 0.49-0.37 (m, 2H), 4H are hidden by solvents. MS (m/z): 605.6 (M + H). |

Scheme 16

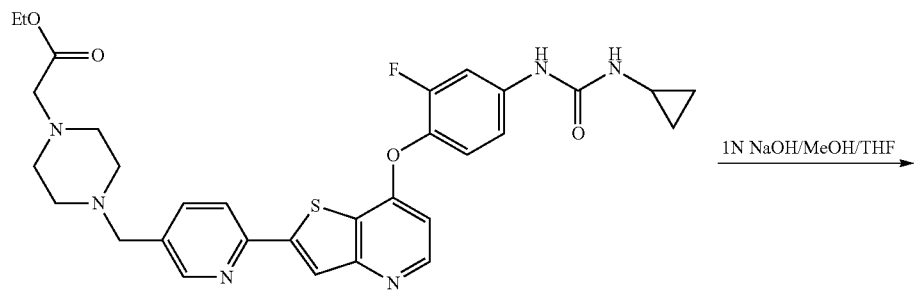

60: Example 43

1N NaOH/MeOH/THF →

-continued

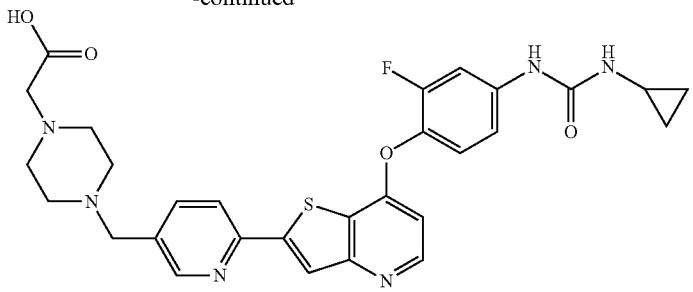

61: Example 44

Example 44

2-(4-((6-(7-(4-(3-cyclopropylureido)-2-fluorophenoxy)thieno[3,2-b]pyridin-2-yl)pyridin-3-yl)methyl)piperazin-1-yl)acetic acid (61)

To a stirred solution of ester 60 (85 mg, 0.14 mmol) in a mixture of MeOH/THF (5/5 mL) was added 1N NaOH (2 mL). The reaction mixture was stirred at RT for 3 h, concentrated, diluted with a minimum of water, quenched with 1N HCl to neutral pH, and concentrated. The residue was purified by Biotage (SNAP 10 g cartridge; 2% of ammonium hydroxide in MeOH/DCM: 5/95 to 30/70 over 20 CV then 100% MeOH over 10 CV), to afford the title compound 44 (72 mg, 0.118 mmol, 84% yield) as an ivory solid. $^1$H NMR (400 MHz, DMSO-$d_6$) δ (ppm): 8.95 (s, 1H), 8.55 (bd, J=1.8 Hz, 1H), 8.52 (d, J=5.5 Hz, 1H), 8.33 (s, 1H), 8.25 (d, J=8.0 Hz, 1H), 7.86 (dd, J=8.1, 2.0 Hz, 1H), 7.73 (dd, J=13.6, 2.4 Hz, 1H), 7.38 (t, J=9.1 Hz, 1H), 7.40-7.00 (m, 1H), 7.20 (bd, J=9.0 Hz, 1H), 6.72 (bd, J=2.7 Hz, 1H), 6.64 (d, J=5.3 Hz, 1H), 3.57 (s, 2H), 2.69 (bs, 4H), 2.59-2.51 (m, 1H), 2.48 (bs, 2H, partially hidden), 0.72-0.58 (m, 2H), 0.49-0.36 (m, 2H), 4H are hidden by water's peak, presence of 1 eq. of methanol. MS (m/z): 577.6 (M+H).

Compounds 62-63 (examples 45-46) were prepared in one step by hydrolysis of the esters 58 and 59 with sodium hydroxide, similarly to compound 61 (example 44, scheme 16) with a final purification by preparative HPLC.

TABLE 7

Characterization of compounds 62 and 63 (examples 45 and 46)

| Cpd | Ex. | Structure | Characterization |
|---|---|---|---|
| 62 | 45 | 1-((6-(7-(4-(3-cyclopropylureido)-2-fluorophenoxy)thieno[3,2-b]pyridin-2-yl)pyridin-3-yl)methyl)piperidine-4-carboxylic acid | $^1$H NMR (400 MHz, DMSO-$d_6$) δ (ppm): 12.12 (bs, 1H), 8.71 (s, 1H), 8.54 (bd, J = 1.4 Hz, 1H), 8.52 (d, J = 5.5 Hz, 1H), 8.33 (s, 1H), 8.24 (d, J = 8.0 Hz, 1H), 7.86 (bd, J = 8.0 Hz, 1H), 7.73 (dd, J = 13.6, 2.4 Hz, 1H), 7.38 (t, J = 9.1 Hz, 1H), 7.20 (bd, J = 8.8 Hz, 1H), 6.65 (d, J = 5.5 Hz, 1H), 6.57 (bd, J = 2.5 Hz, 1H), 3.54 (s, 2H), 2.84-2.70 (m, 2H), 2.59-2.51 (m, 1H), 2.27-2.16 (m, 1H), 2.11-1.98 (m, 2H), 1.85-1.74 (m, 2H), 1.64-1.49 (m, 2H), 0.72-0.58 (m, 2H), 0.50-0.36 (m, 2H). MS (m/z): 562.5 (M + H). |
| 63 | 46 | 2-(1-((6-(7-(4-(3-cyclopropylureido)-2-fluorophenoxy)thieno[3,2-b]pyridin-2-yl)pyridin-3-yl)methyl)piperidin-4-yl)acetic acid | $^1$H NMR (400 MHz, DMSO-$d_6$) δ (ppm): 8.89 (s, 1H)3 8.54 (bd, J = 1.4 Hz, 1H), 8.52 (d, J = 5.5 Hz, 1H), 8.32 (s, 1H), 8.23 (d, J = 8.2 Hz, 1H), 8.19 (bs, 2H, formate salt), 7.85 (dd, J = 8.2, 2.0 Hz, 1H), 7.73 (dd, J = 13.6, 2.4 Hz, 1H), 7.38 (t, J = 9.0 Hz, 1H), 7.21 (bd, J = 9.0 Hz, 1H), 6.73 (bd, J = 2.5 Hz, 1H), 6.64 (d, J = 5.3 Hz, 1H), 3.53 (s, 2H), 2.80 (bd, J = 11.2 Hz, 2H), 2.59-2.51 (m, 1H), 2.14 (bd, J = 6.5 Hz, 2H), 1.98 (bt, J = 10.9 Hz, 2H), 1.64 (bd, J = 10.0 Hz, 3H), 1.28-1.13 (m, 2H), 0.72-0.58 (m, 2H), 0.49-0.36 (m, 2H), one O$\underline{H}$ carboxylic acid is missing, bis-formate salt. MS (m/z): 576.5 (M + H). |

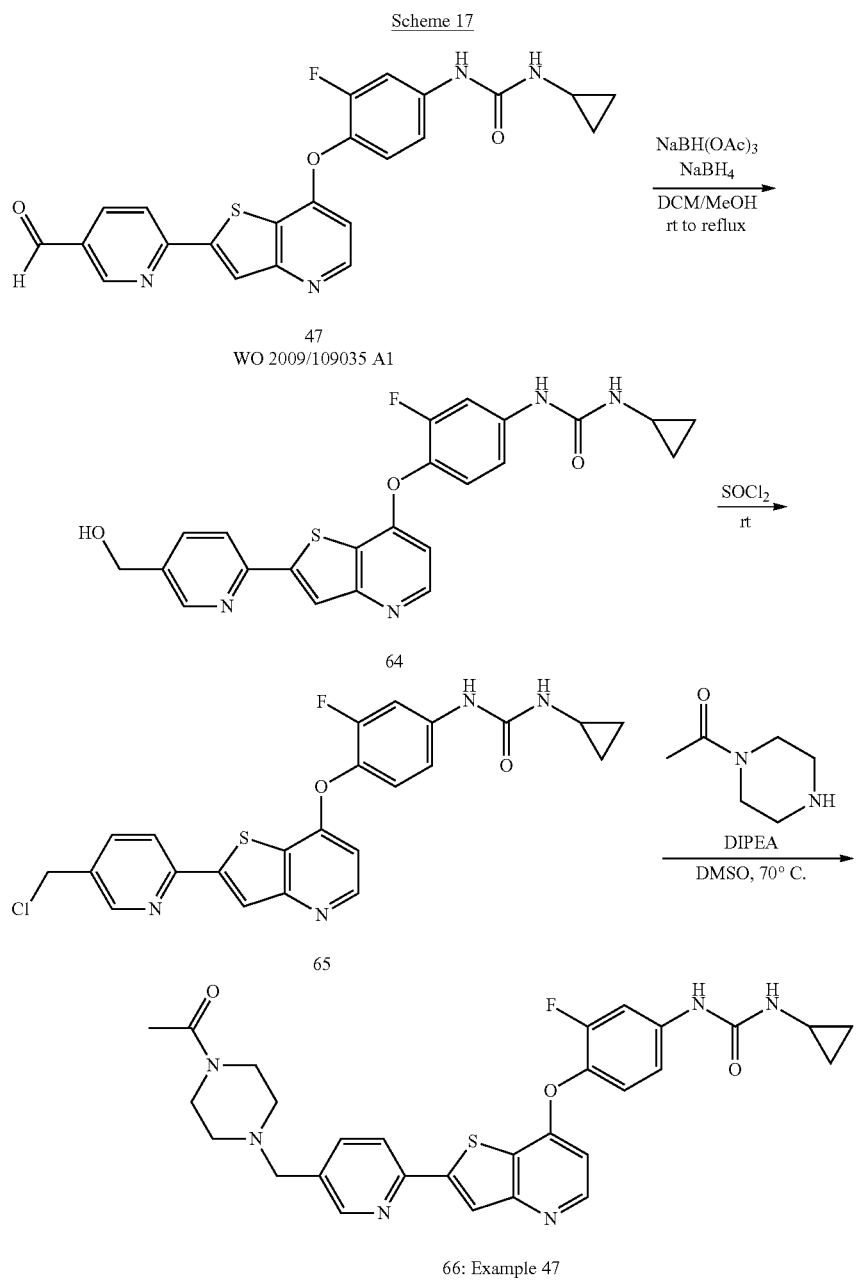

Example 47

1-(4-(2-(5-((4-acetylpiperazin-1-yl)methyl)pyridin-2-yl)thieno[3,2-b]pyridin-7-yloxy)-3-fluorophenyl)-3-cyclopropylurea (66)

Step 1. 1-cyclopropyl-3-(3-fluoro-4-(2-(5-(hydroxymethyl)pyridin-2-yl)thieno[3,2-b]pyridin-7-yloxy)phenyl)urea (64)

To a suspension of 47 (5.60 g, 12.49 mmol) in a mixture of DCM (200 mL)/MeOH (20 mL) in a 1 L round-bottomed flask was added sodium triacetoxyborohydride (5.29 g, 24.97 mmol). The reaction mixture was stirred at RT for 5 h. More sodium triacetoxyborohydride (5.29 g, 24.97 mmol) was added and the mixture was stirred at RT for 16 h. Then NaBH$_4$ (2 g, 52.9 mmol) was added to the reaction mixture that was stirred at RT for 24 h. Finally, more NaBH$_4$ (2 g, 52.9 mmol) was added and the reaction mixture was heated to reflux for 5 h, then cooled to RT, concentrated, quenched with 10% HCl (100 mL), and neutralized slowly with a saturated aqueous solution of NaHCO$_3$ (200 mL) to give a grey precipitate. The suspension was shaken for 15 min and the solid was collected by filtration, rinsed with water (2×25 mL) and dried under high vacuum to afford the title compound 64 (5.34 g, 11.85 mmol, 94% yield) as a light grey solid. MS (m/z): 451.5 (M+H). The material was used in the next step with no additional purification.

Step 2. 1-(4-(2-(5-(chloromethyl)pyridin-2-yl)thieno[3,2-b]pyridin-7-yloxy)-3-fluorophenyl)-3-cyclopropylurea (65)

Into a 500 mL round-bottom flask containing 64 (5.34 g, 11.85 mmol) was added slowly SOCl$_2$ (30 mL, 411 mmol). The yellow solution was stirred at RT for 2 h and cooled to 0° C. The reaction mixture was quenched by addition of ice (150 g) and water (100 mL), and the yellow suspension was shaken at RT for 1 h. The solid was collected by filtration, rinsed with water and dried under high vacuum. The crude product was triturated with AcOEt to afford the title compound 65 (5.55 g, purity ~40% by HPLC, contaminated with the des-cyclopropyl side-product) as a yellow solid. MS (m/z): 469.1 (M+H). The material was used in the next step with no additional purification.

Step 3. 1-(4-(2-(5-((4-acetylpiperazin-1-yl)methyl)pyridin-2-yl)thieno[3,2-b]pyridin-7-yloxy)-3-fluorophenyl)-3-cyclopropylurea (66)

A stirred solution of 65 (1 g, 2.13 mmol, 40%, from the previous step), 1-acetyl-piperazine (328 mg, 2.56 mmol) and DIPEA (1.12 mL, 6.40 mmol) in DMSO (20 mL) was heated at 70° C. overnight, then rt. The reaction mixture was quenched by addition of water and 1N NaOH. The resultant suspension was collected by filtration, rinsed with water and air-dried. The crude product was purified twice by Biotage (SNAP 50 g cartridge; 2% of ammonium hydroxide in MeOH/DCM: 0/100 to 10/90 over 20 CV then 10/90 to 15/85 over 10CV; SiliaFlash 120 g cartridge, 2% of ammonium hydroxide in MeOH/DCM: 0/100 to 10/90 over 20 CV then 10/90 to 20/80 over 10 CV) to produce a material that upon trituration with MeOH afforded the title compound 66 (79 mg, 0.14 mmol, 6% yield) as an off-white solid. $^1$H NMR (400 MHz, DMSO-d$_6$) δ (ppm): 8.71 (s, 1H), 8.57 (d, J=1.8 Hz, 1H), 8.52 (d, J=5.5 Hz, 1H), 8.34 (s, 1H), 8.25 (d, J=8.0 Hz, 1H), 7.88 (dd, J=8.1, 2.1 Hz, 1H), 7.73 (dd, J=13.5, 2.5 Hz, 1H), 7.38 (t, J=9.0 Hz, 1H), 7.20 (bd, J=9.0 Hz, 1H), 6.65 (d, J=5.5 Hz, 1H), 6.57 (bd, J=2.3 Hz, 1H), 3.59 (s, 2H), 3.48-3.40 (m, 4H), 2.59-2.51 (m, 1H), 2.44-2.31 (m, 4H), 1.98 (s, 3H), 0.72-0.58 (m, 2H), 0.50-0.36 (m, 2H). MS (m/z): 561.5 (M+H).

Compounds 67-69 (examples 48-50) were prepared in one step by reacting the appropriate amines with the chloride 65, similarly to compound 66 (example 47, scheme 17).

TABLE 8

Characterization of compounds 67-69 (examples 48-50)

| Cpd | Ex. | Structure | Characterization |
|---|---|---|---|
| 67 | 48 | 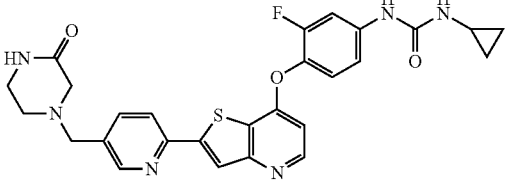<br>1-cyclopropyl-3-(3-fluoro-4-(2-(5-((3-oxopiperazin-1-yl)methyl)pyridin-2-yl)thieno[3,2-b]-pyridin-7-yloxy)phenyl)urea | $^1$H NMR (400 MHz, DMSO-d$_6$) δ (ppm): 8.77 (s, 1H), 8.58 (d, J = 1.6 Hz, 1H), 8.52 (d, J = 5.5 Hz, 1H), 8.34 (s, 1H), 8.26 (d, J = 8.0 Hz, 1H), 7.90 (dd, J = 8.1, 2.0 Hz, 1H), 7.79 (bs, 1H), 7.73 (dd, J = 13.6, 2.4 Hz, 1H), 7.38 (t, J = 9.1 Hz, 1H), 7.20 (dd, J = 8.8, 1.4 Hz, 1H), 6.65 (dd, J = 5.5, 0.8 Hz, 1H), 6.62 (bd, J = 2.5 Hz, 1H), 3.63 (s, 2H), 3.20-3.12 (m, 2H), 2.98 (s, 2H), 2.62-2.51 (m, 3H), 0.72-0.58 (m, 2H), 0.49-0.36 (m, 2H). MS (m/z): 533.6 (M + H). |
| 68 | 49 | 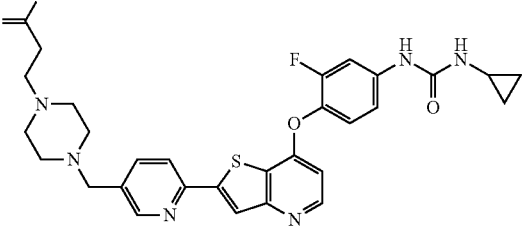<br>ethyl 3-(4-((6-(7-(4-(3-cyclopropyl-ureido)-2-fluorophenoxy)-thieno[3,2-b]-pyridin-2-yl)pyridin-3-yl)methyl)piperazin-1-yl)propanoate | $^1$H NMR (400 MHz, DMSO-d$_6$) δ (ppm): 8.72 (s, 1H), 8.54 (bd, J = 1.6 Hz, 1H), 8.52 (d, J = 5.3 Hz, 1H), 8.32 (s, 1H), 8.24 (d, J = 8.2 Hz, 1H), 7.85 (dd, J = 8.1, 2.1 Hz, 1H), 7.73 (dd, J = 13.6, 2.4 Hz, 1H), 7.38 (t, J = 9.1 Hz, 1H), 7.20 (dd, J = 8.8, 1.4 Hz, 1H), 6.64 (dd, J = 5.5, 0.8 Hz, 1H), 6.58 (bd, J = 2.5 Hz, 1H), 4.05 (q, J = 7.1 Hz, 2H), 3.53 (s, 2H), 2.58-2.30 (m, 13H), 1.17 (t, J = 7.1 Hz, 3H), 0.72-0.58 (m, 2H), 0.49-0.37 (m, 2H). MS (m/z): 619.7 (M + H). |
| 69 | 50 | 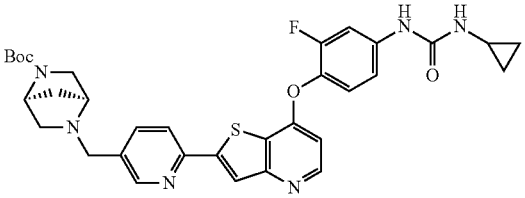 [SMILES: O=C(Nc1ccc(Oc2ccnc3cc(-c4ccc(CN5C[C@@H]6C[C@H]5CN6)cn4)sc23)c(F)c1)NC1CC1]<br>(1S,4S)-tert-butyl 5-((6-(7-(4-(3-cyclopropylureido)-2-fluorophenoxy)thieno[3,2-b]pyridin-2-yl)pyridin-3-yl)methyl)-2,5-diazabicyclo[2.2.1]heptane-2-carboxylate | MS (m/z): 631.7 (M + H). |

Scheme 18

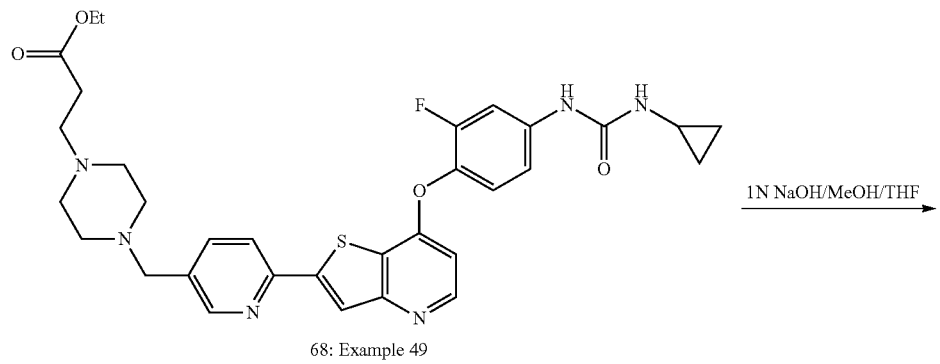

68: Example 49

1N NaOH/MeOH/THF

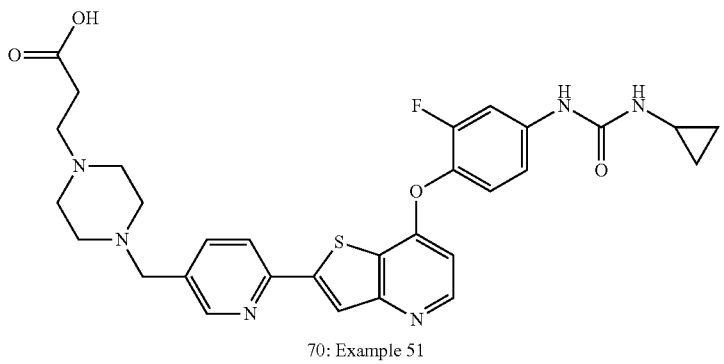

70: Example 51

Example 51

3-(4-((6-(7-(4-(3-cyclopropylureido)-2-fluorophenoxy)thieno[3,2-b]pyridin-2-yl)pyridin-3-yl)methyl)piperazin-1-yl)propanoic acid (70)

To a stirred solution of 68 (100 mg, 0.16 mmol) in a mixture of MeOH/THF (5/5 ml) was added 1N NaOH (2.42 ml). The reaction mixture was heated at 60° C. for 40 min, then rt. The reaction mixture was concentrated, diluted with water, neutralyzed with 1N HCl until formation of a precipitate-gel (pH around 4-5) and sonicated for 1 h. The solid was collected by filtration, rinsed with water, and air-dried. The crude solid was triturated and sonicated in a minimum of methanol. The solid was collected by filtration, rinsed with methanol and dried under high vacuum to afford the desired product (66 mg. 0.11 mmol, 69% yield) as an off-white solid. $^1$H NMR (400 MHz, DMSO-d$_6$) δ (ppm): one O$\underline{H}$ carboxylic acid is missing, 8.72 (s, 1H), 8.54 (bd, J=1.4 Hz, 1H), 8.52 (d, J=5.5 Hz, 1H), 8.33 (s, 1H), 8.24 (d. J=8.0 Hz, 1H), 7.85 (dd, J=8.2, 2.2 Hz, 1H), 7.73 (dd, J=13.5, 2.5 Hz, 1H), 7.38 (t. J=9.0 Hz, 1H), 7.20 (dd, J=9.0, 1.2 Hz, 1H), 6.64 (dd, J=5.5, 0.8 Hz, 1H), 6.58 (bd, J=2.5 Hz, 1H), 3.58 (s, 2H), 2.65-2.30 (m, 13H), 0.72-0.58 (m, 2H), 0.50-0.36 (m, 2H). MS (m/z): 591.5 (M+H).

Scheme 19

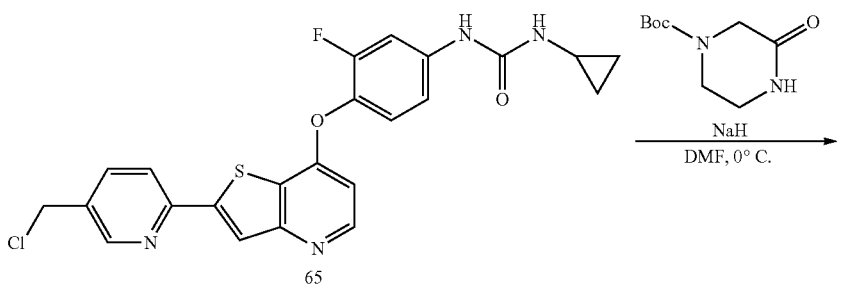

65

-continued

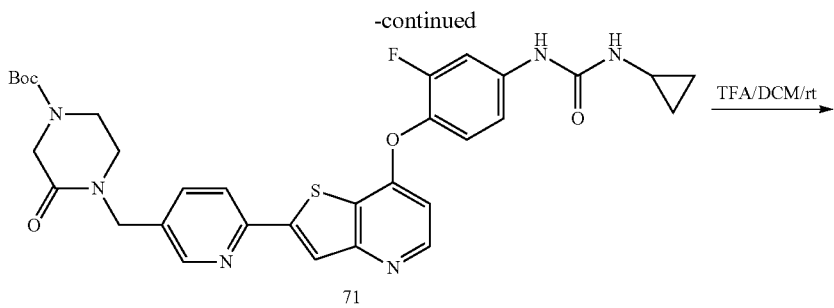

71

TFA/DCM/rt

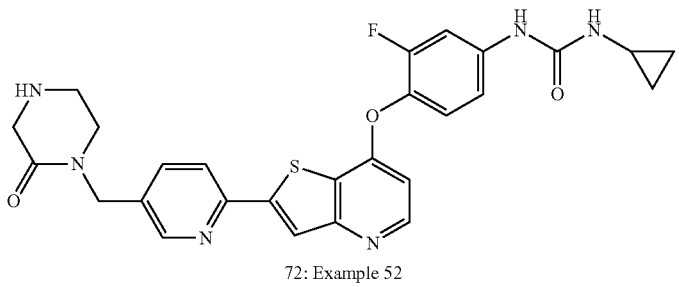

72: Example 52

Example 52

1-cyclopropyl-3-(3-fluoro-4-(2-(5-((2-oxopiperazin-1-yl)methylpyridin-2-yl)thieno[3,2-b]pyridin-7-yloxy)phenyl)urea (72)

Step 1. tert-butyl 4-((6-(7-(4-(3-cyclopropylureido)-2-fluorophenoxy)thieno[3,2-b]pyridin-2-yl)pyridin-3-yl)methyl)-3-oxopiperazine-1-carboxylate (71)

To a stirred suspension of NaH (426 mg, 60% dispersion in mineral oil, 10.66 mmol) in DMF (15 mL) at 0° C. under nitrogen was added a solution of tert-butyl 3-oxopiperazine-1-carboxylate (512 mg, 2.56 mmol) in DMF (5 mL). After 15 min, a solution of chloride 65 (1 g, 2.13 mmol, 40%, scheme 17) in DMF (5 mL) was added. The reaction mixture was stirred at 0° C. for 1.5 h and quenched by addition of 1N HCl and water. The resultant suspension was filtered and the solid material was rinsed with water and air-dried. The crude product was suspended in MeOH and the suspension was stirred for 1 h, filtered, and the filter cake was rinsed with MeOH. The mother liquor and the washings were collected, concentrated and the residue was purified by Biotage (SNAP 25 g cartridge; MeOH/DCM: 0/100 to 10/90 over 20 CV), to afford the title compound 71 (60 mg, 0.095 mmol, 4% yield) as an off-white sticky solid. MS (m/z): 633.6 (M+H).

Step 2. 1-cyclopropyl-3-(3-fluoro-4-(2-(5-((2-oxopiperazin-1-yl)methyl)pyridin-2-yl)thieno[3,2-b]pyridin-7-yloxy)phenyl)urea (72)

A solution of 71 (60 mg, 0.095 mmol) and TFA (5 mL) in DCM (20 mL) was stirred at RT for 5 h. The TFA was removed by co-evaporation with DCM and MeOH, diluted with water, and the pH was adjusted to around 12 with 1N NaOH. The resultant gel was extracted with DCM with traces of MeOH. The combined organic extract was dried over anhydrous magnesium sulfate, filtered and concentrated. The residue was purified by Biotage (SNAP 10 g column; 2% of ammonium hydroxide in MeOH/DCM; 0/100 to 10/90 over 20 CV, 10/90 to 20/80 over 10 CV then 20/80 over 5 CV), to afford the title compound 72 (35 mg, 0.066 mmol, 69% yield, traces of TFA) as a white sticky solid. $^1$H NMR (400 MHz, DMSO-$d_6$) δ (ppm) 8.72 (s, 1H), 8.55 (d, J=1.8 Hz, 1H), 8.52 (d, J=5.3 Hz, 1H), 8.35 (s, 1H), 8.26 (d, J=8.0 Hz, 1H), 7.83 (dd, J=8.2, 2.2 Hz, 1H), 7.73 (dd, J=13.6, 2.4 Hz, 1H), 7.38 (t, J=9.1 Hz, 1H), 7.20 (dd, J=8.9, 1.5 Hz, 1H), 6.65 (dd, J=5.3, 0.6 Hz, 1H), 6.58 (bd, J=2.7 Hz, 1H), 4.59 (s, 2H), 3.37 (s, 2H), 3.28 (t, J=5.5 Hz, 2H), 2.95 (t, J=5.4 Hz, 2H), 2.59-2.51 (m, 1H), 0.72-0.58 (m, 2H), 0.50-0.36 (m, 2H), one NH is missing. MS (m/z): 533.4 (M+H).

Compound 73 (example 53) was prepared in one step by Boc-deprotection of compound 69 (example 50), similarly to compound 72 (example 52, scheme 19).

TABLE 9

Characterization of compound 73 (example 53)

| Cpd | Ex. | Structure | Characterization |
|---|---|---|---|
| 73 | 53 | 1-(4-(2-(5-(((1S,4S)-2,5-diazabicyclo[2.2.1]heptan-2-ylmethyl)-pyridin-2-yl)thieno[3,2-b]pyridin-7-yloxy)-3-fluorophenyl)-3-cyclopropylurea | $^1$H NMR (400 MHz, DMSO-$d_6$) δ (ppm): 9.01 (s, 1H), 8.56 (d, J = 1.6 Hz, 1H), 8.51 (d, J = 5.6 Hz, 1H), 8.31 (s, 1H), 8.22 (d, J = 8.0 Hz, 1H), 7.87 (dd, J = 8.0, 2.0 Hz, 1H), 7.74 (dd, J = 14.0, 2.8 Hz, 1H), 7.37 (t, J = 8.8 Hz, 1H), 7.21 (d, J = 10 Hz, 1H), 6.84 (s, 1H), 6.64 (d, J = 5.6 Hz, 1H), 4.10 (s, 0.5H, NH), 3.38 (s, 1H), 3.17 (s, 1H), 3.03 (d, J = 10.0 Hz, 1H), 2.76 (dd, J = 8.8, 2.0 Hz, 1H), 2.70-2.64 (m, 1H), 2.58-2.51 (m, 1H), 2.35 (d, J = 8.8 Hz, 1H), 1.69 (d, J = 8.8 Hz, 1H), 1.42 (d, J = 8.8 Hz, 1H), 0.67-0.61 (m, 2H), 0.45-0.40 (m, 2H). MS (m/z): 531.5 (M + H). |

Scheme 20

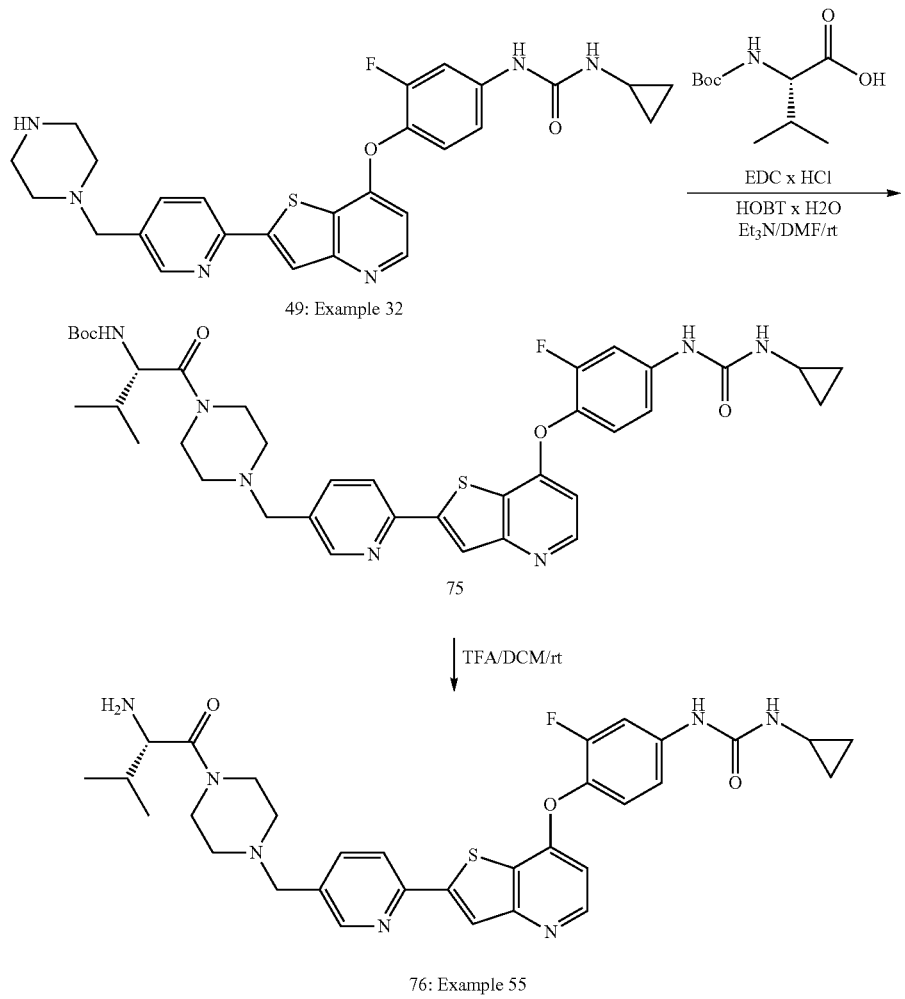

49: Example 32

75

76: Example 55

Example 55

(S)-1-(4-(2-(5-((4-(2-amino-3-methylbutanoyl)piper-azin-1-yl)methyl)pyridin-2-yl)thieno[3,2-b]pyridin-7-yloxy)-3-fluorophenyl)-3-cyclopropylurea (76)

Step 1. (S)-tert-butyl 1-(4-((6-(7-(4-(3-cyclopropy-lureido)-2-fluorophenoxy)thieno[3,2-b]pyridin-2-yl) pyridin-3-yl)methyl)piperazin-1-yl)-3-methyl-1-oxobutan-2-ylcarbamate (75)

To a stirred solution of compound 49 (150 mg, 0.289 mmol, scheme 15), Boc-L-valine (94 mg, 0.43 mmol) and triethylamine (120 µL, 0.87 mmol) in DMF (5 mL) under nitrogen were added HOBT monohydrate (49 mg, 0.32 mmol) and EDC hydrochloride (139 mg, 0.72 mmol) reagents, and the reaction mixture was stirred at RT overnight. The reaction mixture was then partitioned between AcOEt and a saturated aqueous solution of sodium bicarbonate. The organic layer was successively washed with a saturated aqueous solution of sodium bicarbonate, a saturated aqueous solution of ammonium chloride and brine, dried over anhydrous magnesium sulfate, filtered and concentrated. The crude product was purified by Biotage (Snap 25 g; MeOH/DCM: 1/99 to 10/90 over 20 CV), to afford the title compound 75 (171 mg, 0.238 mmol, 82% yield) as a colorless sticky film. MS (m/z): 718.4 (M+H).

Step 2. (S)-1-(4-(2-(5-((4-(2-amino-3-methylbu-tanoyl)piperazin-1-yl)methyl)pyridin-2-yl)thieno[3, 2-b]pyridin-7-yloxy)-3-fluorophenyl)-3-cyclopropy-lurea (76)

A solution of 75 (171 mg, 0.238 mmol) and TFA (2 mL) in DCM (10 mL) was stirred at RT for 2 h. The TFA was removed by co-evaporation with DCM, diluted with a minimum of water, and the pH was adjusted to around 10 with a saturated aqueous solution of sodium bicarbonate and a few drops of 1N NaOH at the end. The resultant suspension was sonicated for 15 min. The solid was collected by filtration, rinsed with water and dried under high vacuum. The crude product was purified by Biotage (SiliaFlash 12 g cartridge; 2% of ammonium hydroxide in MeOH/DCM: 5/95 to 15/85 over 20 CV, then 15/85 to 20/80 over 10 CV), to afford the title compound 76 (110 mg, 0.178 mmol, 74% yield) as a white sticky solid. $^1$H NMR (400 MHz, DMSO-$d_6$) δ (ppm): 8.75 (s, 1H), 8.57 (d, J=1.6 Hz, 1H), 8.52 (d, J=5.3 Hz, 1H), 8.34 (s, 1H), 8.25 (d, J=8.2 Hz, 1H), 7.88 (dd, J=8.1, 2.1 Hz, 1H), 7.73 (dd, J=13.5, 2.5 Hz, 1H), 7.38 (t, J=9.0 Hz, 1H), 7.21 (bd, J=8.8 Hz, 1H), 6.65 (d, J=5.3 Hz, 1H), 6.61 (bd, J=2.5 Hz, 1H), 3.59 (s, 2H), 3.54-3.42 (m, 5H), 2.59-2.51 (m, 1H), 2.48-2.28 (m, 4H), 2.20-1.80 (m, 2H), 1.74-1.62 (m, 1H), 0.87 (d, J=6.8 Hz, 3H), 0.78 (d, J=6.7 Hz, 3H), 0.73-0.58 (m, 2H), 0.50-0.36 (m, 2H). MS (m/z): 519.6 and 618.7 (M+H).

Compound 77 (example 56) was prepared in two steps starting from the piperazine 49, similarly to compound 76 (example 55, scheme 20).

TABLE 10
Characterization of compound 77 (example 56).
| Cpd | Ex. | Structure | Characterization |
| --- | --- | --- | --- |
| 77 | 56 | 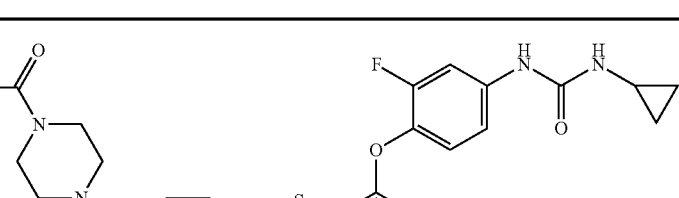<br>1-(4-(2-(5-(((4-(2-aminoacetyl)piperazin-1-yl)methyl)pyridin-2-yl)thieno[3,2-b]-pyridin-7-yloxy)-3-fluorophenyl)-3-cyclopropylurea | $^1$H NMR (400 MHz, DMSO-$d_6$) δ (ppm): 8.81 (s, 1H), 8.58 (d, J = 1.8 Hz, 1H), 8.52 (d, J = 5.5 Hz, 1H), 8.35 (s, 1H), 8.26 (d, J = 8.2 Hz, 1H), 7.88 (dd, J = 8.1, 2.1 Hz, 1H), 7.74 (dd, J = 13.6, 2.4 Hz, 1H), 7.66-7.42 (m, 2H), 7.38 (t, J = 9.1 Hz, 1H), 7.20 (bd, J = 10.2 Hz, 1H), 6.69-6.62 (m, 2H), 3.81 (s, 2H), 3.62 (s, 2H), 3.56-3.48 (m, 2H), 3.42-3.35 (m, 2H), 2.59-2.52 (m, 1H), 2.48-2.35 (m, 4H), 0.72-0.58 (m, 2H), 0.49-0.37 (m, 2H). MS (m/z): 519.5 and 576.5 (M + H). (TFA salt) |
Scheme 21
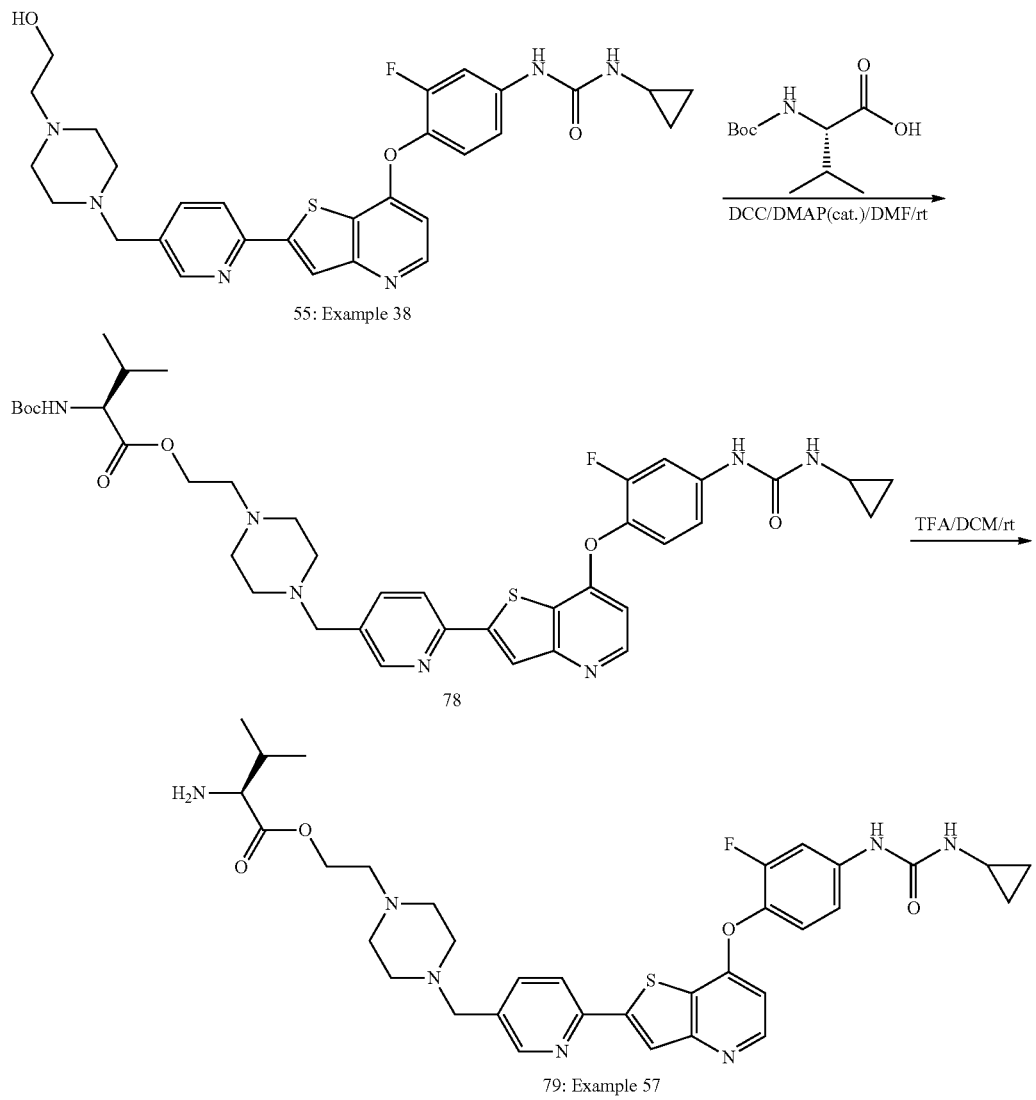

Example 57

(S)-2-(4-((6-(7-(4-(3-cyclopropylureido)-2-fluorophenoxy)thieno[3,2-b]pyridin-2-yl)pyridin-3-yl)methyl)piperazin-1-yl)ethyl 2-amino-3-methylbutanoate (79)

Step 1. (S)-2-(4-((6-(7-(4-(3-cyclopropylureido)-2-fluorophenoxy)thieno[3,2-b]pyridin-2-yl)pyridin-3-yl)methyl)piperazin-1-yl)ethyl 2-(tert-butoxycarbonylamino)-3-methylbutanoate (78)

To a stirred solution of the compound 55 (example 38, table 6) (100 mg, 0.178 mmol), Boc-L-Val-OH (58 mg, 0.27 mmol) and DMAP (4.4 mg, 0.036 mmol) in DMF (4 mL) under nitrogen was added DCC reagent (73 mg, 0.35 mmol), and the reaction mixture was stirred at RT overnight. More Boc-L-Val-OH (60 mg, 0.28 mmol), DCC (95 mg, 0.46 mmol) and DMF (2 mL) were added, respectively. The reaction mixture was stirred at RT overnight. Once again, more Boc-L-Val-OH (60 mg, 0.28 mmol), DCC (95 mg, 0.46 mmol) and DMF (1 mL) were added. The reaction mixture was stirred at RT overnight then partitioned between AcOEt and a saturated aqueous solution of sodium bicarbonate. The organic layer was successively washed with a saturated aqueous solution of sodium bicarbonate, water and brine, dried over anhydrous magnesium sulfate, filtered and concentrated. The residue was purified by Biotage (SNAP 25 g cartridge; MeOH/DCM: 1/99 to 10/90 over 20 CV), to afford the title compound 77 (115 mg, 0.15 mmol, 85% yield) as white sticky solid. MS (m/z): 762.4 (M+H).

Step 2. (S)-2-(4-((6-(7-(4-(3-cyclopropylureido)-2-fluorophenoxy)thieno[3,2-b]pyridin-2-yl)pyridin-3-yl)methyl)piperazin-1-yl)ethyl 2-amino-3-methylbutanoate (79)

A solution of 78 (115 mg. 0.15 mmol) and TFA (2 mL) in DCM (10 mL) was stirred at RT for 3 h. The TFA was removed by co-evaporation with DCM, diluted with a minimum of water, and the pH was adjusted to around 9 with a saturated aqueous solution of sodium bicarbonate (and few drops of 1N NaOH at the end). The aqueous solution was extracted with DCM containing traces of methanol. The organic extract was dried over anhydrous magnesium sulfate, filtered and concentrated. The crude product was purified by Biotage (SNAP 10 g cartridge; 2% of ammonium hydroxide in MeOH/DCM: 5/95 to 20/80 over 20 CV), to afford the title compound 79 (36 mg, 0.05 mmol, 36% yield) as a white sticky solid. $^1$H NMR (400 MHz, DMSO-$d_6$) δ (ppm): 8.72 (s, 1H), 8.54 (d, J=1.4 Hz, 1H), 8.52 (d, J=5.3 Hz, 1H), 8.32 (s, 1H), 8.24 (d, J=8.0 Hz, 1H), 7.85 (dd, J=8.0, 2.0 Hz, 1H), 7.73 (dd, J=13.4, 2.4 Hz, 1H), 7.38 (t, J=9.1 Hz, 1H), 7.20 (bd, J=10.4 Hz, 1H), 6.64 (d, J=5.3 Hz, 1H), 6.58 (bd, J=2.2 Hz, 1H), 4.26-4.18 (m, 1H), 4.11-4.03 (m, 1H), 3.54 (s, 2H), 3.10 (d, J=5.3 Hz, 1H), 2.59-2.30 (m, 11H), 1.88-1.78 (m, 1H), 0.87 (d, J=6.8 Hz, 3H), 0.83 (d, J=6.7 Hz, 3H), 0.69-0.62 (m, 2H), 0.46-0.40 (m, 2H), NH$_2$ is missing. MS (m/z): 662.7 (M+H).

Scheme 22

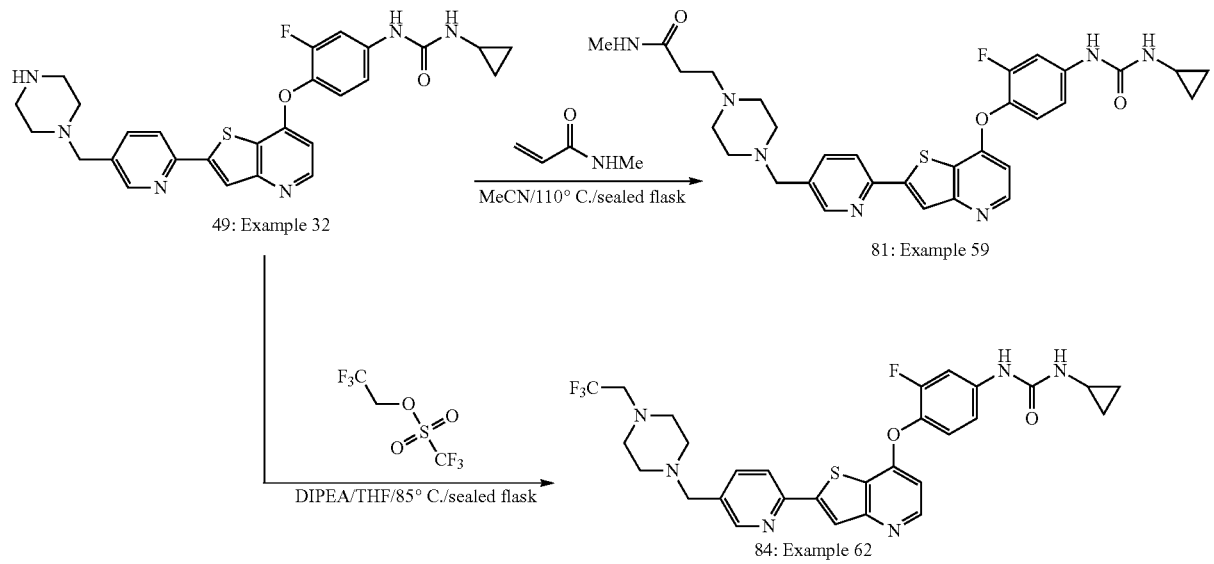

Example 59

3-(4-((6-(7-(4-(3-cyclopropylureido)-2-fluorophenoxy)thieno[3,2-b]pyridin-2-yl)pyridin-3-yl)methyl)piperazin-1-yl)-N-methylpropanamide (81)

A stirred suspension of compound 49 (100 mg, 0.19 mmol, scheme 15) and N-methylacrylamide (1.5 mL) in acetonitrile (20 mL) was heated to 110° C. overnight in a sealed flask. The reaction mixture was cooled to RT, concentrated, and the residue was purified twice by Biotage (SNAP 25 g cartridge; 2% of ammonium hydroxide in MeOH/DCM: 5/95 to 15/85 over 20 CV and SiliaFlash 12 g cartridge; 2% of ammonium hydroxide in MeOH/DCM: 5/95 to 15/85 over 20 CV, then 15/85 over 5 CV), to afford the title compound 81 (50 mg, 0.08 mmol, 43% yield) as a white sticky solid. $^1$H NMR (400 MHz, DMSO-$d_6$) δ (ppm): 8.72 (s, 1H), 8.54 (bd, J=1.4 Hz, 1H), 8.52 (d, J=5.5 Hz, 1H), 8.33 (s, 1H), 8.24 (d, J=8.0 Hz, 1H), 7.85 (dd, J=8.1, 2.1 Hz, 1H), 7.85-7.77 (m, 1H), 7.73 (dd, J=13.6, 2.4 Hz, 1H), 7.38 (t, J=9.1 Hz, 1H), 7.20 (bd, J=8.9 Hz, 1H), 6.64 (bd, J=5.4 Hz, 1H), 6.57 (bd, J=2.5 Hz, 1H), 3.54 (s, 2H), 2.59-2.51 (m, 6H), 2.47-2.11 (m, 10H), 0.72-0.58 (m, 2H), 0.50-0.36 (m, 2H). MS 604.4 (m/z): (M+H).

Compounds 82-83 (examples 60-61) were prepared in one step by reacting compound 49 (example 32) with an appropriate Michael acceptor similarly to compound 81 (example 59, scheme 22).

TABLE 12

Characterization of compounds 82-83 (examples 60-61)

| Cpd | Ex. | Structure | Characterization |
|---|---|---|---|
| 82 | 60 | 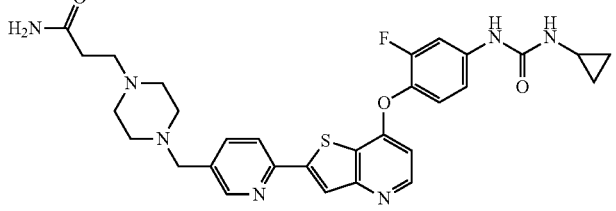<br>3-(4-((6-(7-(4-(3-cyclopropylureido)-2-fluorophenoxy)-thieno[3,2-b]pyridin-2-yl)pyridin-3-yl)methyl)piperazin-1-yl)propanamide | $^1$H NMR (400 MHz, DMSO-$d_6$) δ (ppm): 8.72 (s, 1H), 8.55 (s, 1H), 8.52 (d, J = 5.5 Hz, 1H), 8.33 (s, 1H), 8.25 (d, J = 8.2 Hz, 1H), 7.86 (bd, J = 8.0 Hz, 1H), 7.73 (dd, J = 13.5, 2.5 Hz, 1H), 7.38 (t, J = 9.0 Hz, 2H), 7.20 (bd, J = 8.8 Hz, 1H), 6.77 (bs, 1H), 6.65 (d, J = 5.3 Hz, 1H), 6.58 (bd, J = 2.5 Hz, 1H), 3.56 (bs, 2H), 2.59-2.51 (m, 1H), 2.50-2.15 (m, 8H), two CH$_2$ are hidden by solvent's peak, 0.72-0.58 (m, 2H), 0.50-0.36 (m, 2H). MS (m/z): 590.5 (M + H). |
| 83 | 61 | 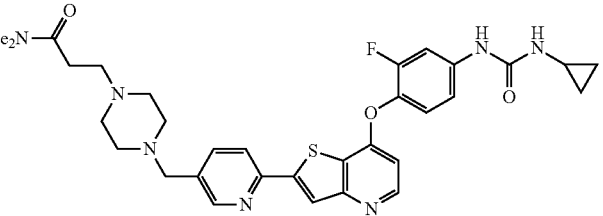<br>3-(4-((6-(7-(4-(3-cyclopropylureido)-2-luorophenoxy)thieno-[3,2-b]pyridin-2-yl)pyridin-3-yl)melhyl)piperazin-1-yl)-N,N-dimethyl-propanamide | $^1$H NMR (400 MHz, DMSO-$d_6$) δ (ppm): 8.72 (s, 1H), 8.54 (bd, J = 1.6 Hz, 1H), 8.52 (d, J = 5.5 Hz, 1H), 8.33 (s, 1H), 8.24 (d, J = 8.2 Hz, 1H), 7.85 (dd, J = 8.1, 2.1 Hz, 1H), 7.73 (dd, J = 13.6, 2.4 Hz, 1 H), 7.38 (t, J = 9.0 Hz, 1H), 7.20 (bd, J = 8.8 Hz, 1H), 6.64 (d, J = 5.5 Hz, 1H), 6.57 (bd, J = 2.5 Hz, 1H), 3.55 (s, 2H), 2.95 (s, 3H), 2.79 (s, 3H), 2.59-2.51 (m, 1H), 2.50-2.20 (m, 8H), two CH$_2$ are hidden by solvent's peak, 0.72-0.59 (m, 2H), 0.49-0.37 (m, 2H). MS (m/z): 618.7 (M + H). |

Example 62

1-cyclopropyl-3-(3-fluoro-4-(2-(5-((4-(2,2,2-trifluoroethyl)piperazin-1-yl)methyl)-pyridin-2-yl)thieno[3,2-b]pyridin-7-yloxy)phenyl)urea (84)

A solution of 49 (200 mg, 0.39 mmol), 2,2,2-trifluoroethyl trifluoromethanesulfonate (134 mg, 0.58 mmol) and DIPEA (0.2 mL, 1.16 mmol) and in THF (15 mL) was stirred and heated at 85° C. for 4 h in a sealed flask, then at RT (scheme 22). The reaction mixture was concentrated, diluted with a minimum of methanol in water. The pH was adjusted to 10-11 with a saturated aqueous solution of sodium bicarbonate and a few drops of 1N NaOH at the end. The suspension was shaken for 15 min and the solid was collected by filtration, rinsed with water and dried under high vacuum. The crude product was purified by Biotage (SiliaFlash 25 g cartridge; 2% of ammonium hydroxide in MeOH/DCM: 1/99 to 10/90 over 20 CV), to afford the title compound 84 (26 mg, 0.043 mmol, 11% yield) as an off-white solid. $^1$H NMR (400 MHz, DMSO-$d_6$) δ (ppm): 8.72 (s, 1H), 8.54 (bd, J=1.4 Hz, 1H), 8.52 (d, J=5.5 Hz, 1H), 8.33 (s, 1H), 8.24 (d, J=8.2 Hz, 1H), 7.85 (dd, J=8.1, 2.1 Hz, 1H), 7.73 (dd, J=13.5, 2.5 Hz, 1H), 7.38 (t, J=9.0 Hz, 1H), 7.20 (dd, J=9.0, 1.4 Hz, 1H), 6.64 (dd, J=5.5, 0.8 Hz, 1H), 6.58 (bd, J=2.5 Hz, 1H), 3.55 (s, 2H), 3.15 (q, J=10.2 Hz, 2H), 2.69-2.51 (m, 5H), 2.48-2.35 (m, 4H), 0.72-0.58 (m, 2H), 0.50-0.36 (m, 2H). MS 601.6 (m/z): (M+H).

Scheme 23

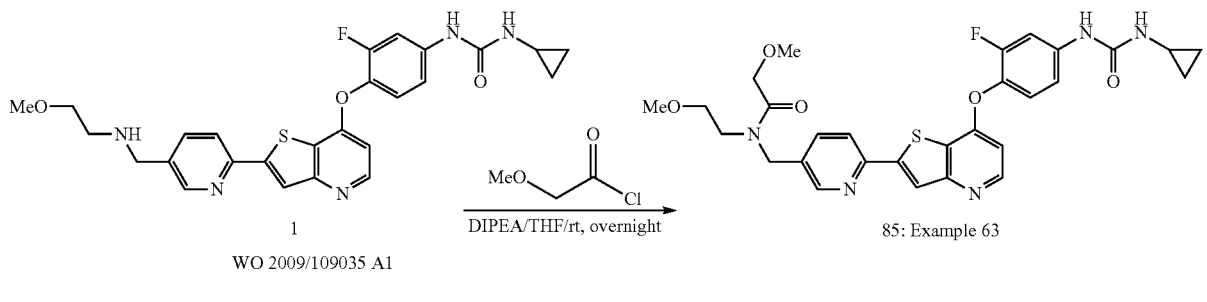

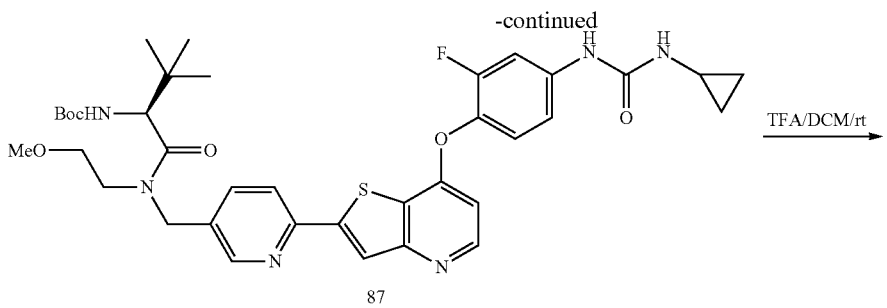

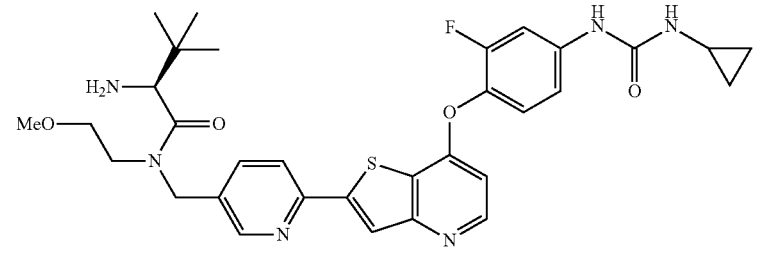

88: Example 65

Example 63

N-(((6-(7-(4-(3-cyclopropylureido)-2-fluorophenoxy)thieno[3,2-b]pyridin-2-yl)pyridin-3-yl)methyl)-2-methoxy-N-(2-methoxyethyl)acetamide (85)

To a solution of 1 (107 mg, 0.211 mmol, scheme 1) and methoxy acetyl chloride (38.5 μl, 0.422 mmol) in THF (4.2 mL) under nitrogen was added DIPEA (110 μl, 0.632 mmol) and the mixture was stirred at RT overnight. Methanol was added and the reaction mixture was concentrated. The residue was purified by Biotage (SNAP 50 g cartridge; MeOH/DCM: 0/100 to 20/80 over 20 CV), to afford the desired product (39 mg, 0.067 mmol, 31% yield) as an off-white solid. $^1$H NMR (400 MHz, DMSO-$d_6$) δ (ppm): mixture of rotamers, 8.71 (s, 1H), 8.54-8.49 (m, 2H), 8.36 and 8.33 (2s, 1H), 8.29 and 8.24 (2d, J=8.4 Hz, 1H), 7.82-7.69 (m, 2H), 7.38 (t, J=8.8 Hz, 1H), 7.20 (d, J=8.0 Hz, 1H), 6.67-6.62 (m, 1H), 6.59-6.55 (m, 1H), 4.66 and 4.61 (2s, 2H), 4.24 and 4.14 (2s, 2H), 3.50-3.18 (m, 10H), 2.60-2.50 (m, 1H), 0.69-0.62 (m, 2H), 0.46-0.40 (m, 2H). MS (m/z): 580.6 (M+H).

Compound 86 (example 64) was prepared in one step by reacting 1 with the corresponding carbonyl chloride reagent similarly to compound 85 (example 63, scheme 23).

Example 65

(S)-2-amino-N-((6-(7-(4-(3-cyclopropylureido)-2-fluorophenoxy)thieno[3,2-b]pyridin-2-yl)pyridin-3-yl)methyl)-N-(2-methoxyethyl)-3,3-dimethylbutanamide (88)

Step 1. (S)-tert-butyl 1-(((6-7-(4-(3-cyclopropylureido)-2-fluorophenoxy)thieno[3,2-b]pyridin-2-yl)pyridin-3-yl)methyl)(2-methoxyethyl)amino)-3,3-dimethyl-1-oxobutan-2-ylcarbamate (87)

To a stirred solution of 1 (100 mg, 0.197 mmol, scheme 1) and Boc-L-TLE-OH (51 mg, 0.22 mmol) under nitrogen in DMF (10 mL) at RT, were added DIPEA (0.120 mL, 0.69 mmol) followed by HATU (225 mg, 0.59 mmol). The reaction mixture was stirred overnight at rt. Ethyl acetate was added, washed with water, saturated ammonium chloride and saturated sodium bicarbonate, dried over anhydrous sodium sulfate, filtered and concentrated. The crude product was purified by Biotage (Snap 25 g; MeOH/DCM: 0/100 to 20/80 over 20 CV), to afford the title compound 87 that used directly for the next step. Yield assumed quantitative.

TABLE 12a

Characterization of compound 86 (example 64)

| Cpd | Ex. | Structure | Characterization |
|---|---|---|---|
| 86 | 64 | N-((6-(7-(4-(3-cyclopropylureido)-2-fluorophenoxy)thieno[3,2-b]pyridin-2-yl)pyridin-3-yl)methyl)-N-(2-methoxyethyl)propionamide | $^1$H NMR (400 MHz, DMSO-$d_6$) δ (ppm): mixture of rotamers, 8.71 (s, 1H), 8.54-8.48 (m, 2H), 8.35 and 8.32 (2s, 1H), 8.28 and 8.23 (2d, J = 8.0 Hz, 1H), 7.80-7.70 (m, 2H), 7.38 (t, J = 8.8 Hz, 1H), 7.20 (d, J = 8.8 Hz, 1H), 6.67-6.62 (m, 1H), 6.57 (d, J = 2.0 Hz, 1H), 6.61-6.54 (m, 1H), 4.72 and 4.60 (2s, 2H), 3.54-3.40 (m, 4H), 3.23 and 3.21 (2s, 3H), 2.59-2.51 (m, 1H), 2.50-2.30 (m, 2H), 1.04-0.95 (m, 3H), 0.69-0.62 (m, 2H), 0.45-0.40 (m, 2H). MS (m/z): 564.6 (M + H). |

Step 2. (S)-2-amino-N-((6-(7-(4-(3-cyclopropylureido)-2-fluorophenoxy)thieno[3,2-b]pyridin-2-yl)pyridin-3-yl)methyl)-N-(2-methoxyethyl)-3,3-dimethylbutanamide (88)

To a solution of 87 (142 mg, 0.197 mmol) in DCM (10 mL) was added TFA (3 mL, 38.9 mmol) and water (0.2 mL). The reaction mixture was stirred overnight at RT, concentrated, diluted with ethyl acetate, and successively washed with a saturated aqueous solution of sodium bicarbonate, 1N NaOH and brine, dried over anhydrous sodium sulfate, filtered and concentrated. The crude product was purified by Biotage (SNAP 50 g cartridge; 2% of ammonium hydroxide in MeOH/DCM: 0/100 to 40/60 over 20 CV), to afford the title compound 88 (39 mg, 0.064 mmol, 32% yield) as an off-white solid. $^1$H NMR (400 MHz, DMSO-$d_6$) δ (ppm): mixture of rotamers, 8.75 (s, 1H), 8.59-8.50 (m, 2H), 8.37 and 8.32 (2s, 1H), 8.28 and 8.24 (2d, J=8.0 Hz, 1H), 7.85 and 7.80 (2dd, J=8.0 and 2.0 Hz, 1H), 7.73 (dd, J=13.6, 2.4 Hz, 1H), 7.38 (t, J=9.2 Hz, 1H), 7.20 (d, J=8.8 Hz, 1H), 6.66-6.57 (m, 2H), 5.18-4.40 (m, 2H), 3.88-2.95 (m, 8H), 2.59-2.51 (m, 1H), 0.93 and 0.91 (2s, 9H), 0.68-0.62 (m, 2H), 0.45-0.40 (m, 2H), primary amine is missing. MS (m/z): 621.7 (M+H).

Compounds 89-91 (examples 66-68) were prepared in one step by coupling 1 with the appropriate carboxylic acid similarly to compound 88 (example 65, scheme 23). Compounds 92 (example 69) and 92-A (example 69-A) were prepared in two steps starting from 2-amino-N-((6-(7-(4-(3-cyclopropylureido)-2-fluorophenoxy)thieno[3,2-b]pyridine-2-yl)pyridine-3-yl)methyl)-N-(2-methoxyethyl)acetamide, similarly to compound 88 (example 65, scheme 23).

TABLE 13

Compounds 89-92 (examples 66-69)

| Cpd | Ex. | Structure | Characterization |
|---|---|---|---|
| 89 | 66 | (S)-N-((6-(7-(4-(3-cyclopropylureido)-2-fluorophenoxy)thieno[3,2-b]pyridin-2-yl)pyridin-3-yl)methyl)-2-hydroxy-N-(2-methoxyethyl)propanamide | $^1$H NMR (400 MHz, DMSO-$d_6$) δ (ppm): mixture of rotamers, 8.76 (s, 1H), 8.56-8.48 (m, 2H), 8.36 and 8.33 (2s, 1H), 8.28 and 8.24 (2d, J = 8.8 Hz, 1H), 7.84-7.70 (m, 2H), 7.38 (t, J = 8.8 Hz, 1H), 7.20 (d, J = 8.8 Hz, 1H), 6.67--6.60 (m, 2H), 5.26-4.40 (M, 4H), 3.78-3.30 (m, 4H), 3.22 and 3.20 (2s, 3H), 2.60-2.50 (m, 1H), 1.25-1.19 (m, 3H), 0.68-0.62 (m, 2H), 0.45-0.40 (m, 2H). MS (m/z): 580.6 (M + H). |
| 90 | 67 | N-((6-(7-(4-(3-cyclopropylureido)-2-fluorophenoxy)thieno[3,2-b]pyridin-2-yl)pyridin-3-yl)methyl)-N-(2-methoxyethyl)-2-(methylsulfonyl)acetamide | $^1$H NMR (400 MHz, DMSO-$d_6$) δ (ppm): 9.14 (s, 1H), 8.57-8.48 (m, 2H), 8.40-8.23 (m, 2H), 7.86-7.70 (m, 2H), 7.37 (t, J = 9.2 Hz, 1H), 7.22 (d, J = 8.8 Hz, 1H), 6.96 (s, 1H), 6.67-6.62 (m, 1H), 4.85-4.53 (m, 4H), 3.65-3.40 (m, 4H), 3.26 (s, 3H), 3.16 (s, 3H), 2.58-2.50 (m, 1H), 0.67-0.61 (m, 2H), 0.45-0.40 (m, 2H). MS (m/z): 628.5 (M + H). |
| 91 | 68 | (S)-benzyl 2-(1-(((6-(7-(4-(3-cyclopropylureido)-2-fluorophenoxy)thieno[3,2-b]pyridin-2-yl)pyridin-3-yl)methyl)(2-methoxyethyl)amino)-3-methyl-1-oxobutan-2-ylamino)-2-oxoethylcarbamate | MS (m/z): 798.4 (M + H). |

TABLE 13-continued

Compounds 89-92 (examples 66-69)

| Cpd | Ex. | Structure | Characterization |
|---|---|---|---|
| 92 | 69 | (S)-2-amino-N-(2-(((6-(7-(4-(3-cyclopropylureido)-2-fluorophenoxy)thieno[3,2-b]pyridin-2-yl)pyridin-3-yl)methyl)(2-methoxyethyl)amino)-2-oxoethyl)-3-methylbutanamide | $^1$H NMR (400 MHz, DMSO-d$_6$) δ (ppm): mixture of rotamers, 8.73 (s, 1H), 8.58-8.50 (m, 2H), 8.38-8.12 (m, 3H), 7.88-7.70 (m, 3H), 7.38 (t, J = 9.2 Hz, 1H), 7.20 (d, J = 8.8 Hz, 1H), 6.67-6.62 (m, 1H), 6.58 (d, J = 1.2 Hz, 1H), 4.74 and 4.63 (2s, 2H), 4.21-3.97 (m, 2H), 3.57-3.30 (m, 4H), 3.24 and 3.21 (2s, 3H), 3.09-3.01 (m, 1H), 2.59-2.50 (m, 1H), 2.02-1.90 (m, 1H), 0.90 (d, J = 6.8 Hz, 3H), 0.79 (d, J = 6.8 Hz, 3H), 0.68-0.61 (m, 2H), 0.45-0.40 (m, 2H). MS (m/z): 664.4 (M + H). |
| 92-A | 69-A | 2-(2-aminoacetamido)-N-((6-(7-(4-(3-cyclopropylureido)-2-fluorophenoxy)thieno[3,2-b]pyridin-2-yl)pyridin-3-yl)methyl)-N-(2-methoxyethyl)acetamide | $^1$H NMR (400 MHz, DMSO-d$_6$) δ (ppm): mixture of rotamers, 8.75 (s, 1H), 8.58-8.48 (m, 2H), 8.38-8.11 (m, 3H), 7.87-7.69 (m, 2H), 7.38 (t, J = 8.8 Hz, 1H), 7.20 (d, J = 9.2 Hz, 1H), 6.67-6.58 (m, 2H), 4.74 and 4.63 (2s, 2H), 4.16 and 4.02 (2d, J = 4.4 Hz, 2H), 3.56-3.10 (m, 9H), 2.59-2.50 (m, 1H), 0.68-0.62 (m, 2H), 0.45-0.40 (m, 2H). MS (m/z): 622.6 (M + H) |

Scheme 24

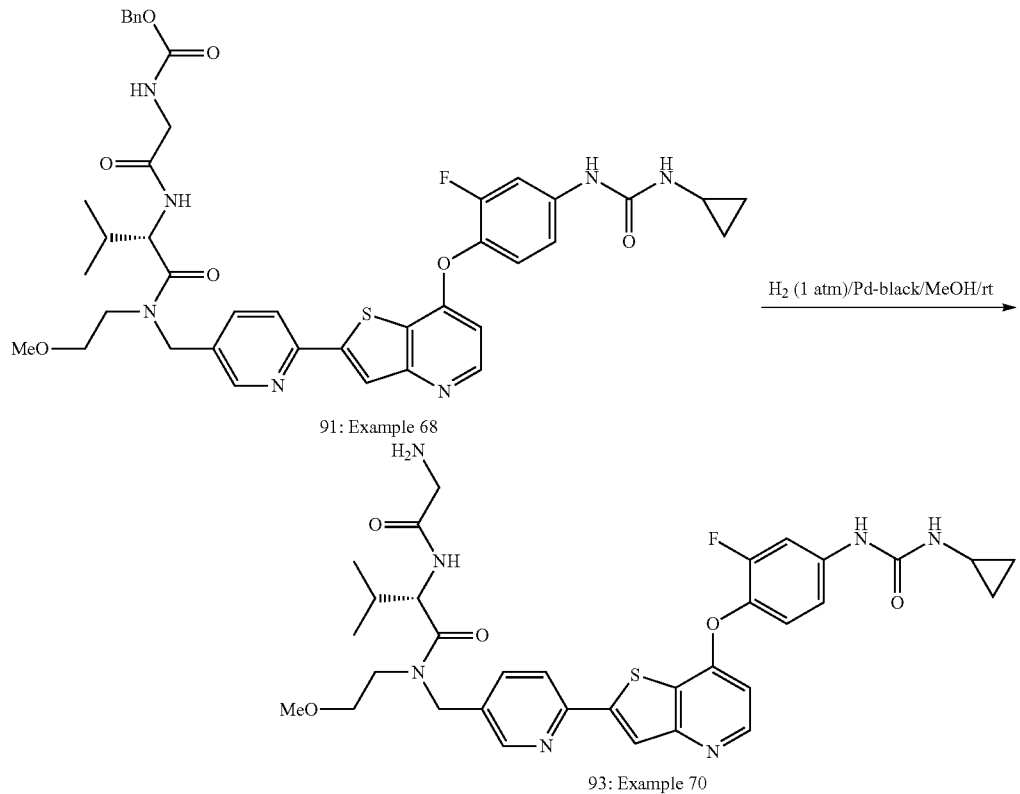

91: Example 68

H$_2$ (1 atm)/Pd-black/MeOH/rt

93: Example 70

Example 70

(S)-2-(2-aminoacetamido)-N-((6-(7-(4-(3-cyclopropylureido)-2-fluorophenoxy)-thieno[3,2-b]pyridin-2-yl)pyridin-3-yl)methyl)-N-(2-methoxyethyl)-3-methylbutanamide (93)

To a solution of 91 (270 mg, 0.338 mmol, table 13) in MeOH (20 mL) was added palladium black (180 mg, 1.692 mmol) and the solution was degassed by bubbling nitrogen for 10 min. The mixture was placed under hydrogen (balloon), stirred overnight under hydrogen, then under nitrogen and pyridine by bubbling nitrogen into the solution. The reaction mixture was filtered through a celite pad, rinsed with methanol, and concentrated. The residue was purified by Gilson (Phenomenex, Luna, 15 Ξ, C18(2) 100A, 250×50.00 mm, 15 μm, 0.05% of formic acid in both MeOH/water:20/80 to 95/5 over 60 min, flow=30 mL/min), then (Phenomenex, Luna, 15μ, C18(2) 100A, 250×5 0.00 mm, 15 μm, 0.05% of formic acid in both MeOH/water (30 mL/min): 20/80 to 95/05 over 60 min), to afford the title compound 93 (24 mg, 0.037 mmol, 10% yield, hydrated formate salt) as a beige solid. $^1$H NMR (400 MHz, DMSO-$d_6$) δ (ppm): mixture of rotamers, 9.10-8.97 (m, 1H), 8.60-8.47 (m, 2H), 8.38-8.05 (m, 4H), 7.88-7.70 (m, 2H), 7.37 (d, J=9.2 Hz, 1H), 7.21 (d, J=8.8 Hz, 1H), 6.92-6.81 (m, 1H), 6.67-6.62 (m, 1H), 5.06-4.50 (m, 3H), 3.90-2.80 (m, 9H), 2.59-2.50 (m, 1H), 2.29-2.19 (m, 2H), 2.10-1.95 (m, 1H), 0.94-0.78 (m, 6H), 0.67-0.61 (m, 2H), 0.45-0.39 (m, 2H). MS (m/z): 664.8 (M+H).

Scheme 26

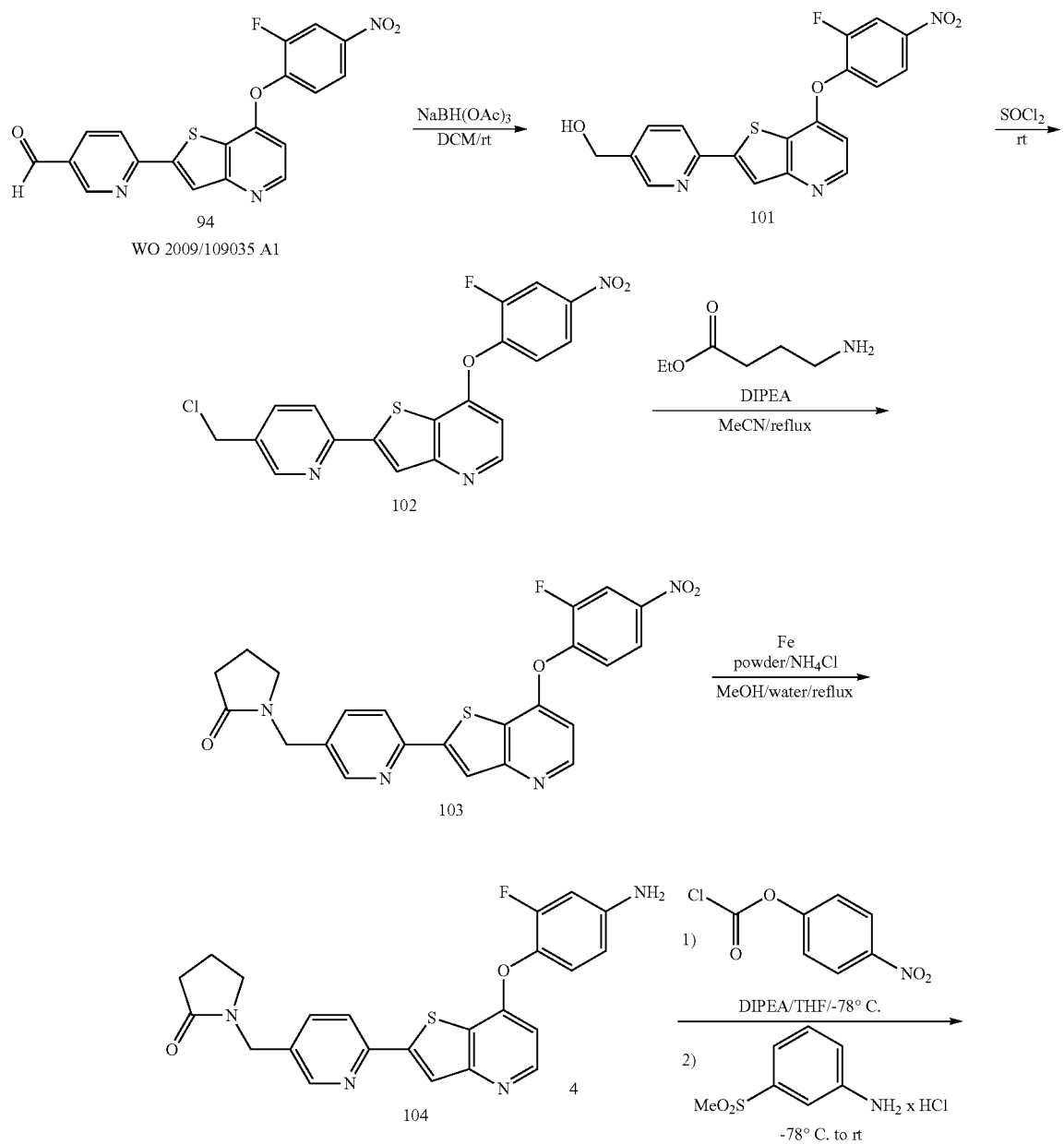

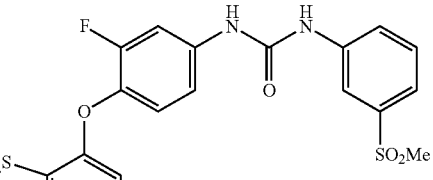

105: Example 72

Example 72

1-(3-fluoro-4-(2-(5-((2-oxopyrrolidin-1-yl)methyl)pyridin-2-yl)thieno[3,2-b]pyridin-7-yloxy)phenyl)-3-(3-(methylsulfonyl phenyl)urea (105)

Step 1. (6-(7-(2-fluoro-4-nitrophenoxy)thieno[3,2-b]pyridin-2-yl)pyridin-3-yl)methanol (101)

To a stirred suspension of 94 (3 g, 7.59 mmol) in DCM (50 mL) at RT under nitrogen was added NaBH(OAc)₃ (3.39 g, 15.99 mmol) in one portion. The reaction mixture was stirred at RT overnight, and quenched by addition of 10% HCl and suspended in a mixture of water and DCM. The solid was collected by filtration, rinsed with water, DCM and dried under high vacuum to afford the title compound 101 (2.26 g, 5.69 mmol, 75% yield) as a yellow-mustard solid which was used in the next step without further purification. MS (m/z): 398.1 (M+H).

Step 2. 2-(5-(chloromethyl)pyridin-2-yl)-7-(2-fluoro-4-nitrophenoxy)thieno[3,2-b]-pyridine (102)

A solution of 101 (2.23 g, 5.61 mmol) in thionyl chloride (8.14 mL) under nitrogen was stirred at RT overnight. The reaction mixture was cooled down to 0° C., and ice was added. The resultant suspension was stirred for 1 h, the solid was collected by filtration, rinsed with water and dried under high vacuum to afford the title compound 102 (2.06 g, 4.96 mmol, 88% yield) as a yellow fluffy solid which was used in the next step without any further purification. MS (m/z): 416.4 and 418.4 (M+H).

Step 3. 1-((6-(7-(2-fluoro-4-nitrophenoxy)thieno[3,2-b]pyridin-2-yl)pyridin-3-yl)methyl)-pyrrolidin-2-one (103)

A mixture of 102 (500 mg, 1.202 mmol), ethyl 4-aminobutanoate (403 mg, 2.405 mmol) and DIPEA (0.630 mL, 3.61 mmol) under nitrogen in acetonitrile (12 mL) was heated to reflux for 3 days, then cooled to RT. The reaction mixture was then concentrated. The crude product was purified by Biotage (25M column; MeOH/DCM: 0/100 to 20/80 over 20 CV). The desired fractions were collected, concentrated and dried under high vacuum to afford the title compound 103 (270 mg, 0.58 mmol, 48% yield). MS (m/z): 465.5 (M+H).

Step 4. 1-((6-(7-(4-amino-2-fluorophenoxy)thieno[3,2-b]pyridin-2-yl)pyridin-3-yl)methyl)pyrrolidin-2-one (104)

A suspension of 103 (270 mg, 0.581 mmol), iron (649 mg, 11.63 mmol), and ammonium chloride (187 mg, 3.49 mmol) in MeOH (10 mL) and water (1 mL), was heated to reflux for 3 h, then cooled to RT. The mixture was then filtered through celite and the cake was rinsed with methanol. The mother liquor was concentrated, and partitioned between a saturated aqueous solution of NaHCO₃ and ethyl acetate. The aqueous phase was extracted 3 times with DCM. The combined organic phase was dried over anhydrous sodium sulfate, filtered, concentrated, re-dissolved in ethyl acetate, washed with 1N NaOH, dried over anhydrous sodium sulfate, filtered and concentrated. The crude product was purified by Biotage (SNAP 50 g cartridge; MeOH/DCM: 0/100 to 20/80 over 20 CV), to afford the title compound 104 (220 mg, 0.50 mmol, 87% yield) as beige solid. MS (m/z): 435.5 (M+H).

Step 5. 1-(3-fluoro-4-(2-(5-((2-oxopyrrolidin-1-yl)methyl)pyridin-2-yl)thieno[3,2-b]pyridin-7-yloxy)phenyl)-3-(3-(methylsulfonyl)phenyl)urea (105)

To a solution of 104 (50 mg, 0.115 mmol) in THF (2.3 mL) under nitrogen at −78° C. was added DIPEA (201 µl, 1.151 mmol) followed by 4-nitrophenyl chloroformate (116 mg, 0.575 mmol). The reaction mixture was kept at −78° C. over 1 hour. 3-(Methylsulfonyl)aniline hydrochloride (143 mg, 0.690 mmol) was added at −78° C. and the reaction mixture was allowed to warm to room temperature slowly. The reaction mixture was then quenched by addition of methanol, concentrated, dissolved in ethyl acetate, and successively washed with NH₄Cl and NaHCO₃, dried over anhydrous sodium sulfate, filtered and concentrated. The crude product was purified by Biotage (SNAP 25 g cartridge; MeOH/DCM: 0/100 to 20/80 over 20 CV), to afford the title compound 105 (14.8 mg, 0.023 mmol, 20% yield) as beige solid. ¹H NMR (400 MHz, DMSO-d₆) δ (ppm): 9.28 (s, 1H), 9.21 (s, 1H), 8.54 (d, J=5.6 Hz, 1H), 8.53 (d, J=2.4 Hz, 1H), 8.36 (s, 1H), 8.27 (d, J=8.4 Hz, 1H), 8.18 (t, J=2.0 Hz, 1H), 7.82-7.74 (m, 2H), 7.70 (dt, J=8.0, 1.6 Hz, 1H), 7.59 (t, J=8.0 Hz, 1H), 7.55 (dt, J=8.0, 1.6 Hz, 1H), 7.47 (t, J=8.8 Hz, 1H), 7.31 (d, J=8.8 Hz, 1H), 6.69 (d, J=5.2 Hz, 1H), 4.46 (s, 2H), 3.40-3.28 (m, 2H, hidden under water peak), 3.21 (s, 3H), 2.31 (t, J=8.0 Hz, 2H), 1.95 (quint, J=7.6 Hz, 2H). MS (m/z): 632.5 (M+H).

Scheme 27

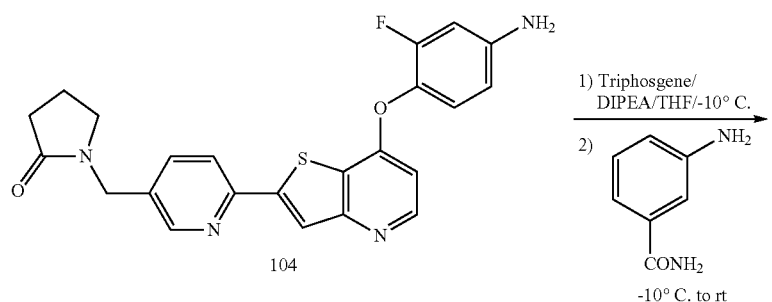

Example 73

3-(3-(3-fluoro-4-(2-(5-((2-oxopyrrolidin-1-yl)methyl)pyridin-2-yl)thieno[3,2-b]pyridin-7-yloxy)phenyl)ureido)benzamide (106)

To a solution of 104 (83 mg, 0.191 mmol, scheme 26) in THF (19 mL) at −10° C. was added DIPEA (334 μl, 1.910 mmol) and triphosgene (56.7 mg, 0.191 mmol). The reaction mixture was stirred for 90 min at −10° C. then 3-aminobenzamide (104 mg, 0.764 mmol) was added. The reaction mixture was allowed to warm to RT, stirred for 3 h, quenched with MeOH, and concentrated. The residue was suspended in 2 mL of MeOH and a saturated aqueous solution of ammonium chloride was added, stirred for 30 min, collected by filtration, and dried. The crude product was purified by Biotage (SNAP 25 g cartridge; MeOH/DCM: 0/100 to 30/70 over 20 CV) to produce a material that was further purified by Gilson (Phenomenex, Luna, 15μ, C18(2) 100A, 250×50.00 mm, 15 μm, 0.05% of formic acid in both MeOH/water (30 mL/min): 30/70 to 95/5 over 60 min), to afford the title compound 106 (8.7 mg, 0.015 mmol, 7% yield, formate salt) as an yellow solid. $^1$H NMR (400 MHz, DMSO-$d_6$) δ (ppm): 11.34 (s, 1H), 11.06 (s, 1H), 8.55-8.50 (m, 2H), 8.41 (s, 4H), 8.35 (s, 1H), 8.26 (d, J=8.0 Hz, 1H), 8.05 (t, J=2.0 Hz, 1H), 7.90-7.77 (m, 3H), 7.71-7.67 (m, 1H), 7.44-7.38 (m, 3H), 7.34-7.27 (m, 2H), 6.68 (dd, J=5.2, 0.8 Hz, 1H), 4.46 (s, 2H), 3.31 (t, J=7.2 Hz, 2H), 2.31 (t, J=8.0 Hz, 2H), 1.95 (quint, J=8.0 Hz, 2H). MS (m/z): 597.5 (M+H).

Scheme 28

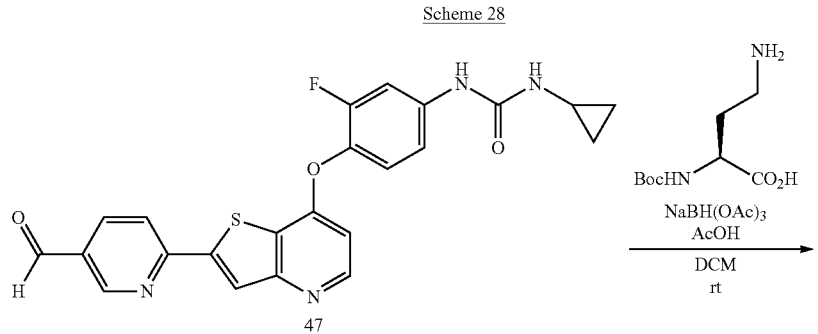

-continued

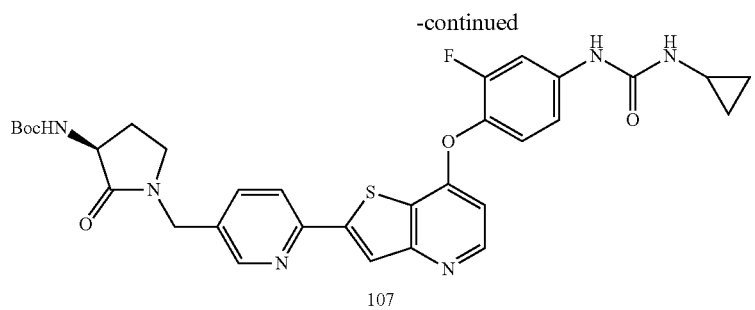

107 wet TFA/DCM/rt →

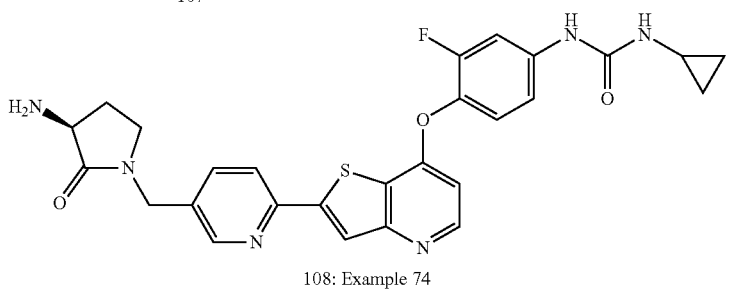

108: Example 74

Example 74
(S)-1-(4-(2-(5-((3-amino-2-oxopyrrolidin-1-yl)methyl)pyridin-2-yl)thieno[3,2-b]pyridin-7-yloxy)-3-fluorophenyl)-3-cyclopropylurea (108)

Step 1. (S)-tert-butyl 1-((6-(7-(4-(3-cyclopropylureido)-2-fluorophenoxy)thieno[3,2-b]-pyridin-2-yl)pyridin-3-yl)methyl)-2-oxopyrrolidin-3-ylcarbamate (107)

To a suspension of 47 (230 mg, 0.51 mmol, scheme 15) in DCM (5.1 mL) were added (S)-4-amino-2-(tert-butoxycarbonylamino)butanoic acid (224 mg, 1.03 mmol) and acetic acid (59 µl, 1.03 mmol). After stirring for 20 min at room temperature, NaBH(OAc)$_3$ (326 mg, 1.54 mmol) was added. The reaction mixture was stirred for 16 h, quenched by addition of 1N NaOH, and concentrated. The solid was collected by filtration and purified by Biotage (SNAP 50 g cartridge; MeOH/DCM: 0/100 to 20/80 over 20 CV), to afford the title compound 107 (120 mg, 0.19 mmol, 37% yield). MS (m/z): 633.7 (M+H).

Step 2. (S)-1-(4-(2-(5-((3-amino-2-oxopyrrolidin-1-yl)methyl)pyridin-2-yl)thieno[3,2-b]pyridin-7-yloxy)-3-fluorophenyl)-3-cyclopropylurea To a solution of 107 (120 mg, 0.19 mmol) in DCM (20 mL) was added water (0.5 mL) and TFA (4 mL, 51.9 mmol). The reaction mixture was stirred at RT for 6 h, concentrated, diluted with ethyl acetate, and washed with 1N NaOH. The organic phase was collected and the aqueous phase was re-extracted with ethyl acetate. The combined organic layers (a lot of unsoluble material stayed on the walls of the separatory funnel which was dissolved in MeOH and combined with the organic layers) were concentrated. A 1N NaOH solution was added; the suspension was stirred for 30 min and the solid was collected by filtration. The crude product was purified by Biotage (SNAP 50 g cartridge; 2% of ammonium hydroxide in MeOH/DCM: 0/100 to 40/60 over 20 CV), to afford the title compound 108 (77 mg, 0.14 mmol, 76% yield) as an off-white solid. $^1$H NMR (400 MHz, DMSO-d$_6$) δ (ppm): 8.77 (s, 1H), 8.55-8.51 (m, 2H), 8.36 (s, 1H), 8.27 (d, J=8.0 Hz, 1H), 7.81 (dd, J=8.0, 2.0 Hz, 1H), 7.73 (dd, J=13.6, 2.4 Hz, 1H), 7.38 (t, J=9.2 Hz, 1H), 7.20 (d, J=8.8 Hz, 1H), 6.65 (d, J=5.6 Hz, 1H), 6.60 (d, J=2.4 Hz, 1H), 4.52 (d, J=15.2 Hz, 1H), 4.45 (d, J=15.2 Hz, 1H), 4.15-3.65 (m, 214), 3.58 (t, J=8.8 Hz, 1H), 3.30-3.14 (m, 2H), 2.59-2.52 (m, 1H), 2.34-2.23 (m, 1H), 1.77-1.65 (m, 1H), 0.68-0.62 (m, 2H), 0.45-0.37 (m, 2H). MS (m/z): 533.6 (M+H).

Compounds 109-111 (examples 75-77) were prepared in two steps by reductive amination of 47 with the appropriately substituted γ-amino-acids similarly to compound 108 (example 74, scheme 28).

TABLE 14

Characterization of compounds 109-111 (examples 75-77)

| Cpd | Ex | Structure | Characterization |
|---|---|---|---|
| 109 | 75 | (R)-1-(4-(2-(5-((3-amino-2-oxopyrrolidin-1-yl)methyl)pyridin-2-yl)thieno[3,2-b]pyridin-7-yloxy)-3-fluorophenyl)-3-cyclopropylurea | $^1$H NMR (400 MHz, DMSO-d$_6$) δ (ppm): mixture of rotamers, 8.98 (s, 1H), 8.55 (d, J = 2.0 Hz, 1 H), 8.53 (d, J = 5.2 Hz, 1H), 8.37 (s, 1H), 8.28 (d, J = 8.4 Hz, 1H), 7.84 (dd, J = 8.4, 2.0 Hz, 1H), 7.73 (dd, J = 13.6, 2.4 Hz, 1H), 7.38 (t, J = 9.2 Hz, 1H), 7.19 (dd, J = 9.2, 1.2 Hz, 1H), 7.14-6.76 (bs, 2H), 6.71 (d, J = 2.8 Hz, 1H), 6.66 (d, J = 5.2 Hz, 1H), 4.58 (d, J = 16.0 Hz, 1H), 4.46 (d, J = 16.0 Hz, 1H), 3.89 (t, J = 9.2 Hz, 1H), 3.4-3.20 (m, hidden under water peak, 2H), 2.59-2.51 (m, 1H), 2.40-2.30 (m, 1H), 1.92-1.80 (m, 1H), 0.68-0.62 (m, 2H), 0.45-0.39 (m, 2H). MS (m/z): 533.6 (M + H). |

TABLE 14-continued

Characterization of compounds 109-111 (examples 75-77)

| Cpd | Ex | Structure | Characterization |
|---|---|---|---|
| 110 | 76 | (S)-1-cyclopropyl-3-(3-fluoro-4-(2-(5-(((3-hydroxy-2-oxopyrrolidin-1-yl)methyl)pyridin-2-yl)thieno[3,2-b]pyridin-7-yloxy)phenyl)urea | $^1$H NMR (400 MHz, DMSO-$d_6$) δ (ppm): 9.70 (s, 1H), 8.54-8.50 (m, 2H), 8.43 (s, 1H), 8.35 (s, 1H), 8.27 (d, J = 8.0 Hz, 1H), 7.81-7.72 (m, 2H), 7.48 (s, 1H), 7.35 (t, J = 9.2 Hz, 1H), 7.24 (dd, J = 8.8, 1.6 Hz, 1H), 6.65 (d, J = 5.2 Hz, 1H), 4.46 (s, 2H), 4.19 (t, J = 8.0 Hz, 1H), 3.30-3.14 (m, 2H), 2.58-2.52 (m, 1H), 2.33-2.24 (m, 1H), 1.79-1.68 (m, 1H), 0.65-0.59 (m, 2H), 0.44-0.38 (m, 2H). MS (m/z): 534.5 (M + H). |
| 111 | 77 | (±)-1-cyclopropyl-3-(3-fluoro-4-(2-(5-((4-hydroxy-2-oxopyrrolidin-1-yl)methyl)pyridin-2-yl)thieno[3,2-b]pyridin-7-yloxy)phenyl)urea | $^1$H NMR (400 MHz, DMSO-$d_6$) δ (ppm): 872 (s, 1H), 8.54-8.51 (m, 2H), 8.35 (s, 1H), 8.27 (d, J = 8.0 Hz, 1H), 7.79 (dd, J = 8.0, 2.4 Hz, 1H), 7.73 (dd, J = 13.6, 2.4 Hz, 1H), 7.38 (t, J = 8.8 Hz, 1H), 7.20 (d, J = 8.8 Hz, 1H), 6.65 (d, J = 5.2 Hz, 1H), 6.58 (d, J = 2.8 Hz, 1H), 5.20 (d, J = 4.0 Hz, 1H), 4.54 (d, J = 15.6 Hz, 1H), 4.42 (d, J = 15.6 Hz, 1H), 4.33-4.27 (m, 1H), 3.54 (dd, J = 10.4, 5.2 Hz, 1H), 3.10 (dd, J = 10.4, 1.6 Hz, 1H), 2.64 (dd, J = 16.8, 6.4 Hz, 1H), 2.59-2.52 (m, 1H), 2.13 (dd, J = 16.8, 2.0 Hz, 1H), 0.68-0.62 (m, 2H), 0.46-0.40 (m, 2H), MS (m/z): 534.6 (M + H). |

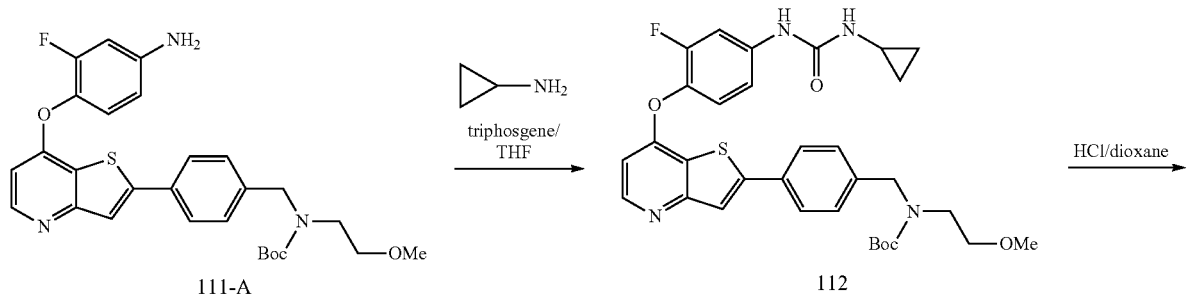

Scheme 29

-continued

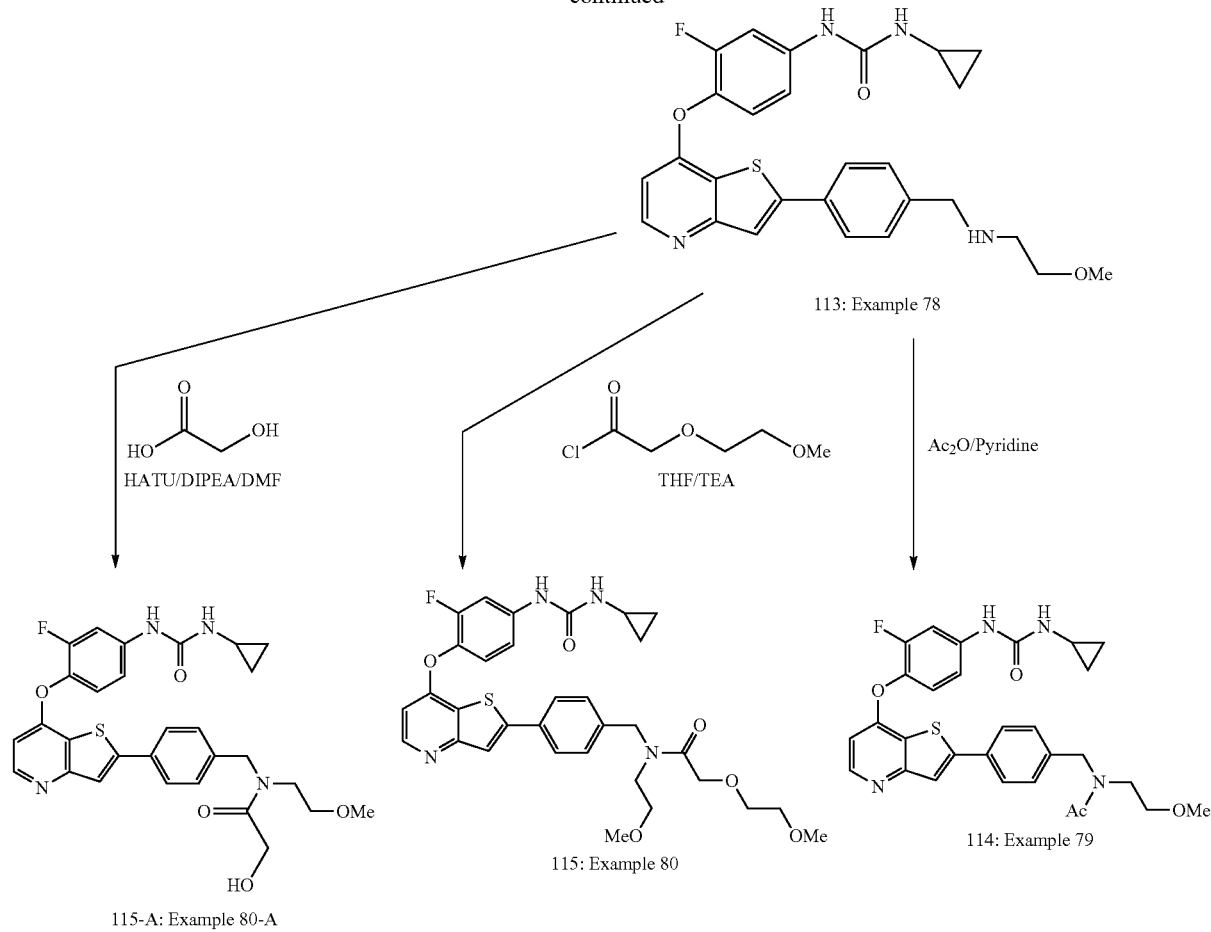

Example 78

1-cyclopropyl-3-(3-fluoro-4-(2-(4-(2-methoxyethylamino)methyl)phenyl)thieno[3,2-b]pyridin-7-yloxy)phenyl)urea (113)

Step 1: tert-butyl 4-(7-(4-(3-cyclopropylureido)-2-fluorophenoxy)thieno[3,2-b]pyridin-2-yl)benzyl(2-methoxyethyl)carbamate (112)

To a solution of 111-A (760 mg, 1.451 mmol) in THF (15 mL) was added TEA (0.607 mL, 4.35 mmol) and triphosgene (431 mg, 1.451 mmol) in THF (5 mL) and the mixture was stirred at RT for an hour. Cyclopropylamine (166 mg, 2.90 mmol) was added and the reaction mixture was stirred at RT overnight. The reaction mixture was concentrated then partitioned between DCM and saturated NaHCO$_3$ solution. The organic phase was collected, dried over anhydrous Na$_2$SO$_4$, filtered and concentrated. Purification of the residue by column chromatography (EtOAc) afforded title compound 112 (560 mg, 64% yield) as a white solid. MS (m/z)=607.2 (M+H).

Step 2: 1-cyclopropyl-3-(3-fluoro-4-(2-(4-((2-methoxyethylamino)methyl)phenyl)thieno[3,2-b]pyridin-7-yloxy)phenyl)urea (113)

To a solution of 112 (560 mg, 0.923 mmol) in DCM (10 mL) was added 4.0M HCl in dioxane (0.923 mL, 3.69 mmol) and the reaction mixture was stirred at RT for 2 hours. The mixture was diluted with saturated NaHCO$_3$ solution and the layers were separated. The organic phase was collected, dried over anhydrous Na$_2$SO$_4$, filtered and concentrated. The resultant solid was triturated with Et$_2$O to afford title compound 113 (350 mg, 75% yield) as a yellow solid. $^1$H NMR (400 MHz, DMSO-d$_6$) δ (ppm): 8.69 (s, 1H), 8.48 (d, J=5.48 Hz, 1H), 8.00 (s, 1H), 7.82 (d, J=8.41 Hz, 1H), 7.70 (m, 1H), 7.44 (d, J=8.22 Hz, 1H), 7.36 (t, J=9.19 Hz, 1H), 7.19 (m, 1H), 6.56 (m, 2H), 3.75 (s, 2H), 3.39 (t, J=5.67 Hz, 2H), 3.22 (s, 3H), 2.64 (t, J=5.67 Hz, 2H), 2.53 (m, 1H), 0.63 (m, 2H), 0.41 (m, 2H). MS (m/z)=507.5 (M+H).

Example 79

N-(4-(7-(4-(3-cyclopropylureido)-2-fluorophenoxy)thieno[3,2-b]pyridin-2-yl)benzyl)-N-(2-methoxyethyl)acetamide (114)

To a suspension of 113 (100 mg, 0.197 mmol) in pyridine (3 mL) was added Ac$_2$O (30.2 mg, 0.296 mmol) and the reaction mixture was stirred for an hour. The mixture was concentrated then re-dissolved in EtOAc and washed with saturated CuSO$_4$ solution then water. The organic phase was collected, dried over anhydrous Na$_2$SO$_4$, filtered and concentrated. The resultant solid was triturated with Et$_2$O to afford title compound 114 (97 mg, 90% yield) as a white solid. $^1$H NMR (400 MHz, DMSO-d$_6$) δ (ppm): 8.68 (s, 1H), 8.48 (m, 1H), 8.03 (s, 1H, rotamer), 7.83 (m, 2H, rotamer), 7.70 (m, 1H), 7.36 (m, 3H), 7.18 (m, 1H), 6.56 (m, 2H), 4.57 (s, 2H, rotamer) 3.43 (s, 3H), 3.29 (s, 2H), 3.20 (s, 2H, rotamer), 2.49 (m, 1H), 2.06 (s, 3H, rotamer), 0.63 (m, 2H), 0.41 (m, 2H). MS (m/z)=549.57 (M+H).

Example 80

N-(4-(7-(4-(3-cyclopropylureido)-2-fluorophenoxy) thieno[3,2-b]pyridin-2-yl)benzyl)-2-(2-methoxyethoxy)-N-(2-methoxyethyl)acetamide (115)

To a suspension of 113 (120 mg, 0.237 mmol) in THF (3 mL) was added 2-(2-methoxyethoxy)acetyl chloride (54.2 mg, 0.355 mmol) and TEA (71.9 mg, 0.711 mmol) and the reaction mixture was stirred overnight at RT. The reaction mixture was diluted with EtOAc then washed with saturated ammonium chloride solution. The organic phase was collected, dried over anhydrous Na$_2$SO$_4$, filtered and concentrated. The resultant solid was triturated with Et$_2$O to give title compound 115 (113 mg, 77% yield) as a white solid. $^1$H NMR (400 MHz, DMSO-d$_6$) δ (ppm): 8.72 (s, 1H), 8.50 (d, J=5.48, 1H), 8.05 (s, 1H, rotamer), 7.90 (m, 2H, rotamer), 7.75 (m, 1H), 7.20 (m, 3H), 7.19 (m, 1H), 6.59 (m, 2H), 4.61 (s, 1H, rotamer), 4.31 (s, 2H, rotamer), 3.61 (m, 2H), 3.49 (m, 6H), 3.23 (m, 7H), 2.55 (m, 1H), 0.64 (m, 2H), 0.43 (m, 2H). MS (m/z)=623.66 (M+H).

Example 80-A

N-(4-(7-(4-(3-cyclopropylureido)-2-fluorophenoxy) thieno[3,2-b]pyridin-2-yl)benzyl)-2-hydroxy-N-(2-methoxyethyl)acetamide (115-A)

To a solution of 113 (168 mg, 0.332 mmol) in DMF (8 mL) at RT was added DIPEA (0.203 mL, 1.161 mmol), followed by HATU reagent (378 mg, 0.995 mmol). The reaction mixture was stirred overnight at RT. Ethyl acetate was added, the reaction mixture was washed with water, saturated ammonium chloride solution and saturated sodium bicarbonate solution, dried over anhydrous sodium sulfate and concentrated. The residue was purified via Biotage (0-50% MeOH/EtOAc; SNAP 50 g cartridge) to give an off-white solid which upon trituration with ether/acetone afforded title compound 115-A (20 mg, 11% yield) as a white solid. $^1$H NMR (400 MHz, DMSO-d$_6$) δ (ppm): contains 2 rotamers: 8.74 (s, 1H), 8.54 (d, 1H, J=5.5 Hz), 8.10, 8.07 (2s, 1H), 7.94, 7.89 (2d, 2H, J=8.2 Hz), 7.78 (dd, 1H, J1=2.4 Hz, J2=13.5 Hz), 7.44-7.38 (m, 3H), 7.25-7.22 (m, 1H), 6.63-6.61 (m, 2H), 4.73-4.61 (m, 3H), 4.28, 4.14 (2d, 2H, J=5.5 Hz), 3.51-3.40 (m, 4H), 3.27 (s, 3H), 2.60-2.56 (m, 1H), 0.71-0.67 (m, 2H), 0.48-0.44 (m, 2H). MS: 565.5 (MH+).

Compounds 116-117 (examples 81-82) were prepared by reacting the corresponding NH-precursors described in WO 2009/109035 A1 with Ac$_2$O, similarly to compound 114 (example 79, scheme 29).

TABLE 15

Characterization of compounds 116 to 117-A (examples 81 to 82-A).

| Cpd | Ex | Structure | Characterization |
| --- | --- | --- | --- |
| 116 | 81 | 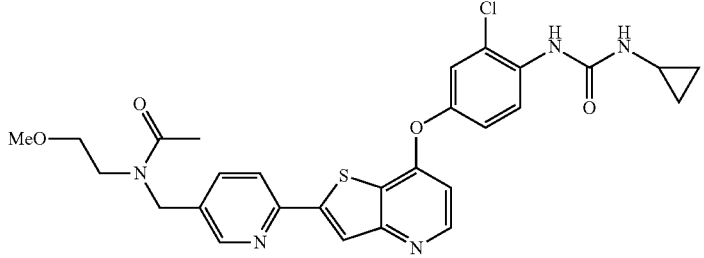 [SMILES: COCCN(Cc1ccc(-c2cc3nccc(Oc4ccc(NC(=O)NC5CC5)c(Cl)c4)c3s2)nc1)C(C)=O]<br>N-((6-(7-(3-chloro-4-(3-cyclopropylureido)phenoxy)thieno[3,2-b]pyridin-2-yl)pyridin-3-yl)methyl)-N-(2-methoxyethyl)acetamide | $^1$H NMR (400 MHz, DMSO-d$_6$) δ (ppm): 8.5 (m, 2H), 8.30-8.20 (m, 3H), 7.97 (s, 1H), 7.76 (m, 1H), 7.25-7.20 (m, 2H), 6.67 (m, 1H), 4.69 (s, 1H), 4.56 (s, 2H), 3.45 (m, 3H), 3.28 (s, 3H), 3.18 (s, 1H), 2.5 (m, 1H), 2.1 (s, 3H), 0.65 (m, 2H), 0.41 (m, 2H). MS (m/z) = 566.617 (M$^+$). |
| 117 | 82 | 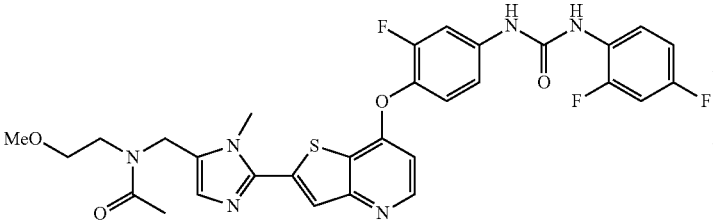<br>N-((2-(7-(4-(3-(2,4-difluorophenyl)ureido)-2-fluorophenoxy)thieno[3,2-b]pyridin-2-yl)-1-methyl-1H-imidazol-5-yl)methyl)-N-(2-methoxyethyl)acetamide | $^1$H NMR (400 MHz, DMSO-d$_6$) δ (ppm): 9.37 (s, 1H), 8.62 (s, 1H), 8.51 (d, J = 5.48 Hz, 1H), 8.03 (m, 1H), 7.89 (s, 1H), 7.73 (m, 1H), 7.43 (t, J = 8.99 Hz, 1H), 7.32 (m, 1H), 7.21 (m, 1H), 7.035 (m, 2H), 6.67 (d J = 5.48 Hz, 1H), 4.65 (s, 2H), 3.81 (s, 3H), 3.40 (s, 2H), 3.23 (s, 2H), 2.086 (s, 3H). MS (m/z) = 652.56 (M + H). |

TABLE 15-continued

Characterization of compounds 116 to 117-A (examples 81 to 82-A).

| Cpd | Ex | Structure | Characterization |
|---|---|---|---|
| 117-A | 82-A | 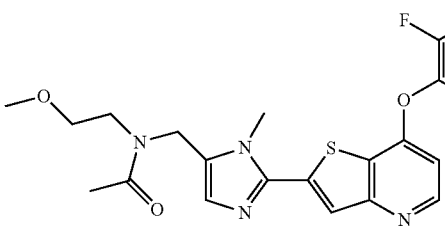<br>N-((2-(7-(2-fluoro-4-(3-isopropylureido)phenoxy)thieno[3,2-b]-pyridin-2-yl)-1-methyl-1H-imidazol-5-yl)methyl)-N-(2-methoxyethyl)acetamide | $^1$H NMR (400 MHz, DMSO-$d_6$) δ (ppm): 9.25(s, 1H), 8.58(s, 1H), 8.55(d, 1H, J = 5.5 Hz), 7.94(s, 1H), 7.76(dd, 1H, J1 = 2.6 Hz, J2 = 13.7 Hz), 7.39(t, 1H, J = 9.0 Hz), 7.21-7.19(m, 1H), 7.08(s, 1H), 6.70-6.68(m, 2H), 4.70(s, 2H), 3.87(s, 3H), 3.81-3.79(m, 1H), 3.46(s, 3H), 3.42(t, 2H), 3.32(t, 2H), 3.29(s, 3H), 2.14(s, 3H), 1.15(s, 3H), 1.13(s, 3H). MS: 555(MH+) |

Scheme 30

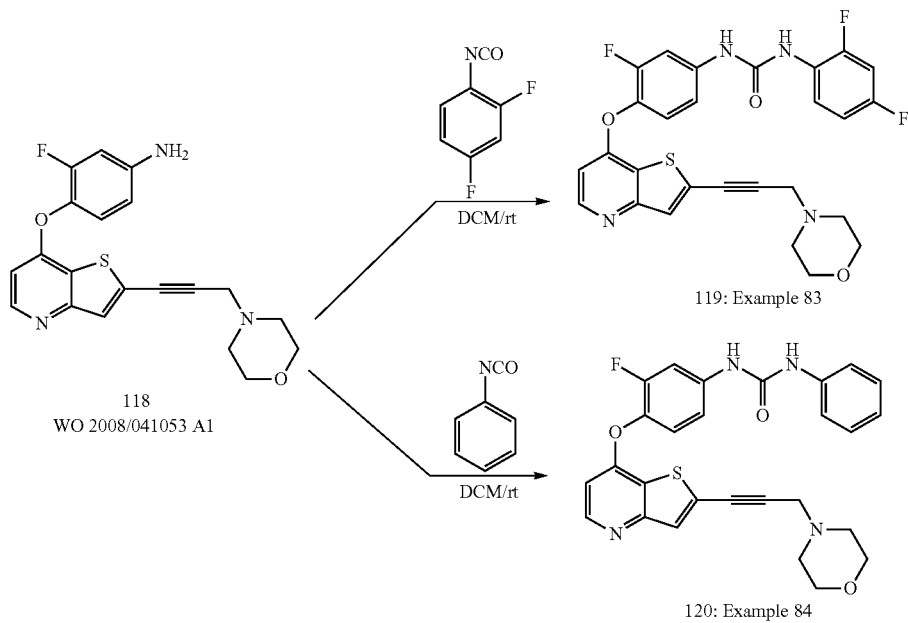

Example 83

1-(2,4-difluorophenyl)-3-(3-fluoro-4-(2-(3-morpholinoprop-1-ynyl)thieno[3,2-b]pyridin-7-yloxy)phenyl)urea (119)

To a solution of 118 (150 mg, 0.391 mmol) in DCM (7 mL) was added the 2,4-difluorophenyl isocyanate (121 mg, 0.782 mmol) and the reaction mixture was stirred at RT overnight. The resultant solid was collected by filtration, dissolved in DCM and purified by column chromatography (EtOAc to 10% MeOH in EtOAc) to afford title compound 119 (71 mg, 34% yield) as a white solid. $^1$H NMR (400 MHz, DMSO-$d_6$) δ (ppm): 9.36 (s, 1H), 8.61 (s, 1H), 8.54 (d, J=5.28, 1H), 8.03 (m, 1H), 7.78 (s, 1H), 7.73 (m, 1H), 7.43 (t, J=8.99 Hz, 1H), 7.34 (m, 1H), 7.23 (m, 1H), 7.05 (m, 1H), 6.71 (d, J=5.48 Hz, 1H), 3.63 (s, 2H), 3.59 (m, 4H), 2.52 (m, 4H). MS (m/z) =539.62 (M+H)

Example 84

1-(3-fluoro-4-(2-(3-morpholinoprop-1-ynyl)thieno[3,2-b]pyridin-7-yloxy)phenyl)-3-phenylurea (120)

To a solution of 118 (150 mg, 0.391 mmol) in DCM (7 mL) was added phenyl isocyanate (93 mg, 0.782 mmol) and the reaction mixture was stirred at RT overnight. The resultant solid was collected by filtration and then purified by column chromatography (EtOAc+1% NH$_4$OH to 10% MeOH in EtOAc+1% NH$_4$OH) to produce title compound 120 (37 mg, 19% yield) as a white solid. $^1$H NMR (400 MHz, DMSO-$d_6$) δ (ppm): 9.06 (s, 1H), 8.81 (s, 1H), 8.54 (d, J=5.48 Hz, 1H), 7.79 (s, 1H), 7.73 (m, 1H), 7.44 (m, 3H), 7.27 (m, 3H), 6.98 (t, J=7.24 Hz, 1H), 6.70 (d, J=5.48 Hz, 1H), 3.63 (s, 2H), 3.60 (m, 4H), 2.48 (m, 4H). MS (m/z)=503.62 (M+H).

Scheme 31

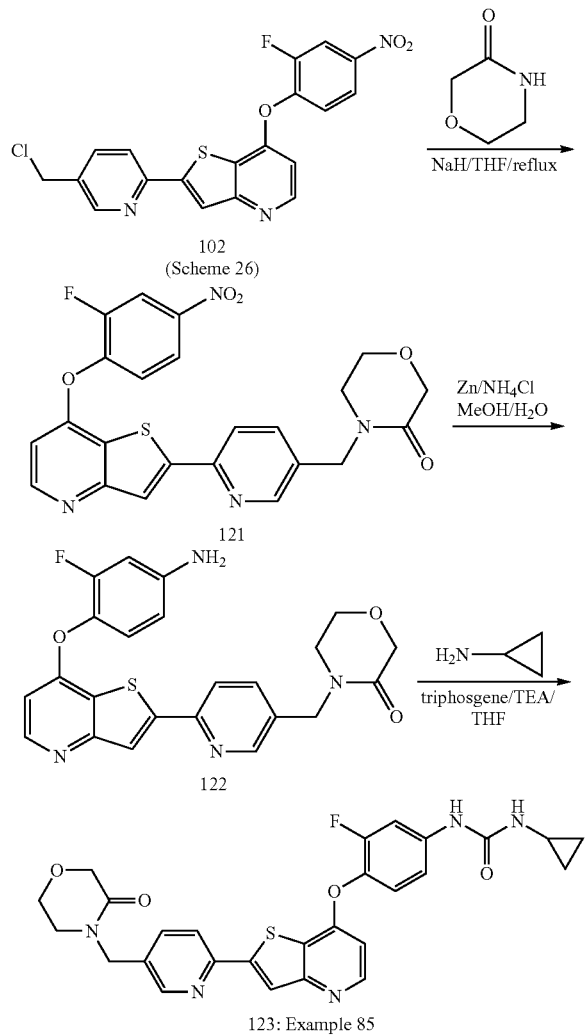

Example 85

1-cyclopropyl-3-(3-fluoro-4-(2-(5-((3-oxomorpholino)methyl)pyridin-2-yl)thieno[3,2-b]pyridin-7-yloxy)phenyl)urea (123)

Step 1: 4-((6-(7-(2-fluoro-4-nitrophenoxy)thieno[3,2-b]pyridin-2-yl)pyridin-3-yl)methyl)morpholin-3-one (121)

To a solution of 102 (350 mg, 0.842 mmol, scheme 26) in THF (10 mL) was added a solution of the anion [made from morpholin-3-one (340 mg, 4 eq., 3.37 mmol) and NaH (81 mg, 4 eq., 3.37 mmol)] in THF (5 mL)) and the mixture was heated to reflux for 8 hours. The mixture was quenched with saturated NH$_4$Cl solution and extracted with DCM. The organic phase was collected, dried over anhydrous Na$_2$SO$_4$, filtered and concentrated. The resultant solid was triturated with acetone to give title compound 121 (135 mg, 33% yield) which was used in the next step with no additional purification. MS (m/z)=481.2 (M+H)

Step 2: 4-((6-(7-(4-amino-2-fluorophenoxy)thieno[3,2-b]pyridin-2-yl)pyridin-3-yl)methyl)morpholin-3-one (122)

To a suspension of 121 (135 mg, 0.281) in MeOH (10 mL) was added Zinc powder (184 mg, 2.81 mmol) and NH$_4$Cl (60.1 mg, 1.124 mmol) in water (1 mL) and the reaction mixture was stirred at reflux for 5 hours then stirred at RT for 2 days. The mixture was filtered, concentrated, dissolved in DCM and MeOH and the resultant solution was then washed with water. The organic phase was collected, dried over anhydrous Na$_2$SO$_4$, filtered and concentrated. The resultant solid 122 (65 mg, 51% yield) was used directly in the next step with no additional purification. MS (m/z)=451.49 (M+H)

Step 3: 1-cyclopropyl-3-(3-fluoro-4-(2-(5-((3-oxomorpholino)methyl)pyridin-2-yl)thieno[3,2-b]pyridin-7-yloxy)phenyl)urea (123)

To a solution of 122 (65 mg, 0.144 mmol) in THF (7 mL) was added TEA (0.06 mL, 0.433 mmol) and triphosgene (42.8 mg, 0.144 mmol) in THF (2 mL) and the mixture was stirred at RT for an hour. Cyclopropylamine (16.48 mg, 0.289 mmol) was added and the reaction mixture was stirred at RT overnight. The reaction mixture was diluted with DCM and washed with saturated NH$_4$Cl solution. The organic phase was collected, dried over anhydrous Na$_2$SO$_4$, filtered and concentrated. The resultant solid was triturated with acetone to afford title compound 123 (18 mg, 23% yield) as an olive colored solid. $^1$H NMR (400 MHz, DMSO-d$_6$) δ (ppm): 8.69 (s, 1H), 8.55 (s, 1H), 8.51 (d, J=5.48 Hz, 1H), 8.34 (s, 1H), 8.25 (d, J=8.22 Hz, 1H), 7.82 (m, 1H), 7.71 (m, 1H), 7.36 (t, J=8.99 Hz, 1H), 7.19 (m, 1H), 6.63 (d, J=5.48 Hz, 1H), 6.55 (s, 1H), 4.60 (s, 2H), 4.12 (s, 2H), 3.83 (m, 2H), 3.36 (m, 2H), 2.49 (m, 1H), 0.64 (m, 2H), 0.42 (m, 2H). MS (m/z)=534.51 (M+H)

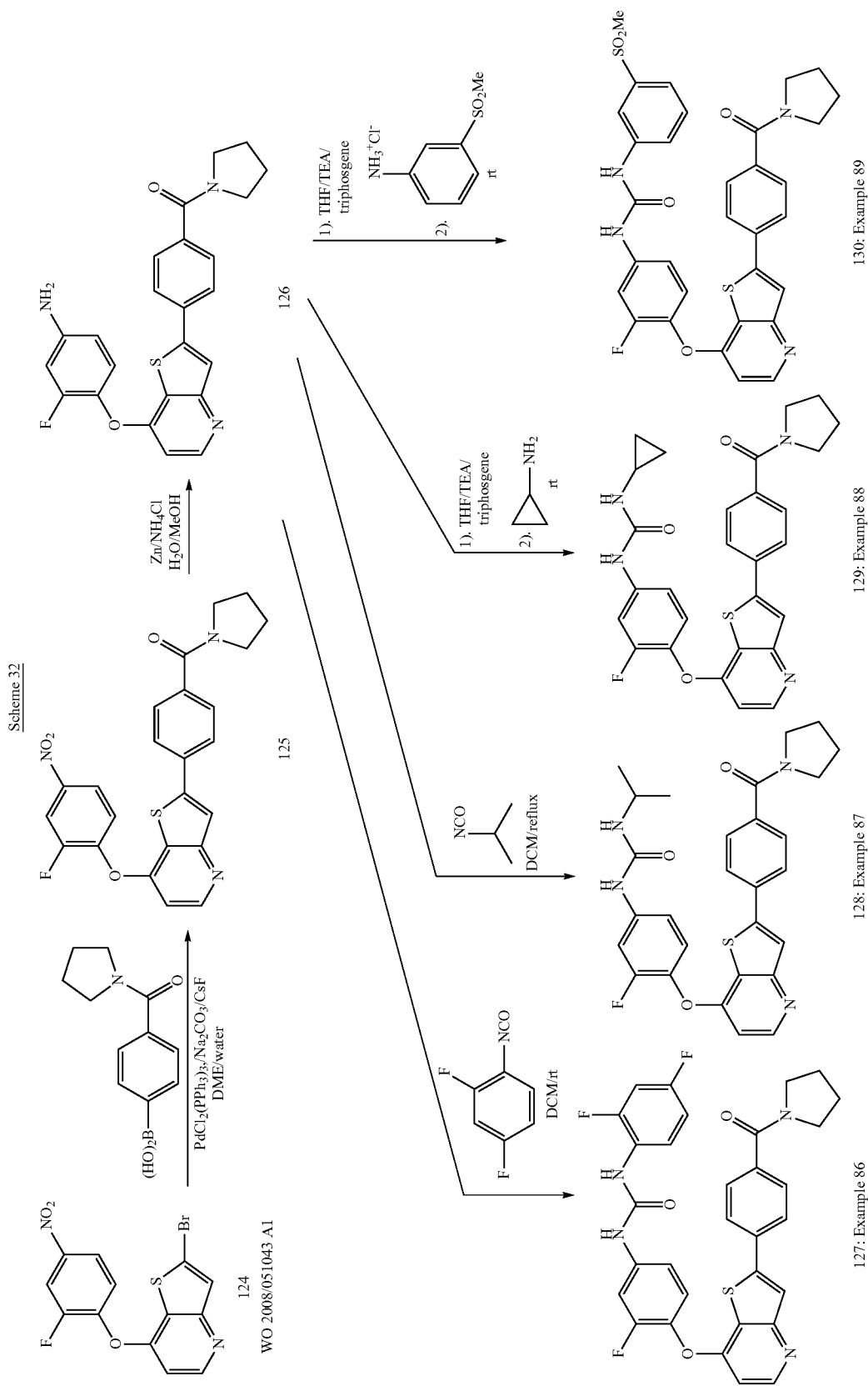

Example 86

1-(2,4-difluorophenyl)-3-(3-fluoro-4-(2-(4-(pyrrolidine-1-carbonyl)phenyl)thieno[3,2-b]pyridin-7-yloxy)phenyl)urea (127)

Step 1: (4-(7-(2-fluoro-4-nitrophenoxy)thieno[3,2-b]pyridin-2-yl)phenyl)(pyrrolidin-1-yl)methanone (125)

To a solution of 124 (1.685 g, 4.57 mmol) in DME (30 mL) was added 4-(pyrrolidine-1-carbonyl)phenylboronic acid (1 g, 4.57 mmol), Pd(PPh$_3$)Cl$_2$ (0.32 g, 0.457 mmol), CsF (2.080 g, 13.70 mmol), Na$_2$CO$_3$ (1.452 g, 13.70 mmol) in water (5 mL) and the reaction mixture was degassed with N$_2$ for 5 min before heating to reflux for 4 hours. The reaction was cooled to RT and diluted with EtOAc and water. The layers were separated and the organic phase was collected, dried over anhydrous Na$_2$SO$_4$, filtered and concentrated. The resultant black solid was triturated with Et$_2$O to afford title compound 125 (1.5 g, 71% yield) as a dark brown solid which was used in the next step with no additional purification. MS (m/z) =464.48 (M+H)

Step 2: (4-(7-(4-amino-2-fluorophenoxy)thieno[3,2-b]pyridin-2-yl)phenyl)(pyrrolidin-1-yl)methanone (126)

To a suspension of 125 (1.5 g, 3.24 mmol) in MeOH (60 mL) was added Zinc powder (1.693 g, 25.9 mmol) and NH$_4$Cl (0.346 g, 6.47 mmol) and the reaction mixture was heated to reflux for 5 hours. The mixture was cooled to RT and filtered. The filtrate was concentrated and the residue was dissolved in DCM and washed with water. The organic phase was collected, dried over anhydrous Na$_2$SO$_4$, filtered and concentrated to give title compound 126 (1.3 g, 93% yield) as a brown oil which became a puffy solid after removal of residual solvent in high vacuum. MS (m/z)=434.50 (M+H)

Step 3: 1-(2,4-difluorophenyl)-3-(3-fluoro-4-(2-(4-(pyrrolidine-1-carbonyl)phenyl)thieno[3,2-b]pyridin-7-yloxy)phenyl)urea (127)

To a solution of 126 (125 mg, 0.288 mmol) in DCM (6 mL) was added the 2,4-difluorophenyl isocyanate (134 mg, 0.865 mmol) and the reaction mixture was stirred at RT overnight. The reaction mixture was then concentrated and the resultant solid was triturated with acetone and collected by filtration to give title compound 127 (100 mg, 59% yield) as a white solid. $^1$H NMR (400 MHz, DMSO-d$_6$) δ (ppm): 9.37 (s, 1H), 8.61 (s, 1H), 8.51 (d, J=5.48 Hz, 1H), 8.14 (s, 1H), 8.04 (m, 1H), 7.94 (m, 2H), 7.76 (m, 1H), 7.64 (m, 2H), 7.45 (t, J=8.99 Hz, 1H), 7.35 (m, 1H), 7.22 (m, 1H), 7.06 (m, 1H), 6.63 (d, J=5.48 Hz, 1H), 3.48-3.37 (m, 4H), 1.85 (m, 4H). MS (m/z)=589.546 (M+H)

Example 87

1-(3-fluoro-4-(2-(4-(pyrrolidine-1-carbonyl)phenyl)thieno[3,2-b]pyridin-7-yloxy)phenyl)-3-isopropylurea (128)

To a solution of 126 (150 mg, 0.346 mmol) in DCM (7 mL) was added isopropyl isocyanate (265 mg, 3.11 mmol) and the reaction mixture was heated to reflux for 8 hours. The mixture was cooled to RT and concentrated. Purification by column chromatography (EtOAc) afforded the title compound 128 which was further triturated with Et$_2$O (90 mg, 50% yield) as a white solid. $^1$H NMR (400 MHz, DMSO-d$_6$) δ (ppm): 8.69 (s, 1H), 8.50 (d, J=5.28 Hz, 1H), 8.49 (s, 1H), 7.93 (d, J=8.41 Hz, 2H), 7.70 (m, 1H), 7.63 (d, J=8.41 Hz, 2H), 7.35 (t, J=9.19 Hz, 1H), 7.11 (m, 1H), 6.60 (d, J=5.48 Hz, 1H), 6.15 (d, J=7.63 Hz, 1H), 3.74 (m, 1H), 3.59-3.40 (m, 4H), 1.88-1.79 (m, 4H), 1.09 (d, J=6.46 Hz, 6H). MS (m/z)=519.65 (M+H)

Example 88

1-cyclopropyl-3-(3-fluoro-4-(2-(4-(pyrrolidine-1-carbonyl)phenyl)thieno[3,2-b]pyridin-7-yloxy)phenyl)urea (129)

To a solution of 126 (150 mg, 0.346 mmol) in DCM (7 mL) was added TEA (105 mg, 1.038 mmol) and triphosgene (103 mg, 0.346 mmol) and the reaction mixture was stirred for 30 minutes. Cyclopropylamine (39.5 mg, 0.692 mmol) was added and the mixture was stirred at RT overnight. The mixture was concentrated and re-dissolved in EtOAc then washed with saturated NH$_4$Cl solution. The organic phase was dried over anhydrous Na$_2$SO$_4$, filtered and concentrated. Purification by column chromatography (10% MeOH in EtOAc) afforded title compound 129 (40 mg, 22% yield) as a white solid. $^1$H NMR (400 MHz, DMSO-d$_6$) δ (ppm): 8.71 (s, 1H), 8.51 (m, 1H), 8.13 (s, 1H), 7.93 (d, J=7.82 Hz, 2H), 7.73 (m, 1H), 7.63 (d, J=7.82 Hz, 2H), 7.37 (t, J=8.61 Hz, 1H), 7.18 (m, 1H), 6.61 (m, 1H), 6.56 (s, 1H), 3.47-3.42 (m, 4H), 1.86-1.81 (m, 4H), 2.53 (m, 1H), 0.64 (m, 2H), 0.411 (m, 2H). MS (m/z)=517.533 (M+H)

Example 89

1-(3-fluoro-4-(2-(4-(pyrrolidine-1-carbonyl)phenyl)thieno[3,2-b]pyridin-7-yloxy)phenyl)-3-(3-(methylsulfonyl)phenyl)urea (130)

To a solution of 126 (150 mg, 0.346 mmol) in THF (6 mL) was added TEA (175 mg, 1.730 mmol) and triphosgene (103 mg, 0.346 mmol) in THF (1 mL) and the mixture was stirred for 30 minutes. 3-(Methylsulfonyl)benzenaminium chloride (144 mg, 0.692 mmol) was added and the mixture was stirred at RT overnight. The mixture was then concentrated and the resultant solid was triturated with acetone, DCM and MeOH, followed by recrystallization from hot DMF. An additional trituration with acetone afforded 130 (25 mg, 11% yield) as a grey powder. $^1$H NMR (400 MHz, DMSO-d$_6$) δ (ppm): 9.32 (s, 1H), 9.24 (s, 1H), 8.52 (d, J=5.48 Hz, 1H), 8.16 (s, 1H), 8.13 (s, 1H), 7.94 (d, J=8.41 Hz, 2H), 7.75 (m, 1H), 7.66-7.62 (m, 3H), 7.56-7.53 (m, 2H), 7.45 (m, 1H), 7.31 (m, 1H), 6.64 (d, J=5.48 Hz, 1H), 3.48-3.37 (m, 4H), 3.19 (s, 3H), 1.86-1.81 (m, 4H). MS (m/z)=631.437 (M+H).

Scheme 33

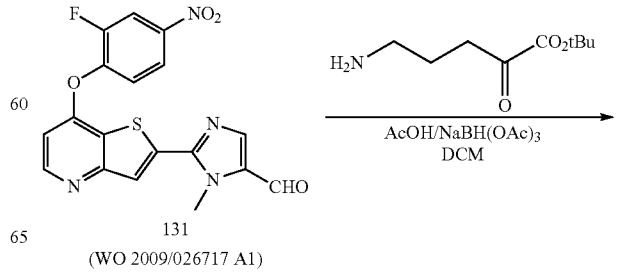

131
(WO 2009/026717 A1)

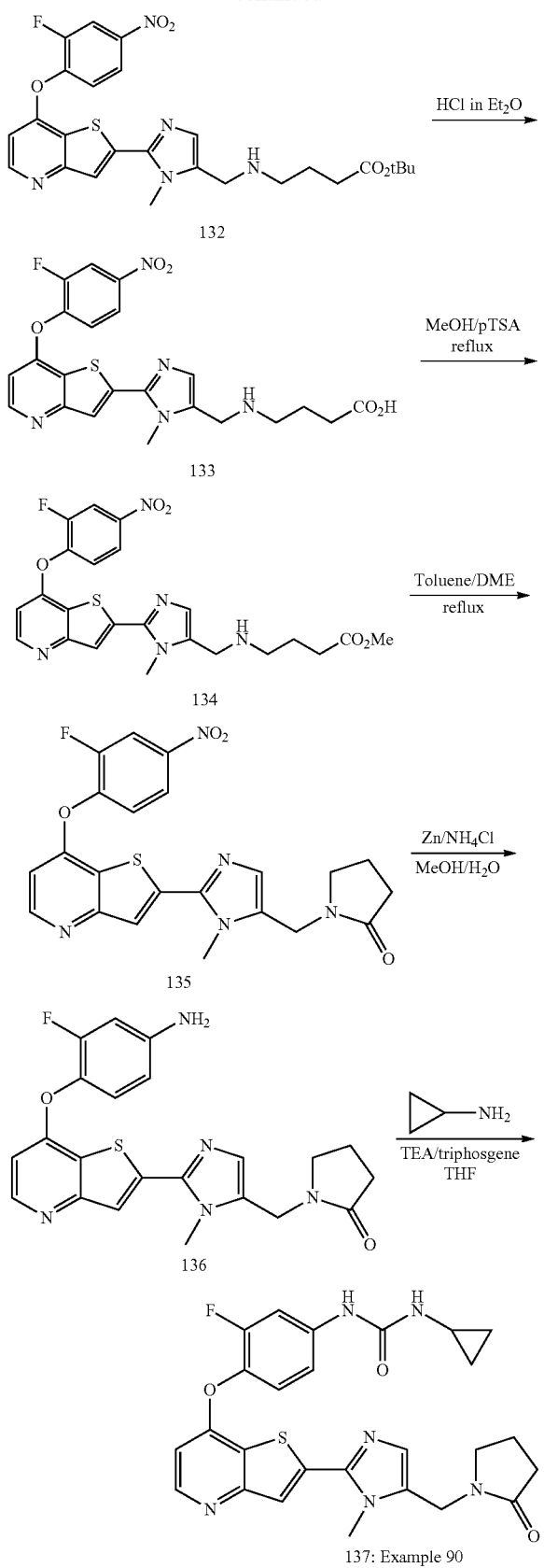

Example 90

1-cyclopropyl-3-(3-fluoro-4-(2-(1-methyl-5-((2-oxopyrrolidin-1-yl)methyl)-1H-imidazol-2-yl)thieno[3,2-b]pyridin-7-yloxy)phenyl)urea (137)

Step 1: tert-butyl 4-((2-(7-(2-fluoro-4-nitrophenoxy)thieno[3,2-b]pyridin-2-yl)-1-methyl-1H-imidazol-5-yl)methylamino)butanoate (132)

To a suspension of aldehyde 131 (200 mg, 0.502 mmol) in DCM (10 mL) was added tert-butyl 5-amino-2-oxopentanoate (282 mg, 1.506 mmol) and AcOH (0.029 mL, 1 eq., 0.502 mmol) and the reaction mixture was stirred for 30 minutes. NaB(OAc)$_3$H (266 g, 1.255 mmol) was added and the reaction mixture was stirred for an additional 24 hours. The reaction mixture was then diluted with excess DCM and washed with water. The organic phase was collected, dried over anhydrous Na$_2$SO$_4$, filtered and concentrated to afford the title compound 132 as an oil (272 mg, 100% yield, crude) that was used in the next step with no additional purification. MS (m/z)=541.59 (M+H).

Step 2: 4-((2-(7-(2-fluoro-4-nitrophenoxy)thieno[3,2-b]pyridin-2-yl)-methyl-1H-imidazol-5-yl)methylamino)butanoic acid (133)

To a solution of 132 (272 mg, 0.502 mmol) in DCM (10 mL) was added HCl (4 M in Et$_2$O) (0.502 mg, 2.009 mmol) and the reaction mixture was stirred at RT for 4 hours. The reaction mixture was then concentrated to afford title compound 133 as a yellow solid (244 mg, 100% yield, crude) that was used in the next step with no additional purification. MS (m/z)=486.1 (M+H).

Step 3: methyl 442-(7-(2-fluoro-4-nitrophenoxy)thieno[3,2-b]pyridin-2-yl)-1-methyl-1H-imidazol-5-yl)methylamino)butanoate (134)

A solution of 133 (242 mg, 0.498 mmol) in dry MeOH (10 mL) was heated in the presence of PTSA (95 mg, 0.498 mmol) for an hour. The reaction mixture was cooled to RT then neutralized with solid sodium bicarbonate. The mixture was then concentrated and partitioned between water and DCM. The organic phase was collected, dried over anhydrous Na$_2$SO$_4$, filtered and concentrated to afford the title compound 134 (249 mg, 100% yield, crude) that was used directly in the next step with no additional purification. MS (m/z)=500.1 (M+H).

Step 4: 1-((2-(7-(2-fluoro-4-nitrophenoxy)thieno[3,2-b]pyridin-2-yl)-1-methyl-1H-imidazol-5-yl)methyl)pyrrolidin-2-one (135)

A solution of 134 (249 mg, 0.498 mmol) in toluene (9 mL) and DME (1 mL) was heated to reflux for 24 hours. The mixture was cooled to RT and concentrated. Purification of the residue by column chromatography (10% MeOH in EtOAc) afforded title compound 135 (125 mg, 54% yield) as a yellow solid. MS (m/z) 467.41 (M+H).

Step 5: 1-((2-(7-(4-amino-2-fluorophenoxy)thieno[3,2-b]pyridin-2-yl)-1-methyl-1H-imidazol-5-yl)methyl)pyrrolidin-2-one (136)

To a solution of 135 (125 mg, 0.267 mmol) in MeOH (10 mL) was added zinc powder (140 mg, 2.14 mmol) and ammonium chloride (42.9 mg, 0.80 mmol) in water (1 mL) and the reaction mixture was heated to reflux for 4 hours. The mixture was cooled to RT, filtered and concentrated. The residue was partitioned between water and DCM/MeOH and the organic phase was collected, dried over anhydrous $Na_2SO_4$, filtered and concentrated to afford title compound 136 (77 mg, 66% yield) that was used crude in the next step with no additional purification. MS (m/z)=438.50 (M+H).

Step 6: 1-cyclopropyl-3-(3-fluoro-4-(2-(1-methyl-5-((2-oxopyrrolidin-1-yl)methyl)-1H-imidazol-2-yl)thieno[3,2-b]pyridin-7-yloxy)phenyl)urea (137)

To a solution of 136 (77 mg, 0.176 mmol) in THF (10 mL) was added TEA (0.074 mL, 0.528 mmol) and triphosgene (52.2 mg, 1.451 mmol) in THF (5 mL) and the mixture was stirred at RT for an hour. Cyclopropylamine (10.5 mg, 0.176 mmol) was added and the reaction mixture was stirred at RT overnight. The reaction mixture was then concentrated and partitioned between with DCM and saturated $NaHCO_3$ solution. The organic phase was collected, dried over anhydrous $Na_2SO_4$, filtered and concentrated. Purification of the residue by column chromatography (10% MeOH in EtOAc) afforded title compound 137 (47 mg, 51% yield) as a white solid. $^1$H NMR (400 MHz, DMSO-$d_6$) δ (ppm): 8.69 (s, 1H), 8.50 (d, J=5.48 Hz, 1H), 7.89 (s, 1H), 7.70 (m, 1H), 7.35 (t, J=8.99 Hz, 1H), 7.17 (m, 1H), 7.05 (s, 1H), 6.65 (d, J=5.48 Hz, 1H), 6.55 (m, 1H), 4.46 (s, 2H), 3.82 (s, 3H), 3.22 (t, J=6.84 Hz, 2H), 2.52 (m, 1H), 2.27 (t, J=7.82 Hz, 2H), 1.90 (m, 2H), 0.63 (m, 2H), 0.40 (m, 2H). MS (m/z)=521.638 (M+H)

Scheme 34

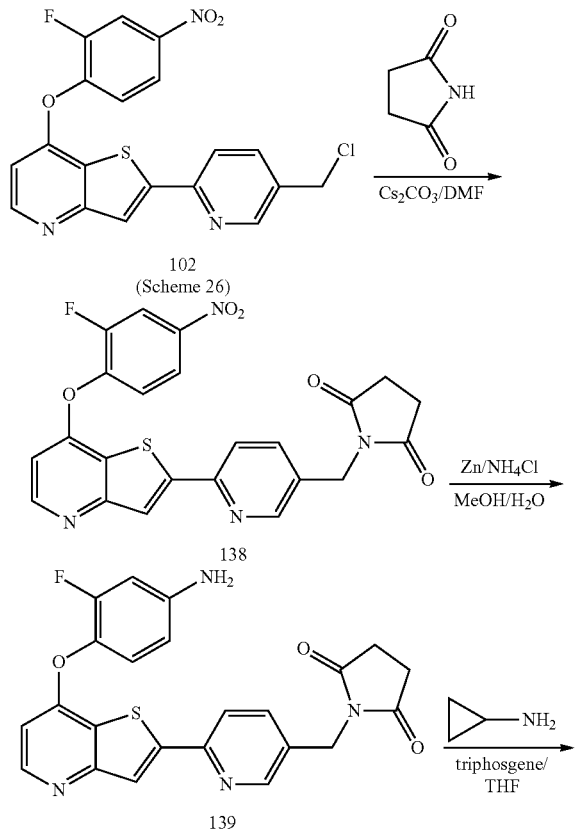

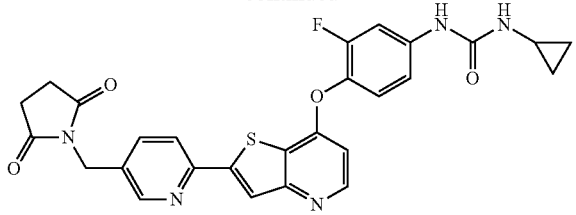

140: Example 91

Example 91

1-cyclopropyl-3-(4-(2-(5-((2,5-dioxopyrrolidin-1-yl)methyl)pyridin-2-yl)thieno[3,2-b]pyridin-7-yloxy)-3-fluorophenyl)urea (140)

Step 1: 1-((6-(7-(2-fluoro-4-nitrophenoxy)thieno[3,2-b]pyridin-2-yl)pyridin-3-yl)methyl)pyrrolidine-2,5-dione (138)

To a solution of 102 (200 mg, 0.481 mmol, scheme 26) in DMF (5 mL) was added $Cs_2CO_3$ (313 mg, 0.962 mmol) and succinimide (95 mg, 0.962 mmol) and the reaction mixture was stirred at RT for 4 hours. The reaction mixture was poured into water and extracted with EtOAc. The organic phase was collected, dried over anhydrous $Na_2SO_4$, filtered and concentrated to afford title compound 138 (100 mg, 43% yield) that was triturated with $Et_2O$ and used with no additional purification. MS (m/z)=479.50 (M+H)

Step 2: 1-((6-(7-(4-amino-2-fluorophenoxy)thieno[3,2-b]pyridin-2-yl)pyridin-3-yl)methyl)pyrrolidine-2,5-dione (139)

To a suspension of 138 (100 mg, 0.209 mmol) in MeOH (10 mL) was added zinc (109 mg, 1.672 mmol) and $NH_4Cl$ (44.7 mg, 0.836 mmol) in water (1 mL) and the reaction mixture was heated to reflux for 48 hrs, cooled to RT and concentrated. The crude product was dissolved in MeOH/DCM and washed with water. The organic phase was collected, dried over anhydrous $Na_2SO_4$, filtered and concentrated to afford title compound 139 (80 mg, 85% yield) that was used without additional purification. MS (m/z)=448.47 (M+H).

Step 3: 1-cyclopropyl-3-(4-(2-(5-((2,5-dioxopyrrolidin-1-yl)methyl)pyridin-2-yl)thieno[3,2-b]pyridin-7-yloxy)-3-fluorophenyl)urea (140)

To a solution of 139 (101 mg, 0.225 mmol) in THF (6 mL) at −35° C. was added TEA (0.094 mL, 1.126 mmol) and triphosgene (80 mg, 0.270 mmol) in THF (1 mL) and the mixture was warmed to −10° C. over an hr. Cyclopropylamine (64.3 mg, 1.126 mmol) was added and the reaction mixture was stirred at RT for 1.5 hrs. The reaction mixture was diluted with EtOAc then washed with saturated $NH_4Cl$ solution. The organic phase was collected, dried over anhydrous $Na_2SO_4$, filtered and concentrated. Purification by column chromatography (10% MeOH in EtOAc) afforded title compound 140 (20 mg, 17% yield) as a white solid. $^1$H NMR (400 MHz, DMSO-$d_6$) δ (ppm): 8.69 (s, 1H), 8.53 (s, 1H), 8.50 (d, J=5.48 Hz, 1H), 8.32 (s, 1H), 8.22 (d, J=8.021, 1H), 7.81 (m, 1H), 7.70 (m, 1H), 7.36 (t, J=9.19 Hz, 1H), 7.18 (m, 1H), 6.62 (d, J=4.89 Hz, 1H), 6.55 (s, 1H), 4.62 (s, 2H), 2.68 (s, 4H), 2.53 (m, 1H), 0.63 (m, 2H), 0.41 (m, 2H). M (m/z)=532.543 (M+H)

Scheme 35

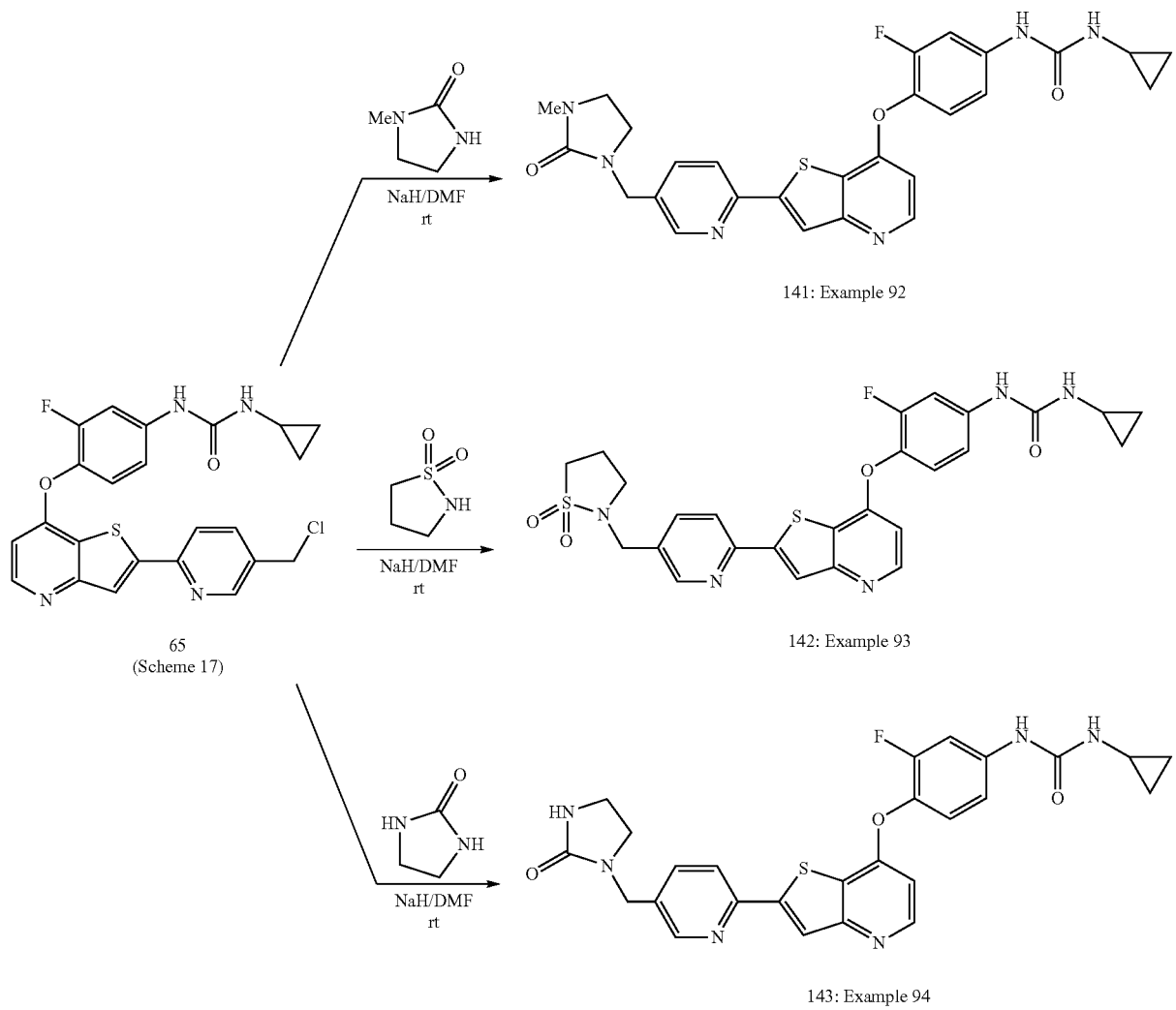

Example 92

1-cyclopropyl-3-(3-fluoro-4-(2-(5-((3-methyl-2-ox-oimidazolidin-1-yl)methyl)pyridin-2-yl)thieno[3,2-b]pyridin-7-yloxy)phenyl)urea (141)

To a solution of 1-methylimidazolidin-2-one (192 mg, 1.919 mmol) in DMF (10 mL) was added NaH (79 mg, 6.2 eq., 0.1.983 mmol) and the mixture was stirred for 15 mins. A solution of 65 (150 mg, 0.320 mmol, scheme 17) in DMF (5 mL) was added and the reaction mixture was stirred at RT for 3 hours. The mixture was then poured into water and extracted well with EtOAc. The organic phase was collected, dried over anhydrous $Na_2SO_4$, filtered and concentrated. Purification by column chromatography (10% MeOH in EtOAc) afforded title compound 141 (17 mg, 10% yield) as a yellow solid. $^1$H NMR (400 MHz, DMSO-$d_6$) δ (ppm): 8.71 (s, 1H), 8.54 (s, 1H), 8.51 (d, J=5.48 hz, 1H), 8.33 (s, 1H), 8.26 (d, J=8.02 Hz, 1H), 7.80 (m, 1H), 7.72 (m, 1H), 7.38 (t, J=8.99 Hz, 1H), 7.20 (m, 1H), 6.65 (m, 1H), 6.56 (s, 1H), 4.35 (s, 2H), 7.33 (m, 4H, partially obscured by $H_2O$ peak), 2.69 (s, 3H), 2.55 (m, 1H), 0.65 (m, 2H), 0.43 (m, 2H). MS (m/z)=533.49 (M+H).

Example 93

1-cyclopropyl-3-(3-fluoro-4-(2-(5-(2,2-dioxo-2-thi-apyrrolidin-1-ylmethyl)pyridin-2-yl)thieno[3,2-b]pyridin-7-yloxy)phenyl)urea (142)

To a solution of 1,3-propanesultam (155 mg, 1.280 mmol) in DMF (10 mL) was added NaH (53.7 mg, 4.2 eq., 1.343 mmol) and the mixture was stirred for 15 mins. A solution of 65 (150 mg, 0.320 mmol, scheme 17) in DMF (5 mL) was added and the reaction mixture was stirred at RT for 3 hours. The mixture was poured into water and extracted with EtOAc. The organic phase was collected, dried over anhydrous $Na_2SO_4$, filtered and concentrated. Purification by column chromatography (10% MeOH in EtOAc) afforded title compound 142 (17 mg, 9% yield) as a yellow solid. $^1$H NMR (400 MHz, DMSO-$d_6$) δ (ppm): 8.83 (s, 1H), 8.58-8.55 (m, 2H), 8.36 (s, 1H), 8.28 (d, 1H, J=8.2 Hz), 8.19 (s, 1H), 7.89 (dd, 1H, J=1.9 Hz, J2=8.2 Hz), 7.77 (dd, 1H, J1=2.3 Hz, J2=13.5 Hz), 7.41 (t, 1H, J=9.0 Hz), 7.25-7.22 (m, 1H), 6.69-6.67 (m, 1H), 3.59-3.57 (m, 6H), 2.62-2.57 (m, 1H), 2.54-2.42 (m, 6H) 0.71-0.66 (m, 2H), 0.48-0.44 (m, 2H). MS (m/z)=554.518 (M+H).

Example 94

1-cyclopropyl-3-(3-fluoro-4-(2-(5-((2-oxoimidazolidin-1-yl)methyl)pyridin-2-yl)thieno[3,2-b]pyridin-7-yloxy)phenyl)urea (143)

To a solution of imidazolidin-2-one (165 mg, 6 eq., 1.919 mmol) in DMF (10 mL) was added NaH (79 mg, 0.1.983 mmol) and the mixture was stirred for 15 min. A solution of 65 (150 mg, 0.320 mmol, scheme 17) in DMF (5 mL) was added and the reaction mixture was stirred at RT for 3 hours. The mixture was poured into water and extracted with EtOAc. The organic phase was collected, dried over anhydrous $Na_2SO_4$, filtered and concentrated. The residue was purified by column chromatography (20% MeOH in DCM) to afford title compound 143 as a yellow solid. $^1$H NMR (400 MHz, DMSO-$d_6$) δ (ppm): 8.74 (s, 1H), 8.58 (m, 1H), 8.56 (d, 1H, J=5.3 Hz), 8.38 (s, 1H), 8.31 (d, 1H, J=8.0 Hz), 7.85 (dd, 1H, J=2.1 Hz and 8.2 Hz), 7.77 (dd, 1H, J=2.5 and 13.7 Hz), 7.42 (t, 1H, J=9.2 Hz), 7.25-7.23 (m, 1H), 6.69 (d, 1H, J=5.3 Hz), 6.60 (m, 1H), 6.57 (s, 1H), 4.36 (s, 2H), 3.34-3.30 (m, 4H), 2.60-2.58 (m, 1H), 0.70-0.67 (m, 2H), 0.48-0.46 (m, 2H). MS (m/z)=519.5 (M+H).

Scheme 37

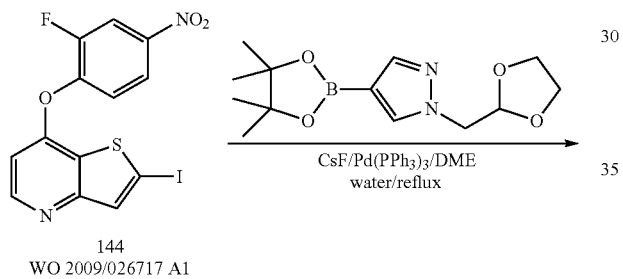

144
WO 2009/026717 A1

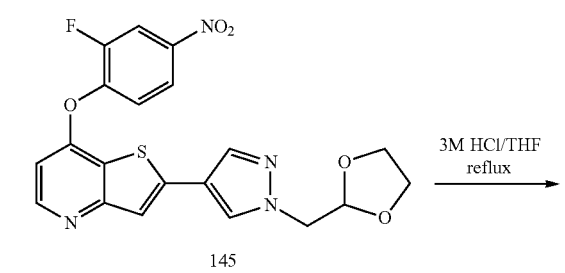

145

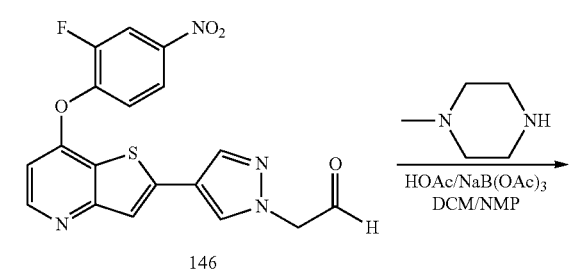

146

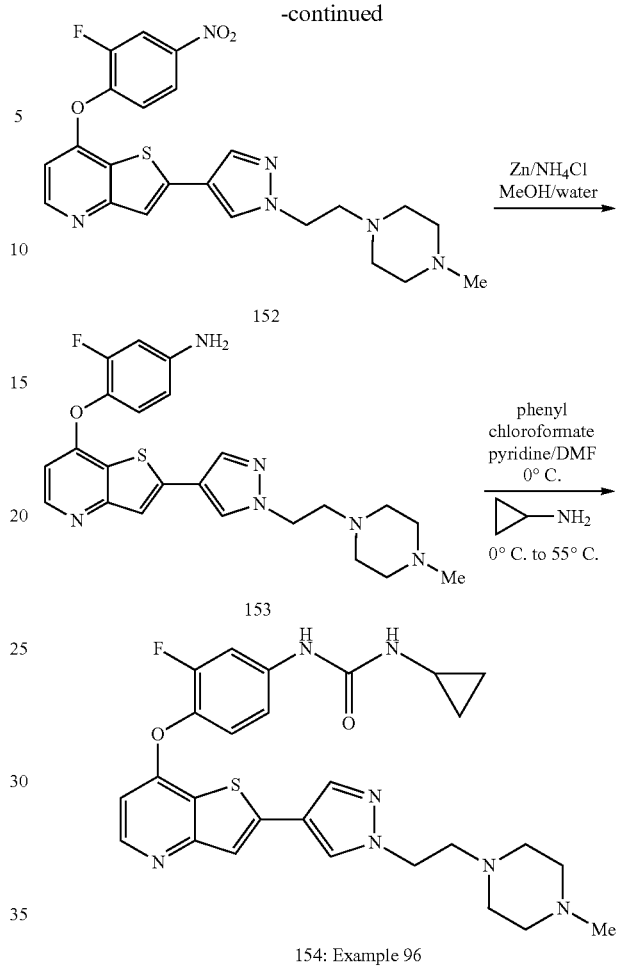

154: Example 96

Example 96

1-cyclopropyl-3-(3-fluoro-4-(2-(1-(2-(4-methylpiperazin-1-yl)ethyl)-1H-pyrazol-4-yl)thieno[3,2-b]pyridin-7-yloxy)phenyl)urea (154)

Step 1: 2-(1-((1,3-dioxolan-2-yl)methyl)-1H-pyrazol-4-yl)-7-(2-fluoro-4-nitrophenoxy)thieno[3,2-b]pyridine (145)

To a suspension 144 (3.57 g, 8.57 mmol) in DME (50 mL) and water (5 mL) was added 1-((1,3-dioxolan-2-yl)methyl)-4-(4,4,5,5-tetramethyl-1,3,2-dioxaborolan-2-O-1H-pyrazole (2 g, 7.14 mmol). CsF (3.25 g, 21.42 mmol). NaHCO$_3$ (1.799 g, 36 mmol) and Pd(PPh$_3$)$_4$ (0.825 g, 0.714 mmol), and the reaction mixture was heated to reflux overnight. The mixture was cooled to RT, diluted with EtOAc and washed with water. The organic phase was collected, dried over anhydrous Na$_2$SO$_4$, filtered and concentrated. The resultant solid was triturated with Et$_2$O to afford title compound 145 (3 g, 95% yield) as a beige solid. MS (m/z)=443.51 (M+H).

Step 2: 2-(4-(7-(2-fluoro-4-nitrophenoxy)thieno[3,2-b]pyridin-2-yl)-1H-pyrazol-1-yl)acetaldehyde (146)

To a solution of 145 (900 mg, 2.034 mmol) in THF (20 mL) was added 3M HCl (30 mL) and the reaction mixture was heated to reflux for 24 hours. The mixture was cooled to RT, and concentrated. The residual aqueous solution was treated with solid sodium bicarbonate and then extracted with DCM. The organic phase was collected, dried over anhydrous Na$_2$SO$_4$, filtered and concentrated. The crude aldehyde 146 (810 mg, 100% yield) was used in the next step with no additional purification. MS (m/z)=399.3 (M+H)

Step 3: 7-(2-fluoro-4-nitrophenoxy)-2-(1-(2-(4-methylpiperazin-1-yl)ethyl)-1H-pyrazol-4-yl)thieno[3,2-b]pyridine (152)

To a solution of 146 (450 mg, 1.13 mmol, Scheme 36) in NMP (10 mL) was added AcOH (0.129 mL, 2.259 mmol) and 1-methylpiperazine (113 mg, 2.259 mmol) and the reaction mixture was stirred at RT for an hour. Sodium triacetoxyborohydride (718 mg, 6.10 mmol) was added and the mixture was stirred at RT overnight. The mixture was diluted with saturated NaHCO$_3$ solution then solid NaHCO$_3$ was added to neutralize the acid. The mixture was extracted with DCM and the extract was dried over anhydrous Na$_2$SO$_4$, filtered and concentrated. The residue was purified by column chromatography (eluent 10% MeOH to 50% MeOH in EtOAc) to afford title compound 152 (250 mg, 27% yield) as a brown oil. MS (m/z)=483.53 (M+H).

Step 4: 3-fluoro-4-(2-(1-(2-(4-methylpiperazin-1-yl)ethyl)-1H-pyrazol-4-yl)thieno[3,2-b]pyridin-7-yloxy)aniline (153)

To a solution of 152 (150 mg, 0.311 mmol) in MeOH (20 mL) was added ammonium chloride (33.3 mg, 0.622 mmol) in water (5 mL) and zinc powder (81 mg, 3.01 mmol) and the reaction mixture was heated to reflux for 3 hours. The mixture was cooled to RT then filtered and the filtrate was concentrated under reduced pressure. The residue was dissolved in DCM and washed with water. The organic phase was collected, dried over anhydrous Na$_2$SO$_4$, filtered and concentrated to afford title compound 153 (132 mg, 92% yield) that was used directly in the next step with no additional purification. MS (m/z)=453.2 (M+H).

Step 5: 1-cyclopropyl-3-(3-fluoro-4-(2-(1-(2-(4-methylpiperazin-1-yl)ethyl)-1H-pyrazol-4-yl)thieno[3,2-b]pyridin-7-yloxy)phenyl)urea (154)

To a stirred solution of 153 (203 mg, 0.449 mmol) and pyridine (0.109 mL, 1.346 mmol) in DMF (10 mL) at 0° C. under nitrogen was added phenyl chloroformate (1.76 mg, 1.121 mmol) and the reaction mixture was stirred at 0° C. for 2 hrs. Cyclopropylamine (128 mg, 2.243 mmol) was added and the reaction mixture was heated at 55° C. for 5 hrs. The reaction mixture was partitioned between EtOAc and saturated sodium bicarbonate solution, then washed with a saturated ammonium chloride solution and brine, dried over anhydrous sodium sulfate, filtered and concentrated. The crude product was purified by column chromatography (eluent EtOAc to 30% MeOH in EtOAc) to afford title compound 154 (30 mg, 12% yield). $^1$H NMR (400 MHz, DMSO-d$_6$) δ (ppm): 8.43 (s, J=5.48 Hz, 1H), 8.33 (s, 1H), 7.99 (s, 1H), 7.74 (m, 1H), 7.67 (s, 1H), 7.60 (bs, 1H), 7.32 (t, J=8.99 Hz, 1H), 7.22 (m, 1H), 6.63 (d, J=5.48 Hz, 1H), 4.25 (t, J=6.46 Hz, 2H), 2.73 (t, J=6.46 Hz, 2H), 2.55 (m, 1H), 2.45 (m, 4H), 2.28 (m, 4H), 2.12 (s, 3H), 0.61 (m, 2H), 0.40 (m, 4H). MS (m/z)=536.54 (M+H).

Example 97

1-cyclopropyl-3-(3-fluoro-4-(2-(1-(2-morpholinoethyl)-1H-pyrazol-4-yl)thieno[3,2-b]pyridin-7-yloxy)phenyl)urea (155)

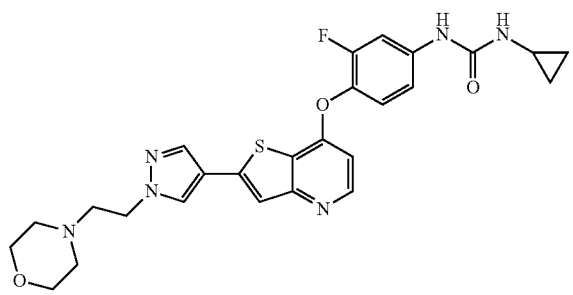

155: Example 97

Title compound 155 was obtained similarly to compound 154 (example 96, Scheme 37) using morpholine in the reductive amination step instead of 1-methylpiperazine. $^1$H NMR (400 MHz, DMSO-d$_6$) δ (ppm): 8.67 (s, 1H), 8.41 (m, 1H), 8.33 (s, 1H), 7.98 (s, 1H), 7.70 (d, J=13.69, 1H), 7.67 (s, 1H), 7.34 (t, J=8.80 Hz, 1H), 7.17 (d, J=8.61 Hz, 1H), 6.54 (bs, 1H), 6.51 (d, J=5.48 Hz, 1H), 4.26 (m, 2H), 3.53 (t, J=4.11 Hz, 4H), 2.72 (t, J=6.45 Hz, 2H), 2.52 (m, 1H), 2.41 (BS, 4H), 0.63 (m, 2H), 0.40 (m, 2H). MS (m/z)=523.57.

Scheme 38

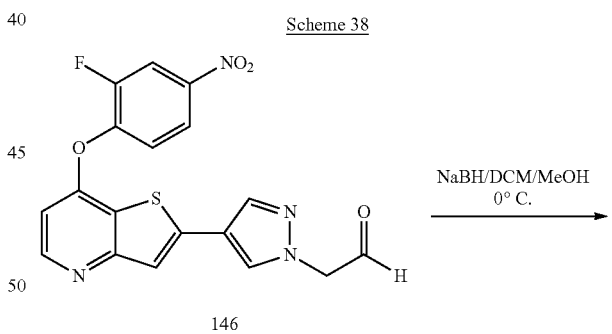

146

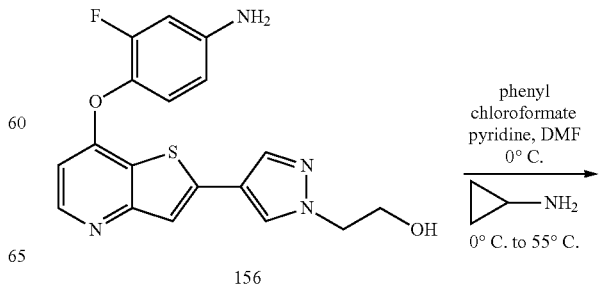

156

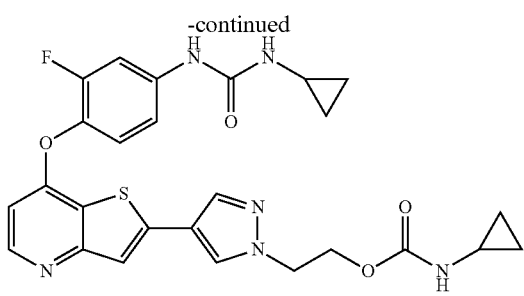

157: Example 98

Example 98

2-(4-(7-(4-(3-cyclopropylureido)-2-fluorophenoxy)thieno[3,2-b]pyridin-2-yl)-1H-pyrazol-1-yl)ethyl cyclopropylcarbamate (157)

Step 1: 2-(4-(7-(4-amino-2-fluorophenoxy)thieno[3,2-b]pyridin-2-yl)-1H-pyrazol-1-yl)ethanol (156)

To a solution of 146 (3 g, 7.53 mmol) in DCM (100 mL) and MeOH (100 mL) was added NaBH₄ (0.57 g, 15.06 mmol) and the reaction mixture was stirred at 0° C. for 20 min. The mixture was quenched with saturated NH₄Cl solution then extracted with DCM. The extract was collected, dried over anhydrous Na₂SO₄, filtered, concentrated and the residue was purified by flash column chromatography (eluent 10% MeOH in EtOAc) to afford title compound 156 (1 g, 36% yield) as white solid. MS (m/z)=371.40 (M+H).

Step 2: 2-(4-(7-(4-(3-cyclopropylureido)-2-fluorophenoxy)thieno[3,2-b]pyridin-2-yl)-1H-pyrazol-1-yl)ethyl cyclopropylcarbamate (157)

To a stirred solution of 156 (900 mg, 2.430 mmol) and pyridine (0.59 mL, 7.29 mmol) in DMF (10 mL) at 0° C. under nitrogen was added phenyl chloroformate (951 mg, 6.07 mmol) and the reaction mixture was stirred at 0° C. for 2 hrs. Cyclopropylamine (694 mg, 12.15 mmol) was added and the reaction mixture was heated at 55° C. for 5 hrs. The reaction mixture was then partitioned between EtOAc and saturated sodium bicarbonate solution. The organic phase was collected then washed a saturated ammonium chloride solution and brine, dried over anhydrous sodium sulfate, filtered and concentrated. The residue was purified by column chromatography (eluent EtOAc to 30% MeOH in EtOAc) to afford title compound 157 (300 mg, 23% yield) as a white solid. $^1$H NMR (400 MHz, DMSO-$d_6$) δ (ppm): 8.69 (s, 1H), 8.43 (d, J=5.47 Hz, 1H), 8.33 (s, 1H), 8.03 (s, 1H), 7.72 (m, 1H), 7.70 (m, 1H), 7.41 (m, 1H), 7.35 (t, J=9.19 Hz, 1H), 7.19 (m, 1H), 6.54 (m, 2H), 4.34 (m, 4H), 2.53 (m, 1H), 2.49 (m, 1H), 0.65 (m, 2H), 0.54 (m, 2H), 0.43 (m, 2H), 0.36 (m, 2H). MS (m/z)=537.58 (M+H).

Scheme 39

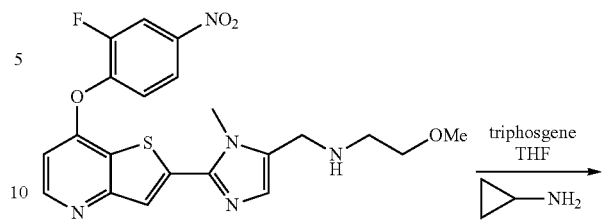

WO 2009/109035 A1

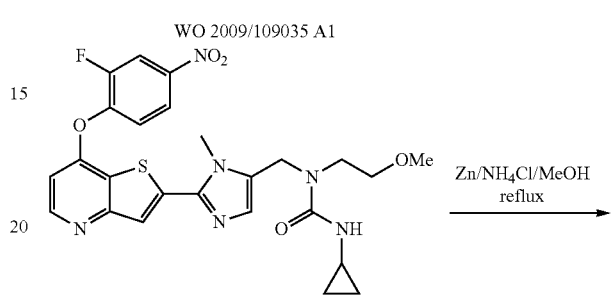

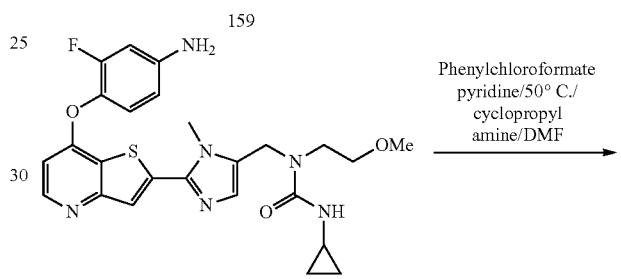

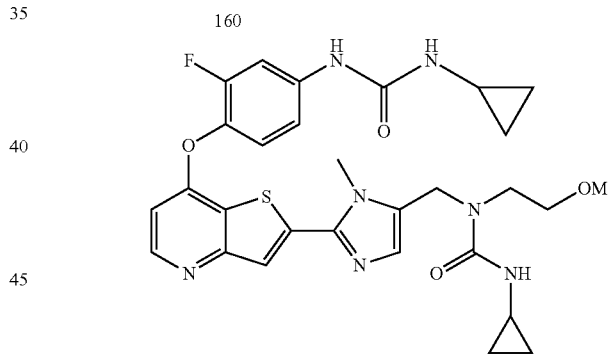

161: Example 99

Example 99

1-((2-(7-(2-fluoro-4-cyclopropylaminocarbonylaminophenoxy)thieno[3,2-b]pyridin-2-yl)-1-methyl-1H-imidazol-5-yl)methyl)-3-cyclopropyl-1-(2-methoxyethyl)urea (161)

Step 1: 3-cyclopropyl-1-((2-(7-(2-fluoro-4-nitrophenoxy)thieno[3,2-b]pyridin-2-yl)-1-methyl-1H-imidazol-5-yl)methyl)-1-(2-methoxyethyl)urea (159)

To a solution of 158 (150 mg, 0.294 mmol) in THF (5 mL) was added TEA (0.123 mL, 0.881 mmol) and triphosgene (43.6 mg, 0.147 mmol) in THF (1 mL) and the mixture was stirred at RT for an hour. Cyclopropylamine (84 mg, 1.469 mmol) was added and the reaction mixture was stirred at RT for 2 hrs. The reaction mixture was concentrated then partitioned between DCM and saturated NaHCO₃ solution. The organic phase was collected, dried over anhydrous Na₂SO₄, filtered and concentrated. The residue was purified by flash column chromatography (leluent 0% MeOH in EtOAc) to afford title compound 159 (40 mg, 25% yield) as an oil. MS (m/z)=541.54 (M+H)

Step 2: 1-((2-(7-(4-amino-2-fluorophenoxy)thieno[3,2-b]pyridin-2-yl)-1-methyl-1H-imidazol-5-yl)methyl)-3-cyclopropyl-1-(2-methoxyethyl)urea (160)

To a solution of 159 (300 mg, 0.555 mmol) in MeOH (10 mL) was added zinc powder (145 mg, 2.22 mmol) and ammonium chloride (59.4 mg, 1.11 mmol) and the reaction mixture was heated to reflux for 3 hours. The mixture was cooled to RT and filtered. The solvent was evaporated and the residue was extracted with DCM. The extract was dried over anhydrous Na₂SO₄, filtered and concentrated. The crude title compound 160 (283 mg, 100% yield) was used in the next step with no additional purification. MS (m/z)=511.2 (M+H).

Step 3: 1-((2-(7-(2-fluoro-4-cyclopropylaminocarbonylaminophenoxy)thieno[3,2-b]pyridin-2-yl)-1-methyl-1H-imidazol-5-yl)methyl)-3-cyclopropyl-1-(2-methoxyethyl)urea (161)

To a stirred solution of 160 (283 mg, 0.554 mmol) and pyridine (0.134 mL, 1.663 mmol) in DMF (10 mL) at 0° C. under nitrogen was added phenyl chloroformate (158 mg, 1.386 mmol) and the reaction mixture was stirred at 0° C. for 2 hrs. Cyclopropylamine (0.195 mL, 2.77 mmol) was added and the reaction mixture was heated at 55° C. for 5 hrs. The reaction mixture was partitioned between EtOAc and saturated sodium bicarbonate solution, then washed a saturated ammonium chloride solution and brine, dried over anhydrous sodium sulfate, filtered and concentrated. The crude product was purified by flash column chromatography (eluent EtOAc to 20% MeOH in EtOAc) to afford title compound 161 (100 mg, 30% yield) as a white solid. ¹H NMR (400 MHz, DMSO-d₆) δ (ppm): 8.70 (s, 1H), 8.50 (d, J=5.48 Hz, 1H), 7.89 (s, 1H), 7.70 (m, 1H), 7.35 (t, J=9.19 Hz, 1H), 7.19 (m, 1H), 6.93 (s, 1H), 6.64 (d, J=5.48 hz, 1H), 6.56 (s, 1H), 6.51 (m, 1H), 4.54 (s, 2H), 3.82 (s, 3H), 3.27 (m, 2H), 3.25 (m, 2H), 3.19 (s, 3H), 2.54 (m, 2H), 0.63 (m, 2H), 0.55 (m, 2H), 0.41 (m, 2H), 0.37 (m, 2H). MS (m/z)=594.61 (M+H).

Example 99-A 1-((2-(7-(4-isopropylaminocarbonylamino-2-fluorophenoxy)thieno[3,2-b]pyridin-2-yl)-1-methyl-1H-imidazol-5-yl)methyl)-3-ethyl-1-(2-methoxyethyl)urea (161-A)

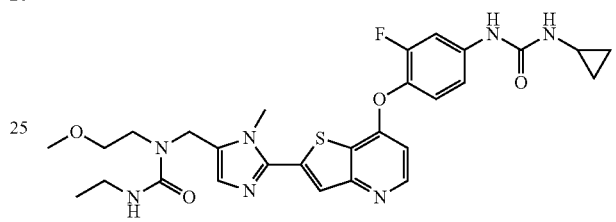

161-A: Example 99-A

Title compound 161-A (example 99-A) was obtained similarly to compound 161 (example 99, scheme 39) starting from the compound 158 and using ethylisocyanate in the first step and isopropylisocyanate in the third step. ¹H NMR (400 MHz, DMSO-d₆) δ (ppm): 8.73 (s, 1H), 8.55 (d, 1H, J=5.5 Hz), 7.93 (s, 1H), 7.73 (dd, 1H, J1=2.5 Hz, J2=13.5 Hz), 7.40 (t, 1H, J=9.0 Hz), 7.17-7.15 (m, 1H), 6.99 (s, 1H), 6.69 (d, 1H, J=5.3 Hz), 6.46 (t, 1H, J=5.5 Hz), 6.18 (d, 1H, J=7.8 Hz), 4.61 (s, 2H), 3.88 (s, 3H), 3.86-3.78 (m, 1H), 3.40-3.38 (m, 2H), 3.35-3.34 (m, 2H), 3.26 (s, 3H), 3.16-3.08 (m, 2H), 1.15 (s, 3H), 1.13 (s, 3H), 1.05 (1, 3H, J=7.2 Hz). MS: 584.6 (MH+).

Example 99-B 1-((2-(7-(4-cyclopropylaminocarbonylamino-2-fluorophenoxy)thieno[3,2-b]pyridin-2-yl)-1-methyl-1H-imidazol-5-yl)methyl)-3-ethyl-1-(2-methoxyethyl)urea (161-B)

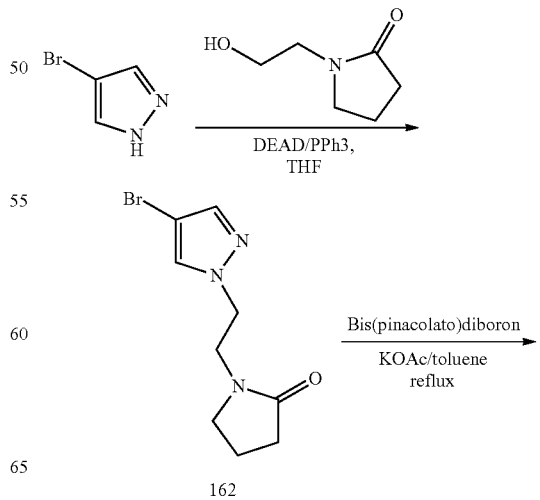

161-B: Example 99-B

Title compound 161-B (example 99-B) was obtained similarly to compound 161 (example 99, scheme 39) starting from the compound 158 and using ethylisocyanate in the first step. ¹H NMR (400 MHz, DMSO-d₆) δ (ppm): 8.75 (s, 1H), 8.55 (d, 1H, J=5.4 Hz), 7.93 (s, 1H), 7.75 (dd, 1H, J1=2.3 Hz, J2=13.5 Hz), 7.41 (t, 1H, J=9.0 Hz), 7.24-7.39 (m, 1H), 6.99 (s, 1H), 6.70 (d, 1H, J=5.3 Hz), 6.60 (m, 1H), 6.46 (t, 1H, J=5.7 Hz), 4.61 (s, 2H), 3.88 (s, 3H), 3.54-3.51 (m, 2H), 3.38-3.33 (m, 2H), 3.26 (s, 3H), 3.13-3.09 (m, 2H), 2.70-2.56 (m, 1H), 1.06 (t, 3H, J=7.2 Hz), 0.71-0.67 (m, 2H), 0.48-0.44 (m, 2H). MS: 582.6 (MH+).

Scheme 40

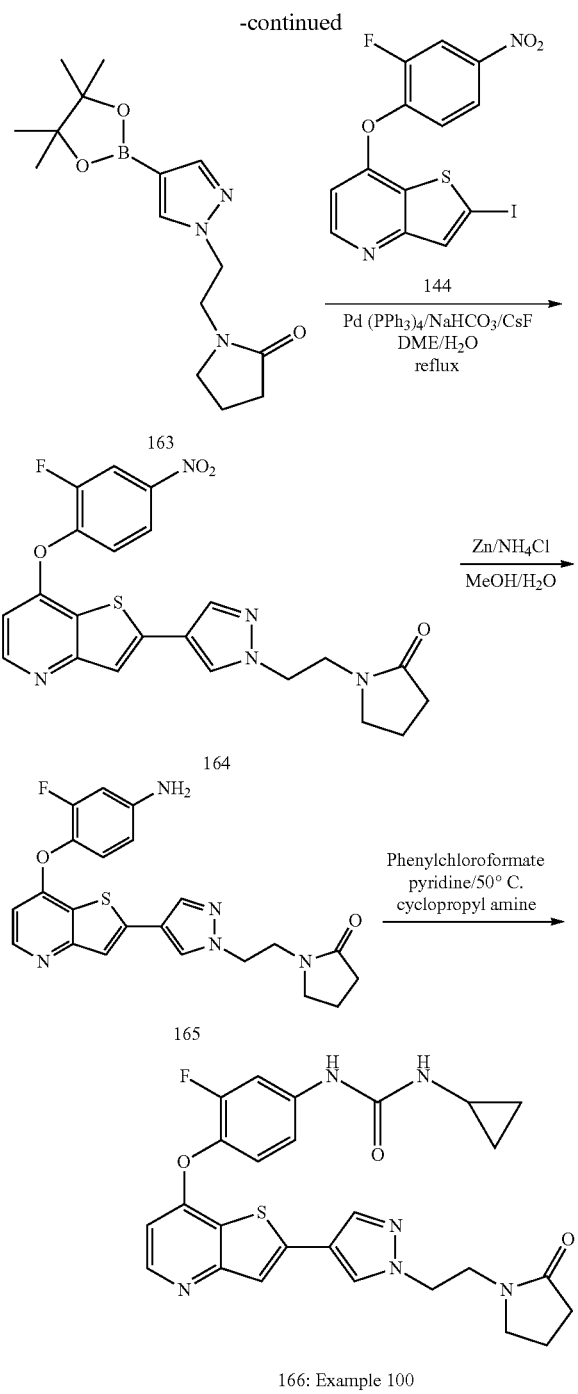

g, 51 mmol) and the reaction mixture was stirred at RT overnight. The mixture was concentrated, co-evaporated with Et$_2$O then dissolved in Et$_2$O and cooled in a fridge for 3 hrs whereupon Ph$_3$P=O precipitated out. The mixture was then filtered and concentrated to afford title compound 162 (8.78 g, 100% yield) which was used in the next step with no additional purification. MS (m/z) 259.12/261.12 (M+H).

Step 2: 1-(2-(4-(4,4,5,5-tetramethyl-1,3,2-dioxaborolan-2-yl)-1H-pyrazol-1-yl)ethyl)pyrrolidin-2-one (163)

To a solution of 162 (8.78 g, 34 mmol) in toluene (150 mL) was added bis(pinacolato)diboron (12.96 g, 51 mmol), KOAc (8.35 g, 85 mmol) and Pd(PPh$_3$)$_4$ (1.96 g, 1.701 mmol) and the reaction mixture was heated to reflux for 4 hours. The mixture was concentrated and the residue was purified by flash column chromatography (eluent EtOAc to 25% MeOH/EtOAc) to afford title compound 163 (6.3 g, 60% yield) as a yellow oil. MS (m/z)=306.4 (M+H).

Step 3: 1-(2-(4-(7-(2-fluoro-4-nitrophenoxy)thieno[3,2-b]pyridin-2-yl)-1H-pyrazol-1-yl)ethyl)pyrrolidin-2-one (164)

To a solution of iodide 144 (2.1 g, 5.05 mmol, scheme 36) in DME (60 mL), at RT, was added boronate 163 (2.31 g, 7.57 mmol), NaHCO$_3$ (1.272 g, 15.14 mmol) in H$_2$O (5 mL), CsF (2.3 g, 15.14 mmol) and Pd (PPh$_3$)$_4$ (0.583 g, 0.505 mmol), and the reaction mixture was degassed with N$_2$ for 10 minutes before being heated to reflux for 4 hrs. The reaction mixture was cooled to RT, and partitioned between EtOAc and H$_2$O. The organic phase was separated and washed with additional H$_2$O then dried over anhydrous sodium sulfate and filtered. The solvent was removed under reduced pressure and the crude product was triturated with diethyl ether to afford title compound 164 (2 g, 85% yield) as a brown solid. MS (m/z)=468.48 (M+H).

Step 4: 1-(2-(4-(7-(4-amino-2-fluorophenoxy)thieno[3,2-b]pyridin-2-yl)-1H-pyrazol-yl)ethyl)pyrrolidin-2-one (165)

To a suspension of 164 (0.5 g, 1.07 mmol) in MeOH (20 mL) was added Zinc (0.28 g, 4.28 mmol) and ammonium chloride (0.114 g, 2.139 mmol) and the reaction mixture was heated to reflux for 3 hours. The mixture was cooled to RT and filtered. The filtrate was concentrated and the resultant oil was partitioned between water and DCM. The organic phase was collected, dried over anhydrous Na$_2$SO$_4$, filtered and concentrated. The resultant solid was triturated with Et$_2$O to give title compound 165 (0.468 mg, 100% yield, crude) as a black solid. MS (m/z) 438.4 (M+H).

Step 5: 1-cyclopropyl-3-(3-fluoro-4-(2-(1-(2-(2-oxopyrrolidin-1-yl)ethyl)-1H-pyrazol-4-yl)thieno[3,2-b]pyridin-7-yloxy)phenyl)urea (166)

To a stirred solution of 165 (400 mg, 0.914 mmol) and pyridine (0.222 mL, 2.74 mmol) in DMF (10 mL) at 0° C. under nitrogen was added phenyl chloroformate (0.287 mg, 2.286 mmol) and the reaction mixture was stirred at 0° C. for 2 hrs. Cyclopropylamine (0.322 mL, 4.57 mmol) was added and the reaction mixture was heated at 55° C. for 5 hrs. The reaction mixture was partitioned between EtOAc and saturated sodium bicarbonate solution, then washed with saturated ammonium chloride solution and brine, dried over

Example 100

1-cyclopropyl-3-(3-fluoro-4-(2-(1-(2-(2-oxopyrrolidin-1-yl)ethyl)-1H-pyrazol-4-yl)thieno[3,2-h]pyridin-7-yloxy)phenyl)urea (166)

Step 1: 1-(2-(4-bromo-1H-pyrazol-1-yl)ethyl)pyrrolidin-2-one (162)

To a solution of 3-bromopyrazole (5 g, 34 mmol), 1-(2-hydroxyethyl)pyrrolidin-2-one (5.75 g, 51 mmol), PPh$_3$ (13.38 g, 51 mmol) in THF (100 mL) was added DEAD (8.89 anhydrous sodium sulfate, filtered and concentrated. The residue was purified by column chromatography (eluent EtOAc to 20% MeOH in EtOAc) to afford title compound 166 (250 mg, 53% yield) as a white solid. $^1$H NMR (400 MHz. DMSO-$d_6$) δ (ppm): 8.69 (s, 1H), 8.44 (d, J=5.48 Hz, 1H), 8.35 (s, 1H), 8.035 (s, 1H), 7.74 (m, 1H), 7.70 (s, 1H), 7.35 (t, J=8.99 Hz, 1H), 7.19 (d, J=8.99 Hz, 1H), 6.55 (m, 2H), 4.28 (t, J=5.87 Hz, 2H), 3.59 (t, J=5.86 Hz, 2H), 3.17 (t, J=6.84 Hz, 2H), 2.55 (m, 1H), 2.15 (t, J=7.83 Hz, 2H), 1.86 (m, 2H), 0.64 (m, 2H), 0.42 (m, 2H). MS (m/z)=521.38 (M+H)

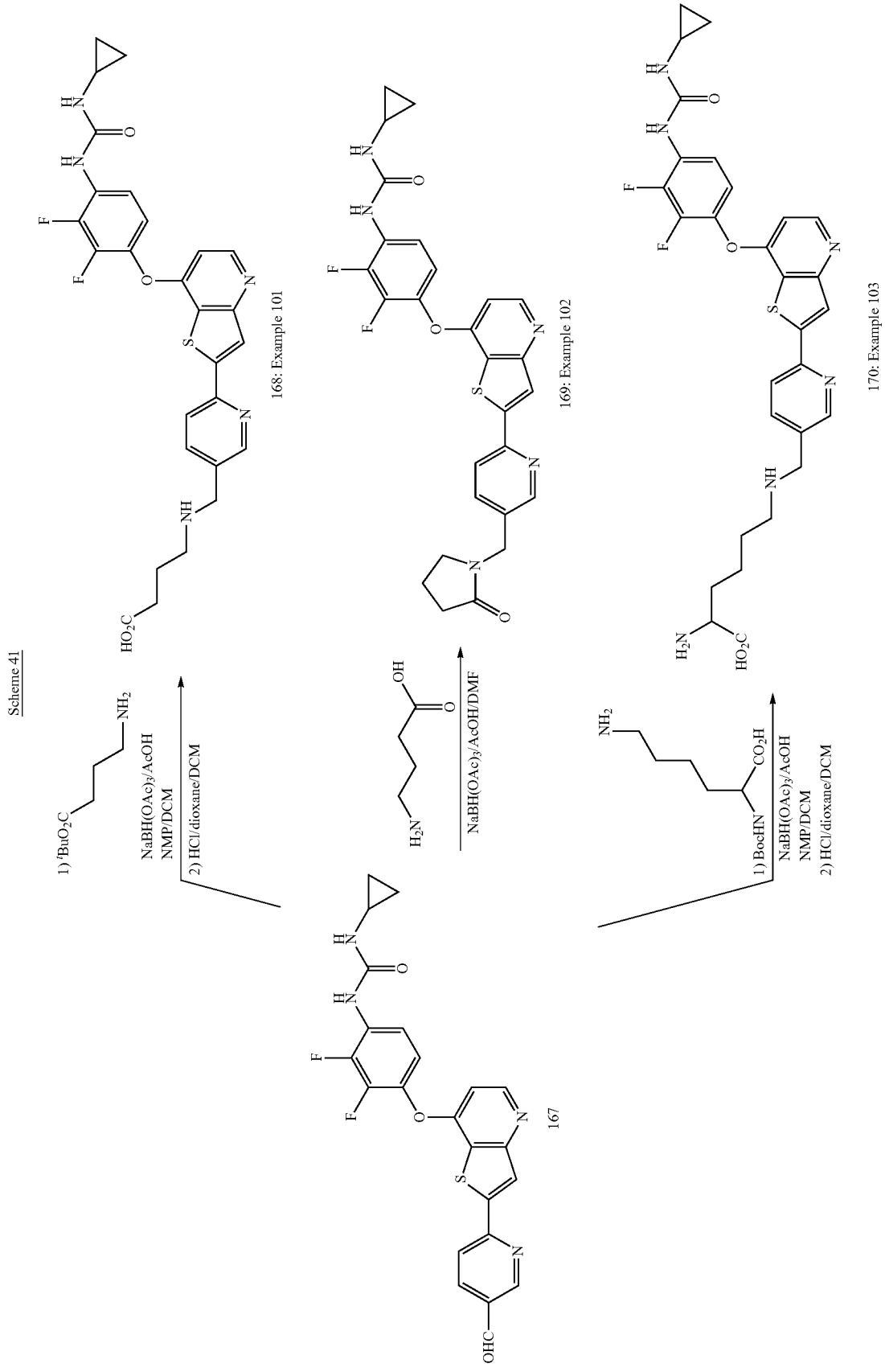

Example 101

4-((6-(7-(4-(3-cyclopropylureido)-2,3-difluorophenoxy)thieno[3,2-b]pyridin-2-yl)pyridin-3-yl)methylamino)butanoic acid (168)

Aldehyde 167 (0.075 g, 0.16 mmol, scheme 67), O-tert-butyl-4-aminobutyric acid (0.077 g, 0.48 mmol) and acetic acid (0.03 mL, 0.5 mmol) were dissolved in 2:1 mixture dichloromethane/NMP (75 mL) to give a colorless solution. This was stirred for 20 min at RT, then sodium triacetoxyborohydride (0.136 g, 0.64 mmol) was added and the mixture was stirred at RT for 3 h. The reaction mixture was then partitioned between ethyl acetate and water, producing a white precipitate isolated by suction filtration. The isolated solid was dissolved in 1:1 mixture methanol/dichloromethane then concentrated. The residue was purified by flash column chromatography (eluent 5-15% methanol/chloroform) to yield a colorless solid. The material was suspended in acetic acid (15 mL), and HCl in dioxane (4M, 1.05 mL) was added, forming a gummy precipitate. This mixture was stirred for 3 h then the supernatant was decanted. The residue was triturated with ethyl acetate, then purified by silica gel chromatography (eluent 60/35/5% chloroform/methanol/NH$_4$OH) to give title compound 168 (29 mg, 31% yield) as a colorless solid. $^1$H NMR (400 MHz, DMSO-d$_6$) δ (ppm): 8.60 (d, J=1.8, 1H); 8.54 (d, J=5.5, 1H); 8.53 (s, 1H); 8.36 (s, 1H); 8.27 (d, J=8.0, 1H); 8.07-8.01 (m, 1H); 7.94 (dd, J=8.0, 2.0, 1H); 7.31-725 (m, 1H); 6.96 (d, J=2.9, 1H); 6.76 (d, J=5.3, 1H); 3.85 (s, 2H); 2.62 (t, J=6.6, 2H); 2.56 (m, 1H); 2.29 (t, J=7.2, 2H); 1.69 (quint, J=6.9, 2H); 0.69-0.63 (m, 2H); 0.44-0.40 (m, 2H). LRMS (M+H): 554.6

Example 102

1-cyclopropyl-3-(2,3-difluoro-4-(2-(5-((2-oxopyrrolidin-1-yl)methyl)pyridin-2-yl)thieno[3,2-b]pyridin-7-yloxy)phenyl)urea (169)

To a solution of aldehyde 167 (200 mg, 0.429 mmol) in DMF (10 mL) were added 4-aminobutyric acid (133 mg, 1.286 mmol) and acetic acid (0.049 mL, 0.858 mmol). After stirring for 20 min at RT, sodium triacetoxyborohydride (454 mg, 2.144 mmol) was added. Stirring was continued for an additional 18 h. Water was added to form a precipitate that was collected by filtration, rinsed with water and purified via Biotage [linear gradient 0-20%, (methanol+2% NH$_4$OH)/dichloromethane; SiliaFlash 25 g cartridge] followed by a trituration with methanol. Title compound 169 was obtained as an off-white solid (131.8 mg, 57.4% yield). $^1$H NMR (400 MHz, MeOH-d$_4$) δ (ppm): 8.54 (d, J=5.2 Hz, 1H), 8.53 (d, J=2.0 Hz, 1H), 8.47 (s, 1H), 8.37 (s, 1H), 8.27 (d, J=8.4 Hz, 1H), 8.04 (t, J=9.2 Hz, 1H), 7.80 (dd, J=8.4, 2.4 Hz, 1H), 7.29 (td, J=8.8, 2.0 Hz, 1H), 6.87 (d, J=2.8 Hz, 1H), 6.77 (d, J=5.2 Hz, 1H), 4.46 (s, 2H), 3.39-3.27 (m, 2H), 2.60-2.53 (m, 1H), 2.31 (t, J=8.0 Hz, 2H), 1.96 (q, J=7.6 Hz, 2H), 0.69-0.63 (m, 2H), 0.45-0.40 (m, 2H). MS (m/z): 536.6 (M+H).

Example 103

2-amino-6-((6-(7-(4-(3-cyclopropylureido)-2,3-difluorophenoxy)thieno[3,2-b]pyridin-2-1)pyridin-3-yl)methylamino)hexanoic acid (170)

Aldehyde 167 (0.110 g, 0.236 mmol), N-Boc-lysine (0.105 g, 0.424 mmol) and acetic acid (0.05 mL, 0.9 mmol) were dissolved in a 2:1 mixture dichloromethane/NMP (75 mL) to give a colorless solution. This was stirred for 20 min at RT, then sodium triacetoxyborohydride (0.150 g, 0.71 mmol) was added and the mixture was stirred at RT for 5 h. The reaction mixture was partitioned between dichloromethane and water, producing a white precipitate that was isolated by suction filtration, dissolved in a 1:1 mixture of methanol/dichloromethane then concentrated and purified by flash column chromatography (eluent 70/25/5% chloroform/methanol/NH$_4$OH) to provide a colorless solid. This material was suspended in acetic acid (20 mL), and HCl in dioxane (4M, 0.6 mL) was added, forming a gummy precipitate. This mixture was stirred for 3 h then the supernatant was decanted. The residue was triturated with ethyl acetate and dried in vacuo yielding the title compound 170 (100 mg, 60% yield) as a colorless solid, presumably as a tri-hydrochloride salt. $^1$H NMR (400 MHz, DMSO-d$_6$) δ (ppm): 9.53 (br s, 2H); 8.81 (d, J=1.8, 1H); 8.62 (d, J=5.7, 1H); 8.60 (s, 1H); 8.46 (s, 1H); 8.41 (d, J=8.2, 1H); 8.38-8.25 (br s, 3H); 8.22 (dd, J=8.4, 2.0, 1H); 8.05-8.01 (m, 1H); 7.33-7.27 (m, 1H); 7.03 (d, J=2.4, 1H); 6.88 (d, J=5.5, 1H); 4.25-4.20 (br s, 2H); 3.90-3.85 (m, 1H); 2.98-2.90 (m, 2H); 2.58-2.52 (m, 1H); 1.85-1.78 (m, 2H); 1.78-1.70 (m, 2H); 1.55-1.45 (m, 1H); 1.45-1.35 (m, 1H); 0.68-0.63 (m, 2H); 0.44-0.40 (m, 2H). LRMS (M+H): 597.5

Compounds 171-172 (examples 104-105) were prepared in one step by reductive amination of aldehyde 167 similarly to compound 48 (example 31, Scheme 15). Compound 173 (example 106) was synthesized similarly to the compound 168 (example 101, Scheme 41) starting from the aldehyde 47 (Scheme 15)

TABLE 16

Characterization of compounds 171-173 (examples 104-106)

| Cpd | Ex | Structure | Characterization |
|---|---|---|---|
| 171 | 104 | 1-(4-(2-(5-5,8,11,14-tetraoxa-2-azapentadecylpyridin-2-yl)thieno[3,2-b]pyridin-7-yloxy)-2,3-diiluorophenyl)-3-cyclopropylurea | $^1$H NMR (400 MHz, MeOH-d$_4$) δ (ppm): 8.61 (d, J = 1.2 Hz, 1H), 8.54 (d, J = 5.6 Hz, 1H), 8.50 (bs, 1H), 8.35 (s, 1H), 8.27 (d, J = 8.4 Hz, 1H), 8.03 (t, J = 8.0 Hz, 1H), 7.95 (dd, J = 8.4, 2.0 Hz, 1H), 7.28 (td, J = 8.4, 2.0 Hz, 1H), 6.91 (d, J = 2.4 Hz, 1H), 6.76 (d, J = 5.6 Hz, 1H), 3.90 (s, 2H), 3.57-3.46 (m, 12H) 3.42-3.36 (m, 2H), 3.21 (s, 3H), 2.77 (t, J = 5.2 Hz, 2H), 2.61-2.53 (m, 1H), 0.69-0.63 (m, 2H), 0.45-0.40 (m, 2H). MS (m/z): 658.4 (M + H). |

TABLE 16-continued

Characterization of compounds 171-173 (examples 104-106)

| Cpd | Ex | Structure | Characterization |
|---|---|---|---|
| 172 | 105 | 3-(4-((6-(7-(4-(3-cyclopropylureido)-2,3-difluorophenoxy)thieno-[3,2-b]pyridin-2-yl)pyridin-3-yl)methyl)piperazin-1-yl)propanoic acid | $^1$H NMR (400 MHz, DMSO-d$_6$) δ (ppm): 8.59 (d, J = 1.6, 1H); 8.49 (d, J = 5.5, 1H); 8.10 (d, J = 8.2, 1H); 8.09 (s, 1H); 7.95-7.90 (m, 2H); 7.21-7.15 (m, 1H); 6.71 (d, J = 4.9, 1H); 3.73 (s, 2H); 3.30-3.20 (m, 6H); 2.85-2.70 (br s, 4H); 2.65-2.55 (m, 3H); 0.79-0.74 (m, 2H); 0.55-0.50 (m, 2H). LRMS (M + H): 609.6 |
| 173 | 106 | (S)-1-((6-(7-(4-(3-cyclopropylureido)-2-fluorophenoxy)thieno[3,2-b]pyridin-2-yl)pyridin-3-yl)methyl)pyrrolidine-2-carboxylic acid | $^1$H NMR (400 MHz, DMSO-d$_6$) δ (ppm): 9.09 (s, 1H); 8.60 (d, J = 1.6, 1H); 8.51 (d, J = 5.5, 1H); 8.33 (s, 1H); 8.26 (s, 1H); 8.25 (d, J = 7.6, 1H); 7.93 (dd, J = 8.2, 2.1, 1H); 7.74 (dd, J = 13.7, 2.5, 1H); 7.37 (t, J = 9.0, 1H); 7.22-7.19 (m, 1H); 6.93 (d, J = 2.4, 1H); 6.63 (d, J = 5.3, 1H); 4.05 (d, J = 13.5, 1H): 3.75 (d, J = 13.7, 1H); 3.34-3.30 (m, 1H); 3.05-3.00 (m, 1H); 2.55-2.50 (m, 2H); 2.15-2.09 (m, 1H); 1.89-1.80 (m, 1H); 1.80-1.71 (m, 2H); 0.66-0.61 (m, 2H); 0.44-0.40 (m, 2H). LRMS (M + H): 548.5 |

Scheme 42

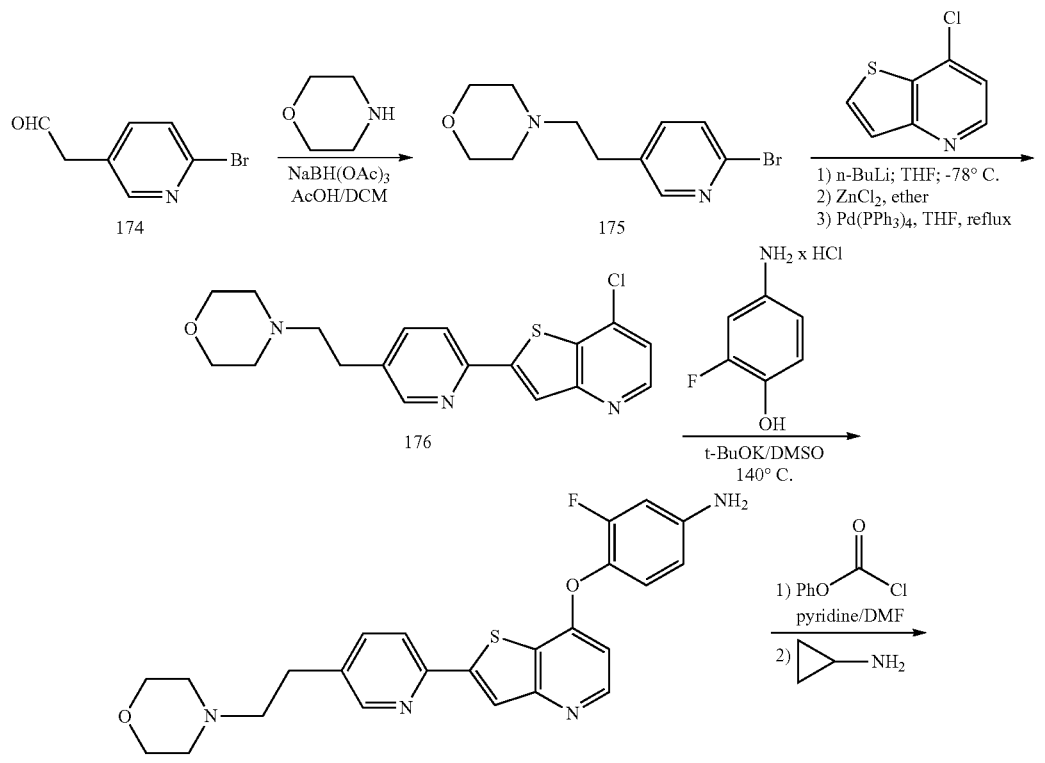

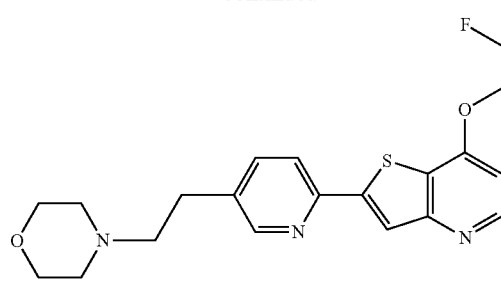

178: Example 107

Example 107

1-cyclopropyl-3-(3-fluoro-4-(2-(5-(2-morpholinoethyl)pyridin-2-yl)thieno[3,2-b]pyridin-7-yloxy)phenyl)urea (178)

Step 1. 4-(2-(6-bromopyridin-3-yl)ethyl)morpholine (175)

Aldehyde 174 (0.76 g, 3.8 mmol), morpholine (3.3 g, 38 mmol) and acetic acid (0.44 L, 7.6 mmol) were dissolved in dichloromethane (100 mL) to give a colorless solution, which was stirred for 20 min. Sodium triacetoxyborohydride (2.42 a, 11.4 mmol) was added and the mixture was stirred at RT for 18 h. The reaction mixture was quenched with 1M HCl (50 mL), the layers were separated, and the organic phase was washed with a further 1M HCl (50 mL). The combined acidic aqueous phase was basified with 3M NaOH, and extracted with dichloromethane. The organic phase was washed with saturated sodium bicarbonate solution and brine, dried over anhydrous $MgSO_4$, filtered and concentrated. The residue was purified by flash column chromatography (eluent 10% methanol/chloroform) to give title compound 175 (1.04 g, 100% yield). $^1$H NMR (400 MHz, $CDCl_3$) δ (ppm): 8.23 (d, J=1.5, 1H); 7.41-7.39 (m, 2H); 3.73-3.70 (m, 4H); 2.75 (t, J=7.0, 2H); 2.56 (t, 6.8, 2H); 2.51-2.47 (m, 4H). LRMS (M+H):271.1, 273.1.

Step 2. 4-(2-(6-(7-chlorothieno[3,2-b]pyridin-2-yl)pyridin-3-yl)ethyl)morpholine (176)

To 7-chlorothienopyridine (0.81 g, 4.8 mmol) in THF (100 mL) at −78° C. was added n-butyllithium (2.5 M in hexanes, 2.1 mL, 5.1 mmol), dropwise. The mixture was allowed to warm to 0° C. then zinc chloride (1.0 M in diethyl ether, 4.8 mL, 4.8 mmol) was added. The mixture was stirred and warmed to room temperature. Bromide 175 (1.0 g, 3.7 mmol) and tetrakis(triphenylphosphine)palladium (0.85 g, 0.74 mmol) in THF (75 mL) were added dropwise, and the resultant mixture was heated to reflux for 2 h. It was then cooled and ammonium chloride (2.0 mL) was added, and the mixture was concentrated. The residue was partitioned between water and ethyl acetate, resulting in a thick precipitate. This was isolated by suction filtration and triturated with ethyl acetate, to provide title compound 176 (1.35 g, 100% yield, crude) as a yellow solid. LRMS (M+H): 360.4

Step 3: 3-fluoro-4-(2-(5-(2-morpholinoethyl)pyridin-2-yl)thieno[3,2-b]pyridin-7-yloxy)aniline (5)

To a solution of 4-amino-2-fluorophenol hydrochloride (0.792 g, 4.84 mmol) in DMSO (50 mL) was added potassium tert-butoxide (1.05 g, 9.31 mmol), and the dark mixture was stirred for 30 min. Then compound 176 (1.34 g, 3.72 mmol) in DMSO (25 mL) was added, and the resultant mixture was heated to 140° C. for 1 h. The reaction mixture was poured into water, which was then extracted with ethyl acetate. The organic phase was washed with water and brine, dried over anhydrous $MgSO_4$, filtered and concentrated. Flash column chromatography of the residue (eluent 10% methanol/chloroform) afforded title compound 177 (0.15 g, 9% yield). LRMS (M+H): 451.5

Step 4: 1-cyclopropyl-3-(3-fluoro-4-(2-(5-(2-morpholinoethyl)pyridin-2-yl)thieno[3,2-b]pyridin-7-yloxy)phenyl)urea (178)

To a solution of 177 (0.15 g, 0.33 mmol) and pyridine (0.06 mL, 0.07 mmol) in DMF (75 mL) at 0° C. was added phenyl chloroformate (0.05 mL, 0.4 mmol). The reaction mixture was stirred at 0° C. for 1 h then cyclopropylamine (0.07 mL, 1.0 mmol) was added. The mixture was warmed to room temperature and stirred for an additional 18 h. It was then poured into water, forming a precipitate which was isolated by suction filtration. The solid was rinsed with ether and dried. Silica gel chromatography (5-10% MeOH/EtOAc) of the material followed by Gilson Reverse Phase HPLC (Luna $C_{18}$, 30-55% MeOH/water, 45 min) and lyophilization, followed by partitioning of the residue between dichloromethane and 1M NaOH, washing the organic phase with brine, drying over anhydrous $MgSO_4$, filtering and concentrating gave title compound 178 (47 mg, 27% yield) as a colorless solid. $^1$H NMR (400 MHz, DMSO-$d_6$) δ (ppm): 8.78 (s, 1H); 8.53 (d, J=1.6, 1H); 8.51 (d, J=5.5, 1H); 8.30 (s, 1H); 8.19 (d, J=8.2, 1H); 7.83 (dd, J=8.2, 2.2, 1H); 7.73 (dd, J=13.7. 2.4, 1H); 7.38 (t, J=9.0, 1H); 7.22-7.18 (m, 1H); 6.65-6.61 (m, 2H); 3.59-3.55 (m, 4H); 2.81 (t, J=7.2, 2H); 2.60-2.51 (m, 3H); 2.48-2.42 (m, 4H); 0.66-0.63 (m, 2H); 0.44-0.41 (m, 2H). LRMS (M+H): 534.3.

Scheme 43

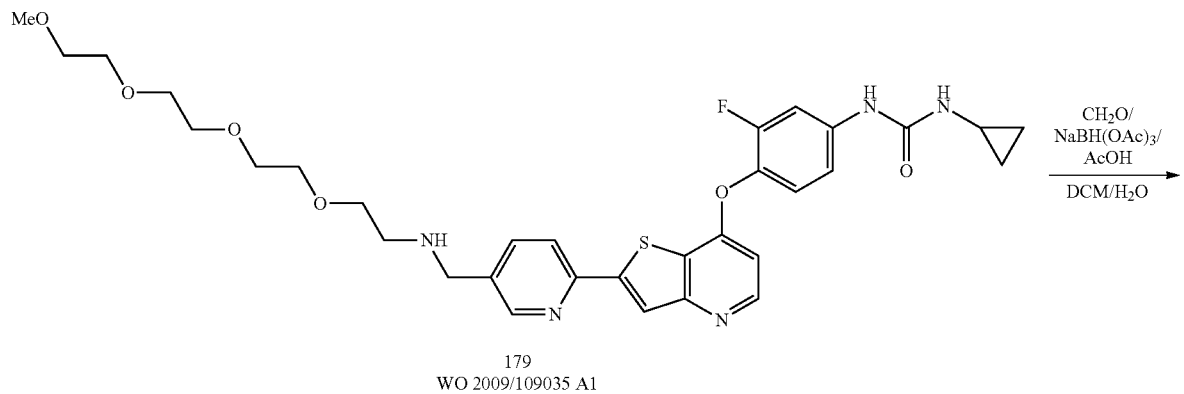

179
WO 2009/109035 A1

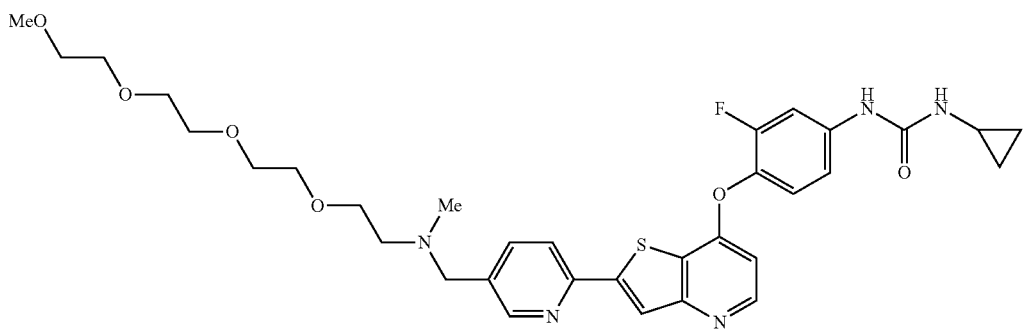

180: Example 108

Example 108

1-cyclopropyl-3-(3-fluoro-4-(2-(5-(2-methyl-5,8,11,14-tetraoxa-2-azapentadecyl)pyridin-2-yl)thieno[3,2-b]pyridin-7-yloxy)phenyl)urea (180)

Amine 179 (0.15 g, 0.23 mmol), 40% aqueous formaldehyde (0.70 g, 23 mmol) and acetic acid (0.13 mL, 2.3 mmol) were dissolved in dichloromethane (25 mL) to give a colorless solution. Sodium triacetoxyborohydride (0.199 g, 0.938 mmol) was added and the mixture was stirred at RT for 10 min. The reaction mixture was then washed with $H_2O$, saturated $NaHCO_3$, and brine, dried over anhydrous $MgSO_4$, filtered and concentrated. Silica gel chromatography of the residue (15% methanol/chloroform) resulted in partially purified product which was further purified by Gilson Reverse Phase HPLC (Luna $C_{18}$, 30-55% MeOH/water, 45 min) then lyophilized. The material was partitioned between 1M NaOH and dichloromethane, and the organic phase was collected and concentrated to yield title compound 180 (0.071 g, 46% yield) as a colorless solid. $^1$H NMR (400 MHz, DMSO-$d_6$) δ (ppm): 8.74 (s, 1H); 8.55 (d, J=1.4, 1H); 8.51 (d, J=5.5, 1H); 8.32 (s, 1H); 8.24 (d, J=8.2, 1H); 7.86 (dd, J=8.2, 2.2, 1H); 7.73 (dd, J=13.5, 2.5, 1H); 7.38 (t, J=8.8, 1H); 7.22-7.18 (m, 1H); 6.64 (d, J=5.3, 1H); 6.60 (d, J=2.4, 1H); 3.60 (s, 2H); 3.55 (t, J=5.9, 2H); 2.53-3.47 (m, 10H); 3.39 (t, J=5.7, 2H); 3.20 (s, 3H); 2.58-2.52 (m, 3H); 2.21 (s, 3H); 0.66-0.63 (m, 21-1); 0.44-0.41 (m, 2H). LRMS (M+H): 654.7

Scheme 44

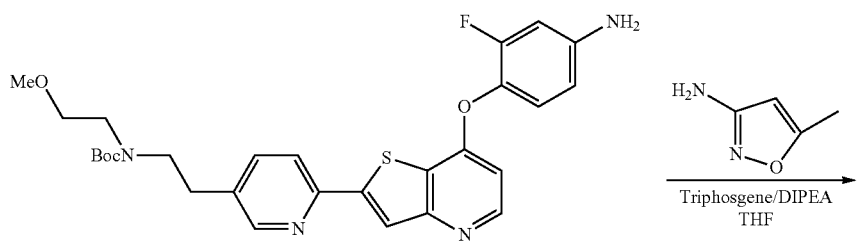

181

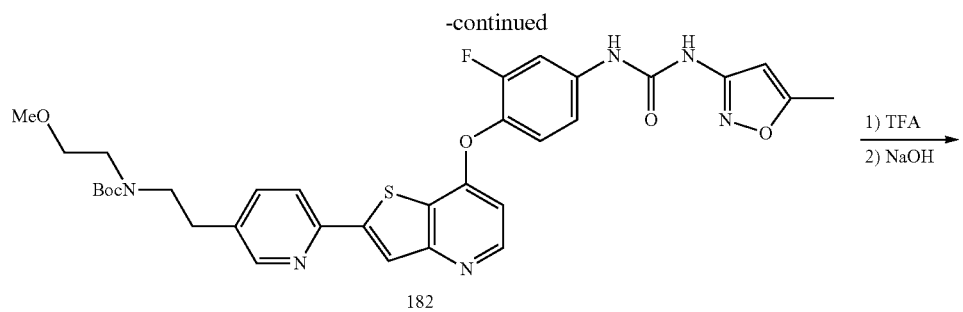

182

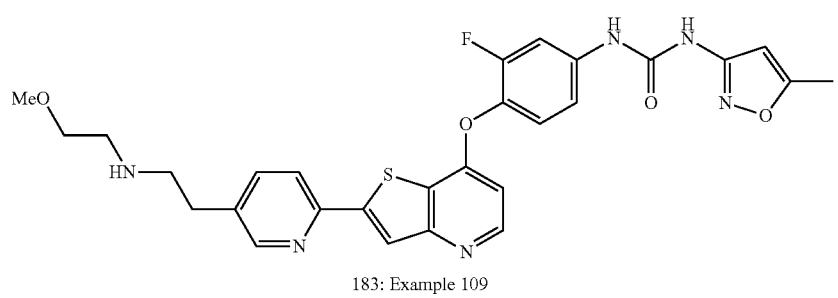

183: Example 109

Example 109

1-(3-fluoro-4-(2-(5-(2-(2-methoxyethylamino)ethyl)pyridin-2-yl)thieno[3,2-b]pyridin-7-yloxy)phenyl)-3-(5-methylisoxazol-3-yl)urea (183)

Step 1: tert-butyl 2-(6-(7-(2-fluoro-4-(3-(5-methylisoxazol-3-yl)ureido)phenoxy)thieno[3,2-b]pyridin-2-yl)pyridin-3-yl)ethyl(2-methoxyethyl)carbamate (182)

To a solution of compound 181 (0.25 g, 0.46 mmol, scheme 64) and DIPEA (0.20 mL, 1.2 mmol) in THF (60 mL) at 0° C. was added triphosgene (0.055 g, 0.19 mmol) and the mixture was stirred for 10 min. Then 3-amino-5-methylisoxazole (0.091 g, 0.93 mmol) was added, the mixture was stirred for an additional 20 min, then warmed to room temperature and stirred for 2 h. Excess triphosgene was quenched with 1 mL water then the mixture was concentrated. The residue was partitioned between water and ethyl acetate, and the organic phase was collected, washed with water, saturated aqueous sodium bicarbonate, and brine. It was then dried over anhydrous MgSO$_4$, filtered, concentrated and purified by flash column chromatography (eluent 3% methanol/ethyl acetate) to give title compound 182 (0.17 g, 56% yield).

Step 2: 1-(3-fluoro-4-(2-(5-(2-(2-methoxyethylamino)ethyl)pyridin-2-yl)thieno[3,2-b]pyridin-7-yloxy)phenyl)-3-(5-methylisoxazol-3-yl)urea (183)

Compound 182 (0.17 g, 0.26 mmol) was suspended in dichloromethane (50 mL) and TFA (1 mL) was added. This solution was stirred for 1 h then the mixture was concentrated. The residue was partitioned between ethyl acetate and water, washed with 3M NaOH and brine, then dried over anhydrous MgSO$_4$, filtered and concentrated. The residue was triturated with diethyl ether and dried in vacuo to afford title compound 183 (0.125 g, 87% yield). $^1$H NMR (400 MHz, DMSO-d$_6$) δ (ppm): 9.74 (s, 1H); 9.33 (s, 1H); 8.52 (d, J=5.5, 1H): 8.51-8.50 (m, 1H); 8.29 (s, 1H); 8.18 (d, J=8.0, 1H): 7.81 (dd, J=8.2, 2.2, 1H); 7.74 (J=12.9, 2.5, 1H); 7.46 (t. J=9.0, 1H); 7.30-7.27 (m, 1H); 6.66 (d, J=5.5, 1H); 6.55 (s, 1H); 3.37 (t, J=5.7, 2H); 3.22 (s, 1H); 2.82-2.75 (m, 4H); 2.68 (t, J=5.5, 2H); 2.37 (s, 3H). LRMS (M+H): 563.5.

Scheme 45

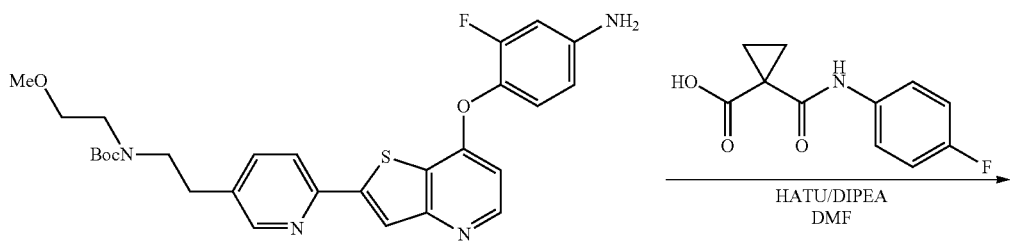

181

-continued

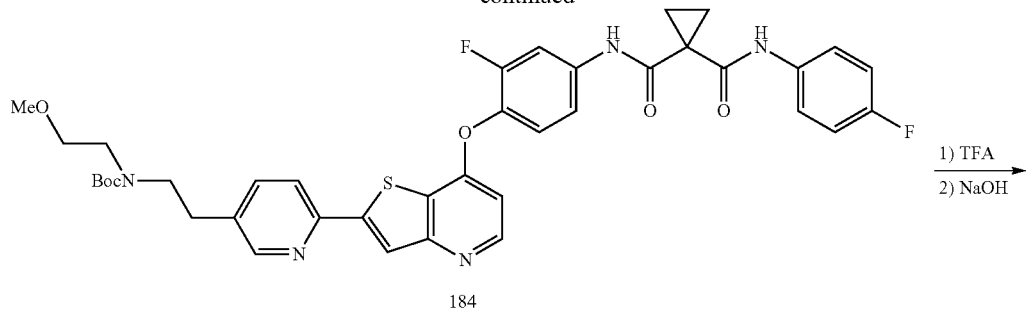

184

1) TFA
2) NaOH

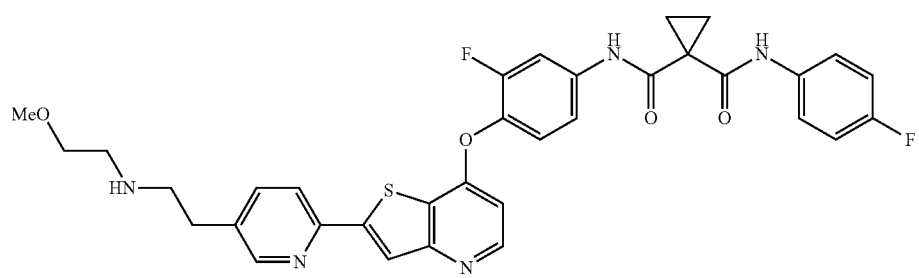

185: Example 110

Example 110

N-(3-fluoro-4-(2-(5-(2-(2-methoxyethylamino)ethyl)pyridin-2-yl)thieno[3,2-b]pyridin-7-yloxy)phenyl)-N-(4-fluorophenyl)cyclopropane-1,1-dicarboxamide (185)

Step 1: tert-butyl 2-(6-(7-(2-fluoro-4-(1-(4-fluorophenylcarbamoyl)cyclopropanecarboxamido)phenoxy)thieno[3,2-b]pyridin-2-yl)pyridin-3-yl)ethyl(2-methoxyethyl)carbamate, (184)

To a solution of compound 181 (0.25 g, 0.46 mmol, scheme 64), 1-(4-fluorophenylcarbamoyl)cyclopropanecarboxylic acid (0.21 g, 0.93 mmol), and DIPEA (0.32 mL, 1.9 mmol) in DMF (25 mL) was added HATU reagent (0.44 g, 1.2 mmol) and the resultant mixture was stirred at room temperature for 48 h. The mixture was partitioned between water and ethyl acetate, and the organic phase washed with water, saturated aqueous sodium bicarbonate, saturated aqueous ammonium chloride, and brine. It was then dried over anhydrous MgSO$_4$, filtered and concentrated. Silica gel chromatography (ethyl acetate) of the residue provided title compound 184 (0.23 g, 67% yield).

Step 2: N-(3-fluoro-4-(2-(5-(2-(2-methoxyethylamino)ethyl)pyridin-2-yl)thieno[3,2-b]pyridin-7-yloxy)phenyl)-N-(4-fluorophenyl)cyclopropane-1,1-dicarboxamide (185)

Compound 184 (0.23 g, 0.31 mmol) was suspended in dichloromethane (50 mL) and TFA (1.1 mL) was added. The reaction mixture was stirred for 18 h then concentrated. The residue was partitioned between ethyl acetate and water, the organic phase was collected, washed with 3M NaOH and brine, then dried over anhydrous MgSO$_4$, filtered and concentrated. The residue was triturated with diethyl ether and dried in vacuo to provide title compound 185 (0.16 g, 81% yield). $^1$H NMR (400 MHz, DMSO-d$_6$) δ (ppm): 10.41 (s, 1H); 10.02 (s, 1H); 8.52 (d, J=5.5, 1H); 8.50-8.48 (m, 1H); 8.29 (s, 1H); 8.18 (d, J=8.2, 1H); 7.90 (dd, J=13.1, 2.2, 1H); 7.81 (dd, J=8.2, 2.2, 1H); 7.64-7.60 (m, 2H); 7.50-7.45 (m, 2H); 7.18-7.12 (m, 2H); 6.65 (d, J=5.5, 1H); 3.37 (t, J=5.7, 2H); 3.22 (s, 3H); 2.82-2.74 (m, 4H); 2.70-2.66 (m, 2H); 1.47 (s, 4H). LRMS (M+H): 644.6

Scheme 46

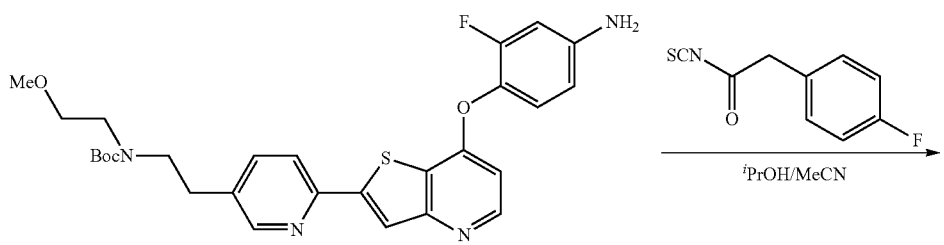

181

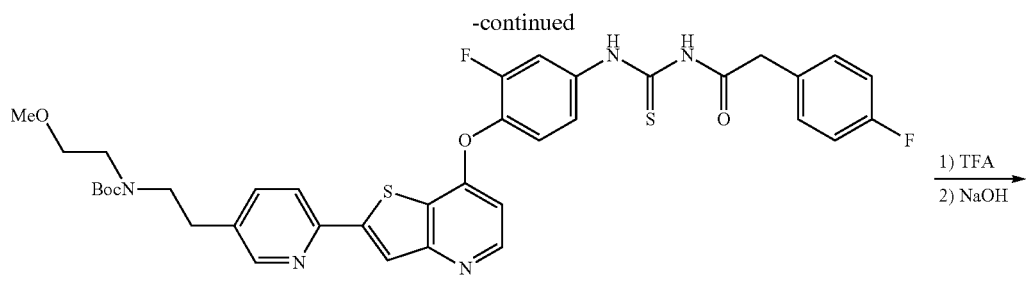

186

1) TFA
2) NaOH

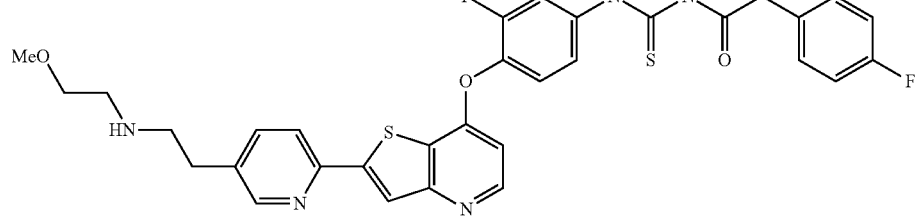

187: Example 111

Example 111

N-(3-fluoro-4-(2-(5-(2-(2-methoxyethyl amino)ethyl)pyridin-2-yl)thieno[3,2-b]pyridin-7-yloxy)phenylcarbamothioyl)-2-(4-fluorophenyl)acetamide (187)

Step 1: tert-butyl 2-(6-(7-(2-fluoro-4-(3-(2-(4-fluorophenyl)acetyl)thioureido)phenoxy)thieno[3,2-b]pyridin-2-yl)pyridin-3-yl)ethyl(2-methoxyethyl)carbamate (186)

To a solution of compound 181 (0.24 g, 0.45 mmol, scheme 64) in 2-propanol (50 mL) was added a solution of 4-fluorophenylacetyl isothiocyanate (0.1M, 0.8 mmol) in acetonitrile (8 mL). The resultant mixture was heated to 70° C. for 1 h, then cooled and concentrated. Silica gel chromatography of the residue (eluent 5% methanol/chloroform) afforded the title compound 186 (0.19 g, 58% yield).

Step 2: N-(3-fluoro-4-(2-(5-(2-(2-methoxyethylamino)ethyl)pyridin-2-yl)thieno[3,2-b]pyridin-7-yloxy)phenylcarbamothioyl)-2-(4-fluorophenyl)acetamide (187)

To a solution of 186 (0.19 g, 0.26 mmol) in acetic acid (10 mL) was added aqueous HCl (3M, 1.0 mL, 3.0 mmol). The mixture was stirred at room temperature for 3 h then partially concentrated. The residue was partitioned between ethyl acetate and water, the organic phase was collected, washed with saturated aqueous sodium bicarbonate and brine. It was then dried over anhydrous MgSO$_4$, filtered and concentrated. The residue was purified by flash column chromatography (eluent 15% methanol/chloroform) to give title compound 187 (80 mg, 49% yield). $^1$H NMR (400 MHz, DMSO-d$_6$) δ (ppm): 8.53 (d, J=5.5, 1H), 8.50 (d, J=1.6, 1H), 8.30 (s, 1H), 8.18 (d, J=7.8, 1H), 8.04 (dd, J=11.2, 1.6, 1H), 7.89 (dd, J=8.2, 2.2, 1H), 7.54-7.50 (m, 2H), 7.40-7.35 (m, 2H), 7.22-7.15 (m, 2H), 6.67 (d, J=5.5, 1H), 3.83 (s, 2H), 3.40 (s, 2H), 3.37 (t, J=5.7, 2H), 3.22 (s, 3H), 2.82-2.75 (m, 4H), 2.69 (t, J=5.7, 2H). LRMS (M+H): 634.4

Scheme 47

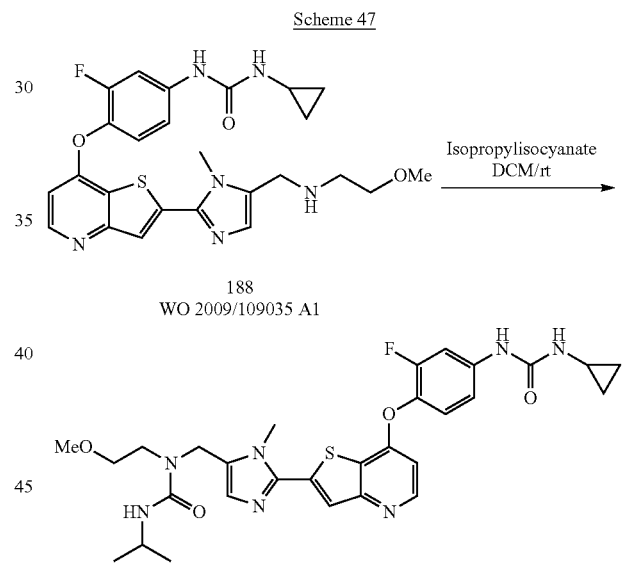

189: Example 112

Example 112

1-((2-(7-(2-fluoro-4-cyclopropylaminocarbonylaminophenoxy)thieno[3,2-b]pyridin-2-yl)-1-methyl-1H-imidazol-5-yl)methyl)-3-isopropyl-1-(2-methoxyethyl (189)

To a solution of 188 (85 mg, 0.166 mmol) in DCM (5 mL) was added isopropyl isocyanate (70.8 mg, 0.832 mmol) and the reaction mixture was stirred at RT overnight. The mixture was diluted with EtOAc then washed with water, dried over anhydrous Na$_2$SO$_4$, filtered and concentrated. The residue was purified by column chromatography (eluent EtOAc to 20% MeOH in EtOAc) to afford title compound 189 (57 mg, 58% yield) as a white solid. $^1$H NMR (400 MHz, DMSO-d$_6$)

δ (ppm): 8.69 (s, 1H), 8.49 (d, J=5.48 Hz, 1H), 7.89 (s, 1H), 7.70 (m, 1H), 7.35 (t, J=8.99 Hz, 1H), 7.19 (m, 1H), 6.94 (s, 1H), 6.64 (d, J=5.28 Hz, 1H), 6.55 (m, 1H), 6.10 (d, J=5.48 Hz, 1H), 4.55 (s, 2H), 3.83 (s, 3H), 3.79 (m, 1H), 3.21 (s, 3H), 2.53 (m, 1H), 1.05 (d, J=6.45 Hz, 6H), 0.63 (m, 2H), 0.40 (m, 2H). MS (m/z)=596.43 (M+H).

Compounds 190, 193-195 (examples 113, 115-117) were prepared similarly to compound 189 (example 112, scheme 47) from precursors described in WO 2009/109035 A1 and compound 113 (example 78, scheme 29).

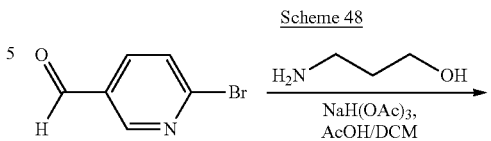

Scheme 48

TABLE 17

Characterization of compounds 190-195 (examples 113-117)

| Cpd | Ex | Structure | Characterization |
|---|---|---|---|
| 190 | 113 | 1-((6-(7-(4-cyclopropylaminocarbonylamino-2-fluorophenoxy)-thieno[3,2-b]pyridin-2-yl)pyridin-3-yl)methyl)-3-isopropyl-1-(2-methoxyethyl)urea | $^1$H NMR (400 MHz, DMSO-$d_6$) δ (ppm): 8.72 (s, 1H), 8.51 (d, J = 5.28 Hz, 1H), 8.48 (m, 1H), 8.301 (s, 1H), 8.23 (d, J = 11.55 hz, 1H), 7.74 (m, 2H), 7.37 (t, J = 9.19 Hz, 1H), 7.20 (m, 1H), 6.64 (d, J = 5.47 Hz, 1H), 6.57 (m, 1H), 6.14 (d, J = 7.62 Hz, 1H), 4.52 (s, 2H), 3.81 (m, 1H), 3.44 (m, 1H), 3.20 (s, 3H), 1.06 (d, J = 6.46 Hz, 6H), 0.65 (m, 2H), 0.42 (m, 2H). MS (m/z) = 593.47 (M + H). |
| 193 | 115 | 1-(4-(7-(4-cyclopropylaminocarbonylamino-2-fluorophenoxy)thieno-[3,2-b]pyridin-2-yl)benzyl)-3-isopropyl-1-(2-methoxyethyl)urea | 1H NMR (400 MHz. DMSO-$d_6$) δ (ppm): 8.74(s, 1H)9 8.53(d, 1H, J = 5.5 Hz), 8.06(s, 1H), 7.90(d, 2H, J = 8.4 Hz), 7.77(dd, 1H, J1 = 2.5 Hz, J2 = 13.7 Hz), 7.41(t, 1H, J = 9.0 Hz), 7.37(d, 2H, J = 8.4 Hz), 7.24-7.22(m, 1H), 6.63-6.60(m, 2H), 6.13(d, 1H, J = 7.4 Hz), 4.65(s, 2H), 3.86-3.81(m, 1H), 3.44(t, 2H, J = 5.7 Hz), 3.36(t, 2H, J = 4.3 Hz), 3.28(s, 3H), 2.61-2.56(m, 1H), 1.11(s, 3H), 1.10(s, 3H), 0.71-0.68(m, 2H), 0.48-0.44(m, 2H). MS: 592.6(MH+). |
| 194 | 116 | 1-(4-(7-(4-cyclopropylaminocarbonylamino-2-fluorophenoxy)thieno-[3,2-b]pyridin-2-yl)benzyl)-3-cyclopentyl-1-(2-methoxyethyl)urea | $^1$H NMR (400 MHz, DMSO-$d_6$) δ (ppm): 8.75 (s, 1), 8.53(d, 1H, J = 5.5 Hz), 8.06(s, 1H), 7.90(d, 1H, J = 8.5 Hz), 7.77(dd, 1H, J1 = 2.3 Hz, J2 = 13.5 Hz), 7.41(t, 1H, J = 9.0 Hz), 7.37(d, 2H, J = 8.41 Hz), 7.25-7.22(m, 1H), 6.36-6.61(m, 2H), 6.18(d, 1H, J = 7.0 Hz), 4.56(s, 2H), 4.02-3.96(m, 1H), 3.45-3.43(m, 2H, J = 5.9 Hz), 3.66(t, 2H, J = 5.9 Hz), 3.23(s, 3H), 2.61-2.56(m, 1H), 1.84-1.78(m, 2H), 1.66-1.62(m, 2H), 1.54-1.49(m, 2H), 1.46-1.40(m, 2H), 0.89-0.66(m, 2H), 0.48-0.44(m, 2H). MS: 618.5(MH+). |
| 195 | 117 | 1-(4-(7-(4-cyclopropylaminocarbonylamino-2-fluorophenoxy)thieno[3,2-b]pyridin-2-yl)benzyl)-3-ethyl-1-(2-methoxyethyl)urea | $^1$H NMR (400 MHz, DMSO-$d_6$) δ (ppm): 8.73(s, 1H), 8.52(d, 1H, J = 5.5 Hz), 8.06(s, 1H), 7.90(d, 2H, J = 8.4 Hz), 7.76(dd, 1H, J = 2.3 Hz, J2 = 13.5 Hz), 7.42(t, 1H, J = 9.0 Hz), 7.36(d, 2H, J = 8.4 Hz), 7.25-7.22(m, 1H), 6.63-6.60(m, 2H), 6.45(t, 1H, J = 5.5 Hz), 4.56(s, 2H), 3.46-3.43(m, 2H), 3.36-3.4(m, 2H), 3.27(s, 3H), 3.14-3.10(m, 2H), 2.60-2.58(m, 1H), 1.06(t, 3H, J = 7.0 Hz), 0.70-0.67(m, 2H), 0.49-0.47(m, 2H). MS: 578.5(MH+). |

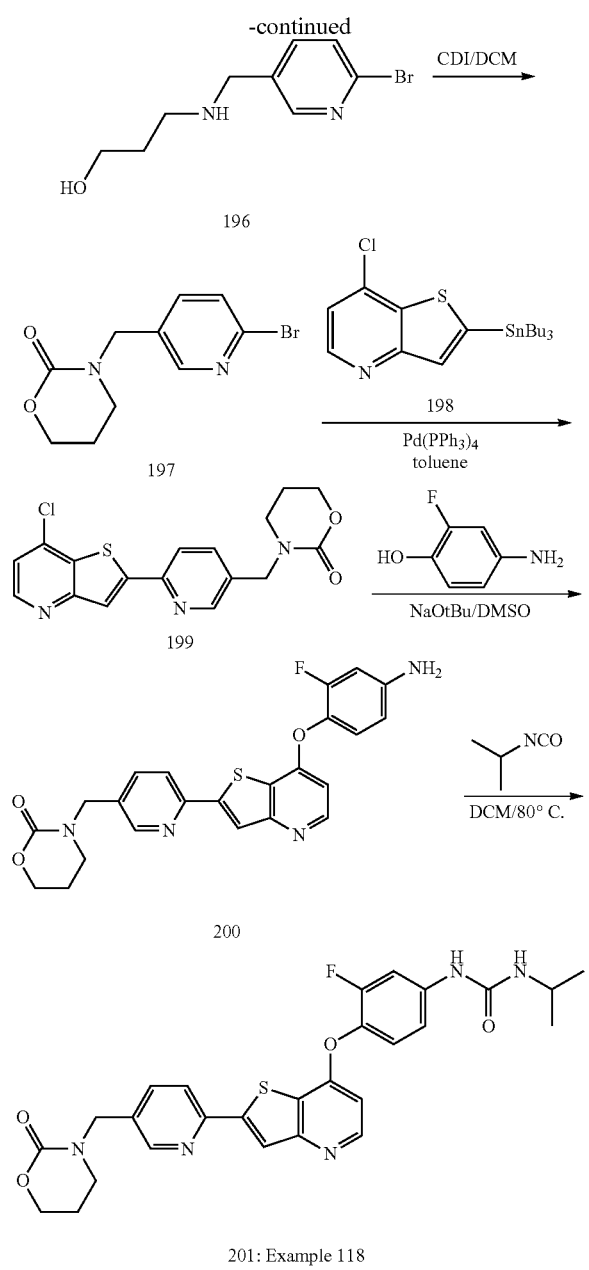

aqueous phase was concentrated and the resultant solid was stirred with a mixture of DCM and acetone then filtered. The filtrate was collected, dried over Na$_2$SO$_4$, and concentrated to give a yellowish material, which upon trituration with Et$_2$O afforded title compound 196 (0.9 g, 55% yield) as an off-white solid. MS: 246 (MH+).

Step 2: 3-((6-bromopyridin-3-yl)methyl)-1,3-oxazinan-2-one (197)

To a solution of 196 (0.9 g, 3.67 mmol) in DCM (30 mL) was added CDI (0.595 g, 3.67 mmol), and the reaction mixture was stirred at RT over weekend. The mixture was then concentrated and the residue was purified by flash column chromatography (eluent EtOAc) to afford the title compound 197 (373 mg, 38% yield) as colorless oil. MS: 271 (HM+).

Step 3: 3-((6-(7-chlorothieno[3,2-b]pyridin-2-yl) pyridin-3-yl)methyl)-1,3-oxazinan-2-one (199)

To a solution of 197 (373 mg, 1.376 mmol) in toluene (10 mL) was added the 7-chloro-2-(tributylstannyl)thieno[3,2-b] pyridine 198 (631 mg, 1.376 mmol) and Pd(PPh$_3$)$_4$ (159 mg, 0.138 mmol). The reaction mixture was heated to reflux for 24 hours. The reaction mixture was then cooled to RT and concentrated. The residue was triturated with Et$_2$O to afford the title compound 199 (363 mg, 73% yield) as beige solid. MS: 360 (MH+).

Step 4: 3-((6-(7-(4-amino-2-fluorophenoxy)thieno[3, 2-b]pyridin-2-yl)pyridin-3-yl)methyl)-1,3-oxazinan-2-one (200)

To a solution of 4-amino-2-fluorophenol (70.7 mg, 0.556 mmol) in DMSO (5 mL) was added sodium tert-butoxide (53.4 mg, 0.556 mmol) and the reaction mixture was stirred for 30 min. Chloride 199 (100 mg, 0.278 mmol) was added and the reaction mixture was heated at 100° C. overnight. The mixture was then cooled to RT and poured into water (20 mL) and the precipitated product was collected by filtration and purified by Biotage (MeOH/EtOAc 0-50%, SNAP 25 g cartridge) to give title compound 200 (147 mg, 33% yield) as a beige solid. MS: 451 (MH+).

Step 5: 1-(3-fluoro-4-(2-(5-((2-oxo-1,3-oxazinan-3-yl)methyl)pyridin-2-yl)thieno[3,2-b]pyridin-7-yloxy) phenyl)-3-isopropylurea (201)

A reaction mixture consisting of amine 200 (100 mg, 0.222 mmol) and 2-isocyanatopropane (434 mg, 5.10 mmol) in DCM (3 mL) was heated to 80° C. in a sealed flask overnight. The mixture was then cooled to RT and purified by Biotage (SiliaFlash 12 g cartridge, 0-12% MeOH/CHCl$_3$) to afford after the separation title compound 201 (35 mg, 29.4% yield) as beige solid. $^1$H NMR (400 MHz, DMSO-d$_6$) δ (ppm): 8.67 (s, 1H), 8.55 (d, 1H, J=1.8 Hz), 8.50 (d, 1H, J=5.3 Hz), 8.33 (s, 1H), 8.25 (d, 1H, J=8.2 Hz), 7.84 (dd, 1H, J1=2.2 Hz, J2=8.2 Hz), 7.69 (dd, J1=2.5 Hz, J2=13.7 Hz), 7.35 (t, 1H, J=9.0 Hz), 7.12-7.10 (m, 1H), 6.62 (d, 1H, J=5.1 Hz), 6.14 (d, 1H, J=7.4 Hz), 4.50 (s, 2H), 4.21 (t, 2H, J=5.1 Hz), 3.77-3.72 (m, 1H), 3.30-3.28 (m, 2H), 1.97-1.92 (m, 2H), 1.10 (s, 3H), 1.08 (s, 3H). MS: 536.4 (MH)+

Example 118

1-(3-fluoro-4-(2-(5-((2-oxo-1,3-oxazinan-3-yl)methyl)pyridin-2-yl)thieno[3,2-b]pyridin-7-yloxy)phenyl)-3-isopropylurea (201)

Step 1: 3-((6-bromopyridin-3-yl)methylamino)propan-1-ol (196)

To a solution of 6-bromonicotinaldehyde (1.25 g, 6.72 mmol) in DCM (25 mL) was added 3-aminopropan-1-ol (1.514 g, 20.16 mmol) and acetic acid (0.385 mL, 6.72 mmol), and the reaction mixture was stirred for 10 min. Sodium triacetoxyborohydride (3.56 g, 16.80 mmol) was added and the reaction mixture was stirred at RT overnight. The reaction mixture was then diluted with EtOAc and extracted with water. The organic phase was discarded. The

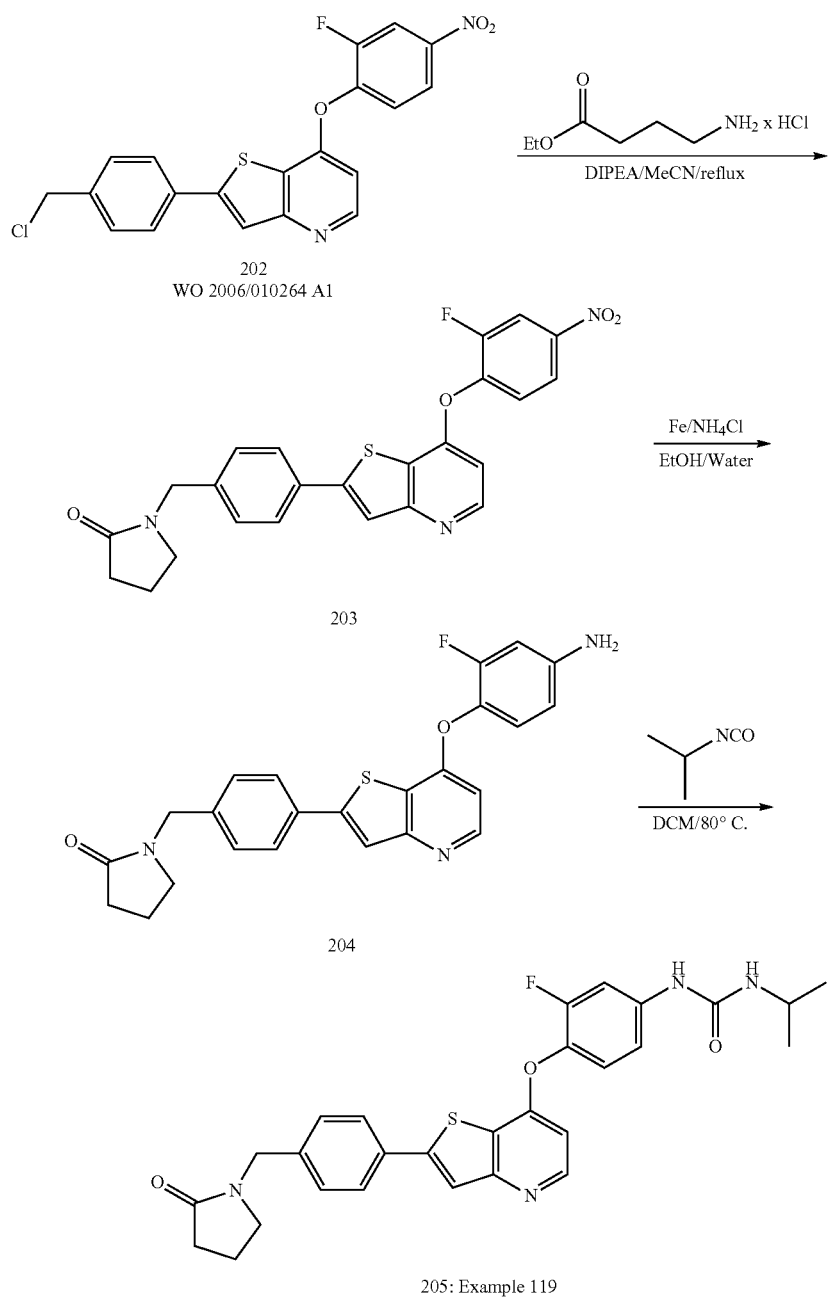

Example 119

1-(3-fluoro-4-(2-(4-((2-oxopyrrolidin-1-yl)methyl)phenyl)thieno[3,2-b]pyridin-7-yloxy)phenyl)-3-isopropylurea (205)

Step 1: 1-(4-(7-(2-fluoro-4-nitrophenoxy)thieno[3,2-b]pyridin-2-yl)benzyl)pyrrolidin-2-one (203)

A mixture of compound 202 (1 g, 2.411 mmol), ethyl 4-aminobutanoate hydrochloride (0.808 g, 4.82 mmol) and DIPEA (1.263 mL, 7.23 mmol) in acetonitrile (12 mL) was heated to reflux for 2 days. The reaction mixture was cooled to room temperature and concentrated. The residue was dissolved in ethyl acetate and washed with saturated ammonium chloride solution. The organic phase was dried over anhydrous sodium sulfate and concentrated. The residue was purified using Biotage (MeOH/EtOAc, 0-20%, SNAP 50 g cartridge) to give the title compound 203 (580 mg, 52% yield) as beige solid. MS: 464 (MH+).

Step 2: 1-(4-(7-(4-amino-2-fluorophenoxy)thieno[3,2-b]pyridin-2-yl)benzyl)pyrrolidin-2-one (204)

The reaction mixture consisting of the nitro compound 203 (580 mg, 1.25 mmol), iron powder (594 mg, 10.64 mmol), and ammonium chloride (57.6 mg, 1.076 mmol) in EtOH/ water mixture (16 mL/8 mL) was stirred for 2 hr at 80° C. The reaction mixture was filtered while hot. The filtrate was concentrated to give title compound 204 (542 mg, 100% yield) as a brown solid. MS: 434 (MH)+.

Step 3: 1-(3-fluoro-4-(2-(4-((2-oxopyrrolidin-1-yl)methyl)phenyl)thieno[3,2-b]pyridin-7-yloxy)phenyl)-3-isopropylurea (205)

Title compound 205 was obtained starting from the compound 204 and following a procedure similar to the one used in the synthesis of compound 201 (example 118, scheme 48).
$^1$H NMR (400 MHz, DMSO-d$_6$) δ (ppm): 1H: 8.66 (s, 1H), 8.48 (d, 1H, J=5.5 Hz), 8.02 (s, 1H), 7.86-7.84 (m, 2H), 7.70 (dd, 1H, J1=2.3 Hz, J2=13.5 Hz), 7.37-7.32 (m, 3H), 7.13-7.10 (m, 1H), 6.58 (dd, 1H, J1=0.8 Hz, J2=5.3 Hz), 6.13 (d, 1H, 0.1=7.4 Hz), 4.41 (s, 2H), 3.78-3.74 (m, 1H), 3.27 (t, 2H, J=7.3 Hz), 2.29 (t, 2H, J=8.2 Hz), 1.94-1.91 (m, 2H), 1.10 (s, 3H), 1.08 (s, 3H). MS: 519.5 (MH+).

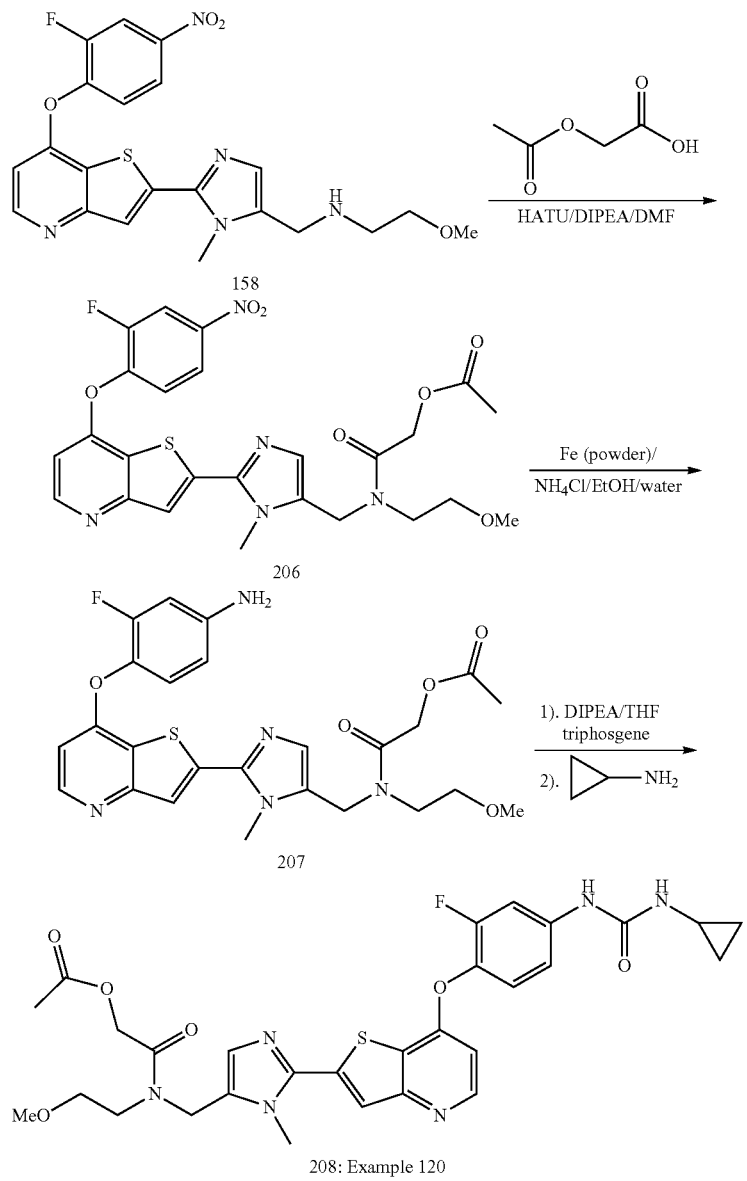

Scheme 50

Example 120

2-(((2-(7-(4-(3-Cyclopropyl ureido)-2-fluorophenoxy)thieno[3,2-b]pyridin-2-yl)-1-methyl-1H-imidazol-5-yl)methyl)(2-methoxyethyl)amino)-2-oxoethyl acetate (208)

Step 1: 2-(((2-(7-(2-fluoro-4-nitrophenoxy)thieno[3,2-b]pyridin-2-yl)-1-methyl-1H-imidazol-5-yl)methyl)(2-methoxyethyl)amino)-2-oxoethyl acetate (206)

To a solution of 158 (423 mg, 0.925 mmol, scheme 39) in DMF (18 mL) was added 2-acetoxyacetic acid (164 mg, 1.387 mmol), DIPEA (0.565 mL, 3.24 mmol) and HATU reagent (1055 mg, 2.77 mmol). The reaction mixture was stirred at room temperature for 1 hr followed by addition of NaHCO₃ saturated solution (200 mL) and EtOAc (300 mL). A white precipitate was formed which was collected by filtration and discarded. The organic layer of the filtrate was collected, dried over anhydrous sodium sulfate and concentrated to give a yellowish solid, which was triturated with ether to give title compound 206 (570 mg, 111% yield, crude) that was used in the next step with no additional purification. MS: 558 (MH)+.

Step 2: 2-(((2-(7-(4-amino-2-fluorophenoxy)thieno[3,2-b]pyridin-2-yl)-1-methyl-1H-imidazol-5-yl)methyl)(2-methoxyethyl)amino)-2-oxoethyl acetate (207)

The reaction mixture consisting of 206 (300 mg, 0.538 mmol), ammonium chloride (24.75 mg, 0.463 mmol) and iron powder (255 mg, 4.57 mmol) in ethanol (6 mL)/water (3.0 mL) was heated to reflux for 1 h. The reaction mixture was filtered while hot and concentrated. The residue was purified by Biotage (MeOH/DCM, 0-20%, SNAP 25 g cartridge) to give the title compound 207 (133 mg, 0.252 mmol, 47% yield) as a white solid. MS: 528 (MH)+.

Step 3: 2-(((2-(7-(4-(3-cyclopropylureido)-2-fluorophenoxy)thieno[3,2-b]pyridin-2-yl)-1-methyl-1H-imidazol-5-yl)methy 1)(2-methoxyethyl)amino)-2-oxoethyl acetate (208)

To a solution of 207 (130 mg, 0.246 mmol) in THF (20 mL) at 0° C. was added. DIPEA (0.172 mL, 0.986 mmol) and triphosgene (43.9 mg, 0.148 mmol). The reaction mixture was stirred for 1 hr at 0° C. before cyclopylamine (70.3 mg, 1.232 mmol) was added. The reaction mixture was allowed to warm up to room temperature and stirred for 1 hr before concentration. The residue was purified by Biotage (MeO/DCM, 0-20%, SNAP 25 g cartridge) to give the title compound 208 (104 mg, 0.170 mmol, 69% yield) as a white solid. MS: 611 (MH)+.

Scheme 51

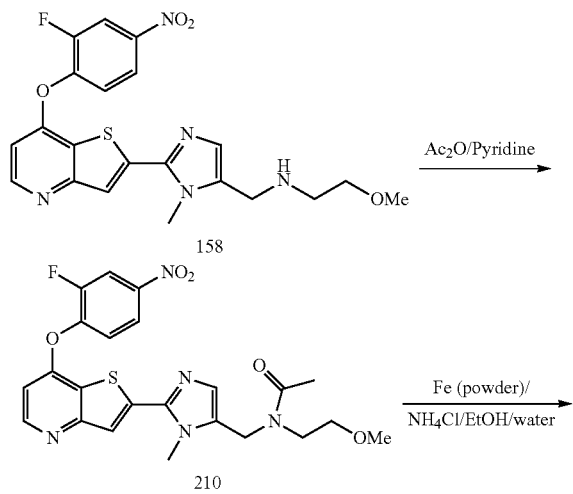

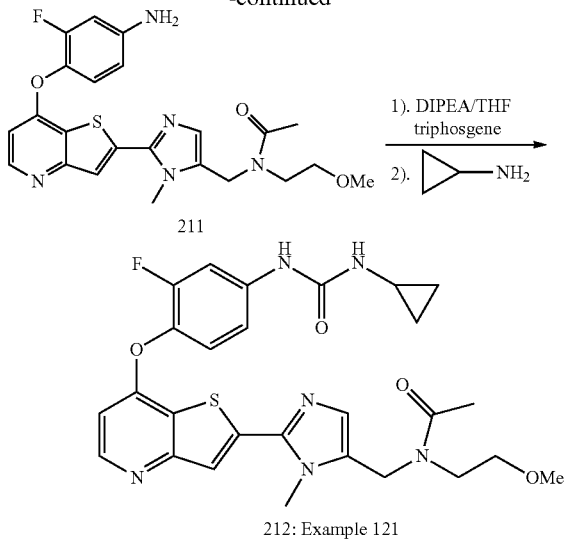

211

212: Example 121

Example 121

N-((2-(7-(4-(3-cyclopropylureido)-2-fluorophenoxy)thieno[3,2-b]pyridin-2-yl)-1-methyl-1H-imidazol-5-yl)methyl)-N-(2-methoxyethyl)acetamide (212)

Step 1: N-((2-(7-(2-fluoro-4-nitrophenoxy)thieno[3,2-b]pyridin-2-yl)-1-methyl-1H-imidazol-5-yl)methyl)-N-(2-methoxyethyl)acetamide (210)

To a solution of 158 (100 mg, 0.219 mmol, scheme 51) in pyridine (6 mL) at 0° C. was added acetic anhydride (0.022 mL, 0.230 mmol) and the reaction mixture was stirred at room temperature for 2 hr. The reaction mixture was partitioned between EtOAc and CuSO₄ (1M) solution, the organic layer was collected, washed with 1N HCl and then water, dried over anhydrous sodium sulfate and concentrated. The residue was purified by Biotage (MeOH/DCM, 0-15%, SNAP 25 g cartridge) to give title compound 210 (80 mg, 0.160 mmol, 73% yield) as a white solid. MS: 500 (MH)+.

Step 2: N-((2-(7-(4-amino-2-fluorophenoxy)thieno[3,2-b]pyridin-2-yl)-1-methyl-1H-imidazol-5-yl)methyl)-N-(2-methoxyethyl)acetamide (211)

Title compound 211 was obtained starting from the compound 210 and following a procedure similar to the one used in the synthesis of compound 207 (scheme 50). MS: 470 (MH)+.

Step 3: N-((2-(7-(4-(3-cyclopropylureido)-2-fluorophenoxy)thieno[3,2-b]pyridin-2-yl)-1-methyl-1H-imidazol-5-yl)methyl)-N-(2-methoxyethyl)acetamide (212)

Title compound 212 was obtained starting from the compound 211 and following a procedure similar to the one used in the synthesis of compound 208 (scheme 50). $^1$H NMR (400 MHz, DMSO-d₆) δ (ppm): 8.75 (s, 1H), 8.55 (d, 1H, J=5.3 Hz), 7.95 and 7.93 (s, 1H), 7.76 (dd, 1H, J1=2.3 Hz, J2=13.5 Hz), 7.41 (t, 1H, J=9.0 Hz), 7.24-7.21 (m, 1H), 7.08 and 6.92 (s, 1H), 6.70 (d, 1H, J=5.5 Hz), 6.60 (m, 1H), 4.74 and 4.70 (s, 2H), 3.88 and 3.86 (s, 3H), 3.45 (m, 2H), 3.36 (m, 1H), 3.28 (s, 3H), 3.24 (m, 1H), 2.60-2.57 (m, 1H), 2.14 and 2.12 (s, 3H), 0.71-0.66 (m, 2H), 0.48-0.44 (m, 2H). MS: 553 (MH)+.

Scheme 52
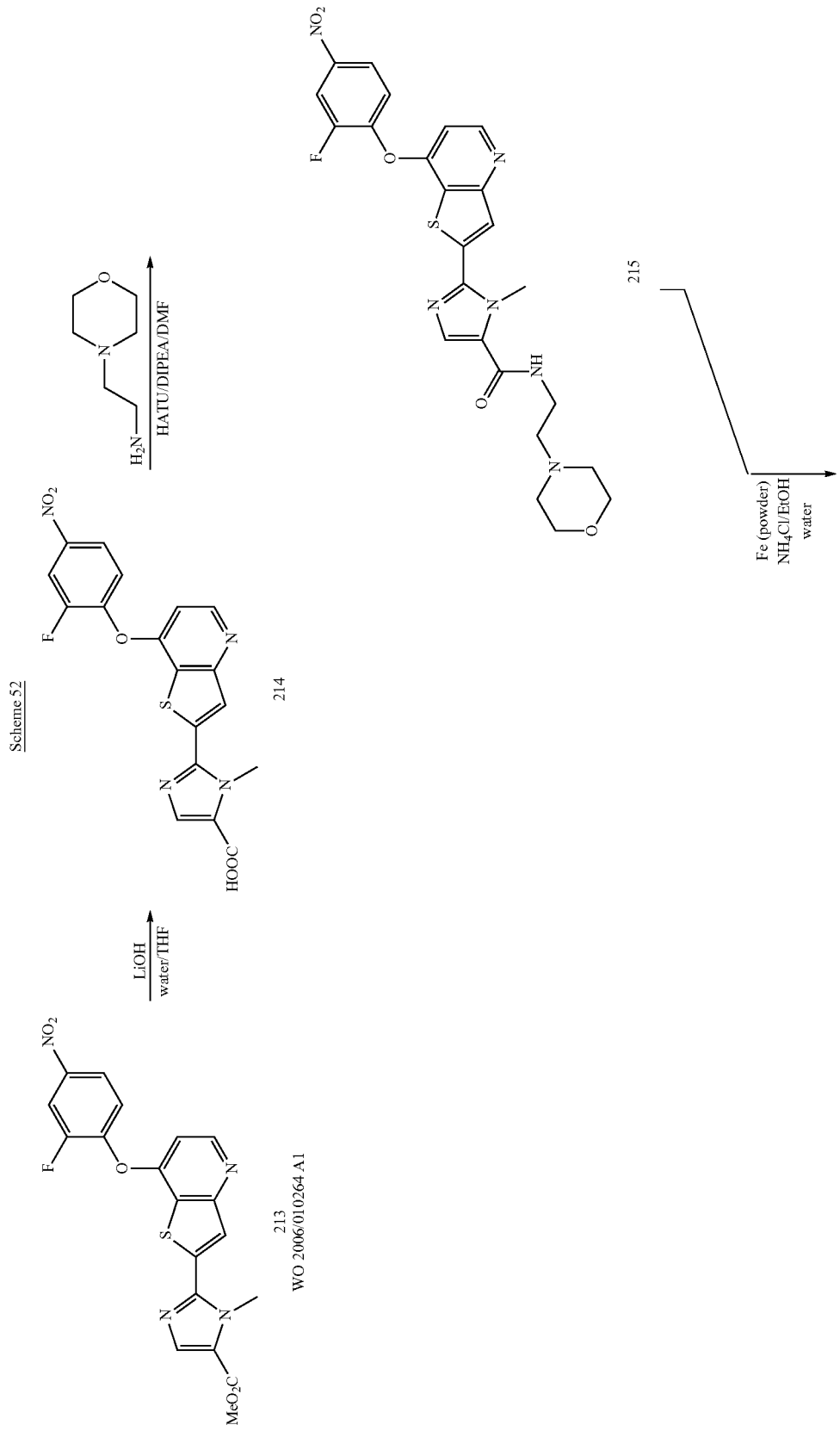

-continued
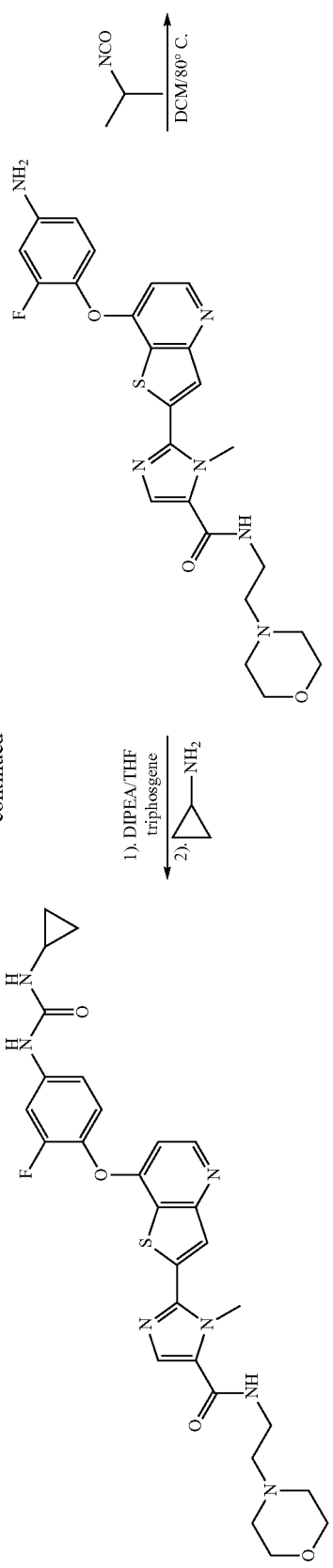
216
217: Example 122
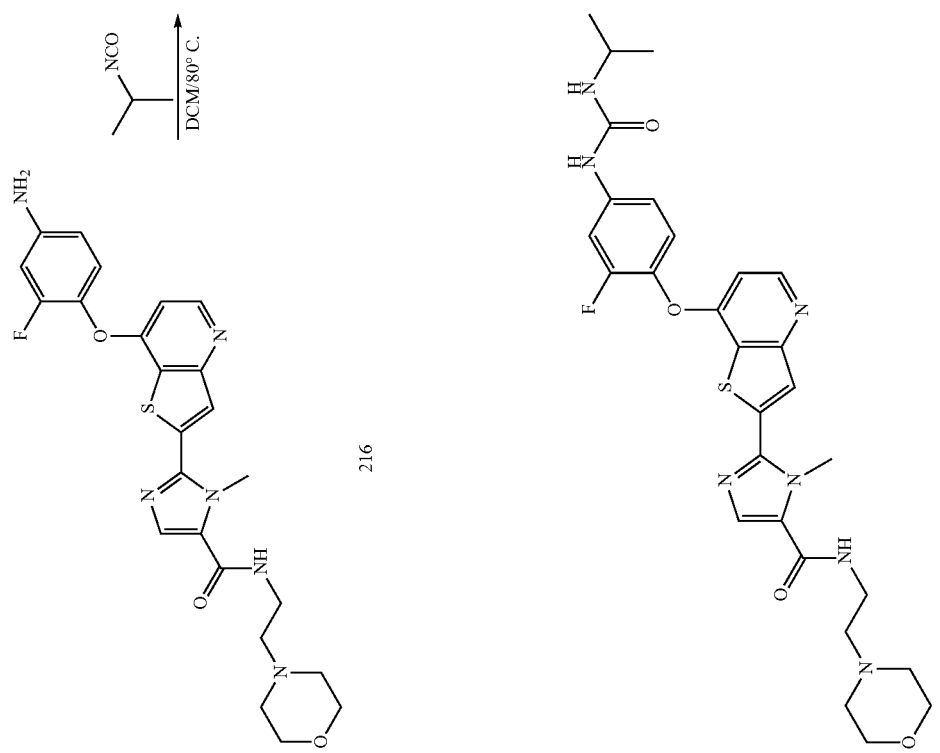
218: Example 123

Example 122

2-(7-(4-(3-cyclopropylureido)-2-fluorophenoxy) thieno[3,2-b]pyridin-2-yl)-1-methyl-N-(2-morpholinoethyl)-1H-imidazole-5-carboxamide (217)

Step 1: 2-(7-(2-fluoro-4-nitrophenoxy)thieno[3,2-b] pyridin-2-yl)-1-methyl-1H-imidazole-5-carboxylic acid (214)

To a suspension of ester 213 (1.5 g, 3.50 mmol) in THF (10 mL) was added a solution of LiOH (0.419 g, 17.51 mmol) in water (10.00 mL) and the reaction mixture was stirred overnight. The THF was evaporated under reduced pressure, water was added and the solution was acidified with 1N HCl to pH 1 to form a precipitate that was collected by filtration and dried to give title compound 214 (1.4 g, 3.38 mmol, 96% yield) as a white solid. MS 415 (MH)+.

Step 2: 2-(7-(2-fluoro-4-nitrophenoxy)thieno[3,2-b] pyridin-2-yl)-1-methyl-N-(2-morpholinoethyl)-1H-imidazole-5-carboxamide (215)

To a solution of acid 214 (180 mg, 0.434 mmol) in DMF (8 mL) was added 2-morpholinoethanamine (0.114 mL, 0.869 mmol), DIPEA (0.266 mL, 1.520 mmol) and HATU reagent (1.303 mmol). The reaction mixture was stirred at RT for 4 hr. NaHCO$_3$ saturated solution (5 mL) and EtOAc (5 mL) were added to form a precipitate that was collected by filtration. The organic layer of the filtrate was separated, dried over anhydrous sodium sulfate, concentrated and the residue was combined with the collected precipitate to give title compound 215 (180 mg, 0.342 mmol, 79% yield) as a white solid. MS: 527.5 (MH)+.

Step 3: 2-(7-(4-amino-2-fluorophenoxy)thieno[3,2-b]pyridin-2-yl)-1-methyl-N-(2-morpholinoethyl)-1H-imidazole-5-carboxamide (216)

The reaction mixture of the nitro compound 215 (180 mg, 0.342 mmol), iron powder (162 mmol), and ammonium chloride (15.7 mg, 0.294 mmol) in EtOH/water mixture (10 mL/5 mL) was heated to reflux for 1 hr. The reaction mixture was filtered while hot. The filtrate was concentrated to give title compound 216 (130 mg, 0.262 mmol, 77% yield) as a white solid. MS: 497.5 (MH)+.

Step 4: 2-(7-(4-(3-cyclopropylureido)-2-fluorophenoxy)thieno[3,2-b]pyridin-2-yl)-1-methyl-N-(2-morpholinoethyl)-1H-imidazole-5-carboxamide (217)

To a suspension of aniline 216 (130 mg, 0.262 mmol) in THF (10 mL) at 0° C. was added DIPEA (0.137 mL, 0.785 mmol) and triphosgene (38.8 mg, 0.131 mmol). The reaction mixture was stirred at 0° C. for 1 hr before cyclopropylamine (0.054 mL, 0.785 mmol) was added and the mixture was stirred for 10 min at 0° C. The reaction mixture was slowly warmed to room temperature and stirred over weekend then partitioned between NaHCO$_3$ saturated solution and EtOAc. The organic layer (suspension) was concentrated, the residue was dry-loaded onto a column (Biotage, MeOH/DCM, 0-25%, SNAP 10 g cartridge), purified twice then triturated with ether and acetone to give title compound 217 (30.4 mg, 0.052 mmol, 20% yield) as a white solid. $^1$H NMR (400 MHz, DMSO-d$_6$) δ (ppm): 8.75 (s, 1H), 8.59 (d, 1H, J=5.5 Hz), 8.48 (m, 1H), 8.07 (s, 1H), 7.78-7.74 (m, 1H), 7.71 (s, 1H), 7.42 (t, 1H, J=9.0 Hz), 7.25-7.22 (m, 1H), 6.74 (d, 1H, J=5.5 Hz), 6.61-6.60 (m, 1H), 4.22 (s, 3H), 3.62 (t, 4H, J=4.5 Hz), inside 3.38-3.33 (m, 2H), 2.60-2.57 (m, 1H), 2.52-2.46 (m, 6H), 0.71-0.67 (m, 2H), 0.48-0.46 (m, 2H). MS: 580.6 (MH)+

Example 123

2-(7-(2-fluoro-4-(3-isopropylureido)phenoxy)thieno [3,2-b]pyridin-2-yl)-1-methyl-N-(2-morpholinoethyl)-1H-imidazole-5-carboxamide (218)

Title compound 218 was obtained starting from the compound 216 and following a procedure similar to the one used in the synthesis of compound 201 (scheme 48). NMR (400 MHz, DMSO-d$_6$) δ (ppm): 8.73 (s, 1H), 8.59 (d, 1H, J=5.3 Hz), 8.48 (t, 1H, J=5.5 Hz), 8.07 (s, 1H), 7.76-7.71 (m, 2H), 7.41 (t, 1H, J=9.01 Hz), 7.17 (d, 1H, J=8.2 Hz), 6.73 (d, 1H, J=5.1 Hz), 6.19 (d, 1H, J=7.71 Hz), 4.21 (s, 3H), 3.83-3.78 (m, 1H), 3.61 (m, 4H), inside 3.39 (m, 2H), 2.51-2.46 (m, 6H), 1.15 (s, 3H), 1.14 (s, 3H). MS: 582.6 (MH)+

Scheme 53

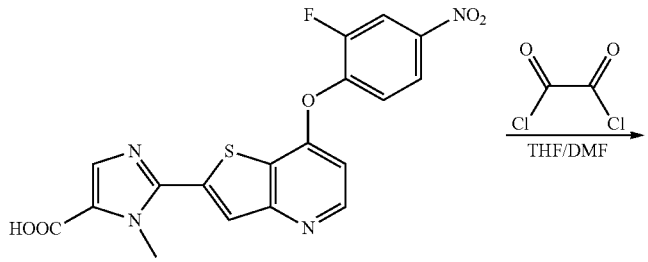

214

-continued

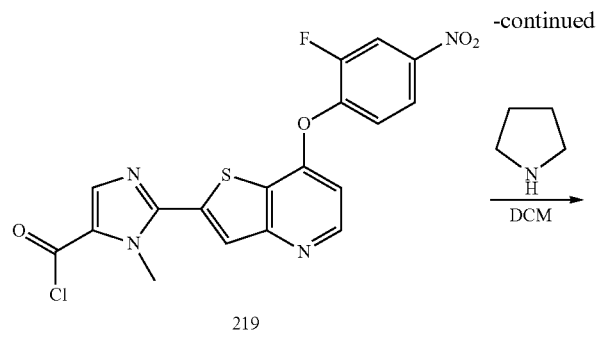
219
220

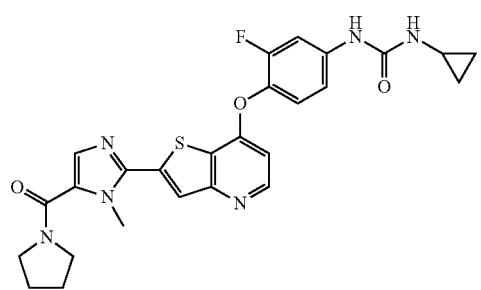
222: Example 124

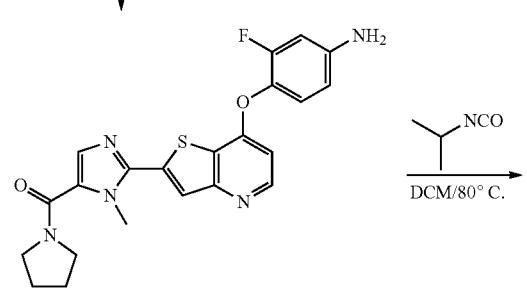
221

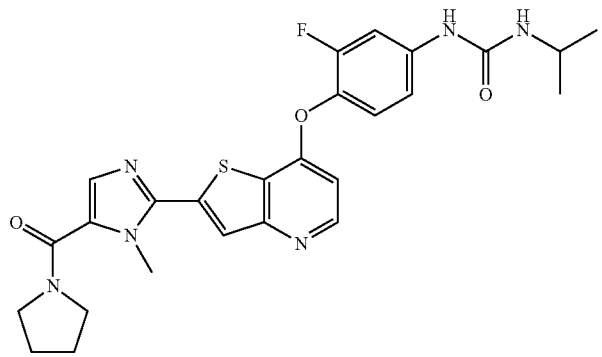
223: Example 125

Example 124

1-cyclopropyl-3-(3-fluoro-4-(2-(1-methyl-5-(pyrrolidine-1-carbonyl)-1H-imidazol-2-yl)thieno[3,2-b]pyridin-7-yloxy)phenyl)urea (222)

Step 1: 2-(7-(2-fluoro-4-nitrophenoxy)thieno[3,2-b]pyridin-2-yl)-1-methyl-1H-imidazole-5-carbonyl chloride (219)

To a pre-cooled solution of acid 214 (1.25 g, 3.02 mmol, scheme 52) in THF (12.07 mL) was added DMF (0.023 mL, 0.302 mmol) and oxalyl chloride (0.660 mL, 7.54 mmol) and the resultant solution was stirred at 0° C. for 30 min. The solvent was evaporated, the residue was triturated with ether and dried under high vacuum to give title compound 219 (1.306 g, 3.02 mmol, 100% yield) as a beige solid. MS: 429.2 (MH+, COOMe), 433.1 (COCl, MH+).

Step 2: (2-(7-(2-fluoro-4-nitrophenoxy)thieno[3,2-b]pyridin-2-yl)-1-methyl-1H-imidazol-5-yl)(pyrrolidin-1-yl)methanone (220)

A suspension of the acyl chloride 219 (700 mg, 1.617 mmol) and pyrrolidine (0.3 mL, 3.63 mmol) in DCM (50 mL) was stirred at room temperature overnight. The reaction mixture was concentrated. The residue was triturated with ether to give title compound 220 (756 mg, 1.617 mmol, 100% yield) as beige solid. MS: 468.3 (MH+).

Step 3: (2-(7-(4-amino-2-fluorophenoxy)thieno[3,2-b]pyridin-2-yl)-1-methyl-1H-imidazol-5-yl)(pyrrolidin-1-yl)methanone (221)

Title compound 221 was obtained starting from the compound 220 and following a procedure similar to the one used in the synthesis of compound 207 (scheme 50). MS: 438.4 (MH+).

Step 4: 1-cyclopropyl-3-(3-fluoro-4-(2-(1-methyl-5-(pyrrolidine-1-carbonyl)-1H-imidazol-2-yl)thieno[3,2-b]pyridin-7-yloxy)phenyl)urea (222)

Title compound 222 was obtained starting from the compound 221 and following a procedure similar to the one used in the synthesis of compound 208 (scheme 50). $^1$H NMR (400 MHz, DMSO-$d_6$) δ (ppm): 8.76 (s, 1H), 8.59 (d, 1H, J=5.3 Hz), 8.06 (s, 1H), 7.76 (dd, 1H, J1=2.1 Hz, J2=13.5 Hz), 7.59 (s, 1H), 7.42 (t, 1H, J=9.0 Hz), 7.24-7.22 (m, 1H), 6.74 (d, 1H, J=5.5 Hz), 6.60 (s, 1H), 4.07 (s, 3H), 3.72-3.69 (m, 4H), 2.60-2.58 (m, 1H), 1.93-1.90 (m, 4H), 0.70-0.67 (m, 2H), 0.47-0.45 (m, 2H). MS: 521.5 (MH)+

Example 125

1-(3-fluoro-4-(2-(1-methyl-5-(pyrrolidine-1-carbonyl)-1H-imidazol-2-yl)thieno[3,2-b]pyridin-7-yloxy)phenyl)-3-isopropylurea (223)

Title compound 223 was obtained starting from the compound 221 and following a procedure similar to the one used in the synthesis of compound 201 (scheme 48). $^1$H NMR (400 MHz, DMSO-$d_6$) δ (ppm): 8.74 (s, 1H), 8.58 (d, 1H, J=5.5 Hz), 8.06 (s, 1H), 7.73 (dd, 1H, J1=2.1 Hz, J2=13.5 Hz), 7.5 (s, 1H), 7.41 (t, 1H, J=9.0 Hz), 7.18-7.16 (m, 2H), 6.74 (d, 1H, J=5.4 Hz), 6.19 (d, 1H, J=7.6 Hz), 4.07 (s, 3H), 3.83-3.78 (m, 1H), 3.70-3.68 (m, 4H), 1.91 (m, 4H), 1.15 (s, 3H), 1.13 (s, 3H). MS: 523.2 (MH)+

Example 126

2-(7-(4-(3-cyclopropylureido)-2-fluorophenoxy)thieno[3,2-b]pyridin-2-yl)-1-ethyl-N-(3-morpholinopropyl)-1H-imidazole-5-carboxamide (224)

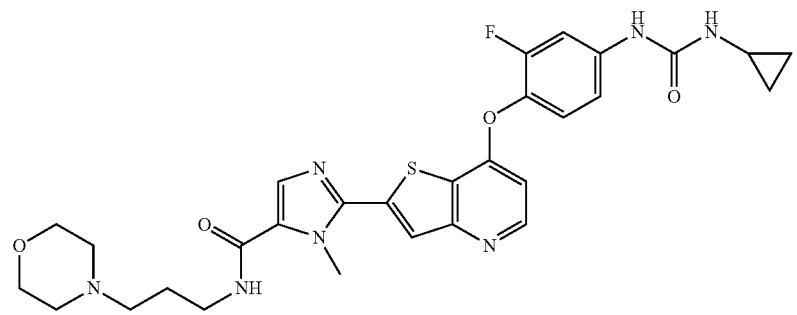

224: Example 126

Title compound 224 was obtained in three steps starting from the acyl chloride 219, similarly to compound 222 (example 123, scheme 53). $^1$H NMR (400 MHz, DMSO-$d_6$) δ (ppm): 8.75 (s, 1H), 8.59 (d, 1H, J=5.3 Hz), 8.53 (m, 1H), 8.07 (s, 1H), 7.76 (dd, 1H, J1=2.3 Hz, J2=13.5 Hz), 7.71 (s, 1H), 7.42 (t, 1H, J=9.0 Hz), 7.25-7.23 (m, 1H), 6.74 (d, 1H, J=5.3 Hz), 6.62-6.61 (m, 1H), 4.22 (s, 3H), 3.62-3.60 (m, 4H), 3.31-3.28 (m, 2H), 2.59-2.58 (m, 1H), 2.38-2.34 (m, 6H), 1.73-1.70 (m, 2H), 0.70-0.68 (m, 2H), 0.48-0.46 (m, 2H). MS: 594.6 (MH)+

Scheme 54

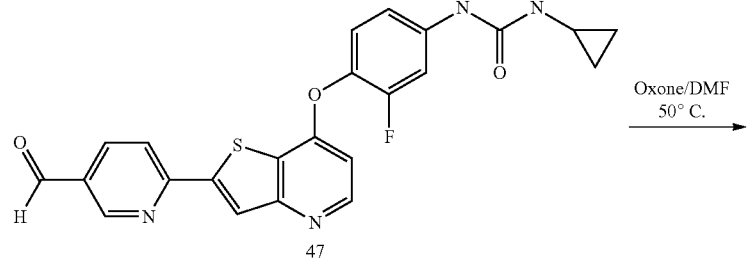

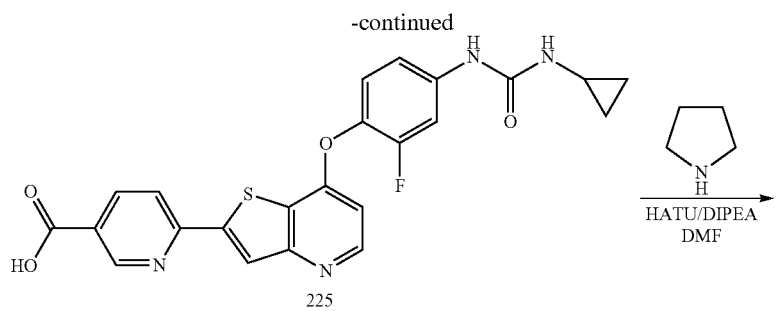

225

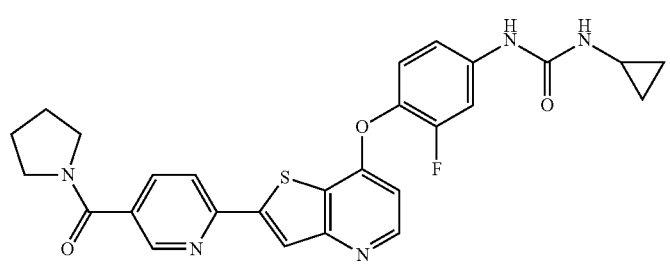 [SMILES: CN(C)[C@@H]1CCN(C(=O)c2ccc(-c3cc4nccc(Oc5ccc(NC(=O)NC6CC6)cc5F)c4s3)nc2)C1]

226: Example 127

Example 127

1-cyclopropyl-3-(3-fluoro-4-(2-(5-(pyrrolidine-1-carbonyl)pyridin-2-yl)thieno[3,2-b]pyridin-7-yloxy)phenyl)urea (226)

Step 1: 6-(7-(4-(3-Cyclopropylureido)-2-fluorophenoxy)thieno[3,2-b]pyridin-2-yl)nicotinic acid (225)

To a suspension of aldehyde 47 (200 mg, 0.446 mmol, scheme 15) in DMF (10 mL) was added Oxone® (330 mg, 0.535 mmol) at RT and the reaction mixture was stirred at 50° C. for 16 hours. The reaction mixture was cooled to 0° C., treated with 1N aqueous HCl (20 mL) and stirred at RT for an additional hour. The resultant precipitate was collected by filtration, washed with water (30 mL) and dried. The crude product was triturated with MeOH to afford title compound 225 (165 mg, 80% yield) as a beige solid. NMR (400 MHz, CD$_3$OD) δ (ppm): 9.66 (bs, 1H), 8.98 (dd, J=1.9, 0.9 Hz, 1H), 8.51 (d, J=5.5 Hz, 1H), 8.31 (s, 1H), 8.22 (dd, J=8.1, 1.9 Hz, 1H), 8.17 (dd, J=8.1, 0.9 Hz, 1H), 7.77 (dd, J=13.7, 2.5 Hz, 1H), 7.45 (bs, 1H), 7.37 (t, J=9.1 Hz, 1H), 7.26 (dd, J=8.9, 1.5 Hz, 1H), 6.62 (d, J=5.3, 0.8 Hz, 1H), 2.60-2.52 (m, 1H), 0.69-0.56 (m, 2H), 0.50-0.37 (m, 2H). [Carboxylic OH is not seen]. MS: 465.3 (MH)$^+$.

Step 2. 1-cyclopropyl-3-(3-fluoro-4-(2-(5-(pyrrolidine-1-carbonyl)pyridin-2-yl)thieno[3,2-b]pyridin-7-yloxy)phenyl)urea (226)

To a solution of acid 225 (70 mg, 0.151 mmol), DIPEA (0.105 mL, 0.603 mmol) and pyrrolidine (0.025 mL, 0.301 mmol) in DMF (4 mL) was added HATU reagent (143 mg, 0.377 mmol). The mixture was stirred for 16 h at RT then partitioned between ethyl acetate and water. The organic phase was collected, washed with water, 1M NaOH, and brine, dried over anhydrous MgSO$_4$, filtered and concentrated. The residue was purified by Biotage (MeOH/DCM, 0-15%, SNAP 10 g cartridge), then using chromatotron (eluent MeOH/DCM, 5-10%) followed by trituration with a mixture Et$_2$O/MeOH/Acetone to give title compound 226 (15 mg, 0.029 mmol, 19% yield) $^1$H NMR (400 MHz, DMSO-d$_6$) δ (ppm): OH from carboxylic acid is missing, 9.66 (bs, 1H), 8.98 (dd, J=1.9, 0.9 Hz, 114), 8.51 (d, J=5.5 Hz, 1H), 8.31 (s, 1H), 8.22 (dd, J=8.1, 1.9 Hz, 1H), 8.17 (dd, J=8.1, 0.9 Hz, 1H), 7.77 (dd, J=13.7, 2.5 Hz, 1H), 7.45 (bs, 1H), 7.37 (t, J=9.1 Hz, 1H), 7.26 (dd, J=8.9, 1.5 Hz, 1H), 6.62 (d, J=5.3, 0.8 Hz, 1H), 2.60-2.52 (m, 1H), 0.69-0.56 (m, 2H), 0.50-0.37 (m, 2H). MS (m/z): 465.3 (M+H)

Compounds 227-233 and 235-238 (examples 128-134 and 136-139) were prepared in one step starting from the acid 225 similarly to compound 226 (example 127, scheme 54). Compounds 239-241 (examples 140-142) were obtained by alkaline hydrolysis of compounds 236-238, respectfully similarly to compound 61 (example 44, scheme 16).

TABLE 18

Characterization of compounds 227-241 (examples 128-142)

| Cpd | Ex | Structure | Characterization |
|---|---|---|---|
| 227 | 128 | (R)-1-cyclopropyl-3-(4-(2-(5-(3-(dimethylamino)pyrrolidine-1-carbonyl)pyridin-2-yl)thieno[3,2-b]pyridin-7-yloxy)-3-fluorophenyl)urea | $^1$H NMR (400 MHz, DMSO-$d_6$) δ (ppm): 8.82 (dd, 1H, J1 = 1.5 Hz, J2 = 5.3 Hz), 8.74(s, 1H), 8.59(dd, 1H, J = 5.4 Hz), 8.50(s, 1H), 8.39(d, 1H, J = 8.1Hz), 8.16-8.12(m, 1H), 7.77(dd, 1H, J1 = 2.3 Hz, J2 = 13.5 Hz), 7.42(t, 1H, J = 9.1 Hz), 7.25-7.23(m, 1H), 6.72(d, 1H, J = 5.5 Hz), 6.61(d, 1H, J = 2.5 Hz), 3.82-3.77 (m, 0.5Hz), 3.69-3.59(m, 2H), 3.56-3.46 (m, 0.5H), 3.32-3.25(m, 1H), 2.84-2.70 (m, 1H), 2.60-2.54(m, 1H), 2.36(s, 3H), 2.16(s, 3H), 2.19-2.07(m, 1H), 0.71-0.68(m, 2H), 0.49-0.45(m, 2H). MS: 561.6(MH)+ |
| 228 | 129 | 1-cyclopropyl-3-(3-fluoro-4-(2-(5-(4-methylpiperazine-1-carbonyl)pyridin-2-yl)thieno[3,2-b]pyridin-7-yloxy)phenyl)urea | $^1$H NMR (400 MHz, DMSO-$d_6$) δ (ppm): 8.75(s, 1H), 8.71-8.70(m, 1H), 8.58(d, 1H, J = 5.5 Hz), 8.49(s, 1H), 8.40(dd, 1H, J1 = 0.8 Hz, J2 = 8.2 Hz), 8.03(dd, 1H, J1 = 2.2 Hz, J2 = 8.2 Hz), 7.77(dd, 1H, J1 = 2.6 Hz, J2 = 13.7 Hz), 7.42(t, 1H, J = 9.0 Hz), 7.25-7.23(m, 1H), 6.71(d, 1H, J = 5.3 Hz), 6.61(m, 1H), 3.69(s, br, 2H), 3.45-3.42(m, 2H), 2.61-2.58(m, 1H), 2.42-2.35(m, 4H), 2.24(s, 3H), 0.71-0.61 (m, 2H), 0.48-0.45(m, 2H). MS: 547 (MH)+ |
| 229 | 130 | 6-(7-(4-(3-cyclopropylureido)-2-fluorophenoxy)thieno[3,2-b]pyridin-2-yl)-N-(2,5,8,11-tetraoxatridecan-13-yl)nicotinamide | $^1$H NMR (400 MHz, DMSO-$d_6$) δ (ppm): 9.08 (dd, 1H, J = 2.1 Hz), 8.86 (t, 1H, J = 5.7 Hz), 8.74 (s, 1H), 8.58 (d, 1H, J = 5.2 Hz), 8.51 (s, 1H), 8.44 (d, 1H, J = 8.2 Hz), 8.37 (dd, 1H, J1 = 2.2 Hz, J2 = 8.8 Hz), 7.77 (dd, 1H, J1 = 2.6 Hz, J2 = 13.7 Hz), 7.42 (t, J = 9.0 Hz), 7.25-7.23 (m, 1H), 6.71 (d, 1H, J = 5.3 Hz), 6.61-6.60 (m, 1H), 3.62-3.54 (m, 6H), 3.54-3.49 (m, 8H), 3.44-3.42 (m, 2H), 3.25 (s, 3H), 2.60-2.58 (m, 1H), 0.70-0.68 (m, 2H), 0.47-0.46 (m, 2H). MS: 654.3(MH)+ |

TABLE 18-continued

Characterization of compounds 227-241 (examples 128-142)

| Cpd | Ex | Structure | Characterization |
|---|---|---|---|
| 230 | 131 | 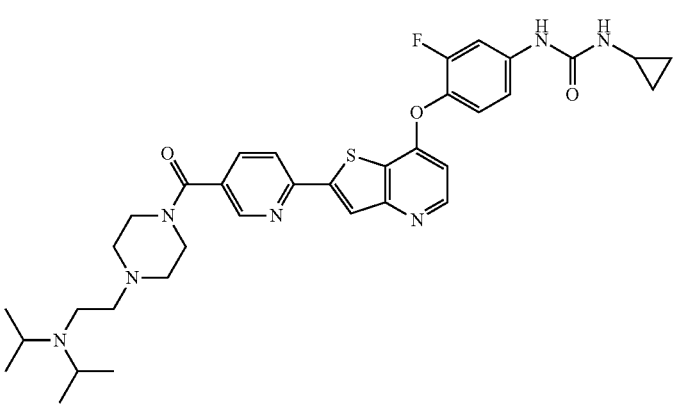 [SMILES: CC(C)N(CCN1CCN(C(=O)c2ccc(-c3cc4nccc(Oc5ccc(NC(=O)NC6CC6)cc5F)c4s3)nc2)CC1)C(C)C]<br>1-cyclopropyl-3-(4-(2-(5-(4-(2-(diisopropylamino)ethyl)piperazine-1-carbonyl)pyridin-2-yl)thieno[3,2-b]pyridin-7-yloxy)-3-fluorophenyl)urea | $^1$H NMR (400 MHz, DMSO-d$_6$) δ (ppm): 8.80(s, 1H), 8.71(dd, 1H, J1 = 0.8 Hz, J2 = 2.2 Hz), 8.58(d, 1H, J = 5.5 Hz), 8.49(s, 1H), 8.39(dd, 1H, J1 = 0.8 Hz, J2 = 8.2 Hz), 8.02(dd, 1H, J1 = 2.1 Hz, J2 = 8.2 Hz), 7.77(dd, 1H, J1 = 2.6 Hz, J2 = 13.7 Hz), 7.42(t, 1H, J = 9.0 Hz), 7.60-7.23(m, 1H), 6.72(d, 1H, J = 4.7 Hz), 6.65-6.64(m, 1H), 3.67(s, br, 1H), 3.43-3.41(m, 2H), 3.00-2.97(m, 2H), 2.60-2.57(m, 1H), 2.57-2.54(m, 2H), 2.49-2.45(m, 2H), 2.37-2.33(m, 2H), 1.00-0.98 (m, 12H), 0.71-0.68 (m, 2H), 0.49-0.47 (m, 2H). MS: 660.7 (MH)+ |
| 231 | 132 | 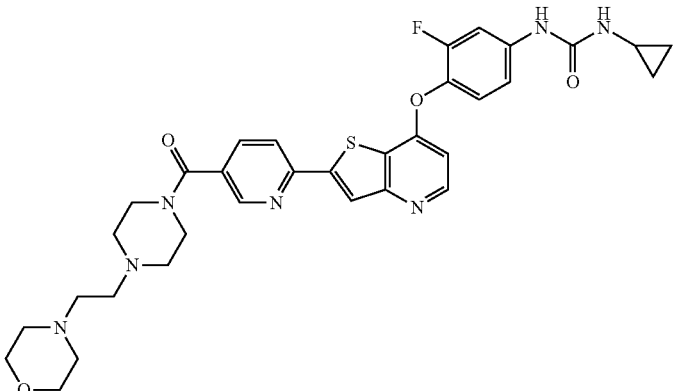<br>1-cyclopropyl-3-(3-fluoro-4-(2-(5-(4-(2-morpholinoethyl)piperazine-1-carbonyl)pyridin-2-yl)thieno[3,2-b]pyridin-7-yloxy)phenyl)urea | $^1$H NMR (400 MHz, DMSO-d$_6$) δ (ppm): 8.82(s, 1H), 8.71(dd, 1H, J1 = 0.8 Hz, J2 = 2.2 Hz), 8.58(d, 1H, J = 5.5 Hz), 8.49(s, 1H), 8.40(dd, 1H, J1 = 0.8 Hz, J2 = 8.2 Hz), 8.02(dd, 1H, J1 = 2.1 Hz, J2 = 8.2 Hz), 7.77(dd, 1H, J1 = 2.4 Hz, J2 = 13.5 Hz), 7.42(t, 1H, J = 9.0 Hz), 7.26-7.23(m, 1H), 6.72(d, 1H, J = 5.3 Hz), 6.68(s, br, 1H), 3.67(d, br, 2H), 3.58(t, 5H, J = 4.5 Hz), 3.44-3.39(m, 3H), 2.60-2.56(m, 1H), 2.53-2.41(m, 10H), 0.71-0.67(m, 2H), 0.49-0.45(m, 2H). MS: 646.6(MH)+ |
| 232 | 133 | 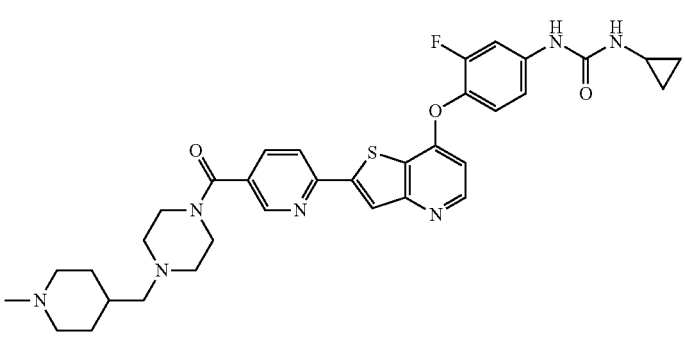 [SMILES: CN1CCC(CN2CCN(C(=O)c3ccc(-c4cc5nccc(Oc6ccc(NC(=O)NC7CC7)cc6F)c5s4)nc3)CC2)CC1]<br>1-cyclopropyl-3-(3-fluoro-4-(2-(5-(4-((1-methylpiperidin-4-yl)methyl)piperazine-1-carbonyl)pyridin-2-yl)thieno[3,2-b]pyridin-7-yloxy)phenyl)urea | $^1$H NMR (400 MHz, DMSO-d$_6$) δ (ppm): 8.76(s, 1H), 8.71(m, 1H), 8.58(d, 1H, J = 5.3 Hz), 8.49(s, 1H), 8.39(d, 1H, J = 8.0 Hz), 8.02(dd, 1H, J1 = 2.1 Hz, J2 = 8.2 Hz), 7.77(dd, 1H, J1 = 2.4 Hz, J2 = 13.5 Hz), 7.42(t, 1H, J = 9.0 Hz), 7.25-7.23(m, 1H), 6.71 (d, 1H, J = 5.2 Hz), 6.63-6.62(m, 1H), 3.68(s, br, 2H), 3.44-3.39(m, 1H), 2.76-2.74(m, 2H), 2.61-2.57(m, 1H), 2.44-2.37(m, 4H), 2.19-2.15(m, 5H), 1.83(t, 2H, J = 10.6 Hz), 1.70-1.67(m, 2H), 1.49-1.44(m, 1H), 1.17-1.10(m, 3H), 0.71-0.67(m, 2H), 0.48-0.45(m, 2H). MS: 644.7 (MH)+ |

TABLE 18-continued

Characterization of compounds 227-241 (examples 128-142)

| Cpd | Ex | Structure | Characterization |
|---|---|---|---|
| 233 | 134 | 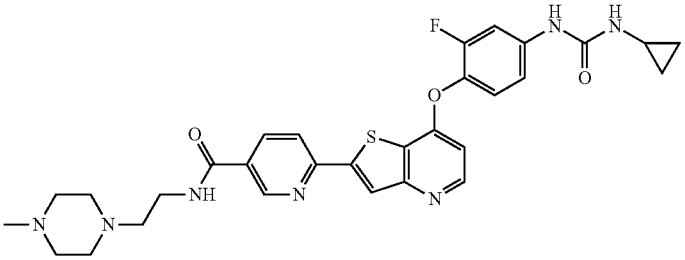 [SMILES: CN1CCN(CCNC(=O)c2ccc(-c3cc4nccc(Oc5ccc(NC(=O)NC6CC6)cc5F)c4s3)nc2)CC1]<br>6-(7-(4-(3-cyclopropylureido)-2-fluorophenoxy)thieno[3,2-b]pyridin-2-yl)-N-(2-(4-methylpiperazin-1-yl)ethyl)nicotinamide formate salt | $^1$H NMR (400 MHz, DMSO-d$_6$) δ (ppm): 9.07(dd, 1H, J = 1.6 Hz), 8.94(s, 1H), 8.73(t, 1H, J = 5.4 Hz), 8.58(d, 1H, J = 5.5 Hz), 8.51(s, 1H), 8.43(d, 1H, J = 8.4 Hz), 8.35(dd, 1H, J1 = 2.1 Hz, J2 = 8.4 Hz), 8.22(s, 1H), 7.78(dd, 1H, J1 = 2.4 Hz, J2 = 13.7 Hz), 7.42(t, 1H, J = 9.0 Hz), 7.25(d, 1H, J = 8.8 Hz), 6.75 (d, 1H, J = 2.4 Hz), 6.71(d, 1H, J = 5.3 Hz), 3.48-3.43(m, 2H), 2.62-2.59(m, 1H), 2.81-2.53(m, 10H), 2.29(s, 3H), 0.71-0.66(m, 2H), 0.48-0.44(m, 2H). MS 590.6 (MH)+ |
| 235 | 136 | 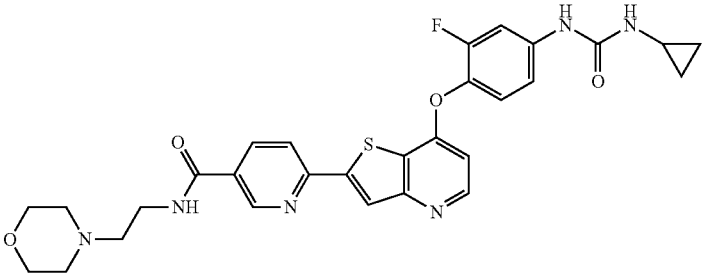 [SMILES: O=C(Nc1ccc(Oc2ccnc3cc(-c4ccc(C(=O)NCCN5CCOCC5)cn4)sc23)c(F)c1)NC1CC1]<br>6-(7-(4-(3-cyclopropylureido)-2-fluorophenoxy)thieno[3,2-b]pyridin-yl)-N-(2-morpholinoethyl)nicotinamide | $^1$H NMR (400 MHz, DMSO-d$_6$) δ (ppm): 9.07-9.06 (m, 1H), 8.75-8.74 (m, 2H), 8.59 (dd, 1H, J = 5.4 Hz), 8.51 (s, 1H), 8.44 (dd, 1H, J = 8.2 Hz), 8.35 (dd, 1H, J1 = 2.21 Hz, J2 = 8.4 Hz), 7.77 (dd, 1H, J1 = 2.4 Hz, J2 = 13.7 Hz), 7.42 (t, 1H, J = 9.1 Hz), 7.25-7.23 (m, 1H), 6.71 (d, 1H, J = 5.3 Hz), 6.62 (m, 1H), 3.62 (m, 4H), 3.49-3.45 (m, 2H), 2.61-2.53 (m, 1H), 2.47 (m, 4H), 0.71-0.67 (m, 2H), 0.47-0.45 (m, 2H). MS: 577.5 (MH)+ |
| 236 | 137 | 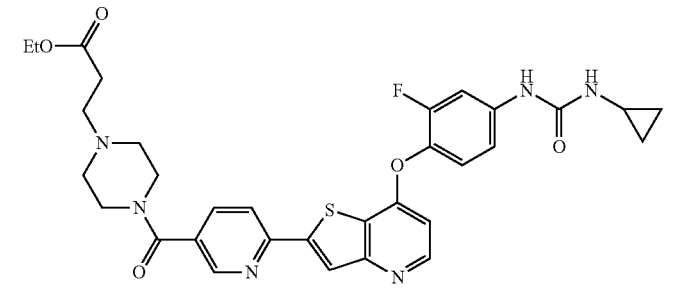 [SMILES: CCOC(=O)CCN1CCN(C(=O)c2ccc(-c3cc4nccc(Oc5ccc(NC(=O)NC6CC6)cc5F)c4s3)nc2)CC1]<br>ethyl 3-(4-(6-(7-(4-(3-cyclopropylureido)-2-fluorophenoxy)thieno-[3,2-b]pyridin-2-yl)nicotinoyl)piperazin-1-yl)propanoate | $^1$H NMR (400 MHz, DMSO-d$_6$) δ (ppm): 8.73 (m, 2H), 8.58 (d, 1H, J = 5.4 Hz), 8.49 (s, 1H), 8.40 (d, 1H, J = 8.2 Hz), 8.03 (dd, 1H, J1 = 2.0 Hz, J2 = 8.2 Hz), 7.77 (dd, 1H, J1 = 2.5 Hz, J2 = 13.5 Hz), 7.42 (t, 1H, J = 9.0 Hz), 7.25-7.23 (m, 1H), 6.72 (d, 1H, J = 5.3 Hz), 6.61-6.60 (m, 1H), 4.10 (q, 2H), 3.66 (m, br, 2H), 3.42-3.39 (m, 2H), 2.67-2.63 (m, 3H), 2.61-2.57 (m, 2H), 2.51-2.49 (m, 3H), 2.43 (m, br, 2H), 1.22 (t, 3H), 0.71-0.68 (m, 2H), 0.48-0.46 (m, 2H). MS: 633.6 (MH)+ |
| 237 | 138 | 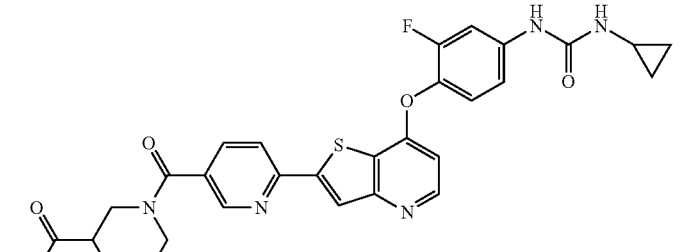<br>ethyl 1-(6-(7-(4-(3-cyclopropylureido)-2-fluorophenoxy)thieno-[3,2-b]pyridin-2-yl)nicotinoyl)piperidine-3-carboxylate | $^1$H NMR (400 MHz, DMSO-d$_6$) δ (ppm): 8.74(s, 1H), 8.71(s, 1H), 8.58(d, 1H, J = 5.5 Hz), 8.49(s, 1H), 8.40(d, 1H, J = 8.2 Hz), 8.03(s, br, 1H), 7.77(dd, 1H, J1 = 2.4 Hz, J2 = 13.5 Hz), 7.43(t, 1H, J = 9.0 Hz), 7.25-7.23(m, 1H), 6.72(d, 1H, J = 5.4 Hz), 6.61-6.60(m, 1H), 4.50-4.48(m, 0.5 Hz), 4.19-4.00(m, 2H), 3.98-3.94(m, 0.5 Hz), 3.68-3.66(m, 0.5 Hz), 3.50-3.48(m, 0.5 Hz), 3.22-3.16(m, 1H), 2.72-2.68(m, 1H), 2.62-2.57(m, 1H), 2.06-2.00(m, 1H), 1.72-1.64(m, 2H), 1.64-1.56(m, 1H), 1.27-1.23(m, 1.5H), 1.20-1.11(m, 1.5H), 0.71-0.67(m, 2H), 0.48-0.45(m, 2H). MS: 604.5 (MH)+ |

TABLE 18-continued

Characterization of compounds 227-241 (examples 128-142)

| Cpd | Ex | Structure | Characterization |
|---|---|---|---|
| 238 | 139 | butyl 4-(6-(7-(4-(3-cyclopropylureido)-2-fluorophenoxy)thieno[3,2-b]pyridin-2-yl)nicotinoyl)morpholine-2-carboxylate | $^1$H NMR (400 MHz, DMSO-$d_6$) δ (ppm): 8.79(s, 1H), 8.74(s, 1H), 8.59(d, 1H, J = 5.3 Hz), 8.51(s, 1H), 8.43(d, 1H, J = 8.2 Hz), 8.08-8.04(m, 1H), 7.77(dd, 1H, J1 = 2.4 Hz, J2 = 13.7 Hz), 7.42(t, 1H, J = 9.0 Hz), 7.26-7.23(m, 1H), 6.72(d, 1H, J = 5.3 Hz), 6.65-6.64(m, 1H), 4.42-4.35(m, 1.5 Hz), 4.22-4.00(m, 2H), 3.96-3.82(m, 1.5H), 3.78-3.44(m, 4H), 2.62-2.56(m, 1H), 1.69-1.44(m, 2H), 1.44-1.18(m, 2H), 0.98-0.78(m, 2H), 0.71-0.64(m, 2H), 0.48-0.44(m, 2H). MS: 634.5(MH)+ |
| 239 | 140 | 3-(4-(6-(7-(4-(3-cyclopropylureido)-2-fluorophenoxy)thieno[3,2-b]pyridin-2-yl)nicotinoyl)piperazin-1-yl)propanoic acid tetraacetate | $^1$H NMR (400 MHz, DMSO-$d_6$) δ (ppm): one OH carboxylic acid is missing, 9.14 (bs, 1H), 8.67 (dd, J = 2.2, 0.8 Hz, 1H), 8.54 (d, J = 5.5 Hz, 1H), 8.45 (s, 1H), 8.36 (d, J = 8.2 Hz, 1H), 7.99 (dd, 8.2, 2.2 Hz, 1H), 7.74 (dd, J = 13.6, 2.4 Hz, 1H), 7.38 (t, J = 9.1 Hz, 1H), 7.22 (bd, J = 8.8 Hz, 1H), 6.97 (bs, 1H), 6.68 (bd, J = 5.5 Hz, 1H), 3.74-3.55 (m, 2H), 2H are hidden by water's peak, 2.66-2.30 (m, 9H), 0.70-0.57 (m, 2H), 0.49-0.36 (m, 2H). MS (m/z): 605.4 (M + H). |
| 240 | 141 | 1-(6-(7-(4-(3-cyclopropylureido)-2-fluorophenoxy)thieno[3,2-b]-pyridin-2-yl)nicotinoyl)piperidine-3-carboxylic acid | $^1$H NMR (400 MHz, DMSO-$d_6$) δ (ppm): 9.28-9.07(m, 1H), 8.71 (s, 1H), 8.60-8.54(m, 1H), 8.48(s, 1H), 8.39(d, 1H, J = 8.4H), 8.06-8.00(m, 1H), 7.77(d, 1H, J = 5.4 Hz), 7.40(t, 1H, J = 9.0 Hz), 7.26-7.20(m, 1H), 7.05-6.85(m, 1H), 6.69(s, 1H), 4.59-4.51(m, 0.4H), 4.08-3.99(m, 0.6 Hz), 3.70-3.62(m, 1H), 3.58-3.51(m, 1H), 3.08-2.98(m, 1H), 2.61-2.57(m, 1H), 2.10-1.97(m, 1H), 1.78-1.64(m, 2H), 1.64-1.52(m, 1H), 1.39-1.27(m, 1H), 0.68-0.67(m, 2H), 0.48-0.44(m, 2H). MS: 576.4 (MH)+ |
| 241 | 142 | 4-(6-(7-(4-(3-cyclopropylureido)-2-fluorophenoxy)thieno[3,2-b]-pyridin-2-yl)nicotinoyl)morpholine-2-carboxylic acid | $^1$H NMR (400 MHz, DMSO-$d_6$) δ (ppm): 9.10-8.98(m, 1H), 8.76(s, 1H), 8.60-8.52(m, 1H), 8.49(s, 1H), 8.41(d, 1H, J = 8.2 Hz), 8.10-8.03(m, 1H), 7.77(d, 1H, J = 5.4 Hz), 7.40(t, 1H, J = 9.0 Hz), 7.26-7.20(m, 1H), 7.05-6.82(m, 1H), 6.69(s, 1H), 4.55-4.40(m, 0.7H), 4.20-4.12(m, 1.3 Hz), 4.00-3.84(m, 2H), 3.70-3.60(m, 2H), 3.60-3.50(m, 1H), 2.61-2.57(m, 1H), 0.68-0.67(m, 2H), 0.48-0.44(m, 2H). MS: 578.1 (MH)+ |

Scheme 55

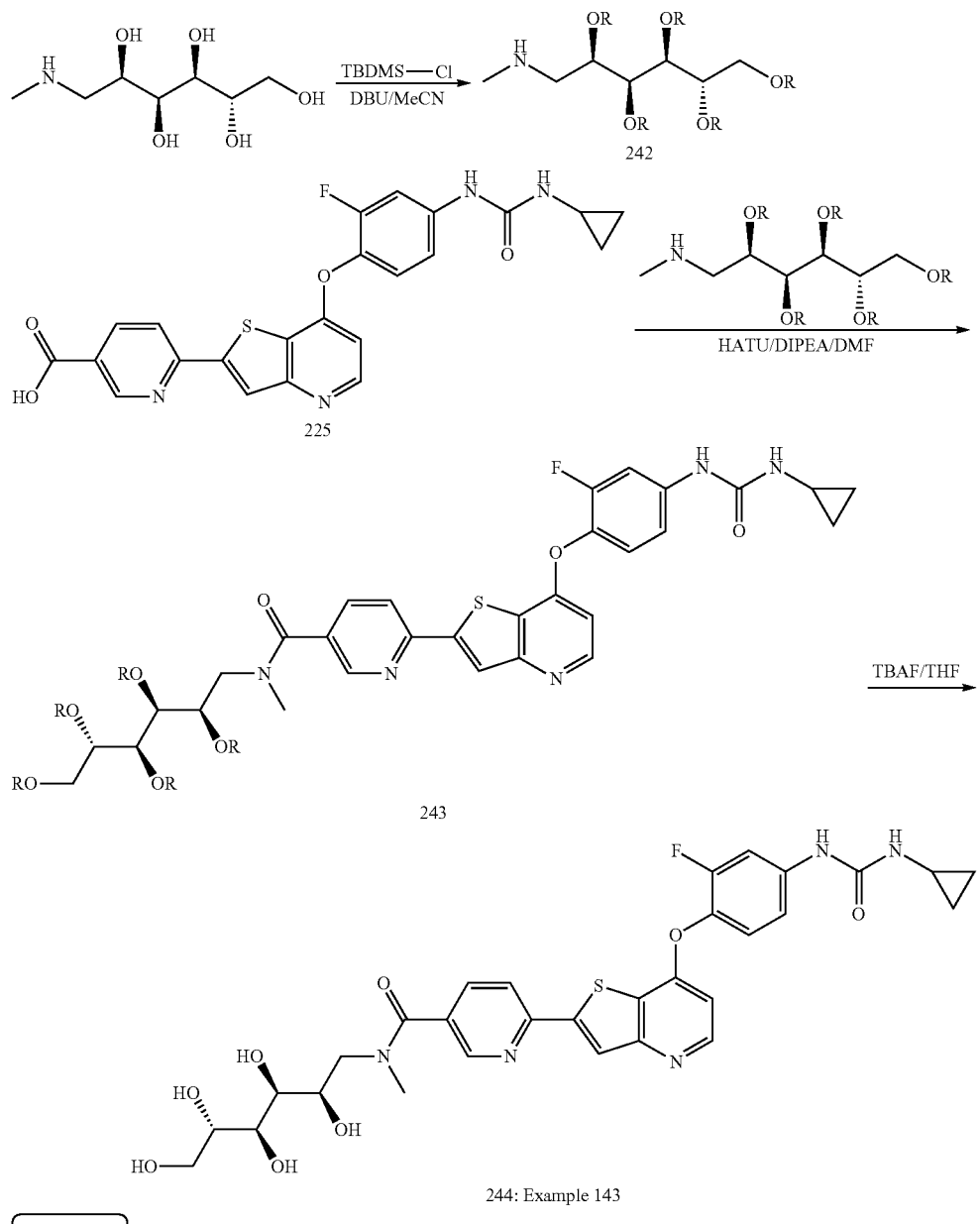

244: Example 143

R = H, TBDMS

Example 143

6-(7-(4-(3-cyclopropylureido)-2-fluorophenoxy) thieno[3,2-b]pyridin-2-yl)-N-methyl-N-((2R,3S,4S, 5S)-2,3,4,5,6-pentahydroxyhexyl)nicotinamide (244)

Step 1: (2R,3S,4S,5S)-2,3,4,5,6-pentakis(tert-butyldimethylsilyloxy)-N-methylhexan-1-amine (242)

To a solution of N-methyl-D-glucamine (0.5 g, 2.56 mmol) in acetonitrile (25.6 mL) at 0° C. was added TBDMSCl (1.930 g, 12.81 mmol) and DBU (1.930 mL, 12.81 mmol). The reaction mixture was stirred for 20 min at 0° C. before it was warmed up to room temperature then stirred overnight. MS showed a mixture of tri- and tetra-TBDMS protected compounds. The reaction mixture was concentrated and the residue was partitioned between EtOAc/H₂O, the organic phase was collected, washed with water, 1N HCl solution and brine, dried and concentrated to give title compound 242 (1.53 g, 2.346 mmol, 92% yield) as a yellowish syrup that was used as is. MS: 538.6, 652.7.

Step 2: 6-(7-(4-(3-cyclopropylureido)-2-fluorophenoxy)thieno[3,2-b]pyridin-2-yl)-N-methyl-N-((2R, 3S,4S,5S)-2,3,4,5,6-pentakis(tert-butyldimethyl silyloxy)hexyl)nicotinamide (243)

To a solution of acid 225 (220 mg, 0.474 mmol, scheme 54), amine 242 (309 mg, 0.474 mmol) and DIPEA (0.331 mL, 1.895 mmol) in DMF (5 mL) was added HATU reagent (270 mg, 0.710 mmol). The mixture was stirred overnight at room temperature then partitioned between ethyl acetate and water. The organic layer was collected, washed with water, 1M NaOH, and brine, dried over anhydrous MgSO₄, filtered and concentrated. The residue was purified by Biotage (MeOH/

8.00 (m, 1H), 7.65 (dd, 1H, J1=2.5 Hz, J2=13.1 Hz), 7.29 (t, 1H, J=8.81 Hz), 7.20-7.17 (m, 1H), 6.64 (d, 1H, J=5.3 Hz), 4.20-4.18 (m, 0.45H), 4.07-4.04 (m, 0.55H), 3.83-3.53 (m, 7H), 3.17 (s, 3H), 2.62-2.57 (m, 1H), 0.78-0.73 (m, 2H), 0.54-0.50 (m, 2H). MS: 642.6 (MH+).

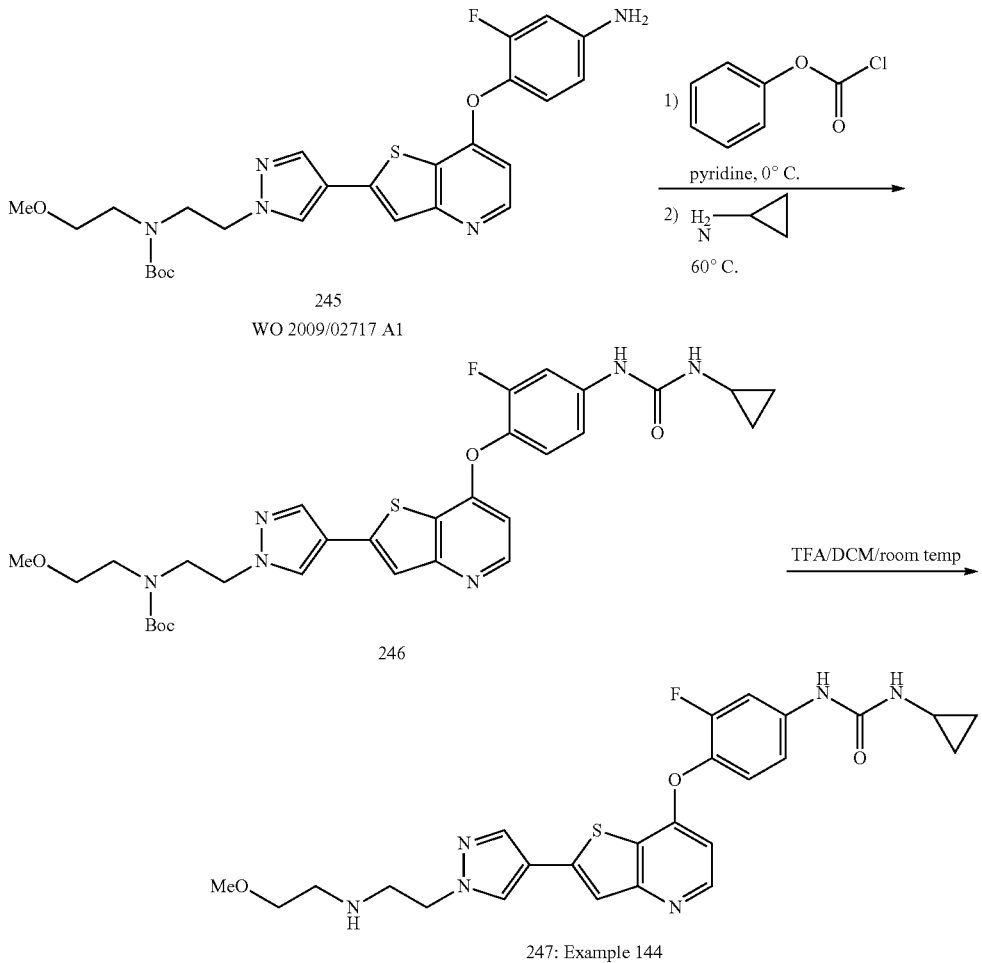

DCM, 0-15%, SNAP 10 g cartridge) to afford title compound 243 (250 mg, 0.254 mmol, 54% yield) as a white solid. MS: 985.4 (MH+).

Step 3: 6-(7-(4-(3-cyclopropylureido)-2-fluorophenoxy)thieno[3,2-b]pyridin-2-yl)-N-methyl-N-((2R,3S,4S,5S)-2,3,4,5,6-pentahydroxyhexyl)nicotinamide (244)

To a solution of 243 (250 mg, 0.228 mmol) in THF (5 mL) was added TBAF (1.0M in THF) (0.273 mL, 0.273 mmol) and the reaction mixture was stirred for 2 hr at RT before concentration. The residue was purified by Biotage, (MeOH/DCM, 20-50%, SNAP 25 g cartridge) and Gilson (Phenomenex, Luna, 15µ, C18(2) 100A, 250×50.00 mm, 15 µm, 0.05% of formic acid in both MeOH/H₂O, 40-90%, flow=30 mL/min), to afford title compound 244 (10 mg, 0.016 mmol, 7% yield) as a white solid. ¹H NMR (400 MHz, CD₃OD) δ (ppm): 8.72 (d, 1H, J=3.9 Hz), 8.47 (s, br, 1H), 8.19-8.13 (m, 2H), 8.13-

Example 144

1-cyclopropyl-3-(3-fluoro-4-(2-(1-(2-(2-methoxyethylamino)ethyl)-1H-pyrazol-4-yl)thieno[3,2-b]pyridin-7-yloxy)phenyl)urea (247)

Step 1. tert-butyl 2-(4-(7-(4-(3-cyclopropylureido)-2-fluorophenoxy)thieno[3,2-b]pyridine-2-yl)-1H-pyrazol-1-yl)ethyl(2-methoxyethyl)carbamate (246)

To a stirred solution of tert-butyl 2-(4-(7-(4-amino-2-fluorophenoxy)thieno[3,2-b]pyridin-2-yl)-1H-pyrazol-1-yl)ethyl(2-methoxyethyl)carbamate (245, 1.22 g, 2.312 mmol) and pyridine (374 µL, 4.62 mmol) in DMF (30 mL) at 0° C. was added phenyl chloroformate (348 µl, 2.77 mmol) and the reaction mixture was stirred for 30 min. Cyclopropylamine (407 µl, 5.78 mmol) was added at 0° C. and the reaction mixture was heated at 60° C. for an additional 30 min. After cooling to RT, the reaction mixture was quenched by addition of water and a saturated solution of ammonium chloride, and extracted with AcOEt. The organic extract was washed with brine, dried over anhydrous sodium sulfate, filtered and concentrated. The residue was purified by Biotage (SNAP 80 g cartridge; MeOH/DCM: 0/100 to 10/90 over 20 CV). The desired fractions were collected and concentrated to afford the title compound 246 (722 mg, 0.18 mmol, 61% yield) as a yellow solid. MS (m/z): 611.63 (M+H).

Step 2. 1-cyclopropyl-3-(3-fluoro-4-(2-(1-(2-(2-methoxyethylamino)ethyl)-1H-pyrazol-4-yl)thieno[3,2-b]pyridin-7-yloxy)phenyl)urea (247)

To a solution of 246 (722 mg, 0.18 mmol) in DCM (30 mL) was added TFA (7 mL) and the reaction mixture was stirred for 45 min. The reaction mixture was concentrated, diluted with water and 4M NaOH to pH 11 and extracted with AcOEt. The extract was washed with water, brine, dried over anhydrous sodium sulfate, filtered and concentrated. The residue was purified by Biotage (SNAP 50 g cartridge; 2% of ammonium hydroxide in MeOH/DCM: 0/100 to 15/85 over 20 CV), to produce a material that upon trituration with AcOEt, afforded the title compound 247 (3.15 mg, 0.617 mmol, 52% yield) as a yellow solid. $^1$H NMR (400 MHz, DMSO-$d_6$) δ(ppm): 8.71 (s, 1H), 8.44 (d, J=5.6 Hz, 1H), 8.33 (s, 1H), 8.01 (d, J=0.8 Hz, 1H), 7.72 (d, J=2.4 and 13.6 Hz, 1H), 7.68 (s, 1H), 7.35 (t, J=9.2 Hz, 1H), 7.22-7.16 (m, 1H), 6.57 (d, J=2.4 Hz, 1H), 6.53 (d, J=5.6 Hz, 1H), 4.21 (t, J=6.0 Hz, 2H), 3.36 (t, J=5.6 Hz, 2H), 2.98 (s, 3H), 2.97 (t, J=6.0 Hz, 2H), 2.68 (t, J=5.6 Hz, 2H), 2.59-2.50 (m, 1H), 0.68-0.62 (m, 2H), 0.45-0.40 (m, 2H). MS (m/z): 511.54 (M+H).

Scheme 57

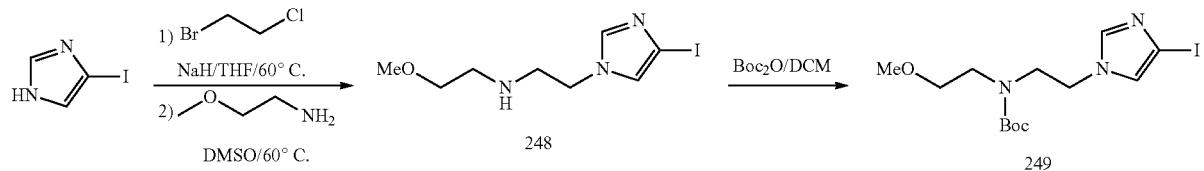

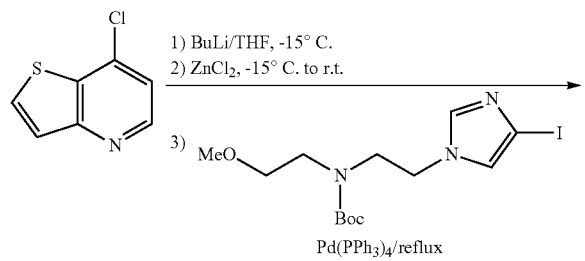

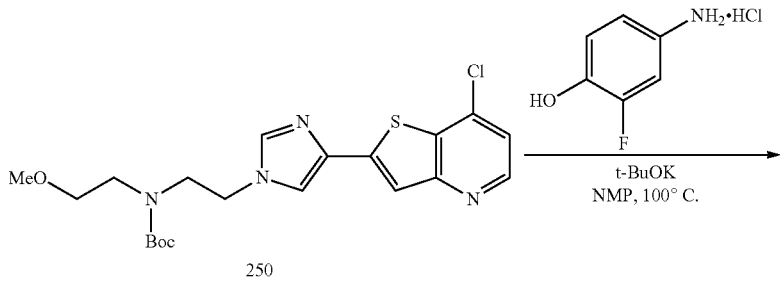

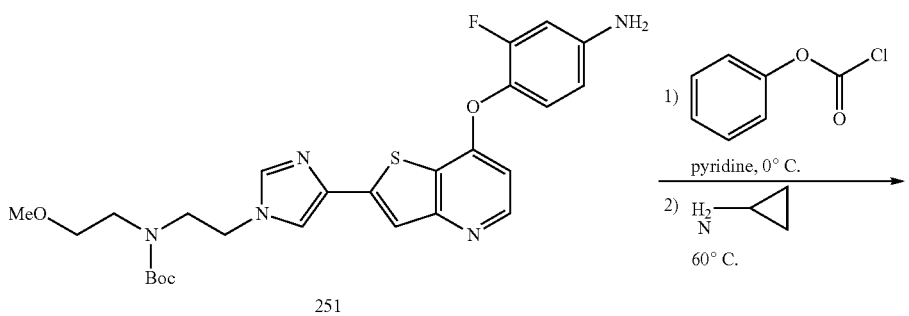

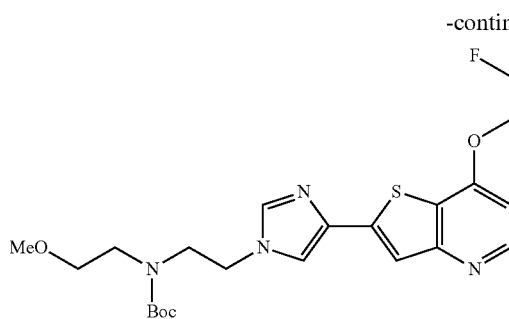
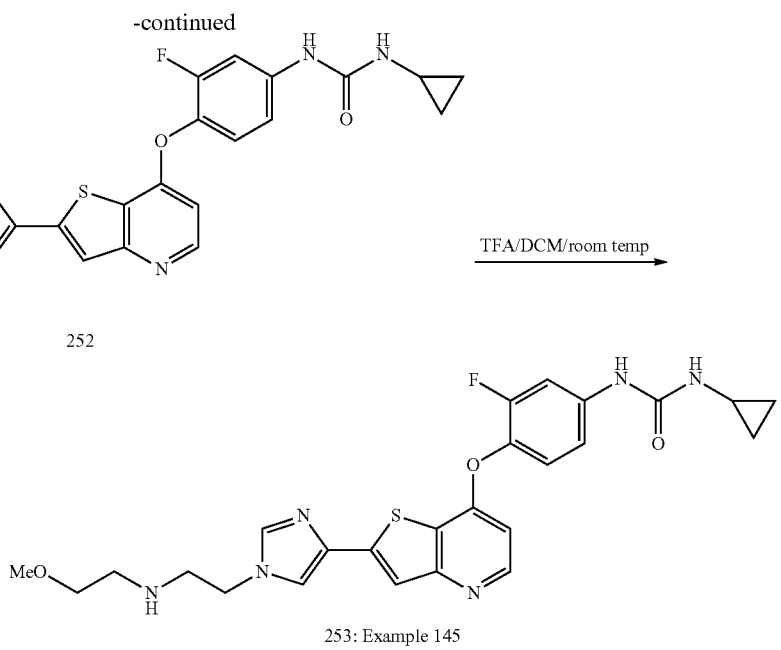

253: Example 145

Example 145

1-cyclopropyl-3-(3-fluoro-4-(2-(1-(2-(2-methoxy-ethylamino)ethyl)-1H-imidazol-4-yl)thieno[3,2-b]pyridin-7-yloxy)phenyl)urea (253)

Step 1. 2-(4-iodo-1H-imidazol-1-yl)-N-(2-methoxyethyl)ethanamine (248)

To a stirred solution of 4-iodoimidazole (8.8 g, 45.4 mmol) in THF (200 mL) at 0° C. under nitrogen was added portionwise NaH 60% (1.99 g, 49.9 mmol). After 15 min, 1-bromo-2-chloroethane (4.53 mL, 54.4 mmol) was added at 0° C. The reaction mixture was heated at 60° C. for 20 h. After cooling to RT, the reaction mixture was diluted with water and extracted with AcOEt. The extract was washed with brine, dried over anhydrous sodium sulfate, filtered and concentrated. The residue was purified by Biotage (SNAP 340 g cartridge; MeOH/AcOEt: 0/100 to 5/95 over 20 CV), to afford crude 1-(2-chloroethyl)-4-iodo-1H-imidazole not shown in the scheme 57 (7 g, 27.26 mmol, 60% yield) as colorless oil. MS (m/z): 256.83 (M+H).

To a stirred solution of crude 1-(2-chloroethyl)-4-iodo-1,1-imidazole (7 g, 27.26 mmol) in DMSO (20 mL) was added 2-methoxyethylamine (7.75 mL, 89 mmol). The reaction mixture was heated at 60° C. for 20 h. After cooling to RT, the reaction mixture was diluted with water and extracted with AcOEt. The extract was washed with brine, dried over anhydrous sodium sulfate, filtered and concentrated. The residue was purified by Biotage (SNAP 340 g cartridge; MeOH/AcOEt: 0/100 to 13/87 over 20 CV), to afford the title compound 248 (2.64 g, 8.94 mmol, 60% yield) as colorless oil. MS (m/z): 296.12 (M+H).

Step 2. tert-butyl 2-(4-iodo-1H-imidazol-1-yl)ethyl(2-methoxyethyl)carbamate (249)

To a stirred solution of 248 (2.64 g, 8.94 mmol) in DCM (30 mL) was added di-tert-butyl dicarbonate (2.75 g, 12.60 mmol). The reaction mixture was stirred at RT for 18 h and concentrated. The residue was purified by Biotage (SNAP 100 g cartridge; AcOEt/Hexane: 20/80 to 100/0 over 20 CV), to afford the title compound 249 (2.16 g, 5.47 mmol, 56% yield) as light yellow oil. MS (m/z): 396.07 (M+H).

Step 3. tert-butyl 2-(4-(7-chlorothieno[3,2-b]pyridin-2-yl)-1H-imidazol-1-yl)ethyl(2-methoxyethyl)carbamate (250)

To a stirred solution of 7-chlorothieno[3,2-b]pyridine (1.39 g, 8.20 mmol) in THF (30 mL) at −15° C. was added n-BuLi (3.28 mL, 8.20 mmol). After 30 min, ZnCl$_2$ (1.12 g, 8.20 mmol) was added at −15° C. and the reaction mixture was allowed to warm to RT over 45 min. A solution of palladium tetrakistriphenylphosphine (0.126 g, 0.11 mmol) and iodide 249 (2.16 g, 5.47 mmol) in THF (10 mL) was added and the mixture was heated to reflux for 45 min then concentrated. The reaction mixture was diluted with water and ammonium hydroxide and extracted with DCM. The extract was washed with brine, dried over anhydrous sodium sulfate, filtered and concentrated. The residue was purified by Biotage (SNAP 340 g cartridge; MeOH/DCM: 0/100 to 10/90 over 20 CV), to afford the title compound 250 (2.37 g, 5.43 mmol, 99% yield) as light brown solid. MS (m/z): 437.45 (M+H).

Step 4. tert-butyl 2-(4-(7-(4-amino-2-fluorophenoxy)thieno[3,2-b]pyridin-2-yl)-1H-imidazol-1-yl)ethyl(2-methoxyethyl)carbamate (251)

To a stirred solution of 4-amino-2-fluorophenol hydrochloride (1.96 g, 11.96 mmol) in NMP (15 mL) was added t-BuOK (2.93 g, 26.1 mmol). After 30 min, chloride 250 (4.75 g, 10.87 mmol) was added and the reaction mixture was heated at 100° C. for 2 h.

In a separate flask a solution of 4-amino-2-fluorophenol HCl (1.96 g, 11.96 mmol) in NMP (15 mL) was treated with t-BuOK (2.93 g, 26.1 mmol) and the resultant phenolate solution was added to the original reaction mixture at 100° C. After 30 min, the reaction was quenched by addition of water and the mixture was extracted with DCM. The organic layer was washed with brine, dried over anhydrous sodium sulfate, filtered and concentrated. The residue was purified by Biotage (SNAP 80 g cartridge; 2% of ammonium hydroxide in MeOH/DCM: 0/100 to 10/90 over 20 CV), to afford the title compound 251 (1.2 g, 2.27 mmol, 21% yield) as light brown solid. MS (m/z): 528.64 (M+H).

Step 5. tert-butyl 2-(4-(7-(4-(3-cyclopropylureido)-2-fluorophenoxy)thieno[3,2-b]pyridin-2-yl)-1H-imidazol-1-yl)ethyl(2-methoxyethyl)carbamate (252)

To a stirred solution of amine 251 (1.2 g, 2.27 mmol) and pyridine (368 μL, 4.55 mmol) in DMF (11 mL) at 0° C. was added phenyl chloroformate (342 μL, 2.73 mmol) and the reaction mixture was stirred for 30 min. Cyclopropylamine (401 μl, 5.69 mmol) was added at 0° C. and the reaction mixture was heated at 60° C. for 45 min. After cooling to RT, the reaction mixture was diluted with water and a saturated solution of ammonium chloride and extracted with AcOEt. The extract was washed with brine, dried over anhydrous sodium sulfate, filtered and concentrated. The residue was purified by Biotage (SNAP 80 g cartridge; MeOH/DCM: 0/100 to 10/90 over 20 CV), to afford the title compound 252 (1 g, 1.63 mmol, 72% yield) as a beige solid. MS (m/z): 611.70 (M+H).

Step 6. 1-cyclopropyl-3-(3-fluoro-4-(2-(1-(2-(2-methoxyethylamino)ethyl)-1H-imidazol-4-yl)thieno[3,2-b]pyridin-7-yloxy)phenyl)urea (253)

To a solution of 252 (1 g, 1.63 mmol) in DCM (50 mL) was added TFA (15 mL) and the reaction mixture was stirred for 1.5 h then concentrated, diluted with water and 4M NaOH to pH 11 and extracted with DCM/MeOH. The extract was washed with water, brine, dried over anhydrous sodium sulfate, filtered and concentrated. The residue was purified by Biotage (SNAP 80 g cartridge; 2% of ammonium hydroxide in MeOH/DCM: 0/100 to 10/90 over 20 CV), to afford the title compound 253 (800 mg, 1.56 mmol, 96% yield) as a beige solid. $^1$H NMR (400 MHz, DMSO-$d_6$) δ(ppm): 8.69 (s, 1H), 8.42 (d, J=5.6 Hz, 1H), 7.91 (d, J=1.2 Hz, 1H), 7.75 (d, J=0.8 Hz, 1H), 7.72 (dd, J=2.4 and 13.6 Hz, 1H), 7.66 (s, 1H), 7.36 (t, J=8.8 Hz, 1H), 7.21-7.16 (m, 1H), 6.57 (d, J=2.85 Hz, 1H), 6.54 (d, J=5.6 Hz, 1H), J=6.4 Hz, 2H), 3.36 (t, J=5.6 Hz, 2H), 3.22 (s, 3H), 2.89 (t, J=6.4 Hz, 2H), 2.67 (t, J=5.6. Hz, 2H), 2.58-2.53 (m, 1H), 0.68-0.61 (m, 2H), 0.45-0.40 (m, 2H). MS (m/z): 511.56 (M+H).

Compound 254 (example 146) was synthesized starting from compound 247 (scheme 56) and following a procedure similar to that described above for the synthesis of compound 114 (example 79, scheme 29). Compound 254-A (example 146-A) was synthesized starting from compound 253 (scheme 57) and following a procedure similar to the described above for the synthesis of compound 114 (example 79, scheme 29). Compounds 255-256 (examples 147-148) were prepared in one step by reacting the corresponding secondary amine precursors 247 (scheme 56) and 253 (scheme 57) with ethyl isocyanate.

TABLE 19

Characterization of compounds 254-256 (examples 146-148)

| Cpd | Ex. | Structure | Characterization |
|---|---|---|---|
| 254 | 146 | 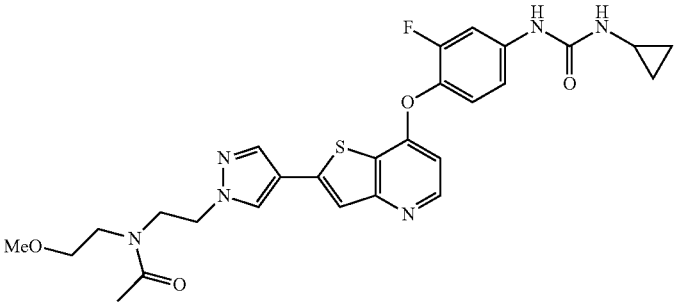 [SMILES: COCCN(CCn1cc(-c2cc3nccc(Oc4ccc(NC(=O)NC5CC5)cc4F)c3s2)cn1)C(C)=O]<br>N-(2-(4-(7-(4-(3-cyclopropylureido)-2-fluorophenoxy)thieno[3,2-b]pyridine-2-yl)-1H-pyrazol-1-yl)ethyl)-N-(2-methoxyethyl)acetamide | 1H NMR (400 MHz, DMSO-d6) δ (ppm): mixture of rotamers, 8.69 (s, 1H), 8.44 (dd, J = 2.0 and 5.6 Hz, 1H), 8.34 and 8.31 (s, 1H), 8.09 and 8.04 (s, 1H), 7.72 (dd, J = 2.0 and 13.6 Hz, 1H), 7.70 (s, 1H), 7.35 (t, J = 9.2 Hz, 1H), 7.22-7.16 (m, 1H), 6.57 (d, J = 2.8 Hz, 1H), 6.54 (t, J = 4.8 Hz, 1H), 4.36 and 4.26 (t, J = 5.6 Hz, 2H), 3.75 and 3.67 (t, J = 5.6 Hz, 2H), 3.43-3.20 (m, 4H), 3.25 and 3.22 (s, 3H), 2.59-2.50 (m, 1H), 2.01 and 1.72 (s, 3H), 0.68-0.62 (m, 2H), 0.45-0.41 (m, 2H). MS (m/z): 553.3 (M + H). |
| 254-A | 146-A | 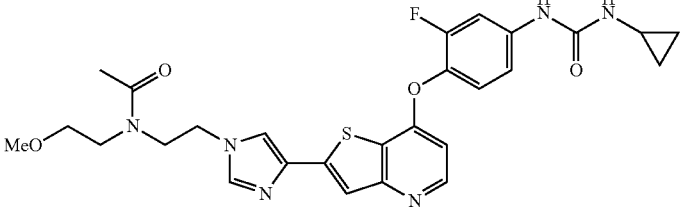<br>N-(2-(4-(7-(4-(3-cyclopropylureido)-2-fluorophenoxy)-thieno[3,2-b]pyridin-2-yl)-1H-imidazol-1-yl)ethyl)-N-(2-methoxyethyl)acetamide | $^1$H NMR (400 MHz, DMSO-$d_6$ δ (ppm): mixture of rotamers, 8.79 (s, 1H), 8.46-8.41 (m, 1H), 7.92 (dd, J = 8.5, 1.1 Hz, 1H), 7.79-7.65 (m, 3H), 7.35 (t, J = 9.1 Hz, 1H), 7.19 (bd, J = 9.0 Hz, 1H), 6.68-6.61 (m, 1H), 6.58-6.53 (m, 1H), 4.24 and 4.14 (2t, J = 6.2 Hz, 2H), 3.69 and 3.62 (2t, J = 6.3 Hz, 2H), 3.41 (bs, 2H), one CH2 is masked by water, 3.25 and 3.24 (2s, 3H), 2.59-2.51 (m, 1H), 2.03 and 1.74 (2s, 3H), 0.71-0.58 (m, 2H), 0.49-0.36 (m, 2H). MS (m/z): 553.6 (M + H). |

TABLE 19-continued

Characterization of compounds 254-256 (examples 146-148)

| Cpd | Ex. | Structure | Characterization |
|---|---|---|---|
| 255 | 147 | 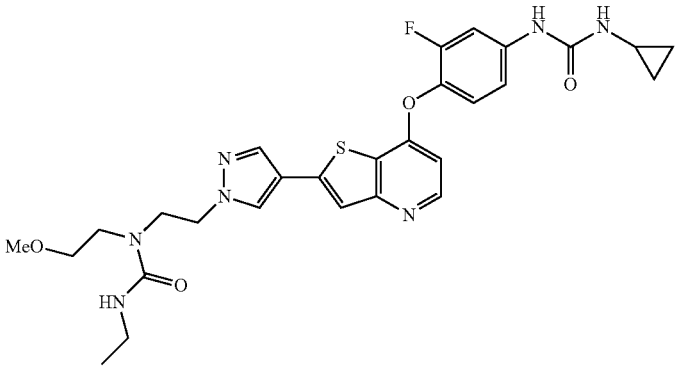 [SMILES: CCNC(=O)N(CCOC)CCn1cc(-c2cc3nccc(Oc4ccc(NC(=O)NC5CC5)cc4F)c3s2)cn1]<br>N-(2-(4-(7-(4-(3-cyclopropylureido)-2-fluorophenoxy)thieno[3,2-b]-pyridine-2-yl)-1H-pyrazol-1-yl)ethyl)-N-(1-ethyl)-N-[3-(2-methoxyethyl)]urea | $^1$H NMR (400 MHz, DMSO-d$_6$ δ (ppm): 8.74 (s, 1H), 8.44 (d, J = 5.4 Hz, 1H), 8.29 (s, 1H), 8.05 (s, 1H), 7.76-7.68 (m, 1H), 7.69 (s, 1H), 7.35 (t, J = 8.8 Hz, 1H), 7.19 (d, J = 8.0 Hz, 1H), 6.61 (bs, 1H), 6.54 (d, J = 5.6 Hz, 1H), 6.21 (t, J = 4.8 Hz, 1H), 4.24 (t, J = 6.0 Hz, 2H), 3.36 (t, J = 6.0 Hz, 2H), 3.28 (t, J = 5.6 Hz, 2H), 3.21 (s, 3H), 3.02 (quint, J = 6.4 Hz, 2H), 2.59-2.50 (m, 1H), 0.98 (t, J = 7.2 Hz, 2H), 0.69-0.61 (m, 2H), 0.46-0.39 (m, 2H). MS (m/z): 582.6 (M + H). |
| 256 | 148 | 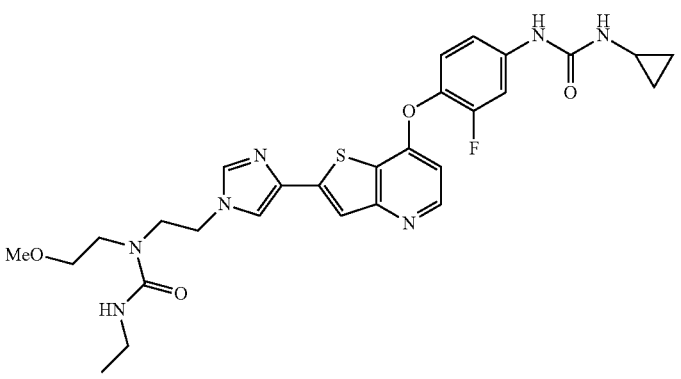 [SMILES: CCNC(=O)N(CCOC)CCn1cnc(-c2cc3nccc(Oc4ccc(NC(=O)NC5CC5)cc4F)c3s2)c1]<br>N-(2-(4-(7-(4-(3-cyclopropylureido)-2-fluorophenoxy)thieno[3,2-b]-pyridin-2-yl)-1H-imidazol-1-yl)ethyl)-N-(1-ethyl)-N-[3-(2-methoxyethyl)]urea | $^1$H NMR (400 MHz, DMSO-d$_6$) δ (ppm): 8.74 (s, 1H), 8.43 (d, J = 5.6 Hz, 1H), 7.88 (d, J = 1.2 Hz, 1H), 7.72 (dd, J = 2.0 and 13.6 Hz, 1H), 7.71 (s, 1H), 7.66 (s, 1H), 7.35 (t, J = 8.8 Hz, 1H), 7.22-7.18 (m, 1H), 6.61 (d, J = 2.4 Hz, 1H), 6.55 (d, J = 5.6 Hz, 1H), 6.29 (t, J = 5.2 Hz, 1H), 4.12 (t, J = 6.4 Hz, 2H), 3.57 (t, J = 6.8 Hz, 2H), 3.31 (t, J = 4.8 Hz, 2H), 3.23 (t, J = 4.8 Hz, 2H), 3.22 (s, 3H), 3.06-2.99 (m, 2H), 2.60-2.51 (m, 1H), 0.98 (t, J = 7.2 Hz, 3H), 0.70-0.62 (m, 2H), 0.45-0.40 (m, 2H). MS (m/z): 582.4 (M + H). |

Compounds 257-259 (examples 149-151) were prepared in two steps from the corresponding secondary amine precursors 247 (scheme 56), 253 (scheme 57) and 171 (Table 16); and acetoxyacetic acid similarly to compound 31 (example 17, scheme 13). Compound 259-A (example 151-A) was prepared from the amine precursor 25 (scheme 11) by following the procedure shown above for the synthesis of compound 115-A (example 80-A, scheme 29).

TABLE 20

Characterization of compounds 257-259 (examples 149-151)

| Cpd | Ex | Structure | Characterization |
|---|---|---|---|
| 257 | 149 | 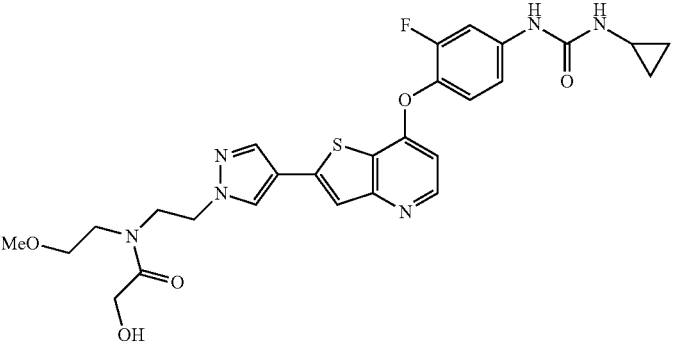 [SMILES: COCCN(CCn1cc(-c2cc3nccc(Oc4ccc(NC(=O)NC5CC5)cc4F)c3s2)cn1)C(=O)CO]<br>N-(2-(4-(7-(4-(3-cyclopropylureido)-2-fluorophenoxy)thieno[3,2-b]-pyridin-2-yl)-1H-pyrazol-1-yl)ethyl)-2-hydroxy-N-(2-methoxyethyl)acetamide | $^1$H NMR (400 MHz, DMSO-d$_6$) δ (ppm): mixture of rotamers, 8.74 (s, 1H), 8.44 (dd, J = 1.6 and 5.6 Hz, 1H), 8.33 and 8.31 (s, 1H), 8.09 and 8.04 (s, 1H), 7.72 (dd, J = 2.0 and 13.6 Hz, 1H), 7.70 (s, 1H), 7.35 (t, J = 9.2 Hz, 1H), 7.22-7.16 (m, 1H), 6.60 (d, J = 2.0 Hz, 1H), 6.54 (t, J = 5.2 Hz, 1H), 4.51 and 4.46 (t, J = 5.6 Hz, 1H), 4.36 and 4.30 (t, J = 6.0 Hz, 2H), 4.11 and 3.80 (d, J = 5.6 Hz, 2H), 3.72 and 3.69 (t, J = 6.0 Hz, 2H), 3.48-3.13 (m, 4H), 3.25 and 3.21 (s, 3H), 2.59-2.50 (m, 1H), 0.68-0.62 (m, 2H), 0.45-0.40 (m, 2H). MS (m/z): 569.2 (M + H). |
| 258 | 150 | 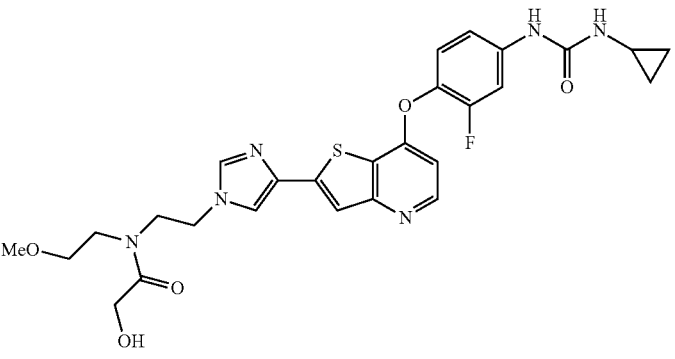 [SMILES: COCCN(CCn1cnc(-c2cc3nccc(Oc4ccc(NC(=O)NC5CC5)cc4F)c3s2)c1)C(=O)CO]<br>N-(2-(4-(7-(4-(3-cyclopropylureido)-2-fluorophenoxy)thieno[3,2-b]-pyridin-2-yl)-1H-imidazol-1-yl)ethyl)-2-hydroxy-N-(2-methoxyethyl)acetamide | $^1$H NMR (400 MHz, DMSO-d$_6$) δ (ppm): mixture of rotamers, 8.80 (s, 1H), 8.43 (dd, J = 2.0 and 5.6 Hz, 1H), 7.92 (dd, J = 1.2 and 8.8 Hz, 1H), 7.78-7.65 (m, 3H), 7.35 (t, J = 9.2 Hz, 1H), 7.22-7.17 (m, 1H), 6.65 (d, J = 2.4 Hz, 1H), 6.55 (dd, J = 1.6 and 5.2 Hz, 1H), 4.55-4.51 (m, 1H), 4.24 and 4.18 (2t, J = 6.0 Hz, 2H), 4.13 and 3.84 (2d, J = 5.6 Hz, 2H), 3.67 and 3.62 (2t, J = 6.0 Hz, 2H), 3.46-3.23 (m, 4H), 3.26 and 3.22 (2s, 3H), 2.58-2.52 (m, 1H), 0.68-0.62 (m, 2H), 0.45-0.40 (m, 2H). MS (m/z): 569.5 (M + H). |
| 259 | 151 | 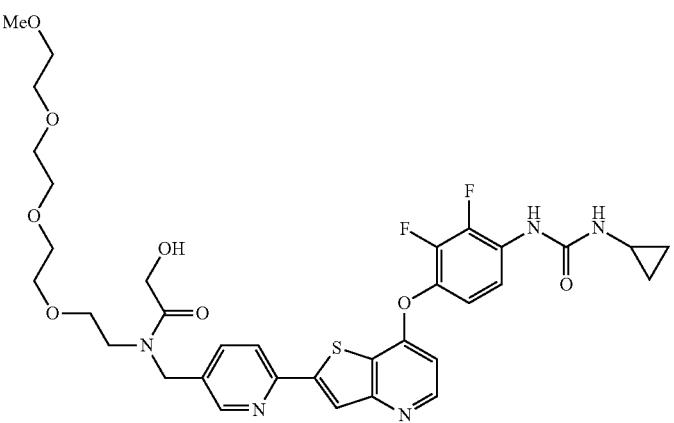 [SMILES: COCCOCCOCCOCCN(Cc1ccc(-c2cc3nccc(Oc4ccc(NC(=O)NC5CC5)c(F)c4F)c3s2)nc1)C(=O)CO]<br>N-((6-(7-(4-(3-cyclopropylureido)-2,3-difluorophenoxy)thieno-[3,2-b]pyridin-2-yl)pyridin-3-yl)methyl)-2-hydroxy-N-(2,5,8,11-tetraoxatridecan-13-yl)acetamide | $^1$H NMR (400 MHz, DMSO-d$_6$) δ (ppm): mixture of rotamers, 8.80 (s, 1H), 8.56-8.50 (m, 2H), 8.38 and 8.35 (s, 1H), 8.29 and 8.24 (d, J = 8.4 Hz, 1H), 8.02 (t, J = 8.4 Hz, 1H), 7.82 and 7.79 (dd, J = 3.2 and 8.0 Hz, 1H), 7.31-7.25 (m, 1H), 6.98 (d, J = 3.2 Hz, 1H), 6.76-6.75 (d, J = 5.6 Hz, 1H), 4.79 and 4.60 (t, J = 5.6 Hz, 1H), 4.66 and 4.65 (s, 2H), 4.25 and 4.15 (d, J = 5.2 Hz, 2H), 3.58-3.37 (m, 17H), 3.21 and 3.20 (s, 3H), 2.60-2.54 (m, 1H), 0.68-0.63 (m, 2H), 0.44-0.40 (m, 2H). MS (m/z): 716.2 (M + H). |

TABLE 20-continued
Characterization of compounds 257-259 (examples 149-151)
| Cpd | Ex | Structure | Characterization |
|---|---|---|---|
| 259-A | 151-A | 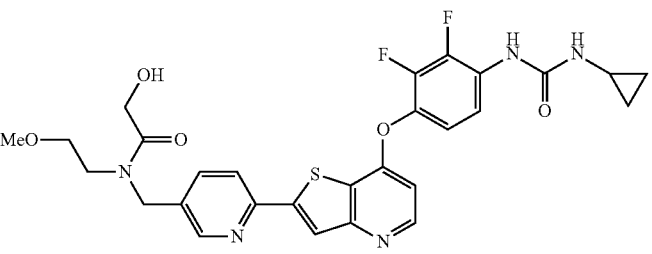 [SMILES: COCCN(Cc1ccc(-c2cc3nccc(Oc4ccc(NC(=O)NC5CC5)c(F)c4F)c3s2)nc1)C(=O)CO] N-((6-(7-(4-(3-cyclopropylureido)-2,3-difluorophenoxy)thieno[3,2-d]pyridin-2-yl)pyridin-3-yl)methyl)-2-hydroxy-N-(2-methoxyethyl)acetamide | $^1$H NMR (400 MHz, DMSO-d$_6$) δ (ppm): mixture of rotamers, 8.57-8.51 (m, 2H), 8.48 (bs, 1H), 8.38 and 8.35 (2s, 1H), 8.30 and 8.25 (2d, J = 8.0 Hz, 1H), 8.03 (bt, J = 7.7 Hz, 1H), 7.84-7.76 (m, 1H), 7.29 (td, J = 8.9, 1.8 Hz, 1H), 6.88 (bd, J = 2.9 Hz, 1H), 6.79-6.74 (m, 1H), 4.82-4.60 (m, 3H), 4.23 and 4.13 (2d, J = 5.8 Hz, 2H), 3.51-3.39 (m, 4H), 3.23 and 3.21 (2s, 3H), 2.61-2.52 (m, 1H), 0.73-0.59 (m, 2H), 0.49-0.36 (m, 2H). MS (m/z): 584.4 (M + H). |
Scheme 58
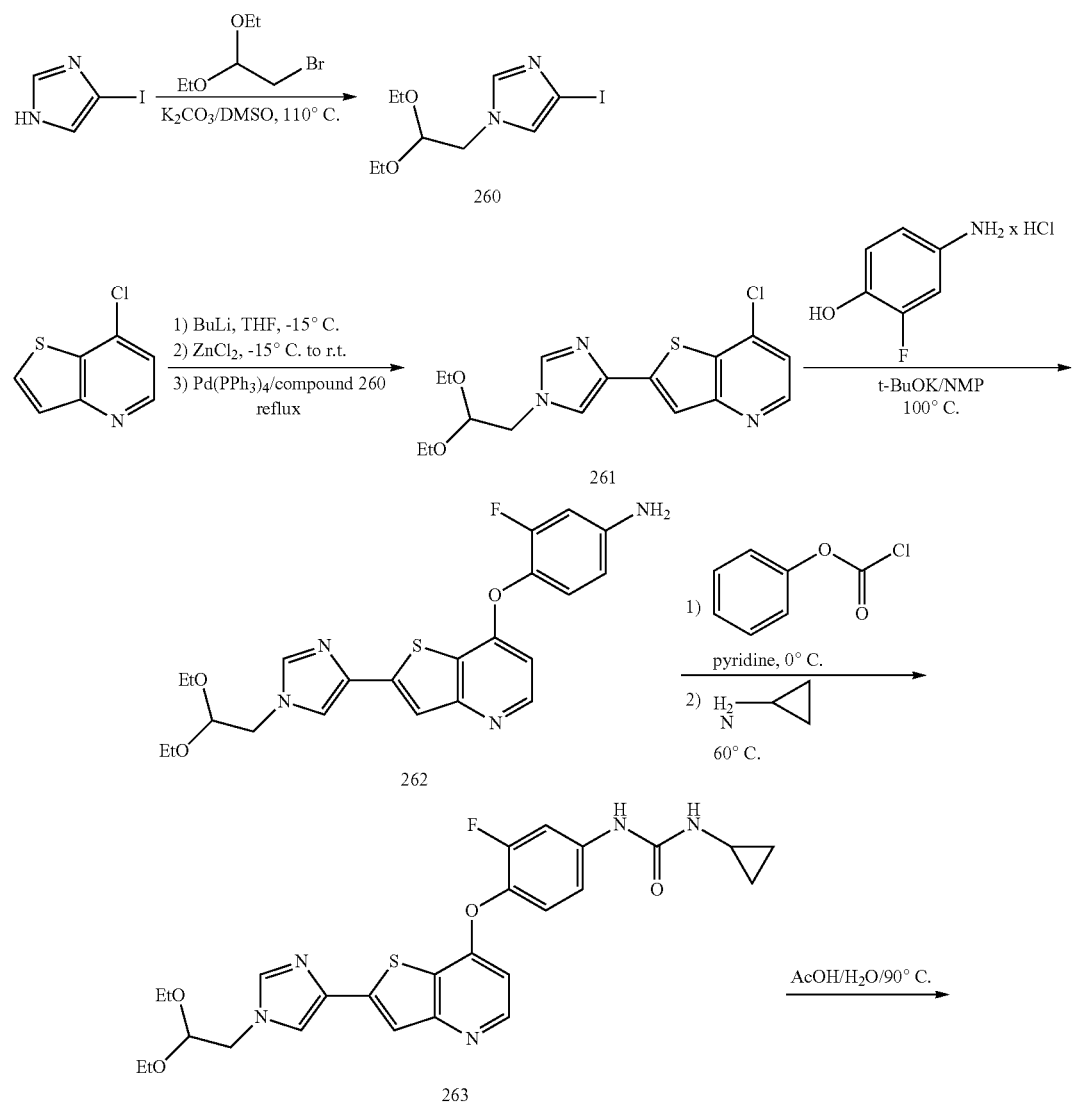

-continued

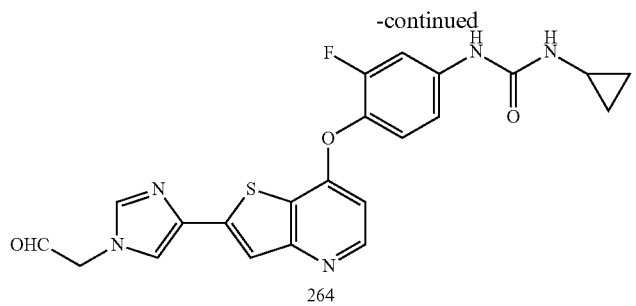

264

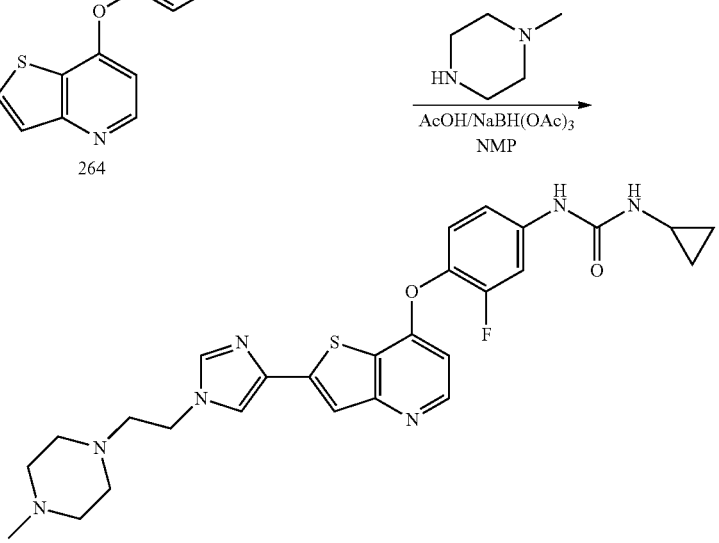

266: Example 153

Example 153

1-Cyclopropyl-3-(3-fluoro-4-(2-(1-(2-(4-methylpiperazin-1-yl)ethyl)-1H-imidazol-4-yl)thieno[3,2-b]pyridin-7-yloxy)phenyl)urea (266)

Step 1. 1-(2,2-diethoxyethyl)-4-iodo-1H-imidazole (260)

To a stirred solution of 4-iodoimidazole (10 g, 51.6 mmol) and bromoacetaldehyde diethyl acetal (9.31 mL) in DMSO (30 mL) was added $K_2CO_3$ (10.69 g, 77 mmol). The reaction mixture was heated at 110° C. for 16 h. After cooling to RT, the reaction mixture was diluted with water and extracted with AcOEt. The organic extract was washed with brine, dried over anhydrous sodium sulfate, filtered and concentrated. The residue was purified by Biotage (SNAP 80 g cartridge; AcOEt/Hex:0/100 to 50/50 over 20 CV). The desired fractions were collected and concentrated to afford title compound 260 (11.29 g, 36.4 mmol, 71% yield) as yellow oil. MS (m/z): 310.97 (M+H).

Step 2. 7-chloro-2-(1-(2,2-diethoxyethyl)-1H-imidazol-4-yl)thieno[3,2-b]pyridine (261)

To a stirred solution of 7-chlorothieno[3,2-]pyridine (9.26 g, 54.6 mmol) in THF (88 mL) at −15° C. was added n-BuLi (21.84 mL, 54.6 mmol). After 30 min, a solution of $ZnCl_2$ 0.5M in THF (109 mL, 54.6 mmol) was added at −15° C. and the reaction mixture was warmed to RT over 45 min. A solution of palladium tetrakistriphenylphosphine (0.841 g, 0.73 mmol) and iodide 260 (11.29 g, 36.4 mmol) in THF (33 mL) was added and the mixture was heated to reflux for 3 h then concentrated. The residue was diluted with water and ammonium hydroxyde and extracted with DCM. The organic extract was washed with brine, dried over anhydrous sodium sulfate, filtered and concentrated. The residue was purified by Biotage (SNAP 80 g cartridge; AcOEt/Hex:0/100 to 100/0 over 20 CV) to produce a material that upon trituration with MTBE afforded the title compound 261 (1.2 g, 3.41 mmol, 9% yield) as light-brown solid. MS (m/z): 437.45 (M+H).

Step 3. 4-(2-(1-(2,2-diethoxyethyl)-1H-imidazol-4-yl)thieno[3,2-b]pyridin-7-yloxy)-3-fluoroaniline (262)

To a stirred solution of 4-amino-2-fluorophenol hydrochloride (1.39 g, 8.53 mmol) in DMSO (20 mL) was added t-BuOK (1.99 g, 17.76 mmol). After 30 min, chloride 261 (2.5 g, 7.11 mmol) was added and the reaction mixture was heated at 100° C. for 1 h.

In a separate flask a solution of 4-amino-2-fluorophenol hydrochloride (1.39 g, 8.53 mmol) in DMSO (20 mL) was treated with t-BuOK (1.99 g, 17.76 mmol) and the resultant phenolate solution was added to the original reaction mixture at 100° C. After 30 min, the mixture was poured into water (300 mL) to form a precipitate that was collected by filtration and dried under high vacuum to afford the title compound 262 (2.86 g, 6.46 mmol, 91% yield) as light brown solid. MS (m/z): 443.44 (M+H).

Step 4. 1-cyclopropyl-3-(4-(2-(1-(2,2-diethoxyethyl)-1H-imidazol-4-yl)thieno[3,2-b]pyridine-7-yloxy)-3-fluorophenyl)urea (263)

To a stirred solution of amine 262 (2.86 g, 6.46 mmol) and pyridine (1.04 mL, 12.93 mmol) in DMF (50 mL) at 0° C. was added phenyl chloroformate (973 μl, 7.76 mmol). After 30 min, cyclopropylamine (1.14 mL, 16.16 mmol) was added at 0° C. and the reaction mixture was heated at 60° C. for 45 min. More cyclopropylamine (1 mL, 14.18 mmol) was added and the reaction mixture was heated at 60° C. for an additional 10 min. After cooling to RT, the reaction mixture was quenched by addition of water to form a precipitate. The solid was collected by filtration, washed with water and dried under vacuum for 2 h. The residue was purified by Biotage (SNAP 80 g cartridge; MeOH/DCM: 0/100 to 10/90 over 20 CV). The desired fractions were collected, concentrated, triturated with MTBE and dried under high vacuum to afford the title compound 263 (2.95 g, 5.61 mmol, 87% yield) as a pink solid. MS (m/z): 526.60 (M+H).

Step 5. 1-cyclopropyl-3-(3-fluoro-4-(2-(1-(2-oxoethyl)-1H-imidazol-4-yl)thieno[3,2-b]pyridin-7-yloxy)phenyl)urea (264)

To a solution of acetal 263 (2.95 g, 5.61 mmol) in AcOH/H$_2$O (20/20 mL) was added concentrated HCl (2 mL) and the reaction mixture was heated at 90° C. for 1 h. The reaction mixture was concentrated, diluted with water and 4M NaOH to pH 10 to form a precipitate that was collected by filtration, washed with water and dried under vacuum. The material was then purified by Biotage (SNAP 100 g cartridge; 2% of ammonium hydroxide in MeOH/DCM: 0/100 to 15/85, over 20 CV) to afford the title compound 264 (1.2 g, 2.66 mmol, 47% yield) as a brown solid. MS (m/z): 484.51 (M+H).

Step 6. 1-Cyclopropyl-3-(3-fluoro-4-(2-(1-(2-(4-methylpiperazin-1-yl)ethyl)-1H-imidazol-4-yl)thieno[3,2-b]pyridin-7-yloxy)phenyl)urea (266)

To a solution of 264 (300 mg, 0.66 mmol), N-methylpiperazine (74 µl, 0.66 mmol) and AcOH (76 µl, 1.33 mmol) in NMP (10 mL) was added sodium triacetoxyborohydride (422 mg, 1.99 mmol) and the reaction mixture was stirred for 2.5 days at RT. The reaction mixture was quenched with saturated sodium bicarbonate solution and extracted with DCM. The organic extract was successively washed with water and brine, dried over anhydrous sodium sulfate, filtered and concentrated. The residue was purified by Biotage (SNAP 40 g cartridge; 2% of ammonium hydroxide in MeOH/DCM: 0/100 to 15/85 over 20 CV) and by Gilson (Phenomenex, Luna 15µ, C18(2) 100A, 250×50.0 mm, 15 µm; 0.05% of formic acid in both MeOH/water:20/80 to 95/5 over 60 min, flow; 30 mL/min) to afford the title compound 266 (180 mg, 0.33 mmol, 51% yield, di-formate salt) as a white solid.

$^1$H NMR (400 MHz, DMSO-d$_6$) δ (ppm): 9.42 (bs, 1H), 8.41 (d, J=5.6 Hz, 1H), 8.29 (bs, 2H), 7.90 (d, J=0.8 Hz, 1H), 7.76 (d, J=1.2 Hz, 1H), 7.73 (dd, J=2.4 and 13.6 Hz, 1H), 7.65 (s, 1H), 7.33 (t, J=8.8 Hz, 1H), 7.23 (bs, 1H), 7.23-7.19 (m, 1H), 6.54 (d, J=5.6 Hz, 1H), 4.13 (t, J=6.0 Hz, 2H), 2.66 (t, J=6.4 Hz, 2H), 2.57-2.52 (m, 1H), 2.50-2.25 (m, 8H), 2.19 (s, 3H), 0.65-0.60 (m, 2H), 0.44-0.39 (m, 2H). MS (m/z): 536.3 (M+H).

Compound 267 was prepared from the aldehyde 264 similarly to compound 169 (example 102, scheme 41).

TABLE 21

Characterization of compound 267 (example 154)

| Cpd | Ex. | Structure | Characterization |
|---|---|---|---|
| 267 | 154 | 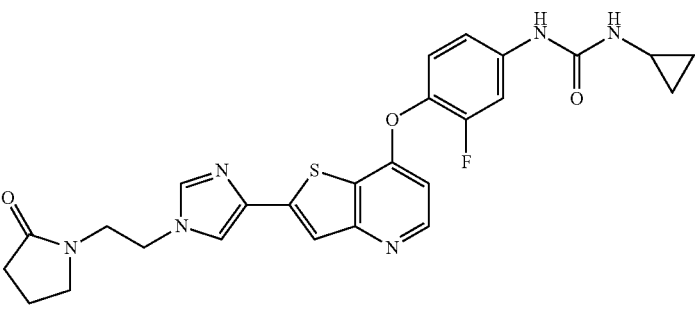 [SMILES: O=C(Nc1ccc(Oc2ccnc3cc(-c4cn(CCN5CCCC5=O)cn4)sc23)c(F)c1)NC1CC1]<br>1-cyclopropyl-3-(3-fluoro-4-(2-(1-(2-(2-oxopyrrolidin-1-yl)ethyl)-1H-imidazol-4-yl)thieno[3,2-b]pyridin-7-yloxy)phenyl)urea | $^1$H NMR (400 MHz, DMSO-d$_6$) δ (ppm): 9.36 (s, 1H), 8.42 (d, J = 5.6 Hz, 1H), 8.38 (bs, 1H), 7.91 (d, J = 0.8 Hz, 1H), 7.75 (d, J = 0.8 Hz, 1H), 7.73 (dd, J = 2.4 and 13.6 Hz, 1H), 7.67 (s, 1H), 7.33 (t, J = 9.2 Hz, 1H), 7.24-7.19 (m, 1H), 7.16 (bs, 1H), 6.55 (d, J = 5.6 Hz, 1H), 4.17 (t, J = 5.6 Hz, 2H), 3.59-3.52 (m, 2H), 3.24 (t, J = 7.2 Hz, 2H), 2.57-2.52 (m, 1H), 2.17 (t, J = 8.0 Hz, 2H), 1.89 (quin, J = 7.6 Hz, 2H), 0.65-0.60 (m, 2H), 0.44-0.40 (m, 2H). MS (m/z): 521.5 (M + 1). |

Scheme 59

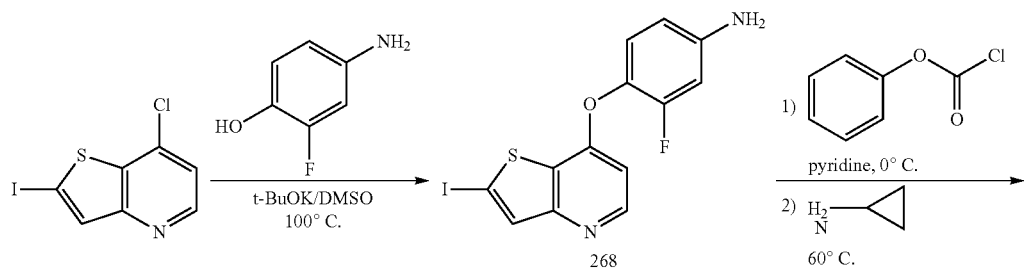

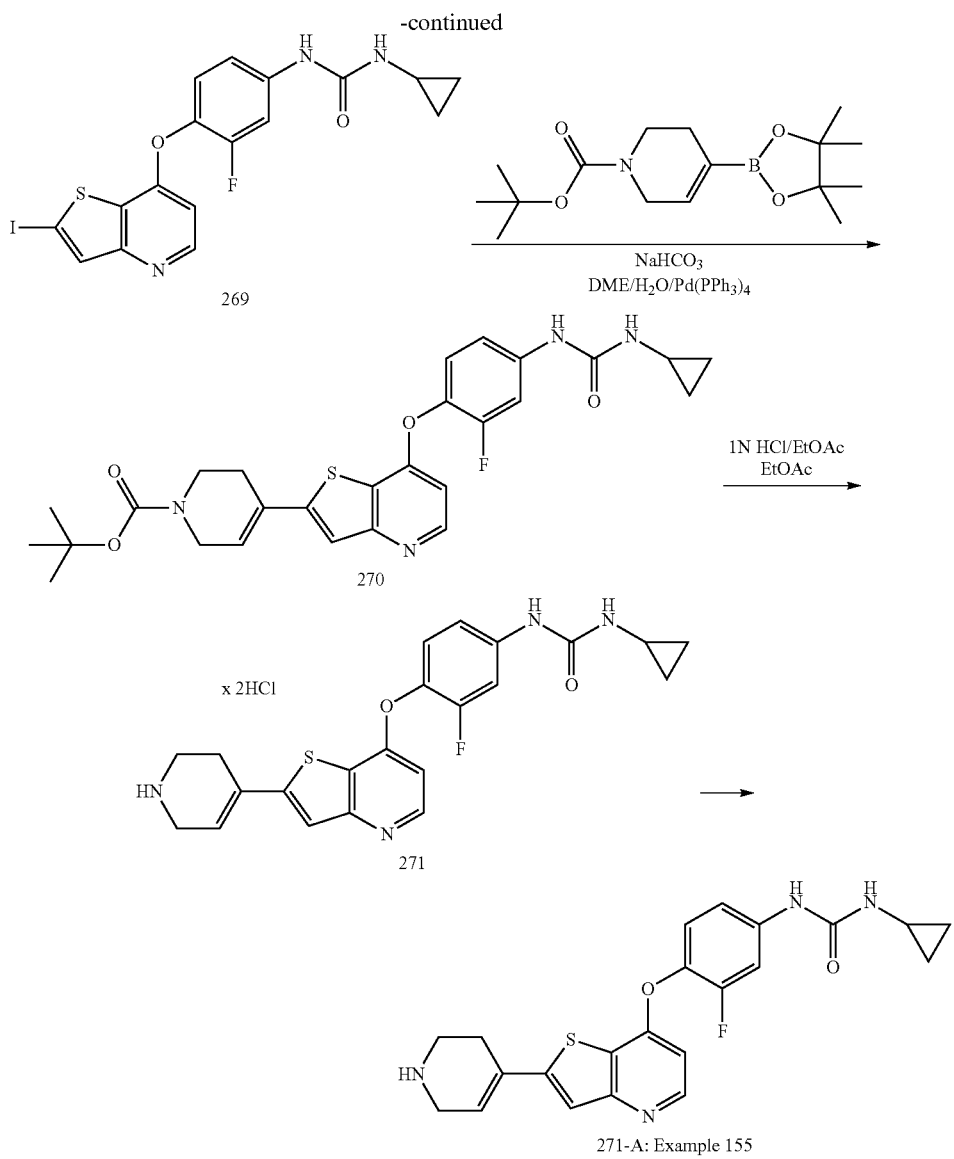

Example 155

1-Cyclopropyl-3-(3-fluoro-4-(2-(1,2,3,6-tetrahydropyridin-4-yl)thieno[3,2-b]pyridin-7-yloxy)phenyl) urea (271-A)

Step 1: 3-Fluoro-4-(2-iodothieno[3,2-b]pyridin-7-yloxy)aniline (268)

To a solution of 4-amino-2-fluorophenol (1.83 g, 14.38 mmol) in DMSO (30 mL) was added potassium tert-butoxide (1.61 g, 14.38 mmol). After 15 min, 7-chloro-2-iodothieno[3,2-b]pyridine (2.5 g, 8.46 mmol, Ragan J. A. et al, Organic Process Research and Development, 2003, 7. 676-683) was added and the reaction mixture was heated at 100° C. for 60 min. The mixture was cooled down to RT then poured into water (250 mL) at 40-45° C. and stirred for 30 min. The precipitate was collected by filtration, washed with water, dried and purified by flash column chromatography on silica gel (eluent 60% EtOAc in Hexane) to afford title compound 268 (1.06 g, 32% yield) as a brown solid. $^1$H NMR (300 MHz, CDCl$_3$) δ (ppm): 8.41 (d, J=5.4 Hz, 1H), 7.75 (s, 1H), 7.03 (t, J=9.0 Hz, 1H), 6.57-6.45 (m, 3H), 3.83 (s, 2H).

Step 2: 1-Cyclopropyl-3-(3-fluoro-4-(2-iodothieno[3,2-b]pyridin-7-yloxy)phenyl)urea (269)

To a solution of amine 268 (1.7 g, 3.98 mmol) in DMF (7 mL) was added pyridine (0.55 mL, 6.77 mmol) at RT and the resultant solution was stirred for 10 min under Ar atmosphere. Phenyl chloroformate (0.75 mL, 5.97 mmol) was added at 0° C. and the mixture was stirred at RT for 40 min. Cyclopropylamine (1.1 mL, 15.9 mmol) was added to the mixture, and the reaction mixture was warmed to 50° C. and stirred for 2 hours. The mixture was then cooled to RT then poured into water (150 mL) and stirred for 30 min. The precipitate was collected by filtration, washed with water and dried. The crude product was triturated with EtOAc to afford title compound 269 (1.75 g, 86% yield) as a pale-violet solid. $^1$H NMR (300 MHz, DMSO-d$_6$) δ (ppm): 8.70 (br, 1H), 8.45 (d, J=5.4 Hz, 1H), 7.91 (s, 1H), 7.72 (dd, J=13.5, 2.4 Hz, 1H), 7.35 (t, J=9.0 Hz, 1H), 7.23 (m, 1H), 6.62 (d, J=5.4 Hz, 1H), 6.56 (br, 1H), 2.60-2.40 (m, 1H), 0.70-0.60 (m, 2H), 0.48-0.35 (m, 2H).

Step 3: tert-Butyl 4-(7-(4-(3-Cyclopropylureido)-2-fluorophenoxy)thieno[3,2-b]pyridin-2-yl)-5,6-dihydropyridine-1(2H)-carboxylate (270)

Iodide 269 (2 g, 4.26 mmol), 1-N-Boc-4-(4,4,5,5-tetramethyl-[1,3,2]dioxaborolan-2-yl)-3,6-dihydro-2H-pyridine (1.85 g, 5.96 mmol), NaHCO$_3$ (1.1 g, 12.8 mmol) and tetrakis(triphenylphosphine)palladium (0.49 g, 0.43 mmol) were suspended in a mixture of DME/water (80 mL/16 mL). The mixture was degassed with an Ar flow, heated at 80° C. and stirred for 16 hours. The mixture was then cooled and filtered through a pad of Celite and washed with EtOAc. The filtrate was diluted with water and extracted with EtOAc. The extract was washed with brine, dried over anhydrous MgSO$_4$, filtered and concentrated. The residue was purified by flash chromatography on silica gel (eluent 3% MeOH in DCM) to afford title compound 270 (1.7 g, 78% yield) as a white solid. $^1$H NMR (300 MHz, DMSO-d$_6$) δ (ppm): 8.73 (s, 1H), 8.45 (d, J=5.4 Hz, 1H), 7.72 (dd, J=13.5, 2.4 Hz, 1H), 7.55 (s, 1H), 7.35 (t, J=9.0 Hz, 1H), 7.24-7.16 (m, 1H), 6.60 (br, 1H), 6.57 (d, =5.4 Hz, 1H), 6.40 (br, 1H), 4.15-4.00 (m, 2H), 3.63-3.54 (m, 2H), 2.70-2.40 (m, 3H), 1.44 (s, 9H), 0.70-0.60 (m, 2H), 0.48-0.35 (m, 2H).

Step 4: 1-Cyclopropyl-3-(3-fluoro-4-(2-(1,2,3,6-tetrahydropyridin-4-yl)thieno[3,2-b]pyridin-7-yloxy)phenyl)urea di-hydrochloride salt (271)

To a suspension of 270 (996 mg, 1.90 mmol) in EtOAc (20 mL) was added 1N HCl-EtOAc (11.4 mL, 11.4 mmol). The reaction mixture was stirred for 18 hours, the precipitate was collected by filtration, washed with EtOAc (30 mL) and dried to afford title compound 271 (962 mg, 100% yield) as a pale yellow solid. $^1$H NMR (300 MHz, DMSO-d$_6$) δ (ppm): 9.22 (br, 2H), 9.03 (s, 1H), 8.58 (d, J=6.0 Hz, 1H), 7.74 (dd, J=13.5, 2.7 Hz, 1H), 7.70 (s, 1H), 7.38 (t, =9.0 Hz, 1H), 7.25-7.15 (m, 1H), 6.77 (d, J=6.0 Hz, 1H), 6.72 (s, 1H), 6.47 (s, 1H), 4.80-4.30 (br, 1H), 3.85-3.75 (m, 2H), 3.42-3.31 (m, 2H), 2.90-2.80 (m, 2H), 2.60-2.40 (m, 1H), 0.70-0.60 (m, 2H), 0.48-0.35 (m, 2H).

Step 5: 1-Cyclopropyl-3-(3-fluoro-4-(2-(1,2,3,6-tetrahydropyridin-4-yl)thieno[3,2-b]pyridin-7-yloxy)phenyl)urea (271-A)

To a stirred solution of the dihydrochloride 271 (150 mg, 0.302 mmol) in EtOAc (50 mL) was added a saturated solution of NaHCO$_3$ (50 mL). The reaction mixture was stirred for 1 h to give a suspension. The solid was collected by filtration, rinsed with water, dried under vacuum and purified by Biotage (SNAP 25 g cartridge; 2% of ammonium hydroxide in MeOH/DCM: 0/100 to 15/85 over 20 CV) to produce a material that upon trituration with AcOEt afforded the title compound 271-A (45 mg, 0.106 mmol, 35% yield) as a white solid. $^1$H NMR (400 MHz, DMSO-d$_6$) δ (ppm): 8.75 (s, 1H), 8.43 (d, =5.6 Hz, 1H), 7.71 (dd, J=2.0 and 13.6 Hz, 1H), 7.47 (s, 1H), 7.34 (t, J=9.2 Hz, 1H), 7.23-7.16 (m, 1H), 6.62 (s, 1H), 6.55 (d, J=5.6 Hz, 1H), 6.43 (s, 1H), 3.40 (bs, 2H), 2.93 (t, J=5.6 Hz, 2H), 2.59-2.50 (m, 1H), 2.46 (bs, 2H), 0.66-0.62 (m, 2H), 0.44-0.40 (m, 2H). MS (m/z): 425.42 (M+H)

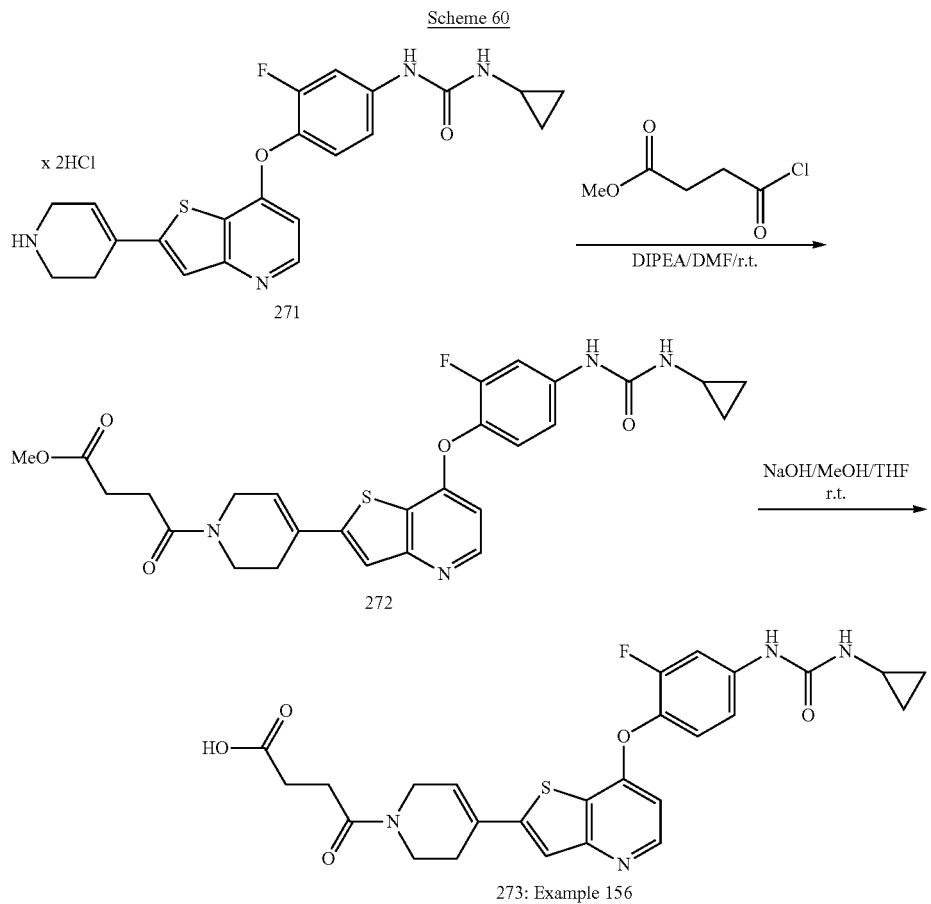

Scheme 60

273: Example 156

Example 156

4-(4-(7-(4-(3-cyclopropylureido)-2-fluorophenoxy)thieno[3,2-b]pyridin-2-yl)-5,6-dihydropyridin-1(2H)-yl)-4-oxobutanoic acid (273)

Step 1. Methyl 4-(4-(7-(4-(3-cyclopropylureido)-2-fluorophenoxy)thieno[3,2-b]pyridin-2-yl)-5,6-dihydropyridin-1(2H)-yl)-4-oxobutanoate (272)

To a stirred suspension of 271 (150 mg, 0.302 mmol) and DIPEA (123 μL, 0.707 mmol) in DMF (10 mL) was added methyl succinyl chloride (65 μl, 0.53 mmol). The reaction mixture was stirred at RT for 2.5 days. Water was added and the reaction mixture was extracted with DCM. The organic layer was successively washed with brine, dried over anhydrous sodium sulfate, filtered and concentrated. The residue was purified by Biotage (SNAP 80 g cartridge; MeOH/DCM: 0/100 to 10/90 over 20 CV), to afford the title compound 272 (120 mg, 0.223 mmol, 63% yield) as an off-white solid. MS (m/z): 539.5 (M+H).

Step 2. 4-(4-(7-(4-(3-cyclopropylureido)-2-fluorophenoxy)thieno[3,2-b]pyridin-2-yl)-5,6-dihydropyridin-1(2H)-yl)-4-oxobutanoic acid (273)

To a stirred suspension of 272 (120 mg, 0.223 mmol) in THF/MeOH (5/5 mL) was added NaOH 1M (3 mL, 3.00 mmol). The reaction mixture was stirred at RT for 16 h and concentrated. The residue was then diluted with water and extracted with DCM/MeOH. The organic layer was successively washed with brine, dried over anhydrous sodium sulfate, filtered and concentrated. The residue was purified by Biotage (SNAP 25 g cartridge; MeOH/DCM: 0/100 to 15/85 over 20 CV) to afford a material that upon trituration with AcOEt afforded the title compound 273 (10 mg, 0.019 mmol, 9% yield) as a white solid. $^1$H NMR (400 MHz, DMSO-d$_6$) δ (ppm): 8.90-8.79 (bs, 1H), 8.35 (d, =5.6 Hz, 1H), 7.64-7.56 (m, 1H), 7.32-7.29 (m, 1H), 7.27-6.96"(m, 4H), 6.68-6.60 (m, 1H), 6.48-6.40 (m, 1H), 5.14-5.01 (m, 1H), 3.94-3.88 (m, 1H), 3.68-3.48 (m, 2H), 2.63-2.56 (m, 2H), 2.50-2.30 (m, 3H), 2.20-2.08 (m, 1H), 1.92-1.79 (m, 1H), 0.57-0.52 (m, 2H), 0.34-0.30 (m, 2H). MS (m/z): 525.39 (M+H).

Compound 274 (example 157) was prepared in one step from compound 271 and 2-(2-methoxyethoxy)acetyl chloride similarly to compound 272 (scheme 60).

TABLE 22

Characterization of compound 274 (example 157)

| Cpd | Ex. | Structure | Characterization |
|---|---|---|---|
| 274 | 157 | 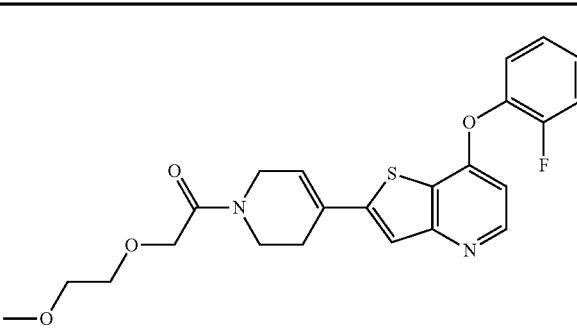<br>1-cyclopropyl-3-(3-fluoro-4-(2-(1-(2-(2-methoxyethoxy(acetyl)-1,2,3,6-tetrahydropyridin-4-yl)thieno[3,2-b]pyridin-7-yloxy)phenyl)urea | $^1$H NMR (400 MHz, DMSO-d$_6$) δ (ppm): 8.83 (s, 1H), 8.45 (d, J = 5.6 Hz, 1H), 7.72 (dd, J = 2.0 and 13.6 Hz, 1H), 7.55 (d, J = 6.8 Hz, 1H), 7.34 (t, J = 9.2 Hz, 1H), 7.19 (d, J = 8.4 Hz, 1H), 6.69 (s, 1H), 6.57 (d, J = 5.6 Hz, 1H), 6.46-6.36 (m, 1H), 4.27-4.12 (m, 4H), 3.73-3.62 (m, 2H), 3.61-3.56 (m, 2H), 3.52-3.47 (m, 2H), 3.25 (s, 3H), 2.73-2.65 (m, 1H), 2.65-2.50 (m, 2H), 0.67-0.62 (m, 2H), 0.44-0.40 (m, 2H). MS (m/z): 541.5 (M + 1). |

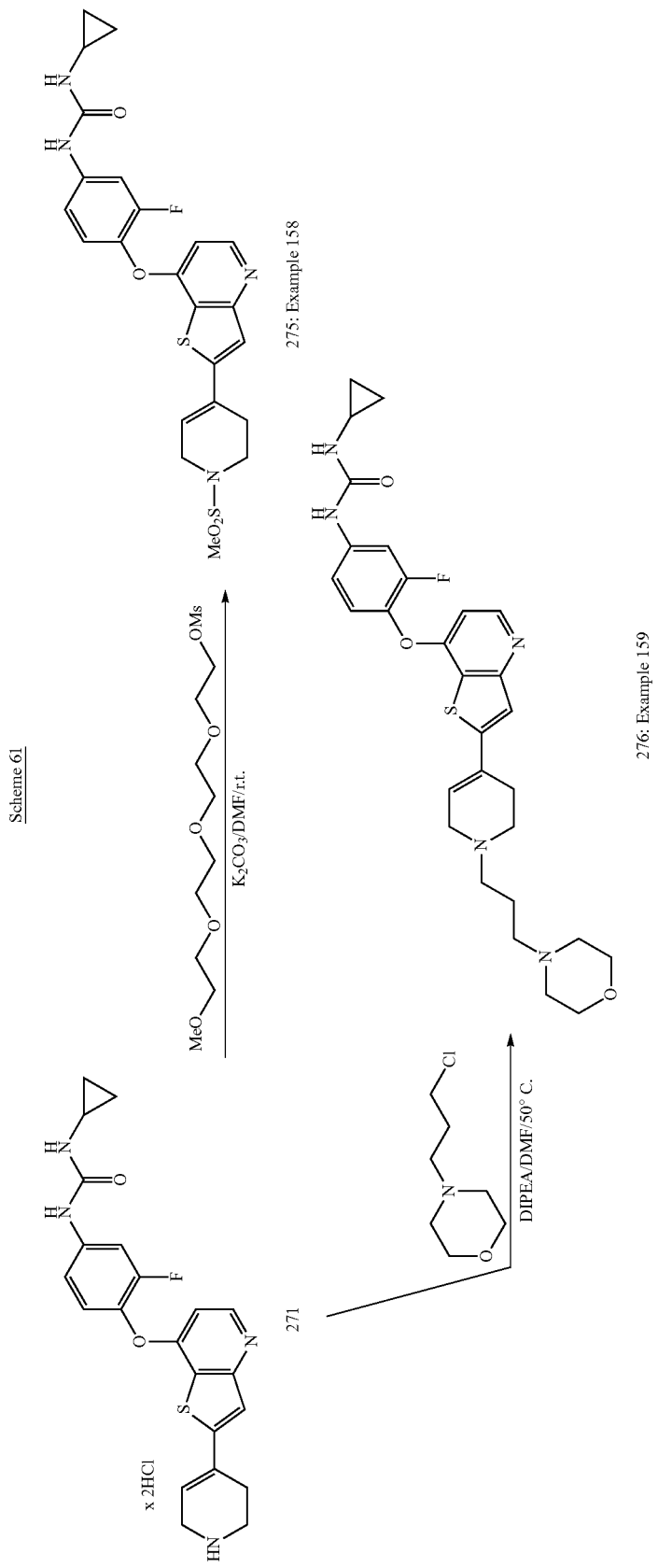

Example 158

1-cyclopropyl-3-(3-fluoro-4-(2-(1-(methylsulfonyl)-1,2,3,6-tetrahydropyridin-4-yl)thieno[3,2-b]pyridin-7-yloxy)phenyl)urea (275)

To a stirred suspension of compound 271 (150 mg, 0.302 mmol) and K$_2$CO$_3$ (180 mg, 1.302 mmol) in DMF (10 mL) was added 2,5,8,11-tetraoxamidecan-13-yl methanesulfonate (112 mg, 0.39 mmol, K. Fukase, et al., SynLett., 2005, 2342-2346). The reaction mixture was stirred at RT for Biotage (SNAP 80 g cartridge; MeOH/DCM: 0/100 to 15/85 over 20 CV) to produce a material that upon trituration with AcOEt afforded title compound 276 (40 mg, 0.07 mmol, 22% yield) as beige solid. $^1$H NMR (400 MHz, DMSO-d$_6$) δ (ppm): 8.77 (s, 1H), 8.44 (d, J=5.2 Hz, 1H), 7.71 (dd, J=2.4 and 13.6 Hz, 1H), 7.48 (s, 1H), 7.34 (t, J=9.2 Hz, 1H), 7.22-7.18 (m, 1H), 6.60 (d, J=2.4 Hz, 1H), 6.55 (d, J=5.2 Hz, 1H), 6.37 (s, 1H), 3.56 (q, J=4.8 Hz, 4H), 3.12 (bs, 2H), 2.70-2.62 (m, 2H), 2.62-2.58 (m, 2H), 2.58-2.50 (m, 1H), 2.43 (t, J=7.2 Hz, 2H), 2.40-2.32 (m, 2H), 2.30 (t, J=7.2 Hz, 2H), 1.64 (quint, J=6.8 Hz, 2H), 0.66-0.62 (m, 2H), 0.44-0.41 (m, 2H). MS (m/z): 552.4. (M+H).

Scheme 62

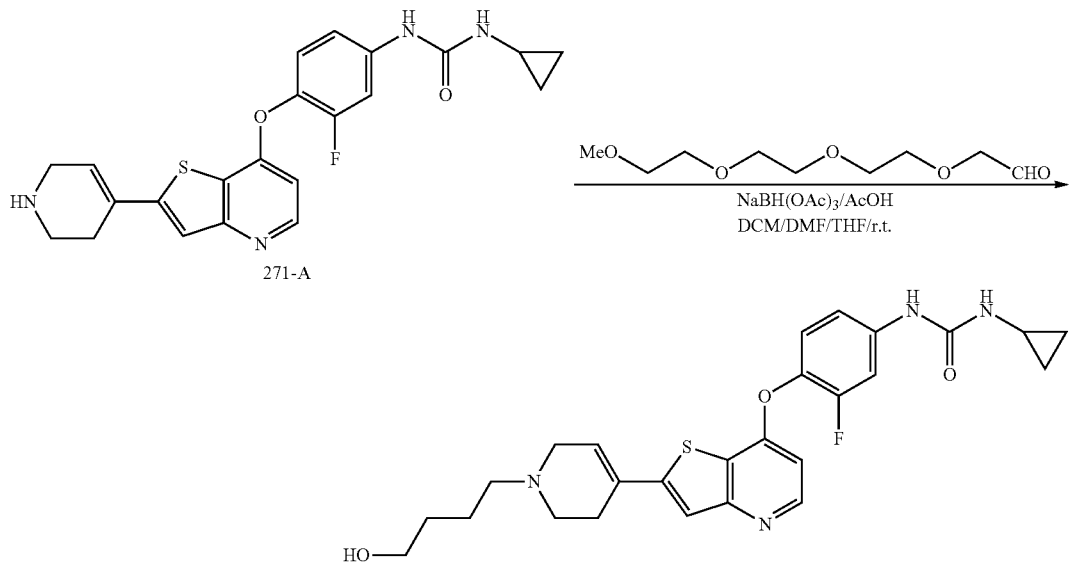

277: Example 160

2.5 days, diluted with water and extracted with EtOAc. The organic extract was washed with brine, dried over anhydrous sodium sulfate, filtered and concentrated. The residue was purified by Biotage (SNAP 80 g cartridge; MeOH/DCM: 0/100 to 15/85 over 20 CV) tp produce a material that upon trituration with Et$_2$O/hexane afforded an unexpected compound 275 (35 mg, 0.07 mmol, 21% yield) as yellow solid. $^1$H NMR (400 MHz, DMSO-d$_6$) δ (ppm): 8.71 (s, 1H), 8.45 (d, J-5.6 Hz, 1H), 7.71 (dd, J=2.8 and 13.6 Hz, 1H), 7.57 (s, 1H), 7.35 (t, J=8.8 Hz, 1H), 7.22-7.16 (m, 1H), 6.02-5.95 (m, 2H), 6.44 (t, J=3.2 Hz, 1H), 3.95-3.90 (m, 2H), 3.42 (t, J=6.4 Hz, 2H), 2.96 (s, 3H), 2.58-2.50 (m, 1H), 0.68-0.62 (m, 2H), 0.44-0.41 (m, 2H). MS (m/z): 503.3 (M+H).

Example 159

1-cyclopropyl-3-(3-fluoro-4-(2-(1-(3-morpholinopropyl)-1,2,3,6-tetrahydropyridin-4-yl)thieno[3,2-b]pyridin-7-yloxy)phenyl)urea (276)

To a stirred solution of compound 271 (150 mg, 0.302 mmol) and DIPEA (227 μl, 1.302 mmol) in DMF (10 mL) was added 4-(3-chloropropyl)morpholine (53.3 mg, 0.325 mmol). The reaction mixture was stirred at 50° C. for 2 h. More 4-(3-chloropropyl)morpholine (212 mg, 1.3 mmol) was added in 4 h and the reaction mixture was heated at 50° C. for an additional 19 h. The reaction mixture was then diluted with water and extracted with EtOAc. The organic extract was washed with brine, dried over anhydrous sodium sulfate, filtered and concentrated. The residue was purified by

Example 160

1-cyclopropyl-3-(3-fluoro-4-(2-(1-(4-hydroxybutyl)-1,2,3,6-tetrahydropyridin-4-yl)thieno[3,2-b]pyridin-7-yloxy)phenyl)urea (277)

To a stirred suspension of compound 271-A (80 mg, 0.188 mmol) and AcOH (12 μl, 0.207 mmol) in DCM (10 mL) was added 2,5,8,11-tetraoxamidecan-13-al (78 mg, 0.377 mmol, L. Gorini, et. al. SynLett., 2006, 948-950). After 30 min, sodium triacetoxyborohydride (120 mg, 0.565 mmol) was added and the reaction mixture was stirred at RT for 1 h. DMF (1 mL) and THF (2 mL) were added to the suspension that was stirred at RT for and additional 18 h. The reaction mixture was diluted with water and concentrated. The residue was purified by Biotage (SNAP 25 g cartridge; MeOH/DCM: 0/100 to 15/85 over 20 CV) to afford a material that upon trituration with MTBE afforded an unexpected compound 277 (30 mg, 0.06 mmol, 32% yield) as beige solid. $^1$H NMR (400 MHz, DMSO-d$_6$) δ (ppm): 8.78 (s, 1H), 8.44 (d, J=5.2 Hz, 1H), 7.71 (dd, J=2.4 and 13.6 Hz, 1H), 7.47 (s, 1H), 7.33 (t, J=9.2 Hz, 1H), 7.22-7.15 (m, 1H), 6.63 (d, J=2.0 Hz, 1H), 6.55 (d, J=5.2 Hz, 1H), 6.37 (s, 1H), 3.40 (t, J=6.4 Hz, 1H), 3.14-3.09 (m, 2H), 2.68-2.50 (m, 5H), 2.40 (t, J=6.4 Hz, 2H), 1.56-1.41 (m, 4H), 0.68-0.61 (m, 2H), 0.44-0.40 (m, 2H). MS (m/z): 497.2 (M+H).

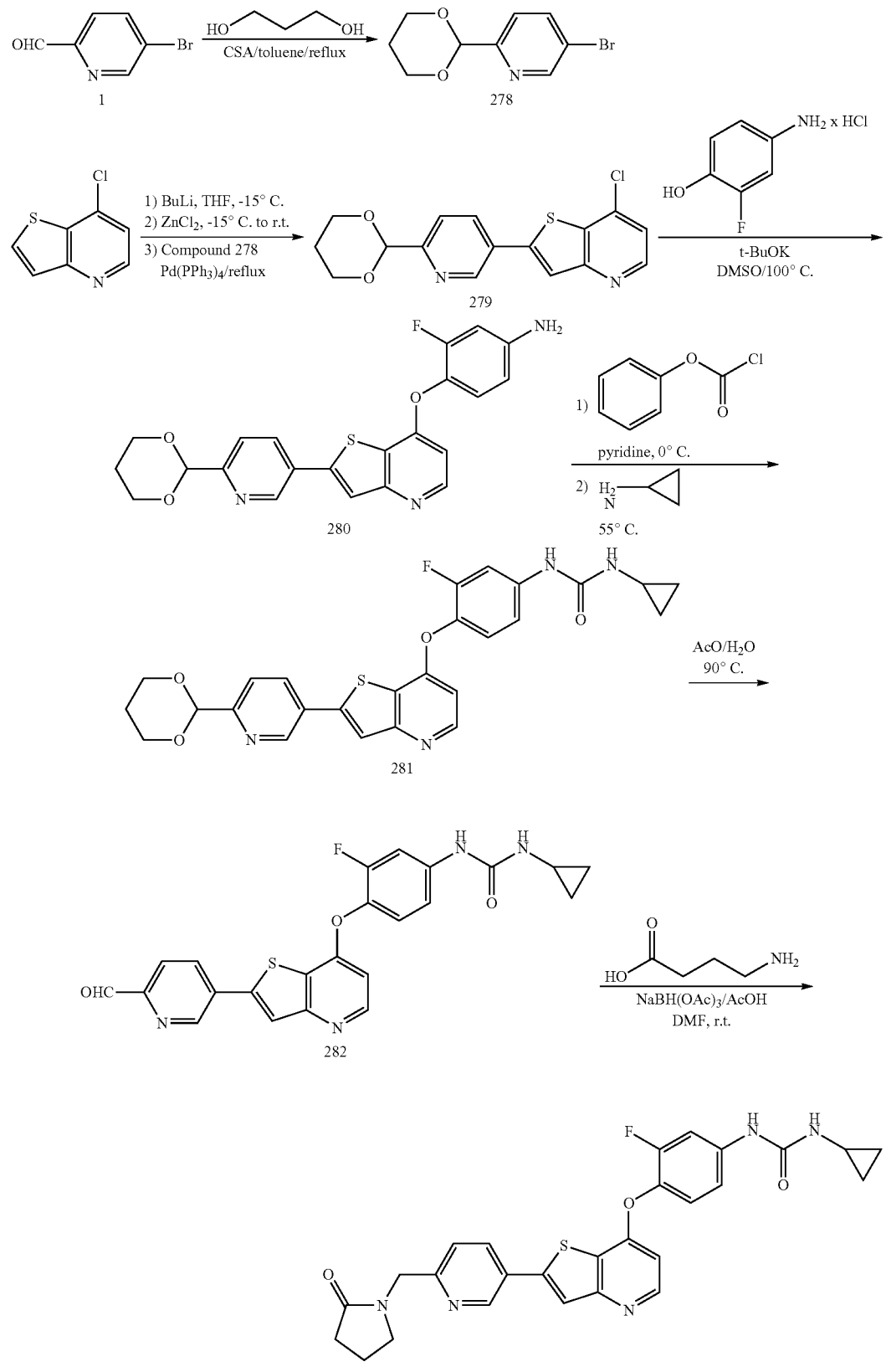

Example 161

1-cyclopropyl-3-(3-fluoro-4-(2-(6-((2-oxopyrrolidin-1-yl)methyl)pyridin-3-yl)thieno[3,2-b]pyridin-7-yloxy)phenyl)urea (283)

Step 1. 5-bromo-2-(1,3-dioxan-2-yl)pyridine (278)

To solution of 5-bromo-2-formylpyridine (10 g, 53.8 mmol), 1,3-propanediol (3.89 mL, 53.8 mmol) in toluene (30 mL) was added CSA (1.249 g, 5.38 mmol). The reaction mixture was heated to reflux for 4 h with a Dean-Stark trap. The reaction mixture was quenched by addition of saturated solution of sodium bicarbonate and extracted with EtOAc. The organic layer was washed with brine, dried over anhydrous sodium sulfate, filtered and concentrated to afford compound 278 (13.37 g, 54.8 mmol, 101% yield, crude) as a brown solid that was used in the next step with no additional purification. MS (m/z): 244.06-246.06 (M+H).

Step 2. 2-(6-(1,3-dioxan-2-yl)pyridin-3-yl)-7-chlorothieno[3,2-b]pyridine (279)

To a stirred solution of 7-chlorothieno[3,2-b]pyridine (12.08 g, 71.2 mmol) in THF (138 mL) at −15° C. was added n-BuLi (30.7 mL, 77.0 mmol). After 30 min, a solution of $ZnCl_2$ 0.5 M in THF (142 mL, 71.2 mmol) was added at −15° C. and the reaction mixture was allowed to warm to RT over 45 min. A solution of palladium tetrakistriphenylphosphine (1.266 g, 1.096 mmol) and bromide 278 (13.37 g, 54.8 mmol) in THF (18.5 mL) was added and the mixture was heated to reflux for 2 h then concentrated. The residue was diluted with water and ammonium hydroxide and extracted with DCM. The organic layer was washed with brine, dried over anhydrous sodium sulfate, filtered and concentrated. The residue was triturated with MTBE to afford the title compound 279 (10.70 g, 32.2 mmol, 59% yield) as light brown solid. MS (m/z): 333.33 (M+H).

Step 3. 4-(2-(6-(1,3-dioxan-2-yl)pyridin-3-yl)thieno[3,2-b]pyridin-7-yloxy)-3-fluoroaniline (280)

To a stirred solution of 4-amino-2-fluorophenol hydrochloride (5.79 g, 35.4 mmol) in DMSO (40 mL) was added t-BuOK (8.66 g, 77.0 mmol). After 30 min, chloride 279 (10.70 g, 32.2 mmol) was added and the reaction mixture was heated at 100° C. for 1.5 h. More solution of 4-amino-2-fluorophenol HCl (860 mg, 7.70 mmol) and t-BuOK (0.86 g, 7.70 mmol) in DMSO (4 mL) was added to the reaction mixture that was heated at 100° C. for an additional 15 min. The reaction mixture was then poured into water (300 mL) to form a precipitate that was collected by filtration, dried under vacuum and triturated with MTBE to afford the title compound 280 (12.39 g, 29.3 mmol, 91% yield) as a beige solid. MS (m/z): 424.39 (M+H).

Step 4. 1-(4-(2-(6-(1,3-dioxan-2-yl)pyridin-3-yl)thieno[3,2-b]pyridin-7-yloxy)-3-fluorophenyl)-3-cyclopropylurea (281)

To a stirred solution of compound 280 (6.32 g, 14.92 mmol) and pyridine (2.41 mL, 17.91 mmol) in DMF (70 mL) at 0° C. was added phenyl chloroformate (2.25 mL, 17.91 mmol). After 30 min cyclopropylamine (2.63 mL, 37.3 mmol) was added at RT and the reaction mixture was heated at 60° C. for 45 min. After cooling to RT the reaction mixture was diluted with water to form a precipitate that was collected by filtration, dried and purified by Biotage (SNAP 100 g cartridge; 2% of ammonium hydroxide in MeOH/DCM: 0/100 to 10/90 over 20 CV), to produce a material that upon trituration with EtOAc afforded the title compound 281 (2.71 g, 5.35 mmol, 36% yield) as a beige solid. MS (m/z): 507.2 (M+H).

Step 5. 1-cyclopropyl-3-(3-fluoro-4-(2-(6-formylpyridin-3-yl)thieno[3,2-b]pyridin-7-yloxy)phenyl)urea (282)

A solution of 281 (2.71 mg, 5.35 mmol) in a mixture AcOH/water (32 mL/8 mL) was heated at 90° C. for 29 h. After cooling to RT the reaction mixture was diluted with water to form a precipitate that was collected by filtration and dried under vacuum to afford the title compound 282 (2.25 g, 5.02 mmol, 94% yield) as a brown solid. MS (m/z): 449.2 (M+H).

Step 6. 1-cyclopropyl-3-(3-fluoro-4-(2-(6-((2-oxopyrrolidin-1-yl)methyl)pyridin-3-yl)thieno[3,2-b]pyridin-7-yloxy)phenyl)urea (283)

To a stirred solution of aldehyde 282 (0.5 g, 1.115 mmol) and AcOH (128 µl, 2.23 mmol) in DMF (10 mL) was added 4-aminobutyric acid (345 mg, 3.34 mmol). After 40 min, sodium triacetoxyborohydride (945 mg, 4.46 mmol) was added and the reaction was stirred at RT for 22 h. The reaction mixture was then diluted with water to form a precipitate that was collected by filtration, dried under vacuum and purified by Biotage (SNAP 50 g cartridge; 2% of ammonium hydroxide in MeOH/DCM: 0/100 to 15/85 over 20 CV) and by Gilson (Phenomenex, Luna 15 µl, C18(2) 100A, 250×50.0 mm, 15 µm; 0.05% of formic acid in both MeOH/water:30/80 to 95/5 over 60 min, flow; 30 mL/min), to afford the title compound 283 (20 mg, 0.04 mmol, 3% yield) as a white solid. $^1$H NMR (400 MHz, DMSO-d$_6$) δ (ppm): 9.28 (s, 1H), 9.06 (d, J=2.4 Hz, 1H), 8.53 (d, J=5.6 Hz, 1H), 8.42 (bs, 1H), 8.26 (dd, J=2.4 and 8.0 Hz, 1H), 8.25 (s, 1H), 7.74 (dd, J=2.0 and 13.6 Hz, 1H), 7.41-7.34 (m, 2H), 7.24-7.20 (m, 1H), 7.08 (bs, 1H), 6.62 (d, J=5.6 Hz, 1H), 4.53 (s, 2H), 2.58-2.51 (m, 1H), 2.32 (t, J=8.0 Hz, 2H), 1.98 (quin, J=7.2 Hz, 2H), 0.65-0.60 (m, 2H), 0.45-0.40 (m, 2H). MS (m/z): 518.5 (M+H).

Scheme 64

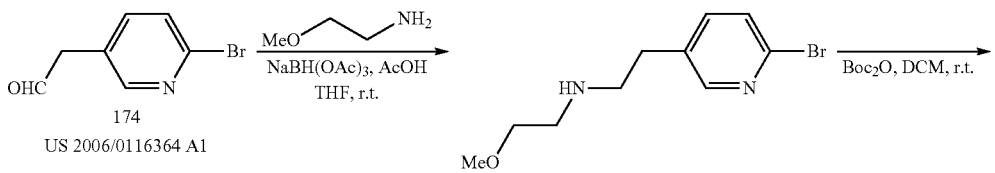

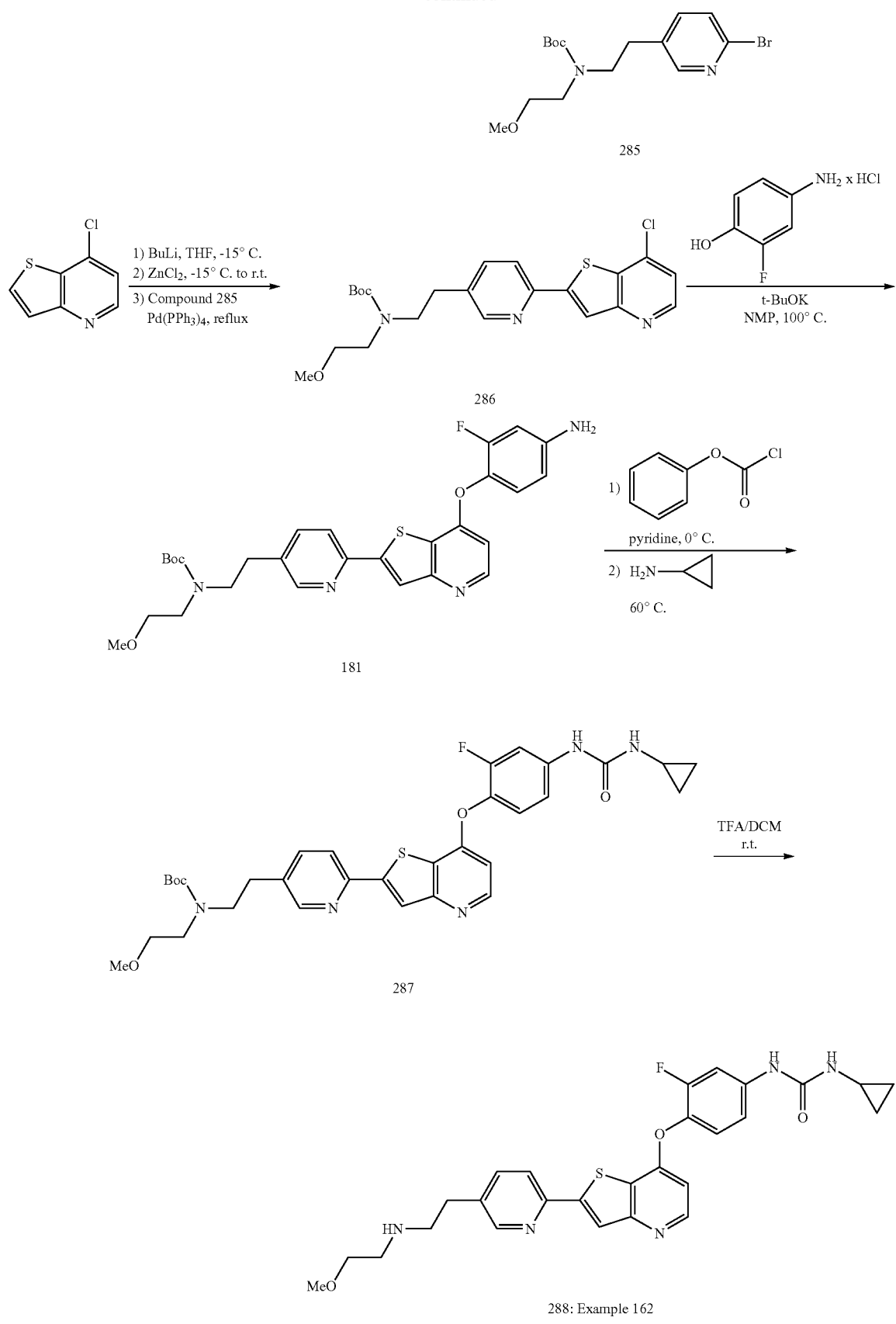

Example 162

1-cyclopropyl-3-(3-fluoro-4-(2-(5-(2-(2-methoxyethylamino)ethyl)pyridin-2-yl)thieno[3,2-b]pyridin-7-yloxy)phenyl)urea (288)

Step 1. 2-(6-bromopyridin-3-yl)-N-(2-methoxyethyl)ethanamine (284)

To solution of aldehyde 174 (6.93 g, 34.6 mmol, scheme 42), 2-methoxyethylamine (9.04 mL, 104 mmol) and AcOH (2.08 mL, 36.4 mmol) in DCM (77 mL) at 0° C. was added sodium triacetoxyborohydride (18.36 g, 87 mmol). The reaction mixture was stirred at RT for 18 h. The reaction was quenched by addition of HCl 10%, and the mixture was extracted with HCl 10%. The acidic aqueous extract was basified at 0° C. with 4M aqueous NaOH solution (pH 10) and further extracted with DCM. The organic layer was successively washed with water, brine, dried over anhydrous sodium sulfate, filtered and concentrated to afford title compound 284 (6.79 g, 26.2 mmol, 76% yield, crude) as an yellow oil that was used in the next step with no additional purification. $^1$H. MS (m/z): 258.9-260.9 (M+H).

Step 2. tert-butyl 2-(6-bromopyridin-3-yl)ethyl(2-methoxyethyl)carbamate (285)

To a solution of crude 284 (6.79 g, 26.2 mmol) in DCM (52 mL) was added di-tert-butyl dicarbonate (9.13 mL, 93.3 mmol). The reaction mixture was stirred at RT for 18 h then concentrated. The residue was purified by Biotage (SNAP 100 g cartridge; AcOEt/Hex:0/100 to 30/70 over 20 CV). The desired fractions were collected and concentrated to afford the title compound 285 (5.53 g, 15.39 mmol, 59% yield) as light yellow oil. MS (m/z): 359.1-361.1 (M+H).

Step 3. tert-butyl 2-(6-(7-chlorothieno[3,2-b]pyridin-2-yl)pyridin-3-yl)ethyl(2-methoxyethyl)carbamate (286)

To a stirred solution of 7-chlorothieno[3,2-b]pyridine (4.26 g, 25.09 mmol) in THF (64 mL) at −15° C. was added n-BuLi (10.77 mL, 25.09 mmol). After 30 min, ZnCl$_2$ (3.42 g, 25.09 mmol) was added at −15° C. and the reaction mixture was allowed to warm to RT over 45 min. A solution of palladium tetrakistriphenylphosphine (0.387 g, 0.335 mmol) and bromide 285 (6.01 g, 16.73 mmol) in THF (20 mL) was added and the mixture was heated to reflux for 1 h and concentrated. The reaction was quenched by addition of water and ammonium hydroxide and the mixture was extracted with DCM. The extract was washed with brine, dried over anhydrous sodium sulfate, filtered and concentrated. The residue was purified by Biotage (SNAP 340 g cartridge; AcOEt/Hex:50/50 to 100/0 over 20 CV), to afford title compound 286 (3.74 g, 8.35 mmol, 50% yield) as yellow oil. MS (m/z): 448.48 (M+H).

Step 4. tert-butyl 2-(6-(7-(4-amino-2-fluorophenoxy)thieno[3,2-b]pyridin-2-yl)pyridin-3-yl)ethyl(2-methoxyethyl)carbamate (181, scheme 44)

To a stirred solution of 4-amino-2-fluorophenol HCl (2.01 g, 12.32 mmol) in NMP (13 mL) was added t-BuOK (3.0 g, 26.7 mmol). After 30 min, chloride 286 (4.6 g, 10.27 mmol) was added and the reaction mixture was heated at 100° C. for 1.5 h. The reaction mixture was poured into water (100 mL) to form a precipitate that was collected by filtration, dried and triturated with MTBE, to afford the title compound 181 (2.98 g, 5.53 mmol, 54% yield) as a beige solid. MS (m/z): 538.8 (M+H).

Step 5. tert-butyl 2-(6-(7-(4-(3-cyclopropylureido)-2-fluorophenoxy)thieno[3,2-b]pyridin-2-yl)pyridin-3-yl)ethyl(2-methoxyethyl)carbamate (287)

To a stirred solution of compound 181 (1.0 g, 1.58 mmol) and pyridine (450 mL, 5.56 mmol) in DMF (25 mL) at 0° C. was added phenyl chloroformate (582 µl, 4.64 mmol). After 2 h cyclopropylamine (643 µl, 9.28 mmol) was added at RT and the reaction mixture was heated at 60° C. for 5 h. After cooling to RT the reaction was quenched by addition of water and the mixture extracted with AcOEt. The extract was successively washed with water, NaOH 1N, saturated solution of ammonium chloride, brine, dried over anhydrous magnesium sulfate, filtered and concentrated. The residue was purified by Biotage (SNAP 80 g cartridge; MeOH/DCM: 1/99 to 10/90 over 20 CV), to afford the title compound 287 (840 mg, 1.35 mmol, 86% yield) as a pink solid. MS (m/z): 622.5 (M+H).

Step 6. 1-cyclopropyl-3-(3-fluoro-4-(2-(5-(2-(2-methoxyethylamino)ethyl)pyridin-2-yl)thieno[3,2-b]pyridin-7-yloxy)phenylurea (288)

To a solution of 287 (840 mg, 1.35 mmol) in DCM (25 mL) was added TFA (10 mL) and the reaction mixture was stirred for 18 h. The reaction mixture was concentrated, diluted with water and 4N NaOH to pH 13 to form a precipitate which was collected by filtration, washed with water, and dried and purified twice by Biotage (SNAP 50 g; MeOH/DCM: 1/99 to 15/85 over 20 CV) to produce a material that upon trituration with MeOH afforded the title compound 288 (338 mg, 0.65 mmol, 48% yield) as a white solid. $^1$H NMR (400 MHz, DMSO-d$_6$) δ (ppm): 8.72 (s, 1H), 8.54-8.49 (m, 2H), 8.30 (s, 1H), 8.19 (d, J=8.2 Hz, 1H), 7.81 (dd, J=8.0, 2.2 Hz, 1H), 7.73 (dd, J=13.5, 2.5 Hz, 1H), 7.38 (t, J=9.1 Hz, 1H), 7.20 (bd, J=8.6 Hz, 1H), 6.63 (d, J=5.5 Hz, 1H), 6.58 (bd, J=2.5 Hz, 1H), 3.37 (t, J=5.7 Hz, 2H), 3.23 (s, 3H), 2.84-2.73 (m, 4H), 2.68 (t, J=5.7 Hz, 2H), 2.59-2.51 (m, 1H), 2.00-1.50 (m, 1H), 0.72-0.58 (m, 2H), 0.50-0.36 (m, 2H).). MS (m/z): 522.6 (M+H).

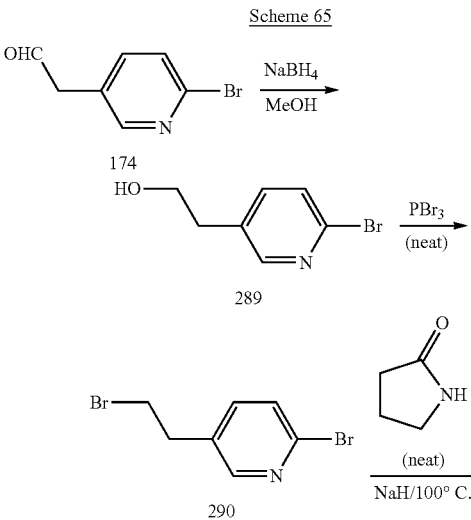

Scheme 65

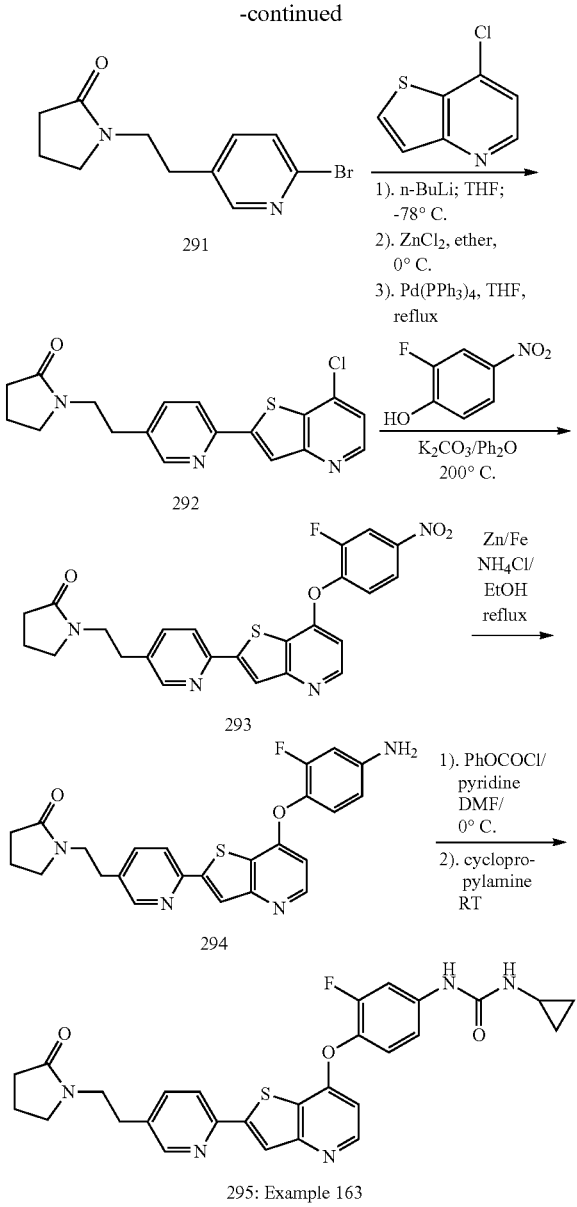

Step 2. 2-bromo-5-(2-bromoethyl)pyridine (290)

Alcohol 289 (1.75 g, 8.66 mmol) was treated with phosphorous tribromide (5.0 mL, 53 mmol) and the mixture was heated for 5 min, until the solid had melted and re-solidified. The mixture was cooled, treated with ice and partitioned between saturated aqueous sodium bicarbonate and dichloromethane. The organic phase was collected, washed with saturated aqueous sodium bicarbonate and brine, dried (anhydrous $MgSO_4$), filtered and concentrated. Silica gel chromatography of the residue (eluent DCM) provided title compound 290 (2.0 g, 7.6 mmol, 87% yield) as a colorless solid. MS (M+H): 266.0

Step 3. 1-(2-(6-bromopyridin-3-yl)ethyl)pyrrolidin-2-one (291)

To a mixture of dibromide 290 (1.7 g, 6.4 mmol) in 2-pyrrolidone (10 mL, 130 mmol) at room temperature was added sodium hydride, 40% dispersion in mineral oil (1.16 g, 19.3 mmol). This reaction mixture was then heated to 100° C. for 2 h, then cooled to RT and partitioned between water and ethyl acetate. The organic phase was collected, washed with water, saturated aqueous ammonium chloride, and brine. It was then dried (anhydrous $MgSO_4$), filtered and concentrated. Silica gel chromatography (10% methanol/ethyl acetate) gave title compound 291 (1.3 g, 75% yield) as a colorless solid. $^1$H NMR (400 MHz, $CDCl_3$) δ (ppm): 8.17-8.16 (m, 1H); 7.42-7.37 (m, 2H); 3.49 (t, J=7.4, 2H); 3.28 (t, J=6.9, 2H); 2.79 (t, J=7.2, 2H); 2.30 (t, J=7.8, 2H); 1.95 (quintet, 7.6, 2H). MS (M+H): 269.1, 271.1

Step 4. 1-(2-(6-(7-chlorothieno[3,2-b]pyridin-2-yl)pyridin-3-yl)ethyl)pyrrolidin-2-one (292)

To 7-chlorothienopyridine (0.95 g, 5.6 mmol) in THF (75 mL) at −78° C. was added n-butyllithium (2.5 M in hexanes, 2.4 mL, 6.0 mmol), dropwise. The solution was stirred for 30 min then warmed to 0° C. and zinc chloride (1.0 M in ether, 6.5 mL, 6.5 mmol) was added. The reaction mixture was stirred for 20 min, then bromide 291 (1.25 g, 4.64 mmol) and tetrakis(triphenylphosphine) palladium (0.5.4 g, 0.46 mmol) in THF (15 mL) were added. The mixture then was heated to reflux for 3 h and cooled to RT. The excess base was quenched with 1 mL saturated aqueous ammonium chloride, and the mixture was concentrated. The residue was partitioned between water and diethyl ether, producing a yellow precipitate, which was isolated by suction filtration, triturated with ethyl acetate and dried in vacuo to give title compound 292 (1.2 g, 72%). MS (M+H): 358.3

Step 5: 1-(2-(6-(7-(2-fluoro-4-nitrophenoxy)thieno[3,2-b]pyridin-2-yl)pyridin-3-yl)ethyl)pyrrolidin-2-one (293)

To chlorothienopyridine 292 (1.2 g, 3.4 mmol) in diphenyl ether (20 mL) was added 2-fluoro-4-nitrophenol (1.58 g, 10.1 mmol) and potassium carbonate (2.32 g, 16.8 mmol) and the resultant mixture was heated to 200° C. for 10 h. Extra 2-fluoro-4-nitrophenol (1.58 g, 10.1 mmol) and potassium carbonate (2.32 g, 16.8 mmol) were added and the mixture was heated at 200° C. for a further 6 h. The mixture was cooled to RT, partitioned between ethyl acetate and 1M aqueous NaOH then filtered through celite. The organic phase was collected, washed with water and brine, dried (anhydrous $MgSO_4$), filtered and concentrated. The residue was purified by silica gel chromatography (10% methanol/ethyl acetate) to afford title compound 293 (0.76 g, 47% yield), contaminated with ~10% starting material 292, as a yellow solid. MS (M+H): 479.5

Example 163

1-cyclopropyl-3-(3-fluoro-4-(2-(5-(2-(2-oxopyrrolidin-1-yl)ethyl)pyridin-2-yl)thieno[3,2-b]pyridin-7-yloxy)phenyl)urea (295)

Step 1. 2-(6-bromopyridin-3-yl)ethanol (289)

To a solution of aldehyde 174 (1.4 g, 7.0 mmol, schemes 42 and 64) in methanol (100 mL) was added sodium borohydride (0.27 g, 7.0 mmol) and the mixture was stirred at room temperature for 30 min. Water (1 mL) was added, and the mixture was concentrated. The residue was then partitioned between ethyl acetate and water. The organic phase was dried (anhydrous $MgSO_4$), filtered and concentrated. Silica gel chromatography (10% methanol/ethyl acetate) of the residue gave title compound 289 (1.0 g, 71% yield) as a colorless solid. MS (M+H): 202.1, 204.1

Step 6: 1-(2-(6-(7-(4-amino-2-fluorophenoxy)thieno[3,2-b]pyridin-2-yl)pyridin-3-yl)ethyl)pyrrolidin-2-one (294)

To impure 293 (0.76 g, 1.6 mmol) in EtOH (75 mL) was added zinc dust (1.04 g, 15.9 mmol), iron filings (0.89 g, 16 mmol) and saturated aqueous ammonium chloride solution (2 mL). The resultant mixture was heated to reflux for 18 h, then cooled, filtered through celite, concentrated and re-dissolved in dichloromethane. The solution was washed with water, 1 M NaOH, and brine, dried (anhydrous MgSO$_4$), filtered, concentrated and the residue was purified by silica gel chromatography (15% MeOH/chloroform) to afford title compound 294 (0.33 g, 46% yield). MS (M+H): 449.2

Step 7: 1-cyclopropyl-3-(3-fluoro-4-(2-(5-(2-(2-oxopyrrolidin-1-yl)ethyl)pyridin-2-yl)thieno[3,2-b]pyridin-7-yloxy)phenyl)urea (295)

To a solution of 294 (0.33 g, 0.74 mmol) and pyridine (0.13 mL, 1.6 mmol) in DMF (15 mL) at 0° C. was added phenyl chloroformate (0.12 mL, 0.96 mmol). The reaction mixture was stirred for 15 min then cyclopropylamine (2.0 mL, 28 mmol) was added. The mixture was warmed to RT, stirred for an additional 18 h and partitioned between water and ethyl acetate. The organic phase was collected, washed with water, 1M NaOH, and brine, dried (anhydrous MgSO$_4$), filtered and concentrated. The residue was purified by silica gel chromatography (20% methanol/ethyl acetate) to afford title compound 295 (0.21 g, 54%). $^1$H NMR (400 MHz, DMSO-d$_6$) δ (ppm): 8.71 (s, 1H); 8.52-8.50 (m, 2H); 8.31 (s, 1H); 8.20 (d, J=8.2, 1H): 7.82 (dd, J=8.2, 2.2, 1H); 7.73 (dd, J=13.5, 2.5, 1H); 7.38 (t, J=9.0, 1H); 7.22-7.18 (m, 1H); 6.64 (d, J=5.5, 1H); 6.59 (d, J=2.5, 1H); 3.48 (t, J=7.0, 2H); 3.35 (t?, obscured by water peak), 2.85 (t, J=6.8, 2H); 2.58-2.52 (m, 1H); 2.16 (t. J=7.8, 2H); 1.89 (quintet, J=7.4, 2H); 0.68-0.63 (m, 2H); 0.45-0.41 (m, 2H). MS: (calc.) 531.17 (found) 532.4 (MH)$^+$ Scheme 66

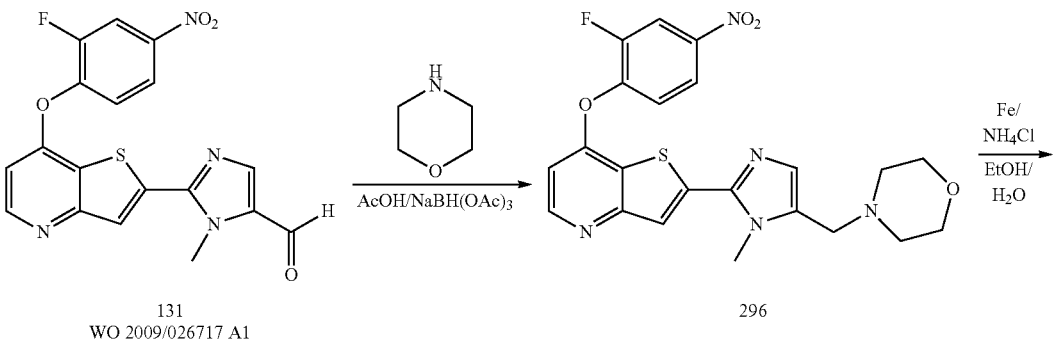

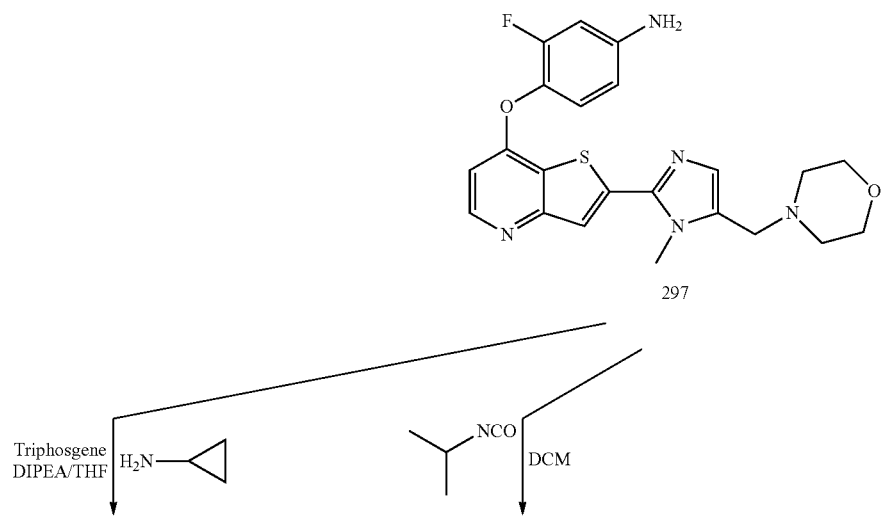

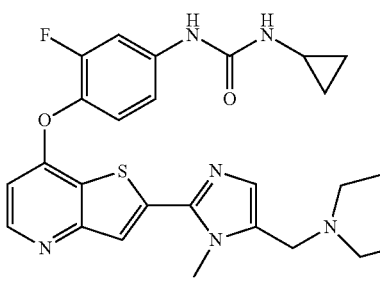

298: Example 164

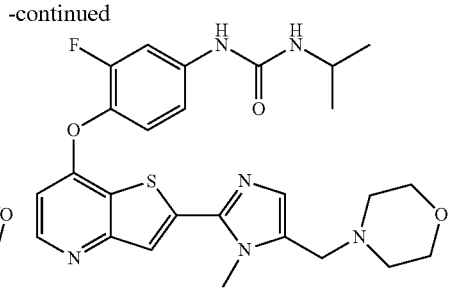

299: Example 165

Example 164

1-cyclopropyl-3-(3-fluoro-4-(2-(1-methyl-5-(morpholinomethyl)-1H-imidazol-2-yl)thieno[3,2-b]pyridin-7-yloxy)phenylurea (298)

Step 1: 4-((2-(7-(2-fluoro-4-nitrophenoxy)thieno[3,2-b]pyridin-2-yl)-1-methyl-1H-imidazol-5-yl)methyl)morpholine (296)

To a suspension of aldehyde 131 (0.8 g, 2.008 mmol, scheme 33) and morpholine (0.437 mL, 5.02 mmol) in dichloromethane (40.2 mL) was added acetic acid (0.230 mL, 4.02 mmol) and the reaction mixture was stirred for 1 h. Sodium triacetoxyborohydride (1.277 g, 6.02 mmol) was added and the mixture was stirred for an additional 4 h. The reaction mixture was extracted with 1M HCl and the organic phase was discarded. The aqueous phase was neutralized with 3M NaOH and extracted with dichloromethane. The DCM extract was washed with brine, dried (anhydrous Na₂SO₄), and evaporated to afford title compound 296 (907 mg, 1.932 mmol, 96% yield, crude). The material was used in the next step with no additional purification. MS: 470 (MH+).

Step 2: 3-fluoro-4-(2-(1-methyl-5-(morpholinomethyl)-1H-imidazol-2-yl)thieno[3,2-b]pyridin-7-yloxy)aniline (297)

A mixture of nitro compound 296 (907 mg, 1.932 mmol), iron powder (917 mg, 16.42 mmol) and ammonium chloride (89 mg, 1.661 mmol) in a solvent system ethanol (24.0 mL) and water (12.0 mL) was heated to 90° C. for 1 hr. The reaction mixture was filtered while hot and concentrated. The residue was purified by Biotage (MeOH.DCM, 0-20%, SNAP 25 g cartridge) to give title compound 297 (700 mg, 1.593 mmol, 82% yield) as a white solid. MS: 440 (MH+).

Step 3: 1-cyclopropyl-3-(3-fluoro-4-(2-(1-methyl-5-(morpholinomethyl)-1H-imidazol-2-yl)thieno[3,2-b]pyridin-7-yloxy)phenyl)urea (298)

To a solution of aniline 297 (200 mg, 0.455 mmol) in THF (20 mL) at 0° C. was added DIPEA (0.318 mL, 1.820 mmol) and triphosgene (81 mg, 0.273 mmol). The mixture was stirred at 0° C. for 1 hr before cyclopropylamine (0.160 mL, 2.275 mmol) was added, and was allowed to warm to RT over 1 hr. The mixture was concentrated and purified by Biotage (MeOH/DCM, 0-22%, SNAP 25 g cartridge) to afford title compound 298 (54 mg, 0.103 mmol, 22.7% yield) as a white solid. ¹H NMR (400 MHz, DMSO-d₆) δ (ppm): 8.69 (s, 1H), 8.50 (d, 1H, J=5.5 Hz), 7.89 (s, 1H), 7.70 (dd, 1H, J1=2.3 Hz, J2=13.9 Hz), 7.35 (t, 1H, J=9.0 Hz), 7.18-7.16 (m, 1H), 6.96 (s, 1H), 6.65 (d, 1H, J=5.5 Hz), 6.55-6.54 (m, 1H), 3.91 (s, 3H), 3.55 (t, 4H, J=3.4 Hz), 3.51 (s, 2H), 2.54-2.51 (m, 1H), 2.37 (m, 4H), 0.65-0.61 (m, 2H), 0.42-0.38 (m, 2H). MS: 523.6 (MH)+

Example 165

1-(3-fluoro-4-(2-(1-methyl-5-(morpholinomethyl)-1H-imidazol-2-yl)thieno[3,2-b]pyridin-7-yloxy)phenyl)-3-isopropylurea (299)

Title compound 299 was obtained starting from the compound 297 and following a procedure similar to the one used in the synthesis of compound 201 (scheme 48). NMR (400 MHz, DMSO-d₆) δ (ppm): 8.73 (s, 1H), 8.55 (d, 1H, J=5.4 Hz), 7.94 (s, 1H), 7.73 (dd, 1H, J1=2.4 Hz, J2=13.5 Hz), 7.40 (t, 1H, J=9.0 Hz), 7.17-7.15 (m, 1H), 7.02 (s, 1H), 6.69 (d, 1H, J=5.5 Hz), 6.19 (d, 1H, 7.6 Hz), 3.97 (s, 3H), 3.83-3.78 (m, 1H), 3.62-3.60 (t, 4H, J=4.1 Hz), 3.57 (s, 2H), 2.43 (m, 4H), 1.15 (s, 3H), 1.14 (s, 3H), 525.5 (MH)+

Scheme 67

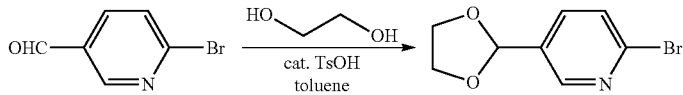

300

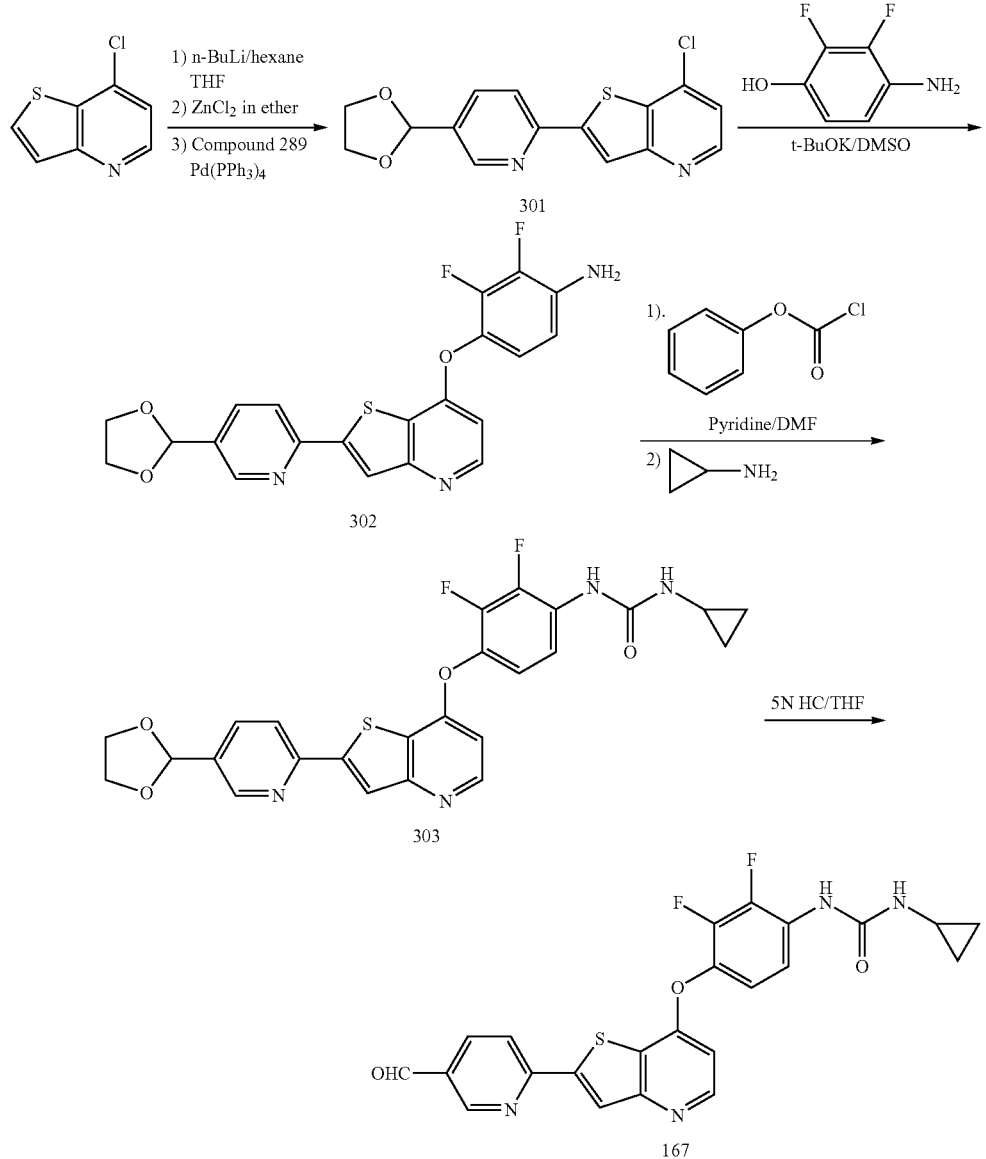

1-Cyclopropyl-3-(2,3-difluoro-4-(2-(5-formylpyri-din-2-yl)thieno[3,2-b]pyridin-7-yloxy)phenyl)urea (167, scheme 41)

Step 1: 2-bromo-5-(1,3-dioxolan-2-yl)pyridine (300)

To a solution of 6-bromonicotinaldehyde (10.1 g, 51.6 mmol) in toluene (400 mL) was added ethylene glycol (11.4 mL, 206 mmol) and p-toluenesulfonic acid (0.98 g, 5.16 mmol), and the reaction mixture was heated to reflux with azeotropic removal of the water using a Dean-Stark trap, for 2.5 h. The mixture was cooled down and washed with saturated NaHCO₃ solution and brine. The organic phase was dried over anhydrous MgSO₄ and concentrated to afford title compound 300 (11.7 g, 98% yield) as a brown solid, which was used in the next step without further purification. $^1$H NMR (300 MHz, DMSO-$d_6$) δ (ppm): 8.46 (d, J=2.7 Hz, 1H), 7.65 (dd, J=8.1, 2.7 Hz, 1H), 7.51 (d, J=8.1 Hz, 1H), 5.83 (s, 1H), 4.20-4.00 (m, 4H).

Step 2: 2-(5-(1,3-Dioxolan-2-yl)pyridin-2-yl)-7-chlorothieno[3,2-b]pyridine (301)

To a solution of 7-chlorothieno[3,2-b]pyridine (14 g, 82.4 mmol) in THF (137 mL) was added, at −78° C., a solution of n-BuLi (34.4 mL, 89.3 mmol, 2.6 M in hexanes) and the reaction mixture was stirred for 10 min. A solution of ZnCl₂ (89 mL, 89.3 mmol, 1.0 M in Et₂O) was added and the mixture was stirred at RT for 10 min. Pd(PPh₃)₄ (3.18 g, 2.75 mmol) was added along with a solution of 300 (15.8 g, 68.7 mmol) in THF (50 mL) and the reaction mixture was heated to reflux under an atmosphere of N₂ gas for 1 hour. The reaction mixture was then cooled to RT, and partitioned between saturated ammonium hydroxide solution and EtOAc. The organic phase was collected, dried over anhydrous Na₂SO₄, filtered and concentrated. The resultant material was triturated with EtOAc to afford the title compound 301 (21.4 g, 98% yield) as a beige solid. $^1$H NMR (300 MHz, DMSO-$d_6$) δ (ppm): 8.71 (d, J=2.1 Hz, 1H), 8.67 (d, J=5.1 Hz, 1H), 8.49 (s, 1H), 8.36 (d, J=8.1 Hz, 1H), 8.01 (dd, J=8.1, 2.1 Hz, 1H), 7.61 (d, J=5.1 Hz, 1H), 5.91 (s, 1H), 4.16-3.96 (m, 4H).

Step 3: 4-(2-(5-(1,3-Dioxolan-2-yl)pyridin-2-yl) thieno[3,2-b]pyridin-7-yloxy)-2,3-difluoroaniline (302)

To a solution of 4-amino-2,3-difluorophenol (1.59 g, 7.49 mmol) in DMSO (10 mL) was added potassium tert-butoxide (1.1 g, 8.98 mmol), and the reaction mixture was stirred for 2 hours. Chloride 301 (1.6 g, 4.99 mmol) was added and the reaction mixture was heated at 100° C. for 2 hours. The mixture was cooled down then poured into water (150 mL) at 40-45° C. and stirred for 30 min. The precipitate was collected by filtration, washed with water and dried overnight. The crude product was triturated with EtOAc/Hexane (2/1, 100 mL) for 1 h, to afford title compound 302 (1.7 g, 79% yield) as a pale violet solid. $^1$H NMR (300 MHz, DMSO-$d_6$) δ (ppm): 8.70 (d, J=2.1 Hz, 1H), 8.53 (d, J=5.4 Hz, 1H), 8.39 (s, 1H), 8.31 (d, J=8.1 Hz, 1H), 7.98 (dd, J=8.1, 2.1 Hz, 1H), 7.10-7.00 (m, 1H), 6.71 (d, J=5.1 Hz, 1H), 6.72-6.61 (m, 1H), 5.90 (s, 1H), 5.64 (s, 2H), 4.16-3.96 (m, 4H).

Step 4: 1-(4-(2-(5-(1,3-Dioxolan-2-yl)pyridin-2-yl) thieno[3,2-b]pyridin-7-yloxy)-2,3-difluorophenyl)-3-cyclopropylurea (303)

To a solution of 302 (1.7 g, 3.98 mmol) in DMF (7 mL) was added pyridine (0.55 mL, 6.77 mmol) at RT and the resultant reaction mixture was stirred for 10 min under Ar atmosphere. Phenyl chloroformate (0.75 mL, 5.97 mmol) was added at 0° C. and the mixture was stirred at RT for an additional 40 min. Cyclopropylamine (1.1 mL, 15.9 mmol) was added to the mixture, and the reaction mixture was warmed to 50° C. and stirred for 2 hours. The mixture was then cooled, poured into water (150 mL) and stirred for 30 min. The precipitate was collected by filtration, washed with water and dried overnight. The crude product was triturated with EtOAc for 1 h and collected by filtration to afford title compound 303 (1.75 g, 86% yield) as a pale violet solid. $^1$H NMR (300 MHz, DMSO-$d_6$) δ (ppm): 8.71 (d, J=2.1 Hz, 1H), 8.55 (d, J=5.4 Hz, 1H), 8.46 (s, 1H), 8.42 (s, 1H), 8.33 (d, J=8.1 Hz, 1H), 8.10-7.95 (m, 1H), 7.99 (dd, J=8.1, 2.1 Hz, 1H), 7.40-7.22 (m, 1H), 6.87 (br, 1H), 6.78 (d, J=5.1 Hz, 1H), 5.90 (s, 1H), 4.16-3.96 (m, 4H), 2.64-2.50 (m, 1H), 0.75-0.60 (m, 2H), 0.50-0.35 (m, 2H)

Step 5: 1-Cyclopropyl-3-(2,3-difluoro-4-(2-(5-formylpyridin-2-yl)thieno[3,2-b]pyridin-7-yloxy) phenyl)urea (167, scheme 41)

To a suspension of 303 (1.75 g, 3.43 mmol) in THF (56 mL) was added aqueous 5N HCl solution (14 mL, 70 mmol) at 0° C. and the reaction mixture was stirred at RT. After 2 hours, the mixture was concentrated, basified with aqueous 5N NaOH solution and stirred at RT for 1 hour. The precipitate was collected by filtration and dried to afford title compound 167 (1.55 g, 97% yield) as a beige solid. $^1$H NMR (300 MHz, DMSO-$d_6$) δ (ppm): 10.14 (s, 1H), 9.14 (d, J=2.1 Hz, 1H), 8.59 (d, J=5.4 Hz, 1H), 8.59 (s, 1H), 8.54 (d, J=8.1 Hz, 1H), 8.49 (s, 1H), 8.10-8.00 (m, 1H), 7.35-7.25 (m, 1H), 6.89 (br, 1H), 6.82 (d, J=5.1 Hz, 1H), 2.64-2.50 (m, 1H), 0.75-0.60 (m, 2H), 0.50-0.35 (m, 2H)

Scheme 68

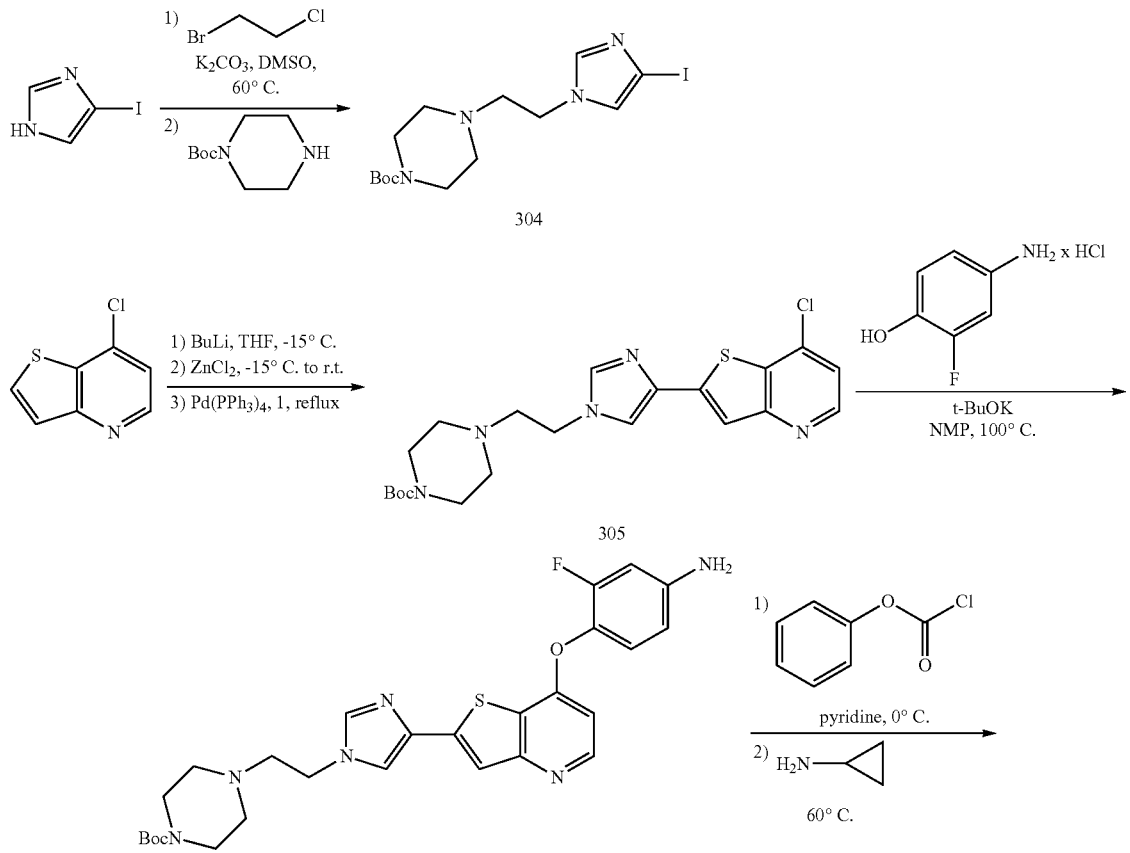

-continued

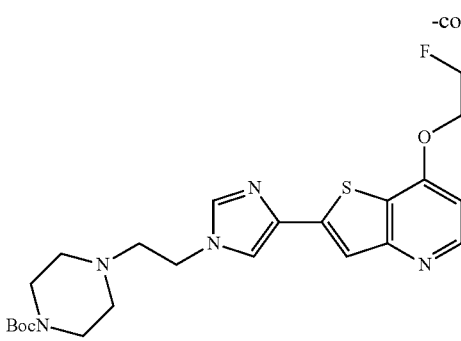

307

TFA/DCM/room temp →

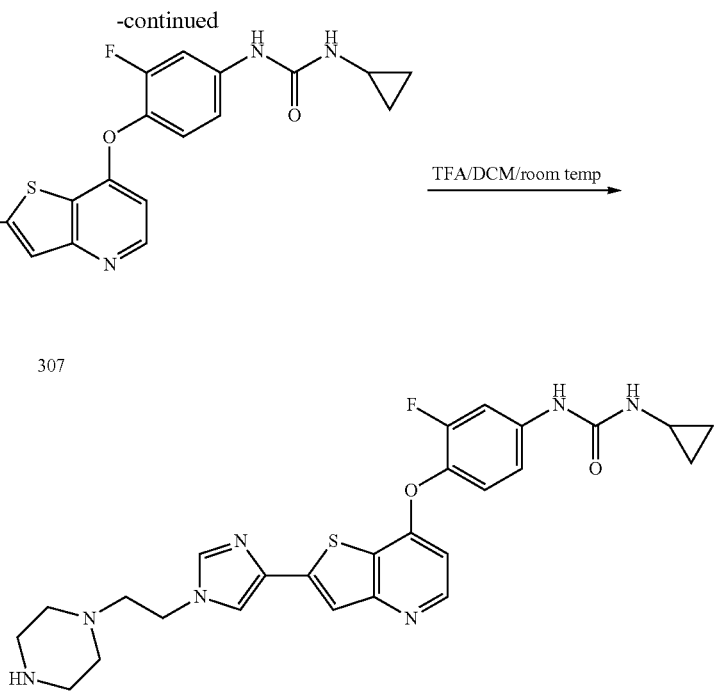

308: Example 166

Example 166

1-cyclopropyl-3-(3-fluoro-4-(2-(1-(2-(piperazin-1-yl)ethyl)-1H-imidazol-4-yl)thieno[3,2-b]pyridin-7-yloxy)phenyl)urea (308)

Step 1. tert-butyl 4-(2-(4-iodo-1H-imidazol-1-yl)ethyl)piperazine-1-carboxylate (304)

To a stirred solution of 4-iodoimidazole (25 g, 129 mmol) and 1-bromo-2-chloroethane (12.87 ml, 155 mmol) in DMSO (250 ml) under nitrogen was added $K_2CO_3$ (26.7 g, 193 mmol). The reaction mixture was heated at 80° C. for 30 min. More 1-bromo-2-chloroethane (1.28 ml, 15.5 mmol) was added and the reaction mixture was heated at 80° C. for an additional 30 min. Finally, 1-Boc-piperazine (28.8 g, 155 mmol) was added and the reaction mixture heated at 80° C. for 1 h, cooled to RT and partitioned between water and AcOEt. The organic layer was collected, washed with brine, dried over anhydrous sodium sulfate, filtered and concentrated. The residue was purified by Biotage (SNAP 340 g cartridge; Hexane/AcOEt:40/60 to 0/100 over 15 CV) followed by another purification under different conditions (SNAP 100 g cartridge; MeOH/DCM: 0/100 to 5/95 over 15 CV), to afford title compound 304 (4 g, 9.85 mmol, 8% yield) as white solid. MS (m/z): 407.18 (M+H).

Step 2. tert-butyl 4-(2-(4-(7-chlorothieno[3,2-b]pyridin-2-yl)-1H-imidazol-1-yl)ethyl)piperazine-1-carboxylate (305)

To a stirred solution of 7-chlorothieno[3,2-b]pyridine (2.95 g, 17.39 mmol) in THF (60 ml) at −15° C. was added n-BuLi (2.5M, 6.96 ml, 17.39 mmol). After 30 min, a solution of $ZnCl_2$ in $Et_2O$ (1M, 17.39 mL, 17.39 mmol) was added at −15° C. and the reaction mixture was warmed to RT over 45 min. A solution of palladium tetrakistriphenylphosphine (0.268 g, 0.232 mmol) and 304 (4.71 g, 11.59 mmol) in THF (18 ml) was added and the mixture was heated to reflux for 1 h then concentrated. The residue was diluted with water and ammonium hydroxide and extracted with DCM. The organic layer was washed with brine, dried over anhydrous sodium sulfate, filtered and concentrated. The residue was triturated with a mixture of MTBE/Hexane, to afford the title compound 305 (3.75 g, 8.37 mmol, 72% yield) as a beige solid. MS (m/z): 448.46 (M+H).

Step 3. tert-butyl 4-(2-(4-(7-(4-amino-2-fluorophenoxy)thieno[3,2-b]pyridin-2-yl)-1H-imidazol-1-yl)ethyl)piperazine-1-carboxylate (306)

To a stirred solution of 4-amino-2-fluorophenol x HCl (1.64 g, 10.05 mmol) in NMP (30 mL) was added t-BuOK (2.25 g, 20.1 mmol). After 30 min, compound 305 (3.75 g, 8.37 mmol) was added and the reaction mixture was heated at 100° C. for 1 h. A solution of 4-amino-2-fluorophenol HCl (1.64 g, 10.05 mmol) in NMP (30 mL) in a separate flask was treated with t-BuOK (2.25 g, 20.1 mmol) and the resultant phenolate solution was added to the reaction mixture at 100° C. After 30 min, the reaction was quenched by addition of water and the precipitate was collected by filtration, dried and triturated with MTBE to afford the title compound 306 (2.10 g, 3.90 mmol, 47% yield) as a beige solid. MS (m/z): 539.39 (M+H).

Step 4. tert-butyl 4-(2-(4-(7-(4-(3-cyclopropylureido)-2-fluorophenoxy)thieno[3,2-b]pyridin-2-yl)-1H-imidazol-1-yl)ethyl)piperazine-1-carboxylate (307)

To a stirred solution of 306 (2.10 g, 3.90 mmol) and pyridine (631 μl, 4.68 mmol) in DMF (20 ml) at 0° C. was added phenyl chloroformate (587 μl, 4.68 mmol). After 45 min cyclopropylamine (687 μl, 9.75 mmol) was added at 0° C. and the reaction mixture was heated at 60° C. for 30 min. After cooling to RT the reaction mixture was quenched by addition of water and extracted with AcOEt. The organic layer was washed with brine, dried over anhydrous sodium sulfate, filtered and concentrated. The residue was purified by Biotage (SNAP 100 g cartridge; MeOH/DCM: 0/100 to 10/90 over 20 CV), to afford the title compound 307 (1.4 g, 2.25 mmol, 58% yield) as a beige solid. MS (m/z): 622.33 (M+H).

Step 5. 1-cyclopropyl-3-(3-fluoro-4-(2-(1-(2-(piperazin-1-yl)ethyl)-1H-imidazol-4-yl)thieno[3,2-b]pyridin-7-yloxy)phen 1 urea (308)

To a solution of 307 (1.4 g, 2.25 mmol) in DCM (30 ml) was added TEA (2 mL) and the reaction mixture was stirred for 1 h. More TFA (3 mL) was added and the reaction mixture was stirred for an additional 3 h then concentrated, diluted with water and 1M NaOH to pH 11. The solid was collected by filtration, rinsed with water and dried. The residue was purified by Biotage (SNAP 80 g cartridge; 2% of ammonium hydroxide in MeOH/DCM: 0/100 to 35/65 over 30 CV), to afford the title compound 308 (870 mg, 1.67 mmol, 74% yield) as a beige solid.

$^1$H NMR (400 MHz, DMSO-d$_6$): δ (ppm): 8.75 (s, 1H), 8.42 (d, J=5.6 Hz, 1H), 7.91 (s, 1H), 7.76 (s, 1H), 7.72 (dd, J=2.4 and 13.6 Hz, 1H), 7.65 (s, 1H), 7.35 (t, J=8.8 Hz, 1H), 7.19 (d, J=8.8 Hz, 1H), 6.60 (bs, 1H), 6.54 (d, J=5.6 Hz, 1H), 4.12 (t, J=6.0 Hz, 2H), 2.68 (t, J=4.8 Hz, 4H), 2.62 (t, J=6.0 Hz, 2H), 2.59-2.50 (m, 1H), 2.41-2.30 (m, 4H), 0.69-0.60 (m, 2H), 0.45-0.40 (m, 2H). MS (m/z): 522.6 (M+H).

Compounds 309 (example 167) and 310 (example 168) were prepared by reacting compounds 307 (scheme 68) and compound 49 (scheme 15) with acetoxyacetic acid, similarly to compound 30 (scheme 13). Compound 311 (example 169) was synthesized by following the procedures described above for the synthesis of compound 49 (scheme 15). Compounds 312 (example 170) and 313 (example 171) were obtained similarly to compound 31 (scheme 13). Compound 314 (example 172) was synthesized by following the procedures described above for the synthesis of compound 75 (scheme 20).

TABLE 23

Characterization of compounds 309-314 (examples 167-172)

| Cpd | Ex. | Structure | Characterization |
|---|---|---|---|
| 309 | 167 | 2-(4-(2-(4-(7-(4-(3-cyclopropylureido)-fluorophenoxy)thieno[3,2-b]pyridin-2-yl)-1H-imidazol-1-yl)ethyl)piperazin-1-yl)-2-oxoethyl acetate | $^1$H NMR (400 MHz, DMSO-d$_6$) δ (ppm): 8.89 (s, 1H), 8.42 (d, J = 5.6 Hz, 1H), 7.93 (d, J = 0.8 Hz, 1H), 7.79 (d, J = 0.8 Hz, 1H), 7.72 (dd, J = 2.4 and 13.6 Hz, 1H), 7.67 (s, 1H), 7.35 (t, J = 9.2 Hz, 1H), 7.22-7.16 (m, 1H), 6.58-6.54 (m, 1H), 6.54 (d, J = 5.6 Hz, 1H), 4.76 (s, 2H), 4.15 (J = 6.0 Hz, 2H), 3.39-3.31 (m, 4H), 2.70 (t, J = 6.0 Hz, 2H), 2.58-2.51 (m, 1H), 2.48-2.40 (m, 4H), 2.06 (s, 3H), 0.69-0.62 (m, 2H), 0.46-0.40 (m, 2H). MS(m/z): 622.7 (M + 1). |
| 310 | 168 | 2-(4-((6-(7-(4-(3-cyclopropylureido)-2-fluorophenoxy)thieno[3,2-b]pyridin-2-yl)pyridin-3-yl)methyl)piperazin-1-yl)-2-oxoethyl acetate | $^1$H NMR (300 MHz, DMSO-d6) δ (ppm): 8.73 (br, 1H), 8.58 (s, 1H), 8.52 (d, J = 5.4 Hz, 1H), 8.34 (s, 1H), 8.26 (d, J = 8.1 Hz, 1H), 7.88 (dd, J = 7.8, 1.8 Hz, 1H), 7.73 (dd, J = 13.8, 2.4 Hz, 1H), 7.38 (t, J = 9.0 Hz, 1H), 7.23-7.19 (m, 1H), 6.65 (d, J = 5.4 Hz, 1H), 6.59 (d, J = 2.1 Hz, 1H), 4.76 (s, 2H), 3.61 (s, 2H), 3.48-3.36 (m, 4H), 2.57-2.53 (m, 1H), 2.44-2.37 (m, 4H), 2.07 (s, 3H), 0.67-0.62 (m, 2H), 0.46-0.41 (m, 2H). MS (m/z): 619.7 (MH)+ |
| 311 | 169 | 1-cyclopropyl-3-(3-fluoro-4-(2-(5-((hexahydropyrrolo[3,4-c]pyrrol-2(1H)-yl)methyl)pyridin-2-yl)thieno[3,2-b]pyridin-7-yloxy)phenyl)urea | $^1$H NMR (400 MHz, DMSO-d$_6$) δ (ppm): 8.78 (bs, 1H), 8.54 (d, J = 1.6 Hz, 1H), 8.52 (d, J = 5.5 Hz, 1H), 8.32 (s, 1H), 8.23 (d, J = 7.6 Hz, 1H), 7.85 (dd, J = 8.1, 2.0 Hz, 1H), 7.73 (dd, J = 13.6, 2.4 Hz, 1H), 7.38 (t, J = 9.0 Hz, 1H), 7.20 (dd, J = 8.7, 1.5 Hz, 1H), 6.64-6.60 (m, 2H), 3.58 (s, 2H), 2.81-2.71 (m, 2H), 2.60-2.50 (m, 7H), 2.31-2.23 (m, 2H), 0.72-0.58 (m, 2H), 0.50-0.37 (m, 2H), one NH is missing. MS (m/z): 545.5 (M + 1). |

TABLE 23-continued

Characterization of compounds 309-314 (examples 167-172)

| Cpd | Ex. | Structure | Characterization |
|---|---|---|---|
| 312 | 170 | 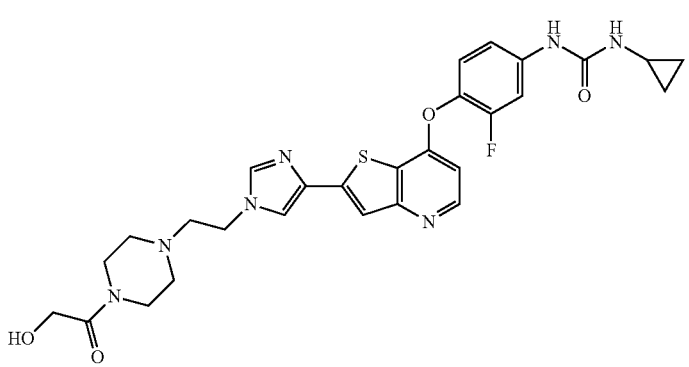 [SMILES: O=C(Nc1ccc(Oc2ccnc3cc(-c4cn(CCN5CCN(C(=O)CO)CC5)cn4)sc23)c(F)c1)NC1CC1]<br>1-cyclopropyl-3-(3-fluoro-4-(2-(1-(2-(4-(2-hydroxyacetyl)piperazin-1-yl)ethyl)-1H-imidazol-4-yl)thieno[3,2-b]pyridin-7-yloxy)phenyl)urea | $^{1}$H NMR (400 MHz, DMSO-$d_6$) δ (ppm): 8.72 (s, 1H), 8.42 (d, J = 5.6 Hz, 1H), 7.93 (d, J = 1.2 Hz, 1H), 7.79 (d, J = 0.8 Hz, 1H), 7.72 (dd, J = 2.4 and 13.6 Hz, 1H), 7.66 (s, 1H), 7.35 (t, J = 9.2 Hz, 1H), 7.21-7.16 (m, 1H), 6.60-6.56 (m, 1H), 6.54 (d, J = 5.6 Hz, 1H), 4.55 (t, J = 5.6 Hz, 2H), 4.14 (t, J = 6.0 Hz, 1H), 4.07 (d, J = 6.0 Hz, 2H), 3.50-3.44 (m, 2H), 3.35-3.30 (m, 2H), 2.69 (t, J = 6.0 Hz, 2H), 2.59-2.51 (m, 1H), 2.49-2.40 (m, 4H), 0.68-0.62 (m, 2H), 0.45-0.41 (m, 2H). MS (m/z): 580.6 (M + 1). |
| 313 | 171 | 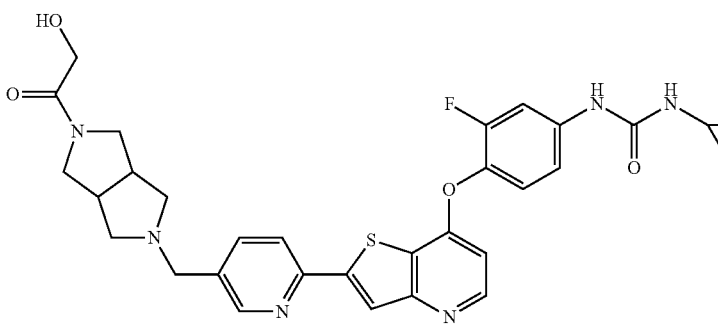<br>1-cyclopropyl-3-(3-fluoro-4-(2-(5-((5-(2-hydroxyacetyl)hexahydropyrrolo[3,4-c]-pyrrol-2(1H)-yl)methyl)pyridin-2-yl)thieno[3,2-b]pyridin-7-yloxy)phenyl)urea | $^{1}$H NMR (400 MHz, DMSO-$d_6$) δ (ppm): 8.72 (s, 1H), 8.55 (bd, J = 1.2 Hz, 1H), 8.52 (d, J = 5.5 Hz, 1H), 8.32 (s, 1H), 8.23 (d, J = 8.2 Hz, 1H), 7.85 (dd, J = 8.1, 1.7 Hz, 1H), 7.73 (dd, J = 13.5, 2.3 Hz, 1H), 7.38 (t, J = 9.1 Hz, 1H), 7.20 (dd, J = 8.8, 1.4 Hz, 1H), 6.65 (d, J = 5.3 Hz, 1H), 6.57 (bd, J = 2.3 Hz, 1H), 4.51 (t, J = 5.6 Hz, 1H), 4.06-3.92 (m, 2H), 3.64 (bs, 2H), 3.62-3.49 (m, 2H), 3.34-3.17 (m, 2H), 2.91-2.69 (m, 2H), 2.61-2.51 (m, 3H), 2.50-2.41 (m, 2H), 0.72-0.59 (m, 2H), 0.50-0.36 (m, 2H). MS (m/z): 603.7 (M + 1). |
| 314 | 172 | 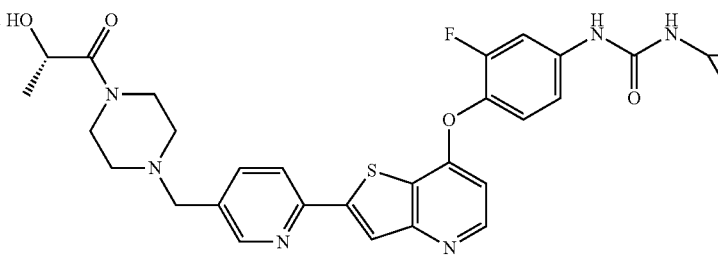<br>(S)-1-cyclopropyl-3-(3-fluoro-4-(2-(5-((4-(2-hydroxypropanoyl)piperazin-1-yl)methyl)pyridin-2-yl)thieno[3,2-b]pyridin-7-yloxy)phenyl)urea | $^{1}$H NMR (400 MHz, DMSO-$d_6$) δ (ppm): 8.74 (s, 1H), 8.57 (bd, J = 1.4 Hz, 1H), 8.52 (d, J = 5.5 Hz, 1H), 8.34 (s, 1H), 8.26 (d, J = 8.0 Hz, 1H), 7.88 (dd, J = 8.2, 2.2 Hz, 1H), 7.73 (dd, J = 13.6, 2.4 Hz, 1H), 7.38 (t, J = 9.1 Hz, 1H), 7.20 (dd, J = 8.8, 1.2 Hz, 1H), 6.65 (d, J = 5.3 Hz, 1H), 6.60 (bd, J = 2.3 Hz, 1H), 4.88 (d, J = 7.0 Hz, 1H), 4.40 (quint, J = 6.7 Hz, 1H), 3.59 (s, 2H), 3.59-3.39 (m, 4H), 2.59-2.51 (m, 1H), 2.47-2.30 (m, 4H), 1.16 (d, J = 6.5 Hz, 3H), 0.72-0.58 (m, 2H), 0.50-0.36 (m, 2H). MS (m/z): 591.7 (M + 1). |

Scheme 69

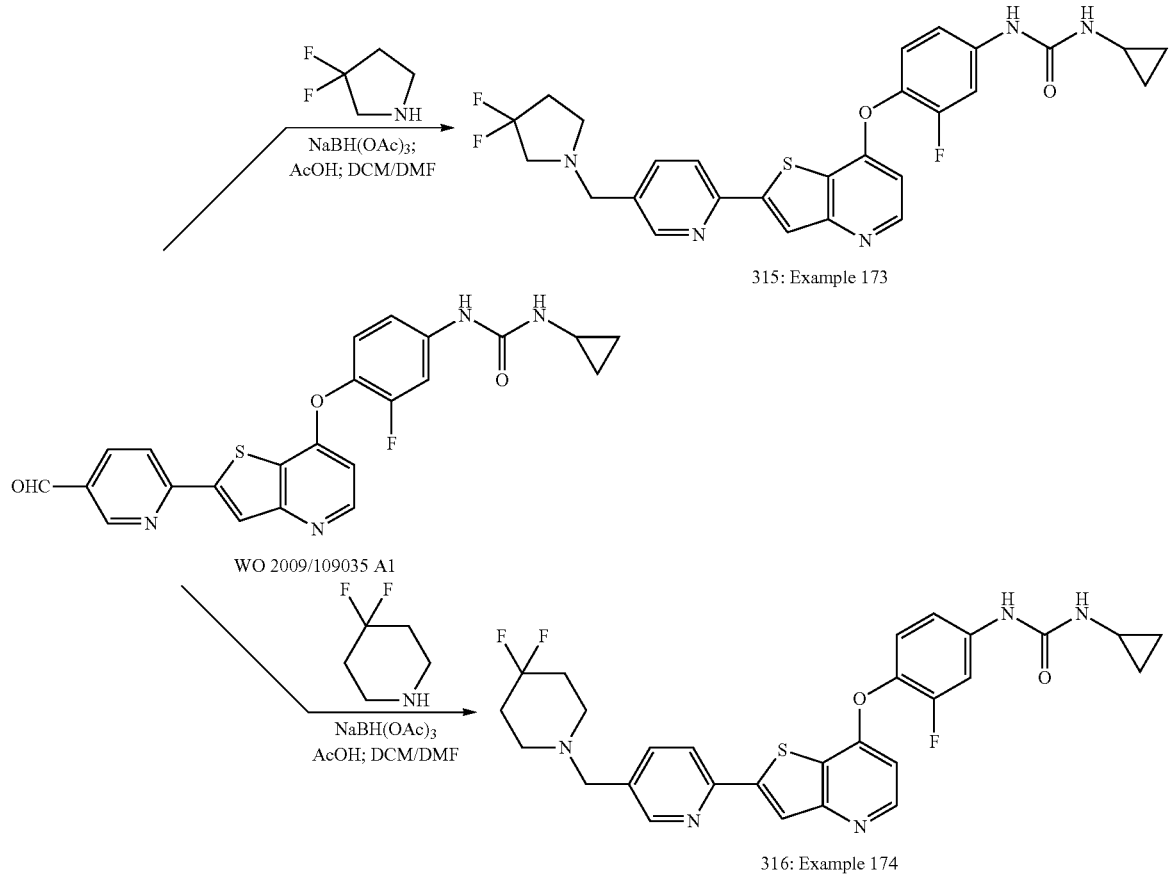

315: Example 173

316: Example 174

Example 173

1-cyclopropyl-3-(4-(2-(5-((3,3-difluoropyrrolidin-1-yl)methyl)pyridin-2-yl)thieno[3,2-b]pyridin-7-yloxy)-3-fluorophenyl)urea, (315)

3,3-Difluoropyrollidine hydrochloride (0.200 g, 1.39 mmol) was suspended in DCM and washed with 3M NaOH. The organic phase was separated, dried over anhydrous MgSO$_4$ and filtered into a solution of aldehyde 47 (0.090 g, 0.20 mmol) and acetic acid (0.03 mL, 0.5 mmol) in a 10:1 dichloromethane/DMF mixture (45 mL), which was stirred for 20 min at RT. Then sodium triacetoxyborohydride (0.128 g, 0.60 mmol) was added and the reaction mixture was stirred at RT for 18 h and partitioned between dichloromethane and water. The organic phase was washed with saturated aqueous NaHCO$_3$, then dried (anhydrous MgSO$_4$) and concentrated. Silica gel chromatography (10% methanol/ethyl acetate), of the residue followed by a second column (10% methanol/chloroform) afforded title compound 315 (0.045 g, 42% yield) as a colorless solid. $^1$H NMR (400 MHz, DMSO-d$_6$) δ (ppm): 8.74 (s, 1H); 8.57 (d, J=2.7, 1H); 8.52 (d, J=5.3, 1H); 8.34 (s, 1H); 8.26 (d, J=8.0, 1H); 7.88 (dd, J=8.2, 2.1, 1H); 7.73 (dd, J=13.7, 2.5, 1H); 7.38 (t, J=9.0, 1H); 7.22-7.19 (m, 1H); 6.65 (d, J=5.3, 1H); 6.60 (d, J=2.7, 1H); 3.71 (s, 2H); 2.92 (t, J=13.3, 2H); 2.73 (t, J=7.0, 2H); 2.57-2.52 (m, 1H); 2.27 (septet, J=7.0, 2H); 0.67-0.63 (m, 2H); 0.45-0.41 (m, 2H). MS (m/z): 540.6 (M+1).

Example 174

1-cyclopropyl-3-(4-(2-(5-((4,4-difluoropiperidin-1-yl)methyl)pyridin-2-yl)thieno[3,2-b]pyridin-7-yloxy)-3-fluorophenyl)urea (316)

3,3-Difluoropiperidine hydrochloride (0.250 g, 2.06 mmol) was suspended in DCM and washed with 3M NaOH. The organic phase was separated, dried over anhydrous MgSO$_4$ and filtered into a solution of aldehyde 47 (0.100 g, 0.22 mmol) and acetic acid (0.04 mL, 0.7 mmol) in a 10:1 dichloromethane/DMF mixture (45 mL) which was stirred for 20 min at RT. Then sodium triacetoxyborohydride (0.142 g, 0.67 mmol) was added and the reaction mixture was stirred at RT for 18 h and partitioned between dichloromethane and water. The organic phase was washed with saturated aqueous NaHCO$_3$, then dried (anhydrous MgSO$_4$) and concentrated. Silica gel chromatography of the residue (10% methanol/chloroform) afforded title compound 316 (0.055 g, 45% yield) as a colorless solid. $^1$H NMR (400 MHz, DMSO-d$_6$) δ (ppm): 8.72 (s, 1H); 8.56 (d, J=2.7, 1H); 8.52 (d, J=5.3, 1H); 8.32 (s, 1H); 8.23 (d, J=8.0, 1H); 7.88 (d, J=8.2, 1H); 7.73 (dd, J=13.7, 1H); 7.38 (t, J=9.0, 1H); 7.22-7.18 (m, 1H); 6.65 (d, J=5.3, 1H); 6.60 (s, 1H); 3.62 (s, 2H); 135-3.30 (m, 4H?, under water peak); 2.57-2.52 (m, 1H); 2.00-1.90 (m 2H); 0.67-0.63 (m, 2H); 0.45-0.41 (m, 2H). MS (m/z): 554.6 (M+1).

Compound 317 (example 175) and 318 (example 176) were synthesized by following the procedures described above for the synthesis of compound 49 (scheme 15). Compounds 319 (example 177) and 320 (example 178) were prepared from compounds 317 and compound 318, similarly to compound 31 (scheme 13). Compound 321 (example 179) was obtained by following the procedure described above for the synthesis of compounds 315 and 316 (scheme 69). Compound 322 (example 180) was synthesized from compound 308 (scheme 68) [alkylation by (2-bromoethoxy)(tert-butyl)dimethylsilane followed by a deprotection of the tert-butyldimethylsilyloxy)ethyl)-intermediate with TBAF].

TABLE 24

Characterization of compounds 317-322 (examples 175-180)

| Cpd | Ex. | Structure | Characterization |
|---|---|---|---|
| 317 | 175 | 1-(4-(2-(5-(2,7-diazaspiro[4.4]nonan-2-ylmethyl)pyridin-2-yl)thieno[3,2-b]pyridin-7-yloxy)-3-fluorophenyl)-3-cyclopropylurea | $^1$H NMR (400 MHz, DMSO-d$_6$) δ (ppm): mixture of rotamers, 8.87 (bs, 1H), 8.56 (bd, J = 1.6 Hz, 1H), 8.51 (d, J = 5.3 Hz, 1H), 8.32 (s, 1H), 8.23 (dd, J = 8.1, 0.7 Hz, 1H), 7.86 (dd, J = 8.0, 2.2 Hz, 1H), 7.73 (dd, J = 13.6, 2.5 Hz, 1H), 7.37 (t, J = 9.0 Hz, 1H), 7.21 (dd, J = 9.0, 1.4 Hz, 1H), 6.71 (bd, J = 2.5 Hz, 1H), 6.64 (dd, J = 5.3, 0.8 Hz, 1H), 3.67 (d, J = 13.7 Hz, 1H), 3.62 (d, J = 13.7 Hz, 1H), 2.88-2.77 (m, 2H), 2.76 (d, J = 10.4 Hz, 1H), 2.68-2.60 (m, 2H), 2.59-2.51 (m, 2H), one CH is masked by water peak, 2.32 (d, J = 9.0 Hz, 1H), 1.80-1.60 (m, 4H), 0.71-0.57 (m, 2H), 0.49-0.36 (m, 2H), one NH is missing. MS(m/z): 559.6 (M + 1). |
| 318 | 176 | 1-(4-(2-(5-(3,9-diazaspiro[5.5]undecan-3-ylmethyl)pyridin-2-yl)thieno-[3,2-b]pyridin-7-yloxy)-3-fluorophenyl)-3-cyclopropylurea | $^1$H NMR (400 MHz, DMSO-d6) δ (ppm): 8.80 (bs, 1H), 8.56-8.48 (m, 2H), 8.31 (s, 1H), 8.22 (d, J = 8.0 Hz, 1H), 7.83 (dd, J = 8.2, 2.0 Hz, 1H), 7.73 (dd, J = 13.6, 2.4 Hz, 1H), 7.38 (t, J = 9.1 Hz, 1H), 7.21 (dd, J = 9.0, 1.2 Hz, 1H), 6.68-6.61 (m, 2H), 3.53 (s, 2H), 2.69-2.59 (m, 4H), 2.58-2.51 (m, 1H), 2.40-2.28 (m, 4H), 1.52-1.24 (m, 8H), 0.72-0.58 (m, 2H), 0.49-0.36 (m, 2H), one NH is missing. MS (m/z): 587.7 (MH)+ |
| 319 | 177 | 1-cyclopropyl-3-(3-fluoro-4-(2-(5-((7-(2-hydroxyacetyl)-2,7-diazaspiro[4.4]nonan-2-yl)methyl)pyridin-2-yl)thieno[3,2-b]pyridin-7-yloxy)phenyl)urea | $^1$H NMR (400 MHz, DMSO-d$_6$) δ (ppm): 8.80 (s, 1H), 8.57 (s, 1H), 8.51 (d, J = 5.3 Hz, 1H), 8.32 (s, 1H), 8.23 (d, J = 8.2 Hz, 1H) 7.87 (dd, J = 8.1, 1.5 Hz, 1H), 7.73 (dd J = 13.6, 2.4 Hz, 1H), 7.38 (t, J = 9.1 Hz, 1H), 7.20 (dd, J = 8.8, 1.2 Hz, 1H), 6.64 (d, J = 5.3 Hz, 1H), 6.61 (bd, J = 2.5 Hz, 1H), 4.52 and 4.48 (2t, J = 5.6 Hz, 1H), 4.02-3.90 (m, 2H), 3.67 (bs, 2H), 3.36-3.18 (m, 4H), 2.74-2.34 (m, 5H), 1.96-1.66 (m, 4H), 0.72-0.58 (m, 2H), 0.49-0.36 (m, 2H). MS (m/z): 617.6 (M + 1). |
| 320 | 178 | 1-cyclopropyl-3-(3-fluoro-4-(2-(5-((9-(2-hydroxyacetyl)-3,9-diazaspiro[5.5]-undecan-3-yl)methyl)pyridin-2-yl)thieno[3,2-b]pyridin-7-yloxy)phenyl)urea | $^1$H NMR (400 MHz, DMSO-d$_6$) δ (ppm): 8.72 (s, 1H), 8.54 (bd, J = 1.6 Hz, 1H), 8.52 (d, J = 5.5 Hz, 1H), 8.32 (s, 1H), 8.23 (d, J = 8.2 Hz, 1H), 7.85 (dd, J = 8.1, 2.1 Hz, 1H), 7.73 (dd, J = 13.6, 2.4 Hz, 1H), 7.38 (t, J = 9.1 Hz, 1H), 7.20 (dd, J = 9.0, 1.4 Hz, 1H), 6.64 (dd, J = 5.4, 0.7 Hz, 1H), 6.57 (bd, J = 2.3 Hz, 1H), 4.42 (t, J = 5.4 Hz, 1H), 4.04 (d, J = 5.3 Hz, 2H), 3.55 (s, 2H), 3.48-3.39 (m, 2H), 3.28-3.20 (m, 2H), 2.59-2.52 (m, 1H), 2.42-2.32 (m, 4H), 1.54-1.30 (m, 8H), 0.72-0.58 (m, 2H), 0.50-0.37 (m, 2H). MS(m/z): 645.8 (M + 1). |

TABLE 24-continued

Characterization of compounds 317-322 (examples 175-180)

| Cpd | Ex. | Structure | Characterization |
|---|---|---|---|
| 321 | 179 | 1-cyclopropyl-3-(3-fluoro-4-(2-(5-((4-fluoropiperidin-1-yl)methyl)pyridin-2-yl)thieno[3,2-b]pyridin-7-yloxy)phenyl)urea | $^1$H NMR (400 MHz, DMSO-$d_6$) δ (ppm): 8.77 (s, 1H); 8.55 (d, J = 1.6, 1H); 8.52 (d, J = 5.5, 1H); 8.33 (s, 1H); 8.24 (d, J = 8.0, 1H); 7.86 (dd, J = 8.2, 2.2, 1H); 7.73 (dd, J = 13.5, 2.5, 1H); 7.38 (t, J = 9.0, 1H); 7.22-7.18 (m, 1H); 6.65-6.60 (m, 2H); 4.80-4.60 (m, 1H); 3.40 (s, 2H); 2.55-2.50 (m, 3H); 2.38-2.30 (m, 2H); 1.92-1.80 (m, 2H); 1.78-1.65 (m, 2H); 0.67-0.62 (m, 2H); 0.44-0.40 (m, 2H). MS (m/z): 536.6 (M + 1). |
| 322 | 180 | 1-cyclopropyl-3-(3-fluoro-4-(2-(1-(2-(4-(2-hydroxyethyl)piperazin-1-yl)ethyl)-1H-imidazol-4-yl)thieno[3,2-b]pyridin-7-yloxy)phenyl)urea | $^1$H NMR (400 MHz, DMSO-$d_6$) δ (ppm): 8.79(s, 1H), 8.42(d, J = 5.6 Hz, 1H), 7.90(s, 1H), 7.76(s, 1H), 7.72(dd, J = 2.4 and 13.6 Hz, 1H), 7.65(s, 1H), 7.35(t, J = 9.2 Hz, 1H), 7.22-7.16(m, 1H), 6.64(s, 1H), 6.54(d, J = 5.6 Hz, 1H), 4.37(bs, 1H), 4.13(t, J = 5.6 Hz, 2H), 3.47(bs, 2H), 2.65(t, J = 6.0 Hz, 2H), 2.59-2.51(m, 1H), 2.50-2.30(m, 8H), 2.36(t, J = 6.0 Hz, 2H), 0.68-0.61 (m, 2H), 0.46-0.40(m, 2H). MS (m/z): 566.6 (M + 1). |

Compound 323 (example 181) was synthesized by following the procedures described above for the synthesis of compound 315 (example 173, scheme 69). Compounds 324-328 (examples 182-186) and 330 (example 188) were prepared in one step from compound 47 similarly to compound 48 (example 31, scheme 15). Compound 329 (example 187) was obtained by alkaline hydrolysis of compound 328 by following the procedure similar to the one described above for the synthesis of compound 31 (example 17, scheme 13).

TABLE 25

Characterization of compounds 323-330 (examples 181-188)

| Cpd | Ex. | Structure | Characterization |
|---|---|---|---|
| 323 | 181 | (S)-1-cyclopropyl-3-(3-fluoro-4-(2-(5-((3-fluoropyrrolidin-1-yl)methyl)pyridin-2-yl)thieno[3,2-b]pyridin-7-yloxy)phenyl)urea | $^1$H NMR (400 MHz, DMSO-$d_6$) δ (ppm): 8.71 (s, 1H); 8.57 (d, J = 1.6 Hz,, 1H); 8.52 (d, J = 5.5 Hz, 1H); 8.33 (s, 1H); 8.25 (d, J = 8.2 Hz, 1H); 7.88 (dd, J = 8.2, 2.2 Hz, 1H); 7.73 (dd, J = 13.5, 2.5 Hz, 1H); 7.38 (t, J = 9.0 Hz, 1H); 7.20 (d, J = 8.4 Hz, 1H); 6.64 (d, J = 5.5 Hz, 1H); 6.57 (d, J = 2.3 Hz, 1H); 5.21 (dt, J = 54.6, 6.5 Hz, 1H); 3.70 (s, 2H); 2.86-2.52 (m, 4H); 2.39-2.34 (m, 1H); 2.22-2.10 (m, 1H); 1.94-1.87 (m 1H); 0.68-0.63 (m, 2H); 0.45-0.41 (m, 2H). MS (m/z): 522.7 (M + 1). |

TABLE 25-continued

Characterization of compounds 323-330 (examples 181-188)

| Cpd | Ex. | Structure | Characterization |
|---|---|---|---|
| 324 | 182 | 1-cyclopropyl-3-(3-fluoro-4-(2-(5-((4-(pyridin-3-ylmethyl)piperazin-1-yl)methyl)pyridin-2-yl)thieno[3,2-b]pyridin-7-yloxy)phenyl)urea | $^1$H NMR (400 MHz, DMSO-$d_6$) δ (ppm): 8.71 (s, 1H); 8.54-8.45 (m, 4H); 8.32 (s, 1H); 8.24 (dd, J = 8.2, 0.6 Hz, 1H); 7.85 (dd, J = 8.4, 2.2 Hz, 1H); 7.75-7.68 (m, 2H); 7.40-7.33 (m, 2H); 7.20 (dd, J = 9.2 1.6 Hz, 1H); 6.64 (dd, J = 5.5, 1.0 Hz, 1H); 6.57 (d, J = 2.7 Hz, 1H); 3.55 (s, 2H); 3.50 (s, 2H); 2.57-2.54 (m, 1H); 2.41 (br. s, 8H); 0.68-0.63 (m, 2H); 0.45-0.41 (m, 2H). MS (m/z): 610.8 (MH)+ |
| 325 | 183 | 1-cyclopropyl-3-(3-fluoro-4-(2-(5-((4-(pyridin-4-ylmethyl)piperazin-1-yl)methyl)pyridin-2-yl)thieno[3,2-b]pyridin-7-yloxy)phenyl)urea | $^1$H NMR (400 MHz, DMSO-$d_6$) δ (ppm): 8.71 (s, 1H); 8.55-8.49 (m, 4H); 8.32 (s, 1H); 8.24 (d, J = 8.2, Hz, 1H); 7.85 (dd, J = 8.0, 2.0 Hz, 1H); 7.73 (dd, J = 13.5, 2.3 Hz, 1H); 7.38 (t, J = 9.0 Hz, 1H); 7.31 (dd, J = 5.7, 1.4 Hz, 2H); 7.20 (br d, J = 8.8 Hz, 1H); 6.64 (dd, J = 5.5, 0.8 Hz, 1H); 6.57 (d, J = 2.7 Hz, 1H); 3.56 (s, 2H); 3.50 (s, 2H); 2.58-2.54 (m, 1H); 2.42 (br. s, 8H); 0.68-0.63 (m, 2H); 0.45-0.41 (m, 2H). MS (m/z): 610.7 (M + 1). |
| 326 | 184 | 1-cyclopropyl-3-(3-fluoro-4-(2-(5-((4-(pyridin-2-ylmethyl)piperazin-1-yl)methyl)pyridin-2-yl)thieno[3,2-b]pyridin-7-yloxy)phenyl)urea | $^1$H NMR (400 MHz, DMSO-$d_6$) δ (ppm): 8.71 (s, 1H); 8.54 (d, J = 1.4 Hz, 1H); 8.52 (d, J = 5.5 Hz, 1H); 8.48 (d, J = 4.1 Hz, 1H); 8.32 (s, 1H); 8.24 (d, J = 8.0, Hz, 1H); 7.85 (dd, J = 8.2, 2.0 Hz, 1H); 7.73-7.71 (dd, m 2H); 7.43-7.36 (m, 2H); 7.26-7.19 (m, 2H); 6.64 (d, J = 5.5 Hz, 1H); 6.57 (d, J = 2.5 Hz, 1H); 3.57 (s, 2H); 3.56 (s, 2H); 2.57-2.53 (m, 1H); 2.45 (br. s, 8H); 0.67-0.64 (m, 2H); 0.45-0.42 (m, 2H). MS (m/z): 610.5 (M + 1). |
| 327 | 185 | 1-cyclopropyl-3-(3-fluoro-4-(2-(5-((4-(pyridin-2-ylmethyl)piperazin-1-yl)methyl)pyridin-2-yl)thieno[3,2-b]pyridin-7-yloxy)phenyl)urea | $^1$H NMR (400 MHz, DMSO-$d_6$) δ (ppm): 8.78 (s, 1H); 8.55 (br. s, 1H); 8.52 (d, J = 5.3 Hz, 1H); 8.33 (s, 1H); 8.24 (d, J = 8.0 Hz, 1H); 7.86 (dd, J = 8.2, 2.0 Hz, 1H); 7.73 (dd, J = 13.5, 2.3 Hz, 1H); 7.38 (t, J = 9.0 Hz, 1H); 7.20 (br. d, J = 9.0 Hz, 1H); 6.65 (d, J = 5.3 Hz, 1H); 6.61 (d, J = 2.3 Hz, 1H); 3.56-3.39 (m, 8H); 2.58-2.45 (m, 11H, overlaps with the residual signal of the solvent); 0.68-0.63 (m, 2H); 0.45-0.42 (m, 2H). [OH-proton is not seen]. MS (m/z): 607.6 (M + 1). |
| 328 | 186 | methyl 2-(1-((6-(7-(4-(3-cyclopropylureido)-2-fluorophenoxy)thieno[3,2-b]pyridin-2-yl)pyridin-3-yl)methyl)piperidin-4-yloxy)acetate | MS (m/z): 606.5 (M + 1). |

TABLE 25-continued
Characterization of compounds 323-330 (examples 181-188)
| Cpd | Ex. | Structure | Characterization |
|---|---|---|---|
| 329 | 187 | 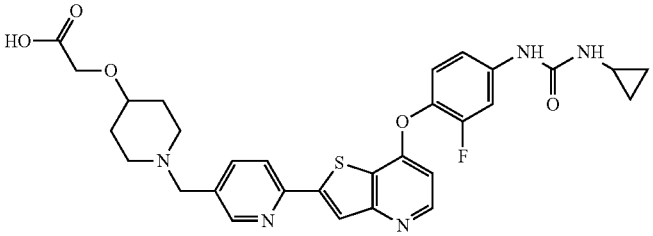 [SMILES: O=C(O)COC1CCN(Cc2ccc(-c3cc4nccc(Oc5ccc(NC(=O)NC6CC6)cc5F)c4s3)nc2)CC1]<br>2-(1-((6-(7-(4-(3-cyclopropylureido)-2-fluorophenoxy)thieno[3,2-b]pyridin-2-yl)pyridin-3-yl)mcthyI)piperidin-4-yloxy)acetic acid | MS (m/z): 592.5 (M + 1). |
| 330 | 188 | 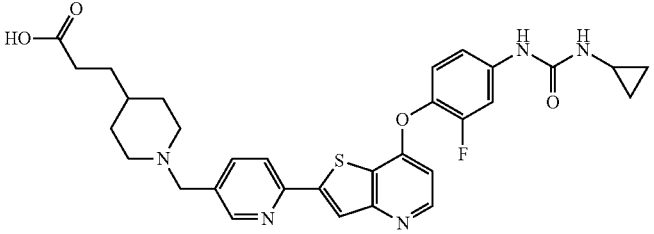 [SMILES: O=C(O)CCC1CCN(Cc2ccc(-c3cc4nccc(Oc5ccc(NC(=O)NC6CC6)cc5F)c4s3)nc2)CC1]<br>3-(1-((6-(7-(4-(3-cyclopropylureido)-2-fluorophenoxy)thieno[3,2-b]pyridin-2-yl)pyridin-3-yl)methyl)piperidin-4-yl)propanoic acid | MS (m/z): 590.6 (M + 1). |
Scheme 70
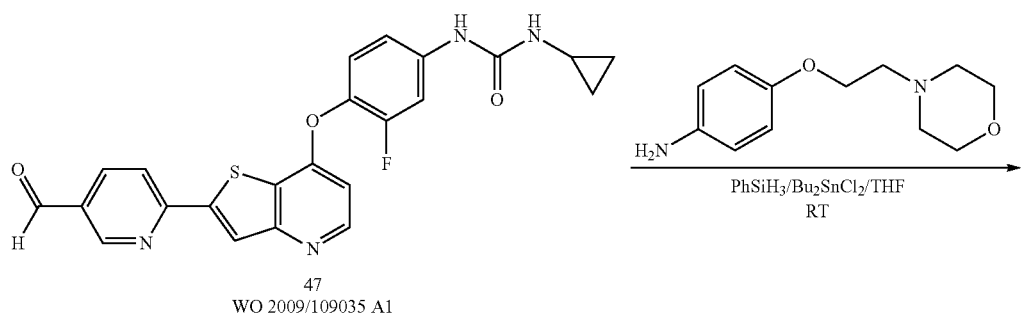
47
WO 2009/109035 A1
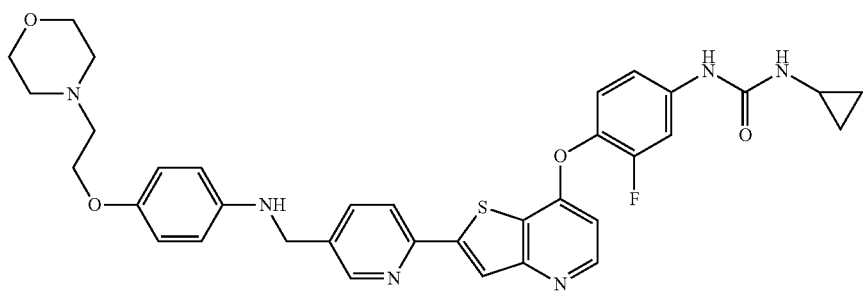
331: Example 189

Example 189

1-Cyclopropyl-3-(3-fluoro-4-(2-(5-((4-(2-morpholinoethoxy)phenylamino)methyl)pyridin-2-yl)thieno[3,2-b]pyridin-7-yloxy)phenyl)urea (331)

To a solution of the aldehyde 47 (0.161 g, 0.359 mmol), 4-(2-morpholinoethoxy)aniline (0.120 g, 0.540 mmol), and dibutyltin dichloride (0.197 g, 0.648 mmol) in DMF (5 mL) was added a solution of phenylsilane (0.047 g, 0.434 mmol) in DMF (2 mL). The reaction mixture was stirred for 3 hours at RT and treated with a mixture of brine/sat. NAHCO$_3$ solution. A precipitate was formed which was collected by filtration, washed with water and dried. Crude material was purified by flash column chromatography, eluent a 10 to 20% gradient of MeOH in AcOEt—to afford the title compound 331 (139 mg, 59.1% yield). $^1$H NMR (400 MHz, DMSO-d$_6$) δ (ppm): 8.72 (s, 1H); 8.62 (d, J=1.6 Hz, 1H); 8.51 (dd, J=5.5 Hz, 1H); 8.30 (s, 1H); 8.22 (d, J=8.2 Hz, 1H); 7.88 (dd, J=8.2, 2.2 Hz, 1H); 7.73 (dd, J=13.5, 2.5 Hz, 1H); 7.38 (t, J=9.2 Hz, 1H); 7.20 (dd, J=8.8 1.2 Hz, 1H); 6.72-6.69 (m, 2H); 6.63 (dd, J=5.5, 0.8 Hz 1H); 6.58-6.54 (m, 3H); 5.95 (t, J=6.3 Hz, 1H); 4.30 (d, J=6.1 Hz, 2H); 3.82 (t, J=5.9 Hz, 2H); 3.55 (t, J=4.5 Hz, 4H); 2.60 (t, J=5.7 Hz, 2H); 2.57-2.62 (m, 1H); 2.42 (t, J=4.5 Hz, 4H); 0.68-0.63 (m, 2H); 0.47-0.41 (m, 2H). MS (m/z): 655.6 (M+1)$^+$ Compounds 332-335 and 339-341 (examples 190-193 and 197-199, table 26) were synthesized by following the procedures similar to the one described above for the synthesis of compound 331 (example 190, scheme 70).

TABLE 26

Characterization of compounds 332-341 (examples 190-199)

| Cpd | Ex. | Structure | Characterization |
|---|---|---|---|
| 332 | 190 | 1-(4-(2-(5-(((1H-Pyrazol-3-ylamino)methyl)pyridin-2-yl)thieno[3,2-b]pyridin-7-yloxy)-3-fluorophenyl)-3-cyclopropylurea | $^1$H NMR (400 MHz, DMSO-d$_6$) δ (ppm): 11.5 (br. s, 1H); 8.69 (s, 1H); 8.60 (d, J = 1.4 Hz, 1H); 8.51 (d, J = 5.5, 1H); 8.28 (s, 1H); 8.20 (d, J = 8.0 Hz, 1H); 7.89 (dd, J = 8.0, 2.2 Hz, 1H); 7.72 (dd, J = 13.5, 2.5 Hz, 1H); 7.38 (t, J = 9.0 Hz, 1H); 7.35 (br. s, 1H); 7.20 (dd, J = 8.6, 1.4 Hz, 1H); 6.63 (dd, J = 5.5, 0.8 Hz, 1H); 6.56 (d, J = 2.7 Hz 1H); 5.83 (br. s, 1H); 5.50 (br. s, 1H); 4.30 (d, J = 6.3 Hz, 2H); 2.57-2.54 (m, 1H); 0.68-0.63 (m, 2H); 0.45-0.41 (m, 2H). MS (m/z): 516.4 (M + 1). |
| 333 | 191 | 1-Cyclopropyl-3-(3-fluoro-4-(2-(5-((5-methyl-1H-pyrazol-3-ylamino)methyl)pyridin-2-yl)thieno[3,2-b]pyridin-7-yloxy)phenyl)urea | $^1$H NMR (400 MHz, DMSO-d$_6$) δ (ppm): 11.19 (br. s, 1H); 8.70 (s, 1H); 8.58 (d, J = 2.0 Hz, 1H); 8.51 (d, J = 5.5, 1H); 8.28 (s, 1H); 8.20 (d, J = 8.0 Hz, 1H); 7.88 (dd, J = 8.0, 2.2 Hz, 1H); 7.73 (dd, J = 13.5, 2.3 Hz, 1H); 7.38 (t, J = 9.0 Hz, 1H); 7.20 (dd, J = 9.0, 1.4 Hz, 1H); 6.63 (d, J = 5.5, Hz, 1H); 6.57 (d, J = 2.5 Hz 1H); 5.72 (br. s, 1H); 5.26 (s, 1H); 4.26 (d, J = 6.1 Hz, 2H); 2.58-2.52 (m, 1H); 0.68-0.63 (m, 2H); 0.45-0.41 (m, 2H). MS (m/z): 530.5 (M + 1) |
| 334 | 192 | 1-Cyclopropyl-3-(3-fluoro-4-(2-(5-((1-methyl-1H-pyrazol-3-ylamino)methyl)pyridin-2-yl)thieno[3,2-b]pyridin-7-yloxy)phenyl)urea | $^1$H NMR (400 MHz, DMSO-d$_6$) δ (ppm): 8.70 (s, 1H); 8.60 (d, J = 2.0 Hz, 1H); 8.51 (d, J = 5.5, 1H); 8.29 (s, 1H); 8.21 (d, J = 8.0 Hz, 1H); 7.89 (dd, J = 8.0, 2.2 Hz, 1H); 7.73 (dd, J = 13.7, 2.5 Hz, 1H); 7.38 (t, J = 9.0 Hz, 1H); 7.31 (d, J = 2.2 Hz 1H); 7.20 (dd, J = 8.8, 1.4 Hz, 1H); 6.63 (dd, J = 5.5, 0.8 Hz, 1H); 6.57 (d, J = 2.3 Hz 1H); 5.83 (t, J = 6.5 Hz, 1H); 5.45 (d, J = 2.3 Hz, 1H); 4.28 (d, J = 6.3 Hz, 2H); 2.58-2.52 (m, 1H); 0.68-0.63 (m, 2H); 0.45-0.41 (m, 2H). MS (m/z): 530.4 (M + 1). |
| 335 | 193 | 1-cyclopropyl-3-(4-(2-(5-((1,5-dimethyl-1H-pyrazol-3-ylamino)methyl)pyridin-2-yl)thieno[3,2-b]pyridin-7-yloxy)-3-fluorophenyl)urea | $^1$H NMR (400 MHz, DMSO-d$_6$) δ (ppm): 8.71 (s, 1H); 8.58 (d, J = 2.0 Hz, 1H); 8.51 (d, J = 5.5, 1H); 8.29 (s, 1H); 8.20 (dd, J = 8.0, 0.6 Hz, 1H); 7.88 (dd, J = 8.2, 2.2 Hz, 1H); 7.73 (dd, J = 13.5, 2.3 Hz, 1H); 7.38 (t, J = 9.0 Hz, 1H); 7.20 (dd, J = 9.0, 1.4 Hz, 1H); 6.63 (dd, J = 5.5, 0.8 Hz, 1H); 6.58 (d, J = 2.5 Hz 1H); 5.71 (t, J = 6.7 Hz, 1H); 5.29 (d, J = 0.6 Hz, 1H); 4.24 (d, J = 6.3 Hz, 2H); 3.46 (s, 3H); 2.58-2.52 (m, 1H); 2.09 (d, J = 0.4 Hz, 3H); 0.68-0.63 (m, 2H); 0.45-0.41 (m, 2H). MS (m/z): 544.3 (M + 1). |

TABLE 26-continued

Characterization of compounds 332-341 (examples 190-199)

| Cpd | Ex. | Structure | Characterization |
|---|---|---|---|
| 339 | 197 | 1-cyclopropyl-3-(4-(2-(5-((4-(3-(dimethylamino)propyl)phenylamino) methyl)pyridin-2-yl)thieno[3,2-b]pyridin-7-yloxy)-3-fluorophenyl)urea | $^1$H NMR (400 MHz, DMSO-d$_6$) δ (ppm): 8.79 (s, 1H); 8.62 (d, J = 1.4 Hz, 1H); 8.51 (d, J = 5.5 Hz, 1H); 8.30 (s, 1H); 8.23 (d, J = 8.2 Hz, 1H); 7.89 (dd, J = 8.2, 2.0 Hz, 1H); 7.73 (dd, J = 13.7, 2.5 Hz, 1H); 7.38 (t, J = 9.0 Hz, 1H); 7.20 (br. d, J = 10.2 Hz, 1H); 6.89 (d, J = 8.4 Hz, 2H); 6.64-6.61 (m, 2H); 6.54 (d, J = 8.4 Hz, 2H); 6.20 (t, J = 6.3 Hz, 1H); 4.33 (d, J = 2.3 Hz, 2H); 2.57-2.53 (m, 1H); 2.42-2.32 (m, 4H); 2.26 (s, 6H); 1.68-1.60 (m, 2H); 0.67-0.63 (m, 2H); 0.44-0.41 (m, 2H). MS (m/z): 611.6 (M + 1). |
| 340 | 198 | 4-((6-(7-(4-(3-cyclopropylureido)-2-fluorophenoxy)thieno[3,2-b] pyridin-2-yl)pyridin-3-yl)methylamino)-N-(2-(diethylamino)ethyl)benzamide | $^1$H NMR (400 MHz, DMSO-d$_6$) δ (ppm): 8.80 (s, 1H); 8.64 (d, J = 1.6 Hz, 1H); 8.51 (d, J = 5.5 Hz, 1H); 8.31 (s, 1H); 8.24 (d, J = 8.2 Hz, 1H); 7.96 (br. t, 1H); 7.89 (dd, J = 8.2, 2.2 Hz, 1H); 7.73 (dd, J = 13.5, 2.5 Hz, 1H); 7.59 (d, J = 8.8 Hz, 2H); 7.38 (t, J = 9.2 Hz, 1H); 7.20 (dd, J = 9.0, 1.2 Hz, 1H); 6.87 (t, J = 6.1 Hz, 1H); 6.64-6.61 (m, 4H); 4.42 (d, J = 5.9 Hz, 2H); 3.30-3.23 (m, 2H), 2.57-2.52 (m, 3H); 0.98-0.67 (m, 6H); 0.66-0.63 (m, 2H); 0.44-0.41 (m, 2H). MS (m/z): 668.5 (M + 1). |
| 341 | 199 | 1-cyclopropyl-3-(3-fluoro-4-(2-(5-((3-(2-morpholinoethoxy)phenylamino) methyl)pyridin-2-yl)thieno[3,2-b]pyridin-7-yloxy)phenyl)urea | $^1$H NMR (400 MHz, DMSO-d$_6$) δ (ppm): 8.81 (s, 1H): 8.62 (d, J = 1.6 Hz, 1H); 8.51 (d, J = 5.3 Hz, 1H); 8.30 (s, 1H); 8.22 (d, J = 8.2 Hz, 1H); 7.88 (dd, J = 8.2, 2.2 Hz, 1H); 7.73 (dd, J = 16.0, 2.5 Hz, 1H); 7.37 (t, J = 9.0 Hz, 1H); 7.20 (br. d, J = 9.0 Hz, 1H); 6.94 (t, J = 8.0 Hz, 1H); 6.66 (d, J = 2.5 Hz, 2H): 6.63 (d, J = 5.5, Hz 1H); 6.35 (t, J = 6.3 Hz, 1H); 6.23 (dd, J = 7.2, 1.4 Hz, 1H); 6.14-6.119 (m, 2H); 4.35 (d, J = 6.1 Hz, 2H); 3.96 (t, J = 5.9 Hz, 2H); 3.54 (t, J = 4.7 Hz, 4H); 2.61 (t, J = 5.9 Hz, 2H); 2.57-2.52 (m, 1H); 2.45-2.41 (t, J = 4.5 Hz, 4H); 0.67-0.63 (m, 2H); 0.44-0.41 (m, 2H). MS (m/z): 655.7 (M + 1). |

*For the synthesis of (2,5,8,11-Tetraoxatridecan-13-yloxy)anilines see scheme 99.

Scheme 71

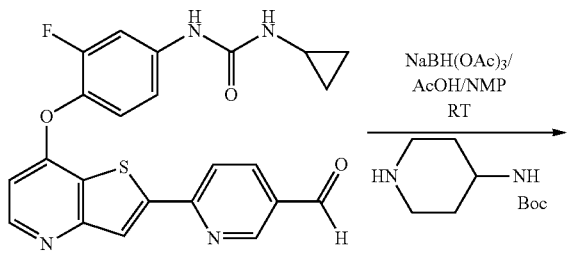

47
WO 2009/109035 A1

-continued

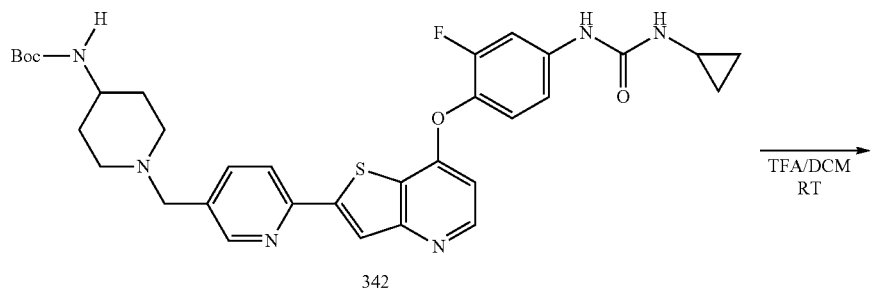

342

TFA/DCM
RT

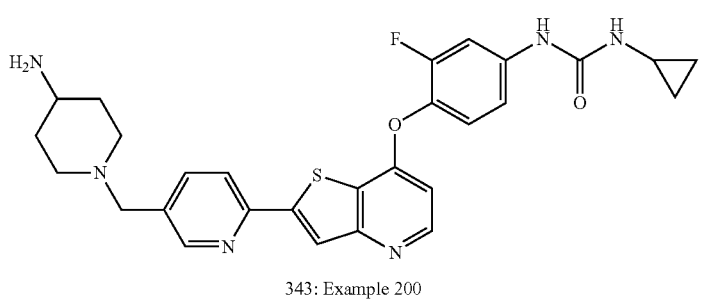

343: Example 200

Example 200

1-(4-(2-(5-((4-Aminopiperidin-1-yl)methyl)pyridin-2-yl)thieno[3,2-b]pyridin-7-yloxy)-3-fluorophenyl)-3-cyclopropylurea (343)

Step 1. tert-Butyl 1-((6-(7-(4-(3-cyclopropylureido)-2-fluorophenoxy)thieno[3,2-b]pyridin-2-yl)pyridin-3-yl)methyl)piperidin-4-ylcarbamate (342)

tert-Butyl piperidin-4-ylcarbamate (1.34 g, 6.69 mmol) was added to a solution of the aldehyde 47 (2.0 g, 4.46 mmol) in a mixture of NMP (20 mL) and glacial AcOH (0.250 mL). The reaction mixture was stirred for 30 min. NaBH(OAc)$_3$ was then added and the reaction mixture was stirred for an additional 2.5 hours. The reaction mixture was then poured into a saturated aqueous NaHCO$_3$ solution. A precipitate was formed which was collected by filtration, washed with water and air-dried. The crude material was purified by column chromatography using a 5 to 20% gradient of MeOH in EtOAc as eluent to afford the title compound 343 (1.45 g, 51.4% yield). MS (m/z): 633.6 (M+1)+.

Step 2. 1-(4-(2-(5-((4-Aminopiperidin-1-yl)methyl)pyridin-2-yl)thieno[3,2-b]pyridin-7-yloxy)-3-fluorophenyl)-3-cyclopropylurea (343)

A solution of the Boc-protected compound 342 in TFA (25 mL) was stirred at RT for 1.5 hours then evaporated. To the residue was added 3N aqueous NaOH solution and the suspension was stirred at RT overnight, collected by filtration, washed with water and dried to afford the title compound 343 (1.177 g, 96% yield). $^1$H NMR (400 MHz, DMSO-d$_6$) δ (ppm): 8.75 (s, 1H); 8.53-8.51 (m, 2H); 8.32 (s, 1H); 8.23 (d, J=8.2 Hz, 1H); 7.84 (dd, J=8.2, 2.2 Hz, 1H); 7.73 (dd, J=13.5, 2.3 Hz, 1H); 7.38 (t, J=9.0 Hz, 1H); 7.20 (dd, J=8.8 1.2 Hz, 1H); 6.64 (d, J=5.5 Hz 1H); 6.61 (d, J=2.3 Hz, 1H); 3.52 (s, 2H); 2.74 (d, J=11.3 Hz, 2H); 2.58-2.52 (m, 1H); 1.99 (t, J=9.8 Hz, 2H); 1.66 (d, J=11.3 Hz, 2H); 1.29-1.20 (m, 2H); 0.68-0.63 (m, 2H); 0.45-0.41 (m, 2H). [Signal of the NH$_2$-group is not seen; NH$_2$—CH-signal is obscured by the peak of residual water]. MS (m/z): 533.5 (M+1)+.

Compound 342-A (example 199-A) was synthesized similarly to compound 342 from the aldehyde 47 and tert-butyl methyl(piperidin-4-yl)carbamate. Compounds 344-350 (examples 201-207) were synthesized starting from the compound 343 (scheme 71), by following the procedures similar to the described above for the synthesis of compounds 30 and 31 (scheme 13). Compounds 351-355 (examples 208-212) were prepared in one step from compound 343 similarly to compound 128 (example 87, scheme 32).

TABLE 27

Characterization of compounds 342-A, 344-355 (examples 199-A, 201-212)

| Cpd | Ex. | Structure | Characterization |
|---|---|---|---|
| 342-A | 199-A | 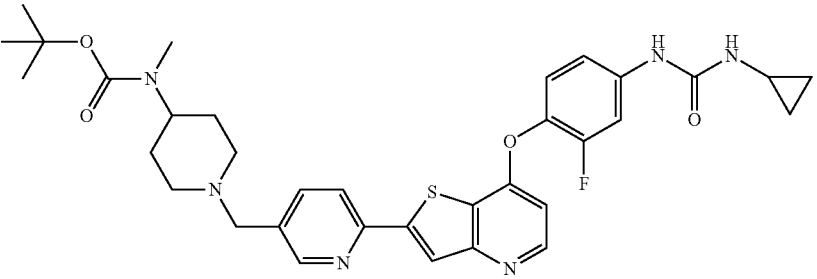<br>tert-butyl 1-((6-(7-(4-(3-cyclopropylureido)-2-fluorophenoxy)thieno[3,2-b]pyridin-2-yl)pyridin-3-yl)methyl)piperidin-4-yl(methyl)carbamate | $^1$H NMR (400 MHz, DMSO-d$_6$) δ (ppm): 8.71(s, 1H), 8.55(d, J = 1.6 Hz, 1H), 8.52(d, J = 5.6 Hz, 1H), 8.33(s, 1H), 8.24(d, J = 8.0 Hz, 1H), 7.86(dd, J = 8.1, 2.0 Hz, 1H), 7.73(dd, J = 13.6, 2.4 Hz, 1H), 7.38 (t, J = 9.2 Hz, 1H), 7.23-7.18(m, 1H), 6.64(d, J = 5.0 Hz, 1H), 6.58(bd, J = 2.8 Hz, 1H), 3.55(s, 2H), 3.35-3.28(m, 1H), 2.93-2.85(m, 2H), 2.67 (s, 3H), 2.60-2.52(m, 1H), 2.07-1.97(m, 2H), 1.75-1.62(m, 2H), 1.55-1.44(m, 2H), 1.39(s, 9H), 0.69-0.62(m, 2H), 0.45-0.40(m, 2H). MS (m/z): 647.6(M + 1). |
| 344 | 201 | 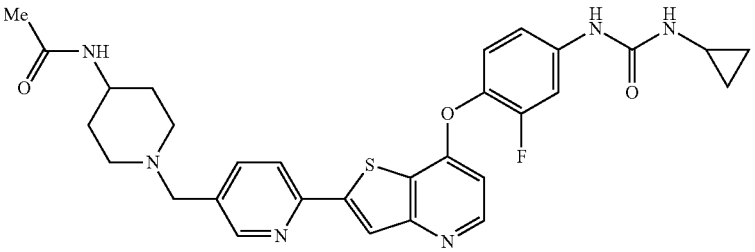<br>N-(1-((6-(7-(4-(3-Cyclopropylureido)-2-fluorophenoxy)thieno[3,2-b]pyridin-2-yl)pyridin-3-yl)methyl)piperidin-4-yl)acetamide | $^1$H NMR (400 MHz, DMSO-d$_6$) δ (ppm): 8.71(s, 1H); 8.54(d, J = 1.6 Hz, 1H); 8.52(d, J = 5.3, 1H); 8.32(s, 1H); 8.24(d, J = 8.2 Hz, 1H); 7.85(dd, J = 8.2, 2.0 Hz, 1H); 7.77(d, J = 7.4 Hz, 1H); 7.73 (dd, J =13.7, 2.5 Hz, 1H); 7.38(t, J = 9.2 Hz, 1H); 7.20(d, J = 8.8 Hz, 1H); 6.64(d, J = 5.3 Hz, 1H); 6.57(d, J = 2.3 Hz, 1H); 3.53(s, 2H); 3.50(br. s, 1H); 2.77(br. d, J = 11.3 Hz, 2H); 2.58-2.51(m, 1H); 2.04(br. t, J =11.0 Hz, 2H); 1.77(s, 3H); 1.71 (br. d, J =11.3 Hz, 2H); 1.42-1.37(m, 2H); 0.68-0.63(m, 2H); 0.45-0.41(m, 2H). MS(m/z): 575.5(M + 1). |
| 345 | 202 | 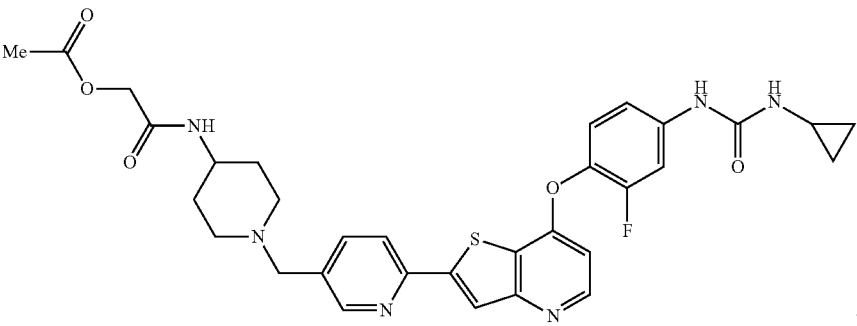<br>2-(1-((6-(7-(4-(3-Cyclopropylureido)-2-fluorophenoxy)thieno[3,2-b]pyridin-2-yl)pyridin-3-yl)methyl)piperidin-4-ylamino)-2-oxoethyl acetate | $^1$H NMR (400 MHz, DMSO-d$_6$) δ (ppm): 8.71(s, 1H); 8.54(d, J = 1.6 Hz, 1H); 8.52(d, J = 5.5, 1H); 8.33 (s, 1H); 8.24(d, J = 8.0 Hz, 1H); 7.92(d, J = 7.8 Hz, 1H); 7.85(dd, J = 8.0, 2.0 Hz, 1H); 7.73(dd, J = 13.5, 2.3 Hz, 1H); 7.38 (t, J = 9.0 Hz, 1H); 7.20 (d, J = 8.8 Hz, 1H); 6.64 (d, J = 5.1 Hz 1H); 6.57 (d, J = 2.5 Hz, 1H); 4.40(s, 2H); 3.58(br. s, 1H); 3.54(s, 2H); 2.78 (br. d, J = 11.5 Hz, 2H); 2.58-2.53(m, 1H); 2.50-2.03(m, 5H); 1.70(br. d, J = 10.2 Hz, 2H); 1.49-1.41(m, 2H); 0.68-0.63 (m, 2H); 0.45-0.41(m, 2H). MS(m/z): 633.6(M + 1) |

TABLE 27-continued

Characterization of compounds 342-A, 344-355 (examples 199-A, 201-212)

| Cpd | Ex. | Structure | Characterization |
|---|---|---|---|
| 346 | 203 | 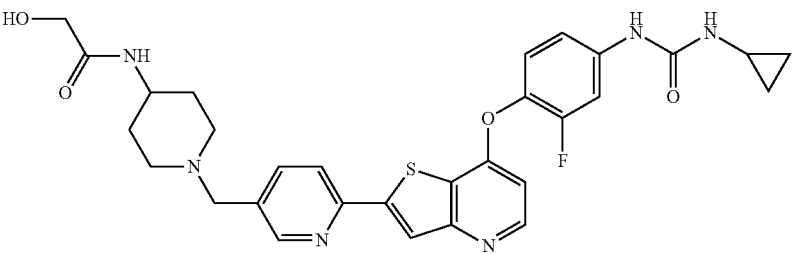<br>N-(1-((6-(7-(4-(3-Cyclopropylureido)-2-fluorophenoxy)thieno[3,2-b]pyridin-2-yl)pyridin-3-yl)methyl)piperidin-4-yl)-2-hydroxyacetamide | $^1$H NMR (400 MHz, DMSO-$d_6$) δ (ppm): 8.71 (s, 1H); 8.54(d, J = 1.4 Hz, 1H); 8.52(d, J = 5.3, 1H); 8.32(s, 1H); 8.24 (d, J = 8.2 Hz, 1H); 7.85 (dd, J = 8.0, 2.0 Hz, 1H); 7.73(dd, J = 13.5, 2.3 Hz, 1H); 7.52(d, J = 8.2 Hz, 1H); 7.38(t, J = 9.0 Hz, 1H); 7.20(d, J = 8.8 Hz, 1H); 6.64(d, J = 5.3 Hz 1H); 6.57(d, J = 2.3 Hz, 1H); 5.41(t, J = 5.9 Hz, 1H); 3.77(d ,J = 5.9 Hz, 2H); 3.62-3.60(m, 1H); 2.78(br. d, J = 11.3 Hz, 2H); 2.57-2.53(m, 1H); 2.06(br. t, J = 11.0 Hz, 2H); 1.67(br. d, J = 9.8 Hz, 2H);1.54-1.49(m, 2H); 0.68-0.63(m, 2H); 0.45-0.41(m, 2H). MS(m/z): 591.5(M + 1). |
| 347 | 204 | 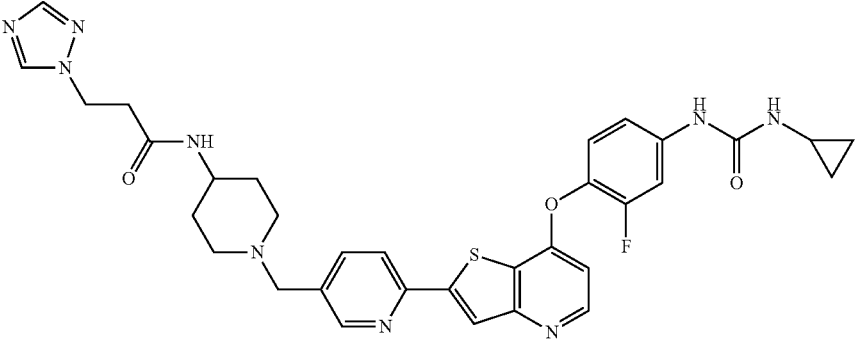<br>N-(1-((6-(7-(4-(3-Cyclopropylureido)-2-fluorophenoxy)thieno[3,2-b]pyridin-2-yl)pyridin-3-yl)methyl)piperidin-4-yl)-3-(1H-1,2,4-triazol-1-yl)propanamide | $^1$H NMR (400 MHz, DMSO-$d_6$) δ (ppm): 8.73 (s, 1H); 8.54(d, J = 1.6 Hz, 1H); 8.52(d, J = 5.5, 1H); 8.39(s, 1H); 8.32(s, 1H); 8.24(d, J = 8.2 Hz, 1H); 7.93 (s, 1H); 7.88(d, J = 7.8 Hz, 1H); 7.84(dd, J = 8.2, 2.2 Hz, 1H); 7.73(dd, J = 13.5, 2.3 Hz, 1H); 7.38(t, J = 9.0 Hz, 1H); 7.20(d, J = 9.0 Hz, 1H); 6.64(d, J = 5.5 Hz, 1H); 6.59(d, J = 2.5 Hz 1H); 4.37(t, J = 6.7 Hz, 2H); 3.52(br. s, 3H); 2.74 (br. d, J = 11.5 Hz, 2H); 2.62(t, J = 6.8 Hz, 2H); 2.58-2.53(m, 1H); 2.03 (br. t, J = 10.8 Hz, 2H); 1.66(br. d, J = 9.6 Hz, 2H); 1.37-1.32(m, 2H); 0.68-0.63(m, 2H); 0.45-0.41(m, 2H). MS(m/z): 656.7(M + 1). |

TABLE 27-continued

Characterization of compounds 342-A, 344-355 (examples 199-A, 201-212)

| Cpd | Ex. | Structure | Characterization |
|---|---|---|---|
| 348 | 205 | N-(1-((6-(7-(4-(3-cyclopropylureido)-2-fluorophenoxy)thieno[3,2-b]pyridin-2-yl)pyridin-3-yl)methyl)piperidin-4-yl)-3-(pyridin-3-yl)propanamide | MS(m/z): 666.5(M + 1). |
| 349 | 206 | N-(1-((6-(7-(4-(3-Cyclopropylureido)-2-fluorophenoxy)thieno[3,2-b]pyridin-2-yl)pyridin-3-yl)methyl)piperidin-4-yl)-3-hydroxypropanamide | MS(m/z): 605.4(M + 1). |
| 350 | 207 | N-(1-((6-(7-(4-(3-cyclopropylureido)-2-fluorophenoxy)thieno[3,2-b]pyridin-2-yl)pyridin-3-yl)methyl)piperidin-4-yl)methanesulfonamide | $^1$H NMR (400 MHz, DMSO-$d_6$) δ (ppm): 8.70(s, 1H); 8.54(s, 1H); 8.52(d, J = 15.3 Hz, 1H); 8.32(s, 1H); 8.24(d, J = 8.0 Hz, 1H); 7.85(d, J = 8.2, Hz, 1H); 7.73(dd, J = 13.5, 2.3 Hz, 1H); 7.38 (t, J = 9.0 Hz, 1H); 7.20 (dd, J = 9.0, 1.2 Hz, 1H); 7.06(d, J = 7.2 Hz, 1H); 6.56(dd, J = 5.5, 0.8 Hz, 1H); 6.56(d, J = 2.5 Hz 1H); 3.54(s, 2H); 2.90(s, 3H); 2.77(br. d, J = 10.6 Hz, 2H); 2.57-2.54(m, 1H); 2.06(br. t, Hz, 2H); 1.82(br. d, J = 9.4 Hz, 2H); 1.49-1.47(m, 2H); 0.67-0.63(m, 2H); 0.45-0.42(m, 2H). [NH—C$\underline{H}$-signal is probably obscured by the peak of residual water]. MS (m/z): 611.6(M + 1). |

TABLE 27-continued

Characterization of compounds 342-A, 344-355 (examples 199-A, 201-212)

| Cpd | Ex. | Structure | Characterization |
|---|---|---|---|
| 351 | 208 | Ethyl 1-((6-(7-(4-(3-cyclopropylureido)-2-fluorophenoxy)thieno[3,2-b]pyridin-2-yl)pyridin-3-yl)methyl)piperidin-4-ylcarbamate | MS(m/s): 605.6(M + 1). |
| 352 | 209 | 1-(4-(2-(5-((4-Methylaminocarbonyl-aminopiperidin-1-yl)methyl)pyridin-2-yl)thieno[3,2-b]pyridin-7-yloxy)-3-fluorophenyl)-3-cyclopropylurea | $^1$H NMR (400 MHz, DMSO-d$_6$) δ (ppm): 8.71(s, 1H); 8.54(d, J = 1.6 Hz, 1H); 8.52(d, J = 5.5 Hz, 1H); 8.32 (s, 1H); 8.24(d, J = 8.2 Hz, 1H); 7.85(dd, J = 8.2, 2.2 Hz, 1H); 7.73(dd, J = 13.5, 2.3 Hz, 1H); 7.38(t, J = 9.0 Hz, 1H); 7.20(dd, J = 9.0, 1.2 Hz, 1H); 6.65(dd, J = 5.3, 0.6 Hz, 1H); 6.57(d, J = 2.5 Hz, 1H); 5.80(d, J = 8.0 Hz, 1H); 5.59(dd, J = 9.2, 4.3 Hz, 1H); 3.53(s, 2H); 2.73-2.70(m, 2H); 2.58-2.53(m, 1H); 2.52(s, 3H); 2.09-2.04(m, 2H); 1.76-1.71(m, 2H); 1.37-1.29(m, 2H); 0.68-0.63 (m, 2H); 0.45-0.41(m, 2H). [The NH—CH-signal is probably obscured by the peak of residual water]. MS (m/z): 590.6(M + 1). |

TABLE 27-continued

Characterization of compounds 342-A, 344-355 (examples 199-A, 201-212)

| Cpd | Ex. | Structure | Characterization |
|---|---|---|---|
| 353 | 210 | 1-(4-(2-(5-((4-Ethylaminocarbonyl-aminopiperidin-1-yl)methyl)pyridin-2-yl)thieno[3,2-b]pyridin-7-yloxy)-3-fluorophenyl)-3-cyclopropylurea | $^1$H NMR (400 MHz, DMSO-$d_6$) δ (ppm): 8.70(s, 1H); 8.54(d, J = 1.4 Hz, 1H); 8.52(d, J = 5.5 Hz, 1H); 8.32(s, 1H); 8.23(d, J = 8.0 Hz, 1H); 7.85(dd, J = 8.0, 2.0 Hz, 1H); 7.73 (dd, J = 13.5, 2.3 Hz, 1H); 7.38(t, J = 9.0 Hz, 1H); 7.20(d, J = 8.8 Hz, 1H); 6.65(d, J = 4.7 Hz, 1H); 6.56(d, J = 2.3 Hz 1H); 5.72(d, J = 7.8 Hz 1H); 5.65(t, J = 5.5 Hz, 1H); 3.53(s, 2H); 3.01-2.94(m, 2H); 2.72(br. d, J = 11.3 Hz, 2H); 2.57-2.54(m, 1H); 2.07(br. t, J =11.2 Hz, 2H); 1.73(br. d, J = 10.0 Hz, 2H); 1.36-1.31(m, 2H); 0.96(t, J = 7.0 Hz, 3H); 0.68-0.63(m, 2H); 0.45-0.41(m, 2H). MS (m/z): 604.6(M + 1). |
| 354 | 211 | 1-(4-(2-(5-((4-Propylaminocarbonyl-aminopiperidin-1-yl)methyl)pyridin-2-yl)thieno[3,2-b]pyridin-7-yloxy)-3-fluorophenyl)-3-cyclopropylurea | $^1$H NMR (400 MHz, DMSO-$d_6$) δ (ppm): 8.72(s, 1H); 8.54(br. s, 1H); 8.52(d, J = 5.5 Hz, 1H); 8.33(s, 1H); 8.24 (d, J = 8.2 Hz, 1H); 7.85 (dd, J = 8.2, 1.8 Hz, 1H); 7.73(dd, J = 13.5, 2.3 Hz, 1H); 7.38(t, J = 9.0 Hz, 1H); 7.20(br. d, J = 8.6 Hz, 1H); 6.64(d, J = 5.5 Hz, 1H); 6.58 (d, J = 2.0 Hz, 1H); 5.74-5.70(m, 2H); 3.53(s, 2H); 2.94-2.89(m, 2H), 2.71(br. d, J = 11.2 Hz, 2H); 2.57-2.52(m, 1H); 2.10-2.05(m, 2H); 1.73(br. d, J = 9.8 Hz, 2H); 1.39-1.27(m, 4H); 0.81(t, J = 7.4 Hz, 3H); 0.68-0.63(m, 2H); 0.45-0.41 (m, 2H). [The NH—CH- signal is probably obscured by the peak of residual water]. MS(m/z): 618.6(M + 1). |

TABLE 27-continued

Characterization of compounds 342-A, 344-355 (examples 199-A, 201-212)

| Cpd | Ex. | Structure | Characterization |
|---|---|---|---|
| 355 | 212 | 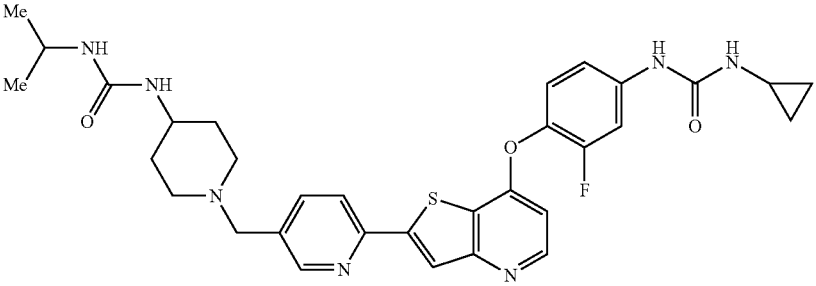<br>1-(4-(2-(5-((4-Isopropylaminocarbonyl-aminopiperidin-1-yl)methyl)pyridin-2-yl)thieno[3,2-b]pyridin-7-yloxy)-3-fluorophenyl)-3-cyclopropylurea | $^1$H NMR (400 MHz, DMSO-d$_6$) δ (ppm): 8.72(s, 1H); 8.54(d, J = 1.4 Hz, 1H); 8.52(d, J = 5.3 Hz, 1H); 8.33 (s, 1H); 8.24(d, J = 8.2 Hz, 1H); 7.85(dd, J = 8.0, 1.9 Hz, 1H); 7.73(dd, J = 16.0, 2.5 Hz, 1H); 7.38(t, J = 9.0 Hz, 1H); 7.20(d, J = 9.0 Hz, 1H); 6.65(d, J = 5.3 Hz, 1H); 6.58(d, J = 2.3 Hz 1H); 5.64(d, J = 7.8 Hz 1H); 5.56(d, J = 7.6 Hz, 1H); 3.65-3.60 (m, 1H); 3.53(s, 2H); 2.70(br. d, J = 11.0 Hz, 2H); 2.57-2.52(m, 1H); 2.10- 2.05(m, 2H); 1.73 (br. d, J = 9.6 Hz, 2H); 1.31-1.29(m, 2H); 1.00(d, J = 6.5 Hz, 6H); 0.68-0.63(m, 2H); 0.45-0.41(m, 2H). [One of NH—C<u>H</u>- signals is probably obscured by the peak of residual water]. MS(m/z): 618.6(M + 1). |

Scheme 72

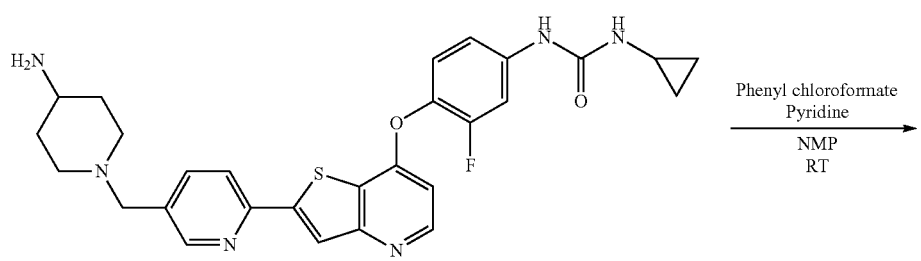

343: Example 200

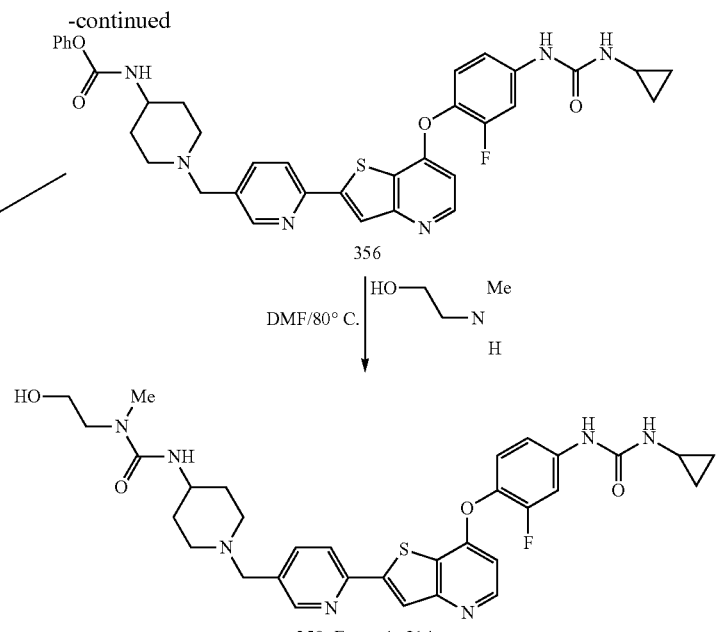

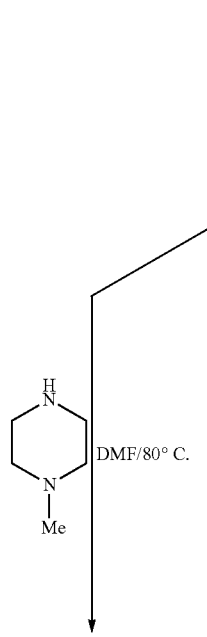

357: Example 213

Example 213

N-(1-((6-(7-(4-(3-Cyclopropylureido)-2-fluorophenoxy)thieno[3,2-b]pyridin-2-yl)pyridin-3-yl)methyl)piperidin-4-yl)-4-methylpiperazine-1-carboxamide (357)

Step 1. Phenyl 1-((6-(7-(4-(3-cyclopropylureido)-2-fluorophenoxy)thieno[3,2-b]pyridin-2-yl)pyridin-3-yl)methyl)piperidin-4-ylcarbamate (356)

To a solution of the amine 343 (0.9 g, 1.69 mmol) in NMP (10 mL) at 0° C. was added pyridine (0.3 ml, 3.71 mmol) followed by the chloroformate (0.3 mL, 2.38 mmol). The mixture was stirred for 40 min at 0° C. then at room temperature for 120 min, quenched by addition of brine/NaHCO₃ solution. A precipitate was formed which was collected by filtration and dried. The crude material was purified by flash column chromatography, eluent a 5 to 10% gradient of MeOH (containing 2% ammonia) in DCM, to afford the title compound 356 (0.528 g, 47.9% yield). MS (m/z): 653.6 (M+1)+.

Step 2. N-(1-((6-(7-(4-(3-Cyclopropylureido)-2-fluorophenoxy)thieno[3,2-b]pyridin-2-yl)pyridin-3-yl)methyl)piperidin-4-yl)-4-methylpiperazine-1-carboxamide (357)

To a solution of the phenylcarbamate 356 (0.11 g, 0.169 mmol) in DMF at RT was added the N-methylpiperazine (0.057 mL, 0.51 mmol). The reaction mixture was heated at 90-95° C. for 2 hours, cooled to RT then treated with brine and saturated NaHCO₃ solution. A precipitate was formed which was collected by filtration and dried. The crude material was purified by flash column chromatography, eluent 12 to 30% MeOH (containing 2% ammonia) in DCM, to afford the title compound 357 (0.088 g, 79% yield). $^1$H NMR (400 MHz, CD$_3$OD-d$_6$) δ (ppm): 8.65 (d, J=1.4 Hz, 1H); 8.47 (d, J=5.5 Hz, 1H); 8.15-8.11 (m, 2H); 7.98 (dd, J=8.2, 2.0 Hz, 1H); 7.67 (dd, J=13.1, 2.3 Hz, 1H); 7.30 (t, J=9.0 Hz, 1H); 7.20 (br. d, J=9.0 Hz, 1H); 6.64 (d, J=5.5 Hz 1H); 3.94 (s, 2H); 3.68-3.65 (m, 1H); 3.57 (br. s, 4H); 3.18 (br. d, J=10.4 Hz, 2H); 2.89 (br. s, 4H); 2.65 (s, 3H); 2.63-2.58 (m, 3H); 1.98 (br. d, J=11.7 Hz, 2H); 1.69 (br. d, J=11.0 Hz, 2H); 0.79-0.74 (m, 2H); 0.55-0.52 (m, 2H). [Signals of NH-protons are not seen]. MS (m/z): 659.5 (M+1)+

Example 214

1-Cyclopropyl-3-(3-fluoro-4-(2-(5-((4-((2-hydroxy-ethyl-methylamino)carbonylamino)piperidin-1-yl)methyl)pyridin-2-yl)thieno[3,2-b]pyridin-7-yloxy)phenyl)urea (358)

Title compound 358 was obtained by following the procedure described above for the synthesis of compound 357 (example 214). $^1$H NMR (400 MHz, CD$_3$OD-d$_6$) δ (ppm): 8.60 (d, J=1.6 Hz, 1H); 8.47 (d, J=5.7 Hz, 1H); 8.12-8.09 (m, 2H); 7.93 (dd, J=8.0, 2.2 Hz, 1H); 7.67 (dd, J=13.1, 2.5 Hz, 1H); 7.30 (t, J=8.8 Hz, 1H); 7.20 (dd, J=8.8, 1.4 Hz, 1H); 6.64 (dd, J=5.5, 1.0 Hz 1H); 3.72 (s, 2H); 3.66 (t, J=5.5 Hz, 2H); 3.63-3.57 (m, 1H); 3.37 (t, J=5.2 Hz, 2H); 2.98 (br. d, J=11.2 Hz, 2H); 2.93 (br. s, 3H); 2.63-2.58 (m, 1H); 2.33 (br. t, J=11.0 Hz, 2H); 1.92 (br. d, J=10.0 Hz, 2H); 1.65-1.55 (m, 2H); 0.90-0.74 (m, 2H); 0.55-0.52 (m, 2H). [Signals of OH- and NH-protons are not seen]. MS (m/z): 634.5 (M+1)+.

Scheme 73

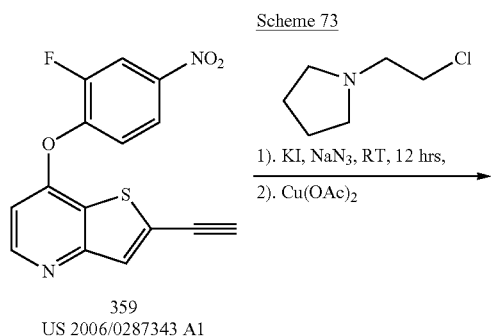

359
US 2006/0287343 A1

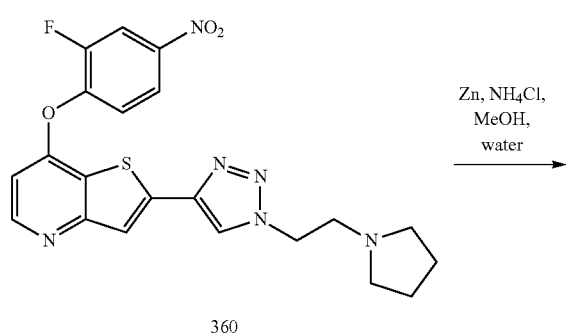

360

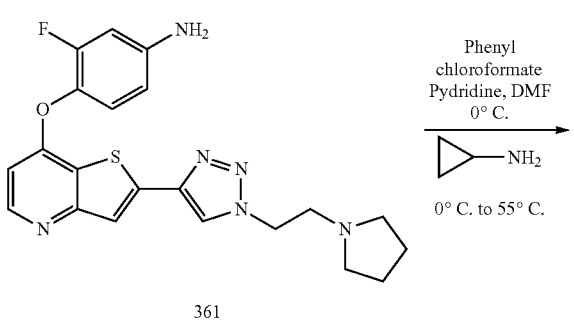

361

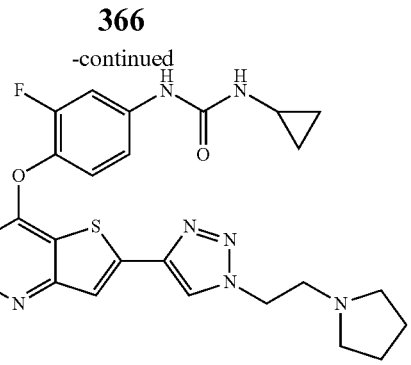

362: Example 215

Example 215

1-Cyclopropyl-3-(3-fluoro-4-(2-(1-(2-(pyrrolidin-1-yl)ethyl)-1H-1,2,3-triazol-4-yl)thieno[3,2-b]pyridin-7-yloxy)phenyl)urea (362)

Step 1: 7-(2-Fluoro-4-nitrophenoxy)-2-(1-(2-(pyrrolidin-1-yl)ethyl)-1H-1,2,3-triazol-4-yl)thieno[3,2-b]pyridine, (360)

To a solution of NaN$_3$ (49.6 mg, 0.764 mmol) in DMSO (5 mL) was added 1-(2-chloroethyl)pyrrolidine (102 mg, 1.2 eq, 0.764 mmol) and KI (127 mg, 1.2 eq, 0.764 mmol) and the reaction mixture was stirred for 12 hrs at RT. Compound 359 (200 mg, 0.636 mmol) and Cu(OAc)$_2$.H$_2$O (34.7 mg, 0.3 eq, 0.191 mmol) were added and the deep red reaction mixture was allowed to stir at RT over 24 hrs. The mixture was then diluted with water and the precipitated solid was collected by filtration to afford the title compound 360 (150 mg, 52% yield) that was used in the next step with no additional purification. MS (m/z): 455.5 (M+H).

Step 2: 3-Fluoro-4-(2-(1-(2-(pyrrolidin-1-yl)ethyl)-1H-1,2,3-triazol-4-yl)thieno[3,2-b]pyridin-7-yloxy)aniline (361)

To a solution of 360 (150 mg, 0.329 mmol) in MeOH (10 mL) was added ammonium chloride (35.3 mg, 2 eq, 0.660 mmol) in water (1 mL) and zinc powder (86 mg, 4 eq, 1.320 mmol) and the reaction mixture was heated to reflux for 3 hours. The mixture was cooled to RT then filtered and the filtrate was concentrated under reduced pressure. The residue was dissolved in DCM and washed with water. The organic phase was collected, dried over anhydrous Na$_2$SO$_4$, filtered and concentrated to afford the title compound 361 (98 mg, 70% yield) that was used in the next step with no additional purification. MS (m/z): 425.5 (M+H)

Step 3: 1-Cyclopropyl-3-(3-fluoro-4-(2-(1-(2-(pyrrolidin-1-yl)ethyl)-1H-1,2,3-triazol-4-yl)thieno[3,2-b]pyridin-7-yloxy)phenyl)urea (362)

To a stirred solution of 361 (98 mg, 0.231 mmol) and pyridine (0.057 mL, 3 eq, 0.9 mmol) in DMF (5 mL) at 0° C. under nitrogen was added phenyl chloroformate (0.072 ml, 2.5 eq, 0.577 mmol) and the reaction mixture was stirred at 0° C. for 2 hrs. Cyclopropylamine (66 mg, 5 eq, 1.154 mmol) was added and the reaction mixture was heated at 55° C. for 5 hrs. The reaction mixture was then diluted with EtOAc, washed sequentially with sodium bicarbonate solution, saturated ammonium chloride solution and brine, then dried over anhydrous Na₂SO₄, filtered and concentrated. The residue was purified by column chromatography (eluent EtOAc to 30% MeOH in EtOAc) to afford the title compound 362 (50 mg, 42% yield) as a while solid after additional trituration with Et₂O. ¹H NMR (400 MHz, DMSO-d₆) δ (ppm): 8.8 (s, 1H), 8.71 (s, 1H), 8.48 (d, J=5.48 Hz, 1H), 7.91 (s, 1H), 7.70 (m, 1H), 7.36 (m, 1H), 7.18 (d, J=8.99 Hz, 1H), 6.61 (d, J=5.48 hz, 1H), 6.55 (s, 1H), 4.55 (m, 2H), 2.93 (m, 2H), 2.50 (m, 1H), 1.67 (m, 4H), 0.65 (m, 2H), 0.41 (m, 2H). MS (m/z): 508.54.

Compounds 363-369 (examples 216-222) were synthesized starting from the compound 359 (scheme 73) by following the procedures similar to the described above for the synthesis of compound 362 (example 215, scheme 73).

TABLE 28

Characterization of compounds 363-369 (examples 216-222)

| Cpd | Ex. | Structure | Characterization |
|---|---|---|---|
| 363 | 216 | 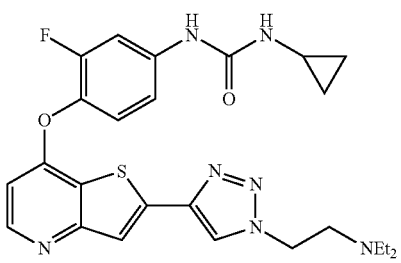<br>1-cyclopropyl-3-(4-(2-(1-(2-(diethylamino)ethyl)-1H-1,2,3-triazol-4-yl)thieno[3,2-b]pyridin-7-yloxy)-3-fluorophenyl)urea | ¹H NMR (400 MHz, DMSO-d₆) δ (ppm): 8.76(s, 1H), 8.71(s, 1H), 8.48 (d, J = 5.28 Hz, 1H), 7.89(s, 1H), 7.71 (m, 1H), 7.36(t, J = 8.99 Hz, 1H), 7.18 (m, 1H), 6.61(d, J = 5.28 Hz, 1H), 6.56 (s, 1H), 4.46(t, J = 6.26 Hz, 2H), 2.84 (t, J = 6.26 Hz, 2H), 2.53(m, 4H), 1.08 (t, J = 7.04 Hz, 6H), 0.64(m, 2H), 0.41 (m, 2H). MS(m/z): 510.15(M + H). |
| 364 | 217 | 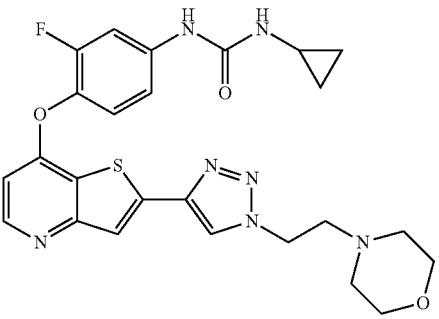<br>1-cyclopropyl-3-(3-fluoro-4-(2-(1-(2-morpholinoethyl)-1H-1,2,3-triazol-4-yl)thieno[3,2-b]pyridin-7-yloxy)phenyl)urea | ¹H NMR (400 MHz, DMSO-d₆) δ (ppm): 8.79(s, 1H), 8.71(s, 1H), 8.50 (d, J = 5.48 hz, 1H), 7.94(s, 1H), 7.72 (m, 1H), 7.38(t, J = 8.99 Hz, 1H), 7.20 (m, 1H), 6.63(m, 1H), 6.57(m, 1H), 458(t, J = 6.26 Hz, 2H), 3.55(m, 4H), 2.80(t, J = 6.26 Hz, 2H), 2.52(m, 1H), 2.45(m, 4H), 0.65(m, 2H), 0.42(m, 2H). MS(m/z): 524.49(M + H). |
| 365 | 218 | 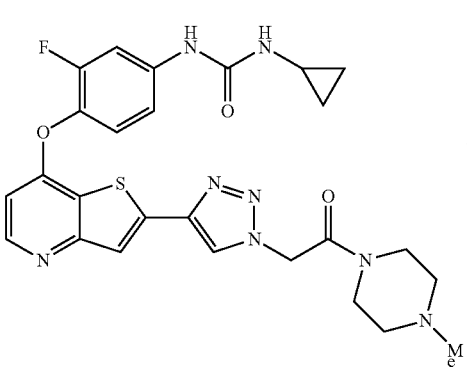<br>1-cyclopropyl-3-(3-fluoro-4-(2-(1-(2-(4-methylpiperazin-1-yl)-2-oxoethyl)-1H-1,2,3-triazol-4-yl)thieno[3,2-b]pyridin-7-yloxy)phenyl)urea | ¹H NMR (400 MHz, DMSO-d₆) δ (ppm): 9.0(s, 1H), 8.67(s, 1H), 8.45(d, J = 5.49 Hz, 1H), 7.92(s, 1H), 7.70(m, 1H), 7.34(t, J = 9.19 Hz, 1H), 6.89(d, J = 5.47 Hz, 1H), 5.57(s, 2H), 3.45(m, 4H), 3.43(m, 4H), 2.49(m, 1H), 2.35 (m, 4H), 2.26(m, 4H), 2.17(s, 3H), 0.6 (m, 2H), 0.42(m, 4H). MS(m/z): 551.53(M + H) |

TABLE 28-continued

Characterization of compounds 363-369 (examples 216-222)

| Cpd | Ex. | Structure | Characterization |
|---|---|---|---|
| 367 | 220 | 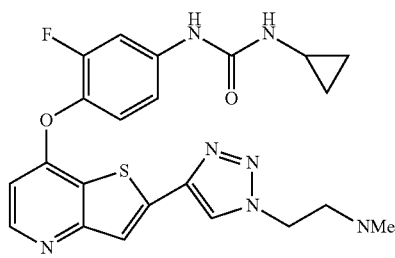<br>1-cyclopropyl-3-(4-(2-(1-(2-(dimethylamino)ethyl)-1H-1,2,3-triazol-4-yl)thieno[3,2-b]pyridin-7-yloxy)-3-fluorophenyl)urea | $^1$H NMR (400 MHz, DMSO-d$_6$) δ (ppm): 8.80(s, 1H), 8.50(d, J = 5.28 Hz, 1H), 7.91(s, 1H), 7.73(m, 1H), 7.38(t, J = 8.99 Hz, 1H), 7.20(m, 1H), 6.63(m, 2H), 4.54(t, J = 6.07 Hz, 2H), 3.35 t, J = 6.07 Hz, 2H), 2.20(s, 6H), 0.65(m, 2H), 0.43(m, 2H). MS(m/z): 482.43(M + H) |
| 368 | 221 | 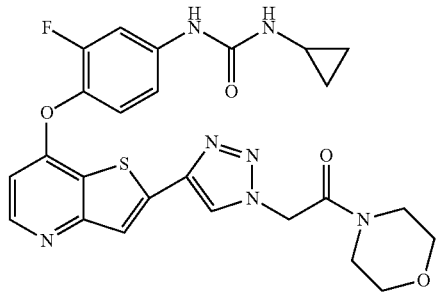<br>1-cyclopropyl-3-(3-fluoro-4-(2-(1-(2-morpholino-2-oxoethyl)-1H-1,2,3-triazol-4-yl)thieno[3,2-b]pyridin-7-yloxy)phenyl)urea | $^1$H NMR (400 MHz, DMSO-d$_6$) δ (ppm): 8.79(s, 1H), 8.71(s, 1H), 8.50 (d, J = 5.48 Hz, 1H), 7.97(s, 1H), 7.70 (m, 1H), 7.39(t, J = 8.99 Hz, 1H), 7.38 (m, 1H), 6.64(m, 2H), 5.62(s, 2H), 3.69(m, 2H), 3.61(m, 2H), 3.55(m, 2H), 3.48(m, 2H), 0.65(m, 2H), 0.42 (m, 2H). MS(m/z): 538.4(M + H) |
| 369 | 222 | 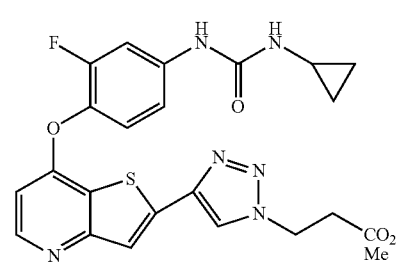<br>Methyl 3-(4-(7-(4-(3-cyclopropylureido)-2-fluorophenoxy)thieno[3,2-b]pyridin-2-yl)-1H-1,2,3-triazol-1-yl)propanoate | $^1$H NMR (400 MHz, DMSO-d$_6$) δ (ppm): 8.82(s, 1H), 8.70(s, 1H), 8.50 (d, J = 5.48 Hz, 1H), 7.91(s, 1H), 7.72 (m, 1H), 7.38(t, J = 9.20 Hz, 1H), 7.20 (m, 1H), 6.63(d, J = 5.48 hz, 1H), 6.56 (s, 1h), 4.68(t, J = 6.65 Hz, 2H), 3.62 (s, 3H), 3.07(t, J = 6.65 hz, 2H), 2.55 (m, 1H), 0.64(m, 2H), 0.43(m, 2H). MS(m/z): 497.41(M + H) |

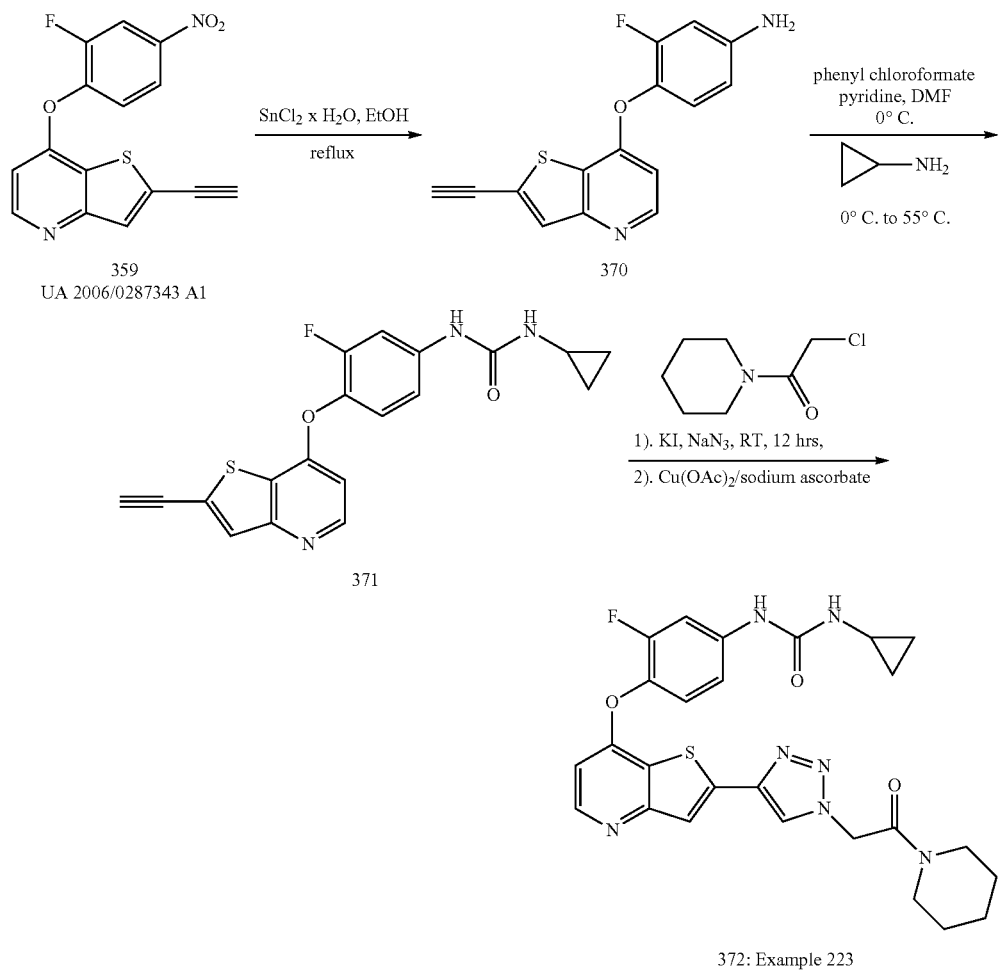

Scheme 74

372: Example 223

Example 223

1-Cyclopropyl-3-(3-fluoro-4-(2-(1-(2-oxo-2-(piperidin-1-yl)ethyl)-1H-1,2,3-triazol-4-yl)thieno[3,2-b]pyridin-7-yloxy)phenyl)urea Step 1: 4-(2-Ethynylthieno[3,2-b]pyridin-7-yloxy)-3-fluoroaniline (370)

To a solution of 359 (120 mg, 0.382 mmol) in EtOH (5 ml) was added SnCl$_2$.2H$_2$O (431 mg, 5 eq, 1.91 mmol) and the reaction mixture was heated to reflux for 30 min (Bellamy, F. D.; Ou, K. *Tetrahedron Lett.* 1984, 25, 839). The mixture was cooled slightly and poured onto ice. A saturated solution of NaHCO$_3$ and DCM were added and the resultant cloudy mixture was stirred for 15 min. The mixture was then filtered and biphasic filtrate was allowed to separate. The aqueous phase was extracted with additional DCM and the organic extracts were combined, dried over anhydrous MgSO$_4$, filtered and concentrated to afford the title compound 370 (102 mg, 94% yield) was used in the next step with no additional purification. MS (m/z): 285.17 (M+H).

Step 2: 1-Cyclopropyl-3-(4-(2-ethynylthieno[3,2-b]pyridin-7-yloxy)-3-fluorophenyl)urea (371)

To a stirred solution of 370 (102 mg, 0.359 mmol) and pyridine (0.058 mL, 2 eq, 0.718 mmol) in THF (5 ml)/DMF (2 ml) at 0° C. under nitrogen was added phenyl chloroformate (0.068 mL, 1.5 eq, 0.538 mmol) and the reaction mixture was stirred at 0° C. for 1 hr. Cyclopropylamine (102 mg, 5 eq, 1.794 mmol) was added and the reaction mixture was heated at 55° C. for 3 hrs. The mixture was then cooled to RT, diluted with EtOAc then washed sequentially with saturated solutions of NH$_4$Cl, NaHCO$_3$ and brine. The organic phase was dried over anhydrous Na$_2$SO$_4$, filtered and concentrated. The residue was purified via column chromatography (eluent EtOAc to 40% MeOH in EtOAc) to afford the title compound 371 (100 mg, 76% yield) as an off-white powder after trituration with Et$_2$O. MS (m/z): 368.23 (M+H)

Step 3: 1-cyclopropyl-3-(3-fluoro-4-(2-(1-(2-oxo-2-(piperidin-1-yl)ethyl)-1H-1,2,3-triazol-4-yl)thieno[3,2-b]pyridin-7-yloxy)phenyl)urea (372)

To a solution of the 2-chloro-1-(piperidin-1-yl)ethanone (106 mg, 2 eq, 0.653 mmol) in DMSO (2 ml) was added sodium azide (42.5 mg, 2 eq, 0.653 mmol) and KI (108 mg, 2 eq, 0.653 mmol) and the reaction mixture was stirred overnight at RT. The alkyne (120 mg, 0.0.327 mmol), Cu(OAc)$_2$·2H$_2$O (17.8 mg, 0.3 eq, 0.098 mmol) and sodium ascorbate (38.8 mg, 0.6 eq, 0.196 mmol) were added and the pale orange mixture was allowed to stir at RT for 15 min. The mixture was then poured onto ice and a few drops of NH$_4$OH were added (~pH 10). The mixture was extracted with DCM and the organic phase was collected, dried over anhydrous Na$_2$SO$_4$, filtered and concentrated. Purification by column chromatography (EtOAc to 20% MeOH in EtOAc) afforded an oil which was dissolved in a mixture of acetone/Et$_2$O. Additional Et$_2$O was added; a precipitate was formed which was collected by filtration to afford the title compound 372 (84 mg, 48% yield) as a white solid. $^1$H NMR (400 MHz, DMSO-d$_6$) δ (ppm): 8.77 (s, 1H), 8.71 (s, 1H), 8.50 (d, J=5.48 Hz, 1H), 7.96 (s, 1H), 7.73 (m, 1H), 7.39 (t. J=8.99 Hz, 1H), 7.38 (m, 1H), 6.64 (6, 1H), 6.63 (s, 1H), 5.58 (s, 2H), 3.38 (m, 4H), 2.55 (m, 1H), 1.61 (m, 4H), 1.48 (m, 2H), 0.64 (m, 2H), 0.43 (m, 2H). MS (m/z): 536.52 (M+H)

Compounds 373, 375-388 (examples 224, 226-239) were synthesized starting from the compound 359 by following the procedures similar to the described above for the synthesis of compound 372 (example 223, scheme 74).

TABLE 29

Characterization of compounds 373-388 (examples 224-239)

| Cpd | Ex. | Structure | Characterization |
|---|---|---|---|
| 373 | 224 | 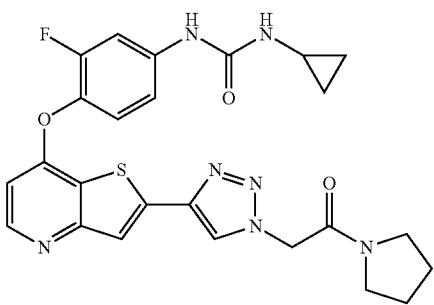<br>1-cyclopropyl-3-(3-fluoro-4-(2-(1-(2-oxo-2-(pyrrolidin-1-yl)ethyl)-1H-1,2,3-triazol-4-yl)thieno[3,2-b]pyridin-7-yloxy)phenyl)urea | $^1$H NMR (400 MHz, DMSO-d$_6$) δ (ppm): 8.71(m, 2H), 8.52(s, 1H), 7.98(s, 1H), 7.73(m, 1H), 7.39(t, J = 8.99 Hz, 1H), 7.20(m, 1H), 6.64(d, J = 5.086 Hz, 1H), 6.56(s, 1H), 5.48(s, 1H), 3.57(t, J = 6.65 Hz, 2H), 3.35(m, 2H, under H$_2$O peak), 2.54(m, 2H), 0.65(m, 2H), 0.43(m, 2H). MS (m/z): 522.54(M + H). |
| 375 | 224 | 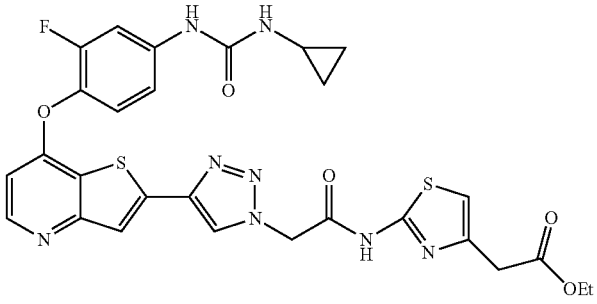<br>ethyl 2-(2-(2-(4-(7-(4-(3-cyclopropylureido)-2-fluorophenoxy)thieno[3,2-b]pyridin-2-yl)-1H-1,2,3-triazol-1-yl)acetamido)thiazol-4-yl)acetate | $^1$H NMR (400 MHz, DMSO-d$_6$) δ (ppm): 12.78(s, 1H), 8.86(s, 1H), 8.71(s, 1H), 8.51(s, 1H), 7.99(s, 1H), 7.73(m, 1H), 7.40(t, J = 8.99 Hz, 1H), 7.19(m, 1H), 7.06(s, 1H), 6.64(d, J = 5.086 Hz, 1H), 6.56(s, 1H), 5.57(s, 2H), 4.10(q, J = 7.043 Hz, 2H), 3.71(s, 2H), 3.40(m, 1H), 1.19(t, J = 7.043 Hz, 3H), 0.64(m, 2H), 0.43(m, 2H). MS (m/z): 637.54(M + H) |

TABLE 29-continued

Characterization of compounds 373-388 (examples 224-239)

| Cpd | Ex. | Structure | Characterization |
|---|---|---|---|
| 376 | 227 | (S)-1-cyclopropyl-3-(4-(2-(1-(2-(3-(dimethylamino)pyrrolidin-1-yl)-2-oxoethyl)-1H-1,2,3-triazol-4-yl)thieno[3,2-b]pyridin-7-yloxy)-3-fluorophenyl)urea | $^1$H NMR (400 MHz, DMSO-d$_6$) δ (ppm): 8.71(m, 2H), 8.50(d, J = 5.48 Hz, 1H), 7.97 (s, 1H), 7.73(m, 1H), 7.39(t, J = 9.19 Hz, 1H), 7.20(m, 1H), 6.64(d, J = 5.48 Hz, 1H), 6.56(s, 1H), 5.59(s, 2H, rotamer), 3.88-3.55(m, 5 H, rotamers), 2.54(m, 1H), 2.28(s, 6H), 2.1-1.7(m, 2H, rotamers), 0.65(m, 2H), 0.43(m, 2H). MS (m/z): 565.58(M + H) |
| 377 | 228 | 1-cyclopropyl-3-(3-fluoro-4-(2-(1-(3-morpholino-3-oxopropyl)-1H-1,2,3-triazol-4-yl)thieno[3,2-b]pyridin-7-yloxy)phenyl)urea | $^1$H NMR (400 MHz, DMSO-d$_6$) δ (ppm): 8.8(s, 1H), 8.71(s, 1H), 7.91(s, 1H), 7.72 (m, 1H), 7.37(t, J = 8.99 hz, 1H), 7.20(m, 1H), 6.64(s, 1H), 6.57(s, 1H), 4.66(t, J = 4.89 Hz, 2H), 3.55(m, 4H), 3.44(m, 4H), 3.08(t, J = 6.84 Hz, 2H), 2.54(m, 1H), 0.65(m, 2H), 0.43(m, 2H). MS(m/z): 552.57(M + H). |
| 378 | 229 | 1-cyclopropyl-3-(3-fluoro-4-(2-(1-(3-(4-methylpiperazin-1-yl)-3-oxopropyl)-1H-1,2,3-triazol-4-yl)thieno[3,2-b]pyridin-7-yloxy)phenyl)urea | $^1$H NMR (400 MHz, DMSO-d$_6$) δ (ppm): 8.96(s, 1H), 8.78(s, 1H), 8.48(d, J = 5.48 Hz, 1H), 7.89(s, 1H), 7.72(m, 1H), 7.35(t, J = 8.99 Hz, 1H), 7.22(m, 1H), 6.80(m, 1H), 6.61(d, J = 5.38 Hz, 1H), 4.63(t, J = 6.45 Hz, 2H), 3.05(t, J = 6.84 Hz, 2H), 2.53(m, 1H), 2.24(m, 4H), 2.13(s, 3H), 0.62(m, 2H), 0.41(m, 2H). MS(m/z): 565.51(M + H) |

TABLE 29-continued

Characterization of compounds 373-388 (examples 224-239)

| Cpd | Ex. | Structure | Characterization |
|---|---|---|---|
| 379 | 230 | 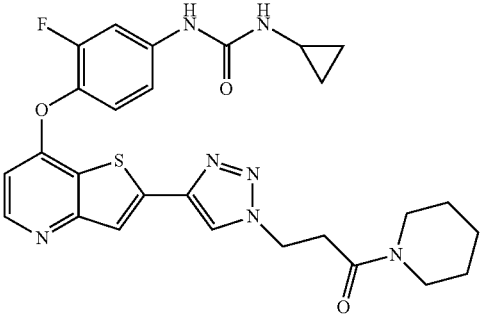<br>1-cyclopropyl-3-(3-fluoro-4-(2-(1-(3-oxo-3-(piperidin-1-yl)propyl)-1H-1,2,3-triazol-4-yl)thieno[3,2-b]pyridin-7-yloxy)phenyl)urea | $^1$H NMR (400 MHz, DMSO-$d_6$) δ (ppm): 8.08(s, 1H), 8.73(s, 1H), 8.50(d, J = 5.48 Hz, 1H), 7.91(s, 1H), 7.72(m, 1H), 7.38(t, J = 8.99 Hz, 1H), 7.20(m, 1H), 6.63(d, J = 5.48 Hz, 1H), 4.64(t, J = 6.65 Hz, 2H), 3.44-3.36(m, 4 H), 3.05(t, J = 6.84 Hz, 2H), 2.54(m, 1H), 1.56-1.40(m, 6H), 0.64(m, 2H), 0.43(m, 2H). MS(m/z): 550.57(M + H) |
| 380 | 231 | 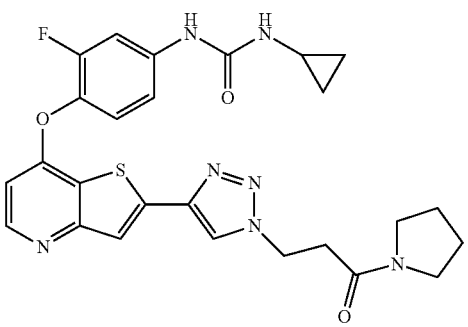<br>1-cyclopropyl-3-(3-fluoro-4-(2-(1-(3-oxo-3-(pyrrolidin-1-yl)propyl)-1H-1,2,3-triazol-4-yl)thieno[3,2-b]pyridin-7-yloxy)phenyl)urea | $^1$H NMR (400 MHz, DMSO-$d_6$) δ (ppm): 8.80(s, 1H), 8.78(s, 1H), 8.50(d, J = 5.47 Hz, 1H), 7.91(s, 1H), 7.72(m, 1H), 7.38(t, J = 8.99 Hz, 1H), 7.20(m, 1H), 6.61(m, 2H), 4.65(t, J = 6.65 Hz, 2H), 3.39(t, J = 6.85 Hz, 2H), 3.28(t, J = 6.83 Hz, 2H), 2.98(t, J = 6.65 Hz, 2H), 2.54(m, 2H), 1.85(m, 2H), 1.75(m, 2H), 0.65(m, 2H), 0.53(m, 2H). MS(m/z): 536.56(M + H) |
| 381 | 232 | 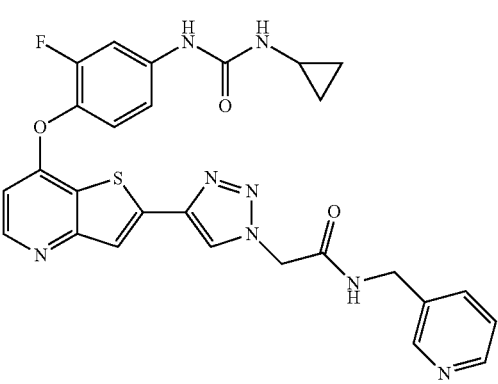<br>2-(4-(7-(4-(3-cyclopropylureido)-2-fluorophenoxy)thieno[3,2-b]pyridin-2-yl)-1H-1,2,3-triazol-1-yl)-N-(pyridin-3-ylmethyl)acetamide | $^1$H NMR (400 MHz, DMSO-$d_6$) δ (ppm): 8.97(t, J = 5.86 Hz, 1H), 8.81(s, 1H), 8.73 (s, 1H), 8.51(m, 3H), 7.98(s, 1H), 7.72(m, 2H), 7.39(m, 2H), 7.21(m, 1H), 6.63(d, J = 5.28 Hz, 1H), 6.59(s, 1H), 5.31(s, 2H), 4.38(d, J = 5.67 Hz, 2H), 2.55(m, 1H), 0.65(m, 2H), 0.43(m, 2H) MS(m/z): 559.41(M + H). |

TABLE 29-continued

Characterization of compounds 373-388 (examples 224-239)

| Cpd | Ex. | Structure | Characterization |
|---|---|---|---|
| 382 | 233 | tert-butyl 1-(2-(4-(7-(4-(3-cyclopropylureido)-2-fluorophenoxy)thieno[3,2-b]pyridin-2-yl)-1H-1,2,3-triazol-1-yl)acetyl)pyrrolidin-3-ylcarbamate | $^1$H NMR (400 MHz, DMSO-d$_6$) δ (ppm): 8.71(m, 2H), 8.48(d, J = 5.49 Hz, 1H), 7.97(m, 1H), 7.71(m, 1H), 7.38(t, J = 8.99 Hz, 1H), 7.20(m, 2H, rotamer), 6.62(d, J = 5.48 Hz, 1H), 6.55(s, 1H), 5.46(m, rotamer, 2H), 4.11-3.99(m, rotamerm 1H), 3.78-3.33(m, rotamers, 4H), 2.65-1.76 (m, rotamers, 2H), 1.38(m, rotamers, 9H), 0.65(m, 2H), 0.43(m, 2H). MS(m/z): 537.59(M + H) |
| 383 | 234 | 2-(4-(7-(4-(3-cyclopropylureido)-2-fluorophenoxy)thieno[3,2-b]pyridin-2-yl)-1H-1,2,3-triazol-1-yl)-N-(pyridin-2-ylmethyl)acetamide | $^1$H NMR (400 MHz, DMSO-d$_6$) δ (ppm): 9.04(m, 1H), 8.82(s, 1H), 8.71(s, 1H), 8.54(s, 1H), 7.99(s, 1H), 7.79(t, J = 7.43 Hz, 1H), 7.73(m, 1H), 7.41(m, 2H), 7.30 (m, 1H), 7.19(m, 1H), 6.64(m, 1H), 6.56 (m, 1H), 5.34(s, 2H), 4.46(d, J = 5.47 Hz, 2H), 2.54(m, 1H), 0.65(m, 2H), 0.42(mn, 2H). MS(m/z): 559.47 |
| 384 | 235 | 1-cyclopropyl-3-(4-(2-(1-(3-(dimethylamino)propyl)-1H-1,2,3-triazol-4-yl)thieno[3,2-b]pyridin-7-yloxy)-3-fluorophenyl)urea | $^1$H NMR (400 MHz, DMSO-d$_6$) δ (ppm): 8.18(s, 1H), 7.32(s, 1H), 8.48(d, J = 5.28 Hz, 1H), 7.89(s, 1H), 7.72(m, 1H), 7.37(t, J = 8.99 Hz, 1H), 7.20(m, 1H), 6.61(d, J = 5.47 Hz, 1H), 6.58(s, 1H), 4.45(t, J = 7.043, 2H), 3.35(m, 1H), 2.23(t, J = 6.8 Hz, 2H), 2.12(s, 6H), 2.00(m, 2H), 0.64 (m, 2H_, 0.41(m, 2H). MS(m/z): 496.43 (M + H) |

TABLE 29-continued

Characterization of compounds 373-388 (examples 224-239)

| Cpd | Ex. | Structure | Characterization |
|---|---|---|---|
| 385 | 236 | 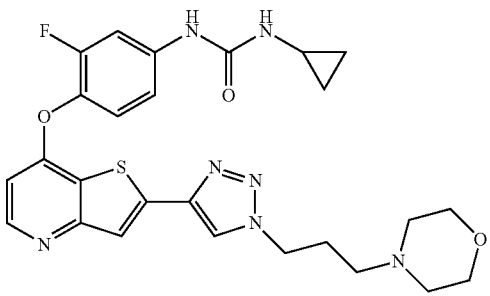<br>1-cyclopropyl-3-(3-fluoro-4-(2-(1-(3-morpholinopropyl)-1H-1,2,3-triazol-4-yl)thieno[3,2-b]pyridin-7-yloxy)phenyl)urea | $^1$H NMR (400 MHz, DMSO-d$_6$) δ (ppm): 8.83(s, 1H), 8.75(s, 1H), 8.50(d, J = 5.47 Hz, 1H), 7.90(s, 1H), 7.72(m, 1H), 7.38(t, J = 8.99 Hz, 1H), 6.63(d, J = 5.48 Hz, 1H), 6.59(s, 1H), 4.48(t, J = 7.04 Hz, 2H), 3.55 (m, 4H), 2.55(m, 1H), 2.29(m, 6H), 2.08 (m, 2H), 0.65(m, 2H), 0.42(m, 2H). MS (m/z): 538.42(M + H). |
| 386 | 237 | 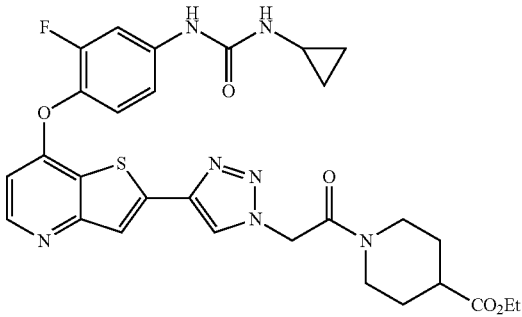<br>Ethyl 1-(2-(4-(7-(4-(3-cyclopropylureido)-2-fluorophenoxy)thieno[3,2-b]pyridin-2-yl)-1H-1,2,3-triazol-1-yl)acetyl)piperidine-4-carboxylate | $^1$H NMR (400 MHz, DMSO-d$_6$) δ (ppm): 8.61(s, 1H), 8.45(m, 1H), 7.91(s, 1H), 7.65(m, 1H), 7.33(t, J = 8.99 Hz, 1H), 7.14(m, 1H), 6.56(d, J = 5.28 hz, 1H), 6.52 (s, 1H), 5.56(d, J = 8.61 Hz, 2H), 4.13(m, 1H), 4.0(q, J = 7.04 Hz, 2H), 3.82(m, 1H), 3.54(m, 1H), 3.14(m, 1H), 2.77(m, 2H), 2.61(m, 2H), 2.50(m, 1H), 1.83(m, 2H), 1.68(m, 1H), 1.21(m, 1H), 1.13(t, J = 7.04 Hz, 3H), 0.59(m, 2H), 0.37(m, 2H). MS (m/z): 538.42(M + H) |
| 387 | 238 | 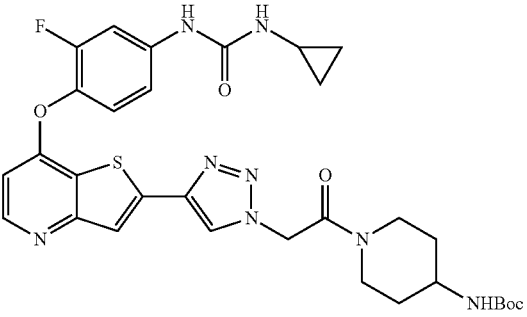<br>tert-butyl 4-(2-(4-(7-(4-(3-cyclopropylureido)-2-fluorophenoxy)thieno[3,2-b]pyridin-2-yl)-1H-1,2,3-triazol-1-yl)acetyl)piperazine-1-carboxylate | $^1$H NMR (400 MHz, DMSO-d$_6$) δ (ppm): 8.74(s, 1H), 8.71(s, 1H), 8.50(d, J = 5.48 hz, 1H), 7.96(s, 1H), 7.72(m, 1H), 7.39(t, J = 8.99 Hz, 1H), 7.20(m, 1H), 6.98(m, 1H), 6.62(d, J = 5.09 Hz, 1H), 6.59(s, 1H), 5.67(d, J = 16.85 Hz, 1H), 5.56(d, J = 16.62 Hz, 1H), 4.18(m, 1H), 3.84(m, 1H), 3.46(m, 2H), 3.17(m, 2H), 2.81(m, 1H), 2.55(m, 1H), 1.80(m, 2H), 1.39(s, 9H), 0.65(m, 2H), 0.45(m, 2H). MS (m/z): 651.58(M + H) |

TABLE 29-continued

Characterization of compounds 373-388 (examples 224-239)

| Cpd | Ex. | Structure | Characterization |
|---|---|---|---|
| 388 | 239 | 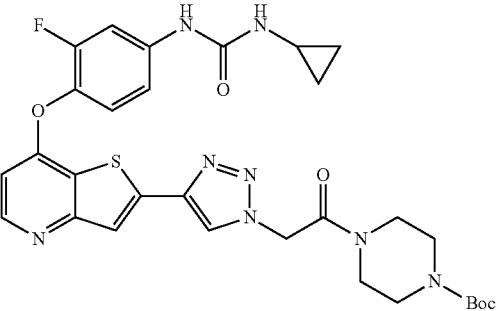<br><br>tert-butyl 4-(2-(4-(7-(4-(3-cyclopropylureido)-2-fluorophenoxy)thieno[3,2-b]pyridin-2-yl)-1H-1,2,3-triazol-1-yl)acetyl)piperazine-1-carboxylate | $^1$H NMR (400 MHz, DMSO-d$_6$) δ (ppm): 8.71(m, 1H), 8.70(s, 1H), 8.48(s, d, J = 5.48 Hz, 1H) 7.95(s, 1H), 7.71(m, 1H), 7.38(t, J = 8.99 Hz, 1H), 7.18(m, 1H), 6.61(d, J = 5.48 Hz, 1H), 6.57(s, 1H), 5.62 (s, 1H)m 3.52(m, 2H), 3.44(m, 4H), 3.35 (m, 2H), 2.55(s, 1H), 1.41(s, 9H), 0.64(m, 2H), 8.41(m, 2H). MS(m/z): 637.45 (M + H) |

Scheme 75

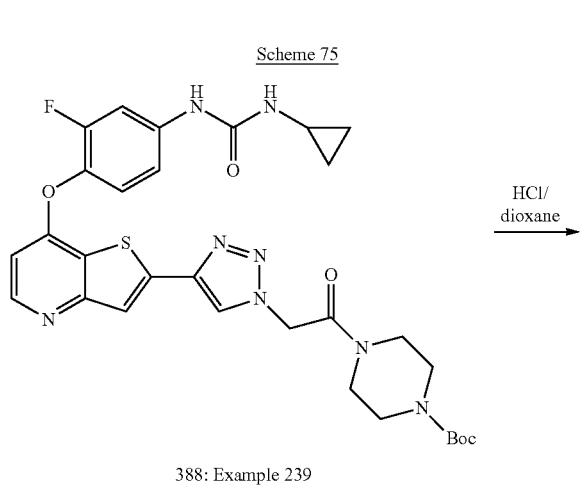

388: Example 239

↓ HCl/dioxane

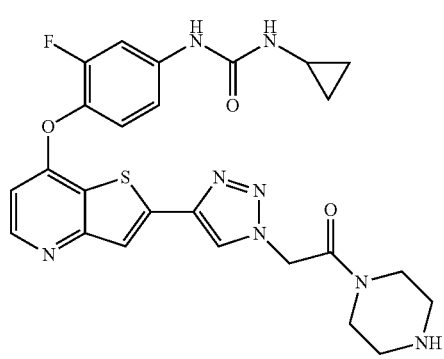

389: Example 240

Example 240

1-Cyclopropyl-3-(3-fluoro-4-(2-(1-(2-oxo-2-(piperazin-1-yl)ethyl)-1H-1,2,3-triazol-4-yl)thieno[3,2-b]pyridin-7-yloxy)phenyl)urea (389)

To a solution of 388 (800 mg, 1.256 mmol) in a solvent mixture of DCM (70 mL) and DMF (10 mL) was added HCl in dioxane (0.882 mL, 10 eq, 12.56 mmol, 4.0 M solution) and the reaction mixture was stirred for 24 hours. The mixture was poured into saturated NaHCO$_3$ solution and the resultant solid was collected by filtration then washed with water and dried to afford the title compound 389 (350 mg, 52% yield) as a white solid. $^1$H NMR (400 MHz, DMSO-d$_6$) δ (ppm): 9.6 (m, 2H), 8.71 (d, J=5.30 Hz, 1H), 8.49 (d, J=4.05 Hz, 1H), 7.95 (m, 1H), 7.76 (d, J=11.50 Hz, 1H), 7.45 (s, 1H), 7.35 (t, J=9.1 Hz, 1H), 7.24 Hz (m, 1H), 6.62 (m, 1H) 4.43 (m, 1H), 4.30 (m, 5H), 2.75 (m, 1H), 2.66 (m, 1H), 2.53 (m, 1H), 1.21 (m, 1H), 0.61 (m, 2H), 0.42 (m, 2H). MS (m/z)=537.4 (M+H).

Compounds 390-392 (examples 241-243) were synthesized starting from the compound 389 (example 239, scheme 75) by following the procedures similar to the ones described above for the synthesis of compounds 30 and 31 (scheme 13). Compound 393 (example 244) was synthesized starting from the compound 392 by following the procedure similar to the one described above for the synthesis of compound 389 (example 240, scheme 75). Compound 394 (example 245) was synthesized starting form the compound 389 by following the procedure similar to the one described above for the synthesis of compound 128 (example 87, scheme 32). Compound 395 (example 246) was synthesized starting from the compound 387 by following the procedure similar to the one described above for the synthesis of compound 13 (example 10, scheme 9).

TABLE 30

Characterization of compounds 390-395 (examples 241-246)

| Cpd | Ex. | Structure | Characterization |
|---|---|---|---|
| 390 | 241 | 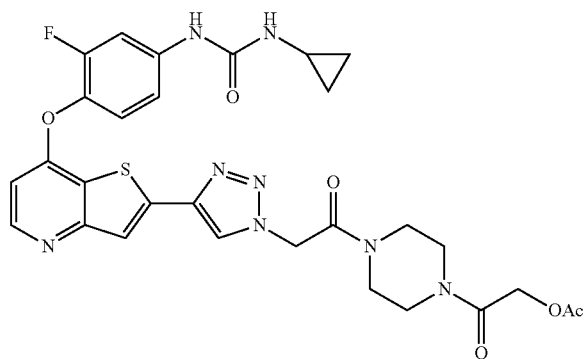<br>4-(2-(4-(7-(4-(3-cyclopropylureido)-2-fluorophenoxy)thieno[3,2-b]pyridin-2-yl)-1H-1,2,3-triazol-1-yl)acetyl)-N-ethylpiperazine-1-carboxamide | MS(m/z): 637.45(M + H) |
| 391 | 242 | 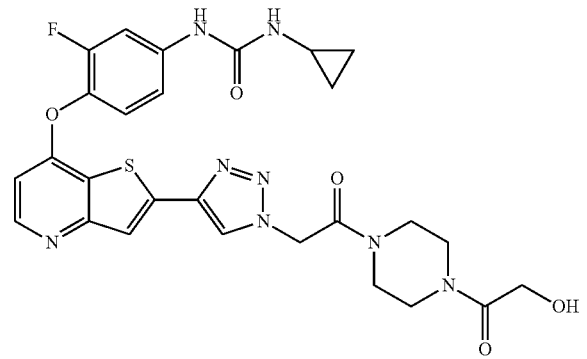<br>1-cyclopropyl-3-(3-fluoro-4-(2-(1-(2-(4-(2-hydroxyacetyl)piperazin-1-yl)-2-oxoethyl)-1H-1,2,3-triazol-4-yl)thieno[3,2-b]pyridin-7-yloxy)phenyl)urea | MS(m/z): 594.35(M + H) |
| 392 | 243 | 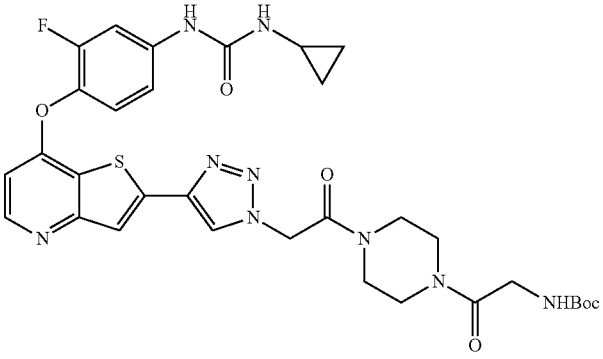<br>tert-butyl 2-(4-(2-(4-(7-(4-(3-cyclopropylureido)-2-fluorophenoxy)thieno[3,2-b]pyridin-2-yl)-1H-1,2,3-triazol-1-yl)acetyl)piperazin-1-yl)-2-oxoethylcarbamate | $^1$H NMR(400 MHz, DMSO-d$_6$) δ (ppm): 8.47(s, 1H), 8.71(s, 1H), 8.50(d, J = 5.48 Hz, 1H), 7.98(s, 1H), 7.73(m, 1H), 7.39(t, J = 8.99 Hz, 1H), 7.20(m, 1H), 6.82(m, 1H), 6.64(m, 2H), 5.56(m, 1H), 3.383(m, 2H), 3.39(m, 7H), 2.54(m, 1H), 0.65(m, 2H), 0.42(m, 1H). MS(m/z): 694.65 (M + H). |

TABLE 30-continued

Characterization of compounds 390-395 (examples 241-246)

| Cpd | Ex. | Structure | Characterization |
|---|---|---|---|
| 293 | 244 | 1-(4-(2-(1-(2-(4-(2-aminoacetyl)piperazin-1-yl)-2-oxoethyl)-1H-1,2,3-triazol-4-yl)thieno[3,2-b]pyridin-7-yloxy)-3-fluorophenyl)-3-cyclopropylurea | $^1$H NMR(400 MHz, DMSO-d$_6$) δ (ppm): 9.73(s, 1H), 8.74(s, 1H), 8.49(d, J = 5.28 Hz, 1H), 7.97(s, 1H), 7.72(m, 1H), 7.37(t, J = 9.19 Hz, 1H), 7.17(m, 1H), 7.08(m, 1H), 6.61(d, J = 5.28 Hz, 1H), 5.57(m, 1H), 3.57(m, 9H), 2.54(m, 1H), 1.98(m, 1H), 1.88(m, 1H), 0.65(m, 2H), 0.40(m, 2H). MS(m/z): 594.55(M + H) |
| 394 | 245 | 4-(2-(4-(7-(4-(3-cyclopropylureido)-2-fluorophenoxy)thieno[3,2-b]pyridin-2-yl)-1H-1,2,3-triazol-1-yl)acetyl)-N-ethylpiperazine-1-carboxamide | $^1$H NMR(400 MHz, DMSO-d$_6$) δ (ppm): 8.75(s, 1H), 8.71(s, 1H), 8.50(d, J = 5.40 Hz, 1H), 7.97(s, 1H), 7.74(m, 1H), 7.41(t, J = 9.05 Hz, 1H), 7.20(m, 1H), 6.62(m, 3H), 5.63(s, 2H), 3.54(m, 2H), 3.45(m, 2H), 3.41(m, 2H), 3.30(m, 2H), 3.05(m, 2H), 2.54(m, 1H), 1.02(t, J = 7.15 Hz, 3H), 0.65(m, 2H), 0.42(m, 2H). MS(m/z): 608.49(M + H) |
| 395 | 246 | 1-(4-(2-(1-(2-(4-aminopiperidine-1-yl)-2-oxoethyl)-1H-1,2,3-triazol-4-yl)thieno[3,2-b]pyridin-7-yloxy)-3-fluorophenyl)-3-cyclopropylurea | $^1$H NMR(400 MHz, DMSO-d$_6$) δ (ppm): 8.74(s, 1H), 8.71(s, 1H), 8.50(d, J = 5.48 hz, 1H), 7.96(s, 1H), 7.72(m, 1H), 7.39(t, J = 8.99 Hz, 1H), 7.20(m, 1H), 6.98(m, 1H), 6.62(d, J = 5.09 Hz, 1H), 6.59(s, 1H), 5.67(d, J = 16.85 Hz, 1H), 5.56(d, J = 16.62 Hz, 1H), 4.18(m, 1H), 3.84(m, 1H), 3.46(m, 2H), 3.17(m, 2H), 2.81(m, 1H), 2.55(m, 1H), 1.80(m, 2H), 0.65(m, 2H), 0.45(m, 2H). MS(m/z): 551.42(M + H). |

Compounds 396-398 (examples 247-249) were prepared similarly to compound 226 (example 127, scheme 54). Compounds 399 and 400 (examples 249 and 250) were prepared in one step by Boc-deprotection of compounds 397 and 398, similarly to compound 72 (example 52, scheme 19). Compounds 401-402 (examples 252-253) were synthesized by following the procedures described above for the synthesis of compound 49 (scheme 15).

TABLE 31

Characterization of compounds 396-401 (examples 247-252)

| Cpd | Ex. | Structure | Characterization |
|---|---|---|---|
| 396 | 247 | 1-cyclopropyl-3-(3-fluoro-4-(2-(5-(4-(2-(2-hydroxyethoxy)ethyl)piperazine-1-carbonyl)pyridin-2-yl)thieno[3,2-b]pyridin-7-yloxy)phenyl)urea | MS(m/z): 621.5(M + H) |
| 397 | 248 | tert-butyl 1-(6-(7-(4-(3-cyclopropylureido)-2-fluorophenoxy)thieno[3,2-b]pyridin-2-yl)nicotinoyl)piperidin-4-yl(methyl)carbamate | $^1$H NMR(400 MHz, DMSO-d$_6$) δ(ppm): 8.73(s, 1H), 8.70(d, J = 2.0 Hz, 1H), 8.54 (d, J = 5.2 Hz, 1H), 8.46(s, 1H), 8.36(d, J = 8.4 Hz, 1H), 8.02(dd, J = 8.0, 2.0 Hz, 1H), 7.73(dd, J = 13.6, 2.8 Hz, 1H), 7.39(t, J = 9.0 Hz, 1H), 7.23-7.18(m, 1H), 6.68(d, J = 4.4 Hz, 1H), 6.58(bd, J = 2.4 Hz, 1H), 4.65-4.53(m, 1H), 3.70-3.60 (m, 1H), 3.40-3.29(m, 1H), 3.24-3.10(m, 1H), 2.85-2.73(m, 1H), 2.70(s, 3H), 2.59-2.51(m, 1H), 1.80-1.60(m, 3H), 1.59-1.43(m, 1H), 1.40 (s, 9H), 0.69-0.62(m, 2H), 0.45-0.40(m, 2H). MS(m/z): 661.48(M + H). |
| 398 | 249 | tert-butyl 1-(6-(7-(4-(3-cycloproylureido)-2-fluorophenoxy)thieno[3,2-b]pyridin-2-yl)nicotinoyl)piperidin-4-ylcarbamate | MS(m/z): 648.6(M + H) |

TABLE 31-continued

Characterization of compounds 396-401 (examples 247-252)

| Cpd | Ex. | Structure | Characterization |
|---|---|---|---|
| 399 | 250 | 1-cyclopropyl-3-(3-fluoro-4-(2-(5-(4-(methylamino)piperidine-1-carbonyl)pyridin-2-yl)thieno[3,2-b]pyridin-7-yloxy)phenyl)urea | $^1$H NMR(400 MHz, DMSO-$d_6$) δ(ppm): 8.75(s, 1H), 8.66 (d, J = 0.8 Hz, 1H), 8.54 (d, J = 5.2 Hz, 1H), 8.45(s, 1H), 8.36(d, J = 8.4 Hz, 1H), 7.97(dd, J = 8.0, 2.0 Hz, 1H), 7.74(dd, J = 13.6, 2.4 Hz, 1H), 7.39(t, J = 9.0 Hz, 1H), 7.23-7.18(m, 1H), 6.68(d, J = 5.2 Hz,1H), 6.60 (bd, J = 2.4 Hz, 1H), 4.30-4.20(m, 1H), 3.63-3.54 (m, 1H), 3.20-3.01(m, 2H), 2.28(s, 3H), 1.94-1.73(m, 2H), 1.33-1.19(m, 2H), 0.69-0.62 (m, 2H), 0.45-0.40(m, 2H). MS(m/z): 561.50(M + H). |
| 400 | 251 | 1-(4-(2-(5-(4-aminopiperidine-1-carbonyl)pyridin-2-yl)thieno[3,2-b]pyridin-7-yloxy)-3-fluorophenyl)-3-cyclopropylurea | $^1$H NMR(400 MHz, DMSO-$d_6$) δ(ppm): 8.71(dd, J = 2.2, 0.8 Hz, 1H); 8.51(dd, J = 5.5 Hz, 1H); 8.23(dd, J = 8.2, 0.8 1H); 8.20(s, 1H); 8.0(dd, J = 8.2, 2.2 Hz, 1H); 7.70(dd, J = 13.1, 2.5 Hz, 1H); 7.33(t, J = 9.0Hz, 1H); 7.23(dd, J = 9.0 1.4 Hz, 1H); 6.69(dd, J = 5.5, 0.8 Hz, 1H); 4.66(br. s, 1H); 3.81(br. d, J = 8.6 Hz, 1H); 3.60(br. s, 2H); 2.66-2.61(m, 1H); 2.03(br. s, 1H); 1.93(br. s, 1H); 1.46(br. s, 2H); 0.82-0.77(m, 2H); 0.58-0.55(m, 2H). [Signals of NH— protons are not seen; NH$_2$—CH-signal is probably, obscured by the peak of residual solvent]. MS(m/z): 547.5 (M + H) |
| 401 | 252 | 1-cyclopropyl-3-(3-fluroo-4-(2-(5-((4-(methylamino)piperidin-1-yl)methyl)pyridin-2-yl)thieno[3,2-b]pyridin-7-yloxy)phenyl)urea | $^1$H NMR(400 MHz, DMSO-$d_6$) δ (ppm): 8.74(s, 1H), 8.53(d, J = 1.2 Hz, 1H), 8.51(d, J = 5.6 Hz, 1H), 8.32(s, 1H), 8.23(d, J = 8.0 Hz, 1H), 7.84 (dd, J = 8.0, 2.0 Hz, 1H), 7.73(dd, J = 13.6, 2.4 Hz, 1H), 7.38(t, J = 9.0 Hz, 1H), 7.23-7.18(m, 1H), 6.64(dd, J = 5.6, 0.8 Hz, 1H), 6.60 (bd, J = 2.4 Hz, 1H), 3.52(s, 2H), 2.80-2.72(m, 2H), 2.60-2.50(m, 1H), 2.30-2.20(m, 1H), 2.24 (s, 3H), 2.05-1.96(m, 2H), 1.80-1.72(m, 2H), 1.38-1.16(m, 2H), 0.69-0.62 (m, 2H), 0.45-0.40(m, 2H). MS(m/z): 547.44(M + H). |

TABLE 31-continued
Characterization of compounds 396-401 (examples 247-252)
| Cpd | Ex. | Structure | Characterization |
|---|---|---|---|
| 402 | 253 | 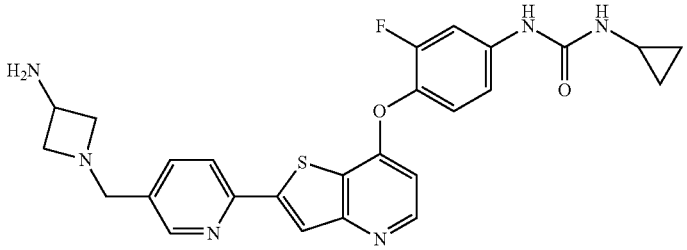<br>1-(4-(2-(5-((3-aminoazetidin-1-yl)methyl)pyridin-2-yl)thieno[3,2-b]pyridin-7-yloxy)-3-fluorophenyl)-3-cyclopropylurea | $^1$H NMR(400 MHz, DMSO-d$_6$) δ(ppm): 8.74(s, 1H), 8.54-8.49(m, 2H), 8.32(s, 1H), 8.22(d, J = 8.4 Hz, 1H), 7.80(dd, J = 8.0, 2.0 Hz, 1H), 7.73(dd, J = 13.2, 2.4 Hz, 1H), 7.38 (t, J = 9.0 Hz, 1H), 7.23-7.17(m, 1H), 6.64(dd, J = 5.2, 0.8 Hz, 1H), 6.60(bd, J = 2.0 Hz, 1H), 3.59(s, 2H), 3.52-3.45 (m, 2H), 3.45-3.30 (m, 1H), 2.69-2.64(m, 2H), 2.59-2.51(m, 1H), 0.68-0.62 (m, 2H), 0.45-0.40(m, 2H). MS(m/z): 505.50(M + H). |
Scheme 76
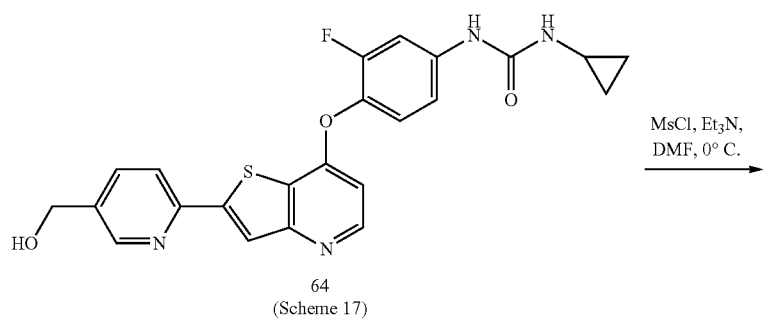
64
(Scheme 17)
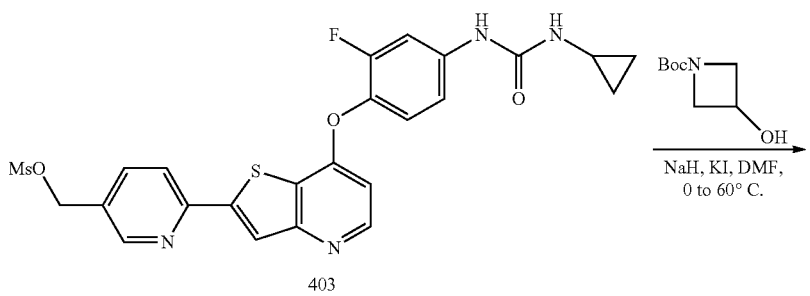
403

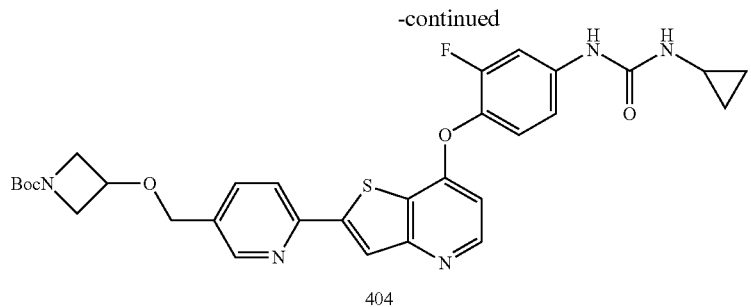

404

TFA, DCM
rt

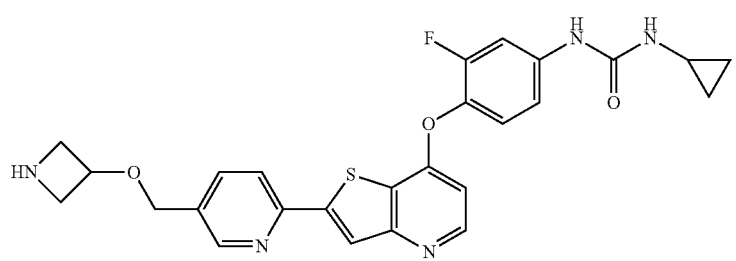

405: Example 254

Example 254

1-(4-(2-(5-((Azetidin-3-yloxy)methyl)pyridin-2-yl)thieno[3,2-b]pyridin-7-yloxy)-3-fluorophenyl)-3-cyclopropylurea (405)

Step 1. (6-(7-(4-(3-cyclopropylureido)-2-fluorophenoxy)thieno[3,2-b]pyridin-2-yl)pyridin-3-yl)methyl methanesulfonate (403)

To a solution of 64 (510 mg, 1.13 mmol, scheme 17) in DMF (15 mL) at 0° C. were added TEA (0.79 mL, 5.65 mmol) and methanesulfonyl chloride (0.35 mL, 4.52 mmol). After 30 min, more TEA (0.48 mL, 3.39 mmol) and methanesulfonyl chloride (0.22 mL, 2.82 mmol) were added at 0° C. The reaction mixture was poured into water to form a precipitate that was collected by filtration, rinsed with water to give the title compound 403 (crude) as a beige powder which was used in the next step with no additional purification. MS (m/z): 529.39 (M+H).

Step 2. tert-butyl 3-((6-(7-(4-(3-cyclopropylureido)-2-fluorophenoxy)thieno[3,2-b]pyridin-2-yl)pyridin-3-yl)methoxy)azetidine-1-carboxylate (404)

To a stirred suspension of NaH (271 mg, 60% dispersion in mineral oil, 6.72 mmol) in DMF (2 mL) at 0° C. was added tert-butyl-3-hydroxyazetidine-1-carboxylate (1.0 g, 5.65 mmol). After 30 min, a solution of 403 (1.13 mmol) in DMF (6 mL) and KI (183 mg, 1.13 mmol) were added at 0° C. The reaction mixture was heated to 80° C. for 30 min. The reaction was then quenched by addition of water and the mixture was extracted with AcOEt/MeOH. The organic phase was washed with brine, dried over anhydrous magnesium sulfate, filtered and concentrated. The residue was purified via Biotage [linear gradient 0-10%, (methanol/dichloromethane: SiliaFlash 25 g cartridge]. Title compound 404 was obtained as a beige solid (221 mg, 32% yield for 2 steps). $^1$H NMR (400 MHz, DMSO-$d_6$) δ (ppm): 8.71 (s, 1H), 8.62 (d, J=2.4 Hz, 1H), 8.52 (d, J=5.2 Hz, 1H), 8.37 (s, 1H), 8.28 (d, J=8.0 Hz, 1H), 7.94 (dd, J=8.0, 2.0 Hz, 1H), 7.73 (dd, J=13.6, 2.4 Hz, 1H), 7.38 (t, J=9.0 Hz, 1H), 7.23-7.18 (m, 1H), 6.64 (d, J=5.2 Hz, 1H), 6.57 (brd, 1H), 4.53 (s, 2H), 4.42-4.36 (m, 1H), 4.09-4.00 (m, 2H), 3.77-3.68 (m, 2H), 2.59-2.50 (m, 1H), 1.37 (s, 9H), 0.68-0.62 (m, 2H), 0.47-0.41 (m, 2H). MS (m/z): 606.48 (M+H).

Step 3. 1-(4-(2-(5-((azetidin-3-yloxy)methyl)pyridin-2-yl)thieno[3,2-b]pyridin-7-yloxy)-3-fluorophenyl)-3-cyclopropylurea (405)

To a suspension of 404 (221 mg, 0.365 mmol) in DCM (5 mL) was added TFA (1 mL) and the reaction mixture was stirred for 4 h then concentrated, diluted with water and 1M NaOH to pH 11. The solid was collected by filtration, rinsed with water and dried. The residue was purified by Biotage (SNAP 25 g cartridge; 2% of ammonium hydroxide in MeOH/DCM: 10/90 to 30/70), to afford the title compound 405 (155 mg, 84% yield) as a beige solid. $^1$H NMR (400 MHz, DMSO-$d_6$) δ (ppm): 8.77 (s, 1H), 8.55 (brd, J=1.6 Hz, 1H), 8.52 (d, J=5.6 Hz, 1H), 8.35 (s, 1H), 8.27 (d, J=7.2 Hz, 1H), 7.91 (dd, J=8.0, 2.4 Hz, 1H), 7.73 (dd, J=13.6, 2.4 Hz, 1H), 7.38 (t, J=9.0 Hz, 1H), 7.24-7.18 (m, 1H), 6.65 (d, J=5.2 Hz, 1H), 6.62 (brd, J=2.8 Hz, 1H), 4.48 (s, 2H), 4.40-4.41 (m, 1H), 3.56-3.49 (m, 2H), 3.47-3.50 (m, 2H), 2.58-2.51 (m, 1H), 0.68-0.62 (m, 2H), 0.47-0.41 (m, 2H). MS (m/z): 506.14 (M+H).

Compounds 406-409 (examples 255-258) were prepared in one step by reacting the corresponding amine precursors 399, 401, 402 (table 31) and 405 (scheme 76) with ethyl isocyanate, similarly to compound 128 (example 87, scheme 32). Compound 410 (example 259) was prepared by reacting compound 401 (table 31) with methyl isocyanate instead of ethyl isocyanate.

TABLE 32

Characterization of compounds 406-410 (examples 255-259)

| Cpd | Ex. | Structure | Characterization |
|---|---|---|---|
| 406 | 255 | 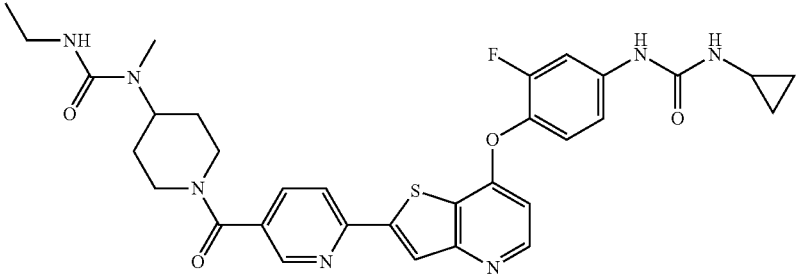<br>Ethyl 1-(6-(7-(4-(3-cyclopropylureido)-2-fluorophenoxy)thieno[3,2-b]pyridin-2-yl)nicotinoyl)piperidin-4-yl(methyl)urea | $^1$H NMR (500 MHz, DMSO-$d_6$) δ (ppm): 8.78(s, 1H), 8.69(d, J = 2.0 Hz, 1H), 8.54 (d, J = 5.4 Hz, 1H), 8.44(s, 1H), 8.34(d, J = 8.2 Hz, 1H), 7.81(dd, J = 8.1, 2.1 Hz, 1H), 7.72(dd, J = 13.5, 2.4 Hz, 1H), 7.38(t, J = 9.0 Hz, 1H), 7.22-7.17(m, 1H), 6.67(d, J = 5.4 Hz, 1H), 4.62-4.55(m, 1H), 4.27-4.18(m, 1H), 3.55(s, 2H), 3.68-3.60(m, 1H), 3.21-3.12(m, 1H), 3.08-3.01(m, 2H), 2.65(s, 3H), 2.59-2.51(m, 1H), 1.70-1.52(m, 3H), 1.47-1.40 (m, 1H), 1.00(t, J = 7.2 Hz, 3H), 0.68-0.62 (m, 2H), 0.45-0.40(m, 2H). MS(m/z): 632.40(M + H). |
| 407 | 256 | 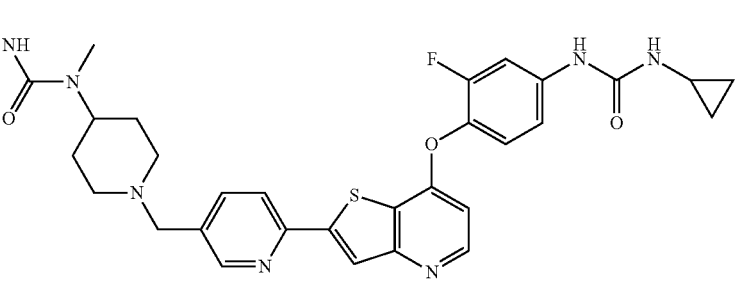<br>1-(4-(2-(5-((4-Ethylaminocarbonyl-methylaminopiperidin-1-yl)methyl)pyridin-2-yl)thieno[3,2-b]pyridin-7-yloxy)-3-fluorophenyl)-3-cyclopropylurea | $^1$H NMR (400 MHz, DMSO-$d_6$) δ (ppm): 8.72(s, 1H), 8.56(d, J = 2.0 Hz, 1H), 8.52(d, J = 5.2 Hz, 1H), 8.34(s, 1H), 8.24(d, J = 8.4 Hz, 1H), 7.86(dd, J = 8.0, 2.0 Hz, 1H), 7.73(dd, J = 13.6, 2.4 Hz, 1H), 7.39(t, J = 9.0 Hz, 1H), 7.23-7.18(m, 1H), 6.64(d, J = 5.2 Hz, 1H), 6.58 (bd, J = 2.0 Hz, 1H), 6.20(t, J = 5.6 Hz, 1H), 3.96-3.87(m, 1H), 3.55(s, 2H), 3.07-2.98(m, 2H), 2.90-2.83(m, 2H), 2.59-2.51(m, 1H), 2.09-2.00 (m, 2H), 1.70-1.59(m, 1H), 1.47-1.39(m, 2H), 0.99 (t, J = 7.2 Hz, 3H), 0.69-0.62 (m, 2H), 0.45-0.40(m, 2H). MS(m/z): 618.58(M + H). |
| 408 | 257 | 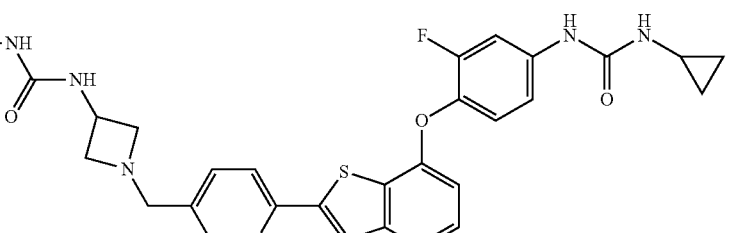<br>1-(4-(2-(5-((3-Ethylaminocarbonylamino)azetidin-1-ny)methyl)pyridin-2-yl)thieno[3,2-b]pyridin-7-yloxy)-3-fluorophenyl)-3-cyclopropylurea | $^1$H NMR (400 MHz, DMSO-$d_6$) δ (ppm): 8.74(s, 1H), 8.54 (brd, 1H), 8.52(d, J = 5.2 Hz, 1H), 8.33(s, 1H), 8.23(d, J = 8.0 Hz, 1H), 7.88-7.80(m, 1H), 7.73(dd, J = 13.6, 2.8 Hz, 1H), 7.38(t, J = 9.0 Hz, 1H), 7.23-7.18(m, 1H), 6.64 (dd, J = 5.2, 0.8 Hz, 1H), 6.58(d, J = 2.4 Hz, 1H), 6.35-6.27(m, 1H), 5.90-5.75(m, 1H), 4.25-4.15(m, 1H), 3.80-3.45(m, 4H), 3.02-2.75(m, 4H), 2.58-2.49(m, 1H), 0.97(t, J = 7.2 Hz, 3H), 0.68-0.62(m, 2H), 0.47-0.40(m, 2H). MS(m/z): 576.50(M + H). |

TABLE 32-continued

Characterization of compounds 406-410 (examples 255-259)

| Cpd | Ex. | Structure | Characterization |
|---|---|---|---|
| 409 | 258 | 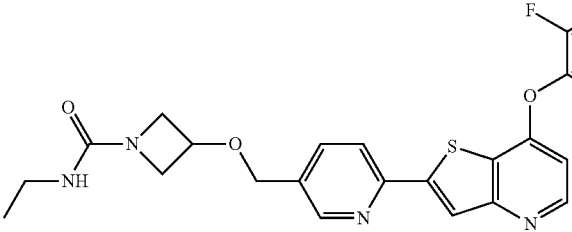<br>3-((6-(7-(4-(3-cyclopropylureido)-2-fluorophenoxy)thieno[3,2-b]pyridin-2-yl)pyridin-3-yl)methoxy)-N-ethylazetidine-1-carboxamide | ¹H NMR (400 MHz, DMSO-d₆) δ (ppm): 8.71(s, 1H), 8.62(d, J = 1.6 Hz, 1H), 8.52(d, J = 5.2 Hz, 1H), 8.37(s, 1H), 8.29(d, J = 8.0 Hz, 1H), 7.94(dd, J = 8.0, 2.0 Hz, 1H), 7.73(dd, J = 13.6, 2.4, Hz 1H), 7.38(t, J = 9.0 Hz, 1H), 7.23-7.18(m, 1H), 6.65(d, J = 5.6 Hz, 1H), 6.57 (bd, J = 2.8 Hz, 1H), 6.31(t, J = 5.6 Hz, 1H), 4.53(s, 2H), 4.41-4.33(m, 1H), 4.00-3.92(m, 2H), 3.65-3.60 (m, 2H), 3.04-2.95(m, 2H), 2.59-2.50(m, 1H), 0.97 (t, J = 7.2 Hz, 3H), 0.68-0.62 (m, 2H), 0.46-0.40(m, 2H). MS(m/z): 577.28(M + H). |
| 410 | 259 | 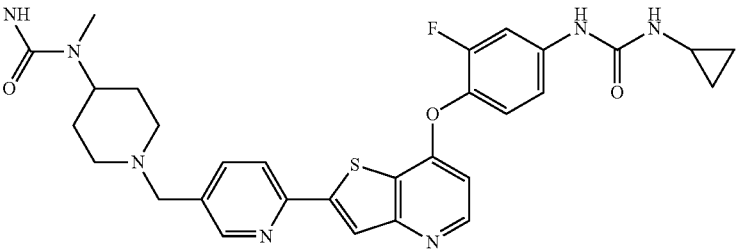<br>1-(4-(2-(5-((4-Methylaminocarbonyl-methylaminopiperidin-1-yl)methyl)pyridin-2-yl)thieno[3,2-b]pyridin-7-yloxy)-3-fluorophenyl)-3-cyclopropylurea | ¹H NMR (500 MHz, DMSO-d₆) δ (ppm): 8.68(s, 1H), 8.54(d, J = 1.7 Hz, 1H), 8.51(d, J = 5.4 Hz, 1H), 8.31(s, 1H), 8.22(d, J = 8.1 Hz, 1H), 7.85(dd, J = 8.1, 2.0 Hz, 1H), 7.72(dd, J = 13.5, 2.5 Hz, 1H), 7.37(t, J = 9.0 Hz, 1H), 7.23-7.18(m, 1H), 6.64(d, J = 5.4 Hz, 1H), 6.54(bd, J = 2.2 Hz, 1H), 6.13(d, J = 4.3 Hz, 1H), 3.95-3.86(m, 1H), 3.54(s, 2H), 2.89-2.83(m, 2H), 2.62(s, 3H), (2.59-2.51(m, 1H), 2.54(d, J = 4.3 Hz, 3H), 2.08-2.00(m, 2H), 1.69-1.58(m, 2H), 1.45-1.38 (m, 2H), 0.68-0.62(m, 2H), 0.45-0.40(m, 2H). MS(m/z): 604.54(M + H). |

Compounds 411-412 (examples 260-261) were prepared in one step by reacting the amine precursor 401 (table 31), similarly to compound 30 (scheme 13). Compound 413 (example 262) was obtained similarly to compound 31 (scheme 13). Compounds 414-415 (examples 263-264) were prepared in two steps by reacting the corresponding amine precursors 402 (table 31) and 405 (scheme 76), similarly to compound 31 (scheme 13).

Compounds 416-418 (examples 265-267) were prepared in one step by reacting the amine precursor 401 (table 31), with the corresponding alkylating agent similarly to compound 275 (scheme 61).

TABLE 33

Characterization of compounds 411-418 (examples 255-267)

| Cpd | Ex. | Structure | Characterization |
|---|---|---|---|
| 411 | 260 | 2-((1-((6-(7-(4-(3-cyclopropylureido)-2-fluorophenoxy)thieno[3,2-b]pyridin-2-yl)pyridin-3-yl)methyl)piperidin-4-yl)(methyl)amino)-2-oxoethyl acetate | ¹H NMR (400 MHz, DMSO-d₆) δ (ppm): 8.73 (s, 1H), 8.56(s, 1H), 8.52(d, J = 5.2 Hz, 1H), 8.34(s, 1H), 8.25(d, J = 8.0 Hz, 1H), 7.86(d, J = 8.4 Hz, 1H) 7.73(dd, J = 13.6, 2.4 Hz, 1H), 7.39(t, J = 9.0 Hz, 1H), 7.24-7.17(m, 1H), 6.64(d, J = 5.2 Hz, 1H), 6.59(bd, J = 2.0 Hz, 1H), 4.80(s, 0.76H), 4.72(s, 1.24H), 4.24-4.10 (m ,1H), 3.58(s, 0.76H), 3.55(s, 1.24H), 2.94-2.85 (m, 2H), 2.78(s, 1.86H), 2.71(s, 1.14H), 2.59-2.51 (m, 1H), 2.18-2.00(m, 2H), 2.06(s, 3H), 1.84-1.38(m, 4H), 0.69-0.62(m, 2H), (0.45-0.40(m, 2H). MS(m/z): 647.51(M + H). |
| 412 | 261 | N-(1-((6-(7-(4-(3-cyclopropylureido)-2-fluorophenoxy)thieno[3,2-b]pyridin-2-yl)pyridin-3-yl)methyl)piperidin-4-yl)-N-methylacrylamide | ¹H NMR (500 MHz, DMSO-d₆) δ (ppm): 8.70(s, 1H), 8.56(brd, 1H), 8.51(d, J = 5.4 Hz, 1H), 8.31(s, 1H), 8.23(d, J = 8.1 Hz, 1H), 7.86(dd, J = 8.1, 1.9 Hz, 1H), 7.72(dd, J = 13.6, 2.4 Hz, 1H), 7.37(t, J = 9.0 Hz, 1H), 7.22-7.18(m, 1H) 6.83-6.68(m, 1H), 6.64(d, J = 5.4 Hz, 1H), 6.55(bd, J = 2.2 Hz, 1H), 6.05(t, J = 17.0 Hz, 1H), 5.67-5.58 (m, 1H), 4.33-4.24(m, 1H), 3.58-3.53(m, 2H), 2.93-2.73(m, 5H), 2.58-2.51(m, 1H), 2.16-2.02 (m, 2H), 1.58-1.41(m, 2H), 0.69-0.62(m, 2H), 0.44-0.40(m, 2H). MS(m/z): 601.48(M + H). |
| 413 | 262 | N-(1-((6-(7-(4-(3-cyclopropylureido)-2-fluorophenoxy)thieno[3,2-b]pyridin-2-yl)pyridin-3-yl)methyl)piperidin-4-yl)-2-hydroxy-N-methylacetamide | ¹H NMR (500 MHz, DMSO-d₆) δ (ppm): 8.68(s, 1H), 8.55 (d, J = 1.4 Hz, 1H), 8.51 (d, J = 5.4 Hz, 1H), 8.32(s, 1H), 8.23(d, J = 8.1 Hz, 1H), 7.86(dd, J = 8.1, 1.9 Hz, 1H), 7.72(dd, J = 13.5, 2.4 Hz, 1H), 7.37(t, J = 9.0 Hz, 1H), 7.22-7.18(m, 1H), 6.62(d, J = 5.4 Hz, 1H), 6.54(bd, J = 2.4 Hz, 1H), 4.41(t, J = 5.2 Hz, 0.4H), 4.33(t, J = 5.2 Hz, 0.6H), 4.27-4.18(m, 1H), 4.10(d, J = 5.1 Hz, 0.8H), 4.02(d, J = 5.3 Hz, 1.2H), 3.59-3.54(m, 2H), 2.94-2.83 (m, 2H), 2.74(s, 1.2H), 2.72(s, 1.8H), 2.58-2.51 (m, 1H), 2.12-2.03(m, 2H), 1.84-1.65(m, 2H), 1.59-1.41(m, 2H), 0.68-0.62 (m, 2H), 0.45-0.40 (m, 2H). MS(m/z): 605.37(M + H). |

TABLE 33-continued

Characterization of compounds 411-418 (examples 255-267)

| Cpd | Ex. | Structure | Characterization |
|---|---|---|---|
| 414 | 263 | N-(1-((6-(7-(4-(3-cyclopropylureido)-2-fluorophenoxy)thieno[3,2-b]pyridin-2-yl)pyridin-3-yl)methyl)azetidin-3-yl)-2-hydroxyacetamide | $^1$H NMR (400 MHz, DMSO-d$_6$) δ (ppm): 8.71(s, 1H), 8.52(brd, 1H), 8.51(d, J = 5.6 Hz, 1H), 8.32(s, 1H), 8.22(d, J = 8.0 Hz, 1H), 8.15(d, J = 7.6 Hz, 1H), 7.82 (dd, J = 8.0, 2.0 Hz, 1H), 7.72(dd, J = 13.6, 2.8 Hz, 1H), 7.38(t, J = 9.0 Hz, 1H), 7.23-7.18 (m, 1H), 6.64(dd, J = 5.2, 0.8 Hz, 1H), 6.57 (d, J = 2.8 Hz, 1H), 5.46(t, J = 2.0 Hz, 1H), 4.43-4.34 (m, 1H), 3.79(d, J = 5.2 Hz, 2H), 3.66(s, 2H), 3.52 (t, 7.2 Hz, 2H), 3.06 (t, J = 7.2 Hz, 2H), 2.58-2.50(m, 1H), 0.69-0.62 (m, 2H), 0.47-0.40(m, 2H). MS(m/z): 563.46(M + H). |
| 415 | 264 | 1-cyclopropyl-3-(3-fluoro-4-(2-(5-((1-(2-hydroxyacetyl)azetidin-3-yloxy)methyl)pyridin-2-yl)thieno[3,2-b]pyridin-7-yloxy)phenyl)urea | $^1$H NMR (400 MHz, DMSO-d$_6$) δ (ppm): 8.81(s, 1H), 8.63(d, J = 1.6 Hz, 1H), 8.52(d, J = 5.2 Hz, 1H), 8.37(s, 1H), 8.29(d, J = 8.0 Hz, 1H), 7.94(dd, J = 8.0, 2.0 Hz, 1H), 7.73(dd, J = 13.6, 2.4 Hz, 1H), 7.38(t, J = 9.0 Hz, 1H), 7.23-7.18(m, 1H), 6.68-6.63(m, 2H), 4.93(t, (J = 6.0 Hz, 1H), 4.55(s, 2), 4.50-4.44 (m, 1H), 4.40-4.34(m, 1H), 4.13-4.04(m, 2H), 3.90(m, J = 6.0 Hz, 2H), 3.78-3.72(m, 1H), 2.58-2.51(m, 1H), 0.68-0.62 (m, 2H), 0.45-0.40(m, 2H). MS(m/z): 564.3(M + H). |
| 416 | 265 | 1-cyclopropyl-3-(3-fluoro-4-(2-(5-((4-((2-methoxyethyl)(methyl)amino)piperidin-1-yl)methyl)pyridin-2-yl)thieno[3,2-b]pyridin-7-yloxy)phenyl)urea | $^1$H NMR (400 MHz, DMSO-d$_6$) δ (ppm): 8.72(s, 1H), 8.54(d, J = 1.6 Hz, 1H), 8.52 (d, J = 5.6 Hz, 1H), 8.33 (s, 1H), 8.24(d, J = 8.0 Hz, 1H), 7.85(dd, J = 8.0, 2.4 Hz, 1H), 7.73(dd, J = 13.6, 2.4 Hz, 1H), 7.38(t, J = 9.0 Hz, 1H), 7.23-7.18(m, 1H), 6.64(dd, J = 5.2, 0.8 Hz, 1H), 6.58(bd, J = 2.4 Hz, 1H), 3.54(s, 2H), 3.45-3.28 (m, 2H), 3.23(s, 3H), 2.90-2.84(m, 2H), 2.59-2.50 (m, 1H), 2.30-2.15(m, 3H), 2.04-1.92(m, 2H), 1.70-1.61(m, 2H), 1.52-1.40(m, 2H), 0.69-0.62(m, 2H), 0.45-0.40(m, 2H). MS(m/z): 605.57(M + H). |

TABLE 33-continued

Characterization of compounds 411-418 (examples 255-267)

| Cpd | Ex. | Structure | Characterization |
|---|---|---|---|
| 417 | 266 | 1-cyclopropyl-3-(3-fluoro-4-(2-(5-((4-((2-hydroxyethyl)(methyl)amino)piperidin-1-yl)methyl)pyridin-2-yl)thieno[3,2-b]pyridin-7-yloxy)phenyl)urea | $^1$H NMR (400 MHz, DMSO-d$_6$) δ (ppm): 8.71(s, 1H), 8.53 (d, J = 1. Hz, 1H), 8.51 (d, J = 5.4 Hz, 1H), 8.31 (s, 1H), 8.22(d, J = 8.2 Hz, 1H), 7.84(dd, J = 8.2, 1.9 Hz, 1H), 7.72(dd, J = 13.5, 2.4 Hz, 1H), 7.37(t, J = 9.0 Hz, 1H), 7.22-7.17(m, 1H), 6.63 (d, J = 5.4 Hz, 1H), 6.68(bd, J = 2.4 Hz, 1H), 3.53(s, 2H), 3.49-3.41(m, 2H), 2.89-2.83(m, 2H), 2.59-2.50(m, 2H), 2.30-2.20(m, 3H), 2.01-1.93 (m, 2H), 1.72-1.65(m, 2H), 1.53-1.40(m, 2H), 0.67-0.62(m,2H), 0.45-0.40(m, 2H). MS(m/z): 591.54(M + H). |
| 418 | 267 | 1-cyclopropyl-3-(3-fluoro-4-(2-(5-((4-(methyl(2,5,8,11-tetraoxatridecan-13-yl)amino)piperidin-1-yl)methyl)pyridin-2-yl)thieno[3,2-b]pyridin-7-yloxy)phenyl)urea | $^1$H NMR (400 MHz, DMSO-d$_6$) δ (ppm): 8.74(s, 1H), 8.54(d, J = 2.0 Hz, 1H), 8.51(d, J = 5.6 Hz, 1H), 8.33(s, 1H), 8.24(d, J = 8.0 Hz, 1H), 7.85(dd, J = 8.4, 2.0 Hz, 1H), 7.73 (dd, J = 13.6, 2.4 Hz, 1H), 7.38(t, J = 9.0 Hz, 1H), 7.23-7.17(m, 1H), 6.64(dd, J = 5.2, 0.8 Hz, 1H), 3.54(s, 2H), 3.52-3.36(m, 17H), 3.22(s, 3H), 2.91-2.82(m, 2H), 2.58-2.51(m, 1H), 2.35-2.15(m, 3H), 2.04-1.92(m, 2H), 1.74-1.60 (m, 2H), 1.51-1.40(m, 2H), 0.68-0.62(m, 2H), 0.45-0.40(m, 2H). MS (m/z): 737.83(M + H). |

Scheme 77

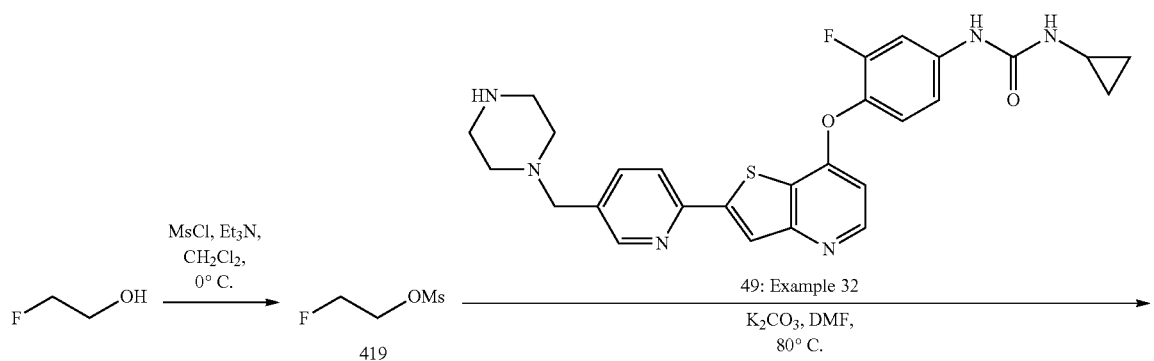

Example 268

1-Cyclopropyl-3-(3-fluoro-4-(2-(5-((4-(2-fluoroethyl)piperazin-1-yl)methyl)pyridin-2-yl)thieno[3,2-b]pyridin-7-yloxy)phenyl)urea (420)

Step 1. 2-Fluoroethyl methanesulfonate (419)

To a stirred solution of 2-fluoroethanol (0.100 mL, 1.72 mmol) in DCM (2 mL) at 0° C. were added TEA (0.312 mL, 2.24 mmol) and methansulfonyl chloride (0.16 mL, 2.06 mmol). The reaction mixture was stirred at 0° C. for 0.5 h, quenched with water and extracted with DCM. The organic phase was collected, dried over anhydrous $Na_2SO_4$, filtered and concentrated to afford the title compound 419 (140 mg, 57% yield) as an orange oil which was used in the next step

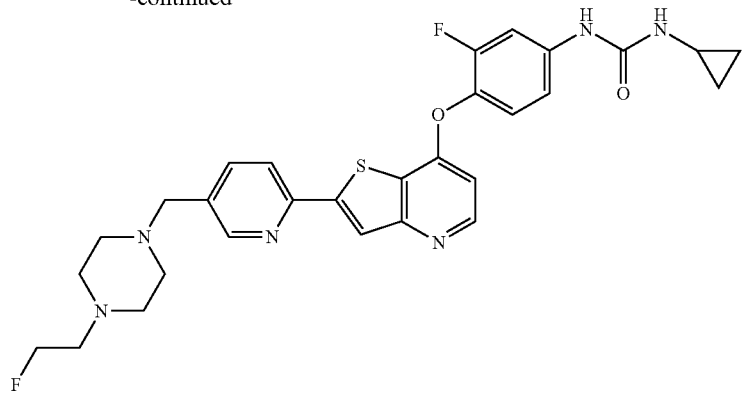

420: Example 268 with no additional purification. $^1$H NMR (400 MHz, $CDCl_3$) δ (ppm): 4.75-4.72 (m, 1H), 4.63-4.60 (m, 1H), 4.52-4.49 (m, 1H), 4.45-4.42 (m, 3.08 (s, 3H).

Step 2. 1-cyclopropyl-3-(3-fluoro-4-(2-(5-((4-(2-fluoroethyl)piperazin-1-yl)methyl)pyridin-2-yl)thieno[3,2-b]pyridin-7-yloxy)phenyl)urea (420)

To a solution of 49 (70 mg, 0.111 mmol, scheme 26) in DMF (2 mL) were added $K_2CO_3$ (77 mg, 0.555 mmol) and 419 (79 mg, 0.555 mmol). The mixture was heated to 80° C. for 16 hours. Water was added to form a precipitate that was collected by filtration, rinsed with water and purified via Biotage [linear gradient 0-20%, (methanol/dichloromethane; SiliaFlash 10 g cartridge]. Title compound 420 was obtained as a white solid (38.9 mg, 62% yield). $^1$H NMR (500 MHz, DMSO-$d_6$) δ (ppm): 8.68 (s, 1H), 8.53 (d, J=1.7 Hz, 1H), 8.51 (d, J=5.4 Hz, 1H), 8.31 (s, 1H), 8.23 (d, J=8.2 Hz, 1H), 7.85 (dd, J=8.1, 2.0 Hz, 1H), 7.72 (dd, J=13.5, 2.4 Hz, 1H), 7.37 (t, J=9.0 Hz, 1H), 7.22-7.17 (m, 1H), 6.64 (d, J=5.4 Hz, 1H), 6.54 (bd, J=2.3 Hz, 1H), 4.55 (t, J=4.9 Hz, 1H), 4.45 (t, J=4.9 Hz, 1H), 3.54 (s, 2H), 2.89-2.83 (m, 2H), 2.62 (t, J=5.0 Hz, 1H), 2.59-2.51 (m, 1H), 2.56 (t, J=5.1 Hz, 1H), 2.50-2.32 (m, 8H), 0.68-0.62 (m, 2H), 0.45-0.40 (m, 2H). MS (m/z): 565.23 (M+H).

Example 269

1-Cyclopropyl-3-(3-fluoro-4-(2-(5-((4-((2-fluoroethyl)(methyl)amino)piperidin-1-yl)methyl)pyridin-2-yl)thieno[3,2-b]pyridin-7-yloxy)phenyl)urea (421)

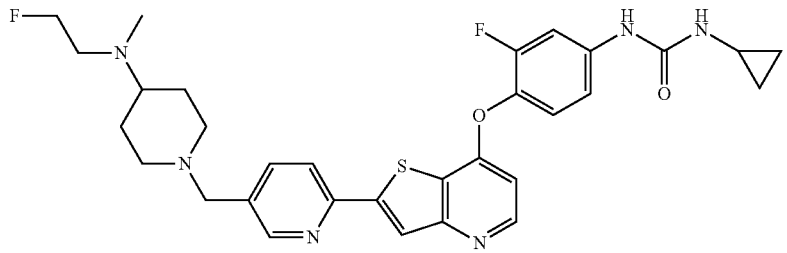

421: Example 269

Compound 421 (example 269) was prepared in one step by reacting the amine precursor 401 (table 31) with compound 419, similarly to compound 420 (example 268, scheme 77). $^1$H NMR (400 MHz, DMSO-$d_6$) δ (ppm): 8.73 (s, 1H), 8.54 (d, J=1.6 Hz, 1H), 8.52 (d, J=5.6 Hz, 1H), 8.33 (s, 1H), 8.24 (d, J=8.0 Hz, 1H), 7.85 (dd, J=8.0, 2.0 Hz, 1H), 7.73 (dd, J=13.6, 2.4 Hz, 1H), 7.38 (t, J=9.0 Hz, 1H), 7.22-7.18 (m, 1H), 6.64 (d, J=5.2 Hz, 1H), 6.56 (bd, J=2.8 Hz, 1H), 4.51 (t, J=5.2 Hz, 1H), 4.39 (t, J=5.2 Hz, 1H), 3.54 (s, 2H), 2.90-2.82 (m, 2H), 2.77-2.63 (m, 2H), 2.59-2.50 (m, 1H), 2.40-2.30 (m, 1H), 2.22 (s, 3H), 2.02-1.91 (m, 2H), 1.69-1.61 (m, 2H), 1.50-1.38 (m, 2H), 0.68-0.62 (m, 2H), 0.45-0.40 (m, 2H). MS (m/z): 593.59 (M+H).

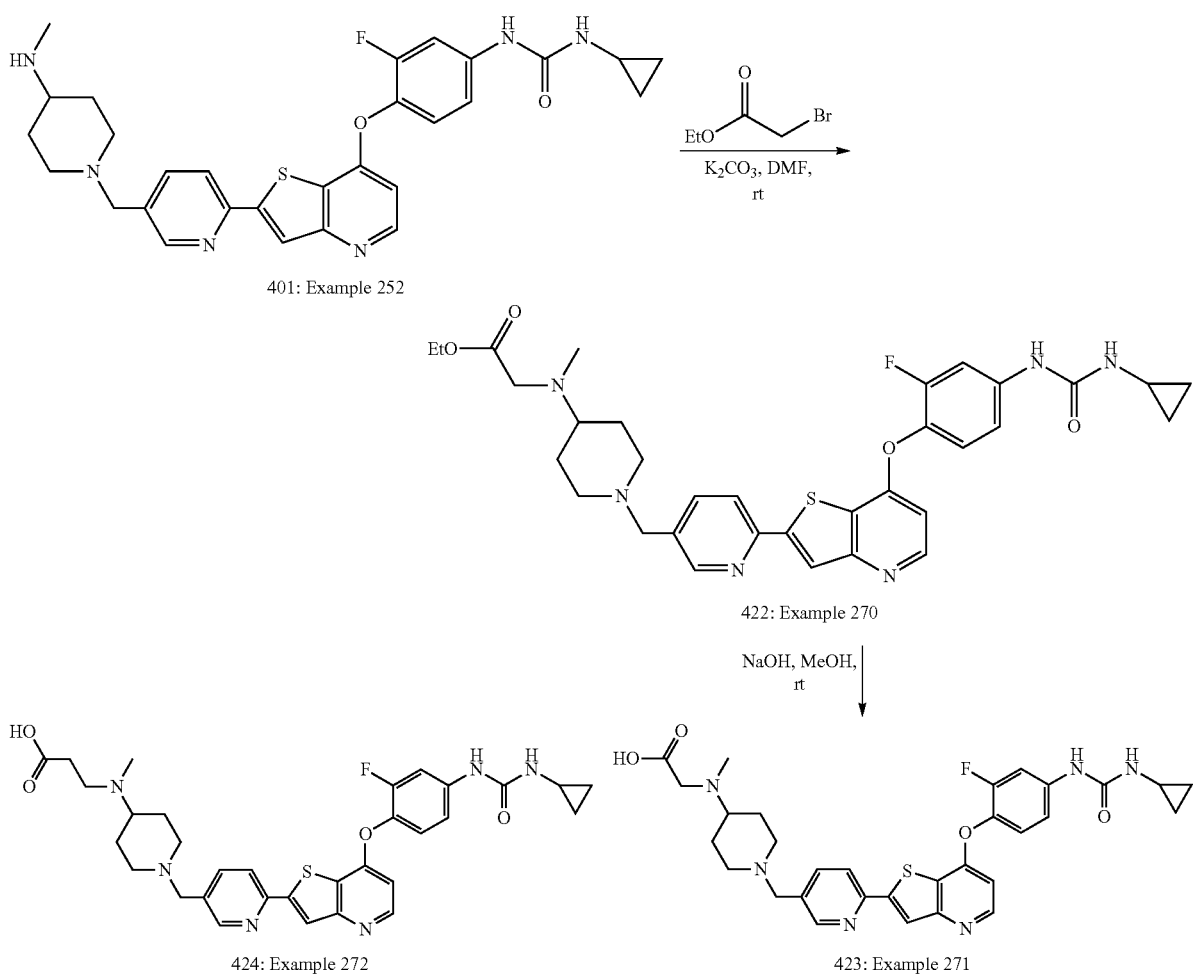

Scheme 78

401: Example 252

422: Example 270

424: Example 272

423: Example 271

Example 270

Ethyl 2-((1-((6-(7-(4-(3-cyclopropylureido)-2-fluorophenoxy)thieno[3,2-b]pyridin-2-yl)pyridin-3-yl)methyl)piperidin-4-yl)(methyl)amino)acetate (422)

To a suspension of 401 (109 mg, 0.20 mmol) in DMF (2 mL) were added K2CO3 (33 mg, 0.24 mmol) and Ethyl bromoacetate (33 mg, 0.22 mmol). The reaction mixture was stirred at RT for 1 h. Water was added to form a precipitate that was collected by filtration, rinsed with water and purified via Biotage [linear gradient 0-20%, (methanol/dichloromethane; SiliaFlash 10 g cartridge]. Title compound 422 was obtained as a beige solid (92 mg, 72% yield). $^1$H NMR (500 MHz, DMSO-$d_6$) δ (ppm): 8.71 (s, 1H), 8.54 (d, J=1.8 Hz, 1H), 8.51 (d, J=5.4 Hz, 1H), 8.32 (s, 1H), 8.24 (d, J=8.1 Hz, 1H), 7.84 (dd, J=8.2, 2.0 Hz, 1H), 7.72 (dd, J=13.5, 2.5 Hz, 1H), 7.38 (t, J=9.0 Hz, 1H), 7.22-7.18 (m, 1H), 6.63 (d, J=5.4 Hz, 1H), 6.56 (bd, J=2.0 Hz, 1H), 4.05 (q, J=7.1 Hz, 2H), 3.52 (s, 2H), 3.28 (s, 2H), 2.86-2.79 (m, 2H), 2.58-2.51 (m, 1H), 2.45-2.37 (m, 1H), 2.26 (s, 3H), 1.98-1.91 (m, 2H), 1.72-1.66 (m, 2H), 1.42-1.32 (m, 2H), 1.16 (t, J=7.1 Hz, 3H), 1.45-1.38 (m, 2H), 0.68-0.62 (m, 2H), 0.45-0.40 (m, 2H). MS (m/z): 633.45 (M+H).

Example 271

2-((1-((6-(7-(4-(3-Cyclopropylureido)-2-fluorophenoxy)thieno[3,2-b]pyridin-2-yl)pyridin-3-yl)methyl)piperidin-4-yl)(methyl)amino)acetic acid (423)

To a suspension of 422 (78 mg, 0.12 mmol) in MeOH (3 mL) was added 1N NaOH (0.6 mL, 0.6 mmol). The reaction mixture was stirred at RT for 2 h. The reaction mixture was then concentrated, diluted with water and the pH was adjusted to 6-7 by addition of 1N HCl. The resulting suspension was stirred for 30 min, and the solid was collected by filtration, rinsed with water, air-dried and dried under high vacuum to afford the title compound 423 (50.3 mg, 67% yield) as a beige solid. $^1$H NMR (400 MHz, DMSO-$d_6$) δ (ppm): 8.81 (s, 1H), 8.55 (brd, 1H), 8.51 (d, J=5.6 Hz, 1H), 8.33 (s, 1H), 8.24 (d, J=8.0 Hz, 1H), 7.85 (dd, J=8.2, 2.0 Hz, 1H), 7.73 (dd, J=13.6, 2.4 Hz, 1H), 7.38 (t, J=9.0 Hz, 1H), 7.24-7.18 (m, 1H), 6.59-6.42 (m, 2H), 3.56 (s, 2H), 3.26 (s, 2H), 2.93-2.84 (m, 3H), 2.58-2.51 (m, 1H), 2.53 (s, 3H), 2.06-1.95 (m, 2H), 1.88-1.80 (m, 2H), 1.61-1.49 (m, 2H), 0.68-0.62 (m, 2H), 0.47-0.41 (m, 2H). MS (m/z): 605.59 (M+H).

Example 272

3-((1-((6-(7-(4-(3-Cyclopropylureido)-2-fluorophenoxy)thieno[3,2-b]pyridin-2-yl)pyridin-3-yl)methyl)piperidin-4-yl)(methyl)amino)propanoic acid (424)

Compound 424 (example 272) was prepared in two steps starting from the amine precursor 401 (table 31), similarly to compound 423 (example 271, scheme 77). $^1$H NMR (400 MHz, DMSO-$d_6$) δ (ppm): 8.78 (s, 1H), 8.55 (brd, 1H), 8.51 (d, J=5.2 Hz, 1H), 8.33 (s, 1H), 8.24 (d, J=8.0 Hz, 1H), 7.85 (dd, J=8.0, 2.0 Hz, 1H), 7.73 (dd. J=13.6, 2.4 Hz, 1H), 7.38 (t, J=9.0 Hz, 1H), 7.23-7.18 (m, 1H), 6.64 (d, J=5.2 Hz, 1H), 6.67-6.62 (m, 1H), 3.54 (s, 2H), 3.17 (s, 2H), 2.90-2.83 (m, 2H), 2.74 (t, J=6.8 Hz, 2H), 2.58-2.45 (m, 2H), 2.30 (t, J=6.8 Hz, 2H), 2.26 (s, 3H), 2.04-1.95 (m, 2H), 1.70-1.63 (m, 2H), 1.57-1.46 (m, 2H), 0.68-0.62 (m, 2H), 0.47-0.40 (m, 2H). MS (m/z): 619.54 (M+H).

Example 273

Ethyl 2-(3-(1-((6-(7-(4-(3-cyclopropylureido)-2-fluorophenoxy)thieno[3,2-b]pyridin-2-yl)pyridin-3-yl)methyl)piperidin-4-yl)ureido)acetate (425)

To a suspension of 343 (106 mg, 0.20 mmol, scheme 71) in THF (3 mL) was added ethoxycarbonylmethyl isocyanate (0.068 mL, 0.6 mmol) and stirred at RT for 3 h. To the mixture was added DMF (2 mL) and stirred for 1 h. The mixture was then concentrated, water was added to form a precipitate that was collected by filtration, rinsed with water and purified via Biotage [linear gradient 2-20%, (methanol/dichloromethane; SiliaFlash 10 g cartridge]. Title compound 425 was obtained as a white solid (79.5 mg, 60% yield). $^1$H NMR (400 MHz, DMSO-$d_6$) δ (ppm): 8.73 (s, 1H), 8.54 (brd, 1H), 8.52 (d, J=5.6 Hz, 1H), 8.33 (s, 1H), 8.24 (d, J=8.0 Hz, 1H), 7.85 (dd, J=8.0, 2.0 Hz, 1H), 7.73 (dd, J=13.6, 2.4 Hz, 1H), 7.38 (t,

Scheme 79

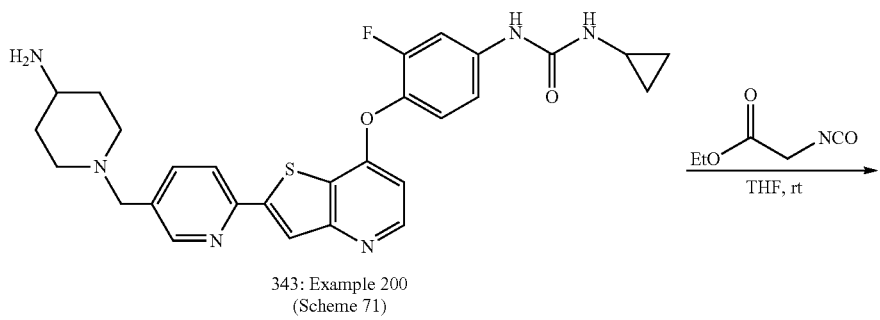

343: Example 200
(Scheme 71)

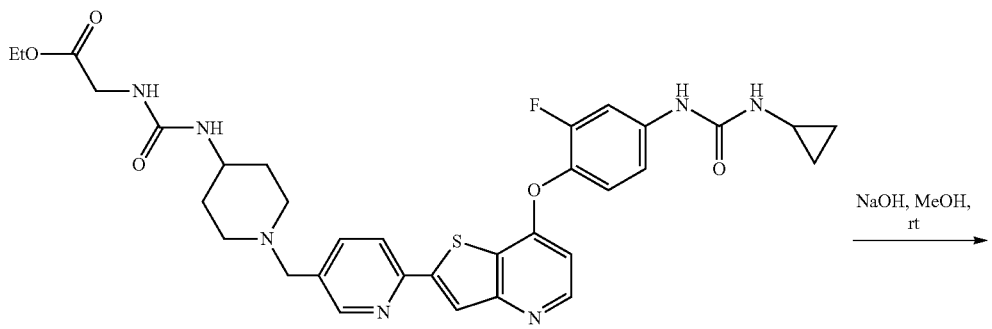

425: Example 273

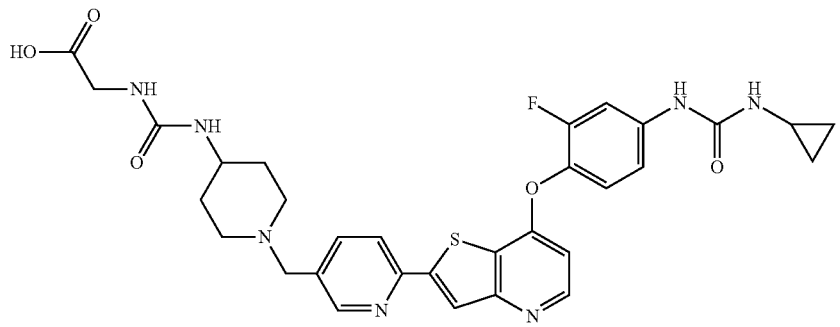

426: Example 274

J=9.0 Hz, 1H), 7.23-7.18 (m, 1H), 6.64 (d, J=5.2 Hz, 1H), 6.59 (bd, 1H), 6.15 (d, J=8.0 Hz, 1H), 6.06 (t, J=8.0 Hz, 1H), 4.06 (q, J=6.4 Hz, 2H), 3.74 (d, J=6.50 Hz, 2H), 3.54 (s, 2H), 2.77-2.66 (m, 2H), 2.58-2.51 (m, 2H), 2.13-2.04 (m, 2H), 1.78-1.70 (m, 2H), 1.40-1.30 (m, 2H), 1.18 (t, J=6.8 Hz, 3H), 0.68-0.62 (m, 2H), 0.45-0.40 (m, 2H). MS (m/z): 662.28 (M+H).

Example 274

2-(3-(1-((6-(7-(4-(3-Cyclopropylureido)-2-fluorophenoxy)thieno[3,2-b]pyridin-2-yl)pyridin-3-yl)methyl)piperidin-4-yl)ureido)acetic acid (426)

To a suspension of 425 (78 mg, 0.12 mmol) in MeOH (3 mL) was added 1N NaOH (0.6 mL, 0.6 mmol). The reaction mixture was stirred at RT for 20 h. The reaction mixture was then concentrated, diluted with water and the pH was adjusted to 6-7 by addition of 1N HCl. To the resulting suspension was added MeOH to dissolve the mixture clearly, and purified via Biotage [KP-C18-HS 30 g, gradient 20-95% (methanol/water)]. Title compound 426 was obtained as a white solid (79.5 mg, 60% yield). $^1$H NMR (400 MHz, DMSO-$d_6$) δ (ppm): one H of carboxylic acid is missing, 10.17 (brs, 1H), 8.53 (d, J=1.6 Hz, 1H), 8.51 (d, J=5.2 Hz, 1H), 8.29 (s, 1H), 8.20 (d, J=8.0 Hz, 1H), 8.02 (brs, 1H), 7.81 (dd, J=8.0, 2.0 Hz, 1H), 7.76 (dd, J=14.0, 2.4 Hz, 1H), 7.33 (t, J=9.0 Hz, 1H), 7.28 (dd, J=9.2, 2.0 Hz, 1H), 6.65 (d, J=4.4 Hz, 1H), 6.25 (d, J=7.6 Hz, 1H), 5.59 (t, J=3.6 Hz, 1H), 4.15-4.09 (m, 1H), 3.51 (s, 2H), 3.28 (d, J=4.4 Hz, 2H), 2.72-2.65 (m, 2H), 2.58-2.51 (m, 1H), 2.11-2.02 (m, 2H), 1.76-1.66 (m, 2H), 1.38-1.25 (m, 2H), 0.63-0.56 (m, 2H), 0.44-0.38 (m, 2H). MS (m/z): 634.5 (M+H).

Compounds 427-428 (examples 275-276) were prepared in two steps starting from the corresponding amine precursors 401 and 402 (table 31), similarly to compound 426 (example 274, scheme 79). Compound 429 (example 277) was prepared similarly to compound 426 (example 274, scheme 79) using ethyl 3-isocyanatopropanoate instead of ethoxycarbonylmethyl isocyanate in the first step.

TABLE 34

Characterization of compounds 427-429 (examples 275-277)

| Cpd | Ex. | Structure | Characterization |
|---|---|---|---|
| 427 | 275 | 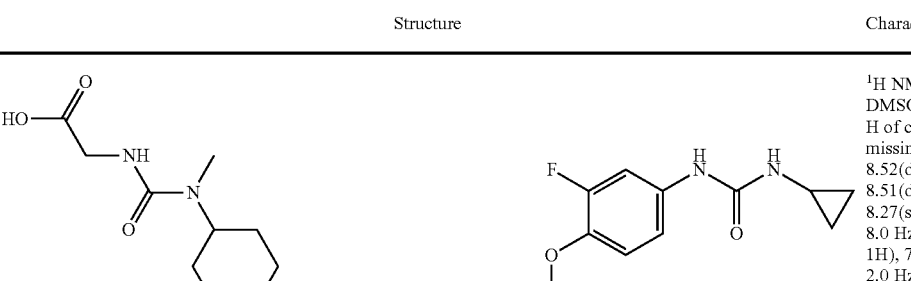<br>2-(3-(1-((6-(7-(4-(3-cyclopropylureido)-2-fluorophenoxy)thieno[3,2-b]pyridin-2-yl)pyridin-3-yl)methyl)piperidin-4-yl)-3-methylureido)acetic acid | $^1$H NMR (400 MHz, DMSO-$d_6$) δ (ppm): one H of carboxylic acid is missing, 10.21(brs, 1H), 8.52(d, J = 2.0 Hz, 1H), 8.51(d, J = 5.2 Hz, 1H), 8.27(s, 1H), 8.16(d, J = 8.0 Hz, 1H), 7.93(brs, 1H), 7.79(dd, J = 8.0, 2.0 Hz, 1H), 7.73 (dd, J = 13.6, 2.4 Hz, 1H), 7.32(t, J = 9.0 Hz, 1H), 7.28(dd, J = 8.8, 2.4 Hz, 1H), 6.62(dd, J = 5.2, 0.8 Hz, 1H), 5.77(t, J = 3.6 Hz, 1H), 3.93-3.82(m, 1H), 3.50(s, 2H), 3.29 (d, J = 3.6 Hz, 2H), 2.89-2.81(m, 2H), 2.67 (s, 3H), 2.58-2.51 (m, 1H), 2.08-1.98 (m, 1H), 1.71-1.58 (m, 2H), 1.50-1.43 (m, 2H), 0.63-0.56(m, 2H), 0.44-0.38(m, 2H). MS(m/z): 648.37(M + H). |

TABLE 34-continued

Characterization of compounds 427-429 (examples 275-277)

| Cpd | Ex. | Structure | Characterization |
|---|---|---|---|
| 428 | 276 | 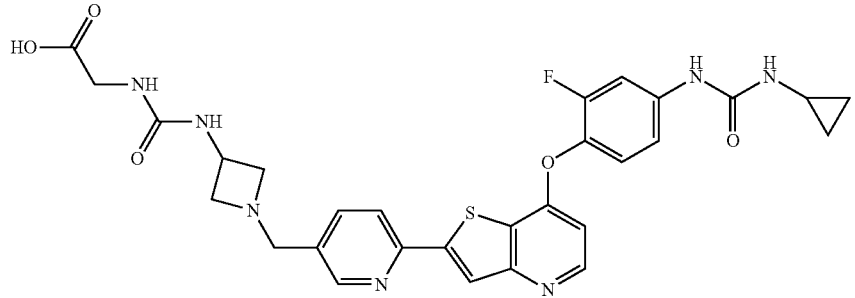<br>2-(3-(1-((6-(7-(4-(3-cyclopropylureido)-2-fluorophenoxy)thieno[3,2-b]pyridin-2-yl)pyridin-3-yl)methyl)azetidin-3-yl)ureido)acetic acid | $^1$H NMR (400 MHz, DMSO-$d_6$) δ (ppm): one H of carboxylic acid is missing, 10.03(brs, 1H), 8.52-8.49(m, 2H), 8.29 (s, 1H), 8.20(d, J = 8.0 Hz, 1H), 7.87(brs, 1H), 7.81(dd, J = 8.4, 2.0 Hz, 1H), 7.76(dd, J = 14.0, 2.4 Hz, 1H), 7.33 (t, J = 9.0 Hz, 1H), 7.25(dd, J = 9.0, 2.0 Hz, 1H), 6.76(d, J = 8.0 Hz, 1H), 6.56(d, J = 5.6 Hz, 1H), 5.65(t, J = 4.0 Hz, 1H), 4.20-4.11(m, 1H), 3.60(s, 2H), 3.49(t, J = 7.2 Hz, 2H), 3.26 (d, J = 4.0 Hz, 2H), 2.77(t, J = 7.2 Hz, 2H), 2.58-2.51(m, 1H), 0.64-0.56(m, 2H), 0.44-0.38(m, 2H). MS (m/z): 606.40(M + H). |
| 429 | 277 | 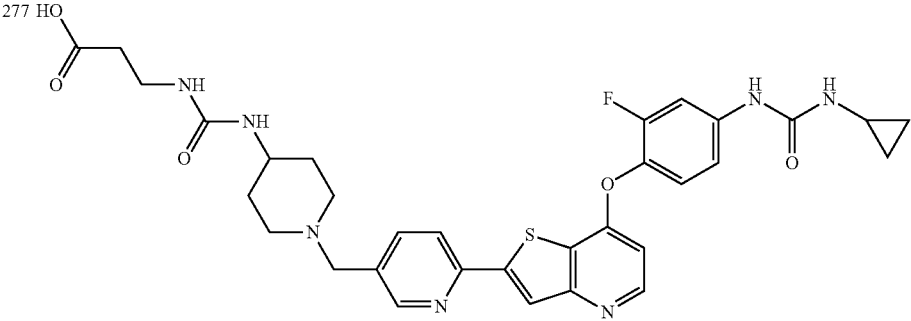<br>3-(3-(1-((6-(7-(4-(3-cyclopropylureido)-2-fluorophenoxy)thieno[3,2-b]pyridin-2-yl)pyridin-3-yl)methyl)piperidin-4-yl)ureido)propanoic acid | $^1$H NMR (400 MHz, DMSO-$d_6$) δ (ppm): (400 MHz, DMSO-$d_6$) d(ppm): one H of carboxylic acid is missing, 9.79 (brs, 1H), 8.54-8.50(m, 2H), 8.29(s, 1H), 8.20(d, J = 8.0 Hz, 1H), 7.82(dd, J = 8.0, 2.0 Hz, 1H), 7.73(dd, J = 13.6, 2.4 Hz, 1H), 7.60(brs, 1H), 7.34 (t, J = 9.0 Hz, 1H), 7.28-7.21(m, 1H), 6.69 (d, J = 5.2Hz, 1H), 6.02 (brd, J = 7.6 Hz, 1H), 5.78(brs, 1H), 3.54(s, 2H), 3.20-3.18(m, 3H), 2.68-2.59(m, 2H), 2.58-2.51(m, 1H), 2.17 (t, J = 6.4 Hz, 2H), 2.14-2.05(m, 2H), 1.75-1.66(m,2H), 1.38-1.25(m, 2H), 0.64-0.58(m, 2H), 0.43-0.39(m, 2H). MS (m/z): 648.22(M + H). |

Scheme 80
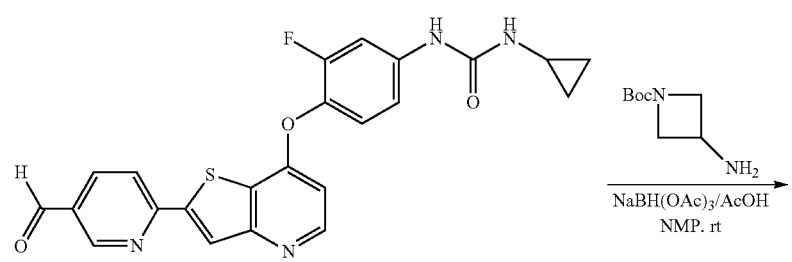
47
Scheme 15
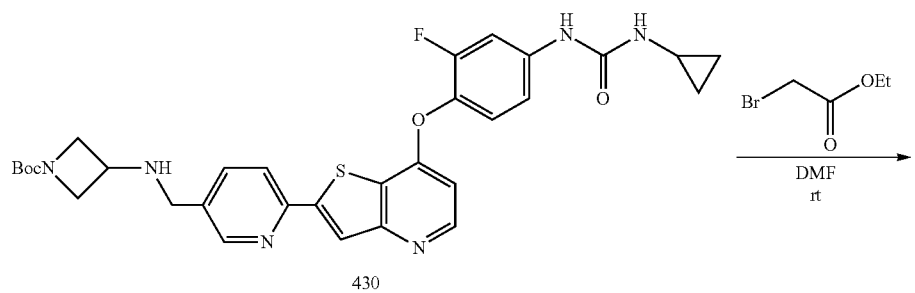
430
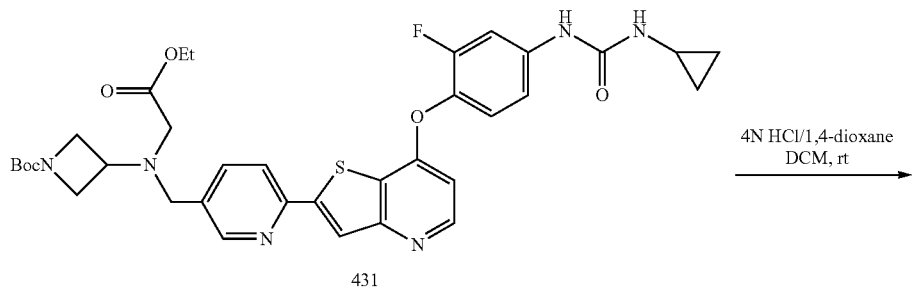
431
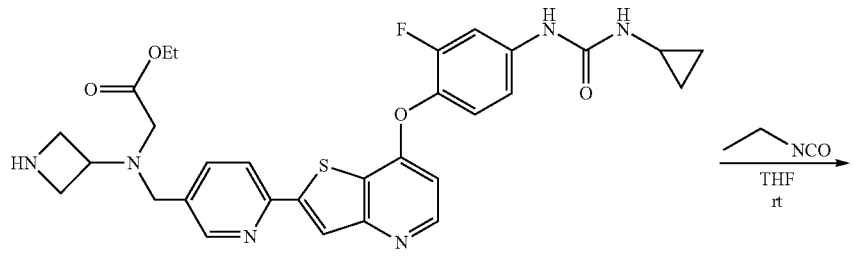
432
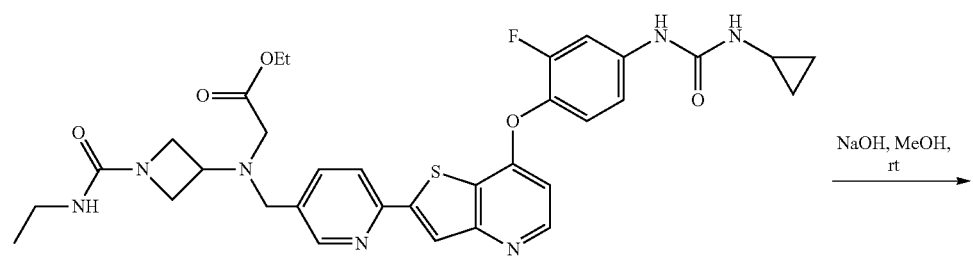
433

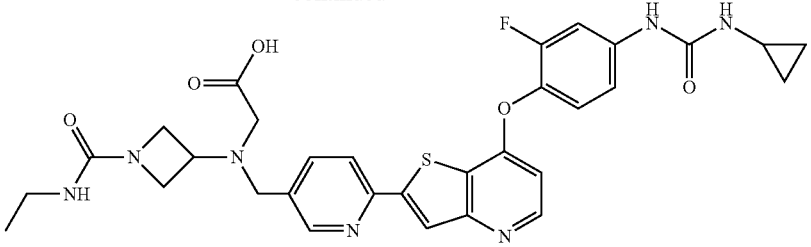

434: Example 278

Example 278

2-(((6-(7-(4-(3-Cyclopropylureido)-2-fluorophenoxy)thieno[3,2-b]pyridin-2-yl)pyridin-3-yl)methyl)(1-(ethylcarbamoyl)azetidin-3-yl)-amino)acetic acid (434)

Step 1. tert-butyl 3-((6-(7-(4-(3-cyclopropylureido)-2-fluorophenoxy)thieno[3,2-b]pyridin-2-yl)pyridin-3-yl)methylamino)azetidine-1-carboxylate (430)

To a suspension of the aldehyde 47 (1.0 g, 2.25 mmol, scheme 15) in NMP (12 mL) were added 3-amino-1-N-Boc-azetidine (0.600 g, 3.38 mmol) and acetic acid (0.19 mL, 3.38 mmol) at RT and stirred for 30 mill. Then NaBH(OAc)$_3$ (1.2 g, 5.63 mmol) was added and stirred for 3 days. The reaction mixture was poured into saturated aqueous solution of NaHCO$_3$ to form a precipitate that was collected by filtration, rinsed with water and purified via Biotage [linear gradient 2-20%, (methanol/dichloromethane; SiliaFlash 25 g cartridge]. Title compound 430 was obtained as a beige solid (960 mg, 71% yield). $^1$H NMR (400 MHz, DMSO-d$_6$) δ (ppm): 8.71 (s, 1H), 8.56 (d, J=1.2 Hz, 1H), 8.51 (d, J=5.2 Hz, 1H), 8.32 (s, 1H), 8.23 (d, J=8.0 Hz, 1H), 7.89 (dd, J=8.0, 2.0 Hz, 1H), 7.73 (dd, J=13.6, 2.4 Hz, 1H), 7.38 (t, J=9.0 Hz, 1H), 7.23-7.18 (m, 1H), 6.64 (dd, J=5.2, 1.2 Hz, 1H), 6.56 (bd, J=2.4 Hz, 1H), 3.98-3.83 (m, 2H), 3.69 (s, 2H), 3.62-3.47 (m, 3H), 2.58-2.51 (m, 1H), 1.36 (s, 9H), 0.68-0.62 (m, 2H), 0.45-0.40 (m, 2H), one NH is missing. MS (m/z): 605.46 (M+H).

Step 2. tert-butyl 3-(((6-(7-(4-(3-cyclopropylureido)-2-fluorophenoxy)thieno[3,2-b]pyridin-2-yl)pyridin-3-yl)methyl)(2-ethoxy-2-oxoethyl)amino)azetidine-1-carboxylate (431)

To a solution of 430 (300 mg, 0.496 mmol) in DMF (6 mL) was added ethyl bromoacetate (0.06 mL, 0.546 mmol). The reaction mixture was stirred at RT for 3 days, quenched with water and extracted with DCM. The organic phase was collected, dried over anhydrous Na$_2$SO$_4$, filtered and concentrated. The residue was purified by Biotage (SNAP 10 g cartridge; MeOH/DCM: 0/100 to 10/90), to afford the title compound 431 (93 mg, 27% yield) as a beige solid. $^1$H NMR (400 MHz, DMSO-d$_6$) δ (ppm): 8.76 (s, 1H), 8.54 (brd, J=1.6 Hz, 1H), 8.52 (d, J=5.6 Hz, 1H), 8.35 (s, 1H), 8.25 (d, J=8.0 Hz, 1H), 7.88 (dd, J=8.0, 2.0 Hz, 1H), 7.73 (dd, J=13.6, 2.4 Hz, 1H), 7.38 (t, J=9.0 Hz, 1H), 7.23-7.18 (m, 1H), 6.65 (dd, J=5.2, 0.8 Hz, 1H), 6.61 (bd, J=2.8 Hz, 1H), 4.05 (q, 7.2 Hz, 2H), 3.93-3.75 (m, 5H), 3.79 (s, 2H), 3.31 (s, 2H), 2.58-2.52 (m, 1H), 1.37 (s, 9H), 1.17 (t, J=7.2 Hz, 3H), 0.68-0.62 (m, 2H), 0.47-0.41 (m, 2H). MS (m/z): 691.64 (M+H).

Step 3. ethyl 2-(azetidin-3-yl-((6-(7-(4-(3-cyclopropylureido)-2-fluorophenoxy)thieno[3,2-b]pyridin-2-yl)pyridin-3-yl)methyl)amino)acetate (432)

To a solution of 431 (93 mg, 0.135 mmol) in DCM (5 mL) was added 4M HCl in 1,4-dioxane solution (0.17 mL, 0.675 mmol) and stirred at RT for 6 h. The mixture was then concentrated to afford the title compound 432 (presumably the hydrochloride salt) as beige solid which was used in the next step with no additional purification. $^1$H NMR (400 MHz, DMSO-d$_6$) δ (ppm): 9.13 (s, 1H), 8.98-8.86 (m, 1H), 8.78-8.66 (m, 1H), 8.69 (d, J=6.0 Hz, 1H), 8.63 (d, J=1.2 Hz, 1H), 8.40 (s, 1H), 8.34 (d, J=8.4 Hz, 1H), 7.94 (dd, J=8.0, 2.0 Hz, 1H), 7.77 (dd, J=13.6, 2.4 Hz, 1H), 7.44 (t, J=9.0 Hz, 1H), 7.25-7.21 (m, 1H), 6.92 (d, J=5.2 Hz, 1H), 6.77 (brs, 1H), 4.08 (q, J=7.2 Hz, 2H), 4.15-3.80 (m, 7H), 3.16 (s, 2H), 2.58-2.51 (m, 1H), 1.19 (t, J=7.2 Hz, 3H), 0.68-0.62 (m, 2H), 0.45-0.39 (m, 2H). MS (m/z): 591.58 (M+H).

Step 4. ethyl 2-(((6-(7-(4-(3-cyclopropylureido)-2-fluorophenoxy)thieno[3,2-b]pyridin-2-yl)pyridin-3-yl)methyl)(1-(ethylcarbamoyl)azetidin-3-yl)amino)acetate (433)

To a suspension of 432 (0.135 mmol) in THF (5 mL) were added TEA (0.094 mL, 0.675 mmol) and ethyl isocyanate (0.032 mL, 0.405 mmol) and stirred at RT for 1 h. The mixture was then concentrated, water was added to form a precipitate that was collected by filtration, rinsed with water, air-dried to afford the title compound 433 (78 mg, 88% yield for 2 steps) as a beige solid. $^1$H NMR (400 MHz, DMSO-d$_6$) δ (ppm): 8.71 (s, 1H), 8.55 (d, J=1.6 Hz, 1H), 8.52 (d, J=5.6 Hz, 1H), 8.34 (s, 1H), 8.25 (d, J=8.4 Hz, 1H), 7.88 (dd, J=8.0, 2.0 Hz, 1H), 7.73 (dd, J=13.6, 2.4 Hz, 1H), 7.38 (t, J=9.0 Hz, 1H), 6.65 (dd, J=5.6, 0.8 Hz, 1H), 6.57 (bd, J=2.8 Hz, 1H), 6.27 (t, J=5.6 Hz, 1H), 4.06 (q, J=7.2 Hz, 2H), 3.84-3.75 (m, 5H), 3.69-3.61 (m, 2H), 3.02-2.94 (m, 2H), 2.59-2.51 (m, 1H), 1.18 (t, J=7.2 Hz, 3H), 0.97 (t, J=7.2 Hz, 3H), 0.68-0.62 (m, 2H), 0.45-0.40 (m, 2H). MS (m/z): 662.60 (M+H).

Step 5. 2-(((6-(7-(4-(3-cyclopropylureido)-2-fluorophenoxy)thieno[3,2-b]pyridin-2-yl)pyridin-3-yl)methyl)(1-(ethylcarbamoyl)azetidin-3-yl)amino)acetic acid (434)

To a solution of 433 (78 mg, 0.118 mmol) in MeOH (3 mL) was added 1N NaOH (0.59 mL, 0.59 mmol) and stirred at RT for 3 h. The mixture was then concentrated, diluted with water and the pH was adjusted to 6-7 by addition of 1N HCl. To the resulting suspension was added MeOH to dissolve the mixture clearly, and purified via Biotage [KP-C18-HS 30 g, gradient 20-95% (methanol/water)]. Title compound 434 was obtained as a white solid (79.5 mg, 60% yield). $^1$H NMR (400

MHz, DMSO-d$_6$) δ (ppm): 10.94 (brs, 1H), 8.71 (s, 1H), 8.62-8.57 (m, 1H), 8.38 (d, J=5.6 Hz, 1H), 8.19 (s, 1H), 8.15 (d, J=8.0 Hz, 1H), 7.89 (dd, J=8.0, 2.0 Hz, 1H), 7.82 (dd, J=14.0, 2.4 Hz, 1H), 7.20 (t, J=9.2 Hz, 1H), 7.09-7.05 (m, 1H), 6.42 (d, J=4.8 Hz, 1H), 6.22 (t, J=5.6 Hz, 1H), 3.84-3.72 (m, 5H), 3.63-3.58 (m, 2H), 3.01-2.94 (m, 2H), 2.86 (s, 2H), 2.59-2.50 (m, 1H), 0.97 (t, J=7.2 Hz, 3H), 0.61-0.56 (m, 2H), 0.45-0.40 (m, 2H). MS (m/z): 634.60 (M+H).

Scheme 81

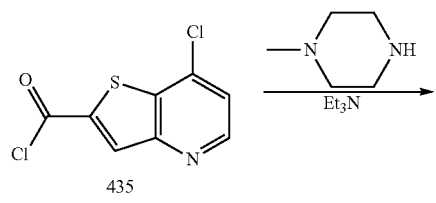

435
WO 2006/010264 A1

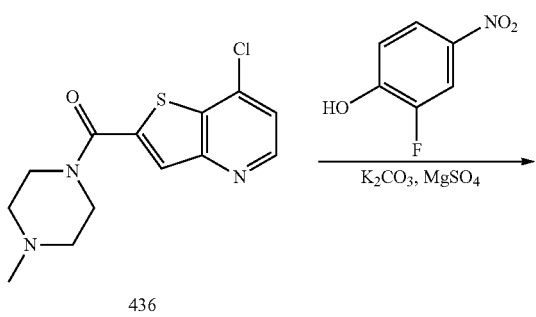

436

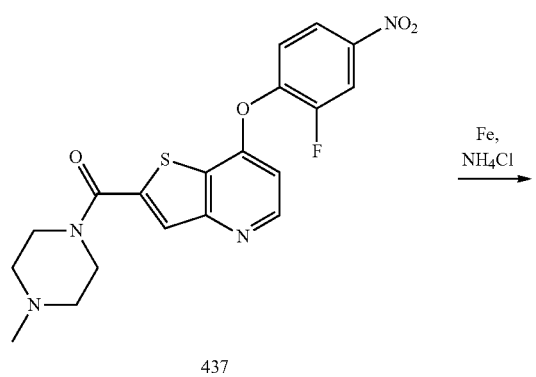

437

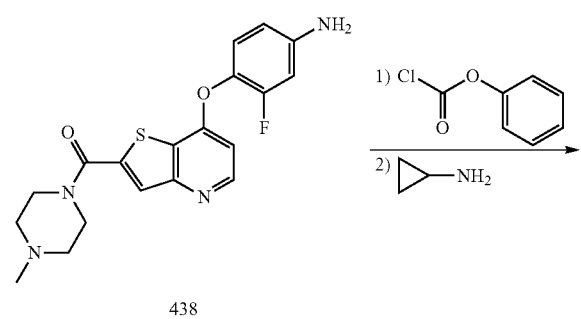

438

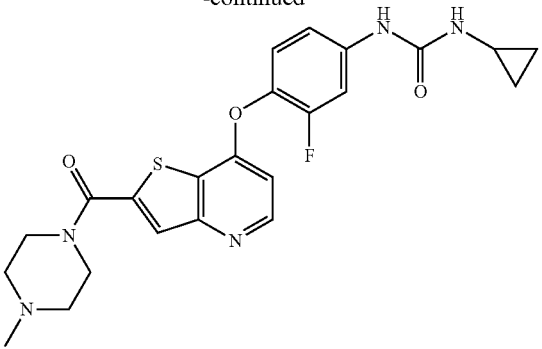

439: Example 279

Example 279

1-Cyclopropyl-3-(3-fluoro-4-(2-(4-methylpiperazine-1-carbonyl)thieno[3,2-b]pyridin-7-yloxy)phenyl)urea (429)

Step 1. (7-chlorothieno[3,2-b]pyridin-2-yl)(4-methylpiperazin-1-yl)methanone (436)

1-Methylpiperazine (0.574 mL, 5.17 mmol) was added to a suspension of 7-chlorothieno[3,2-b]pyridine-2-carbonyl chloride (435, 1 g, 4.31 mmol) and Et$_3$N (1.80 mL, 12.93 mmol) in DCM (50 mL). The reaction mixture was stirred for 1 h at room temperature, diluted with water and a saturated aqueous solution of ammonium chloride and extracted with DCM. The organic layer was successively washed with a saturated aqueous solution of ammonium chloride and brine, dried over sodium sulfate, filtered and concentrated. The residue was purified by biotage (SNAP 25 g cartridge; MeOH/DCM: 0/100 to 10/90 over 20CV), to afford the title compound 436 (1.16 g, 3.93 mmol, 91% yield) as a yellow solid. MS (m/z): 296.2 (M+H).

Step 2. (7-(2-fluoro-4-nitrophenoxy)thieno[3,2-b]pyridin-2-yl)(4-methylpiperazin-1-yl)methanone (437)

MgSO$_4$ (1.41 g, 11.78 mmol) was added to a suspension of 436 (1.16 g, 3.93 mmol), 2-fluoro-4-nitrophenol (1.23 g, 7.85 mmol) and Na$_2$CO$_3$ (1.24 g, 11.78 mmol) in Ph$_2$O (10 mL). The suspension was heated at 160° C. for 1.5 h and at 190° C. for 2 h. After cooling to room temperature, DCM (30 mL) was added and the reaction mixture was filtered and concentrated. The residue was purified by biotage (SNAP 25 g cartridge; AcOEt/Hexane:10/90 over 5 CV then MeOH/DCM: 0/100 to 10/90 over 20CV), to afford the title compound 437 (1.20 g, 2.88 mmol, 73% yield) as a yellow solid. MS (m/z): 417.2 (M+H).

Step 3: (7-(4-amino-2-fluorophenoxy)thieno[3,2-b]pyridin-2-yl)(4-methylpiperazin-1-yl)methanone (438)

Zinc (0.75 g, 11.53 mmol) was added to a suspension of 437 (1.2 g, 2.88 mmol) and ammonium chloride (0.31 g, 5.76 mmol) in a mixture of MeOH (30 mL) and water (5.10 mL). The suspension was heated to reflux for 50 min. After cooling to room temperature, the reaction mixture was filtered and concentrated. The residue was partitioned between DCM, water and ammonium hydroxide. The organic layer was collected, successively washed with water and brine, dried over sodium sulfate, filtered and concentrated. The residue was purified by biotage (SNAP 50 g cartridge; MeOH/DCM: 0/100 to 20/80 over 30CV), to afford the title compound 438 (733 mg, 1.89 mmol, 66% yield) as a yellow solid. MS (m/z): 387.4 (M+H).

Step 4: 1-cyclopropyl-3-(3-fluoro-4-(2-(4-methyl) piperazine-1-carbonyl)thieno[3, 2-b]pyridine-7-yloxy)phenyl)urea (439)

Phenylchloroformate (0.136 mL, 1.08 mmol) was added to a solution of 438 (350 mg, 0.91 mmol) and pyridine (0.147 mL, 1.81 mmol) in DMF (10 mL) at 0° C. After 20 min, cyclopropylamine (0.16 mL, 2.26 mmol) was added at 0° C. and the reaction mixture was heated at 60° C. for 30 min. More cyclopropylamine (0.16 mL, 2.26 mmol) was added and the reaction mixture was heated at 60° C. for 30 min. After cooling to room temperature, the reaction mixture was diluted with water and a saturated aqueous solution of ammonium chloride, and extracted with AcOEt. The organic layer was washed with brine, dried over sodium sulfate, filtered and concentrated. The residue was purified by biotage (SNAP 25 g cartridge; MeOH/DCM: 0/100 to 10/90 over 20CV), triturated with MTBE (25 mL) and dried to afford the title compound 439 (330 mg, 0.70 mmol, 78% yield) as a white solid. $^1$H NMR (400 MHz, DMSO-$d_6$) δ(ppm) 1H, 8.71 (s, 1H), 8.58 (d, J=5.6 Hz, 1H), 7.83 (s, H), 7.73 (dd, J=2.4 and 13.6 Hz, 1H), 7.37 (t, J=8.8 Hz, 1H), 7.23-7.17 (m, 1H), 6.72 (d, J=5.6 Hz, 1H), 6.57 (d, J=2.4 Hz, 1H), 3.72-3.66 (m, 4H), 2.58-2.51 (m, 1H), 2.41-2.35 (m, 4H), 2.21 (s, H), 0.68-0.62 (m, 2H), 0.45-0.41 (m, 2H). MS (m/z): 470.4 (M+H).

Compounds 440-458 (examples 280-298) were prepared in four steps by following the procedures similar to the ones used for the synthesis of compound 439 (example 279, scheme 81).

TABLE 35

Characterization of compounds 440-458 (examples 280-298)

| Cpd | Ex. | Structure | Characterization |
|---|---|---|---|
| 440 | 280 | 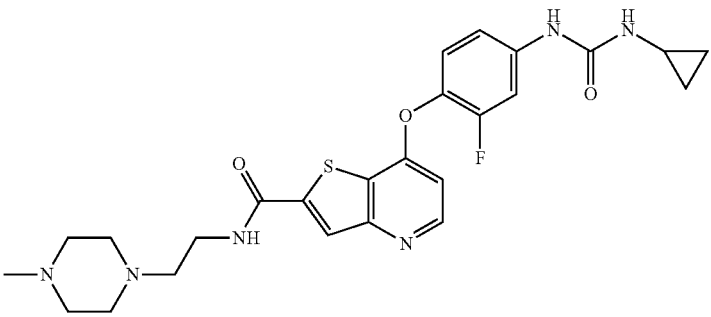<br>7-(4-(3-cyclopropylureido)-2-fluorophenoxy)-N-(2-(4-methylpiperazin-1-yl)ethyl)thieno[3,2-b]pyridin-2-carboxamide | $^1$H NMR (400 MHz, DMSO-$d_6$) δ (ppm): 8.91 (t, J = 6.0 Hz, 1H), 8.81(s, 1H), 8.57(d, J = 5.6 Hz, 1H), 8.23(s, 1H), 7.73(dd, J = 2.4 and 13.6 Hz, 1H), 7.37(t, J = 8.8 Hz, 1H), 7.20(d, J = 8.8 Hz, 1H), 6.71(d, J = 5.6 Hz, 1H), 6.66(d, J = 2.4 Hz, 1H), 3.40(q, J = 6.4 Hz, 2H), 2.59-2.50(m, 1H), 2.52-2.20(m, 10H), 2.13(s, 3H), 0.68-0.61(m, 2H), 0.45-0.40(m, 2H). MS(m/z): 513.4(M + 1). |
| 441 | 281 | 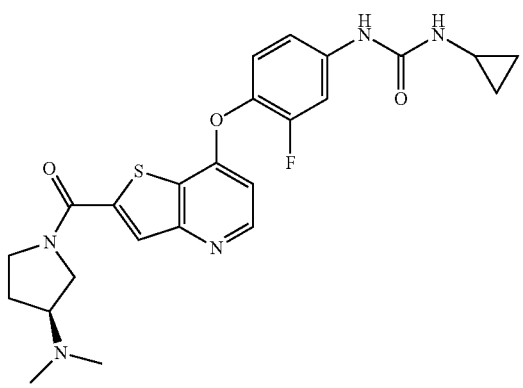<br>(S)-1-cyclopropyl-3-(4-(2-(3-(dimethylamino)pyrrolidine-1-carbonyl)thieno[3,2-b]pyridin-7-yloxy)-3-fluorophenyl)urea | $^1$H NMR (400 MHz, DMSO-$d_6$) δ (ppm): 8.72(s, 1H), 8.58(dd, J = 1.6 and 5.2 Hz, 1H), 8.09 and 8.02(s, 1H), 7.73(dd, J = 2.4 and 13.6 Hz, 1H), 7.37(t, J = 8.8 Hz, 1H), 7.24-7.11(m, 1H), 6.72(d, J = 5.2 Hz, 1H), 6.57(d, J = 2.0 Hz, 1H), 4.08-3.98(m, 1H), 3.94-3.75(m, 1H), 3.75-3.62(m, 1H), 3.52-3.24(m, 1H), 2.82-2.68(m, 1H), 2.59-2.51 (m, 1H), 2.26-2.05(m, 1H), 2.19(s, 3H), 2.18 (s, 3H), 1.90-1.68(m, 1H), 0.68-0.62(m, 2H), 0.45-0.40(m, 2H). MS (m/z): 484.4 (M + 1). |

TABLE 35-continued

Characterization of compounds 440-458 (examples 280-298)

| Cpd | Ex. | Structure | Characterization |
|---|---|---|---|
| 442 | 282 | 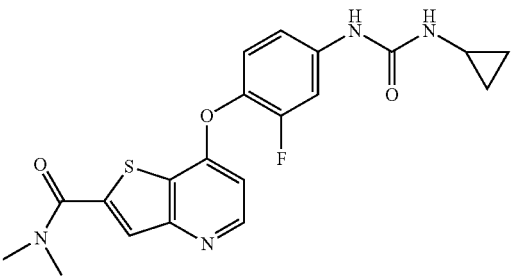<br>7-(4-(3-cyclopropylureido)-2-fluorophenoxy)-N,N-dimethylthieno[3,2-b]pyridine-2-carboxamide | $^1$H NMR (400 MHz, DMSO-d$_6$) δ (ppm): 8.71 (s, 1H), 8.57(d, J = 5.6 Hz, 1H), 7.93(s, 1H), 7.73(dd, J = 2.4 and 13.6 Hz, 1H), 7.37(J = 9.2 Hz, 1H), 7.22-7.17(m, 1H), 6.71(d, J = 5.6 Hz, 1H), 6.57(d, J = 2.4 Hz, 1H), 3.26 (brs, 3H), 3.05(bs, 3H), 2.59-2.51(m, 1H), 0.68-0.62(m, 2H), 0.45-0.40(m, 2H). MS (m/z): 415.3(M + 1). |
| 443 | 283 | 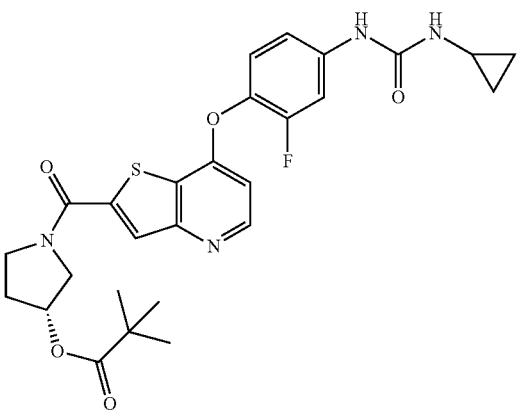<br>(R)-1-(7-(4-(3-cyclopropylureido)-2-fluorophenoxy)thieno[3,2-b]pyridine-2-carbonyl)pyrrolidin-3-yl pivalate | $^1$H NMR (400 MHz, DMSO-d$_6$) δ (ppm): 8.71 (s, 1H), 8.59(d, J = 5.6 Hz, 1H), 8.12 and 8.05(s, 1H), 7.73(dd, J = 2.4 and 13.6 Hz, 1H), 7.37(t, J = 8.8 Hz, 1H), 7.23-7.17(m, 1H), 6.73(d, J = 5.6 Hz, 1H), 6.57(d, J = 2.4 Hz, 1H), 5.35-5.25(m, 1H), 4.25-3.57(m, 4H), 2.30-2.12(m, 1H), 2.11-1.97(m, 1H), 1.15 and 1.10(s, 9H), 0.68-0.62(m, 1H), 0.45-0.40(m, 1H). MS(m/z): 514.4 (M + 1). |
| 444 | 284 | 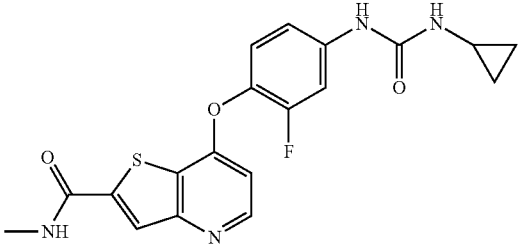<br>7-(4-(3-cyclopropylureido)-2-fluorophenoxy)-N-methylthieno[3,2-b]pyridine-2-carboxamide | $^1$H NMR (400 MHz, DMSO-d$_6$) δ (ppm): 8.94 (q, J = 4.4 Hz, 1H), 8.70(s, 1H), 8.56(d, J = 5.6 Hz, 1H), 8.19(s, 1H), 7.72(dd, J = 2.4 and 13.6 Hz, 1H), 7.37(t, J = 8.8 Hz, 1H), 7.22-7.17(m, 1H), 6.70(d, J = 5.6 Hz, 1H), 6.57(d, J = 2.4 Hz, 1H), 2.84(d, J = 4.8 Hz, 3H), 2.58-2.51(m, 2H), 0.68-0.62(m, 2H), 0.45-0.40(m, 2H). MS(m/z): 401.2(M + 1). |

TABLE 35-continued

Characterization of compounds 440-458 (examples 280-298)

| Cpd | Ex. | Structure | Characterization |
|---|---|---|---|
| 445 | 285 | 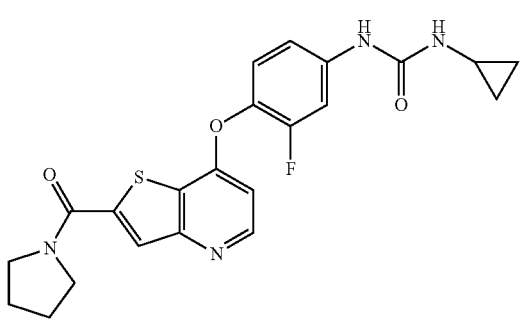<br>1-cyclopropyl-3-(3-fluoro-4-(2-(pyrrolidine-1-carbonyl)thieno[3,2-b]pyridin-7-yloxy)phenyl)urea | $^1$H NMR (400 MHz, DMSO-d$_6$) δ (ppm): 8.71 (s, 1H), 8.58(d, J = 5.6 Hz, 1H), 8.03(s, 1H), 7.72(dd, J = 2.4 and 13.2 Hz, 1H), 7.37(t, J = 9.2 Hz, 1H), 7.22-7.17(m, 1H), 6.72(dd, J = 0.8 and 5.6 Hz, 1H), 6.56(d, J = 2.8 Hz, 1H), 3.86(t, J = 6.8 Hz, 2H), 3.54(t, J = 6.8 Hz, 2H), 2.58-2.52(m, 1H), 1.96(quin, J = 6.8 Hz, 2H), 1.88(quin, J = 6.8 Hz, 2H), 0.68-0.62(m, 2H), 0.45-0.40(m, 2H). MS (m/z): 441.3(M + 1). |
| 446 | 286 | 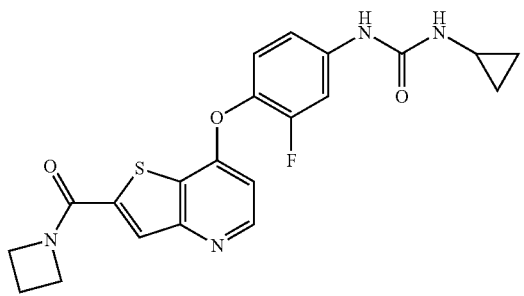<br>1-(4-(2-(azetidine-1-carbonyl)thieno[3,2-b]pyridin-7-yloxy)-3-fluorophenyl)-3-cyclopropylurea | $^1$H NMR (400 MHz, DMSO-d$_6$) δ (ppm): 8.77 (s, 1H), 8.59(d, J = 5.6 Hz, 1H), 7.89(s, 1H), 7.73(dd, J = 2.4 and 12.6 Hz, 1H), 7.37(t, J = 9.2 Hz, 1H), 7.23-7.18(m, 1H), 6.72(dd, J = 0.8 and 5.6 Hz, 1H), 4.63(t, J = 7.6 Hz, 2H), 4.12(t, J = 7.6 Hz, 2H), 2.58-2.51(m, 1H), 2.35(quin, J = 7.6 Hz, 2H), 0.67-0.62 (m, 2H), 0.45-0.40(m, 2H). MS(m/z): 427.3 (M + 1). |
| 447 | 287 | 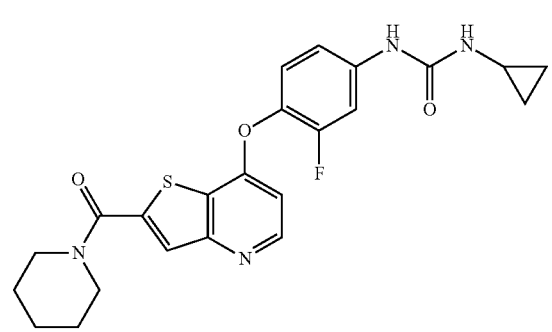<br>1-cyclopropyl-3-(3-fluoro-4-(2-(piperidin-1-carbonyl)thieno[3,2-b]pyridin-7-yloxy)phenyl)urea | $^1$H NMR (400 MHz, DMSO-d$_6$) δ (ppm): 8.96 (s, 1H), 8.67(d, J = 5.6 Hz, 1H), 7.82(s, 1H), 7.75(dd, J = 2.4 and 11.2 Hz, 1H), 7.40(t, J = 9.2 Hz, 1H), 7.24-7.18(m, 1H), 6.87(d, J = 5.6 Hz, 1H), 6.68(bs, 1H), 3.65-3.58(m, 4H), 2.58-2.51(m, 1H), 1.70-1.53(m, 4H), 0.38-0.62(m, 2H), 0.44-0.40(m, 2H). MS(m/z): 455.3(M + 1). |

TABLE 35-continued

Characterization of compounds 440-458 (examples 280-298)

| Cpd | Ex. | Structure | Characterization |
|-----|-----|-----------|------------------|
| 448 | 288 | 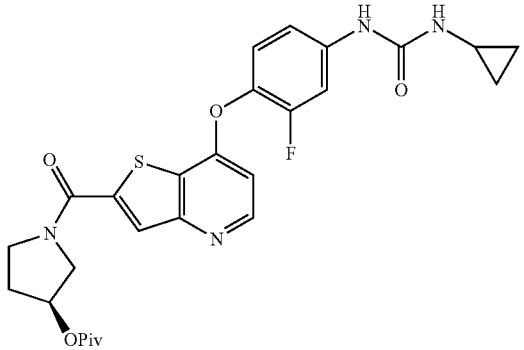<br>(S)-1-(7-(4-(3-cyclopropylureido)-2-fluorophenoxy)thieno[3,2-b]pyridine-2-carbonyl)pyrrolidin-3-yl pivalate | $^1$H NMR (400 MHz, DMSO-d$_6$) δ (ppm): 8.70 (s, 1H), 8.59(d, J = 5.6 Hz, 1H), 8.11 and 8.04(s, 1H), 7.72(dd, J = 2.4 and 11.2 Hz, 1H), 7.37(t, J = 8.8 Hz, 1H), 7.24-7.18(m, 1H), 6.73(d, J = 5.6 Hz, 1H), 6.56(d, J = 2.4 Hz, 1H), 5.33-5.26(m, 1H), 4.23-3.58(m, 4H), 2.58-2.51(m, 1H), 2.30-1.98(m, 2H), 1.15 and 1.10(s, 9H), 0.67-0.629m, 2H), 0.44-0.40(m, 2H). MS(m/z): 514.4(M + 1). |
| 449 | 289 | 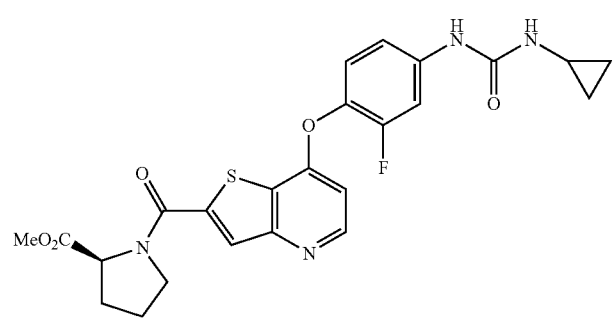<br>(S)-methyl 1-(7-(4-(3-cyclopropylureido)-2-fluorophenoxy)thieno[3,2-b]pyridine-2-carbonyl)pyrrolidine-2-carboxylate | $^1$H NMR (400 MHz, DMSO-d$_6$) δ (ppm): 8.72 (s, 1H), 8.60 and 8.58(d, J = 5.6 Hz, 1H), 8.11 and 7.79(s, 1H), 7.72(dd, J = 2.4 and 11.2 Hz, 1H), 7.37(t, J = 9.2 Hz, 1H), 7.23-7.17(m, 1H), 6.76 and 6.73(d, J = 5.6 Hz, 1H), 6.56(d, J = 2.0 Hz, 1H), 5.12 and 4.55 (dd, J = 5.6 and 8.8 Hz, 1H), 4.03-3.98 and 3.51-3.48(m, 2H), 3.67 and 3.55(s, 3H), 2.57-2.51(m, 1H), 2.34-2.249m, 1H), 2.06-1.99(m, 2H), 1.96-1.89(m, 1H), 0.68-0.62 (m, 2H), 0.45-0.40(m, 2H). MS(m/z): 499.4 (M + 1). |
| 450 | 290 | 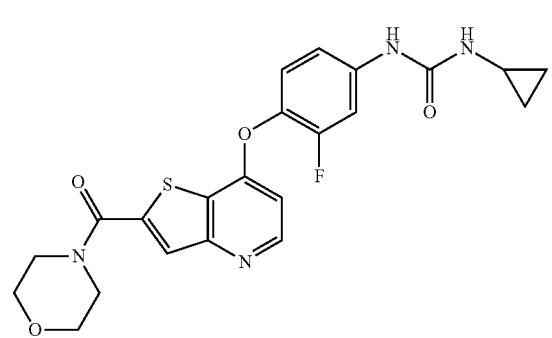<br>1-cyclopropyl-3-(3-fluoro-4-(2-(morpholine-4-carbonyl)thieno[3,2-b]pyridin-7-yloxy)phenyl)urea | $^1$H NMR (400 MHz, DMSO-d$_6$) δ (ppm): 8.70 (s, 1H), 8.58(d, J = 5.6 Hz, 1H), 7.88(s, 1H), 7.73(dd, J = 2.4 and 13.6 Hz, 1H), 7.37(t, J = 9.2 Hz, 1H), 7.23-7.18(m, 1H), 6.73(d, J = 5.6 Hz, 1H), 6.56(d, J = 2.4 Hz, 1H), 3.75-3.61(m, 8H), 2.59-2.51(m, 1H), 0.68-0.62 (m, 2H), 0.45-0.40(m, 2H). MS(m/z): 457.4 (M + 1). |

TABLE 35-continued

Characterization of compounds 440-458 (examples 280-298)

| Cpd | Ex. | Structure | Characterization |
|---|---|---|---|
| 451 | 291 | 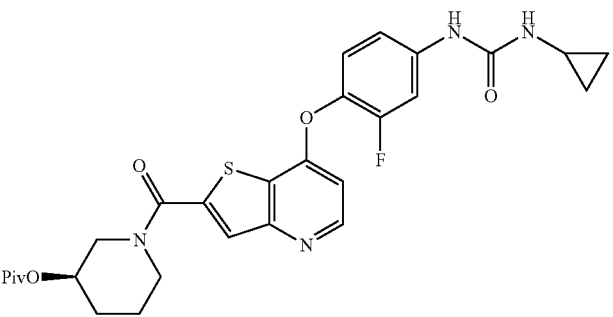<br>(R)-1-(7-(4-(3-cyclopropylureido)-2-fluorophenoxy)thieno[3,2-b]pyridine-2-carbonyl)piperidin-3-yl pivalate | ¹H NMR (400 MHz, DMSO-d₆) δ (ppm): 8.72 (s, 1H), 8.58(d, J = 5.6 Hz, 1H), 7.79(bs, 1H), 7.73(dd, J = 2.4 and 13.6 Hz, 1H), 7.37 (t, J = 8.8 Hz, 1H), 7.23-7.18(m, 1H), 6.75 (d, J = 5.6 Hz, 1H), 6.57(d, J = 2.0 Hz, 1H), 4.83(bs, 1H), 4.25-3.10(m, 2H), 2.58-2.52 (m, 1H), 1.92-1.55(m, 4H), 1.29-1.21(m, 1H), 1.10.(s, 9H), 0.87-0.81(m, 1H), 0.68-0.62(m, 2H), 0.45-0.40(m, 2H). MS(m/z): 555.4(M + 1). |
| 452 | 292 | 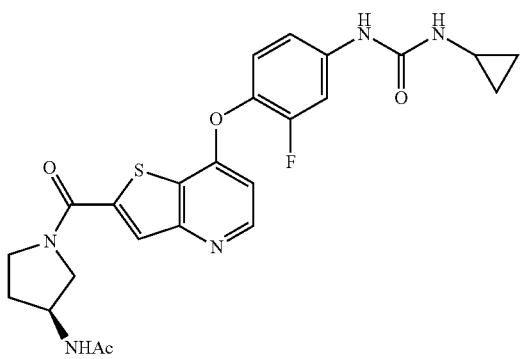<br>(S)-N-(1-(7-(4-(3-cyclopropylureido)-2-fluorophenoxy)thieno[3,2-b]pyridine-2-carbonyl)pyrrolidin-3-yl)acetamide | ¹H NMR (400 MHz, DMSO-d₆) δ (ppm): 8.78 (s, 1H), 8.59(d, J = 5.6 Hz, 1H), 8.20(d, J = 6.4 Hz, 1H, 8.03 and 7.98(s, 1H), 7.73(dd, J = 2.0 and 13.6 Hz, 1H), 7.37(t, J = 8.8 Hz, 1H), 7.24-7.16(m, 1H), 6.74(d, J = 5.6 Hz, 1H), 6.58(s, 1H), 4.35-4.27(m, 1H), 4.13-3.40(m, 3H), 3.96(t, J = 6.8 Hz, 1H), 2.57-2.51(m, 1H), 2.22-2.05(m, 1H), 1.97-1.80 (m, 1H), 1.83 and 1.79(s, 3H), 0.68-0.62(m, 2H), 0.45-0.40(m, 2H). MS(m/z): 498.1 (M + 1). |
| 453 | 293 | 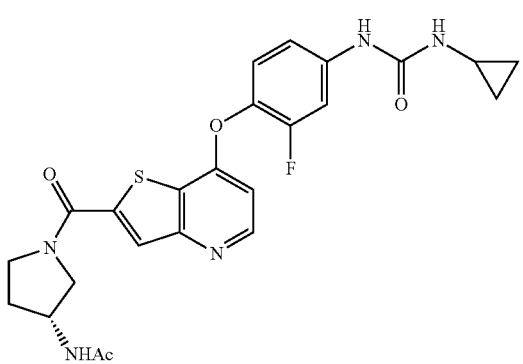<br>(R)-N-(1-(7-(4-(3-cyclopropylureido)-2-fluorophenoxy)thieno[3,2-b]pyridine-2-carbonyl)pyrrolidin-3-yl)acetamide | ¹H NMR (400 MHz, DMSO-d₆) δ (ppm): 8.86 (s, 1H), 8.58(d, J = 5.6 Hz, 1H), 8.20(d, J = 6.4 Hz, 1H), 8.03 and 7.98(s, 1H), 7.73(dd, J = 2.4 and 13.6 Hz, 1H), 7.37(t, J = 9.2 Hz, 1H), 7.24-7.18(m, 1H), 6.73(d, J = 5.6 Hz, 1H), 6.69(d, J = 2.4 Hz, 1H), 4.29(quin, J = 6.4 Hz, 1H), 4.13-3.40(m, 3H), 3.96(t, J = 7.2 Hz, 1H), 2.58-2.51(m, 1H), 2.20-2.07(m, 1H), 1.92-1.86(m, 1H), 1.83 and 1.79(s, 3H), 0.67-0.62(m, 1H), 0.45-0.40(m, 1H). MS (m/z): 498.1 (M +1). |

TABLE 35-continued

Characterization of compounds 440-458 (examples 280-298)

| Cpd | Ex. | Structure | Characterization |
|---|---|---|---|
| 454 | 294 | 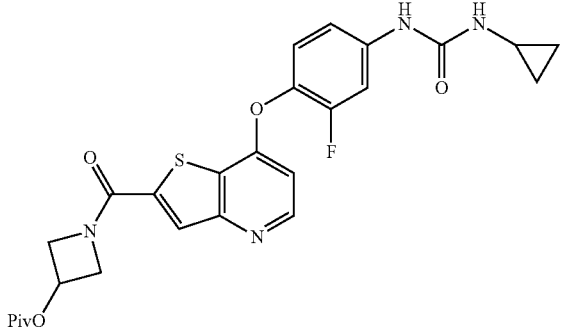<br>1-(7-(4-(3-cyclopropylureido)-2-fluorophenoxy)thieno[3,2-b]pyridine-2-carbonyl)azetidin-3-yl pivalate | $^1$H NMR (400 MHz, DMSO-d$_6$) δ (ppm): 8.70 (s, 1H), 8.60(d, J = 5.6 Hz, 1H), 7.97(s, 1H), 7.72(dd, J = 2.4 and 13.6 Hz, 1H), 7.37(t, J = 9.2 Hz, 1H), 7.23-7.18(m, 2H), 6.74(d, J = 5.6 Hz, 1H), 6.56(d, J = 2.8 Hz, 1H), 5.27-5.21(m, 1H), 4.98-4.91(m, 1H), 4.65-4.58 (m, 1H), 4.52-4.45(m, 1H), 4.07-3.99(m, 1H), 2.59-2.51(m, 1H), 1.19(s, 9H), 0.67-0.62(m, 2H), 0.45-0.40(m, 2H). MS(m/z): 527.4(M + 1). |
| 455 | 295 | 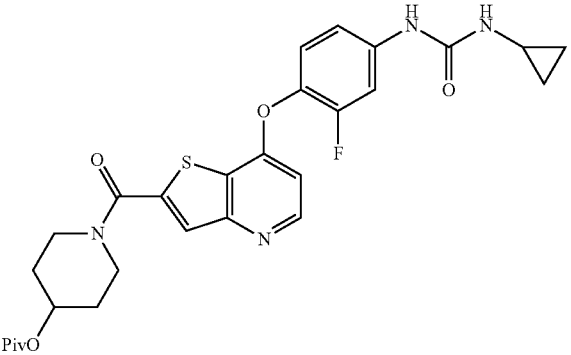<br>1-(7-(4-(3-cyclopropylureido)-2-fluorophenoxy)thieno[3,2-b]pyridine-2-carbonyl)piperidin-4-yl pivalate | $^1$H NMR (400 MHz, DMSO-d$_6$) δ (ppm): 8.71 (s, 1H), 8.58(d, J = 5.6 Hz, 1H), 7.85(s, 1H), 7.73(dd, J = 2.4 and 13.2 Hz, 1H), 7.37(t, J = 9.2 Hz, 1H), 7.23-7.18(m, 1H), 6.72(d, J = 5.6 Hz, 1H), 6.57(d, J = 2.4 Hz, 1H), 4.98-4.92(m, 1H), 3.82-3.63(m, 4H), 2.57-2.51 (m, 1H), 1.96-1.86(m, 2H), 1.69-1.62(m, 2H), 1.16(s, 9H), 0.67-0.62(m, 2H), 0.45-0.40(m, 2H). MS(m/z): 555.4(M + 1). |
| 456 | 296 | 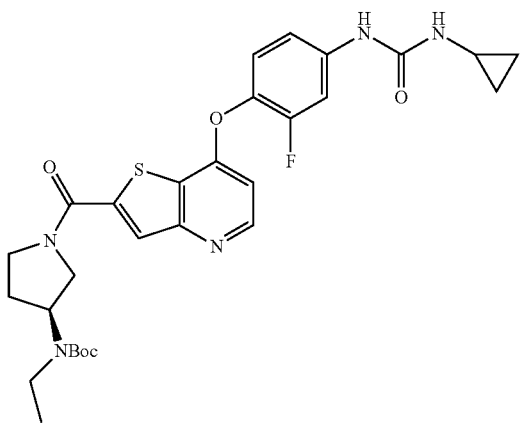<br>(S)-tert-butyl 1-(7-(4-(3-cyclopropylureido)-2-fluorophenoxy)thieno[3,2-b]pyridine-2-carbonyl)pyrrolidin-3-yl(ethyl)carbamate | $^1$H NMR (400 MHz, DMSO-d$_6$) δ (ppm): 8.72 (s, 1H), 8.58(d, J = 5.6 Hz, 1H), 8.05(d, J = 11.6 Hz, 1H), 7.73(dd, J = 2.4 and 13.6 Hz, 1H), 7.37(t, J = 9.2 Hz, 1H), 7.23-7.17(m, 1H), 6.73(d, J = 5.6 Hz, 1H), 6.57(d, J = 2.4 Hz, 1H), 4.51(bs, 1H), 4.01(t, J = 8.0 Hz, 1H), 3.95-3.40(m, 3H), 3.25-3.15(m, 2H), 2.58-2.51(m, 1H), 2.20-2.03(m, 2H), 1.43 and 1.39(s, 9H), 1.06(t, J = 6.4 Hz, 3H), 0.68-0.62(m, 2H), 0.45-0.40(m, 2H). MS (m/z): 584.5(M +1). |

TABLE 35-continued

Characterization of compounds 440-458 (examples 280-298)

| Cpd | Ex. | Structure | Characterization |
|---|---|---|---|
| 457 | 297 | 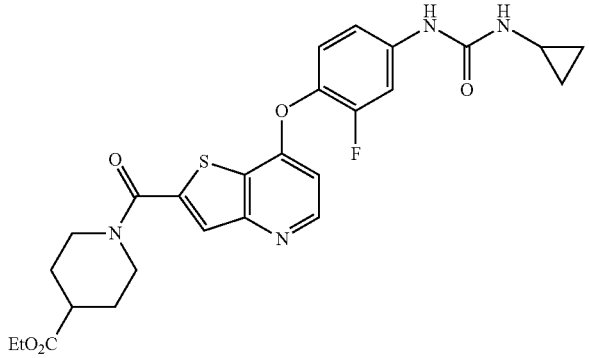<br>ethyl 1-(7-(4-(3-cyclopropylureido)-2-fluorophenoxy)thieno[3,2-b]pyridine-2-carbonyl)piperidine-4-carboxylate | $^1$H NMR (400 MHz, DMSO-d$_6$) δ (ppm): 8.71 (s, 1H), 8.57(d, J = 5.6 Hz, 1H), 7.82(s, 1H), 7.73(dd, J = 2.4 and 13.6 Hz, 1H), 7.37(t, J = 9.2 Hz, 1H), 7.22-7.18(m, 1H), 6.71(d, J = 5.6 Hz, 1H), 6.57(d, J = 2.8 Hz, 1H), 4.40-3.95(m, 2H), 4.07(t, J =7.2 Hz, 2H), 3.45-2.95(m, 2H), 2.72-2.66(m, 1H), 2.57-2.51 (m, 1H), 1.98-1.87(m, 2H), 1.68-1.55(m, 2H), 0.68-0.62(m, 2H), 0.44-0.40(m, 2H). MS(m/z): 527.4(M + 1). |
| 458 | 298 | 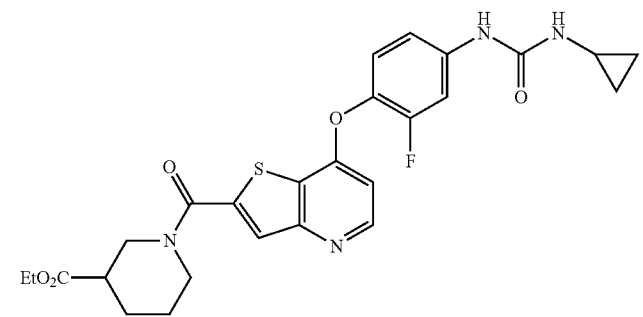<br>ethyl 1-(7-(4-(3-cyclopropylureido)-2-fluorophenoxy)thieno[3,2-b]pyridine-2-carbonyl)piperidine-3-carboxylate | $^1$H NMR (400 MHz, DMSO-d$_6$) δ (ppm): 8.71 (s, 1H), 8.58(d, J = 5.6 Hz, 1H), 7.84(bs, 1H), 7.73(dd, J = 2.4 and 13.6 Hz, 1H), 7.37 (t, J = 9.2 Hz, 1H), 7.23-7.17(m, 1H), 6.72 (d, J = 5.6 Hz, 1H), 6.57(d, J = 2.0 Hz, 1H), 4.20-3.05(m, 3H), 4.07(bs, 2H), 3.91-3.83 (m, 1H), 2.78-2.61(m, 1H), 2.58-2.51(m, 1H), 2.04-1.96(m, 1H), 1.80-1.63(m, 2HJ), 1.62-1.51(m, 1H), 1.15(bs, 3H), 0.68-0.62 (m, 2H), 0.45-0.40(m, 2H). MS(m/z): 527.4 (M + 1). |

Compounds 460-466 (examples 300-306) were synthesized by following the procedures described above for the synthesis of compound 31 (example 17) (scheme 13). Compounds 467-470 (examples 307-310) were synthesized by following the procedures described above for the synthesis of compound 114 (example 79) (scheme 29). Compounds 471-474 (examples 311-314) were synthesized using the corresponding amines by following the procedures described above for the synthesis of compound 13 (example 10) (scheme 9).

TABLE 36

Characterization of compounds 460-474 (examples 300-314)

| Cpd | Ex. | Structure | Characterization |
|---|---|---|---|
| 460 | 300 | 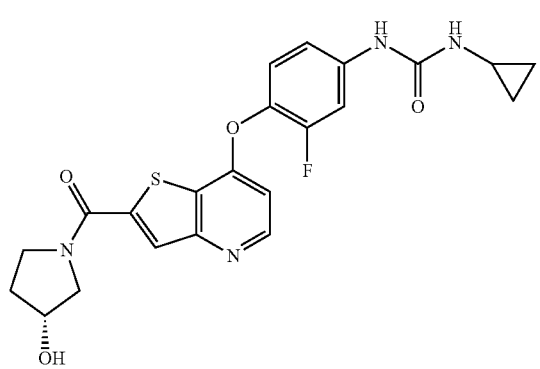 [SMILES: O=C(Nc1ccc(Oc2ccnc3cc(C(=O)N4CC[C@@H](O)C4)sc23)c(F)c1)NC1CC1]<br>(R)-1-cyclopropyl-3-(3-fluoro-4-(2-(3-hydroxypyrrolidine-1-carbonyl)thieno[3,2-b]pyridin-7-yloxy)phenyl)urea | $^1$H NMR (400 MHz, DMSO-d$_6$) δ (ppm): 8.71 (s, 1H), 8.58 (d, J = 5.6 Hz, 1H), 8.07 and 8.00 (s, 1H), 7.73 (dd, J = 2.4 and 13.2 Hz, 1H), 7.38 (t, J = 9.2 Hz, 1H), 7.23-7.17 (m, 1H), 6.72 (d, J = 5.6 Hz, 1H), 6.56 (d, J = 2.0 Hz, 1H), 5.11-5.08 (m, 1H), 4.42-4.32 (m, 1H), 4.03-3.45 (m, 4H), 2.59-2.51 (m, 1H), 2.09-1.81 (m, 2H), 0.68-0.62 (m, 2H), 0.45-0.40 (m, 2H), MS (m/z): 457.4 (M + 1). |
| 461 | 301 | 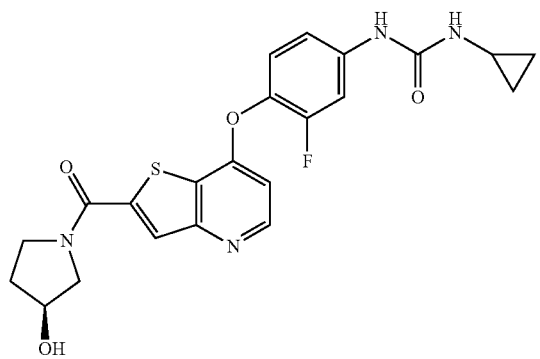 [SMILES: O=C(Nc1ccc(Oc2ccnc3cc(C(=O)N4CC[C@H](O)C4)sc23)c(F)c1)NC1CC1]<br>(S)-1-cyclopropyl-3-(3-fluoro-4-(2-(3-hydroxypyrrolidine-1-carbonyl)thieno[3,2-b]pyridin-7-yloxy)phenyl)urea | $^1$H NMR (400 MHz, DMSO-d6) δ (ppm): 8.76 (s, 1H), 8.58 (d, J = 5.6 Hz, 1H), 8.06 and 8.00 (s, 1H), 7.72 (dd, J = 2.4 and 11.2 Hz, 1H), 7.37 (t, J = 9.2 Hz, 1H), 7.23-7.18 (m, 1H), 6.73 (d, J = 5.6 Hz, 1H), 6.62 (d, J = 2.4 Hz, 1H), 5.10-5.07 (m, 1H), 4.41-4.32 (m, 1H), 4.03-3.45 (m, 4H), 2.58-2.51 (m, 1H), 2.09-1.82 (m, 2H), 0.68-0.62 (m, 2H), 0.45-0.40 (m, 2H). MS (m/z): 457.4 (M + 1). |
| 462 | 302 | 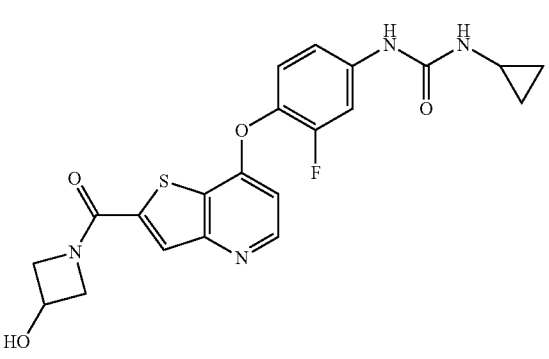 [SMILES: O=C(Nc1ccc(Oc2ccnc3cc(C(=O)N4CC(O)C4)sc23)c(F)c1)NC1CC1]<br>(1-cyclopropyl-3-(3-fluoro-4-(2-(3-hydroxyazetidine-1-carbonyl)thieno[3,2-b]pyridin-7-yloxy)phenyl)urea | $^1$H NMR (400 MHz, DMSO-d6) δ (ppm): 8.71 (s, 1H), 8.59 (d, J = 5.6 Hz, 1H), 7.92 (s, 1H), 7.72 (dd, J = 2.4 and 13.6 Hz, 1H), 7.37(t, J = 9.2 Hz, 1H), 7.23-7.17 (m, 1H), 6.73 (d, J = 5.6 Hz, 1H), 6.57 (bs, 1H), 5.88 (d, J = 6.8 Hz, 1H), 4.80 (t, J = 8.0 Hz, 1H), 4.62-4.55 (m, 1H), 4.38-4.29 (m, 2H), 3.85 (dd, J = 3.2 and 10.4 Hz, 1H), 2.58-2.51 (m, 1H), 0.68-0.62 (m, 2H), 0.45-0.40 (m, 2H). MS (m/z): 443.2 (M + 1). |

TABLE 36-continued

Characterization of compounds 460-474 (examples 300-314)

| Cpd | Ex. | Structure | Characterization |
|---|---|---|---|
| 463 | 303 | 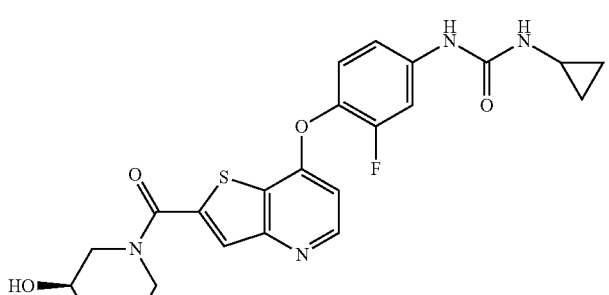<br>(R)-1-cyclopropyl-3-(3-fluoro-4-(2-(3-hydroxypiperidine-1-carbonyl)thieno-[3,2-b]pyridine-7-yloxy)phenyl)urea | $^1$H NMR (400 MHz, DMSO-d6) δ (ppm): 8.73 (s, 1H), 8.56 (d, J = 5.6 Hz, 1H), 7.85 (bs, 1H), 7.73 (dd, J = 2.4 and 13.6 Hz, 1H), 7.37 (t, J = 8.8 Hz, 1H), 7.23-7.18 (m, 1H), 6.71 (d, J = 5.6 Hz, 1H), 6.58 (d, J = 2.4 Hz, 1H), 5.00 (bs, 1H), 4.20-2.90 (m, 4H), 2.59-2.51 (m, 1H), 1.95-1.70 (m, 2H), 1.60-1.40 (m, 2H), 0.67-0.62 (m, 2H), 0.43-0.40 (m, 2H). MS (m/z): 471.0 (M + 1). |
| 464 | 304 | 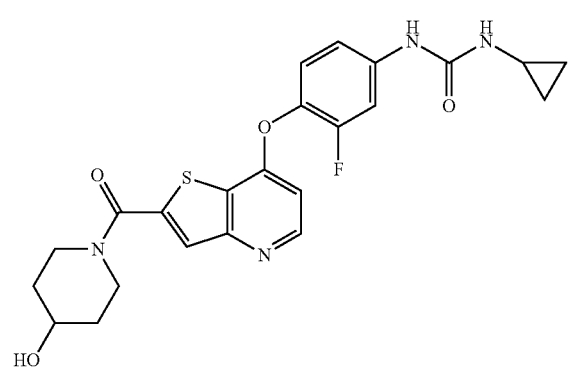 [SMILES: O=C(Nc1ccc(Oc2ccnc3cc(C(=O)N4CCC(O)CC4)sc23)c(F)c1)NC1CC1]<br>1-cyclopropyl-3-(3-fluoro-4-(2-(4-hydroxypiperidine-1-carbonyl)thieno-[3,2-b]pyridine-7-yloxy)phenyl)urea | $^1$H NMR (400 MHz, DMSO-d6) δ (ppm): 8.83 (s, 1H), 8.57 (d, J = 5.6 Hz, 1H), 7.80 (s, 1H), 7.73 (dd, J = 2.4 and 13.6 Hz, 1H), 7.37 (t, J = 9.2 Hz, 1H), 7.22-7.16 (m, 1H), 6.71 (d, J = 5.6 Hz, 1H), 6.64 (d, J = 2.0 Hz, 1H), 4.86 (d, J = 4.0 Hz, 1H), 4.02-3.83 (m, 2H), 3.82-3.75 (m, 1H), 3.12-3.08 (m, 1H), 2.57-2.50 (m, 1H), 2.0-1.68 (m, 3H), 1.49-1.38 (m, 2H), 0.66-0.62 (m, 2H), 0.43-0.40 (m, 2H). MS (m/z): 471.3 (M + 1). |
| 465 | 305 | 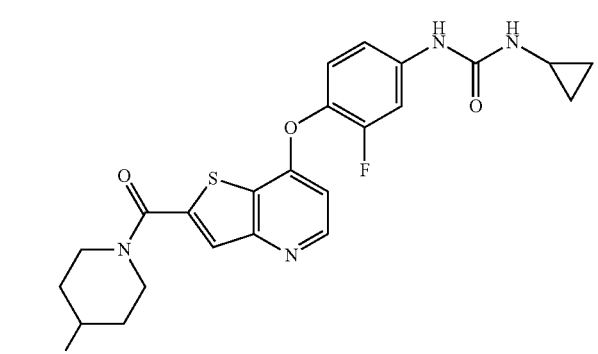<br>1-(7-(4-(3-cyclopropylureido)-2-fluorophenoxy)thieno[3,2-b]pyridine-2-carbonyl)piperidine-4-carboxylic acid | $^1$H NMR (400 MHz, DMSO-d6) δ (ppm): 9.10 (bs, 1H), 8.57 (d, J = 5.6 Hz, 1H), 7.81 (s, 1H), 7.74 (dd, J = 2.4 and 13.6 Hz, 1H), 7.36 (t, J = 8.8 Hz, 1H), 7.24-7.19 (m, 1H), 6.93 (bs, 1H), 6.71 (d, J = 5.6 Hz, 1H), 4.40-2.90 (m, 4H), 2.58-2.51 (m, 1H), 1.96-1.87 (m, 2H), 1.66-1.53 (m, 2H), 0.66-0.61 (m, 2H), 0.44-0.40 (m, 2H), MS (m/z): 499.2 (M + 1). |

TABLE 36-continued

Characterization of compounds 460-474 (examples 300-314)

| Cpd | Ex. | Structure | Characterization |
|---|---|---|---|
| 466 | 306 | 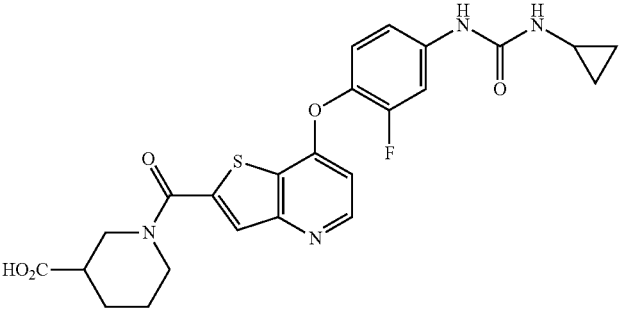 [SMILES: O=C(Nc1ccc(Oc2ccnc3cc(C(=O)N4CCCC(C(=O)O)C4)sc23)c(F)c1)NC1CC1]<br>1-(7-(4-(3-cyclopropylureido)-2-fluorophenoxy)thieno[3,2-b]pyridine-2-carbonyl)piperidine-3-carboxylic acid | $^1$H NMR (400 MHz, DMSO-d6) δ (ppm): 8.82 (s, 1H), 8.61 (d, J = 5.6 Hz, 1H), 7.86 (bs, 1H), 7.74 (dd, J = 2.4 and 13.6 Hz, 1H), 7.39 (t, J = 9.2 Hz, 1H), 7.23-7.17 (m, 1H), 6.77 (d, J = 5.6 Hz, 1H), 6.62 (bs, 1H), 4.52-3.88 (m, 2H), 3.35-2.90 (m, 2H), 2.68-2.51 (m, 2H), 2.05-1.95 (m, 1H), 1.68-1.62 (m, 2H), 1.62-1.48 (m, 1H), 0.68-0.60 (m, 2H), 0.45-0.40 (m, 2H). MS (m/z): 499.3 (M + 1). |
| 467 | 307 | 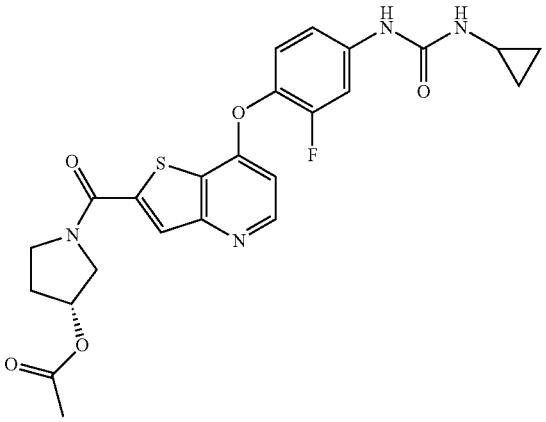 [SMILES: CC(=O)O[C@@H]1CCN(C(=O)c2cc3nccc(Oc4ccc(NC(=O)NC5CC5)cc4F)c3s2)C1]<br>(R)-1-(7-(4-(3-cyclopropylureido)-2-fluorophenoxy)thieno[3,2-b]pyridine-2-carbonyl)pyrrolidin-3-yl acetate | $^1$H NMR (400 MHz, DMSO-d$_6$) δ (ppm): 8.75 (s, 1H), 8.59 (d, J = 5.6 Hz, 1H), 8.09 and 8.04 (s, 1H), 7.73 (dd, J = 2.4 and 13.6 Hz, 1H), 7.37 (t, J = 9.2 Hz, 1H), 7.24-7.17 (m, 1H), 6.73 (d, J = 5.6 Hz, 1H), 6.61 (d, J = 2.4 Hz, 1H), 5.36-5.27 (m, 1H), 4.24-3.58 (m, 4H), 2.59-2.51 (m, 1H), 2.32-2.00 (m, 2H), 2.03 (d, J = 17.6 Hz, 3H), 0.68-0.62 (m, 2H), 0.45-0.40 (m, 2H). MS (m/z): 499.3 (M + 1). |
| 468 | 308 | 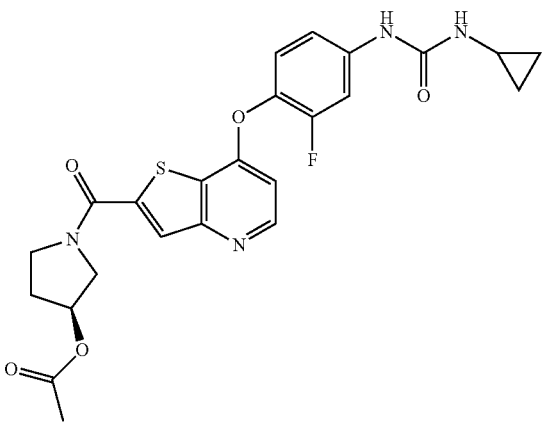 [SMILES: CC(=O)O[C@H]1CCN(C(=O)c2cc3nccc(Oc4ccc(NC(=O)NC5CC5)cc4F)c3s2)C1]<br>(S)-1-(7-(4-(3-cyclopropylureido)-2-fluorophenoxy)thieno[3,2-b]pyridine-2-carbonyl)pyrrolidin-3-yl acetate | 1H NMR (400 MHz, DMSO-d6) δ (ppm): 8.75 (s, 1H), 8.59 (d, J = 5.6 Hz, 1H), 8.09 and 8.03 (s, 1H), 7.72 (dd, J = 2.4 and 11.2 Hz, 1H), 7.37 (t, J = 8.8 Hz, 1H), 7.23-7.18 (m, 1H), 6.73 (d, J = 5.6 Hz, 1H), 6.60 (d, J = 2.4 Hz, 1H), 5.36-5.27 (m, 1H), 4.25-3.55 (m, 4H), 2.59-2.51 (m, 1H), 2.33-2.08 (m, 2H), 2.05 and 2.00 (s, 3H), 0.68-0.62 (m, 2H), 0.45-0.40 (m, 2H). MS (m/z): 499.3 (M + 1). |

TABLE 36-continued

Characterization of compounds 460-474 (examples 300-314)

| Cpd | Ex. | Structure | Characterization |
|---|---|---|---|
| 469 | 309 | 1-(7-(4-(3-cyclopropylureido)-2-fluorophenoxy)thieno[3,2-b]pyridine-2-carbonyl)azetidin-3-yl acetate | $^1$H NMR (400 MHz, DMSO-d6) δ (ppm): 8.71 (s, 1H), 8.60 (d, J = 5.6 Hz, 1H), 7.95 (s, 1H), 7.73 (dd, J = 2.4 and 13.6 Hz, 1H), 7.37 (t, J = 9.2 Hz, 1H), 7.23-7.18 (m, 1H), 6.73 (d, J = 5.6 Hz, 1H), 6.57 (d, J = 2.4 Hz, 1H), 5.27-5.20 (m, 1H), 4.97-4.90 (m, 1H), 4.68-4.61 (m, 1H), 4.46 (dd, J = 7.2 and 11.2 Hz, 1H), 4.09-4.02 (m, 1H), 2.58-2.51 (m, 1H), 2.09 (s, 3H), 0.68-0.62 (m, 2H), 0.45-0.40 (m, 2H). MS (m/z): 485.4 (M + 1). |
| 470 | 310 | (R)-1-(7-(4-(3-cyclopropylureido)-2-fluorophenoxy)thieno[3,2-b]pyridine-2-carbonyl)piperidin-3-yl acetate | $^1$H NMR (400 MHz, DMSO-d6) δ (ppm): 8.73 (s, 1H), 8.58 (d, J= 5.6 Hz, 1H), 7.81 (s, 1H), 7.73 (dd, J = 2.4 and 13.6 Hz, 1H), 7.38 (t, J = 5.2 Hz, 1H), 7.23-7.17 (m, 1H), 6.74 (d, J = 5.6 Hz, 1H), 6.58 (d, J = 0.8 Hz, 1H), 4.79 (bs, 1H), 4.01-3.55 (m, 4H), 2.57-2.51 (m, 1H), 2.08-1.85 (m, 4H), 1.84-1.70 (m, 3H), 1.65-1.53 (m, 1H), 0.66-0.62 (m, 2H), 0.44-0.40 (m, 2H). MS (m/z): 513.4 (M + 1). |
| 471 | 311 | 1-(7-(4-(3-cyclopropylureido)-2-fluorophenoxy)thieno[3,2-b]pyridine-2-carbonyl)-N-(2-(dimethylamino)ethyl)piperidine-4-carboxamide | $^1$H NMR (400 MHz, CD$_3$OD-d$_4$) δ (ppm): 7.57 (d, J = 5.6 Hz, 1H), 7.74 (s, 1H), 7.71 (dd, J = 2.4 and 13.2 Hz, 1H), 7.33 (t, J = 8.8 Hz, 1H), 7.25-7.21 (m, 1H), 6.76 (d, J = 5.6 Hz, 1H), 4.90-2.95 (m, 4H), 3.50 (t, J = 6.4 Hz, 2H), 2.96 (t, J = 6.4 Hz, 2H), 2.68-2.60 (m, 2H), 2.04-1.93 (m, 2H), 1.86-1.64 (m, 2H), 0.83-0.77 (m, 2H), 0.60-0.55 (m, 21H). MS (m/z): 569.3 (M + 1). |

TABLE 36-continued

Characterization of compounds 460-474 (examples 300-314)

| Cpd | Ex. | Structure | Characterization |
|---|---|---|---|
| 472 | 312 | 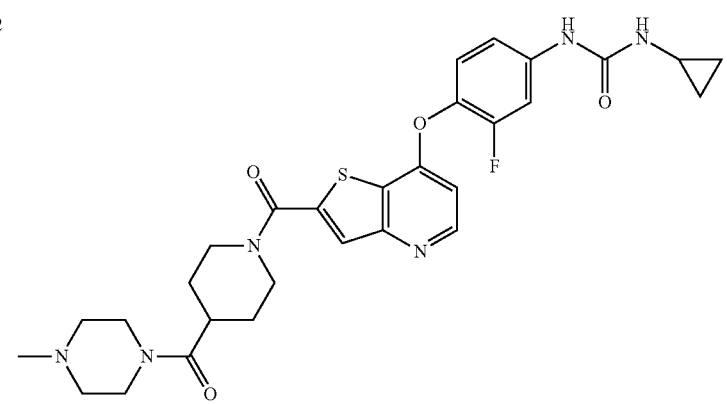<br>1-cyclopropyl-3-(3-fluoro-4-(2-(4-(4-methylpiperazine-1-carbonyl)piperidine-1-carbonyl)thieno[3,2-b]pyridin-7-yloxy)phenyl)urea | $^1$H NMR (400 MHz, DMSO-d6) δ (ppm): 8.73 (s, 1H), 8.57 (d, J = 5.6 Hz, 1H), 7.82 (s, 1H), 7.73 (dd, J = 2.4 and 13.6 Hz, 1H), 7.37 (t, J = 9.2 Hz, 1H), 7.23-7.18 (m, 1H), 6.71 (d, J = 5.6 Hz, 1H), 6.58 (d, J = 2.0 Hz, 1H), 3.56-3.49 (m, 2H), 3.49-3.42 (m, 2H), 3.41-3.28 (m, 4H), 3.05-2.96 (m, 1H), 2.59-2.51 (m, 1H), 2.34-2.28 (m, 2H), 2.28-2.20 (m, 2H), 2.18 (s, 3H), 1.76-1.66 (m, 2H), 1.64-1.50 (m, 2H), 1.10 (s, 2H), 0.68-0.62 (m, 2H), 0.45-0.40 (m, 2H). MS (m/z): 581.5 (M + 1). |
| 473 | 313 | 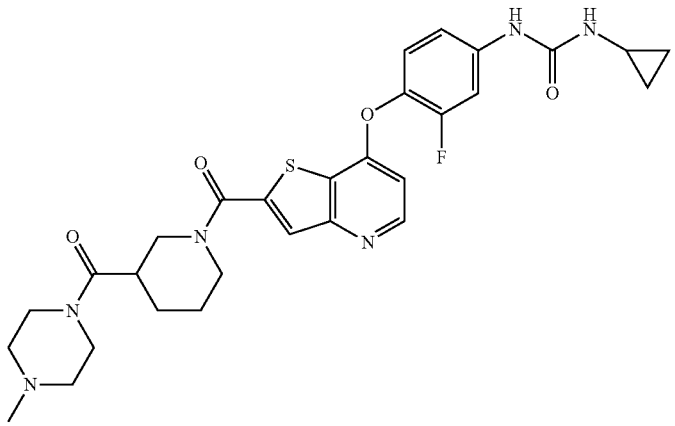 [SMILES: CN1CCN(C(=O)C2CCCN(C(=O)c3cc4nccc(Oc5ccc(NC(=O)NC6CC6)cc5F)c4s3)C2)CC1]<br>1-cyclopropyl-3-(3-fluoro-4-(2-(3-(4-methylpiperazine-1-carbonyl)piperidine-1-carbonyl)thieno[3,2-b]pyridin-7-yloxy)phenyl)urea | $^1$H NMR (400 MHz, DMSO-d6) δ (ppm): 8.72 (s, 1H), 8.57 (d, J = 5.6 Hz, 1H), 7.82 (bs, 1H), 7.73 (dd, J = 2.4 and 13.6 Hz, 1H), 7.37 (t, J = 9.2 Hz, 1H), 7.22-7.17 (m, 1H); 6.72 (d, J = 5.6 Hz, 1H), 6.59 (d, J = 2.4 Hz, 1H), 4.45-3.80 (m, 2H), 3.70-3.15 (m, 5H), 3.14-2.85 (m, 2H), 2.58-2.51 (m, 1H), 2.47-1.52 (m, 12H), 0.68-0.62 (m, 2H), 0.45-0.40 (m, 2H). MS (m/z): 581.2 (M + 1). |
| 474 | 314 | 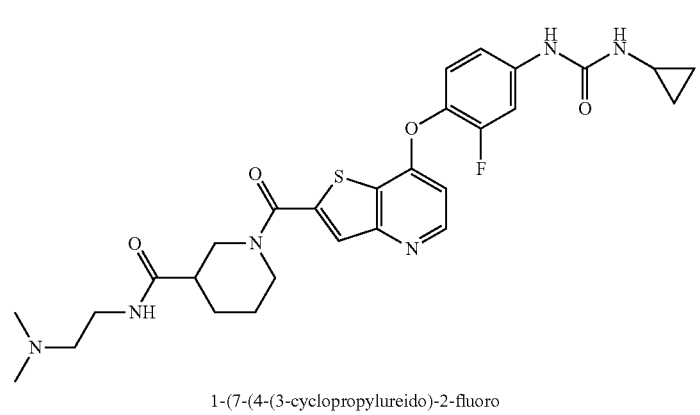<br>1-(7-(4-(3-cyclopropylureido)-2-fluoro phenoxy)thieno[3,2-b]pyridine-2-carbonyl)-N-(2-(dimethylamino)ethyl)piperidine-3-carboxamide | $^1$H NMR (400 MHz, DMSO-d6) δ (ppm): 8.81 (s, 1H), 8.57 (d, J = 5.6 Hz, 1H), 7.87 (bs, 1H), 7.82 (s, 1H), 7.73 (dd, J = 2.0 and 9.6 Hz, 1H), 7.36 (t, J = 9.6 Hz, 1H), 7.24-7.17 (m, 1H), 6.72 (d, J = 5.6 Hz, 1H), 6.65 (s, 1H), 4.50-3.90 (m, 3H), 3.21-2.85 (m, 4H), 2.58-2.51 (m, 1H), 2.49-2.36 (m, 1H), 2.36-2.00 (m, 7H), 1.93-1.84 (m, 1H), 1.83-1.60 (m, 2H), 1.57-1.42 (m, 1H), 0.67-0.62 (m, 2H), 0.45-0.40 (m, 2H). MS (m/z): 569.4 (M + 1). |

Compounds 475-481 (example 315-321) were synthesized using the corresponding amines by following the procedures described above for the synthesis of compound 48 (example 31) (scheme 15).

TABLE 37

Characterization of compounds 475-481 (examples 315-321)

| Cpd | Ex. | Structure | Characterization |
|---|---|---|---|
| 475 | 315 | 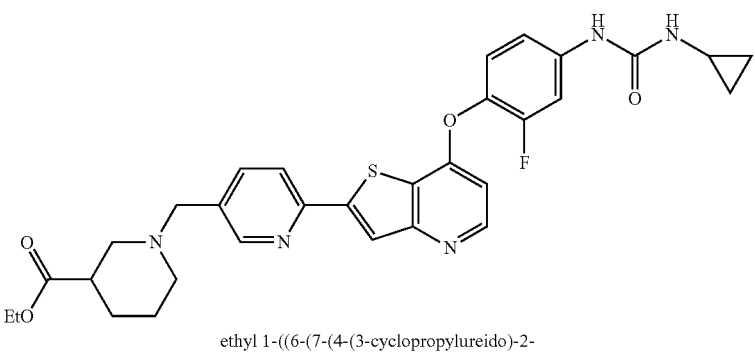<br>ethyl 1-((6-(7-(4-(3-cyclopropylureido)-2-fluorophenoxy)thieno[3,2-b]pyridin-2-yl)pyridino-yl)methyl)piperidine-3-carboxylate | $^1$H NMR (400 MHz, DMSO-d$_6$) δ (ppm): 8.68 (s, 1H), 8.52 (d, J = 1.7 Hz, 1H), 8.51 (d, J = 5.6 Hz, 1H), 8.31 (s, 1H), 8.22 (d, J = 8.0 Hz, 1H), 7.83 (dd, J = 2.0 and 8.0 Hz, 1H), 7.72 (dd, J = 2.4 and 13.6 Hz, 1H), 7.36 (t, J = 9.0 Hz, 1H), 7.22-7.18 (m, 1H), 6.63 (d, J = 5.6 Hz, 1H), 6.65 (d, J = 2.4 Hz, 1H), 4.03 (q, J = 7.0 Hz, 2H), 3.58 (d, J = 14.0, 1H), 3.51 (d, J = 14 Hz, 1H), 2.78-2.72 (m, 1H), 2.65-2.50 (m, 3H), 2.31-2.24 (m, 1H), 2.18-2.10 (m, 1H), 1.78-1.72 (m, 1H), 1.69-1.63 (m, 1H), 1.53-1.39 (m, 2H), 0.67-0.62 (m, 2H), 0.45-0.40 (m. 2H). MS (m/z): 590.4 (M + 1). |
| 476 | 315 | 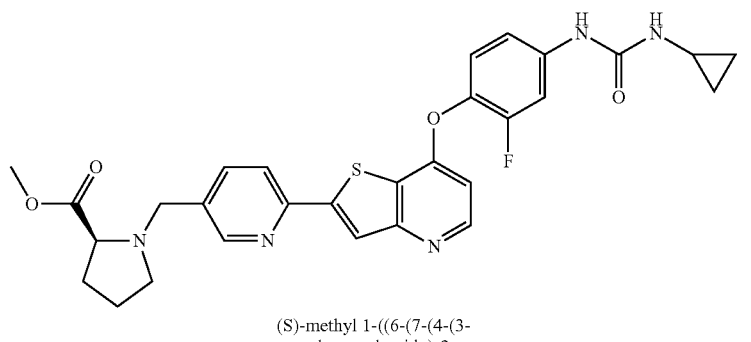<br>(S)-methyl 1-((6-(7-(4-(3-cyclopropylureido)-2-fluorophenoxy)thieno[3,2-b]pyridin-2-yl)pyridin-3-yl(methyl)pyrrolidine-2-carboxylate | $^1$H NMR (400 MHz, DMSO-d6) δ (ppm): 8.68 (s, 1H), 8.53 (d, J = 1.2 Hz, 1H), 8.51 (d, J = 5.6 Hz, 1H), 8.30 (s, 1H), 8.22 (d, J = 8.0 Hz, 1H), 7.85 (dd, J = 1.8 and 8.0 Hz, 1H), 7.72 (dd, J = 2.4 and 13.6 Hz, 1H), 7.36 (t, J = 9.0 Hz, 1H), 7.22-7.17 (m, 1H), 6.63 (d, J = 5.6 Hz, 1H), 6.54 (d, J = 2.0 Hz, 1H), 3.95 (d, J = 13.6 Hz, 1H), 6.41 (d, J = 13.6 Hz, 1H), 3.35-3.31 (m, 1H), 2.93-2.86 (m, 1H), 2.58-2.51 (m, 1H), 2.43 (q, J = 8.4 Hz, 1H), 2.08 (qd, J = 6.5 and 12.4 Hz, 1H), 1.87-1.79 (m, 1H), 1.79-1.72 (m, 2H), 0.67-0.62 (m, 2H), 0.45-0.40 (m, 2H). MS (m/z): 562.3 (M + 1). |
| 477 | 317 | 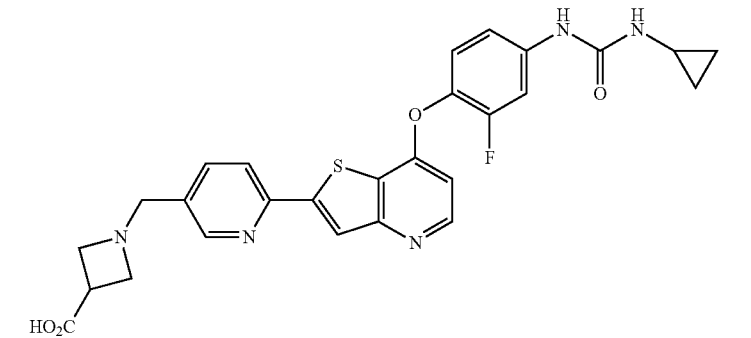 [SMILES: O=C(Nc1ccc(Oc2ccnc3cc(-c4ccc(CN5CC(C(=O)O)C5)cn4)sc23)c(F)c1)NC1CC1]<br>1-((6-(7-(4-(3-cyclopropylureido)-2-fluorophenoxy)thieno[3,2-b]pyridin-2-yl)pyridin-3-yl)methyl)azetidine-3-carboxylic acid | $^1$H NMR (400 MHz, DMSO-d6) δ (ppm): 8.76 (s, 1H), 8.53 (d, J = 1.6 Hz, 1H), 8.51 (d, J = 5.6 Hz, 1H), 8.32 (s, 1H), 8.22 (d, J = 8.4 Hz, 1H), 7.83 (dd, J = 2.0 and 8.0 Hz, 1H), 7.73 (dd, J = 2.4 and 13.6 Hz, 1H), 7.37 (t, J = 9.2 Hz, 1H), 7.23-7.18 (m, 1H), 6.64 (d, J = 5.6 Hz, 1H), 6.60 (d, J = 1.2 Hz, 1H), 3.63 (s, 2H), 3.48-3.40 (m, 2H), 3.38-3.29 (m, 3H), 2.57-2.51 (m, 1H), 0.68-0.62 (m, 2H), 0.45-0.40 (m, 2H). MS (m/z): 534.3 (M + 1). |

TABLE 37-continued

Characterization of compounds 475-481 (examples 315-321)

| Cpd | Ex. | Structure | Characterization |
|---|---|---|---|
| 478 | 318 | 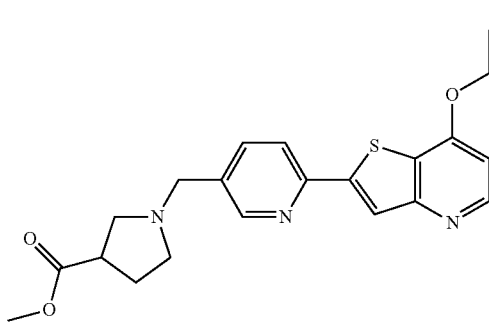<br>methyl 1-((6-(7-(4-(3-cyclopropylureido)-2-fluorophenoxy)thieno[3,2-b]pyridin-2-yl)pyridin-3-yl)methyl)pyrrolidine-3-carboxylate | $^1$H NMR (400 MHz, DMSO-d6) δ (ppm): 8.71 (s, 1H), 8.55 (d, J = 1.2 Hz, 1H), 8.52 (d, J = 5.6 Hz, 1H), 8.32 (s, 1H), 8.24 (d, J = 8.0 Hz, 1H), 7.86 (dd, J = 2.0 and 8.4 Hz, 1H), 7.73 (dd, J = 2.4 and 13.6 Hz, 1H), 7.38 (t, J = 9.2 Hz, 1H), 7.24-7.18 (m, 1H), 6.64 (d, J = 5.6 Hz, 1H), 6.57 (d, J = 2.4 Hz, 1H), 3.68 (d, J = 13.6 Hz, 1H), 3.63 (d, J = 13.6 Hz, 1H), 3.10-3.01 (m, 1H), 2.74 (t, J = 9.2 Hz, 1H), 2.66 (dd, J = 2.4 and 9.2 Hz, 1H), 2.59-2.51 (m, 3H), 2.07-1.91 (m, 2H), 0.68-0.63 (m, 2H), 0.45-0.41 (m, 2H). MS (m/z): 562.5 (M + 1). |
| 480 | 320 | 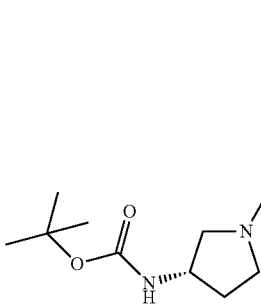<br>(S)-tert-butyl 1-((6-(7-(4-(3-cyclopropylureido)-2-fluorophenoxy)thieno[3,2-b]pyridin-2-yl)pyridin-3-yl)methyl)pyrrolidin-3-ylcarbamate<br>$^1$H NMR (400 MHz, DMSO-d6) δ (ppm): 8.70 (s, 1H), 8.56 (d, J = 1.6 Hz, 1H), 8.51 (d, J = 5.6 Hz, 1H), 8.32 (s, 1H), 8.22 (d, J = 8.0 Hz, 1H), 7.86 (dd, J = 2.0 and 8.4 Hz, 1H), 7.73 (dd, J = 2.4 and 13.6 Hz, 1H), 7.38 (t, J = 9.2 Hz, 1H), 7.23-7.18 (m, 1H), 7.01 (d, J = 7.2 Hz, 1H), 6.64 (d, J = 5.6 Hz, 1H), 6.56 (d, J = 2.4 Hz, 1H), 3.96-3.88 (m, 1H), 3.66 (d, J = 13.6 Hz, 1H), 3.60 (d, J = 13.6 Hz, 1H), 2.74-2.68 (m, 1H), 2.59-2.51 (m, 2H), 2.49-2.42 (m, 1H), 2.34-2.26 (m, 1H), 2.10-1.99 (m, 1H), 1.62-1.51 (m, 1H), 1.36 (m, 9H), 0.68-0.63 (m, 2H), 0.45-0.41 (m, 2H). MS (m/z): 619.3 (M + 1). | |
| 481 | 321 | 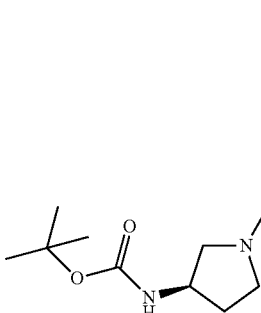<br>(R)-tert-butyl 1-((6-(7-(4-(3-cyclopropylureido)-2-fluorophenoxy)thieno[3,2-b]pyridin-2-yl)pyridin-3-yl)methyl)pyrrolidin-3-ylcarbamate<br>$^1$H NMR (400 MHz, DMSO-d6) δ (ppm): 8.71 (s, 1H), 8.56 (d, J = 1.6 Hz, 1H), 8.51 (d, J = 5.6 Hz, 1H), 8.32 (s, 1H), 8.23 (d, J = 8.4 Hz, 1H), 7.86 dd, J = 1.6 and 8.0 Hz, 1H), 7.73 (dd, J = 2.4 and 13.6 Hz, 1H), 7.37 (t, J = 9.2 Hz, 1H), 7.23-7.18 (m, 1H), 7.02 (d, J = 6.8 Hz, 1H), 6.64 (d, J = 5.6 Hz, 1H), 6.57 (d, J = 2.4 Hz, 1H), 3.97-3.88 (m, 1H), 3.66 (d, J = 13.6 Hz, 1H), 3.60 (d, J = 13.6 Hz, 1H), 2.71 (t, J = 8.8 Hz, 1H), 2.59-2.51 (m, 2H), 2.49-2.42 (m, 1H), 2.30 (dd, J = 5.2 and 9.2 Hz, 1H), 2.10-1.99 (m, 1H), 1.62-1.51 (m, 1H), 1.36 (s, 9H), 0.68-0.63 (m, 2H), 0.45-0.41 (m, 2H). MS (m/z): 619.3 (M + 1). | |

Compounds 482-494 (example 322-334) were synthesized starting from the acid 62 (example 45, Table 7) and the corresponding amines by following the procedures described above for the synthesis of compound 12 (scheme 9).

TABLE 38

Characterization of compounds 482-494 (examples 322-334)

| Cpd | Ex. | Structure | Characterization |
|---|---|---|---|
| 482 | 322 | 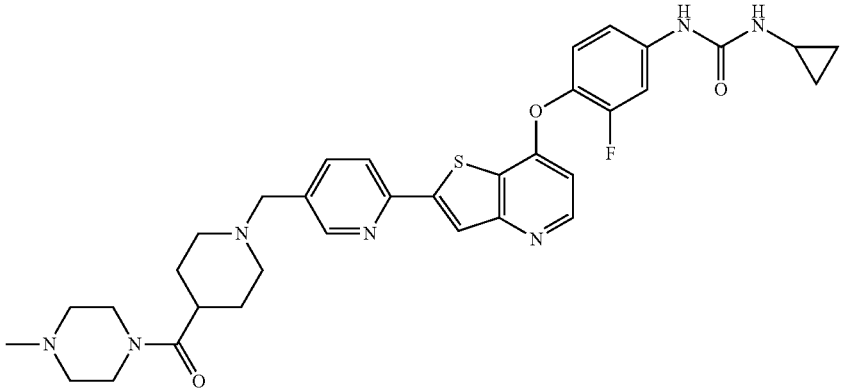 [SMILES: CN1CCN(C(=O)C2CCN(Cc3ccc(-c4cc5nccc(Oc6ccc(NC(=O)NC7CC7)cc6F)c5s4)nc3)CC2)CC1]<br>1-cyclopropyl-3-(3-fluoro-4-(2-(5-((4-(4-methylpiperazine-1-carbonyl)piperidin-1-yl)methyl)pyridin-2-yl)thieno[3,2-b]pyridin-7-yloxy)phenyl)urea | $^1$H NMR (400 MHz, DMSO-d$_6$) δ (ppm): 8.76 (s, 1H), 8.51 (d, J = 1.4 Hz, 1H), 8.50 (d, J = 5.6 Hz, 1H), 8.31 (s, 1H), 8.23 (d, J = 8.0 Hz, 1H), 7.85 (dd, J = 1.8 and 8.0 Hz, 1H), 7.73 (dd, J = 2.4 and 13.6 Hz, 1H), 7.36 (t, J = 9.0 Hz, 1H), 7.22-7.16 (m, 1H), 6.64 (d, J = 5.6 Hz, 1H), 6.59 (d, J = 2.4 Hz, 1H), 3.54 (s, 2H), 3.47-3.38 (m, 4H), 2.85-2.79 (m, 2H), 2.59-2.51 (m, 2H), 2.29-2.18 (m, 5H), 2.15 (s, 3H), 2.07-2.00 (m, 2H), 1.61-1.53 (m, 4H), 0.67-.62 (m, 2H), 0.45-0.40 (m, 2H). MS (m/z): 644.4 (M + 1). |
| 483 | 323 | 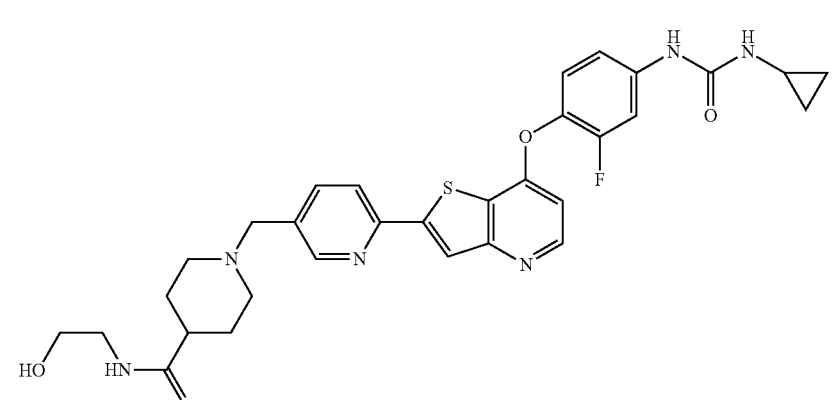<br>1-((6-(7-(4-(3-cyclopropylureido)-2-fluoro phenoxy)thieno[3,2-b]pyridin-2-yl)pyridin-3-yl)methyl)-N-(2-hydroxyethyl)piperidine-4-carboxamide | $^1$H NMR (400 MHz, DMSO-d6) δ (ppm): 8.75 (s, 1H), 8.53 (s, 1H), 8.10 (d, J = 5.6 Hz, 1H), 8.31 (s, 1H), 8.23 (d, J = 8.2 Hz, 1H), 7.87-7.83 (m, 1H), 7.74-7.69 (m, 2H), 7.36 (t, J = 9.0 Hz, 1H), 7.22-7.16 (m, 1H), 6.65-6.62 (m, 2H), 4.62 (t, J = 5.6 Hz, 1H), 3.53 (bs, 2H), 3.35 (q, J = 6.0 Hz, 2H), 3.08 (q, J = 6.0 Hz, 2H), 2.86-2.80 (m, 2H), 2.57-2.51 (m, 1H), 2.13-2.05 (m, 1H), 2.00-1.90 (m, 2H), 1.67-1.53 (m, 4H), 0.67-0.62 (m, 2H), 0.44-0.39 (m, 2H). MS (m/z): 605.3 (M + 1). |

TABLE 38-continued

Characterization of compounds 482-494 (examples 322-334)

| Cpd | Ex. | Structure | Characterization |
|---|---|---|---|
| 484 | 324 | 1-((6-(7-(4-(3-cyclopropylureido)-2-fluorophenoxy)thieno[3,2-b]pyridin-2-yl)pyridin-3-yl)methyl)-N-(2-hydroxyethyl)-N-methylpiperidine-4-carboxamide | $^1$H NMR (400 MHz, DMSO-d6) δ (ppm): 8.77 (s, 1H), 8.54 (bs, 1H), 8.51 (d, J = 5.6 Hz, 1H), 8.32 (s, 1H), 8.26-8.21 (m, 1H), 7.91-7.82 (m, 1H), 7.72 (dd, J = 2.4 and 13.6 Hz, 1H), 7.37 (t, J = 9.0 Hz, 1H), 7.22-7.17 (m, 1H), 6.64 (d, J = 5.6 Hz, 1H), 6.58 (d, J = 1.4 Hz, 1H), 4.78 and 4.60 (t, J = 5.4 Hz, 1H), 3.60-3.27 (m, 6H), 3.02 and 2.78 (s, 3H), 2.92-2.77 (m, 2H), 2.70-2.58 (m, 1H), 2.57-2.51 (m, 1H), 2.10-1.93 (m, 2H), 1.69-1.53 (m, 4H), 0.67-0.62 (m, 2H), 0.45-0.40 (m, 2H). MS (m/z): 619.4 (M + 1). |
| 484-A | 324-A | 1-((6-(7-(4-(3-cyclopropylureido)-2-fluorophenoxy)thieno[3,2-b]pyridin-2-yl)pyridin-3-yl)methyl)-N-(2-(dimethylamino)ethyl)piperidine-4-carboxamide | $^1$H NMR (400 MHz, DMSO-d6) δ (ppm): 8.74 (s, 1H), 8.52 (s, 1H), 8.51 (d, J = 5.6 Hz, 1H), 8.30 (s, 1H), 8.23 (d, J = 8.0 Hz, 1H), 7.85 (dd, J = .6 and 8.0 Hz, 1H), 7.73 (dd, J = 2.4 and 13.6 Hz, 1H), 7.63 (t, J = 5.6 Hz, 1H), 7.22-7.17 (m, 1H), 6.64 (d, J = 5.6 Hz, 1H), 6.59 (d, J = 2.0 Hz, 1H), 3.51 (s, 2H), 3.10 (q, J = 6.6 Hz, 2H), 2.85-2.79 (m, 2H), 2.57-2.51 (m, 1H), 1.23 (t, J = 6.8 Hz, 2H), 2.14-2.08 (m, 1H), 2.11 (s, 6H), 1.98-1.91 (m, 2H), 1.65-1.52 (m, 4H), 0.66-0.62 (m, 2H), 0.45-0.40 (m, 2H). MS (m/z): 632.4 (M + 1). |

TABLE 38-continued

Characterization of compounds 482-494 (examples 322-334)

| Cpd | Ex. | Structure | Characterization |
|---|---|---|---|
| 485 | 325 | 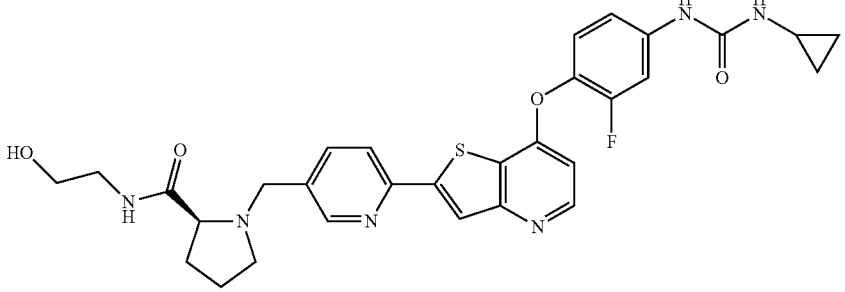<br>(S)-1-((6-(7-(4-(3-cyclopropylureido)-2-fluoro phenoxy)thieno[3,2-b]pyridin-2-yl)pyridin-3-yl)methyl)-N-(2-hydroxyethyl)pyrrolidine-2-carboxamide | $^1$H NMR (400 MHz, DMSO-d6) δ (ppm): 8.89 (s, 1H), 8.64 (d, J = 1.2 Hz, 1H), 8.52 (d, J = 5.6 Hz, 1H), 8.35 (s, 1H), 8.24 (d, J = 8.4 Hz, 1H), 7.94 (dd, J = 2.0 and 8.4 Hz, 1H), 7.85 (t, J = 5.6 Hz, 1H), 7.73 (dd, J = 2.4 and 13.6 Hz, 1H), 7.38 (t, J = 5.2 Hz, 1H), 7.24-7.18 (m, 1H), 6.65 (d, J = 5.6 Hz, 1H), 4.74 (t, J = 5.2 Hz, 1H), 3.86 (d, J = 13.2 Hz, 1H), 3.53 (d, J = 13.2 Hz, 1H), 3.39 (q, J = 5.6 Hz, 2H), 3.25-3.16 (m, 1H), 3.13-3.06 (m, 2H), 2.95-2.88 (m, 1H), 2.59-2.51 (m, 1H), 2.36-2.28 (m, 1H), 2.13-2.05 (m, 1H), 1.76-1.62 (m, 3H), 0.68-0.62 (m, 2H), 0.45-0.40 (m, 2H). MS (m/z): 591.4 (M + 1). |
| 486 | 326 | 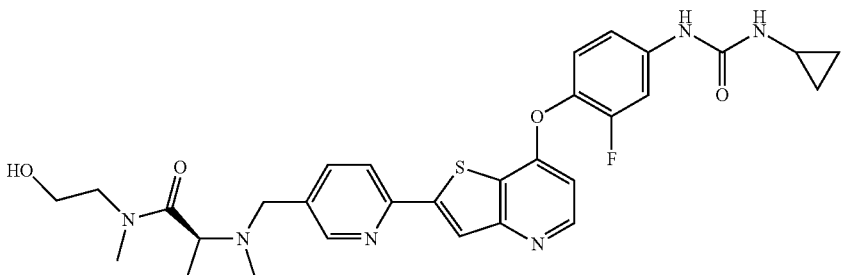<br>(S)-1-((6-(7-(4-(3-cyclopropylureido)-2-fluoro phenoxy)thieno[3,2-b]pyridin-2-yl)pyridin-3-yl)methyl)-N-(2-hydroxyethyl)-N-methylpyrrolidine-2-carboxamide | $^1$H NMR (400 MHz, DMSO-d6) δ (ppm): 8.89 (s, 1H), 8.54 (s, 1H), 8.51 (d, J = 5.6 Hz, 1H), 8.31 (s, 1H), 8.22 (d, J = 8.0 Hz, 1H), 7.88 (d, J = 8.0 Hz, 1H), 7.73 (dd, J = 2.4 and 13.6 Hz, 1H), 7.37 (t, J = 8.8 Hz, 1H), 7.23-7.18 (m, 1H), 6.66 (d, J = 2.4 Hz, 1H), 6.64 (d, J = 5.6 Hz, 1H), 4.83 and 4.65 (t, J = 5.6 Hz, 1H), 3.90-3.65 (m, 2H), 3.61-3.25 (m, 5H), 3.02 and 2.79 (s, 3H), 2.98-2.58 (m, 1H), 2.58-2.51 (m, 1H), 2.47-2.30 (m, 1H), 2.18-2.04 (m, 1H), 1.81-1.63 (m, 3H), 0.68-0.62 (m, 2H), 0.45-0.40 (m, 2H). MS (m/z): 605.5 (M + 1). |

TABLE 38-continued

Characterization of compounds 482-494 (examples 322-334)

| Cpd | Ex. | Structure | Characterization |
|---|---|---|---|
| 487 | 327 | 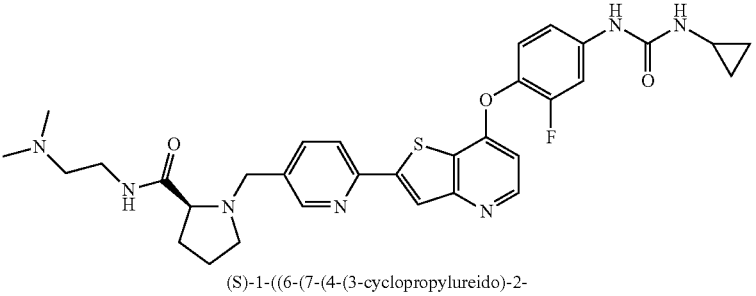<br>(S)-1-((6-(7-(4-(3-cyclopropylureido)-2-fluorophenoxy)thieno[3,2-6]pyridin-2-yl)pyridin-3-yl)methyl)-N-(2-(dimethylamino)ethyl)pyrrolidine-2-carboxamide | $^1$H NMR (400 MHz, DMSO-d6) δ (ppm): 8.94 (s, 1H), 8.68 (d, J = 1.2 Hz, 1H), 8.52 (d, J = 5.6 Hz, 1H), 8.36 (s, 1H), 8.25 (d, J = 8.0 Hz, 1H), 8.15-8.07 (m, 1H), 7.97 (dd, J = 1.6 and 8.0 Hz, 1H), 7.73 (dd, J = 2.0 and 13.6 Hz, 1H), 7.37 (t, J = 9.2 Hz, 1H), 7.23-7.18 (m, 1H), 6.69 (d, J = 2.4 Hz, 1H), 6.66 (d, J = 5.6 Hz, 1H), 3.87 (d, J = 13.2 Hz, 1H), 3.56 (d, J = 13.2 Hz, 1H), 3.13-3.08 (m, 1H), 2.97-2.80 (m, 3H), 2.57 (bs, 6H), 2.57-2.51 (m, 1H), 2.37-2.29 (m, 1H), 2.18-2.06 (m, 1H), 1.78-1.64 (m, 3H), 0.68-0.62 (m, 2H), 0.44-0.40 (m, 2H). MS (m/z): 618.1 (M + 1). |
| 488 | 328 | 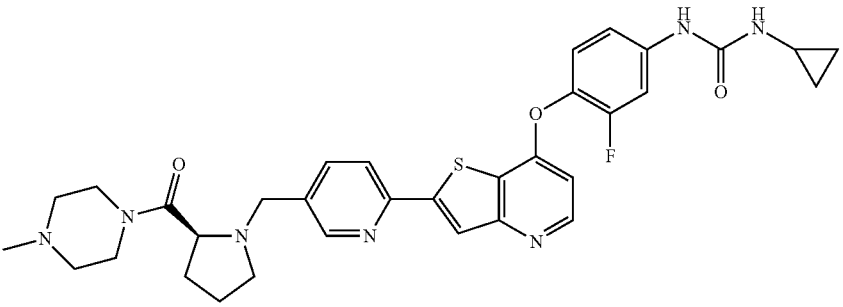 [SMILES: CN1CCN(C(=O)[C@@H]2CCCN2Cc2ccc(-c3cc4nccc(Oc5ccc(NC(=O)NC6CC6)cc5F)c4s3)nc2)CC1]<br>(S)-1-cyclopropyl-3-(3-fluoro-4-(2-(5-((2-(4-methylpiperazine-1-carbonyl)pyrrolidin-1-yl)methyl)pyridin-2-yl)thieno[3,2-b]pyridin-7-yloxy)phenyl)urea | $^1$H NMR (400 MHz, DMSO-d6) δ (ppm): 8.75 (s, 1H), 8.55 (s, 1 H), 8.52 (d, J = 5.6 Hz, 8.33 (s, 1H), 8.24 (d, J = 8.0 Hz, 1H), 7.90-7.84 (m, 1H), 7.73 (dd, J = 2.4 and 13.6 Hz, 1H), 7.37 (t, J = 9.2 Hz, 1H), 7.24-7.17 (m, 1H), 6.64 (d, J = 5.6 Hz, 1H), 6.59 (d, J = 2.4 Hz, 1H), 3.90-3.80 (m, 1H), 3.65-3.25 (m, 5H), 3.02-2.90 (m, 1H), 0.59-2.51 (m, 1H), 2.48-2.02 (m, 10H), 1.82-1.65 (m, 3H), 0.68-0.63 (m, 2H), 0.44-0.40 (m, 2H). MS (m/z): 630.6 (M + 1). |

TABLE 38-continued

Characterization of compounds 482-494 (examples 322-334)

| Cpd | Ex. | Structure | Characterization |
|---|---|---|---|
| 489 | 329 | 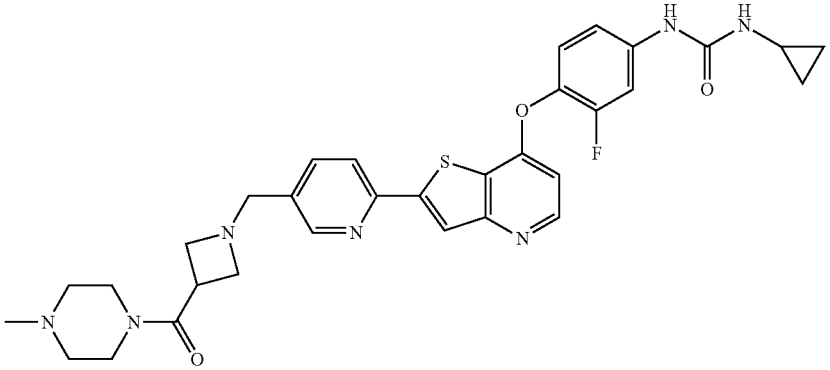 [SMILES: CN1CCN(C(=O)C2CN(Cc3ccc(-c4cc5nccc(Oc6ccc(NC(=O)NC7CC7)cc6F)c5s4)nc3)C2)CC1]<br>1-cyclopropyl-3-(3-fluoro-4-(2-(5-((3-(4-methyl piperazine-1-carbonyl)azetidin-1-yl)methyl) pyridin-2-yl)thieno[3,2-b]pyridin-7-yloxy)phenyl)urea | $^1$H NMR (400 MHz, DMSO-d6) δ (ppm): 8.79 (s, 1H), 8.54 (d, J = 1.6 Hz, 1H), 8.52 (d, J = 5.6 Hz, 1H), 8.33 (s, 1H), 8.23 (d, J = 8.0 Hz, 1H), 8.34 (dd, J = 1.6 and 8.0 Hz, 1H), 7.73 (dd, J = 2.4 and 13.6 Hz, 1H), 7.37 (t, J = 9.2 Hz, 1H), 7.23-7.18 (m, 1H), 6.64 (d, J = 5.6 Hz, 1H), 6.61 (d, J = 2.4 Hz, 1H), 3.65 (bs, 2H), 3.55-3.42 (m, 5H), 3.26 (bs, 4H), 2.59-2.51 (m, 1H), 2.41-2.25 (m, 4H), 2.22 (bs, 3H), 0.68-0.62 (m, 2H), 0.44-0.40 (m, 2H). MS (m/z): 616.4 (M + 1). |
| 490 | 330 | 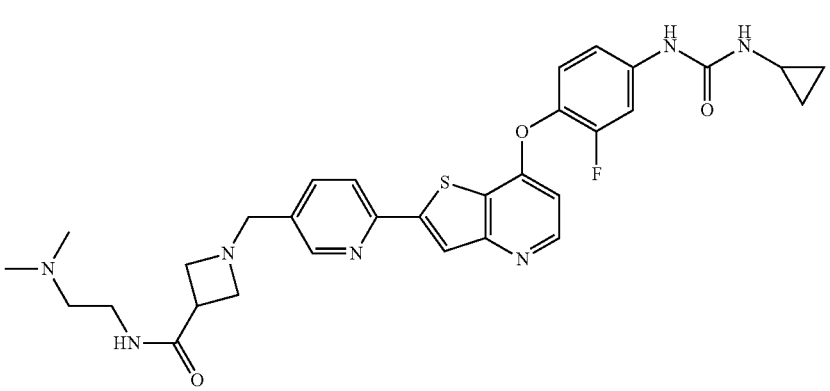 [SMILES: CN(C)CCNC(=O)C1CN(Cc2ccc(-c3cc4nccc(Oc5ccc(NC(=O)NC6CC6)cc5F)c4s3)nc2)C1]<br>1-((6-(7-(4-(3-cyclopropylureido)-2-fluoro phenoxy)thieno[3,2-b]pyridin-2-yl)pyridin-3-yl)methyl)-N-(2-(dimethylamino)ethyl)azetidine-3-carboxamide | $^1$H NMR (400 MHz, DMSO-d6) δ (ppm): 8.74 (s, 1H), 8.57-8.50 (m, 2H), 8.32 (s, 1H), 8.21 (d, J = 8.0 Hz, 1H), 7.82 (dd, J = 2.0 and 8.0 Hz, 1H), 7.79 (t, J = 7.6 Hz, 1H), 7.73 (dd, J = 1.6 and 13.6 Hz, 1H), 7.37 (t, J = 9.2 Hz, 1H), 7.24-7.18 (m, 1H), 6.64 (d, J = 5.6 Hz, 1H), 6.59 (d, J = 2.0 Hz, 1H), 3.59 (s, 2H), 3.41-3.35 (m, 2H), 3.20-3.10 (m, 5H), 2.59-2.51 (m, 1H), 2.25 (t, J = 6.8 Hz, 2H), 2.12 (s, 6H), 0.68-0.62 (m, 2H), 0.45-0.40 (m, 2H). MS (m/z): 604.4 (M + 1). |

TABLE 38-continued

Characterization of compounds 482-494 (examples 322-334)

| Cpd | Ex. | Structure | Characterization |
|---|---|---|---|
| 491 | 331 | 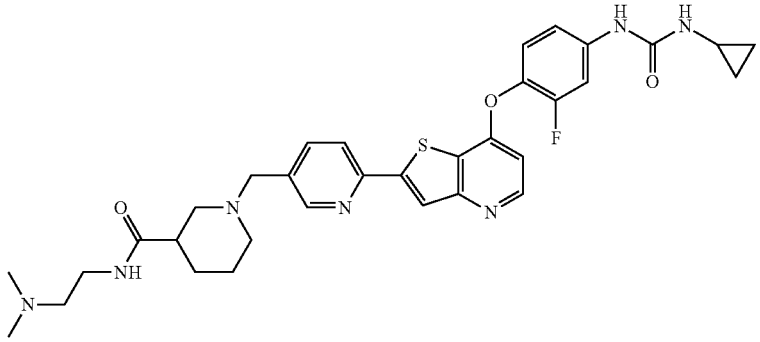 [SMILES: CN(C)CCNC(=O)C1CCCN(Cc2ccc(-c3cc4nccc(Oc5ccc(NC(=O)NC6CC6)cc5F)c4s3)nc2)C1]<br>1-((6-(7-(4-(3-cyclopropylureido)-2-fluoro phenoxy)thieno[3,2-b]pyridin-2-yl)pyridin-3-yl)methyl)-N-(2-(dimethylamino)ethyl)piperidine-3-carboxamide | $^1$H NMR (400 MHz, DMSO-d6) δ (ppm): 8.92 (s, 1H), 8.58 (bs, 1H), 8.52 (d, J = 5.6 Hz, 1H), 8.35 (bs, 1H), 8.26 (bs, 1H), 8.13 (bs, 1H), 7.87 (bs, 1H), 7.73 (dd, J = 2.4 and 13.6 Hz, 1H), 7.37 (t, J = 9.2 Hz, 1H), 7.23-7.18 (m, 1H), 6.68 (d, J = 2.8 Hz, 1H), 6.66 (d, J = 5.6 Hz, 1H), 3.72-3.45 (m, 2H), 3.03 (bs, 2H), 2.92-2.66 (m, 3H), 2.71 (s, 6H), 2.58-2.51 (m, 1H), 2.48-1.22 (m, 8H), 0.68-0.62 (m, 2H), 0.44-0.40 (m, 2H). MS (m/z): 632.4 (M + 1). |
| 492 | 332 | 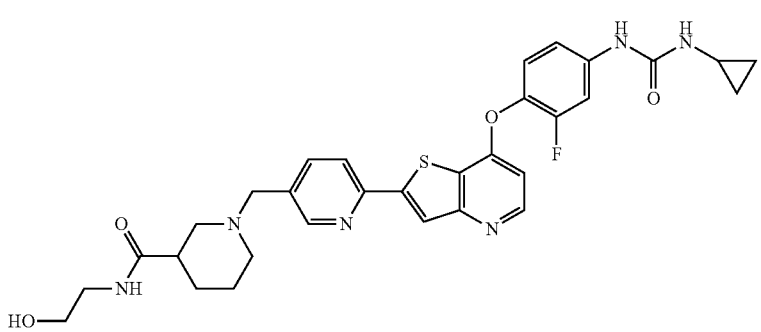 [SMILES: O=C(Nc1ccc(Oc2ccnc3cc(-c4ccc(CN5CCCC(C(=O)NCCO)C5)cn4)sc23)c(F)c1)NC1CC1]<br>1-((6-(7-(4-(3-cyclopropylureido)-2-fluoro phenoxy)thieno[3,2-b]pyridin-2-yl)pyridin-3-yl)methyl)-N-(2-hydroxyethyl)piperidine-3-carboxamide | $^1$H NMR (400 MHz, DMSO-d6) δ (ppm): 8.73 (s, 1H), 8.55 (s, 1H), 8.52 (d, J = 5.6 Hz, 1H), 8.32 (s, 1H), 8.24 (d, J = 8.0 Hz, 1H), 7.99-7.84 (m, 2H), 7.73 (dd, J = 2.4 and 13.6 Hz, 1H), 7.38 (t, J = 9.2 Hz, 1H), 7.23-7.18 (m, 1H), 6.64 (d, J = 5.6 Hz, 1H), 6.58 (d, J = 2.4 Hz, 1H), 4.63 (t, J = 5.6 Hz, 1H), 3.60-3.49 (m, 2H), 3.40-3.28 (m, 2H), 3.07 (q, J = 6.0 Hz, 2H), 2.78-2.68 (m, 2H), 2.58-2.51 (m, 1H), 2.42-2.33 (m, 1H), 2.13-1.96 (m, 2H), 1.73-1.59 (m, 2H), 1.55-1.32 (m, 2H), 0.68-0.63 (m, 2H), 0.45-0.41 (m, 2H). MS (m/z): 605.4 (M + 1). |

| Cpd | Ex. | Structure | Characterization |
|---|---|---|---|
| 493 | 333 | 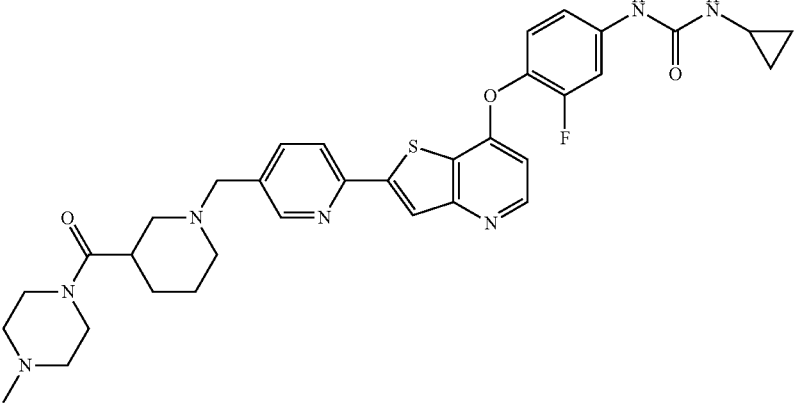<br>1-cyclopropyl-3-(3-fluoro-4-(2-(5-((3-(4-methyl piperazine-1-carbonyl)piperidin-1-yl)methyl) pyridin-2-yl)thieno[3,2-b]pyridin-7-yloxy) phenyl)urea | $^1$H NMR (400 MHz, DMSO-d6) δ (ppm): 8.76 (s, 1H), 8.55 (s, 1H), 8.52 (d, J = 5.6 Hz, 1H), 8.32 (s, 1H), 8.24 (d, J = 8.4 Hz, 1H), 7.91-7.83 (m, 1H), 7.72 (dd, J = 2.4 and 13.6 Hz, 1H), 7.37 (t, J = 9.2 Hz, 1H), 7.24-7.16 (m, 1H), 6.64 (d, J = 5.6 Hz, 1H), 6.06 (d, J = 2.4 Hz, 1H), 3.65-3.50 (m, 2H), 3.50-3.37 (m, 4H), 2.87-2.66 (m, 3H), 2.58-2.51 (m, 1H), 2.38-1.90 (m, 9H), 1.73-1.50 (m, 3H), 1.35-1.21 (m, 1H), 0.68-0.63 (m, 2H), 0.45-0.40 (m, 2H). MS (m/z): 644.5 (M + 1). |
| 494 | 334 | 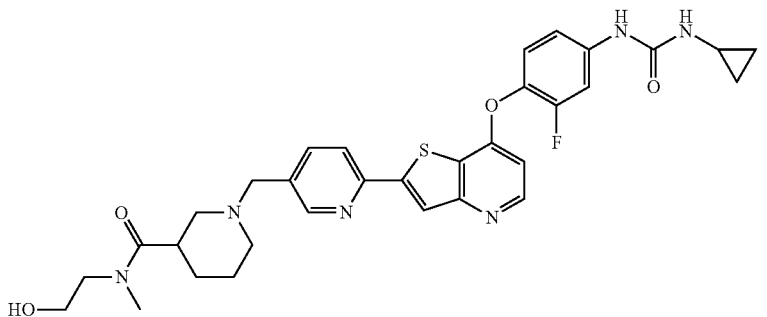 [SMILES: CN(CCO)C(=O)C1CCCN(Cc2ccc(-c3cc4nccc(Oc5ccc(NC(=O)NC6CC6)cc5F)c4s3)nc2)C1]<br>1-((6-(7-(4-(3-cyclopropylureido)-2-fluoro phenoxy)thieno[3,2-b]pyridin-2-yl)pyridin-3-yl)methyl)-N-(2-hydroxyethyl)-N-methylpiperidine-3-carboxamide | $^1$H NMR (400 MHz, DMSO-d6) δ (ppm): 8.75 (s, 1H), 8.57-8.53 (m, 1H), 8.52 (d, J = 5.6 Hz, 1H), 8.32 (s, 1H), 8.23 (d, J = 8.0 Hz, 1H), 7.88-7.83 (m, 1H), 7.73 (dd, J = 2.4 and 13.6 Hz, 1H), 7.37 (t, J = 9.2 Hz, 1H), 7.23-7.18 (m, 1H), 6.64 (d, J = 5.6 Hz, 1H), 6.61 (d, J = 2.4 Hz, 1H), 4.81 and 4.59 (t, J = 5.6 Hz, 1H), 3.56 (s, 2H), 3.51-3.23 (m, 4H), 3.01 and 2.76 (s, 3H), 2.94-2.74 (m, 3H), 2.09-1.88 (m, 2H), 1.78-1.48 (m, 3H), 1.35-1.21 (m, 1H), 0.68-0.62 (m, 2H), 0.45-0.41 (m, 2H). MS (m/z): 619.5 (M + 1). |

Compounds 495-496 (example 335-336) were synthesized by following the procedures described above for the synthesis of compound 13 (example 10, scheme 9). Compounds 497-499 (example 337-339) were synthesized by following the procedures described above for the synthesis of compound 17 (example 31, scheme 13). Compound 500 (example 340) was synthesized by following the procedures described for the synthesis of compound 582 (example 412, scheme 91).

TABLE 39

Characterization of compounds 495-500 (examples 335-340)

| Cpd | Ex. | Structure | Characterization |
|---|---|---|---|
| 495 | 335 | (S)-1-(4-(2-(5-((3-aminopyrrolidin-1-yl)methyl)pyridin-2-yl)thieno[3,2-b]-pyridin-7-yloxy)-3-fluorophenyl)-3-cyclopropylurea | $^1$H NMR (400 MHz, DMSO-d$_6$) δ (ppm): 8.76 (s, 1H), 8.55(d, J = 1.2 Hz, 1H), 8.51 (d, J = 5.6 Hz, 1H), 8.31 (s, 1H), 8.22 (d, J = 8.4 Hz, 1H), 7.86 (dd, J = 2.0 and 8.0 Hz, 1H), 7.73 (dd, J = 2.4 and 13.6 Hz, 1H), 7.37 (t, J = 9.2 Hz, 1H), 7.23-7.18 (m, 1H), 6.64 (d, J = 5.6 Hz, 1H), 6.61 (d, J = 2.8 Hz, 1H), 3.66 (d, J = 13.6 Hz, 1H), 3.59 (d, J = 13.6 Hz, 1H), 3.39-3.29 (m, 1H), 2.66 (dd, J = 6.4 and 8.8 Hz, 1H), 2.62-2.51 (m, 2H), 2.48-2.42 (m, 1H), 2.16 (dd, J = 5.2 and 13.2 Hz, 1H), 2.06-1.97 (m, 1H), 1.75-1.42 (m, 2H), 1.41-1.32 (m, 1H), 0.68-0.62 (m, 2H), 0.45-0.41 (m, 2H). MS (m/z): 519.4 (M + 1). |
| 496 | 336 | 1-cyclopropyl-3-(4-(2-(5-((3,3-dimethylpiperazin-1-yl)methyl)pyridin-2-yl)thieno[3,2-b]pyridin-7-yloxy)-3-fluorophenyl)urea | $^1$H NMR (400 MHz, DMSO-d6) δ (ppm): 8.72 (s, 1H), 8.54 (d, J = 1.2 Hz, 1H), 8.51 (d, J = 5.6 Hz, 1H), 8.32 (s, 1H), 8.24 (d, J = 8.0 Hz, 1H), 7.85 (dd, J = 2.0 and 8.0 Hz, 1H), 7.73 (dd, J = 13.6 Hz, 1H), 7.38 (t, J = 9.2 Hz, 1H), 7.23-7.18 (m, 1H), 6.64 (d, J = 5.6 Hz, 1H), 6.58 (d, J = 2.8 Hz, 1H), 3.49 (s, 1H), 2.73 (t, J = 4.4 Hz, 1H), 2.58-2.51 (m, 1H), 2.27 (bs, 2H), 2.05 (bs, 2H), 1.03 (s, 6H), 0.68-0.62 (m, 2H), 0.45-0.41 (m, 2H). MS (m/z): 547.5 (M + 1). |
| 497 | 337 | (S)-N-(1-((6-(7-(4-(3-cyclopropylureido)-2-fluorophenoxy)thieno[3,2-b]pyridin-2-yl)-pyridin-3-yl)methyl)pyrrolidin-3-yl)-2-hydroxyacetamide | $^1$H NMR (400 MHz, DMSO-d$_6$) δ (ppm): 8.79 (s, 1H), 8.58 (d, J = 1.6 Hz, 1H), 8.52 (d, J = 5.6 Hz, 1H), 8.32 (s, 1H), 8.24 (d, J = 8.0 Hz, 1H), 7.87 (dd, J = 2.0 and 8.4 Hz, 1H), 7.73 (dd, J = 2.4 and 13.6 Hz, 1H), 7.69 (bs, 1H), 7.37 (t, J = 9.2 Hz, 1H), 7.23-7.18 (m, 1H), 6.65 (d, J = 5.6 Hz, 1H), 6.61 (d, J = 2.4 Hz, 1H), 5.40 (t, J = 6.0 Hz, 1H), 4.30-4.20 (m, 1H), 3.77 (d, J = 5.6 Hz, 2H), 3.75-3.60 (m, 2H), 2.78-2.66 (m, 2H), 2.58-2.51 (m, 1H), 2.50-2.40 (m, 2H), 2.18-2.08 (m, 1H), 1.71-1.60 (m, 1H), 0.68-0.62 (m, 2H), 0.45-0.40 (m, 2H). MS (m/z): 577.5 (M + 1). |

TABLE 39-continued

Characterization of compounds 495-500 (examples 335-340)

| Cpd | Ex. | Structure | Characterization |
|---|---|---|---|
| 498 | 338 | 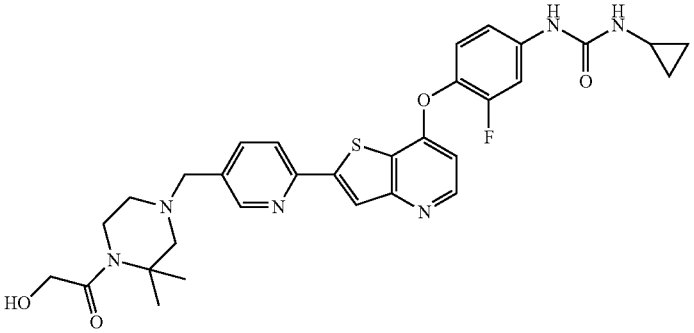 [SMILES: CC1(C)CN(Cc2ccc(-c3cc4nccc(Oc5ccc(NC(=O)NC6CC6)cc5F)c4s3)nc2)CCN1C(=O)CO]<br>1-cyclopropyl-3-(3-fluoro-4-(2-(5-((4-(2-hydroxyacetyl)-3,3-dimethylpiperazin-1-yl)methyl)pyridin-2-yl)thieno[3,2-b]pyridin-7-yloxy)phenyl)urea | $^1$H NMR (400 MHz, DMSO-d6) δ (ppm): 8.70 (s, 1H), 8.58 (d, J = 1.6 Hz, 1H), 8.52 (d, J = 5.6 Hz, 1H), 8.33 (s, 1H), 8.26 (d, J = 8.4 Hz, 1H), 7.89 (dd, J = 2.0 and 8.0 Hz, 1H), 7.73 (dd, J = 2.4 and 13.6 Hz, 1H), 7.38 (t, J = 9.2 Hz, 1H), 7.23-7.18 (m, 1H), 6.65 (d, J = 5.6 Hz, 1H), 6.57 (d, J = 2.4 Hz, 1H), 4.31 (t, J = 5.2 Hz, 1H), 3.98 (d, J = 5.6 Hz, 2H), 3.57 (s, 2H), 3.28 (t, J = 5.2 Hz, 2H), 2.58-2.51 (m, 1H), 2.46 (t, J = 5.2 Hz, 2H), 2.21 (s, 2H), 1.40 (s, 6H), 0.68-0.63 (m, 2H), 0.45-0.40 (m, 2H). MS (m/z): 605.4 (M + 1). |
| 499 | 339 | 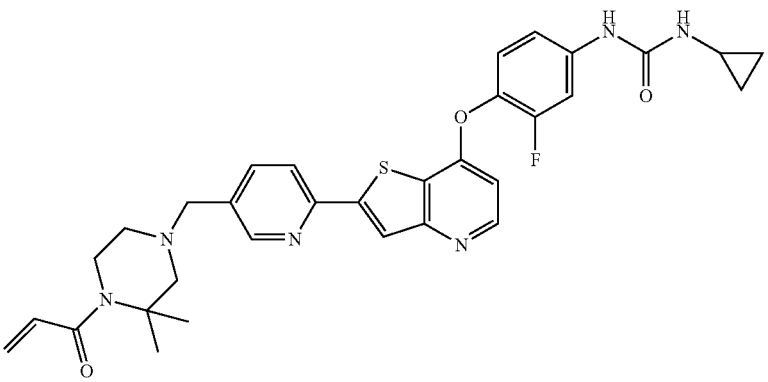 [SMILES: C=CC(=O)N1CCN(Cc2ccc(-c3cc4nccc(Oc5ccc(NC(=O)NC6CC6)cc5F)c4s3)nc2)CC1(C)C]<br>1-(4-(2-(5-((4-acryloyl-3,3-dimethylpiperazin-1-yl)methyl)pyridin-2-yl)thieno[3,2-b]pyridin-7-yloxy)-3-fluorophenyl)-3-cyclopropylurea | $^1$H NMR (400 MHz, DMSO-d6) δ (ppm): 8.71 (s, 1H), 8.58 (s, 1H), 8.52 (d, J = 5.6 Hz, 1H), 8.33 (s, 1H), 8.26 (d, J = 8.0 Hz, 1H), 7.89 (dd, J = 2.0 and 8.0 Hz, 1H), 7.73 (dd, J = 2.4 and 13.6 Hz, 1H), 7.38 (t, J = 9.2 Hz, 1H), 7.23-7.18 (m, 1H), 6.67 (dd, J = 10.4 and 16.4 Hz, 1H), 6.66 (d, J = 5.6 Hz, 1H), 6.57 (d, J = 2.8 Hz, 1H), 5.96 (dd, J = 2.4 and 16.4 Hz, 1H), 5.55 (dd, J = 2.4 and 10.4 Hz, 1H), 3.57 (s, 2H), 3.45 (t, J = 5.2 Hz, 2H), 2.60-2.51 (m, 1H), 2.47 (t, J = 5.2 Hz, 2H), 2.21 (s, 2H), 1.38 (s, 6H), 0.68-0.62 (m, 2H), 0.45-0.41 (m, 2H). MS (m/z): 601.5 (M + 1). |
| 500 | 340 | 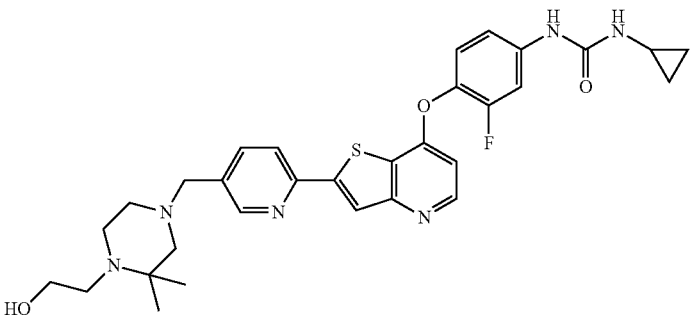 [SMILES: CC1(C)CN(Cc2ccc(-c3cc4nccc(Oc5ccc(NC(=O)NC6CC6)cc5F)c4s3)nc2)CCN1CCO]<br>1-cyclopropyl-3-(3-fluoro-4-(2-(5-((4-(2-hydroxyethyl)-3,3-dimethylpiperazin-1-yl)methyl)pyridin-2-yl)thieno[3,2-b]pyridin-7-yloxy)phenyl)urea | $^1$H NMR (400 MHz, CD3OD-d$_4$) δ (ppm): 8.61 (d, J = 1.6 Hz, 1H), 8.50 (d, J = 5.6 Hz, 1H), 8.11 (d, J = 7.6 Hz, 1H), 8.10 (s, 1H), 7.95 (dd, J = 2.0 and 8.4 Hz, 1H), 7.71 (dd, J = 2.4 and 13.2 Hz, 1H), 7.34 (t, J = 8.8 Hz, 1H), 7.23-7.21 (m, 1H), 6.67 (d, J = 5.6 Hz, 1H), 3.63 (t, J = 5.6 Hz, 2H), 3.61 (s, 2H), 2.90-2.10 (m, 9H), 1.14 (s, 6H), 0.82-0.78 (m, 2H), 0.60-0.55 (m, 2H). MS (m/z): 591.4 (M + 1). |

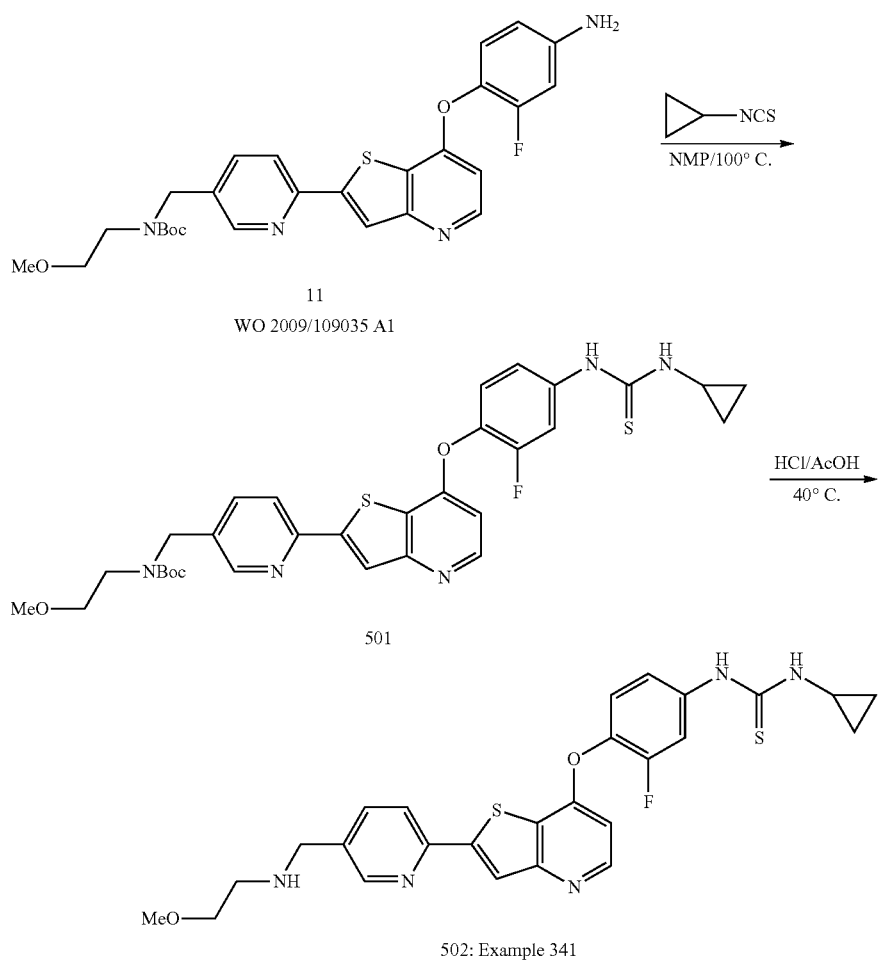

Scheme 82

502: Example 341

Example 502

1-Cyclopropyl-3-(3-fluoro-4-(2-(5-((2-methoxyethylamino)methyl)pyridin-2-yl)thieno[3,2-b]pyridin-7-yloxy)phenyl)thiourea (502)

Step 1. tert-butyl (6-(7-(4-(3-cyclopropylthioureido)-2-fluorophenoxy)thieno[3,2-b]pyridin-2-yl)pyridin-3-yl)ethyl(2-methoxyethyl)carbamate (501)

Cyclopropyl isothiocyanate (0.353 mL, 3.81 mmol) was added to a solution of compound 11 [1 g, 1.91 mmol scheme 9] in NMP (20 mL). The solution was heated at 80° C. for 3 h and at 100° C. for 4 h. After cooling to room temperature, the reaction mixture was quenched by addition of water and extracted with DCM. The organic layer was successively washed with water, brine, dried over sodium sulphate, filtered and concentrated. The residue was purified by biotage (SNAP 100 g cartridge; MeOH/DCM: 0/100 to 5/95 over 20CV), to afford the title compound 501 (1.3 g) as a brown oil. MS (m/z): 624.7 (M+H).

Step 2. 1-cyclopropyl-3-(3-fluoro-4-(2-(5-((2-methoxyethylamino)methyl)pyridin-2-yl) thieno[3,2-b]pyridin-7-yloxy)phenyl)thiourea (502)

To a solution of 501 (1.3 g) in AcOH (10 mL) was added. HCl 1M (5.72 mL, 5.72 mmol). The reaction mixture was heated at 40° C. for 1 h. More HCl 1M (2 mL) was added and the reaction mixture was heated at 40° C. for 1 h. After cooling to room temperature, the reaction mixture was diluted with water and pH was adjusted to pH 9 by addition of NaOH 4M. Finally, the mixture was extracted with EtOAc, the extract was washed brine, dried over sodium sulfate, filtered and concentrated. The residue was purified by biotage (SNAP 100 g cartridge; MeOH/DCM: 0/100 to 10/90 over 20CV) and triturated with MTBE/EtOAc to afford the title compound 502 (325 mg, 0.62 mmol, 33% yield) as a light yellow solid. $^1$H NMR (400 MHz, DMSO-d$_6$) δ (ppm): 9.62 (bs, 1H), 8.57 (s, 1H), 8.54 (d, J=5.6 Hz, 1H), 8.33 (s, 1H), 8.23 (d, J=8.8 Hz, 1H), 7.92-7.85 (m, 2H), 7.46 (t, J=9.2 Hz, 1H), 7.37 (bs, 1H), 6.66 (d, J=5.6 Hz, 1H), 3.78 (s, 2H), 3.41 (t, J=5.6 Hz, 2H), 3.24 (s, 3H), 2.65 (t, J=5.6 Hz, 2H), 0.81-0.75 (m, 2H), 0.63-0.57 (m, 2H). MS (m/z): 524.6 (M+1).

Compound 503 (example 342) was synthesized by following the procedures described above for the synthesis of compound 128 (example 87) (scheme 32). Compound 504 (example 343) was synthesized by following the procedures described above for the synthesis of compound 114 (example 79) (scheme 29). Compounds 505 (example 344) was synthesized by following the procedures described above for the synthesis of compound 17 (example 31) (scheme 13).

TABLE 40

Characterization of compounds 503-505 (examples 342-344)

| Cpd | Ex. | Structure | Characterization |
|-----|-----|-----------|------------------|
| 503 | 342 | 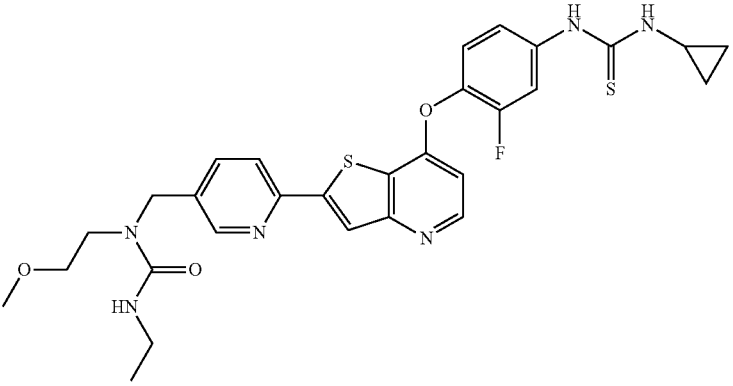 [SMILES: CCNC(=O)N(CCOC)Cc1ccc(-c2cc3nccc(Oc4ccc(NC(=S)NC5CC5)cc4F)c3s2)nc1]<br>1-((6-(7-(4-(3-cyclopropylthioureido)-2-fluorophenoxy)thieno[3,2-b]pyridin-2-yl)pyridin-3-yl)methyl)-3-ethyl-1-(2-methoxyethyl)urea | $^1$H NMR (400 MHz, DMSO-d$_6$) δ (ppm): 8.54 (d, J = 5.6 Hz, 1H), 8.48 (d, J= 2.0 Hz, 1H), 8.32 (s, 1H), 8.24 (d, J = 8.0 Hz. 1H), 7.88 (dd, J = 2.0 and 12.8 Hz, 1H), 7.75 (dd, J = 2.0 and 8.0 Hz, 1H), 7.46 (t, J = 9.2 Hz, 1H), 7.36 (bs, 1H), 6.66 (d, J = 5.6 Hz, 1H), 6.43 (t, J = 5.6 Hz, 1H), 4.53 (s, 2H), 3.44-3.33 (m, 4H), 3.22 (s, 3H), 3.08 (td, J = 5.2 and 6.8 Hz, 2H), 1.01 (t, J = 7.2 Hz, 3H), 0.81-0.74 (m, 2H), 0.63-0.57 (m, 2H). MS (m/z): 595.5 (M + 1). |
| 504 | 343 | 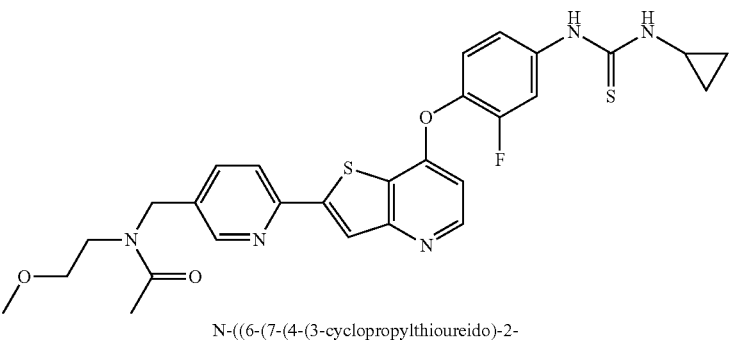<br>N-((6-(7-(4-(3-cyclopropylthioureido)-2-fluorophenoxy)thieno[3,2-b]pyridin-2-yl)pyridin-3-yl)methyl)-N-(2-methoxyethyl)acetamide | $^1$H NMR (400 MHz, DMSO-d$_6$) δ (ppm): 8.58-8.53 (m, 1H), 8.53-8.50 (m, 1H), 8.37 and 8.34 (s, 1H), 8.29 and 8.23 (d, J = 8.0 Hz, 1H), 7.89 (d, J = 12.8 Hz, 1H), 7.82-7.75 (m, 1H), 7.46 (t, J = 8.8 Hz, 1H),7.38 (bs, 1H), 6.67 and 6.66 (d, J = 5.6 Hz, 1H), 4.71 and 4.59 (s, 2H), 3.52-3.40 (m, 4H), 3.24 and 3.21 (s, 3H), 2.12 and 2.05 (s, 3H), 0.81-0.75 (m, 2H), 0.63-0.58 (m, 2H). MS (m/z): 566.3 (M + 1). |
| 505 | 344 | 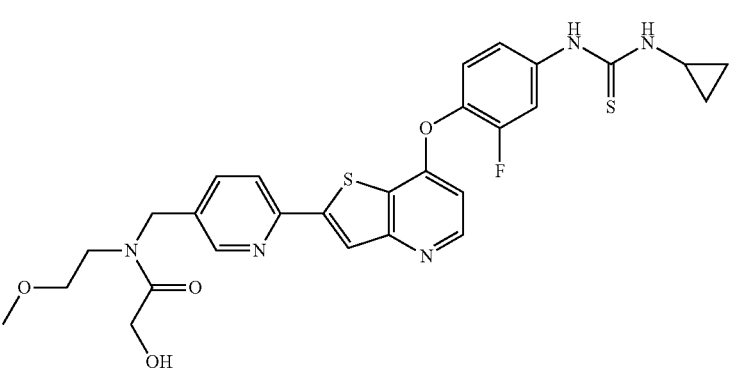 [SMILES: COCCN(Cc1ccc(-c2cc3nccc(Oc4ccc(NC(=S)NC5CC5)cc4F)c3s2)nc1)C(=O)CO]<br>N-((6-(7-(4-(3-cyclopropylthioureido)-2-fluorophenoxy)thieno[3,2-b]pyridin-2-yl)pyridin-3-yl)methyl)-2-hydroxy-N-(2-methoxyethyl)acetamide | $^1$H NMR (400 MHz, DMSO-d$_6$) δ (ppm): 8.57-8.52 (m, 2H), 8.37 and 8.35 (s, 1H), 8.29 and 8.25 (d, J = 8.0 Hz, 1H), 7.88 (dd, J = 2.0 and 15.2 Hz, 1H), 7.79 (dd, J = 2.0 and 8.4 Hz, 1H), 7.46 (t, J = 9.2 Hz, 1H), 7.37 (bs, 1H), 6.66 (d, J = 5.6 Hz, 1H), 4.80 and 4.62 (t, J = 5.6 Hz, 1H), 4.63 (bs, 2H), 4.23 and 4.13 (d, J = 5.2 Hz, 1H), 3.52-3.41 (m, 4H), 3.22 and 3.21 (s, 3H), 0.80-0.73 (m, 2H), 0.63-0.57 (m, 2H). MS (m/z): 582.5 (M + 1). |

Compound 506 (example 345) was prepared in one step by reacting compound 49 (example 32, scheme 15,) with methyl malonyl chloride reagent similarly to compound 85 (example 63, scheme 23). Compounds 507-509 (examples 346-348) were prepared in one step by reacting compound 49 (example 32, scheme 15) with an appropriate Michael acceptor similarly to compound 81 (example 59, scheme 22). Compounds 510-511 (examples 349-350) were prepared in one step by hydrolysis of the esters 506 and 509 with sodium hydroxide at room temperature or at 60° C., similarly to compound 61 (example 44, scheme 16) with a final purification by preparative HPLC.

TABLE 41

Characterization of compounds 506-511 (examples 345-350)

| Cpd | Ex. | Structure | Characterization |
|---|---|---|---|
| 506 | 345 | | methyl 3-(4-((6-(7-(4-(3-cyclopropylureido)-2-fluorophenoxy)thieno[3,2-b]pyridin-2-yl)pyridin-3-yl)methyl)piperazin-1-yl)-3-oxopropanoate<br>$^1$H NMR (400 MHz, DMSO-d$_6$) δ (ppm): 8.72 (s, 1H), 8.57 (bd, J = 1.4 Hz, 1H), 8.52 (d, J = 5.5 Hz, 1H), 8.34 (s, 1H), 8.25 (d, J = 8.2 Hz, 1H), 7.88 (dd, J = 8.1, 2.1 Hz, 1H), 7.73 (dd, J = 13.6, 2.4 Hz, 1H), 7.38 (t, J = 9.1 Hz, 1H), 7.20 (dd, J = 8.9, 1.3 Hz, 1H), 6.65 (dd, J = 5.3, 0.8 Hz, 1H), 6.58 (bd, J = 2.5 Hz, 1H), 3.62 (s, 3H), 3.60 (s, 2H), 3.54 (s, 2H), 3.50-3.38 (m, 4H), 2.59-2.51 (m, 1H), 2.46-2.33 (m, 4H), 0.72-0.58 (m, 2H), 0.50-0.36 (m, 2H). MS (m/z): 619.76 (M + H). |
| 507 | 346 | | methyl 3-(4-((6-(7-(4-(3-cyclopropylureido)-2-fluorophenoxy)thieno[3,2-b]pyridin-2-yl)pyridin-3-yl)methyl)piperazin-1-yl)propanoate<br>$^1$H NMR (400 MHz, DMSO-d$_6$) δ (ppm): 8.74 (s, 1H), 8.54 (bd, J = 1.4 Hz, 1H), 8.52 (d, J = 5.5 Hz, 1H), 8.32 (s, 1H), 8.24 (d, J = 8.0 Hz, 1H), 7.85 (dd, J = 8.2, 2.2 Hz, 1H), 7.73 (dd, J = 13.6, 2.4 Hz, 1H), 7.38 (t, J = 9.1 Hz, 1H), 7.20 (dd, J = 9.0, 1.4 Hz, 1H), 6.64 (dd, J = 5.5, 0.8 Hz, 1H), 6.60 (bd, J = 2.5 Hz, 1H), 3.58 (s, 3H), 3.53 (s, 2H), one CH$_2$ is hidden, 2.59-2.51 (m, 3H), 2.48-2.31 (m, 8H), 0.72-0.58 (m, 2H), 0.50-0.36 (m, 2H). MS (m/z): 605.8 (M + H). |
| 508 | 347 | | methyl 3-(4-((6-(7-(4-(3-cyclopropylureido)-2-fluorophenoxy)thieno[3,2-b]pyridin-2-yl)pyridin-3-yl)methyl)piperazin-1-yl)butanoate<br>$^1$H NMR (400 MHz, DMSO-d$_6$) δ (ppm): 8.75 (s, 1H), 8.53 (bd, J = 1.6 Hz, 1H), 8.52 (d, J = 5.5 Hz, 1H), 8.32 (s, 1H), 8.23 (d, J = 8.2 Hz, 1H), 7.84 (dd, J = 8.1, 2.1 Hz, 1H), 7.73 (dd, J = 13.6, 2.4 Hz, 1H), 7.38 (t, J = 9.0 Hz, 1H), 7.20 (dd, J = 8.9, 1.3 Hz, 1H), 6.64 (dd, J = 5.5, 0.8 Hz, 1H), 6.61 (bd, J = 2.3 Hz, 1H), 3.57 (s, 3H) 3.52 (s, 2H), 3.01 (hex, J = 7.0 Hz, 1H), 2.59-2.51 (m, 1H), one CH is hidden, 2.48-2.30 (m, 8H), 2.24 (dd, J = 14.4, 7.9 Hz, 1H), 0.96 (d, J = 6.7 Hz, 3H), 0.72-0.58 (m, 2H), 0.49-0.37 (m, 2H). MS (m/z): 619.7 (M + H). |

TABLE 41-continued

Characterization of compounds 506-511 (examples 345-350)

| Cpd | Ex. | Structure | Characterization |
|---|---|---|---|
| 509 | 348 | 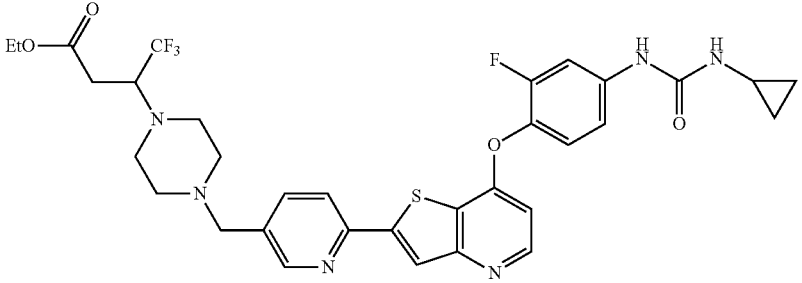 [SMILES: CCOC(=O)CC(N1CCN(Cc2ccc(-c3cc4nccc(Oc5ccc(NC(=O)NC6CC6)cc5F)c4s3)nc2)CC1)C(F)(F)F] | ethyl 3-(4-((6-(7-(4-(3-cyclopropylureido)-2-fluorophenoxy)thieno[3,2-b]pyridin-2-yl)pyridin-3-yl)methyl)piperazin-1-yl)-4,4,4-trifluorobutanoate<br>$^1$H NMR (400 MHz, DMSO-d$_6$) δ (ppm): 8.72 (s, 1H), 8.53 (bd, J = 1.4 Hz, 1H), 8.52 (d, J = 5.5 Hz, 1H), 8.33 (s, 1H), 8.24 (dd, J = 8.1, 0.7 Hz, 1H), 7.85 (dd, J = 8.1, 2.1 Hz, 1H), 7.73 (dd, J = 13.6, 2.4 Hz, 1H), 7.38 (t, J = 9.1 Hz, 1H), 7.20 (dd, J = 9.0, 1.4 Hz, 1H), 6.64 (dd, J = 5.5, 0.8 Hz, 1H), 6.58 (bd, J = 2.5 Hz, 1H), 4.17-4.04 (m, 2H), 3.82-3.69 (m, 1H), 3.54 (s, 2H), 2.86-2.52 (m, 7H), 2.44-2.24 (m, 4H), 1.19 (t, J = 7.0 Hz, 3H), 0.72-0.59 (m, 2H), 0.49-0.37 (m, 2H). MS (m/z): 687.6 (M + H). |
| 510 | 349 | 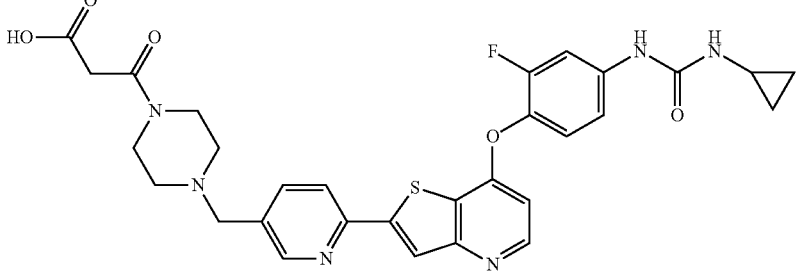 | 3-(4-((6-(7-(4-(3-cyclopropylureido)-2-fluorophenoxy)thieno[3,2-b]pyridin-2-yl)pyridin-3-yl)methyl)piperazin-1-yl)-3-oxopropanoic acid<br>$^1$H NMR (400 MHz, DMSO-d$_6$) δ (ppm): 9.33 (bs, 1H), 8.57 (bd, J = 1.4 Hz, 1H), 8.51 (d, J = 5.5 Hz, 1H), 8.33 (s, 1H), 8.25 (d, J = 8.2 Hz, 1H), 7.87 (dd, J = 8.1, 2.0 Hz, 1H), 7.73 (dd, J = 13.7, 2.5 Hz, 1H), 7.37 (t, J = 9.1 Hz, 1H), 7.33 (bs, ammonium salt), 7.19 (bd, J = 8.8 Hz, 1H), 6.93 (bd, J = 2.7 Hz, 1H), 6.64 (dd, J = 5.5, 0.8 Hz, 1H), 3.58 (bs, 2H), 3.50-3.40 (m, 4H), one CH$_2$ is hidden, 2.58-2.51 (m, 1H), 2.45-2.32 (m, 4H), 0.71-0.58 (m, 2H), 0.49-0.34 (m, 2H). MS (m/z): 605.5 (M + H). |
| 511 | 350 | 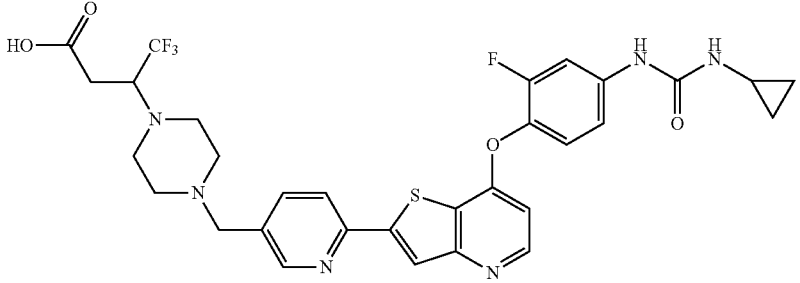 [SMILES: O=C(O)CC(N1CCN(Cc2ccc(-c3cc4nccc(Oc5ccc(NC(=O)NC6CC6)cc5F)c4s3)nc2)CC1)C(F)(F)F] | 3-(4-((6-(7-(4-(3-cyclopropylureido)-2-fluorophenoxy)thieno[3,2-b]pyridin-2-yl)pyridin-yl)methyl)piperazin-1-yl)-4,4,4-trifluorobutanoic acid<br>$^1$H NMR (400 MHz, DMSO-d$_6$) δ (ppm): one O$\underline{H}$ carboxylic acid is missing, 8.74 (s, 1H), 8.54 (bd, J = 1.4 Hz, 1H), 8.52 (d, J = 5.3 Hz, 1H), 8.32 (s, 1H), 8.24 (d, J = 8.0 Hz, 1H), 7.85 (dd, J = 8.1, 2.1 Hz, 1H), 7.73 (dd, J = 13.5, 2.5 Hz, 1H), 7.38 (t, J = 9.1 Hz, 1H), 7.20 (bd, J = 10.3 Hz, 1H), 6.64 (dd, J = 5.5, 0.8 Hz. 1H), 6.60 (bd, J = 2.3 Hz, 1H), 3.78-3.66 (m, 1H), 3.54 (s, 2H), 2.84-2.74 (m, 2H), 2.70-2.60 (m, 3H), 2.59-2.51 (m, 1H), 2.48-2.28 (m, 5H), 0.72-0.58 (m, 2H), 0.49-0.37 (m, 2H).<br>MS (m/z): 659.6 (M + H). |

Scheme 83

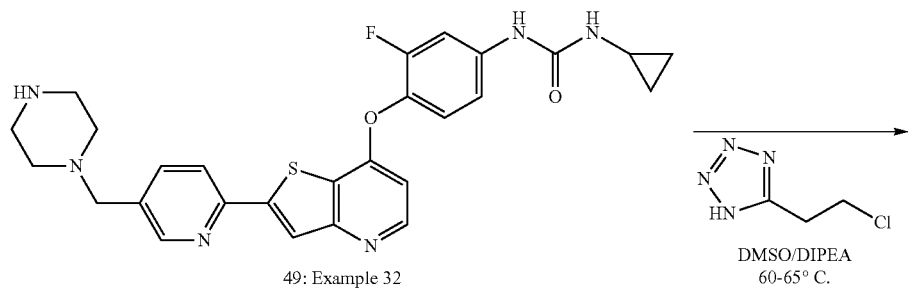

49: Example 32

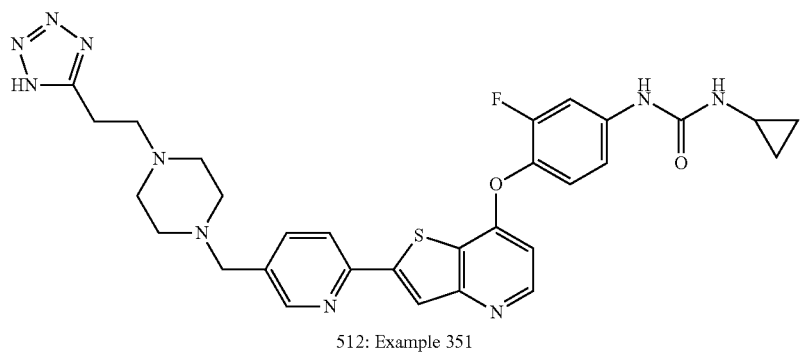

512: Example 351

Example 351

1-(4-(2-(5-((4-(2-(1H-tetrazol-5-yl)ethyl)piperazin-1-yl)methyl)pyridin-2-yl)thieno[3,2-b]pyridin-7-yloxy)-3-fluorophenyl)-3-cyclopropylurea (512)

To a stirred suspension of 49 (300 mg, 0.578 mmol, scheme 15) and DIPEA (303 μl, 1.74 mmol) in DMSO (5 ml) under nitrogen at rt was added 5-(2-chloroethyl)-1H-tetrazole (137 mg, 1.03 mmol), and the reaction mixture was stirred at rt for 1 h, heated at 60° C. overnight, then at rt. More 5-(2-chloroethyl)-1H-tetrazole (300 mg, 2.27 mmol) was added and the reaction mixture was heated at 60-65° C. for 24 h, then rt. The reaction mixture was diluted with water, and sonicated. The solid was collected by filtration, rinsed with water and air-dried. The crude material was purified three times by Biotage (Snap 25 g cartridge: 2% of ammonium hydroxide in MeOH/DCM: 5/95 to 25/75 over 20 CV, then 25/75 to 50/50 over 20 CV; Silia Sep HP 12 g cartridge: 2% of ammonium hydroxide in MeOH/DCM: 10/90 to 30/70 over 20 CV, then 30/70 to 40/60 over 20 CV; Snap 30 g KP-C18-HS (reverse phase): MeOH/water (millipore): 20/80 to 95/05 over 40 CV), to afford the desired product 512 (14 mg, 0.02 mmol, 3.9% yield) as a beige sticky solid. $^1$H NMR (400 MHz, DMSO-$d_6$) δ (ppm): one NH is missing, 8.74 (s, 1H), 8.54 (bd, J=1.6 Hz, 1H), 8.52 (d, J=5.5 Hz, 1H), 8.32 (s, 1H), 8.24 (d, J=8.0 Hz, 1H), 7.85 (dd, J=8.2, 2.2 Hz, 1H), 7.73 (dd, J=13.6, 2.4 Hz, 1H), 7.38 (t, J=9.0 Hz, 1H), 7.20 (dd, J=9.0, 1.4 Hz, 1H), 6.64 (dd, J=5.4, 0.7 Hz, 1H), 6.60 (bd, J=2.5 Hz, 1H), 3.55 (s, 2H), 2.95 (t, J=7.4 Hz, 2H), 2.68 (t, J=7.5 Hz, 2H), 2.59-2.32 (m, 9H), 0.72-0.58 (m, 2H), 0.50-0.37 (m, 2H). MS (m/z): 615.7 (M+H).

Scheme 84

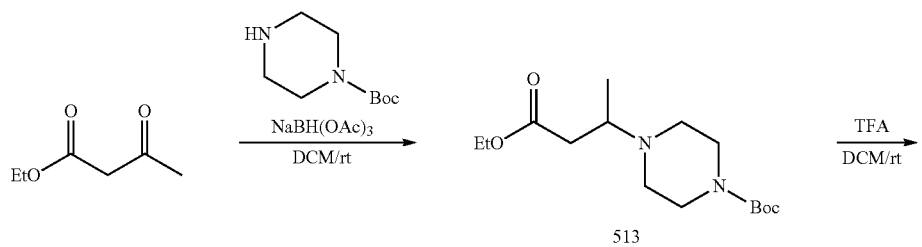

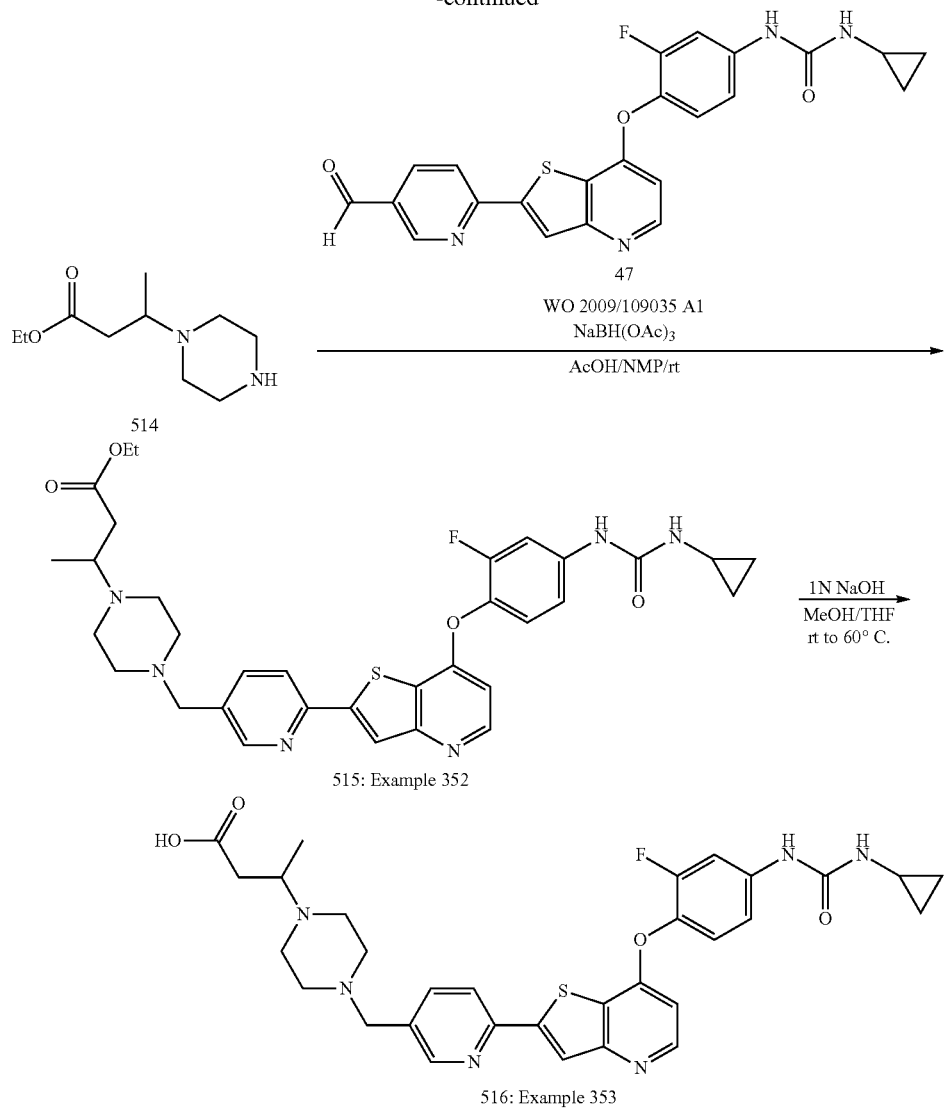

Example 352

Ethyl 3-(4-((6-(7-(4-(3-cyclopropylureido)-2-fluorophenoxy)thieno[3,2-b]pyridin-2-yl)pyridin-3-yl)methyl)piperazin-1-yl)butanoate (515)

Step 1. tert-butyl 4-(4-ethoxy-4-oxobutan-2-yl)piperazine-1-carboxylate (513)

A solution of tert-butyl piperazine-1-carboxylate (1 g, 5.37 mmol), ethyl acetoacetate (883 µl, 6.98 mmol) in DCM (30 ml) was stirred for 30 min at rt under nitrogen, then (2.4 g, 10.74 mmol) NaBH(OAc)$_3$ was added. The reaction mixture was stirred at rt overnight, quenched by addition of water, stirred for 15 min and slowly diluted with a saturated aqueous solution of sodium bicarbonate (pH around 8-9). The reaction mixture was shaken for 1 h. After separation, the aqueous layer was extracted with DCM. The organic layer was dried over anhydrous magnesium sulfate, filtered and concentrated. The residue was purified by Biotage (Snap 50 g cartridge, MeOH/DCM: 0/100 to 5/95 over 20 CV, not UV active) to afford the desired product 513 (1.03 g, 3.43 mmol, 63% yield) as a colorless sticky oil. MS (m/z): 301.4 (M+H).

Step 2. ethyl 3-(piperazin-1-yl)butanoate (514)

A solution of 513 (1.02 g, 3.40 mmol) and TFA (10 ml) in DCM (50 ml) was stirred at rt for 3 h. The reaction mixture was concentrated (azeotropes with DCM), diluted in water, and the pH was adjusted to around 8-9 with a saturated aqueous solution of sodium bicarbonate and 1N NaOH, and extracted with DCM. The organic layer was dried over anhydrous magnesium sulfate, filtered and concentrated to afford the desired product 514 (411 mg, 2.05 mmol, 60% yield) as a yellow sticky oil that was used crude in the next step without any further purification. MS (m/z): 201.3 (M+H).

Step 3. ethyl 3-(4-((6-(7-(4-(3-cyclopropylureido)-2-fluorophenoxy)thieno[3,2-b]pyridin-2-yl)pyridin-3-yl)methyl)piperazin-1-yl)butanoate (515)

A solution of 47 (500 mg, 1.12 mmol, scheme 15), 514 (268 mg, 1.34 mmol) and acetic acid (128 µl, 2.23 mmol) in NMP (5 ml) at rt under nitrogen was sonicated and stirred for 1 h. Then NaBH(OAc)$_3$ (746 mg, 3.34 mmol) was added and the reaction mixture was stirred at rt overnight, quenched by addition of water, stirred for 20 min and slowly diluted with a saturated aqueous solution of sodium bicarbonate. The resultant mixture was shaken for 10 min and sonicated. The solid was collected by filtration, rinsed with water and air-dried then purified twice by Biotage (Snap 50 g cartridge, MeOH/DCM: 1/99 to 12/88 over 20 CV; Silia Flash 40 g cartridge, MeOH/DCM: 1/99 to 15/85 over 30 CV) to afford the desired product 514 (297 mg, 0.469 mmol, 42% yield) as an ivory sticky solid.). $^1$H NMR (400 MHz, DMSO-d$_6$) δ (ppm): 8.71 (s, 1H), 8.53 (bd, J=1.6 Hz, 1H), 8.52 (d, J=5.5 Hz, 1H), 8.32 (s, 1H), 8.23 (d, J=8.2 Hz, 1H), 7.84 (dd, J=8.2, 2.0 Hz, 1H), 7.73 (dd, J=13.6, 2.4 Hz, 1H), 7.38 (t, J=9.0 Hz, 1H), 7.20 (dd, J=8.9, 1.5 Hz, 1H), 6.64 (dd, J=5.5, 0.8 Hz, 1H), 6.58 (bd, J=2.5 Hz, 1H), 4.10-3.98 (m, 2H), 3.52 (s, 2H), 3.01 (hex, J=7.0 Hz, 1H), 2.59-2.51 (m, 1H), 2.50-2.30 (m, 9H), 2.22 (dd, J=14.3, 7.6 Hz, 1H), 1.17 (t, J=7.0 Hz, 3H), 0.96 (d, J=6.7 Hz, 3H), 0.72-0.58 (m, 2H), 0.49-0.36 (m, 2H). MS (m/z): 633.5 (M+H).

Example 353

3-(4-((6-(7-(4-(3-cyclopropylureido-2-fluorophenoxy)thieno[3,2-b]pyridin-2-yl)pyridin-3-yl)methyl)piperazin-1-yl)butanoic acid (516)

To a stirred solution of 515 (252 mg, 0.40 mmol) in a mixture of MeOH/THF (10/10 ml) was added 1N NaOH (3.19 ml). The reaction mixture was heated at 60° C. for 2 h, concentrated, diluted with water, neutralyzed with a saturated aqueous solution of ammonium chloride (pH around 5-6), and triturated for 30 min with sonication. The resultant gel was isolated by filtration and air-dried. The solid residue was suspended in MeOH and water, collected by filtration, rinsed with water, air-dried and dried under high vacuum. The dry solid was re-dissolved in a mixture of DCM and MeOH, the solution was filtered, the filtrate was concentrated, and the residue was triturated in a minimum of MeOH, sonicated for 10 min, collected by filtration, rinsed with MeOH, air-dried and dried under high vacuum to afford the desired product 515 (130 mg, 0.206 mmol, 51% yield) as an off-white-grey solid. $^1$H NMR (400 MHz, DMSO-d$_6$) a (ppm): one OH from carboxylic acid is missing, 8.75 (s, 1H), 8.56 (bd, J=1.6 Hz, 1H), 8.52 (d, J=5.3 Hz, 1H), 8.33 (s, 1H), 8.25 (d, J=8.0 Hz, 1H), 7.86 (dd, J=8.0, 2.0 Hz, 1H), 7.73 (dd, 0.1=13.6, 2.4 Hz, 1H), 7.38 (t, J=9.1 Hz, 1H), 7.20 (bd, J=9.0 Hz, 1H), 6.65 (d, J=4.9 Hz, 1H), 6.60 (bd, J=2.5 Hz, 1H), 3.58 (s, 2H), 3.14-3.04 (m, 1H), 2.74-2.64 (m, 2H), 2.62-2.34 (m, 8H), 2.15 (dd, J=15.6, 6.3 Hz, 1H), 1.00 (d, J=6.7 Hz, 3H), 0.72-0.58 (m, 2H), 0.49-0.36 (m, 2H). MS (m/z): 605.5 (M+H).

Scheme 85

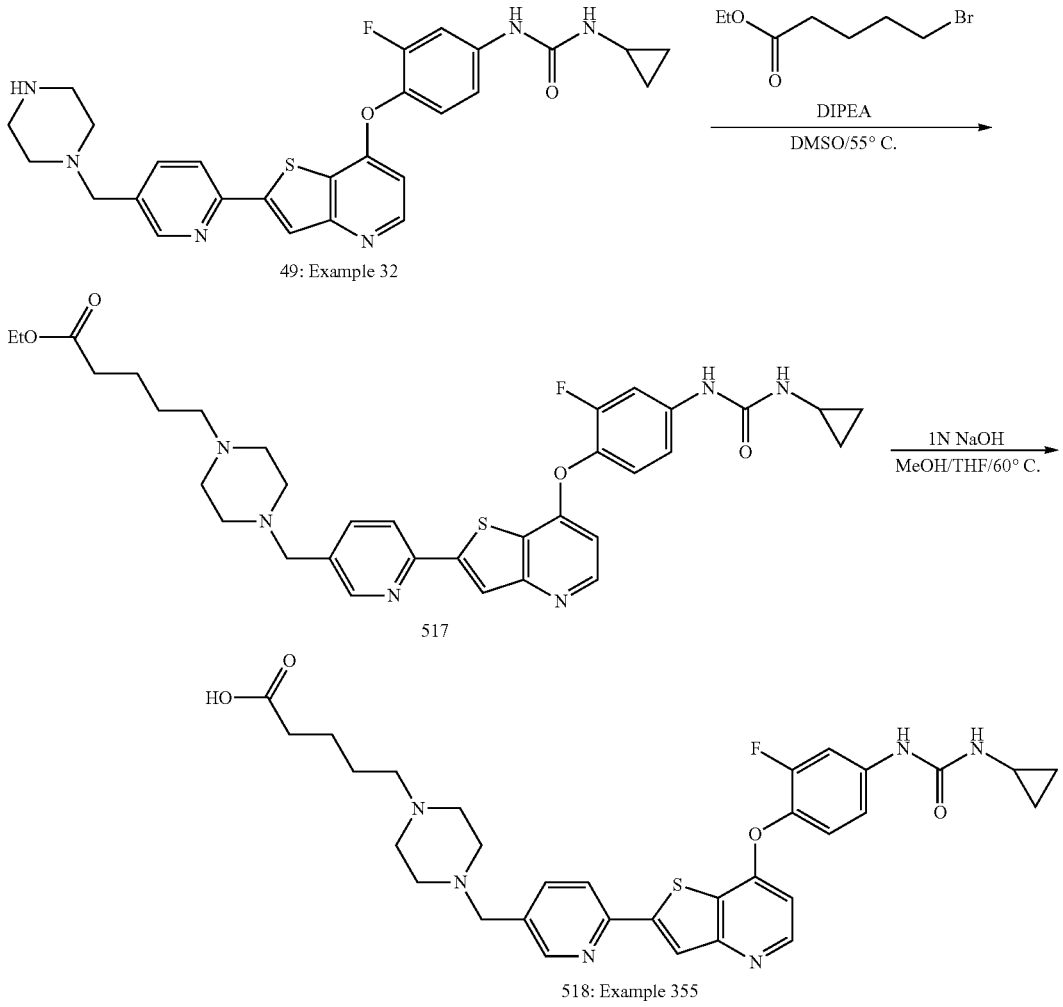

49: Example 32

517

518: Example 355

Example 355

5-(4-((6-(7-(4-(3-cyclopropylureido)-2-fluorophenoxy)thieno[3,2-b]pyridin-2-yl)pyridin-3-yl)methyl)piperazin-1-yl)pentanoic acid (518)

Step 1. ethyl 5-(4-((6-(7-(4-(3-cyclopropylureido)-2-fluorophenoxy)thieno[3,2-b]pyridin-2-yl)pyridin-3-yl)methyl)piperazin-1-yl)pentanoate (517)

To a stirred solution of 49 (200 mg, 0.39 mmol, scheme 15) and DIPEA (202 µl, 1.16 mmol) in DMSO (5 ml) at rt under nitrogen was added ethyl 4-bromovalerate (85 µl, 0.58 mmol), and the reaction mixture was heated at 50-55° C. for 1 h, then at rt. The reaction mixture was diluted with AcOEt, and successively washed with water, a saturated aqueous solution of sodium bicarbonate and brine, dried over anhydrous magnesium sulfate, filtered and concentrated. The residue was purified twice by Biotage (SiliaFlash 25 g cartridge: 2% of ammonium hydroxide in MeOH/DCM: 1/99 to 10/90 over 20 CV, then 10/90 to 15/85 over 10 CV; Snap 25 g cartridge: 2% of ammonium hydroxide in MeOH/DCM: 1/99 to 15/85 over 30 CV) to afford the desired product 517 (94 mg, 0.145 mmol, 37% yield) as a colorless sticky solid. MS (m/z): 647.75 (M+H).

Step 2. 5-(4-((6-(7-(4-(3-cyclopropylureido)-2-fluorophenoxy)thieno[3,2-b]pyridin-2-yl)pyridin-3-yl)methyl)piperazin-1-yl)pentanoic acid (518)

To a stirred solution of 517 (94 mg, 0.145 mmol) in a mixture of MeOH/THF (5/5 mL) was added 1N NaOH (1.45 mL). The reaction mixture was heated at 60° C. for 1.5 h, then at rt. The reaction mixture was concentrated, diluted with water, neutralyzed with 1N HCl (pH around 5-6) until precipitation occurred. The suspension was shaken for 15 min and the gel was collected by filtration, rinsed with water, and dried under high vacuum to afford the desired product 518 (66 mg, 0.107 mmol, 73% yield) as a white fluffy solid. $^1$H NMR (400 MHz, DMSO-$d_6$) δ (ppm): the carboxylic O$\underline{H}$ is missing, 8.78 (s, 1H), 8.56 (bd, J=1.4 Hz, 1H), 8.52 (d, J=5.5 Hz, 1H), 8.33 (s, 1H), 8.25 (d, J=8.0 Hz, 1H), 7.86 (dd, J=8.2, 2.0 Hz, 1H), 7.73 (dd, J=13.6, 2.4 Hz, 1H), 7.38 (t, J=9.1 Hz, 1H), 7.20 (dd, J=8.9, 1.3 Hz, 1H), 6.65 (dd, J=5.4, 0.7 Hz, 1H), 6.60 (bd, J=2.5 Hz, 1H), 3.58 (s, 2H), 2.70-2.30 (m, 11H), 2.26-2.18 (m, 2H), 1.56-1.40 (m, 4H), 0.72-0.58 (m, 2H), 0.49-0.36 (m, 2H). MS (m/z): 619.5 (M+H).

Compounds 519-522 (examples 356-359) were prepared in two steps starting from 49 (example 32, scheme 15) similarly to compound 518 (example 355, scheme 85).

TABLE 43

Characterization of compounds 519-522 (examples 356-359)

| Cpd | Ex. | Structure | Characterization |
|---|---|---|---|
| 519 | 356 | 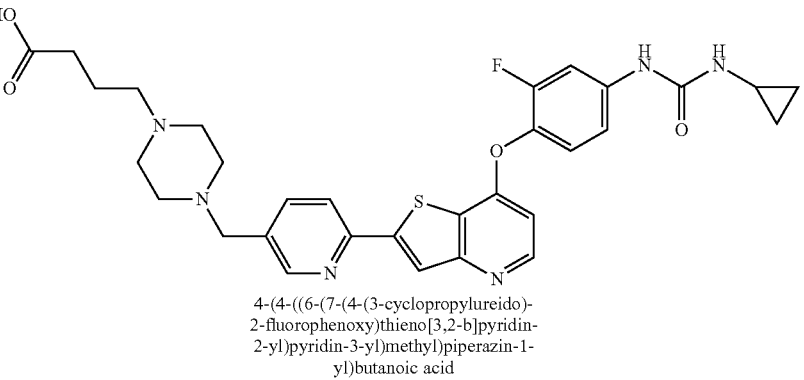<br>4-(4-((6-(7-(4-(3-cyclopropylureido)-2-fluorophenoxy)thieno[3,2-b]pyridin-2-yl)pyridin-3-yl)methyl)piperazin-1-yl)butanoic acid | $^1$H NMR (400 MHz, DMSO-$d_6$) δ (ppm): one O$\underline{H}$ carboxylic acid is missing, 8.72 (s, 1H), 8.55 (bd, J = 1.8 Hz, 1H), 8.52 (d, J = 5.3 Hz, 1H), 8.32 (s, 1H), 8.24 (d, J = 8.2 Hz, 1H), 7.85 (dd, J = 8.1, 2.1 Hz, 1H), 7.73 (dd, J = 13.6, 2.4 Hz, 1H), 7.38 (t, J = 9.0 Hz, 1H), 7.20 (bd, J = 8.8 Hz, 1H), 6.64 (d, J = 5.3 Hz, 1H), 6.58 (bd, J = 2.5 Hz, 1H), 3.55 (s, 2H), 2.59-2.52 (m, 1H), 2.49-2.33 (m, 8H), 2.30 (t, J = 6.9 Hz, 2H), 2.23 (t, J = 7.1 Hz, 2H), 1.63 (quint, J = 7.0 Hz, 2H), 0.72-0.59 (m, 2H), 0.49-0.37 (m, 2H). MS (m/z): 605.7 (M + H). |
| 520 | 357 | 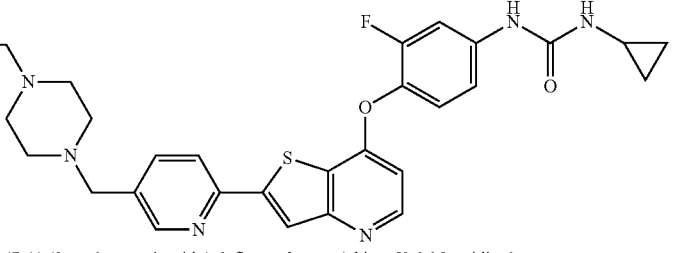<br>6-(4-((6-(7-(4-(3-cyclopropylureido)-2-fluorophenoxy)thieno[3,2-b]pyridin-2-yl)pyridin-3-yl)methyl)piperazin-1-yl)hexanoic acid<br>$^1$H NMR (400 MHz, DMSO-$d_6$) δ (ppm): one O$\underline{H}$ carboxylic acid is missing, 8.74 (s, 1H), 8.55 (bd, J = 1.6 Hz, 1H), 8.52 (d, J = 5.5 Hz, 1H), 8.33 (s, 1H), 8.24 (d, J = 8.2 Hz, 1H), 7.85 (dd, J = 8.2, 2.0 Hz, 1H), 7.73 (dd, J = 13.6, 2.4 Hz, 1H), 7.38 (t, J = 9.1 Hz, 1H), 7.20 (dd, J = 9.0, 1.2 Hz, 1H), 6.64 (d, J = 5.3 Hz, 1H), 6.58 (bd, J = 2.5 Hz, 1H), 3.56 (s, 2H), 2.65-2.24 (m, 11H), 2.19 (t, J = 7.3 Hz, 2H), 1.56-1.36 (m, 4H), 1.31-1.20 (m, 2H), 0.72-0.58 (m, 2H), 0.49-0.37 (m, 2H). MS (m/z): 633.6 (M + H). | |

TABLE 43-continued

Characterization of compounds 519-522 (examples 356-359)

| Cpd | Ex. | Structure | Characterization |
|---|---|---|---|
| 521 | 358 | 7-(4-((6-(7-(4-(3-cyclopropylureido)-2-fluorophenoxy)thieno[3,2-b]pyridin-2-yl)pyridin-3-yl)methyl)piperazin-1-yl)heptanoic acid | $^1$H NMR (400 MHz, DMSO-d$_6$) δ (ppm): one O$\underline{H}$ carboxylic acid is missing, 8.76 (s, 1H), 8.54 (bd, J = 1.6 Hz, 1H), 8.52 ( d, J = 5.3 Hz, 1H), 8.32 (s, 1H), 8.24 (d, J = 8.0 Hz, 1H), 7.85 (dd, J = 8.2, 2.0 Hz, 1H), 7.73 (dd, J = 13.6, 2.4 Hz, 1H), 7.38 (t, J = 9.1 Hz, 1H), 7.20 (dd, J = 8.9, 1.3 Hz, 1H), 6.64 (dd, J = 5.4. 0.7 Hz, 1H), 6.62 (bd, J = 2.2 Hz, 1H), 3.54 (s, 2H), 2.59-2.51 (m, 1H), 2.48-2.20 (m, 10H), 2.17 (t, J = 7.3 Hz, 2H), 1.56-1.18 (m, 8H), 0.72-0.58 (m, 2H), 0.49-0.36 (m, 2H). MS (m/z): 647.7 (M + H). |
| 522 | 359 | 8-(4-((6-(7-(4-(3-cyclopropylureido)-2-fluorophenoxy)thieno[3,2-b]pyridin-2-yl)pyridin-3-yl)methyl)piperazin-1-yl)octanoic acid | $^1$H NMR (400 MHz, DMSO-d$_6$) δ (ppm): one O$\underline{H}$ carboxylic acid is missing, 8.86 (bs, 1H), 8.54 (bd, J = 1.6 Hz, 1H), 8.52 (d, J = 5.3 Hz, 1H), 8.32 (s, 1H), 8.23 (d, J = 8.0 Hz, 1H), 7.84 (dd, J = 8.2, 2.0 Hz, 1H), 7.73 (dd, J = 13.5, 2.5 Hz, 1H), 7.38 (t, J= 9.1 Hz, 1H), 7.21 (dd, J = 9.0, 1.4 Hz, 1H), 6.71 (bs, 1H), 6.65 (dd, J = 5.4, 0.7 Hz, 1H), 3.54 (s, 2H), 2.59-2.51 (m, 1H), 2.48-2.27 (m, 8H), 2.23 (dd, J = 7.2 Hz, 2H), 2.17 (t, J = 7.3 Hz, 2H), 1.53-1.32 (m, 4H), 1.25 (bs, 6H), 0.72-0.58 (m, 2H), 0.49-0.36 (m, 2H). MS (m/z): 661.6 (M + H). |

Compounds 523, 525, 527 and 530 (examples 360, 362, 364 and 367) were prepared in two steps similarly to compound 49 (example 32, scheme 15). Compounds 524, 526, 529 and 531 (examples 361, 363, 366 and 368) were prepared in two steps starting from 523, 525, 527 and 530, respectively similarly to compound 31 (example 17, scheme 13). Compound 528 (example 365) is a precursor of compound 529 (example 366) was prepared similarly to compound 30 (scheme 13).

TABLE 44

Characterization of compounds 523-531 (examples 360-368)

| Cpd | Ex. | Structure | Characterization |
|---|---|---|---|
| 523 | 360 | 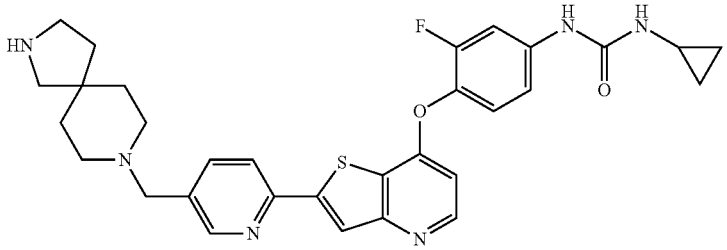 [SMILES: O=C(Nc1ccc(Oc2ccnc3cc(-c4ccc(CN5CCC6(CCNC6)CC5)cn4)sc23)c(F)c1)NC1CC1]<br>1-(4-(2-(5-(2,8-diazaspiro[4.5]decan-8-ylmethyl)pyridin-2-yl)thieno[3,2-b]-pyridin-7-yloxy)-3-fluorophenyl)-3-cyclopropylurea | MS (m/z): 573.6 (M + H). |
| 524 | 361 | 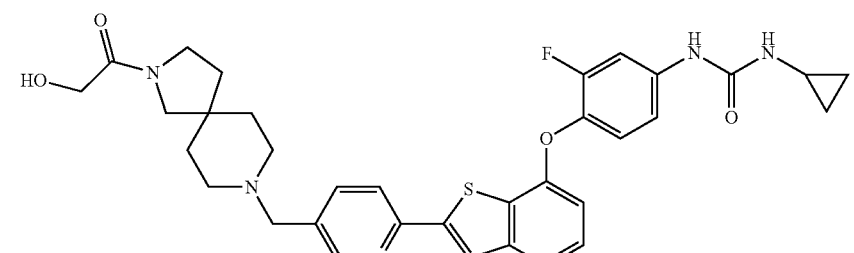<br>1-cyclopropyl-3-(3-fluoro-4-(2-(5-((2-(2-hydroxyacetyl)-2,8-diazaspiro[4.5]decan-8-yl)methyl)pyridin-2-yl)thieno[3,2-b]pyridin-7-yloxy)phenyl)urea<br>$^1$H NMR (400 MHz, DMSO-$d_6$) δ (ppm): 8.73 (s, 1H), 8.55 (bd, J = 1.4 Hz, 1H), 8.52 (d, J = 5.5 Hz, 1H), 8.32 (s, 1H), 8.24 (d, J = 8.0 Hz, 1H), 7.85 (dd, J = 8.2, 2.0 Hz, 1H), 7.73 (dd, J = 13.6, 2.4 Hz, 1H), 7.38 (t, J = 9.0 Hz, 1H), 7.20 (dd, J = 8.9, 1.3 Hz, 1H), 6.64 (dd, J = 5.4, 0.7 Hz, 1H), 6.58 (bd, J = 2.5 Hz, 1H), 4.49 and 4.46 (2t, 5.6 Hz, 1H), 3.97 (d, J = 5.7 Hz, 2H), 3.56 (s, 2H), 3.41-3.33 (m, 2H), 3.18 (d, J = 6.8 Hz, 2H), 2.59-2.52 (m, 1H), 2.49-2.25 (m, 4H), 1.75 (t, J = 7.0 Hz, 1H), 1.66 (t, J = 7.1 Hz, 1H), 1.58-1.44 (m, 4H), 0.72-0.58 (m, 2H), 0.49-0.37 (m, 2H). MS (m/z): 631.6 (M + H). |
| 525 | 362 | 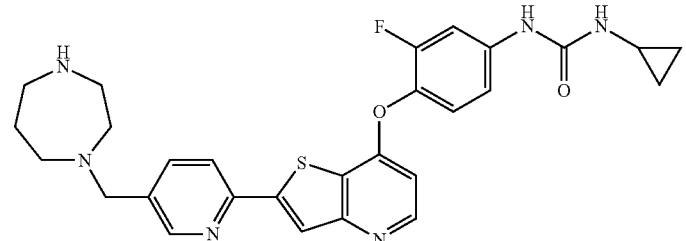<br>1-(4-(2-(5-((1,4-diazepan-1-yl)methyl)pyridin-2-yl)thieno[3,2-b]-pyridin-7-yloxy)-3-fluorophenyl)-3-cyclopropylurea | MS (m/z): 533.4 (M + H). |

TABLE 44-continued

Characterization of compounds 523-531 (examples 360-368)

| Cpd | Ex. | Structure | Characterization |
|---|---|---|---|
| 526 | 363 | 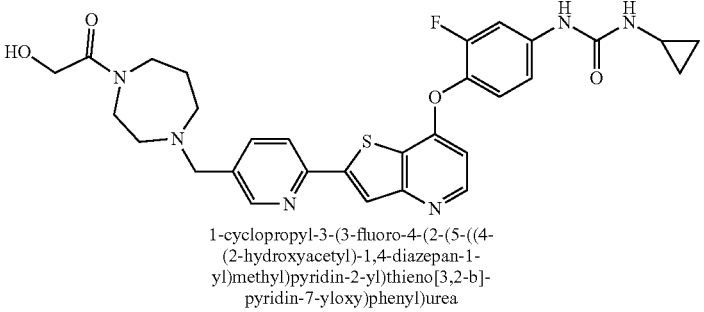<br>1-cyclopropyl-3-(3-fluoro-4-(2-(5-((4-(2-hydroxyacetyl)-1,4-diazepan-1-yl)methyl)pyridin-2-yl)thieno[3,2-b]-pyridin-7-yloxy)phenyl)urea | $^1$H NMR (400 MHz, DMSO-$d_6$) δ (ppm): 8.74 (s, 1H), 8.59-8.55 (m, 1H), 8.52 (d, J = 5.5 Hz, 1H), 8.33 (s, 1H), 8.24 (d, J = 8.0 Hz, 1H), 7.91-7.85 (m, 1H), 7.73 (dd, J = 13.6, 2.4 Hz, 1H), 7.38 (t, J = 9.1 Hz, 1H), 7.20 (dd, J = 9.0, 1.4 Hz, 1H), 6.65 (d, J = 5.3 Hz, 1H), 6.60 (d, J = 2.7 Hz, 1H), 4.43 (dt, J = 10.2, 5.2 Hz, 1H), 4.08 (dd, J = 7.6, 5.5 Hz, 2H), 3.70 (bd, J = 5.9 Hz, 2H), 3.59-3.50 (m, 2H), 3.43-3.37 (m, 2H), 2.72-2.52 (m, 5H), 1.86-1.71 (m, 2H), 0.72-0.58 (m, 2H), 0.50-0.36 (m, 2H). MS (m/z): 591.5 (M + H). |
| 527 | 364 | 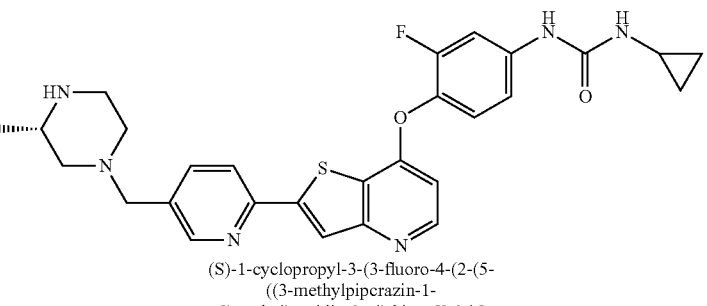<br>(S)-1-cyclopropyl-3-(3-fluoro-4-(2-(5-((3-methylpiperazin-1-yl)methyl)pyridin-2-yl)thieno[3,2-b]-pyridin-7-yloxy)phenyl)urea | $^1$H NMR (400 MHz, DMSO-$d_6$) δ (ppm): 8.73 (s, 1H), 8.54 (d, J = 1.4 Hz, 1H), 8.52 (d, 5.3 Hz, 1H), 8.32 (s, 1H), 8.24 (dd, J = 8.0, 0.6 Hz, 1H), 7.85 (dd, J = 8.0, 2.2 Hz, 1H), 7.73 (dd, J = 13.6, 2.4 Hz, 1H), 7.38 (t, J = 9.0 Hz, 1H), 7.20 (dd, J = 8.9, 1.3 Hz, 1H), 6.64 (dd, J = 5.4, 0.9 Hz, 1H), 6.59 (bd, J = 2.5 Hz, 1H), AB system ($δ_A$ = 3.53, $δ_B$ = 3.49, J = 13.7 Hz, 2H), 2.83-2.76 (m, 1H), 2.74-2.60 (m, 4H), 2.59-2.52 (m, 1H), 1.99-1.89 (m, 1H), 1.61 (t, J = 10.2 Hz, 1H), 0.90 (d, J = 6.3 Hz, 3H), 0.72-0.58 (m, 2H), 0.49-0.36 (m, 2H), one NH is missing. MS (m/z): 533.4 (M + H). |

TABLE 44-continued

Characterization of compounds 523-531 (examples 360-368)

| Cpd | Ex. | Structure | Characterization |
|-----|-----|-----------|------------------|
| 528 | 365 | 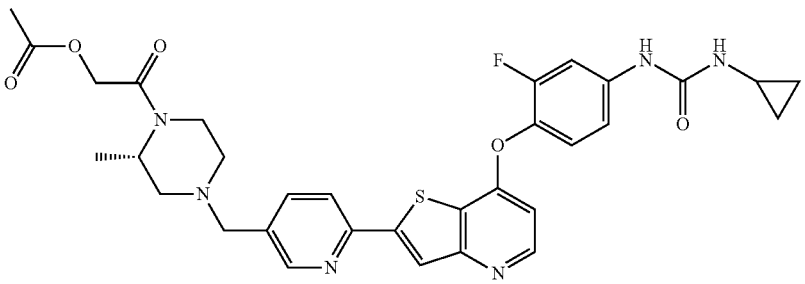 [SMILES: CC(=O)OCC(=O)N1CCN(Cc2ccc(-c3cc4nccc(Oc5ccc(NC(=O)NC6CC6)cc5F)c4s3)nc2)C[C@@H]1C]<br>(S)-2-(4-((6-(7-(4-(3-cyclopropylureido)-2-fluorophenoxy)thieno[3,2-b]pyridin-2-yl)pyridin-3-yl)methyl)-2-methylpiperazin-1-yl)-2-oxoethyl acetate | $^1$H NMR (400 MHz, DMSO-d$_6$) δ (ppm): mixture of rotamers, 8.72 (s, 1H), 8.58 (bd, J = 1.0 Hz, 1H), 8.52 (d, J = 5.3 Hz, 1H), 8.34 (s, 1H), 8.27 (d, J = 8.2 Hz, 1H), 7.89 (dd, J = 8.2, 2.2 Hz, 1H), 7.73 (dd, J = 13.5, 2.5 Hz, 1H), 7.38 (t, J = 9.1 Hz, 1H), 7.20 (dd, J = 9.0, 1.4 Hz, 1H), 6.65 (dd, J = 5.3. 0.8 Hz, 1H), 6.58 (bd, J = 2.5 Hz, 1H), 4.98-4.54 (m, 2H), 4.52-4.35 (m, 0.5H), 4.20-3.82 (m, 1H), AB system (δ$_A$ = 3.62, δ$_B$ = 3.53, J = 13.9 Hz. 2H), one H is hidden by water's peak, 3.00-2.74 (m, 1.5H), 2.65 (d, J = 11.2 Hz, 1H), 2.59-2.51 (m, 1H), 2.27-1.82 (m, 5H), 1.40-1.07 (m, 3H), 0.72-0.58 (m, 2H), 0.50-0.36 (m, 2H). MS (m/z): 633.5 (M + H). |
| 529 | 366 | 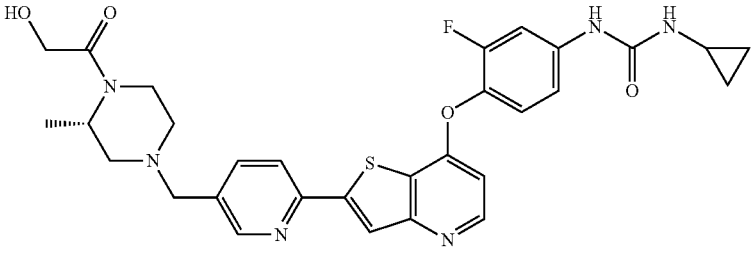 [SMILES: C[C@H]1CN(Cc2ccc(-c3cc4nccc(Oc5ccc(NC(=O)NC6CC6)cc5F)c4s3)nc2)CCN1C(=O)CO]<br>(S)-1-cyclopropyl-3-(3-fluoro-4-(2-(5-((4-(2-hydroxyacetyl)-3-methylpiperazin-1-yl)methyl)pyridin-2-yl)thieno[3,2-b]pyridin-7-yloxy)phenyl)urea | $^1$H NMR (400 MHz, DMSO-d$_6$) δ (ppm): mixture of rotamers, 8.74 (s, 1H), 8.58 (bd, J = 1.4 Hz, 1H), 8.52 (d, J = 5.5 Hz, 1H), 8.34 (s, 1H), 8.26 (d, J = 8.0 Hz, 1H), 7.88 (dd, J = 8.2, 2.0 Hz, 1H), 7.73 (dd, J = 13.5, 2.5 Hz, 1H), 7.38 (t, J = 9.1 Hz, 1H), 7.20 (dd, J = 8.9, 1.3 Hz, 1H), 6.65 (dd, J = 5.3, 0.8 Hz, 1H), 6.60 (bd, J = 2.5 Hz, 1H), 4.51 (bt, J = 5.5 Hz, 1.5H), 4.28-3.82 (m, 3H), 3.70-3.40 (m, 2.5H), 3.30-2.74 (m, 2H), 2.65 (d, J = 11.5 Hz, 1H), 2.59-2.51 (m, 1H), 2.24-1.83 (m, 2H), 1.40-1.06 (m, 3H), 0.72-0.58 (m, 2H), 0.50-0.36 (m, 2H). MS (m/z): 591.5 (M + H). |
| 530 | 367 | 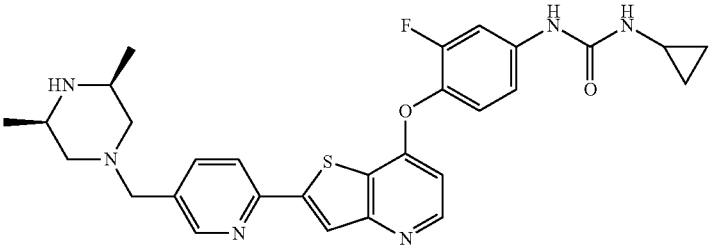 [SMILES: C[C@@H]1CN(Cc2ccc(-c3cc4nccc(Oc5ccc(NC(=O)NC6CC6)cc5F)c4s3)nc2)C[C@H](C)N1]<br>1-cyclopropyl-3-(4-(2-(5-(((3S,5R)-3,5-dimethylpiperazin-1-yl)methyl)pyridin-2-yl)thieno[3,2-b]-pyridin-7-yloxy)-3-fluorophenyl)urea | $^1$H NMR (400 MHz, DMSO-d$_6$) δ (ppm): 8.72 (s, 1H), 8.53 (bd, J = 1.4 Hz, 1H), 8.52 (d, J = 5.3 Hz, 1H), 8.32 (s, 1H), 8.24 (d, J = 8.2 Hz, 1H), 7.84 (dd, J = 8.1, 2.1 Hz, 1H), 7.73 (dd, J = 13.5, 2.5 Hz, 1H), 7.38 (t, J = 9.0 Hz, 1H), 7.20 (dd, J = 8.9, 1.3 Hz, 1H), 6.65 (dd, J = 5.4, 0.7 Hz, 1H), 6.58 (bd, J = 2.5 Hz, 1H), 3.52 (s, 2H), 2.82-2.72 (m, 2H), 2.70-2.62 (m, 2H), 2.59-2.51 (m, 1H), 1.55 (t, J = 10.4 Hz, 2H), 0.91 (d, J = 6.3 Hz, 6H), 0.72-0.58 (m, 2H), 0.50-0.36 (m, 2H), one NH is missing. MS (m/z): 547.5 (M + H). |

TABLE 44-continued

Characterization of compounds 523-531 (examples 360-368)

| Cpd | Ex. | Structure | Characterization |
|---|---|---|---|
| 531 | 368 | 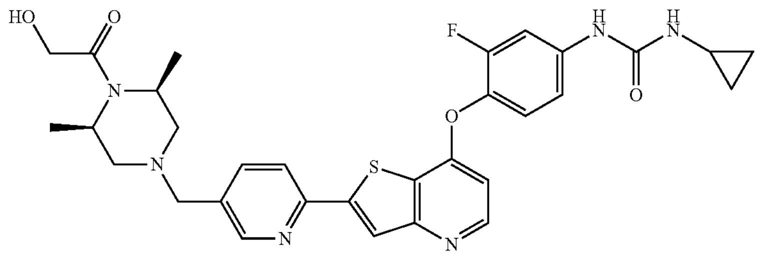 [SMILES: C[C@@H]1CN(Cc2ccc(-c3cc4nccc(Oc5ccc(NC(=O)NC6CC6)cc5F)c4s3)nc2)C[C@H](C)N1C(=O)CO] | 1-cyclopropyl-3-(3-fluoro-4-(2-(5-(((3S,5R)-4-(2-hydroxyacetyl)-3,5-dimethylpiperazin-1-yl)methyl)pyyridin-2-yl)thieno[3,2-b]pyridin-7-yloxy)phenyl)urea<br>$^1$H NMR (400 MHz, DMSO-d$_6$) δ (ppm): 8.72 (s, 1H), 8.61 (bd, J = 1.6 Hz, 1H), 8.52 (d, J = 5.5 Hz, 1H), 8.34 (s, 1H), 8.28 (d, J = 8.2 Hz, 1H), 7.93 (dd, J = 8.2, 2.0 Hz, 1H), 7.73 (dd, J = 13.5, 2.5 Hz, 1H), 7.38 (t, J = 9.1 Hz, 1H), 7.20 (dd, J = 9.0, 1.4 Hz, 1H), 6.65 (dd, J = 5.4, 0.7 Hz, 1H), 6.58 (bd, J = 2.3 Hz, 1H), 4.44 (t, J = 5.4 Hz, 1H), 4.50-3.70 (m, 4H), 3.60 (s, 2H), 2.67 (bd, J = 11.2 Hz, 2H), 2.59-2.51 (m, 1H), 2.25-2.02 (m, 2H), 1.50-1.10 (m, 6H), 0.72-0.58 (m, 2H), 0.50-0.36 (m, 2H).<br>MS (m/z): 605.4 (M + H). |

Compounds 532-533 (examples 369-370) were prepared in one step by reductive amination of compound 47 with the appropriate amine similarly to compound 48 (example 31, scheme 15).

TABLE 45

Characterization of compounds 532-534 (examples 369-371)

| Cpd | Ex. | Structure | Characterization |
|---|---|---|---|
| 532 | 369 | 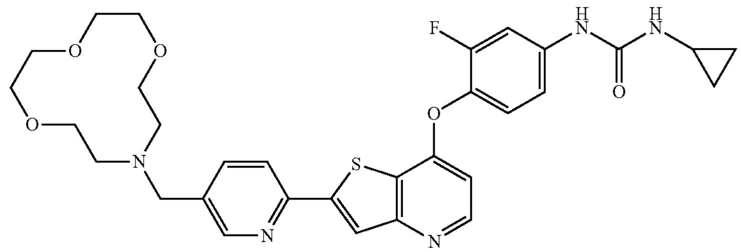 | 1-(4-(2-(5-((1,4,7-trioxa-10-azacyclododecan-10-yl)methyl)pyridin-2-yl)thieno[3,2-b]pyridin-7-yloxy)-3-fluorophenyl)-3-cyclopropylurea<br>$^1$H NMR (500 MHz, DMSO-d$_6$) δ (ppm): 8.72 (s, 1H), 8.59 (bd, J = 1.4 Hz, 1H), 8.50 (d, J = 5.4 Hz, 1H), 8.30 (s, 1H), 8.22 (d, J = 8.2 Hz, 1H), 7.93 (dd, J = 8.2, 1.9 Hz, 1H), 7.72 (dd, J = 13.5, 2.4 Hz, 1H), 7.37 (t, J = 9.1 Hz, 1H), 7.20 (bd, J = 8.6 Hz, 1H), 6.63 (d, J = 5.4 Hz, 1H), 6.58 (bd, J = 2.4 Hz, 1H), 3.69 (s, 2H), 3.63-3.52 (m, 12H), 2.66 (t, J = 4.7 Hz, 4H), 2.58-2.52 (m, 1H), 0.70-0.59 (m, 2H), 0.47-0.37 (m, 2H). MS (m/z): 608.5 (M + H). |
| 533 | 370 | 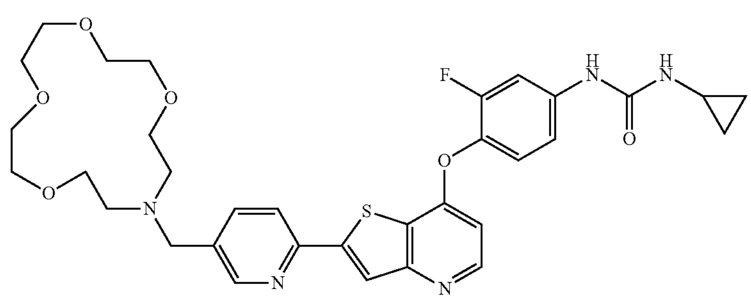 | 1-(4-(2-(5-((1,4,7,10-tetraoxa-13-azacyclopentadecan-13-yl)methyl)pyridin-2-yl)thieno[3,2-b]pyridin-7-yloxy)-3-fluorophenyl)-3-cyclopropylurea<br>$^1$H NMR (400 MHz, DMSO-d$_6$) δ (ppm): 8.71 (s, 1H), 8.56 (bd, J = 1.6 Hz, 1H), 8.52 (d, J = 5.5 Hz, 1H), 8.32 (s, 1H), 8.23 (d, J = 8.0 Hz, 1H), 7.90 (dd, J = 8.2, 2.2 Hz, 1H), 7.73 (dd, J = 13.5, 2.5 Hz, 1H), 7.38 (t, J = 9.0 Hz, 1H), 7.20 (dd, J = 8.8, 1.4 Hz, |

TABLE 45-continued

Characterization of compounds 532-534 (examples 369-371)

| Cpd | Ex. | Structure | Characterization |
|---|---|---|---|
| | | | 1H), 6.64 (d, J = 5.3 Hz, 1H), 6.57 (bd, J = 2.5 Hz, 1H), 3.72 (s, 2H), 3.62-3.48 (m, 16H), 2.69 (t, J = 5.9 Hz, 4H), 2.59-2.51 (m, 1H), 0.72-0.58 (m, 2H), 0.50-0.36 (m, 2H). MS (m/z): 652.6 (M + H). |

Compounds 535-543 (examples 372-380) were prepared in one step by the amide coupling reaction of compound 49 with the appropriate carboxylic acid similarly to compound 75 (scheme 20).

TABLE 46

Characterization of compounds 535-543 (examples 372-380)

| Cpd | Ex. | Structure | Characterization |
|---|---|---|---|
| 535 | 372 | 1-cyclopropyl-3-(3-fluoro-4-(2-(5-((4-(5-(((3aR,4R,6aS)-2-oxohexahydro-1H-thieno[3,4-d]imidazol-4-yl)pentanoyl)piperazin-1-yl)methyl)pyridin-2-yl)thieno[3,2-b]pyridin-7-yloxy)phenyl)urea | $^1$H NMR (400 MHz, DMSO-d$_6$) δ (ppm): 8.72 (s, 1H), 8.57 (bd, J = 1.4 Hz, 1H), 8.52 (d, J = 5.5 Hz, 1H), 8.34 (s, 1H), 8.26 (d, J = 8.0 Hz, 1H), 7.88 (dd, J = 8.1, 2.0 Hz, 1H), 7.73 (dd, J = 13.6, 2.4 Hz, 1H), 7.38 (t, J = 9.1 Hz, 1H), 7.20 (bd, J = 8.8 Hz, 1H), 6.65 (dd, J = 5.4, 0.7 Hz, 1H), 6.58 (bd, J = 2.5 Hz, 1H), 6.44 (s, 1H), 6.36 (s, 1H), 4.33-4.27 (m, 1H), 4.16-4.10 (m, 1H), 3.59 (s, 2H), 3.52-3.40 (m, 4H), 3.13-3.06 (m, 1H), 2.82 (dd, J = 12.4, 5.0 Hz, 1H), 2.61-2.51 (m, 2H), 2.44-2.25 (m, 6H), 1.67-1.25 (m, 6H), 0.72-0.58 (m, 2H), 0.50-0.37 (m, 2H). MS (m/z): 745.7 (M + H). |
| 536 | 373 | (S)-1-cyclopropyl-3-(4-(2-(5-((4-(2,3-dihydroxypropanoyl)piperazin-1-yl)methyl)pyridin-2-yl)thieno[3,2-b]pyridin-7-yloxy)-3-fluorophenyl)urea | $^1$H NMR (400 MHz, DMSO-d$_6$) δ (ppm): 9.18 (bs, 1H), 8.58 (bd, J = 1.6 Hz, 1H), 8.52 (d, J = 5.3 Hz, 1H), 8.36 (bs, 1H), 8.34 (s, 1H), 8.26 (d, J = 8.2 Hz, 1H), 7.88 (dd, J = 8.1, 2.1 Hz, 1H), 7.74 (dd, J = 13.6, 2.4 Hz, 1H), 7.37 (t, J = 9.1 Hz, 1H), 7.22 (dd, J = 8.9, 1.5 Hz, 1H), 7.01 (bs, 1H), 6.65 (dd, J = 5.5, 0.8 Hz, 1H), 5.05-4.54 (m, 1H), 4.31 (t, J = 5.6 Hz, 1H), 3.59 (s, 2H), 3.58-3.36 (m, 6H), 2.59-2.52 (m, 1H), 2.46-2.34 (m, 4H), 0.70-0.57 (m, 2H), 0.49-0.36 (m, 2H). MS (m/z): 607.6 (M + H). |

TABLE 46-continued

Characterization of compounds 535-543 (examples 372-380)

| Cpd | Ex. | Structure | Characterization |
|---|---|---|---|
| 537 | 374 | 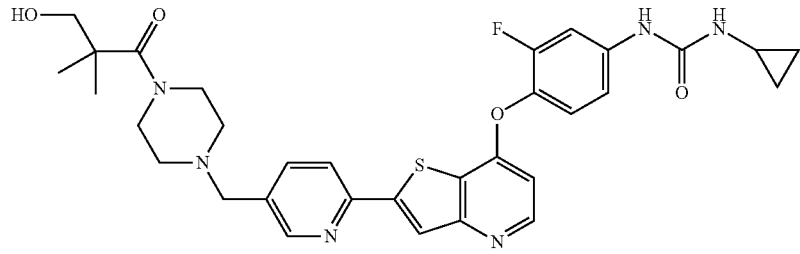 | 1-cyclopropyl-3-(3-fluoro-4-(2-(5-((4-(3-hydroxy-2,2-dimethylpropanoyl)piperazin-1-yl)methyl)pyridin-2-yl)thieno[3,2-b]pyridin-7-yloxy)phenyl)urea<br>$^1$H NMR (400 MHz, DMSO-d$_6$) δ (ppm): 8.72 (s, 1H), 8.57 (bd, J = 1.6 Hz, 1H), 8.52 (d, J = 5.5 Hz, 1H), 8.34 (s, 1H), 8.26 (d, J = 8.2 Hz, 1H), 7.88 (dd, J = 8.2, 2.2 Hz, 1H), 7.73 (dd, J = 13.6, 2.4 Hz, 1H), 7.38 (t, J = 9.1 Hz, 1H), 7.20 (dd, J = 8.9, 1.3 Hz, 1H), 6.65 (dd, J = 5.3, 0.8 Hz, 1H), 6.58 (bd, J = 2.5 Hz, 1H), 4.52 (t, J = 5.9 Hz, 1H), 3.62-3.48 (m, 6H), 3.39 (d, J = 6.1 Hz, 2H), 2.58-2.51 (m, 1H), 2.46-2.34 (m, 4H), 1.13 (s, 6H), 0.72-0.58 (m, 2H), 0.50-0.36 (m, 2H). MS (m/z): 619.6 (M + H). |
| 538 | 375 | 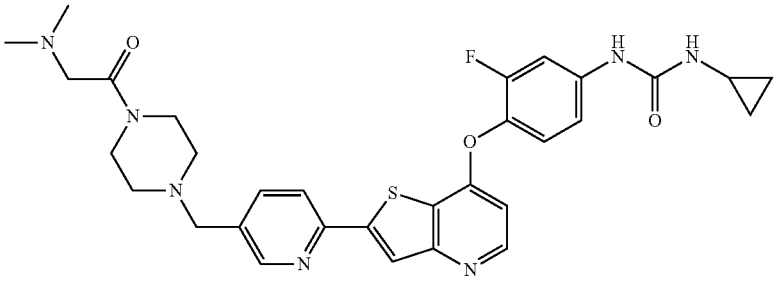 | 1-cyclopropyl-3-(4-(2-(5-((4-(2-(dimethylamino)acetyl)piperazin-1-yl)methyl)pyridin-2-yl)thieno[3,2-b]pyridin-7-yloxy)-3-fluorophenyl)urea<br>$^1$H NMR (400 MHz, DMSO-d$_6$) δ (ppm): 8.73 (s, 1H), 8.57 (bd, J = 1.4 Hz, 1H), 8.52 (d, J = 5.5 Hz, 1H), 8.34 (s, 1H), 8.25 (d, J = 8.0 Hz, 1H), 7.88 (dd, J = 8.1, 2.1 Hz, 1H), 7.73 (dd, J = 13.5, 2.3 Hz, 1H), 7.38 (t, J = 9.0 Hz, 1H), 7.20 (dd, J = 8.8, 1.4 Hz, 1H), 6.65 (dd, J = 5.4, 0.7 Hz, 1H), 6.59 (bd, J = 2.5 Hz, 1H), 3.58 (s, 2H), 3.57-3.41 (m, 4H), 3.04 (s, 2H), 2.59-2.52 (m, 1H), 2.44-2.31 (m, 4H), 2.15 (s, 6H), 0.72-0.58 (m, 2H), 0.49-0.36 (m, 2H). MS (m/z): 604.6 (M + H). |
| 539 | 376 | 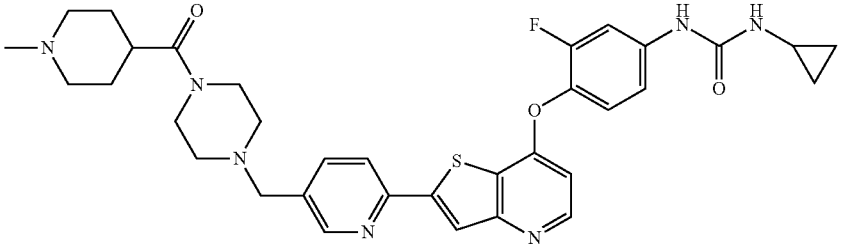 | 1-cyclopropyl-3-(3-fluoro-4-(2-(5-((4-(1-methylpiperidine-4-carbonyl)piperazin-1-yl)methyl)pyridin-2-yl)thieno[3,2-b]pyridin-7-yloxy)phenyl)urea<br>$^1$H NMR (400 MHz, DMSO-d$_6$) δ (ppm): 8.81 (s, 1H), 8.57 (bd, J = 1.6 Hz, 1H), 8.52 (d, J = 5.5 Hz, 1H), 8.34 (s, 1H), 8.25 (d, J = 8.2 Hz, 1H), 7.87 (dd, J = 8.2, 2.2 Hz, 1H), 7.73 (dd, J = 13.6, 2.4 Hz, 1H), 7.38 (t, J = 9.1 Hz, 1H), 7.21 (dd, J = 8.9, 1.3 Hz, 1H), 6.69-6.62 (m, 2H), 3.58 (s, 2H), 3.54-3.40 (m, 4H), 2.81-2.72 (m, 2H), 2.59-2.51 (m, 1H), one CH is hidden, 2.44-2.30 (m, 4H), 2.14 (s, 3H), 1.96-1.84 (m, 2H), 1.62-1.50 (m, 4H), 0.72-0.58 (m, 2H), 0.49-0.36 (m, 2H). MS (m/z): 644.8 (M + H). |

TABLE 46-continued

Characterization of compounds 535-543 (examples 372-380)

| Cpd | Ex. | Structure | Characterization |
|---|---|---|---|
| 540 | 377 | 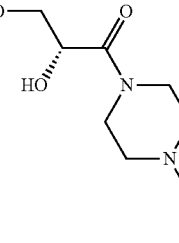 (R)-1-cyclopropyl-3-(4-(2-(5-((4-(2,3-dihydroxypropanoyl)piperazin-1-yl)methyl)pyridin-2-yl)thieno[3,2-b]pyridin-7-yloxy)-3-fluorophenyl)urea | $^1$H NMR (400 MHz, DMSO-d$_6$) δ (ppm): 8.78 (s, 1H), 8.57 (bd, J = 1.6 Hz, 1H), 8.52 (d, J = 5.3 Hz, 1H), 8.34 (s, 1H), 8.25 (d, J = 8.0 Hz, 1H), 7.88 (dd, J = 8.2, 2.0 Hz, 1H), 7.73 (dd, J = 13.6, 2.4 Hz, 1H), 7.38 (t, J = 9.1 Hz, 1H), 7.21 (dd, J = 8.8, 1.4 Hz, 1H), 6.69-6.58 (m, 2H), 4.89 (d, J = 7.0 Hz, 1H), 4.68 (t, J = 5.9 Hz, 1H), 4.31 (q, J = 5.9 Hz, 1H), 3.64-3.37 (m, 8H), 2.59-2.52 (m, 1H), 2.47-2.33 (m, 4H), 0.72-0.58 (m, 2H), 0.50-0.36 (m, 2H). MS (m/z): 607.6 (M + H). |
| 541 | 378 | 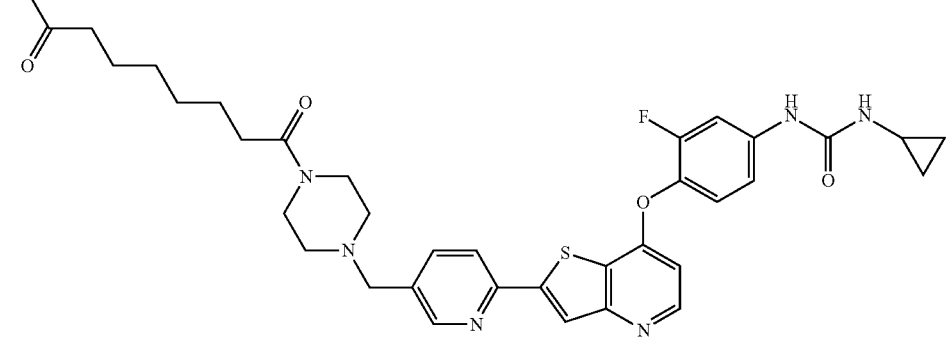 methyl 8-(4-((6-(7-(4-(3-cyclopropylureido)-2-fluorophenoxy)thieno[3,2-b]pyridin-2-yl)pyridin-3-yl)methyl)piperazin-1-yl)-8-oxooctanoate | MS (m/z): 689.7 (M + H). |
| 542 | 379 | 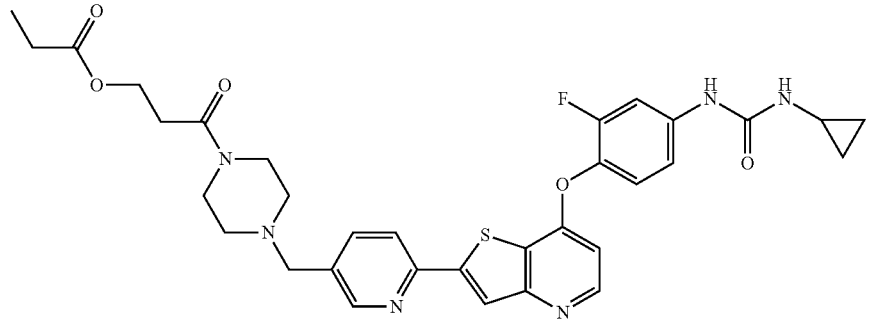 3-(4-((6-(7-(4-(3-cyclopropylureido)-2-fluorophenoxy)thieno[3,2-b]pyridin-2-yl)pyridin-3-yl)methyl)piperazin-1-yl)-3-oxopropyl propionate | MS (m/z): 647.3 (M + H). |

TABLE 46-continued

Characterization of compounds 535-543 (examples 372-380)

| Cpd | Ex. | Structure | Characterization |
|---|---|---|---|
| 543 | 380 | 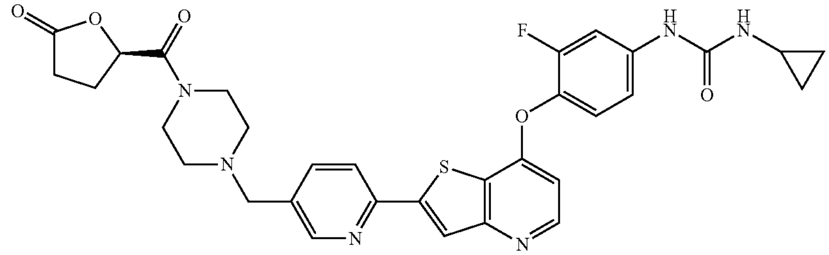 | (R)-1-cyclopropyl-3-(3-fluoro-4-(2-(5-((4-(5-oxotetrahydrofuran-2-carbonyl)piperazin-1-yl)methyl)pyridin-2-yl)thieno[3,2-b]pyridin-7-yloxy)phenyl)urea<br>$^1$H NMR (400 MHz, DMSO-$d_6$) δ (ppm): 8.71 (s, 1H), 8.58 (bd, J = 1.4 Hz, 1H), 8.52 (d, J = 5.5 Hz, 1H), 8.34 (s, 1H), 8.26 (d, J = 8.0 Hz, 1H), 7.88 (dd, J = 8.2, 2.0 Hz, 1H), 7.73 (dd, J = 13.6, 2.4 Hz, 1H), 7.38 (t, J = 9.0 Hz, 1H), 7.20 (bd, J = 8.8 Hz, 1H), 6.65 (dd, J = 5.4, 0.7 Hz, 1H), 6.57 (bd, J = 2.3 Hz, 1H), 5.52-5.44 (m, 1H), 3.61 (s, 2H), 3.60-3.40 (m, 4H), 2.59-2.51 (m, 1H), 2.49-2.31 (m, 7H), 2.19-2.09 (m, 1H), 0.72-0.58 (m, 2H), 0.49-0.36 (m, 2H). MS (m/z): 631.2 (M + H). |

Compounds 544-546 (examples 381-383) were prepared in one step by hydrolysis of the esters 541 and 542 or lactone 543, respectively, in the presence of sodium hydroxide at 45-60° C., similarly to compound 61 (example 44, scheme 16) with a final purification by preparative HPLC.

TABLE 47

Characterization of compounds 544-546 (examples 381-383).

| Cpd | Ex. | Structure | Characterization |
|---|---|---|---|
| 544 | 381 | 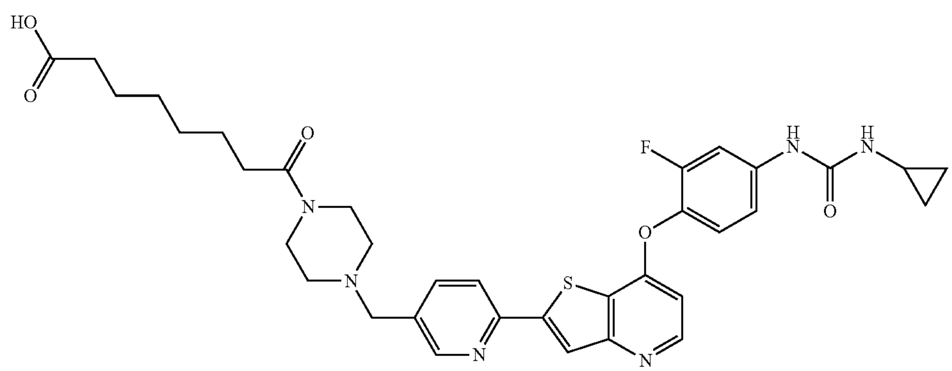 | 8-(4-((6-(7-(4-(3-cyclopropylureido)-2-fluorophenoxy)thieno[3,2-b]pyridin-2-yl)pyridin-3-yl)methyl)piperazin-1-yl)-8-oxooctanoic acid<br>$^1$H NMR (400 MHz, DMSO-$d_6$) δ (ppm): one OH carboxylic acid is missing, 8.81 (bs, 1H), 8.57 (bd, J = 1.4 Hz, 1H), 8.52 (d, J = 5.5 Hz, 1H), 8.33 (s, 1H), 8.25 (d, J = 8.0 Hz, 1H), 7.87 (dd, J = 8.2, 2.2 Hz, 1H), 7.73 (dd, J = 13.6, 2.4 Hz, 1H), 7.38 (t, J = 9.1 Hz, 1H), 7.21 (dd, J = 9.0, 1.4 Hz, 1H), 6.72-6.61 (m, 2H), 3.59 (s, 2H), 3.49-3.41 (m, 4H), 2.59-2.52 (m, 1H), 2.43-2.23 (m, 6H), 2.17 (t, J = 7.3 Hz, 2H), 1.53-1.40 (m, 4H), 1.32-1.20 (m, 4H), 0.72-0.58 (m, 2H), 0.49-0.36 (m, 2H). MS (m/z): 675.7 (M + H). |

TABLE 47-continued

Characterization of compounds 544-546 (examples 381-383).

| Cpd | Ex. | Structure | Characterization |
|-----|-----|-----------|------------------|
| 545 | 382 | 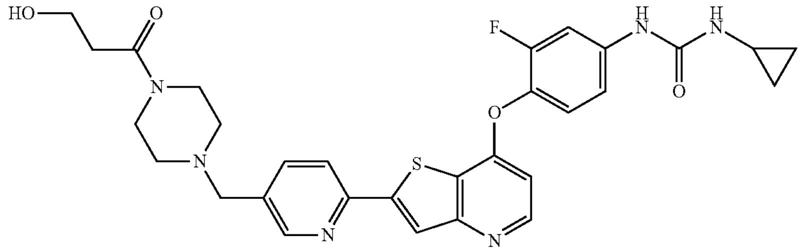 | 1-cyclopropyl-3-(3-fluoro-4-(2-(5-((4-(3-hydroxypropanoyl)piperazin-1-yl)methyl)pyridin-2-yl)thieno[3,2-b]pyridin-7-yloxy)phenyl)urea<br><br>$^1$H NMR (400 MHz, DMSO-d$_6$) δ (ppm): 8.71 (s, 1H), 8.57 (bd, J = 1.4 Hz, 1H), 8.52 (d, J = 5.5 Hz, 1H), 8.33 (s, 1H), 8.25 (dd, J = 8.1, 0.7 Hz, 1H), 7.88 (dd, J = 8.1, 2.1 Hz, 1H), 7.73 (dd, J = 13.5, 2.5 Hz, 1H), 7.38 (t, J = 9.1 Hz, 1H), 7.20 (dd, J = 8.9, 1.3 Hz, 1H), 6.65 (dd, J = 5.3, 0.8 Hz, 1H), 6.57 (bd, J = 2.7 Hz, 1H), 4.50 (t, J = 5.4 Hz, 1H), 3.66-3.56 (m, 4H), 3.52-3.42 (m, 4H), 2.58-2.52 (m, 1H), 2.46 (t, J = 6.6 Hz, 2H), 2.43-2.32 (m, 4H), 0.72-0.58 (m, 2H), 0.50-0.36 (m, 2H). MS (m/z): 591.4 (M + H). |
| 546 | 383 | 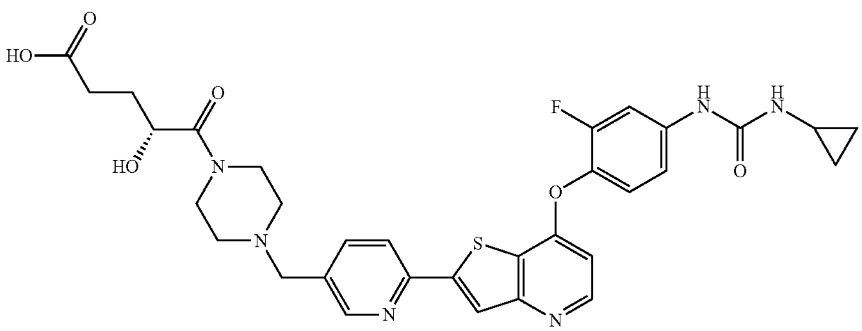 | (R)-5-(4-((6-(7-(4-(3-cyclopropylureido)-2-fluorophenoxy)thieno[3,2-b]pyridin-2-yl)pyridin-3-yl)methyl)piperazin-1-yl)-4-hydroxy-5-oxopentanoic acid<br><br>$^1$H NMR (400 MHz, DMSO-d$_6$) δ (ppm): 12.40-11.80 (m, 1H), 8.73 (s, 1H), 8.57 (d, J = 1.4 Hz, 1H), 8.52 (d, J = 5.5 Hz, 1H), 8.34 (s, 1H), 8.26 (d, J = 8.2 Hz, 1H), 7.88 (dd, J = 8.1, 2.1 Hz, 1H), 7.73 (dd, J = 13.5, 2.5 Hz, 1H), 7.38 (t, J = 9.1 Hz, 1H), 7.20 (bd, J = 9.0 Hz, 1H), 6.65 (dd, J = 5.4, 0.9 Hz, 1H), 6.59 (bd, J = 2.5 Hz, 1H), 5.06-4.66 (m, 1H), 4.33-4.21 (m, 1H), 3.59 (s, 2H), 3.59-3.43 (m, 4H), 2.59-2.51 (m, 1H), 2.47-2.26 (m, 6H), 1.85-1.73 (m, 1H), 1.65-1.53 (m, 1H), 0.72-0.58 (m, 2H), 0.49-0.36 (m, 2H). MS (m/z): 649.4 (M + H). |

Scheme 86

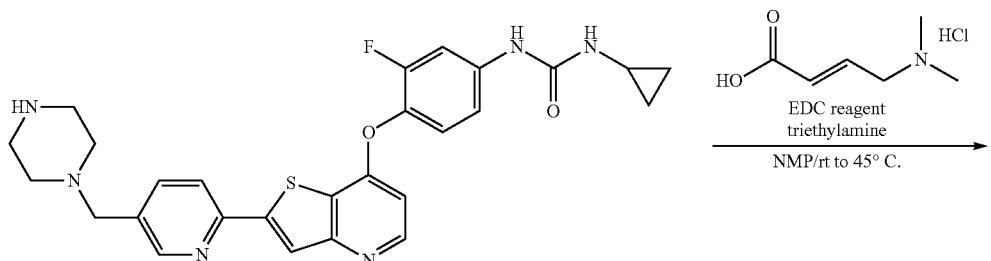

49: Example 32

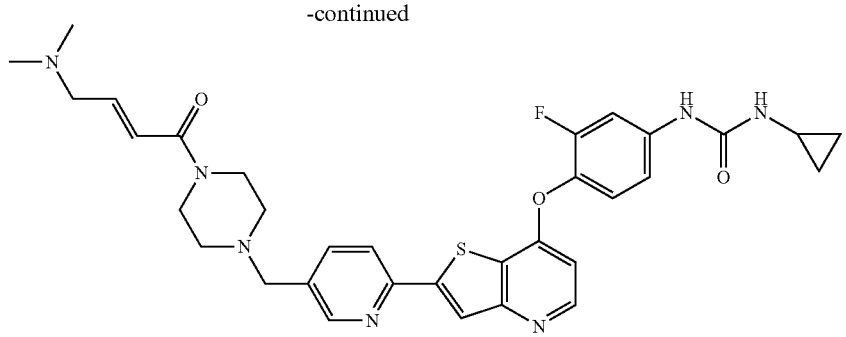

547: Example 384

Example 384

(E)-1-cyclopropyl-3-(4-(2-(5-((4-(4-(dimethylamino)but-2-enoyl)piperazin-1-yl)methyl)pyridin-2-yl)thieno[3,2-b]pyridin-7-yloxy)-3-fluorophenyl)urea (547)

A solution of trans-4-dimethylaminocrotonic acid hydrochloride (124 mg, 0.75 mmol), EDC-hydrochloride (248 mg, 1.29 mmol) and triethylamine (139 μl, 0.995 mmol) in NMP (10 ml) under nitrogen was stirred at rt for 40 min. Then 49 (150 mg, 0.25 mmol, 0.7 TFA salt) was added and the reaction mixture was stirred at rt overnight. More trans-4-dimethylaminocrotonic acid hydrochloride (124 mg, 0.75 mmol), EDC-hydrochloride (248 mg, 1.29 mmol) were added and the reaction mixture was stirred at 45° C. overnight, then at rt. Finally, the reaction was quenched by addition of water and a saturated aqueous solution of sodium bicarbonate (formation of a gel). The gel was collected by filtration, rinsed with water and air-dried. The crude product was purified by Biotage (Snap 25 g cartridge: 2% of ammonium hydroxide in MeOH/DCM: 1/99 to 30/70 over 30 CV) to afford the desired product 547 (38 mg, 0.06 mmol, 24% yield) as a pale ivory sticky solid. $^1$H NMR (500 MHz, DMSO-$d_6$) δ (ppm): 8.78 (s, 1H), 8.56 (bd, J=1.7 Hz, 1H), 8.51 (d, J=5.4 Hz, 1H), 8.34 (s, 1H), 8.25 (d, J=8.2 Hz, 1H), 7.87 (dd, J=8.2, 2.0 Hz, 1H), 7.72 (dd, J=13.6, 2.4 Hz, 1H), 7.37 (t, J=9.1 Hz, 1H), 7.19 (bd, J=8.9 Hz, 1H), 6.64 (d, J=5.4 Hz, 1H), 6.60 (bs, 1H), 6.36 (bd, J=11.6 Hz, 1H), 5.95 (dt, J=11.6, 6.9 Hz, 1H), 3.59 (s, 2H), 3.55-3.43 (m, 4H), 2H are hidden by water's peak, 2.59-2.23 (m, 11H), 0.69-0.58 (m, 2H), 0.47-0.36 (m, 2H). MS (m/z): 630.6 (M+H).

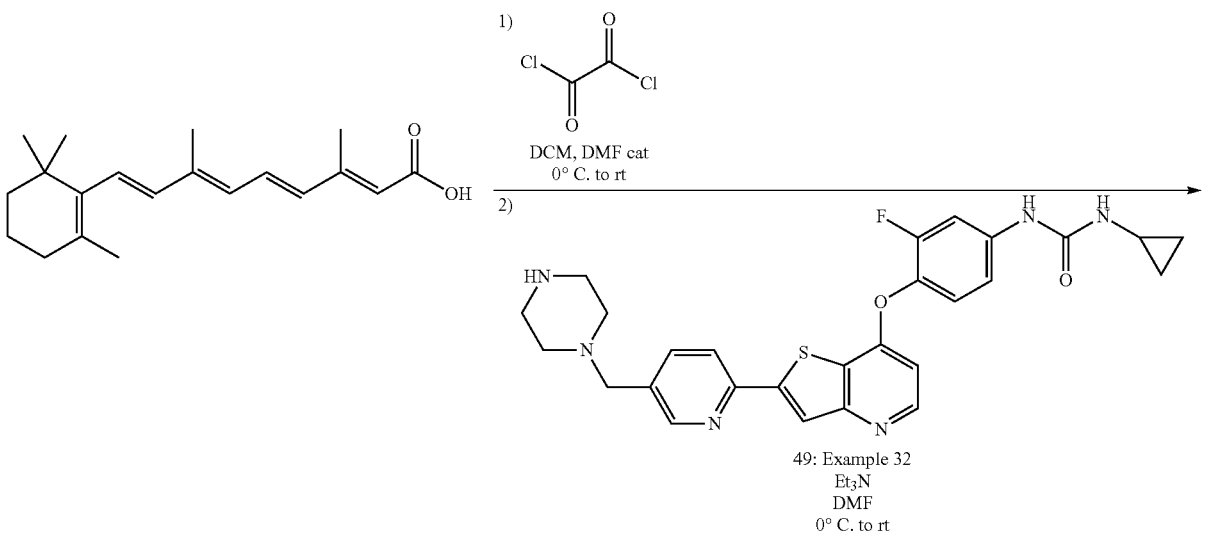

Scheme 87

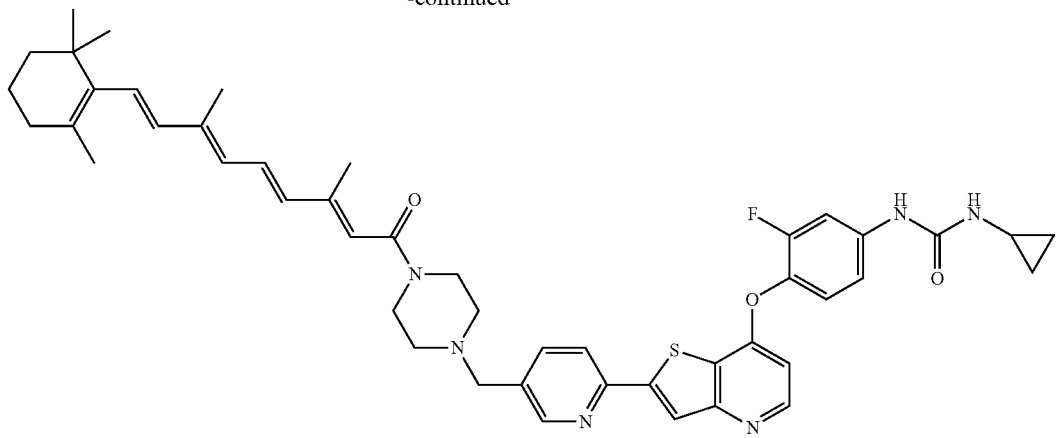

548: Example 385

Example 385

1-cyclopropyl-3-(4-(2-(5-((4-(((2E,4E,6E,8E)-3,7-dimethyl-9-(2,6,6-trimethylcyclohex-1-enyl)nona-2,4,6,8-tetraenoyl)piperazin-1-yl)methyl)pyridin-2-yl)thieno[3,2-b]pyridin-7-yloxy)-3-fluorophenyl)urea (548)

To a stirred solution of all-trans retinoic acid (ATRA) (130 mg, 0.43 mmol) in a mixture of DMF (1 ml) and DCM (6.5 ml) at 0° C. under nitrogen was added dropwise oxalyl chloride (76 µl, 0.87 mmol). The reaction mixture was stirred at rt for 50 min. DCM was removed under reduced pressure (no heat!) and the remaining solution was diluted with DMF (2 ml). To a stirred solution of 49 (150 mg, 0.29 mmol) and triethylamine (120 µl, 0.87 mmol) in DMF (5 ml) at 0° C. under nitrogen was slowly added the solution of the acyl chloride intermediate. After one hour, the reaction mixture at 0° C. was quenched by addition of water. The resulting suspension was shaken then the solid was collected by filtration, rinsed with water and air-dried. The crude material was purified twice by Biotage (Snap 25 g cartridge; MeOH/DCM: 0/100 to 5/95 over 30 CV, then 05/95 to 10/90 over 10 CV; Snap 25 g cartridge; MeOH/DCM: 1/99 to 10/90 over 30 CV). The desired fractions were combined and concentrated. The residue was dissolved in MeOH, concentrated until precipitation was occurred. The solid was collected by filtration, rinsed with MeOH and dried to afford the desired product 548 (56 mg, 0.07 mmol, 24% yield) as a bright yellow fluffy solid. $^1$H NMR (400 MHz, DMSO-$d_6$) δ (ppm): 8.72 (s, 1H), 8.57 (bd, J=1.8 Hz, 1H), 8.52 (d, J=5.5 Hz, 1H), 8.34 (s, 1H), 8.26 (d, J=8.2 Hz, 1H), 7.88 (dd, J=8.2, 1.9 Hz, 1H), 7.73 (dd, J=13.6, 2.4 Hz, 1H), 7.38 (t, J=9.1 Hz, 1H), 7.19 (dd, J=9.0, 1.4 Hz, 1H), 6.82 (dd, J=15.3, 11.3 Hz, 1H), 6.65 (dd, J=5.5, 0.8 Hz, 1H), 6.59 (bd, J=2.5 Hz, 1H), 6.39 (d, J=15.1 Hz, 1H), 6.25-6.10 (m, 4H), 3.60 (s, 2H), 3.57-3.43 (m, 4H), 2.59-2.51 (m, 1H), 2.45-2.34 (m, 4H), 2.04-1.96 (m, 5H), 1.95 (s, 3H), 1.68 (s, 3H), 1.61-1.52 (m, 2H), 1.46-1.40 (m, 2H), 1.00 (s, 6H), 0.72-0.58 (m, 2H), 0.49-0.36 (m, 2H). MS (m/z): 801.8 (M+H).

Scheme 88

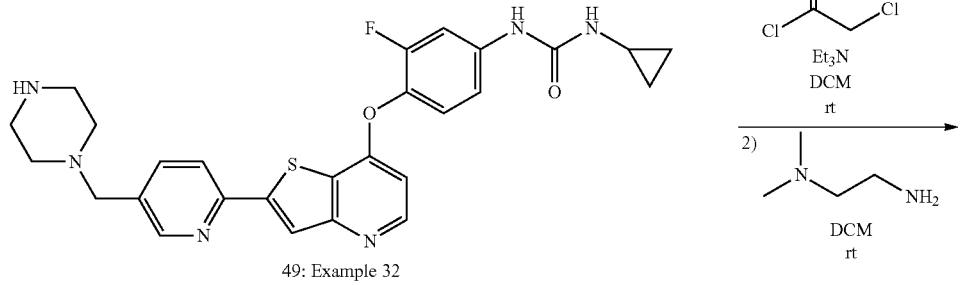

49: Example 32

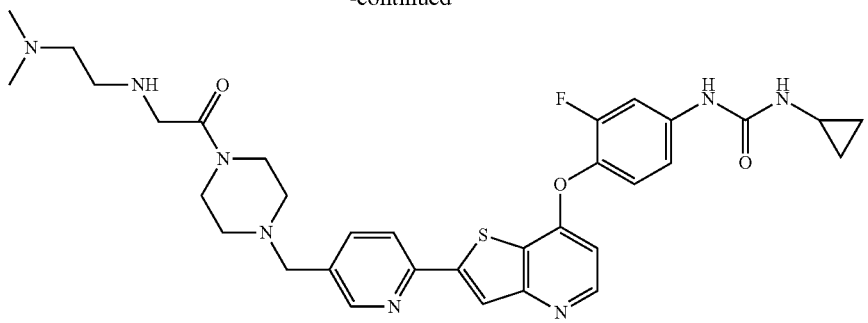

549: Example 386

Example 386

1-cyclopropyl-3-(4-(2-(5-((4-(2-(2-(dimethylamino) ethylamino)acetyl)piperazin-1-yl)methyl)pyridin-2-yl)thieno[3,2-b]pyridin-7-yloxy)-3-fluorophenyl)urea (549)

To a stirred solution of 49 (100 mg, 0.19 mmol) and triethylamine (107 µl, 0.77 mmol) in DCM (10 ml) under nitrogen was added chloroacetyl chloride (19 µl, 0.23 mmol), and the reaction mixture was stirred at rt for 25 min. N,N-Dimethylethylene diamine (134 µl, 1.16 mmol) was added, and the reaction mixture was stirred at rt overnight, heated at 40° C. for 5 h, then at rt. The reaction mixture was concentrated, diluted with water and few drops of 1N NaOH and sonicated. The resulting gel was collected by filtration, rinsed with water and air-dried. The crude product was purified three times by Biotage [Snap 30 g cartridge KP-C18-HS (reverse phase) ×2: MeOH/water (Millipore): 20/80 to 95/05 over 40 CV; Analogix SF 25-40 g cartridge; 2% of ammonium hydroxide in MeOH/DCM: 1/99 to 50/50 over 60 CV], to afford the desired compound 549 (13 mg, 0.02 mmol, 10% yield) as a pale yellow sticky solid. $^1$H NMR (500 MHz, DMSO-d$_6$) δ (ppm): 8.75 (s, 1H), 8.56 (bd, J=1.7 Hz, 1H), 8.51 (d, J=5.4 Hz, 1H), 8.32 (s, 1H), 8.24 (d, J=8.1 Hz, 1H), 7.87 (dd, J=8.2, 1.9 Hz, 1H), 7.72 (dd, J=13.6, 2.4 Hz, 1H), 7.37 (t, J=9.1 Hz, 1H), 7.20 (bd, J=8.9 Hz, 1H), 6.64 (d, J=5.4 Hz, 1H), 6.61 (bd, J=1.9 Hz, 1H), 3.58 (s, 2H), 3.50-3.36 (m, 4H), 3.33 (s, 2H), 2.59-2.51 (m, 1H), 2.52 (t, J=6.3 Hz, 2H), 2.43-2.31 (m, 4H), 2.27 (t, J=6.3 Hz, 2H), 2.10 (s, 6H), 0.70-0.58 (m, 2H), 0.47-0.37 (m, 2H), one NH secondary amine is missing. MS (m/z): 647.6 (M+H).

Compound 550 (example 387) was prepared in two steps by coupling 225 (scheme 54) with 1-Boc-piperazine similarly to compound 226 (example 127, scheme 54) followed by Boc-deprotection similarly to compound 49 (example 32, scheme 15).

TABLE 48

Characterization of compound 550 (example 387).

| Cpd | Ex. | Structure | Characterization |
|---|---|---|---|
| 550 | 387 | 1-cyclopropyl-3-(3-fluoro-4-(2-(5-(piperazine-1-carbonyl)pyridin-2-yl)thieno[3,2-b]pyridin-7-yloxy)phenyl)urea | $^1$H NMR (400 MHz, DMSO-d$_6$) δ (ppm): 8.75 (bs, 1H), 8.66 (dd, J = 2.2, 1.0 Hz, 1H), 8.54 (d, J = 5.5 Hz, 1H), 8.46 (s, 1H), 8.36 (dd, J = 8.1, 0.7 Hz, 1H), 7.98 (dd, J = 8.2, 2.2 Hz, 1H), 7.74 (dd, J = 13.6, 2.4 Hz, 1H), 7.39 (t, J = 9.0 Hz, 1H), 7.20 (bd, J = 8.8 Hz, 1H), 6.68 (dd, J = 5.4, 0.7 Hz, 1H), 6.65-6.58 (m, 1H), 3.57 (bs, 2H), 3.30 (bs, 2H), 2.81-2.62 (m, 4H), 2.59-2.51 (m, 1H), 0.72-0.58 (m, 2H), 0.49-0.36 (m, 2H), NH is missing. MS (m/z): 533.2 (M + H). |

Compounds 551-555 (examples 388-392) were prepared in one step by reacting 49 (example 32) with isocyanate reagents similarly to compound 128 (example 87, scheme 32). Compounds 556 and 557 (examples 393 and 394) were prepared in one step by reacting 527 (example 364, table 44) and 550 (example 387, table 48), respectively, with ethyl isocyanate.

TABLE 49

Characterization of compounds 551-557 (examples 388-394)

| Cpd | Ex. | Structure | Characterization |
| --- | --- | --- | --- |
| 551 | 388 | 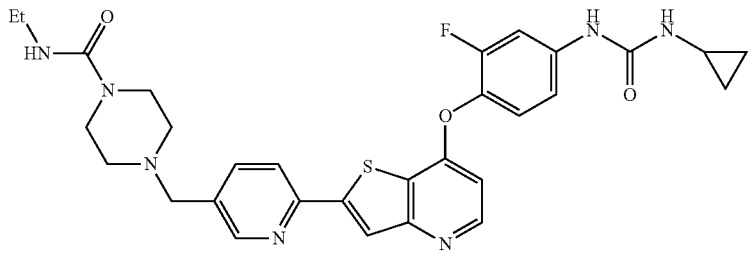 4-((6-(7-(4-(3-cyclopropylureido)-2-fluorophenoxy)thieno[3,2-b]pyridin-2-yl)pyridin-3-yl)methyl)-N-ethylpiperazine-1-carboxamide | $^1$H NMR (400 MHz, DMSO-d$_6$) δ (ppm): 8.74 (s, 1H), 8.56 (bd, J = 1.4 Hz, 1H), 8.52 (d, J = 5.3 Hz, 1H), 8.33 (s, 1H), 8.25 (d, J = 8.2 Hz, 1H), 7.87 (dd, J = 8.2, 2.0 Hz, 1H), 7.73 (dd, J = 13.5, 2.5 Hz, 1H), 7.38 (t, J = 9.1 Hz, 1H), 7.20 (dd, J = 8.8, 1.4 Hz, 1H), 6.65 (dd, J = 5.5, 0.8 Hz, 1H), 6.60 (bd, J = 2.5 Hz, 1H), 6.46 (t, J = 5.4 Hz, 1H), 3.57 (s, 2H), 3.31-3.24 (m, 4H), 3.07-2.98 (m, 2H), 2.58-2.51 (m, 1H), 2.38-2.31 (m, 4H), 0.99 (t, J = 7.1 Hz, 3H), 0.72-0.58 (m, 2H), 0.49-0.36 (m, 2H). MS (m/z): 590.6 (M + H). |
| 552 | 389 | 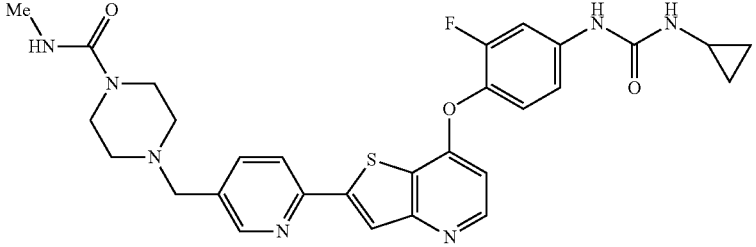 4-((6-(7-(4-(3-cyclopropylureido)-2-fluorophenoxy)thieno[3,2-b]pyridin-2-yl)pyridin-3-yl)methyl)-N-methylpiperazine-1-carboxamide | $^1$H NMR (500 MHz, DMSO-d$_6$) δ (ppm): 8.69 (s, 1H), 8.55 (bd, J = 1.7 Hz, 1H), 8.51 (d, J = 5.4 Hz, 1H), 8.32 (s, 1H), 8.23 (d, J = 8.1 Hz, 1H), 7.86 (dd, J = 8.2, 2.0 Hz, 1H), 7.72 (dd, J = 13.5, 2.4 Hz, 1H), 7.37 (t, J = 9.1 Hz, 1H), 7.19 (dd, J = 8.8, 1.3 Hz, 1H), 6.64 (d, J = 5.4 Hz, 1H), 6.56 (bd, J = 2.4 Hz, 1H), 6.39 (q, J = 4.3 Hz, 1H), 3.55 (s, 2H), 3.30-3.20 (m, 4H), 2.58-2.52 (m, 1H), 2.54 (d, J = 4.3 Hz, 3H), 2.37-2.30 (m, 4H), 0.70-0.59 (m, 2H), 0.47-0.37 (m, 2H). MS (m/z): 576.4 (M + H). |
| 553 | 390 | 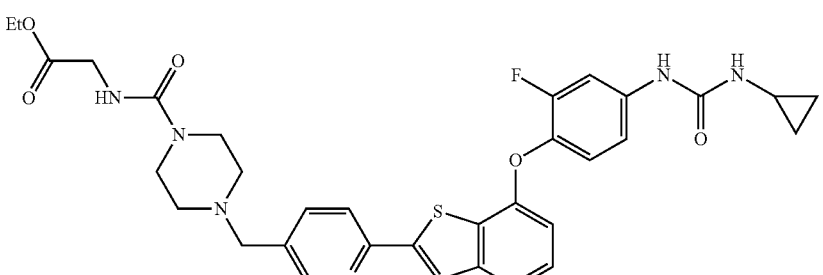 ethyl 2-(4-((6-(7-(4-(3-cyclopropylureido)-2-fluorophenoxy)thieno[3,2-b]pyridin-2-yl)pyridin-3-yl)methyl)piperazine-1-carboxamido)acetate | MS (m/z): 648.3 (M + H). |

TABLE 49-continued

Characterization of compounds 551-557 (examples 388-394)

| Cpd | Ex. | Structure | Characterization |
| --- | --- | --- | --- |
| 554 | 391 | 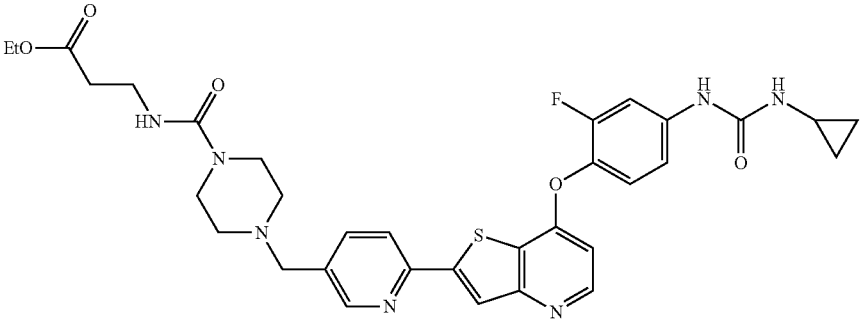 ethyl 3-(4-((6-(7-(4-(3-cyclopropylureido)-2-fluorophenoxy)thieno[3,2-b]pyridin-2-yl)pyridin-3-yl)methyl)piperazine-1-carboxamido)propanoate | MS (m/z): 662.3 (M + H). |
| 555 | 392 | 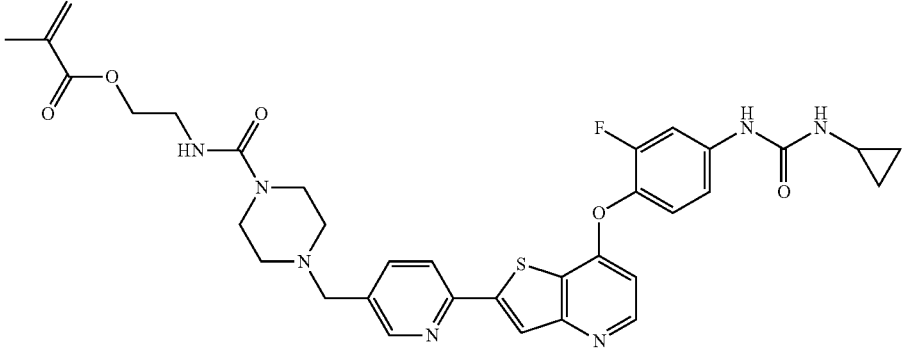 2-(4-((6-(7-(4-(3-cyclopropylureido)-2-fluorophenoxy)thieno[3,2-b]pyridin-2-yl)pyridin-3-yl)methyl)piperazine-1-carboxamido)ethyl methacrylate | MS (m/z): 674.4 (M + H). |
| 556 | 393 | 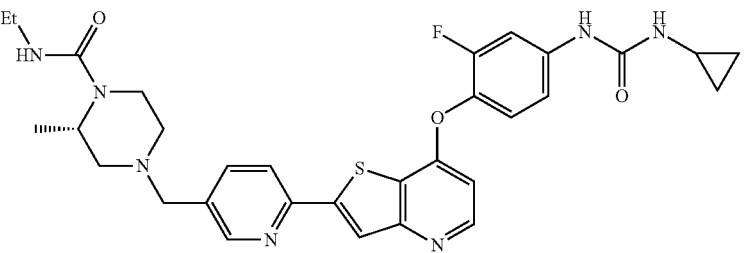 (S)-4-((6-(7-(4-(3-cyclopropylureido)-2-fluorophenoxy)thieno[3,2-b]pyridin-2-yl)pyridin-3-yl)methyl)-N-ethyl-2-methylpiperazine-1-carboxamide | $^1$H NMR (400 MHz, DMSO-d$_6$) δ (ppm): 8.72 (s, 1H), 8.57 (bd, J = 1.6 Hz, 1H), 8.52 (d, J = 5.3 Hz, 1H), 8.34 (s, 1H), 8.26 (dd, J = 8.1, 0.7 Hz, 1H), 7.88 (dd, J = 8.2, 2.2 Hz, 1H), 7.73 (dd, J = 13.6, 2.4 Hz, 1H), 7.38 (t, J = 9.1 Hz, 1H), 7.20 (dd, J = 8.9, 1.3 Hz, 1H), 6.65 (dd, J = 5.4, 0.9 Hz, 1H), 6.58 (bd, J = 2.5 Hz, 1H), 6.39 (t, J = 5.4 Hz, 1H), 4.14-4.04 (m, 1H), 3.67 (bd, J = 12.9 Hz, 1H), AB system (δ$_A$ = 3.59, δ$_B$ = 3.49, J = 14.0 Hz, 2H), 3.10-2.98 (m, 2H), 2.94 (td, J = 12.6, 3.1 Hz, 1H), 2.78 (bd, J = 10.8 Hz, 1H), 2.61 (bd, J = 11.0 Hz, 1H), 2.59-2.51 (m, 1H), 2.08 (dd, J = 11.1, 3.5 Hz, 1H), 1.95 (td, J = 11.6, 3.2 Hz, 1H), 1.13 (d, J = 6.7 Hz, 3H), 0.99 (t, J = 7.1 Hz, 3H), 0.72-0.58 (m, 2H), 0.49-0.36 (m, 2H). MS (m/z): 604.5 (M + H). |

TABLE 49-continued

Characterization of compounds 551-557 (examples 388-394)

| Cpd | Ex. | Structure | Characterization |
|---|---|---|---|
| 557 | 394 | 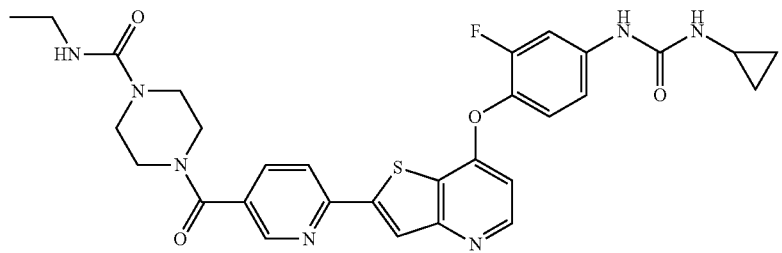 4-(6-(7-(4-(3-cyclopropylureido)-2-fluorophenoxy)thieno[3,2-b]pyridin-2-yl)nicotinoyl)-N-ethylpiperazine-1-carboxamide | $^1$H NMR (400 MHz, DMSO-d$_6$) δ (ppm): 8.73 (s, 1H), 8.70 (dd, J = 2.0, 0.8 Hz, 1H), 8.55 (d, J = 5.5 Hz, 1H), 8.47 (s, 1H), 8.38 (dd, J = 8.2, 0.8 Hz, 1H), 8.02 (dd, J = 8.2, 2.2 Hz, 1H), 7.74 (dd, J = 13.6, 2.4 Hz, 1H), 7.39 (t, J = 9.1 Hz, 1H), 7.20 (bd, J = 9.0 Hz, 1H), 6.68 (dd, J = 5.5, 0.8 Hz, 1H), 6.63-6.56 (m, 2H), 3.61 (bs, 2H), 3.48-3.30 (m, 6H), 3.10-3.01 (m, 2H), 2.59-2.51 (m, 1H), 1.01 (t, J = 7.1 Hz, 3H), 0.72-0.58 (m, 2H), 0.49-0.36 (m, 2H). MS (m/z): 604.5 (M + H). |

Compounds 558-560 (examples 395-397) were prepared in one step by hydrolysis of the esters 553-555 in the presence of sodium hydroxide at room temperature, similarly to compound 61 (example 44, scheme 16) with a final purification by preparative HPLC.

TABLE 50

Characterization of compounds 558-560 (examples 395-397)

| Cpd | Ex. | Structure | Characterization |
|---|---|---|---|
| 558 | 395 | 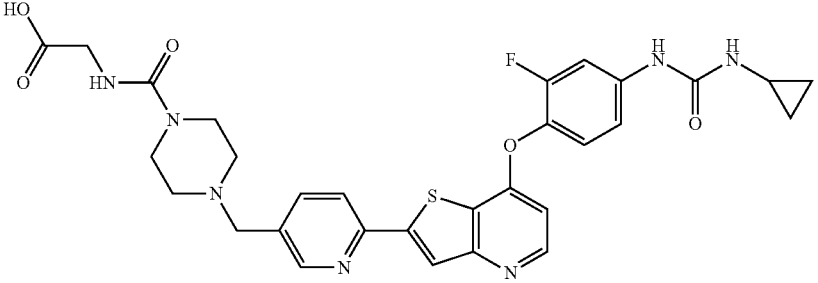 2-(4-((6-(7-(4-(3-cyclopropylureido)-2-fluorophenoxy)thieno[3,2-b]pyridin-2-yl)pyridin-3-yl)methyl)piperazine-1-carboxamido)acetic acid | $^1$H NMR (400 MHz, DMSO-d$_6$) δ (ppm): one OH carboxylic acid is missing, 9.55 (bs, 1H), 8.55 (bd, J = 1.4 Hz, 1H), 8.51 (d, J = 5.5 Hz, 1H), 8.32 (s, 1H), 8.23 (d, J = 8.0 Hz, 1H), 7.86 (dd, J = 8.2, 2.0 Hz, 1H), 7.75 (dd, J = 13.7, 2.3 Hz, 1H), 7.36 (t, J = 9.1 Hz, 1H), 7.35 (bs, 1H), 7.24 (dd, J = 9.0, 1.4 Hz, 1H), 6.63 (dd, J = 5.5, 0.8 Hz, 1H), 6.55-6.40 (m, 1H), 3.56 (s, 2H), 3.49 (d, J = 5.1 Hz, 2H), 3.40-3.20 (m, 4H), 2.59-2.51 (m, 1H), 2.44-2.28 (m, 4H), 0.69-0.55 (m, 2H), 0.49-0.35 (m, 2H MS (m/z): 620.5 (M + H). |

TABLE 50-continued

Characterization of compounds 558-560 (examples 395-397)

| Cpd | Ex. | Structure | Characterization |
|---|---|---|---|
| 559 | 396 | 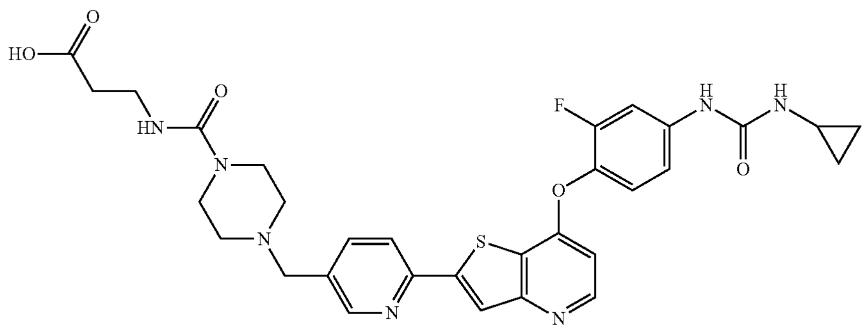 | 3-(4-((6-(7-(4-(3-cyclopropylureido)-2-fluorophenoxy)thieno[3,2-b]pyridin-2-yl)pyridin-3-yl)methyl)piperazine-1-carboxamido)propanoic acid<br>$^1$H NMR (400 MHz, DMSO-d$_6$) δ (ppm): one O<u>H</u> carboxylic acid is missing, 10.12 (bs, 1H), 8.55-8.42 (m, 2H), 8.26 (s, 1H), 8.16 (d, J = 8.0 Hz, 1H), 7.90 (bs, 1H), 7.81 (dd, J = 8.1, 1.9 Hz, 1H), 7.74 (dd, J = 13.8, 2.2 Hz, 1H), 7.33 (t, J = 9.0 Hz, 1H), 7.26 (dd, J = 9.0, 1.8 Hz, 1H), 6.77 (bs, 1H), 6.62 (d, J = 4.9 Hz, 1H), 3.52 (s, 2H), 3.26 (bs, 4H), 3.16 (m, 2H), 2.58-2.51 (m, 1H), 2.38-2.27 (m, 4H), 2.24-2.14 (m, 2H), 0.67-0.53 (m, 2H), 0.47-0.34 (m, 2H). MS (m/z): 634.6 (M + H). |
| 560 | 397 | 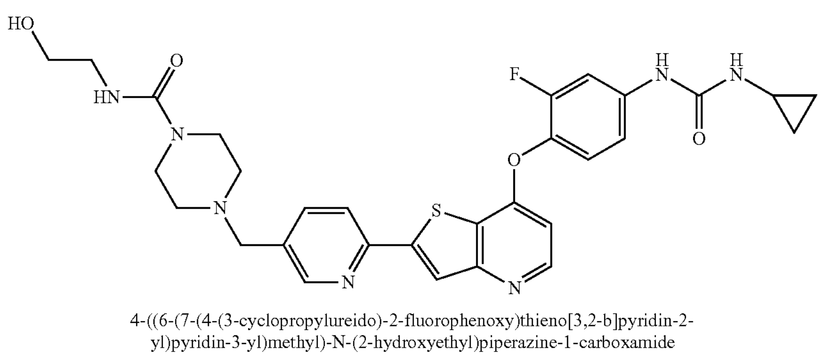 [SMILES: O=C(Nc1ccc(Oc2ccnc3cc(-c4ccc(CN5CCN(C(=O)NCCO)CC5)cn4)sc23)c(F)c1)NC1CC1] | 4-((6-(7-(4-(3-cyclopropylureido)-2-fluorophenoxy)thieno[3,2-b]pyridin-2-yl)pyridin-3-yl)methyl)-N-(2-hydroxyethyl)piperazine-1-carboxamide<br>$^1$H NMR (400 MHz, DMSO-d$_6$) δ (ppm): 8.74 (s, 1H), 8.56 (bd, J = 1.4 Hz, 1H), 8.52 (d, J = 5.5 Hz, 1H), 8.33 (s, 1H), 8.25 (d, J = 8.2 Hz, 1H), 7.87 (dd, J = 8.1, 1.9 Hz, 1H), 7.73 (dd, J = 13.6, 2.4 Hz, 1H), 7.38 (t, J = 9.1 Hz, 1H), 7.20 (dd, J = 8.9, 1.3 Hz, 1H), 6.65 (dd, J = 5.5, 0.8 Hz, 1H), 6.58 (bd, J = 2.7 Hz, 1H), 6.48 (t, J = 5.4 Hz, 1H), 4.61 (t, J = 5.5 Hz, 1H), 3.57 (s, 2H), 2H are hidden by water's peak, 3.36-3.24 (m, 4H), 3.07 (q, J = 6.1 Hz, 2H), 2.59-2.51 (m, 1H), 2.42-2.27 (m, 4H), 0.72-0.58 (m, 2H), 0.50-0.36 (m, 2H). MS (m/z): 606.5 (M + H). |

Compound 562 (example 399) was prepared in one step starting from 49 (example 32, scheme 15) and the corresponding alkylating reagent similarly to compound 512 (example 351, scheme 83).

TABLE 51

Characterization of compound 562 (example 399).

| Cpd | Ex. | Structure | Characterization |
|---|---|---|---|
| 562 | 399 | 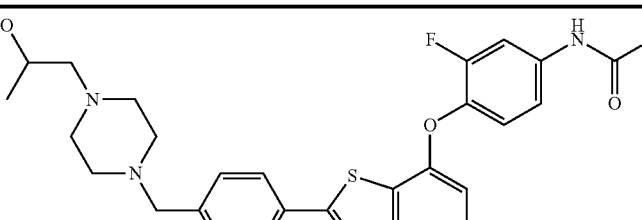 | 1-cyclopropyl-3-(3-fluoro-4-(2-(5-((4-(2-hydroxypropyl)piperazin-1-yl)methyl)pyridin-2-yl)thieno[3,2-b]pyridin-7-yloxy)phenyl)urea<br>$^1$H NMR (400 MHz, DMSO-$d_6$) δ (ppm): 8.77 (s, 1H), 8.54 (bd, J = 1.6 Hz, 1H), 8.52 (d, J = 5.5 Hz, 1H), 8.32 (s, 1H), 8.23 (d, J = 8.2 Hz, 1H), 7.85 (dd, J = 8.1, 2.1 Hz, 1H), 7.73 (dd, J = 13.6, 2.4 Hz, 1H), 7.38 (t, J = 9.1 Hz, 1H), 7.20 (dd, J = 8.9, 1.3 Hz, 1H), 6.64 (dd, J = 5.3, 0.8 Hz, 1H), 6.62 (bd, J = 2.7 Hz, 1H), 4.23 (bd, J = 3.7 Hz, 1H), 3.78-3.67 (m, 1H), 3.54 (s, 2H), 2.59-2.52 (m, 1H), 2.49-2.33 (m, 8H), 2.23 (dd, J = 12.1, 7.0 Hz, 1H), 2.14 (dd, J = 12.2, 5.6 Hz, 1H), 1.02 (d, J = 6.3 Hz, 3H), 0.72-0.58 (m, 2H), 0.49-0.37 (m, 2H). MS (m/z): 577.6 (M + H). |

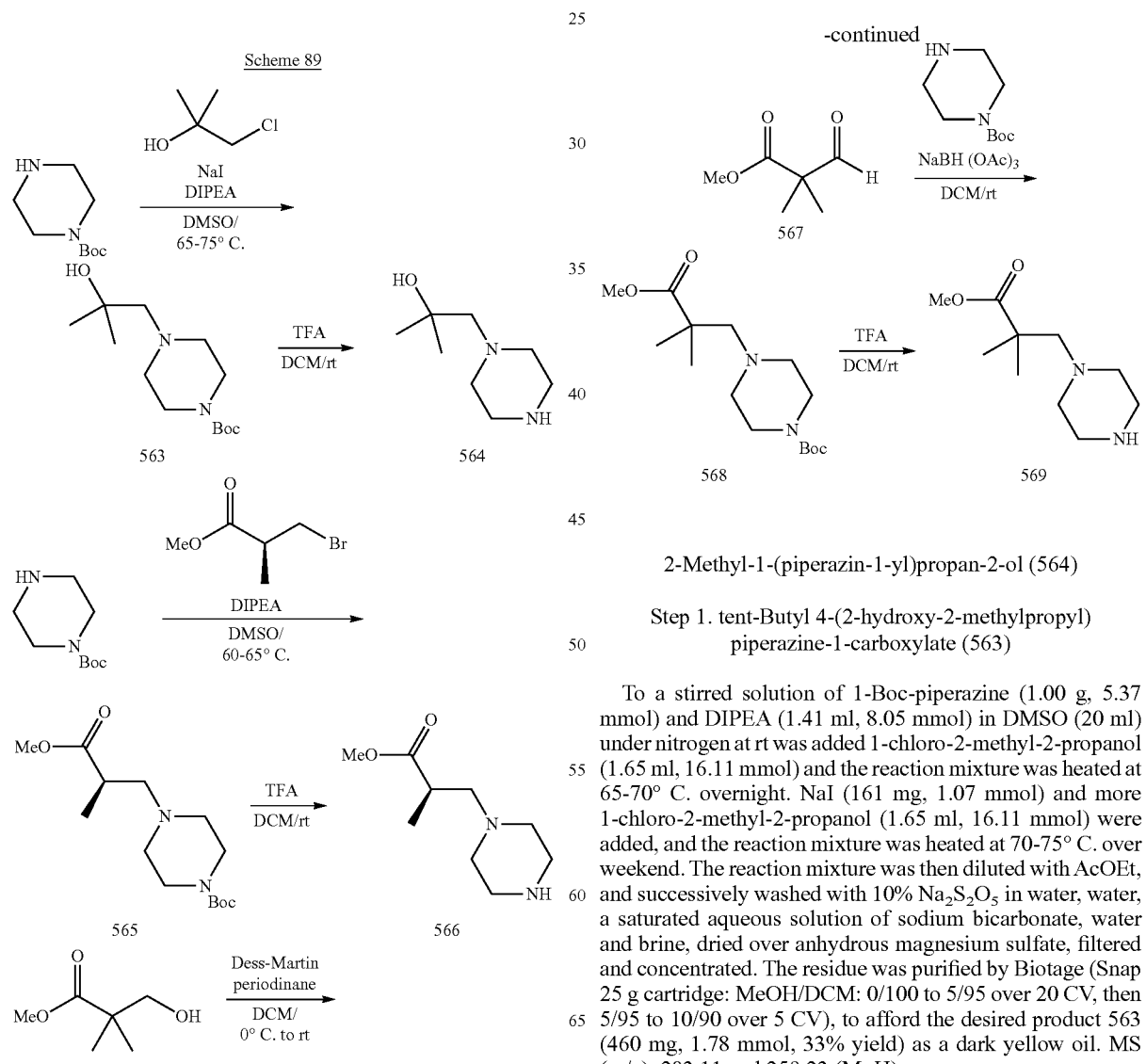

Scheme 89

2-Methyl-1-(piperazin-1-yl)propan-2-ol (564)

Step 1. tent-Butyl 4-(2-hydroxy-2-methylpropyl)piperazine-1-carboxylate (563)

To a stirred solution of 1-Boc-piperazine (1.00 g, 5.37 mmol) and DIPEA (1.41 ml, 8.05 mmol) in DMSO (20 ml) under nitrogen at rt was added 1-chloro-2-methyl-2-propanol (1.65 ml, 16.11 mmol) and the reaction mixture was heated at 65-70° C. overnight. NaI (161 mg, 1.07 mmol) and more 1-chloro-2-methyl-2-propanol (1.65 ml, 16.11 mmol) were added, and the reaction mixture was heated at 70-75° C. over weekend. The reaction mixture was then diluted with AcOEt, and successively washed with 10% $Na_2S_2O_5$ in water, water, a saturated aqueous solution of sodium bicarbonate, water and brine, dried over anhydrous magnesium sulfate, filtered and concentrated. The residue was purified by Biotage (Snap 25 g cartridge: MeOH/DCM: 0/100 to 5/95 over 20 CV, then 5/95 to 10/90 over 5 CV), to afford the desired product 563 (460 mg, 1.78 mmol, 33% yield) as a dark yellow oil. MS (m/z): 203.11 and 259.23 (M+H).

Step 2. 2-Methyl-1-(piperazin-1-yl)propan-2-ol (564)

A solution of 563 (460 mg, 1.78 mmol) and TFA (5 ml) in DCM (20 ml) was stirred at rt for 5 h. The reaction mixture was concentrated (azeotropes with DCM), diluted with water, stirred for 10 min. The pH was adjusted to around 10 with 1N NaOH, and the alkaline solution was extracted with DCM. The organic extract was dried over anhydrous magnesium sulfate, filtered, concentrated under high vacuum to afford the desired product 564 (170 mg, 1.07 mmol, 60% yield) as a dark orange sticky solid. The crude product was used in the next step without any further purification. MS (m/z): 159.13 (M+H).

(R)-Methyl 2-methyl-3-(piperazin-1-yl)propanoate (566)

Step 1. (R)-tert-butyl 4-(3-methoxy-2-methyl-3-oxopropyl)piperazine-1-carboxylate (565)

To a stirred solution of 1-Boc-piperazine (1.00 g, 5.37 mmol) and DIPEA (2.81 ml, 16.11 mmol) in DMSO (20 ml) under nitrogen at rt was added methyl (S)-(−)-3-bromo-2-methyl propionate (1.03 ml, 8.05 mmol), and the reaction mixture was heated at 60-65° C. over weekend. More methyl (S)-(−)-3-bromo-2-methyl propionate (1.03 ml, 8.05 mmol) was added, and the reaction mixture was heated at 65° C. overnight. The reaction mixture was diluted with AcOEt, and successively washed with water, a saturated aqueous solution of sodium bicarbonate and brine. The aqueous layers were combined, extracted with ethyl acetate, and successively washed with water and brine. The organic layer was dried over anhydrous magnesium sulfate, filtered and concentrated. The residue was purified by Biotage (Snap 25 g cartridge: MeOH/DCM: 0/100 to 5/95 over 20 CV, then 05/95 to 10/90 over 5 CV), to afford the desired product 565 (523 mg, 1.83 mmol, 34% yield) as a yellow oil. MS (m/z): 231.13 and 287.27 (M+H).

Step 2. (R)-Methyl 2-methyl-3-(piperazin-1-yl)propanoate (566)

A solution of 565 (523 mg, 1.83 mmol) and TFA (5 ml) in DCM (15 ml) was stirred at rt for 3.5 h. The reaction mixture was concentrated (azeotropes with DCM), diluted with water, stirred for 10 min, and the pH was adjusted to around 9 with a saturated aqueous solution of sodium bicarbonate and 1N NaOH. The alkaline solution was extracted with DCM; the extract was dried over anhydrous magnesium sulfate, filtered, and concentrated under high vacuum to afford the desired product 566 (314 mg, 1.68 mmol, 92% yield) as a yellow oil that was used crude in the next step without any further purification. MS (m/z): 187.2 (M+H).

Methyl 2,2-dimethyl-3-(piperazin-1-yl)propanoate (569)

Step 1. Methyl 2,2-dimethyl-3-oxopropanoate (567)

To a stirred solution of methyl 2,2-dimethyl-3-hydroxypropionate (1 g, 7.57 mmol) in DCM (50 ml) at 0° C. under nitrogen was added Dess-Martin periodinane (3.21 g, 7.57 mmol) in one portion and the reaction mixture was stirred at 0° C. for 1 h then rt for 45 min. The reaction mixture was cooled down to 0° C. and poured into 1N NaOH solution (30 mL) and extracted with DCM. The organic layer was collected, dried over anhydrous magnesium sulfate, filtered, and partially evaporated (at around 25° C.) under reduced pressure, to afford a solution of 567 that was stored in the freezer and used in the next step without any further purification.

Step 2. tert-Butyl 4-(3-methoxy-2,2-dimethyl-3-oxopropyl)piperazine-1-carboxylate (568)

A solution of 567 (0.57 mmol, crude in 25 ml of DCM) and 1-Boc-piperazine (1.175 g, 6.31 mmol) in DCM (50 ml) was stirred for 1 h at rt under nitrogen, then cooled down to 0° C. To the cold solution NaBH(OAc)$_3$ (4.22 g, 18.93 mmol) was added in one portion. The reaction mixture was stirred at 0° C. for 1 h, then at rt overnight, quenched by addition of water, stirred for 1 h and slowly neutralyzed with a saturated aqueous solution of sodium bicarbonate (pH=7-8). The alkaline solution was extracted with DCM. The organic extract was dried over anhydrous magnesium sulfate, filtered and concentrated. The residue was purified by Biotage (Snap 25 g cartridge, MeOH/DCM: 0/100 to 10/90 over 30 CV), to afford the desired product 568 (1.137 g, 3.79 mmol, 60% yield) as colorless oily liquid. MS (m/z): 301.3 (M+H).

Step 3. Methyl 2,2-dimethyl-3-(piperazin-1-yl)propanoate (569)

A solution of 568 (1.137 g, 3.79 mmol) and TFA (15 ml) in DCM (30 ml) was stirred at rt for 2.5 h. The reaction mixture was concentrated (azeotropes with DCM), diluted with water, stirred for 1 h, and the pH was adjusted to around 9-10 with 1N NaOH. The alkaline solution was extracted with DCM. The extract was dried over anhydrous magnesium sulfate, filtered, concentrated and dried under high vacuum to afford the desired product 569 (667 mg, 3.33 mmol, 88% yield) as a pale-yellow viscous liquid. The crude material was used in the next step without any further purification. MS (z): 201.1 (M+H).

Compounds 570-572 (examples 400-402) were prepared in one step by reductive amination of compound 47 with the appropriate amine described above similarly to compound 48 (example 31, scheme 15). Compound 573 (example 403) was prepared in one step by coupling 225 (scheme 54) with methyl 2,2-dimethyl-3-(piperazin-1-yl)propanoate 569 similarly to compound 226 (example 127, scheme 54).

TABLE 52

Characterization of compounds 570-573 (examples 400-403)

| Cpd | Ex. | Structure | Characterization |
|---|---|---|---|
| 570 | 400 | 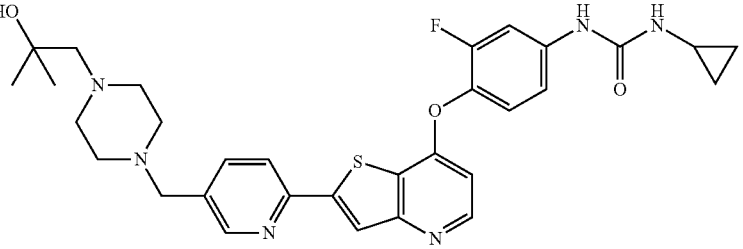 | 1-cyclopropyl-3-(3-fluoro-4-(2-(5-((4-(2-hydroxy-2-methylpropyl)piperazin-1-yl)methyl)pyridin-2-yl)thieno[3,2-b]pyridin-7-yloxy)phenyl)urea<br>$^1$H NMR (400 MHz, DMSO-$d_6$) δ (ppm): 8.76 (bs, 1H), 8.54 (bd, J = 1.4 Hz, 1H), 8.52 (d, J = 5.5 Hz, 1H), 8.32 (s, 1H), 8.23 (d, J = 8.2 Hz, 1H), 7.85 (dd, J = 8.1, 2.1 Hz, 1H), 7.73 (dd, J = 13.6, 2.4 Hz, 1H), 7.38 (t, J = 9.1 Hz, 1H), 7.20 (bdd, J = 8.8, 1.4 Hz, 1H), 6.64 (dd, J = 5.4, 0.7 Hz, 1H), 6.62 (bs, 1H), 4.04 (s, 1H), 3.53 (s, 2H), 2.64-2.50 (m, 5H), 2.48-2.32 (m, 4H), 2.18 (s, 2H), 1.06 (s, 6H), 0.72-0.58 (m, 2H), 0.49-0.37 (m, 2H). MS (m/z): 591.6 (M + H). |
| 571 | 401 | 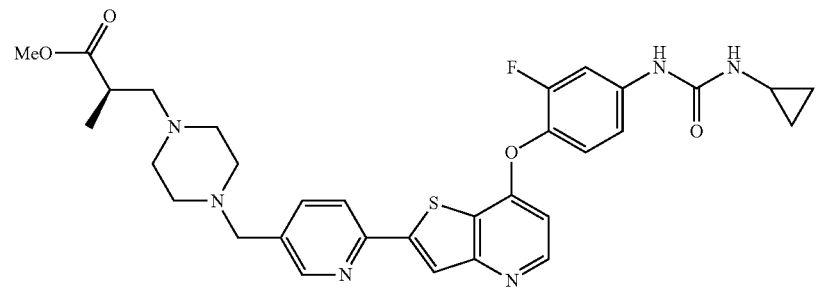 | (R)-methyl 3-(4-((6-(7-(4-(3-cyclopropylureido)-2-fluorophenoxy)thieno[3,2-b]pyridin-2-yl)pyridin-3-yl)methyl)piperazin-1-yl)-2-methylpropanoate<br>MS (m/z): 619.7 (M + H). |
| 572 | 402 | 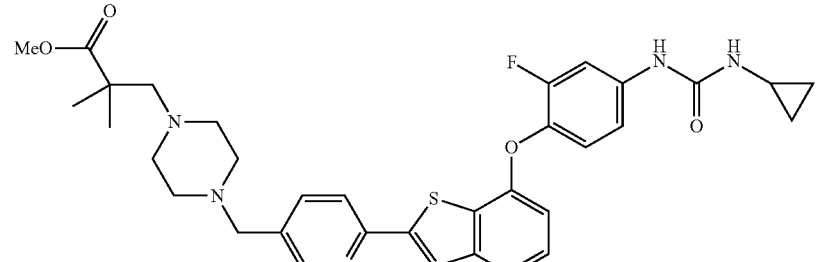 | methyl 3-(4-((6-(7-(4-(3-cyclopropylureido)-2-fluorophenoxy)thieno[3,2-b]pyridin-2-yl)pyridin-3-yl)methyl)piperazin-1-yl)-2,2-dimethylpropanoate<br>MS (m/z): 633.6 (M + H). |
| 573 | 403 | 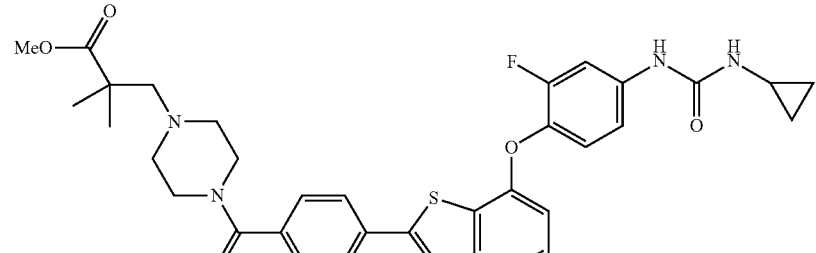 | methyl 3-(4-(6-(7-(4-(3-cyclopropylureido)-2-fluorophenoxy)thieno[3,2-b]pyridin-2-yl)nicotinoyl)piperazin-1-yl)-2,2-dimethylpropanoate<br>MS (m/z): 647.6 (M + H). |

Compounds 574-576 (examples 404-406) were prepared in one step by hydrolysis of the esters 571-573, in the presence of excess sodium hydroxide at 65-70° C., similarly to compound 61 (example 44, scheme 16) with a final purification by preparative HPLC.

TABLE 53

Characterization of compounds 4574-576 (examples 404-406).

| Cpd | Ex. | Structure | Characterization |
|---|---|---|---|
| 574 | 404 | 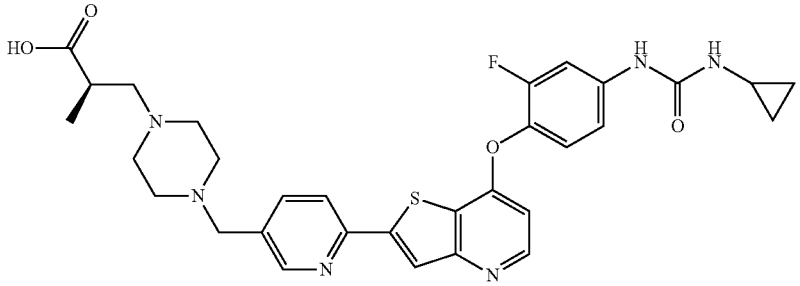 (R)-3-(4-((6-(7-(4-(3-cyclopropylureido)-2-fluorophenoxy)thieno[3,2-b]pyridin-2-yl)pyridin-3-yl)methyl)piperazin-1-yl)-2-methylpropanoic acid | $^1$H NMR (400 MHz, MeOH-d$_4$) δ (ppm): one O$\underline{H}$ carboxylic acid is missing, 10.34 (bs, 1H), 8.53 (bd, J = 1.4 Hz, 1H), 8.50 (d, J = 5.3 Hz, 1H), 8.29 (s, 1H), 8.21 (d, J = 8.2 Hz, 1H), 8.06 (bs, 1H), 7.83 (dd, J = 8.1, 2.1 Hz, 1H), 7.76 (dd, J = 13.8, 2.4 Hz, 1H), 7.33 (t, J = 9.0 Hz, 1H), 7.26 (dd, J = 9.0, 1.8 Hz, 1H), 6.62 (dd, J = 5.3, 0.8 Hz, 1H), 3.52 (s, 2H), 2.58-2.51 (m, 1H), one CH is hidden, 2.49-2.18 (m, 10H), 0.97 (d, J = 6.8 Hz, 3H), 0.66-0.52 (m, 2H), 0.47-0.34 (m, 2H). MS (m/z): 605.6 (M + H). |
| 575 | 405 | 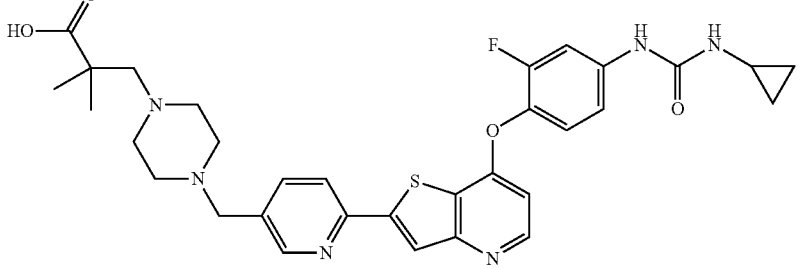 3-(4-((6-(7-(4-(3-cyclopropylureido)-2-fluorophenoxy)thieno[3,2-b]pyridin-2-yl)pyridin-3-yl)methyl)piperazin-1-yl)-2,2-dimethylpropanoic acid | $^1$H NMR (400 MHz, DMSO-d$_6$) δ (ppm): 12.54 (bs, 1H), 8.73 (s, 1H), 8.53 (bd, J = 1.4 Hz, 1H), 8.52 (d, J = 5.3 Hz, 1H), 8.33 (s, 1H), 8.24 (d, J = 8.0 Hz, 1H), 7.84 (dd, J = 8.1, 2.1 Hz, 1H), 7.73 (dd, J = 13.6, 2.4 Hz, 1H), 7.38 (t, J = 9.1 Hz, 1H), 7.20 (bd, J = 8.8 Hz, 1H), 6.64 (dd, J = 5.5, 0.6 Hz, 1H), 6.59 (bd, J = 2.3 Hz, 1H), 3.53 (s, 2H), 2.59-2.52 (m, 1H), 4$\underline{H}$ are hidden by solvent peak's, 2.44 (s, 2H), 2.39 (bs, 4H), 1.05 (s, 6H), 0.72-0.58 (m, 2H), 0.49-0.36 (m, 2H). MS (m/z): 619.6 (M + H). |
| 576 | 406 | 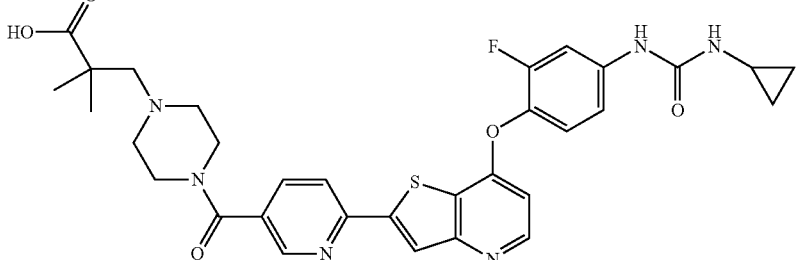 3-(4-(6-(7-(4-(3-cyclopropylureido)-2-fluorophenoxy)thieno[3,2-b]pyridin-2-yl)nicotinoyl)piperazin-1-yl)-2,2-dimethylpropanoic acid | $^1$H NMR (400 MHz, DMSO-d$_6$) δ (ppm): OH from carboxylic acid is missing, 11.22 (bs, 1H), 8.89 (bs, 1H), 8.58 (dd, J = 2.1, 0.7 Hz, 1H), 8.43 (d, J = 5.5 Hz, 1H), 8.30 (s, 1H), 8.23 (d, J = 8.2 Hz, 1H), 7.89 (dd, J = 8.1, 2.1 Hz, 1H), 7.73 (dd, J = 13.9, 2.2 Hz, 1H), 7.34-7.24 (m, 2H), 6.46 (d, J = 5.3 Hz, 1H), 3.64-3.50 (m, 2H), 3.30-3.18 (m, 2H), 5$\underline{H}$ are hidden by solvent peak's, 2.43 (s, 2H), 1.00 (s, 6H), 0.64-0.50 (m, 2H), 0.45-0.32 (m, 2H). MS (m/z): 633.6 (M + H). |

Intermediates 577-579 (examples 407-409) were prepared in one step starting from 550 (example 387), 527 (example 364) and 530 (example 367), respectively, and excess (2-bromoethoxy)-tert-butyldimethylsilane similarly to compound 512 (example 351, scheme 83). Compound 580 (example 410) was prepared in one step starting from 550 (example 351) and excess methyl 3-bromopropionate similarly to compound 512 (example 351, scheme 83).

TABLE 54

Characterization of Intermediates 577-579 and Final compound 580 (example 410).

| Cpd | Ex. | Structure | Characterization |
|---|---|---|---|
| 577 | 407 | 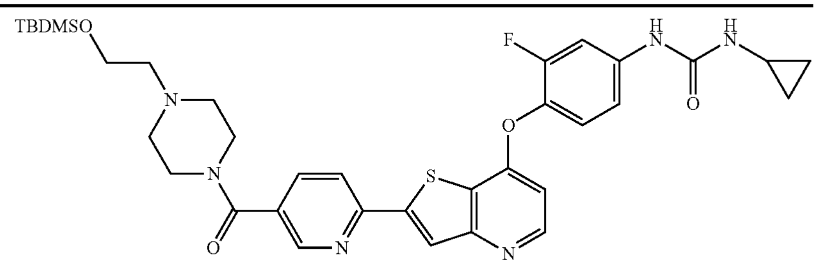 | 1-(4-(2-(5-(4-(2-(tert-butyldimethylsilyloxy)ethyl)piperazine-1-carbonyl)pyridin-2-yl)thieno[3,2-b]pyridin-7-yloxy)-3-fluorophenyl)-3-cyclopropylurea<br>MS (m/z): 691.6 (M + H). |
| 578 | 408 | 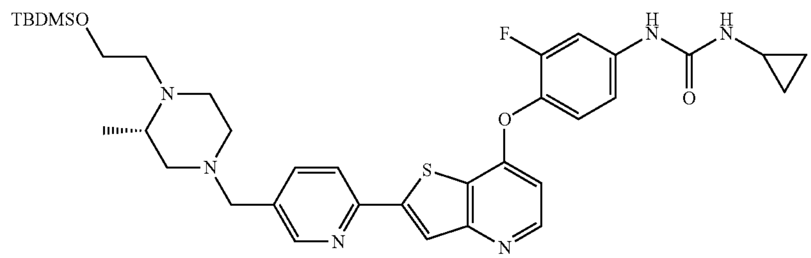 | (S)-1-(4-(2-(5-((4-(2-(tert-butyldimethylsilyloxy)ethyl)-3-methylpiperazin-1-yl)methyl)pyridin-2-yl)thieno[3,2-b]pyridin-7-yloxy)-3-fluorophenyl)-3-cyclopropylurea<br>MS (m/z): 691.6 (M + H). |
| 579 | 409 | 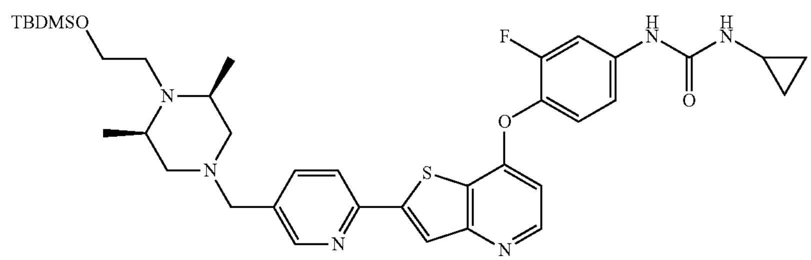 | 1-(4-(2-(5-(((3S,5R)-4-(2-(tert-butyldimethylsilyloxy)ethyl)-3,5-dimethylpiperazin-1-yl)methyl)pyridin-2-yl)thieno[3,2-b]pyridin-7-yloxy)-3-fluorophenyl)-3-cyclopropylurea<br>MS (m/z): 705.7 (M + H). |
| 580 | 410 | 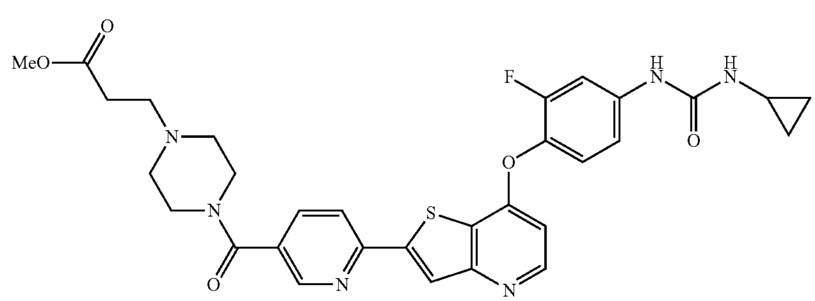 | methyl 3-(4-(6-(7-(4-(3-cyclopropylureido)-2-fluorophenoxy)thieno[3,2-b]pyridin-2-yl)nicotinoyl)piperazin-1-yl)propanoate<br>¹H NMR (400 MHz, DMSO-d₆) δ (ppm): 8.74 (s, 1H), 8.67 (dd, J = 2.2, 0.8 Hz, 1H), 8.55 (d, J = 5.3 Hz, 1H), 8.46 (s, 1H), 8.36 (dd, J = 8.2, 0.8 Hz, 1H), 7.99 (dd, J = 8.2, |

TABLE 54-continued

Characterization of Intermediates 577-579 and Final compound 580 (example 410).

| Cpd | Ex. | Structure | Characterization |
|---|---|---|---|
| | | | 2.2 Hz, 1H), 7.73 (dd, J = 13.6, 2.4 Hz, 1H), 7.39 (t, J = 9.0 Hz, 1H), 7.21 (dd, J = 8.9, 1.3 Hz, 1H), 6.68 (dd, J = 5.4, 0.7 Hz, 1H), 6.60 (bd, J = 2.5 Hz, 1H), 3.74-3.52 (m, 5H), 2H are hidden by the water peak, 2.65-2.32 (m, 9H), 0.72-0.58 (m, 2H), 0.50-0.36 (m, 2H). MS (m/z): 619.3 (M + H). |

Scheme 90

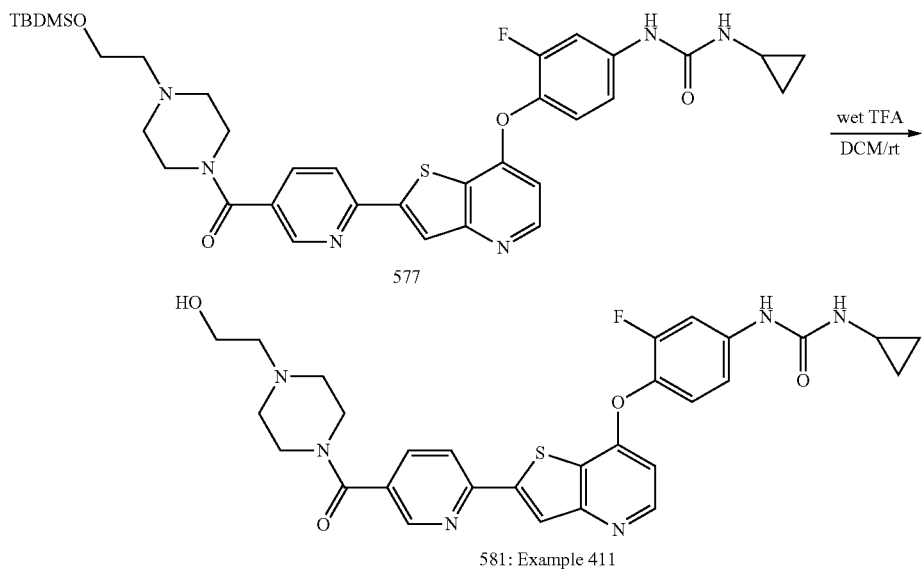

Example 411

1-cyclopropyl-3-(3-fluoro-4-(2-(5-(4-(2-hydroxy-ethyl)piperazine-1-carbonyl)pyridin-2-yl)thieno[3,2-b]pyridin-7-yloxy)phenyl)urea (581)

A solution of 577 (190 mg, 0.275 mmol) and wet TFA (2 ml) in DCM (5 ml) was stirred at rt for 1.5 h. More TFA (2 mL) were added and the reaction mixture was stirred at rt for 3.5 h and stored in the freezer overnight. The reaction mixture was then concentrated (azeotropes with DCM), diluted in water, stirred for 5 min and the pH was adjusted to around 12-13 with 1N NaOH. The resulting suspension was stirred and sonicated for 30 min: the solid was collected by filtration, rinsed with water, and air-dried. The crude product was purified by Biotage (Snap 25 g cartridge, 2% of ammonium hydroxide in MeOH/DCM: 1/99 to 15/85 over 30 CV), to afford the desired product 581 (109 mg, 0.19 mmol, 68% yield) as an off-white powder. $^1$H NMR (400 MHz, DMSO-$d_6$) δ (ppm): 8.72 (s, 1H), 8.67 (dd, J=2.2, 0.8 Hz, 1H), 8.54 (d, J=5.5 Hz, 1H), 8.46 (s, 1H), 8.36 (dd, J=8.1, 0.9 Hz, 1H), 7.99 (dd, J=8.2, 2.2 Hz, 1H), 7.73 (dd, J=13.5, 2.5 Hz, 1H), 7.39 (t, J=9.0 Hz, 1H), 7.21 (dd, J=9.0, 1.2 Hz, 1H), 6.68 (dd, J=5.3, 0.8 Hz, 1H), 6.58 (bd, J=2.5 Hz, 1H), 4.46 (t, J=5.4 Hz, 1H), 3.74-3.56 (m, 2H), 3.51 (q, J=5.9 Hz, 2H), 3.44-3.32 (m, 2H), 2.59-2.51 (m, 1H), one CH$_2$ is hidden, 2.43 (t, J=6.2 Hz, 4H), 0.72-0.58 (m, 2H), 0.49-0.37 (m, 2H). MS (m/z): 577.4 (M+H).

Scheme 91

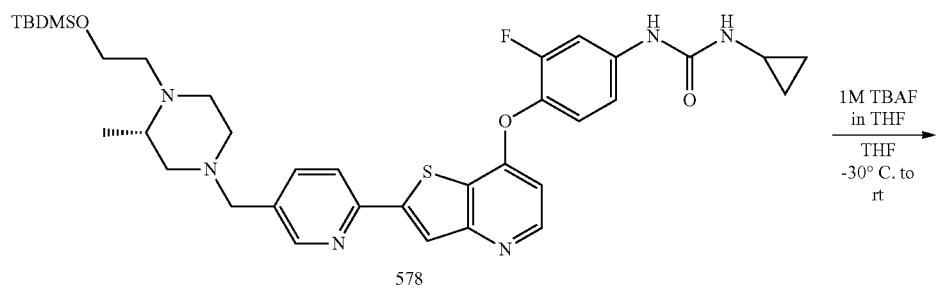

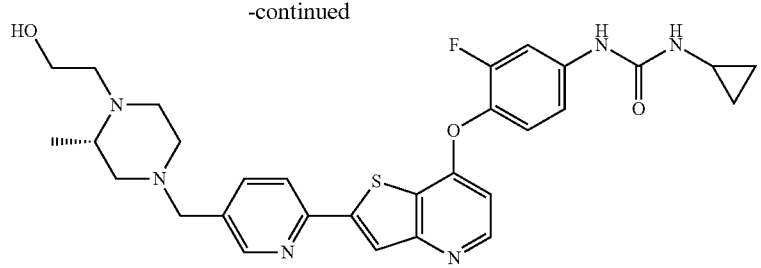

582: Example 412

Example 412

(S)-1-cyclopropyl-3-(3-fluoro-4-(2-(5-((4-(2-hydroxyethyl)-3-methylpiperazin-1-yl)methyl)pyridin-2-yl)thieno[3,2-b]pyridin-7-yloxy)phenyl)urea (582)

To a stirred solution of 578 (134 mg, 0.20 mmol) in THF (5 ml) at −30° C. was added a solution of TBAF (0.4 ml, 0.4 mmol). The reaction mixture was allowed to warm to rt over 2 hrs, and more TBAF (1 ml, 1 mmol) was added. After 2 hrs at rt, the reaction mixture was concentrated, diluted with water and sonicated for 30 min. The solid was collected by filtration, rinsed with water and air-dried. The crude product was purified twice by Biotage (Snap 25 g cartridge, 2% of ammonium hydroxide in MeOH/DCM: 1/99 to 20/80 over 20 CV), to afford the desired product 578 (99 mg, 0.17 mmol, 86% yield) as a white sticky solid. $^1$H NMR (400 MHz, DMSO-$d_6$) δ (ppm): 8.72 (s, 1H), 8.54 (bd, J=1.6 Hz, 1H), 8.52 (d, J=5.5 Hz, 1H), 8.32 (s, 1H), 8.24 (dd, J=8.1, 0.7 Hz, 1H), 7.85 (dd, J=8.1, 2.1 Hz, 1H), 7.73 (dd, J=13.5, 2.5 Hz, 1H), 7.38 (t, J=9.0 Hz, 1H), 7.20 (dd, J=8.8, 1.4 Hz, 1H), 6.64 (dd, J=5.3, 0.8 Hz, 1H), 6.57 (bd, J=2.5 Hz, 1H), 4.50-4.22 (m, 1H), 3.51 (s, 2H), 3.49-3.41 (m, 2H), 2.88-2.51 (m, 5H), 2.48-2.10 (m, 4H), 1.98-1.80 (m, 1H), 0.96 (d, J=6.3 Hz, 3H), 0.72-0.58 (m, 2H), 0.50-0.36 (m, 2H). MS (m/z): 577.5 (M+H).

Compound 583 (example 413) was prepared in one step starting from 579 (example 409) by deprotection with TBAF, similarly to compound 582 (example 412). Compound 584 (example 414) was prepared in two steps starting from 550 (example 387) similarly to compound 31 (example 17, scheme 13). Compound 585 (example 415) were prepared in one step by coupling 74 (example 54, scheme 20) with a corresponding protected aminoacid similarly to compound 78 (scheme 21) in the presence of DMAP and DCC.

TABLE 55

Characterization of compounds 583-585 (examples 413-415)

| Cpd | Ex. | Structure | Characterization |
|---|---|---|---|
| 583 | 413 | (structure shown) | 1-cyclopropyl-3-(3-fluoro-4-(2-(5-(((3S,5R)-4-(2-hydroxyethyl)-3,5-dimethylpiperazin-1-yl)methyl)pyridin-2-yl)thieno[3,2-b]pyridin-7-yloxy)phenyl)urea<br>$^1$H NMR (400 MHz. DMSO-$d_6$) δ (ppm): 8.79 (s, 1H), 8.55 (s, 1H), 8.52 (d, J = 5.5 Hz, 1H), 8.33 (s, 1H), 8.25 (d, J = 8.2 Hz, 1H), 7.85 (bd, J = 7.2 Hz, 1H), 7.73 (dd, J = 13.5, 2.5 Hz, 1H), 7.38 (t, J = 9.1 Hz, 1H), 7.20 (dd, J = 8.7, 1.3 Hz, 1H), 6.65 (dd, J = 5.4, 0.7 Hz, 1H), 6.61 (bd, J = 2.5 Hz, 1H), 4.60-4.20 (m, 0.6H), 3.60-3.40 (m, 2H), two CH$_2$ are hidden, 2.80-2.51 (m, 5H), 1.95-0.80 (m, 8H), 0.72-0.58 (m, 2H), 0.49-0.36 (m, 2H). MS (m/z): 591.3 (M + H). |
| 584 | 414 | (structure shown) | 1-cyclopropyl-3-(3-fluoro-4-(2-(5-(4-(2-hydroxyacetyl)piperazine-1-carbonyl)pyridin-2-yl)thieno[3,2-b]pyridin-7-yloxy)phenyl)urea<br>$^1$H NMR (400 MHz, DMSO-$d_6$) δ (ppm): 8.77-8.70 (m, 2H), 8.55 (d, J = 5.5 Hz, 1H), 8.47 |

TABLE 55-continued
Characterization of compounds 583-585 (examples 413-415)
| Cpd | Ex. | Structure | Characterization |
|---|---|---|---|
| | | | (s, 1H), 8.38 (dd, J = 8.2, 0.8 Hz, 1H), 8.03 (dd, J = 8.1, 2.1 Hz, 1H), 7.73 (dd, J = 13.5, 2.5 Hz, 1H), 7.39 (t, J = 9.1 Hz, 1H), 7.21 (dd, J = 9.1, 1.3 Hz, 1H), 6.68 (dd, J = 5.4, 0.7 Hz, 1H), 6.59 (bd, J = 2.3 Hz, 1H), 4.70 (t, J = 5.6 Hz, 1H), 4.21-4.04 (m, 2H), 3.75-3.37 (m, 8H), 2.59-2.51 (m, 1H), 0.72-0.58 (m, 2H), 0.50-0.36 (m, 2H). MS (m/z): 591.4 (M + H). |
| 585 | 415 | 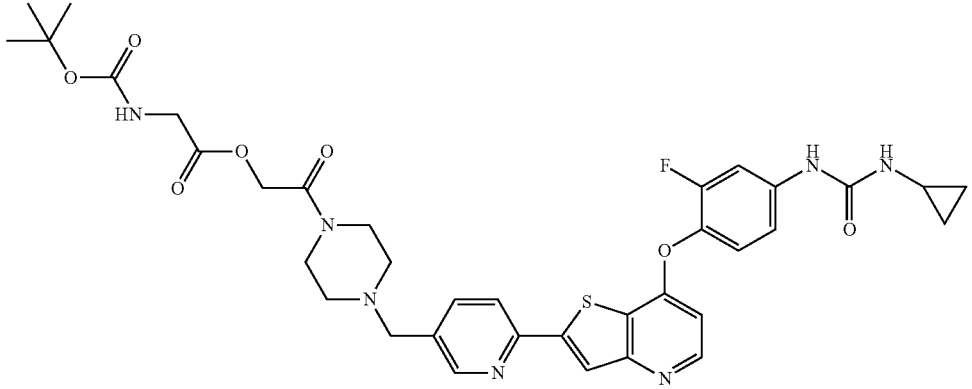 2-(4-((6-(7-(4-(3-cyclopropylureido)-2-fluorophenoxy)thieno[3,2-b]pyridin-2-yl)pyridin-3-yl)methyl)piperazin-1-yl)-2-oxoethyl 2-(tert-butoxycarbonylamino)acetate | MS (m/z): 734.4 (M + H). |
Scheme 92
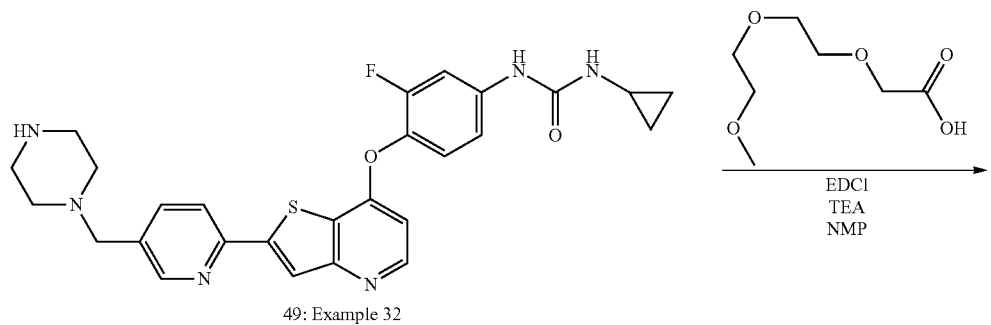
49: Example 32
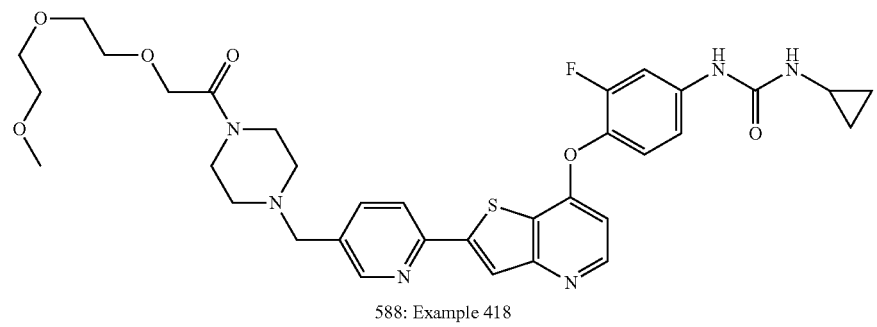
588: Example 418

Example 418

1-Cyclopropyl-3-(3-fluoro-4-(2-(5-((4-(2-(2-(2-methoxyethoxy)ethoxy)acetyl)piperazin-1-yl)methyl)pyridin-2-yl)thieno[3,2-b]pyridin-7-yloxy)phenyl)urea (588)

To a solution of compound 49 (0.050 g, 0.10 mmol, scheme 15), 24242-methoxyethoxy)ethoxy)acetyl acid (0.35 g, 0.20 mmol), and TEA (0.040 g, 0.40 mmol) in NMP (1 was added EDCI (0.037 g, 1.9 mmol). The resultant mixture was stirred at room temperature for 24 h, diluted with water and extracted with EtOAc. The organic layer was washed with water, brine; dried over MgSO₄ and concentrated. The residue was purified by flash chromatography on silica gel (EtOAc/MeOH) to afford title compound 588 (0.022 g, 34% yield) as a white powder. ¹H NMR (300 MHz, MeOH-d₄) δ (ppm): 8.62 (d, J=1.5 Hz, 1H), 8.50 (d, J=5.4 Hz, 1H), 8.12 (d, J=7.2 Hz, 1H), 8.11 (s, 1H), 7.96 (dd, J=1.8, 8.1 Hz, 1H), 7.70 (dd, J=2.7, 13.2 Hz, 1H), 7.33 (t, J=8.7 Hz, 1H), 7.25-7.21 (m, 1H), 6.67 (d, J=5.7 Hz, 1H), 4.28 (s, 2H), 3.70-3.54 (m, 14H), 3.68 (s, 3H), 2.63 (tt, J=3.9 Hz, 1H), 2.61-2.54 (m, 4H), 0.83-0.75 (m, 2H), 0.60-0.53 (m, 2H). [Peaks of the two NH protons were not observed]. MS (m/z): 679.2 (M+H).

Compound 589 (example 419) was prepared in one step by coupling of compound 49 with an appropriate acid similarly to compound 588 (example 418, scheme 92).

TABLE 56

Characterization of compounds 589-591 (examples 419-421).

| Cpd | Ex. | Structure | Characterization |
|---|---|---|---|
| 589 | 419 | 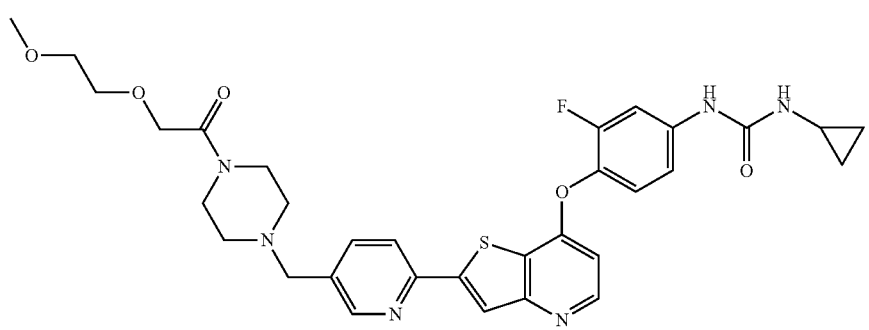 | 1-cyclopropyl-3-(3-fluoro-4-(2-(5-((4-(2-(2-methoxyethoxy)acetyl)piperazin-1-yl)methyl)pyridin-2-yl)thieno[3,2-b]pyridin-7-yloxy)phenyl)urea<br>¹H NMR (300 MHz, MeOH-d₄) δ (ppm): 8.62 (s, 1H), 8.50 (d, J = 5.4 Hz, 1H), 8.12 (d, J = 7.8 Hz, 1H), 8.11 (s, 1H), 7.96 (dd, J = 2.4, 8.1 Hz, 1H), 7.70 (dd, J = 2.4, 12.9 Hz, 1H), 7.33 (t, J = 8.7 Hz, 1H), 7.25-7.21 (m, 1H), 6.67 (dd, J = 1.2, 5.4 Hz, 1H), 4.27 (s, 2H), 3.72-3.54 (m, 10H), 3.39 (s, 3H), 2.64 (tt, J = 3.6 Hz, 1H), 2.59-2.52 (m, 4H), 0.84-0.76 (m, 2H), 0.60-0.54 (m, 2H). Peaks of the two NH protons were not observed. MS (m/z): 635.3 (M + H). |

Scheme 94

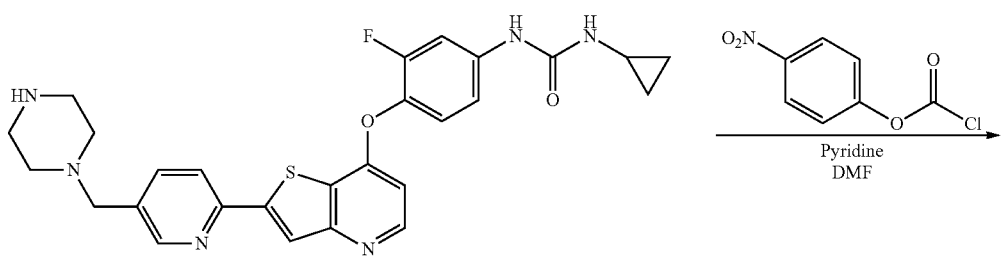

49: Example 32

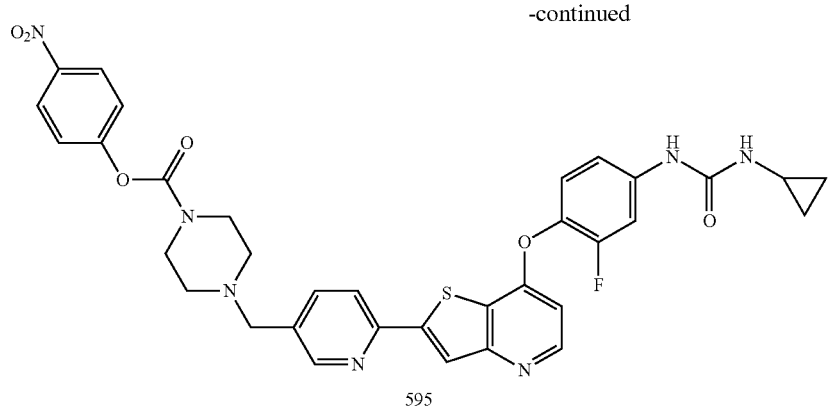
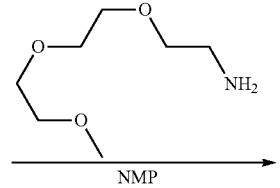

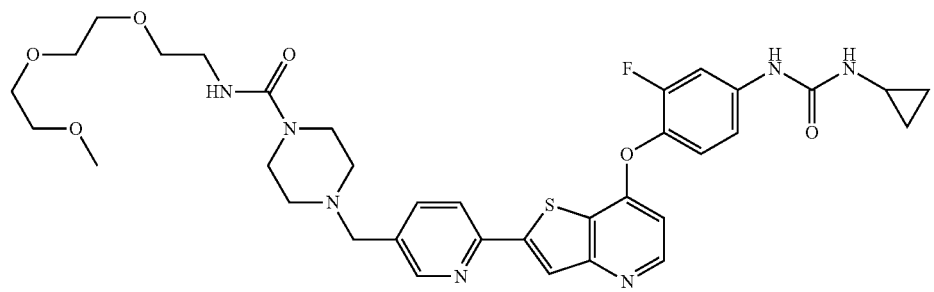

596: Example 495

Example 495

4-((6-(7-(4-(3-Cyclopropylureido)-2-fluorophenoxy)thieno[3,2-b]pyridin-2-yl)pyridin-3-yl)methyl)-N-(2-(2-(2-methoxyethoxy)ethoxy)ethyl)piperazine-1-carboxamide (596)

Step 1. 4-Nitrophenyl 4-((6-(7-(4-(3-cyclopropylureido)-2-fluorophenoxy)thieno[3,2-b]pyridin-2-yl)pyridin-3-yl)methyl)piperazine-1-carboxylate (595)

To a solution of compound 49 (0.50 g, 0.96 mmol, scheme 15) and pyridine (0.11 g, 1.4 mmol) in DMF (4 mL) was added 4-nitrophenyl chlorocarbonate (0.23 g, 1.1 mmol). The resultant mixture was stirred at room temperature for 1 h, diluted with saturated NH$_4$Cl aqueous solution and extracted with EtOAc-THF (4:1 mixture). The organic layer was collected, washed with saturated NaHCO$_3$ aqueous solution, water and brine, dried over MgSO$_4$ and concentrated. The residue was triturated with t-BuOMe, to afford title compound 595 (0.42 g, 64% yield) as a beige solid. $^1$H NMR (300 MHz, DMSO-d$_6$) δ (ppm): 8.72 (s, 1H), 8.60 (s, 1H), 8.53 (d, J=5.4 Hz, 1H), 8.35 (s, 1H), 8.30-8.26 (m, 3H), 7.91 (d, J=8.1 Hz, 1H), 7.74 (dd, J=2.4, 10.8 Hz, 1H), 7.45 (d, J=8.7 Hz, 2H), 7.39 (t, J=9.0 Hz, 1H), 7.21 (d, J=9.0 Hz, 1H), 6.66 (d, J=5.1 Hz, 1H), 6.58 (s, 1H), 3.65 (brs, 4H), 3.49 (brs, 2H), 3.34 (brs, 4H), 2.58-2.54 (m, 1H), 0.70-0.63 (m, 2H), 0.47-0.43 (m, 2H).

Step 2. 4-((6-(7-(4-(3-Cyclopropylureido)-2-fluorophenoxy)thieno[3,2-b]pyridin-2-yl)pyridin-3-yl)methyl)-N-(2-(2-(2-methoxyethoxy)ethoxy)ethyl)piperazine-1-carboxamide (596)

To a solution of 595 (0.10 g, 0.15 mmol) in NMP (4 mL) was added 2-(2-(2-methoxyethoxy)ethoxy)ethanamine (0.073 g, 45 mmol). The resultant mixture was stirred at 70° C. for 32 h, diluted with saturated NH$_4$Cl aqueous solution and extracted with EtOAc-THF (4:1 mixture). The organic layer was collected, washed with saturated NaHCO$_3$ aqueous solution, water and brine, dried over MgSO$_4$ and concentrated. The residue was purified by flash chromatography on silica gel (EtOAc/MeOH) to afford title compound 596 (0.058 g, 56% yield) as an amorphous solid. $^1$H NMR (300 MHz, MeOH-d$_4$) δ (ppm): 8.61 (d, J=1.8 Hz, 1H), 8.49 (d, J=5.4 Hz, 1H), 8.12 (d, J=7.8 Hz, 1H), 8.11 (s, 1H), 7.95 (dd, J=2.4, 8.1 Hz, 1H), 7.70 (dd, J=2.7, 13.2 Hz, 1H), 7.33 (t, J=8.7 Hz, 1H), 7.25-7.21 (m, 1H), 6.67 (dd, J=1.2, 5.4 Hz, 1H), 3.70-3.61 (m, 8H), 3.57-3.52 (m, 4H), 3.50-3.43 (m, 4H), 3.40-3.25 (m, 5H), 2.64 (tt, J=3.6 Hz, 1H), 2.62-2.49 (m, 4H), 0.82-0.76 (m, 2H), 0.60-0.54 (m, 2H). [Peaks of the two NH protons were not observed]. MS (m/z): 708.4 (M+H).

Scheme 95

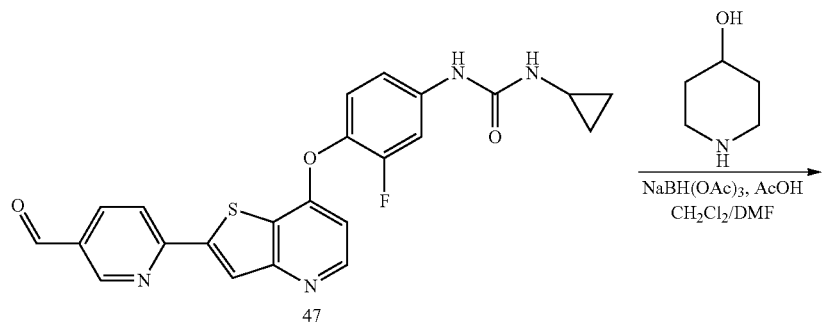

Example 498

1-Cyclopropyl-3-(3-fluoro-4-(2-(5-((4-hydroxypiperidin-1-yl)methyl)pyridin-2-yl)thieno[3,2-b]pyridin-7-yloxy)phenyl)urea (599)

To a suspension of the aldehyde 47 (0.3 g, 0.669 mmol) in a mixture of DCM (9 mL) and DMF (3 mL) were added 4-hydroxypiperidine (0.135 g, 1.34 mmol) and acetic acid (0.08 mL, 1.34 mmol) at RT. The reaction mixture was stirred for 30 min; NaBH(OAc)$_3$ (0.425 g, 2.00 mmol) was added and the reaction mixture was stirred overnight. More 4-hydroxypiperidine (0.135 g, 1.34 mmol) and NaBH(OAc)$_3$ (0.425 g, 2.00 mmol) were added to the reaction mixture that was stirred at room temperature for 4 hr, then quenched by addition of saturated NaHCO$_3$ solution and extracted with DCM/MeOH. The organic layer was washed with brine and dried over MgSO$_4$ and concentrated. The crude product was purified by flash chromatography on silica gel (DCM/MeOH: 90/10 to 75/25) then triturated with MeOH to afford title compound 599 (0.17 g, 48% yield) as a brown solid. $^1$H NMR (300 MHz, DMSO-d$_6$) δ (ppm): 8.71 (s, 1H), 8.56-8.53 (m, 1H), 8.52 (d, J=5.4 Hz, 1H), 8.31 (s, 1H), 8.23 (d, J=8.1 Hz, 1H), 7.85 (dd, J=8.4, 2.4 Hz, 1H), 7.73 (dd, J=13.5, 2.4 Hz, 1H), 7.38 (t, J=9.0 Hz, 1H), 7.24-7.18 (m, 1H), 6.65 (d, J=5.4 Hz, 1H), 6.56 (d, J=2.1 Hz, 1H), 4.58 (d, J=4.2 Hz, 1H), 3.54 (s, 2H), 3.50-3.40 (m, 1H), 2.75-2.65 (m, 2H), 2.60-2.50 (m, 1H), 2.19-2.05 (m, 2H), 1.80-1.65 (m, 2H), 1.50-1.35 (m, 2H), 0.71-0.64 (m, 2H), 0.48-0.40 (m, 2H).

Scheme 98

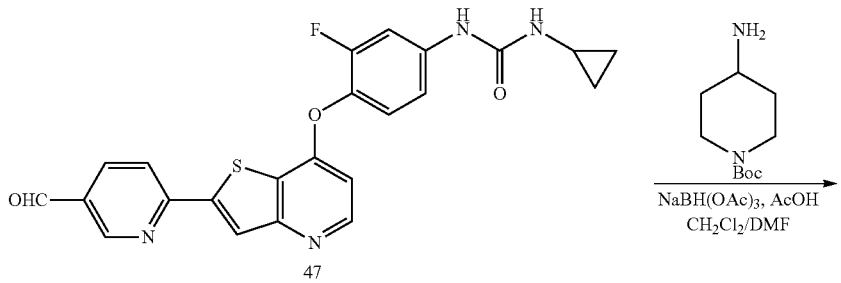

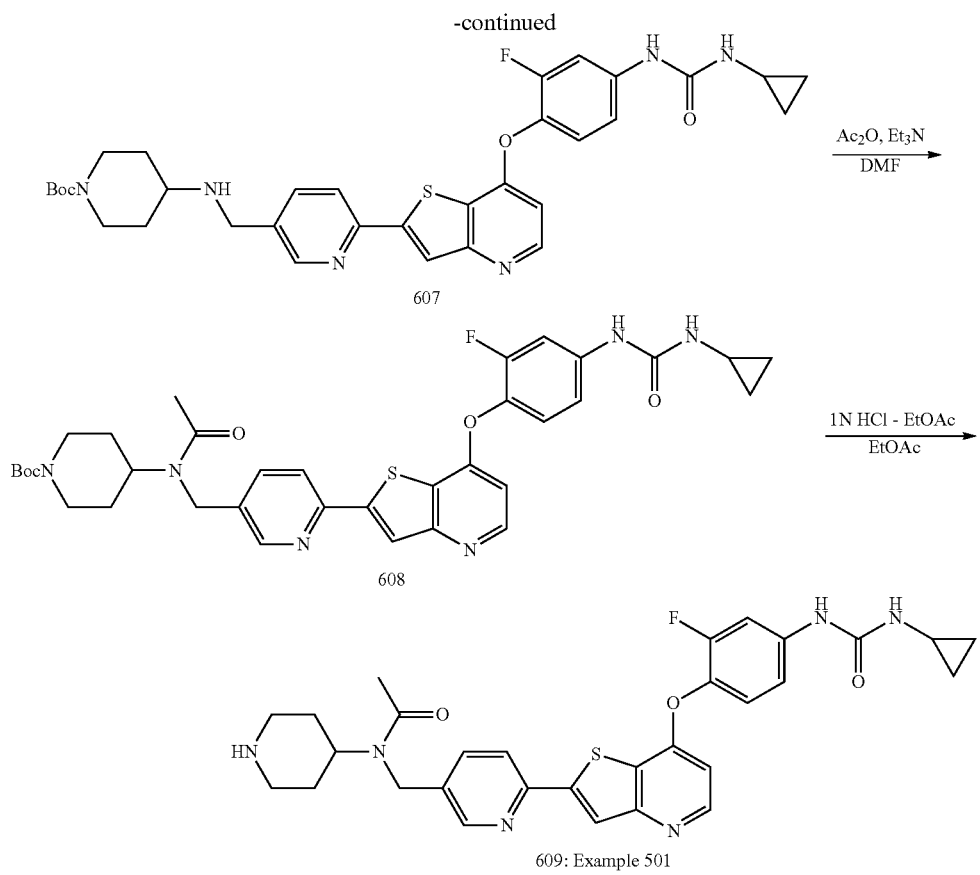

609: Example 501

Example 501

N-((6-(7-(4-(3-Cyclopropyl ureido)-2-fluorophenoxy)thieno[3,2-b]pyridin-2-yl)pyridin-3-yl)methyl)-N-(piperidin-4-yl)acetamide (609)

Step 1. tert-butyl 4-((6-(7-(4-(3-cyclopropylureido)-2-fluorophenoxy)thieno[3,2-b]pyridin-2-yl)pyridin-3-yl)methylamino)piperidine-1-carboxylate (607)

To a suspension of aldehyde 47 (0.3 g, 0.669 mmol) in a mixture of DCM (9 mL) and DMF (3 mL) were added 4-amino—Boc-piperidine (0.27 g, 1.34 mmol) and acetic acid (80 µL, 1.34 mmol) at RT. The reaction mixture was stirred for 1.5 hr, treated with NaBH(OAc)$_3$ (0.425 g, 2.00 mmol) and stirred overnight, then quenched by addition of saturated NaHCO$_3$ solution and extracted with DCM/MeOH. The extract was washed with brine, dried over MgSO$_4$ and concentrated. The residue was purified by flash chromatography on silica gel (EtOAc/MeOH: 93/7 to 84/16) to afford title compound 607 (0.355 g, 84% yield) as a pale brown solid. $^1$H NMR (300 MHz, DMSO-d$_6$) δ (ppm): 8.69 (s, 1H), 8.58 (brs, 1H), 8.51 (d, J=5.7 Hz, 1H), 8.30 (s, 1H), 8.22 (d, J=8.1 Hz, 1H), 7.91 (dd, J=8.4, 1.8 Hz, 1H), 7.72 (dd, J=13.5, 1.8 Hz, 1H), 7.37 (t, J=9.0 Hz, 1H), 7.25-7.15 (m, 1H), 6.64 (d, J=5.4 Hz, 1H), 6.55 (d, J=2.7 Hz, 1H), 3.85-3.75 (m, 2H), 3.81 (s, 2H), 2.90-2.65 (m, 2H), 1.85-1.75 (m, 2H), 1.45-1.35 (m, 1H), 1.39 (s, 9H), 1.25-1.10 (m, 2H), 0.71-0.62 (m, 2 Hz, 0.48-0.40 (m, 2H).

Step 2. tort-butyl 4-(N-((6-(7-(4-(3-cyclopropylureido)-2-fluorophenoxy)thieno[3,2-b]pyridin-2-yl)pyridin-3-yl)methyl)acetamido)piperidine-1-carboxylate (608)

To a solution of 607 (0.355 g, 0.561 mmol) in DMF (5 mL) were added TEA (0.2 mL, 1.4 mmol) and Ac$_2$O (0.12 mL, 1.12 mmol) at RT. The reaction mixture was stirred at 55° C. overnight, diluted with water and extracted with EtOAc/MeOH. The organic layer was washed with brine, dried over MgSO$_4$ and concentrated. The residue was purified by flash chromatography on silica gel (EtOAc/MeOH:90/10) to afford title compound 608 (0.314 g, 83%) as a white amorphous solid. $^1$H NMR (300 MHz, DMSO-d$_6$) δ (ppm): 8.70 (s, 1H), 8.55-8.47 (m, 2H), 8.34 (s, 0.32H), 8.30 (s, 0.78H), 8.26 (d, J=8.4 Hz, 0.3H), 8.18 (d, J=8.4 Hz, 0.7H), 7.83-7.69 (m, 2H), 7.38 (t, J=9.0 Hz, 1H), 7.25-7.15 (m, 1H), 6.68-6.62 (m, 1H), 6.56 (d, J=2.7 Hz, 1H), 4.67 (s, 0.7H), 4.54 (s, 1.3H), 4.05-3.85 (m, 3H), 2.85-2.65 (m, 2H), 2.61-2.50 (m, 1H), 2.23 (s, 2H), 2.01 (s, 1H), 1.70-1.40 (m, 4H), 1.40-1.32 (m, 9H), 0.71-0.62 (m, 2H), 0.48-0.40 (m, 2H).

Step 3. N-((6-(7-(4-(3-Cyclopropylureido)-2-fluorophenoxy)thieno[3,2-b]pyridin-2-yl)pyridin-3-yl)methyl)-N-(piperidin-4-yl)acetamide (609)

To a suspension of 608 (0.314 g, 0.465 mmol) in EtOAc (6 mL) was added 1N HCl-EtOAc (2.0 ml, 2.0 mmol) at RT. The reaction mixture was stirred overnight then concentrated and co-evaporated with EtOAc. The residue was purified by flash chromatography using Hi-Flash column (Yamazen Corporation) packed with amino silica gel (DCM/MeOH:96/4 to 80/20) to afford title compound 609 (0.193 g, 72% yield) as a white amorphous solid. $^1$H NMR (300 MHz, DMSO-$d_6$) δ (ppm): 8.71 (s, 1H), 8.54-8.46 (m, 2H), 8.34 (s, 0.3H), 8.30 (s, 0.7H), 8.26 (d, J=8.1 Hz, 0.3H), 8.18 (d, J=8.1 Hz, 0.7H), 7.82-7.69 (m, 2H), 7.38 (t, J=9.0 Hz, 1H), 7.25-7.15 (m, 1H), 6.68-6.62 (m, 1H), 6.57 (d, J=3.0 Hz, 1H), 4.66 (s, 0.7H), 4.54 (s, 1.3H), 3.90-3.75 (m, 1H), 3.00-2.90 (m, 2H), 2.61-2.40 (m, 3H), 2.20 (s, 2H), 1.99 (s, 1H), 1.65-1.40 (m, 4H), 0.71-0.62 (m, 2H), 0.48-0.40 (m, 2H).

Compound 611 (example 503) was prepared in one step via an amide coupling reaction of compound 49 (scheme 15) with 1-hydroxycyclopropanecarboxylic acid similarly to compound 115-A (example 80-A, scheme 29). Compound 612 (example 504) was obtained in two steps similarly to compound 31 (example 17, scheme 13). Compound 613 (example 504) was prepared via an amide coupling reaction of compound 343 (example 200, scheme 71) with 2[2-(2-methoxyethoxy)ethoxy]acetic acid.

TABLE 59

Characterization of compound 611-613 (example 503-505)

| Cpd | Ex. | Structure | Characterization |
|---|---|---|---|
| 611 | 503 | 1-cyclopropyl-3-(3-fluoro-4-(2-(5-((4-(1-hydroxycyclopropanecarbonyl)piperazin-1-yl)methyl)pyridin-2-yl)thieno[3,2-b]pyridin-7-yloxy)phenyl)urea | $^1$H NMR (400 MHz, DMSO-$d_6$) δ (ppm): 8.72 (s, 1H), 8.57 (bd, J = 1.4 Hz, 1H), 8.52 (d, J = 5.5 Hz, 1H), 8.34 (s, 1H), 8.26 (d, J = 8.0 Hz, 1H), 7.88 (dd J = 8.1, 2.0 Hz, 1H), 7.73 (dd, J = 13.6, 2.4 Hz, 1H), 7.38 (t, J = 9.1 Hz, 1H), 7.20 (bd, J = 8.8 Hz, 1H), 6.65 (dd, J = 5.4, 0.7 Hz, 1H), 6.58 (bd, J = 2.5 Hz, 1H), 6.44 (s, 1H), 6.36 (s, 1H), 4.33-4.27 (m, 1H), 4.16-4.10 (m, 1H), 3.59 (s, 2H), 3.52-3.40 (m, 4H), 3.13-3.06 (m, 1H), 2.82 (dd, J = 12.4, 5.0 Hz, 1H), 2.61-2.51 (m, 2H), 2.44-2.25 (m, 6H), 1.67-1.25 (m, 6H), 0.72-0.58 (m, 2H), 0.50-0.37 (m, 2H). MS (m/z): 745.7 (M + H). |
| 612 | 504 | 1-cyclopropyl-3-(3-fluoro-4-(2-(5-((4-(2-hydroxy-2-methylpropanoyl)piperazin-1-yl)methyl)pyridin-2-yl)thieno[3,2-b]pyridin-7-yloxy)phenyl)urea | $^1$H NMR (400 MHz, DMSO-$d_6$) δ (ppm): 9.10 (bs, 1H), 8.57 (bd, J = 1.4 Hz, 1H), 8.52 (d, J = 5.3 Hz, 1H), 8.33 (s, 1H), 8.25 (d, J = 8.0 Hz, 1H), 7.88 (dd, J = 8.1, 2.1 Hz, 1H), 7.74 (dd, J = 13.6, 2.4 Hz, 1H), 7.37 (t, J = 9.1 Hz, 1H), 7.22 (dd, J = 8.9, 1.5 Hz, 1H), 6.93 (bd, J = 2.2 Hz, 1H), 6.65 (dd, J = 5.5, 0.6 Hz, 1H), 5.39 (s, 1H), 4.10-3.40 (m, 6H), 2.59-2.51 (m, 1H), 2.46-2.32 (m, 4H), 1.29 (s, 6H), 0.71-0.57 (m, 2H), 0.49-0.36 (m, 2H). MS (m/z): 605.53 (M + H). |
| 613 | 505 | N-(1-((6-(7-(4-(3-cyclopropylureido)-2-fluorophenoxy)thieno[3,2-b]pyridin-2-yl)pyridin-3-yl)methyl)piperidin-4-yl)-2-(2-(2-methoxyethoxy)ethoxy)acetamide | $^1$H NMR (400 MHz, DMSO-$d_6$) δ (ppm): 8.88 (s, 1H), 8.54 (brd, J = 1.2 Hz, 1H), 8.51 (d, J = 5.2 Hz, 1H), 8.33 (s, 1H), 8.24 (d, J = 8.0 Hz, 1H), 7.84 (dd, J = 8.0, 2.0 Hz, 1H), 7.73 (dd, J = 13.6, 2.4 Hz, 1H), 7.47 (d, J = 8.4 Hz, 1H), 7.38 (t, J = 9.0 Hz, 1H), 7.23-7.18 (m, 1H), 6.73 (brd, J = 2.4 Hz, 1H), 6.64 (dd, J = 5.2, 0.8 Hz, 1H), 3.85 (s, 2H), 3.66-3.56 (m, 1H), 3.56-3.52 (m, 8H), 3.47-3.44 (m, 2H), 3.25 (s, 3H), 2.83-2.76 (m, 2H), 2.58-2.51 (m, 1H), 2.11-2.03 (m, 2H), 1.73-1.67 (m, 2H), 1.57-1.44 (m, 2H), 0.68-0.62 (m, 2H), 0.45-0.40 (m, 2H). MS (m/z): 693.69 (M + H). |

Pharmaceutical Compositions

In some embodiments, the invention provides pharmaceutical compositions comprising a compound according to the invention and a pharmaceutically acceptable carrier, excipient, or diluent. Compositions of the invention may be formulated by any method well known in the art and may be prepared for administration by any route, including, without limitation, parenteral, oral, sublingual, transdermal, topical, intranasal, intratracheal, or intrarectal. In some embodiments, compositions of the invention are administered intravenously in a hospital setting. In some embodiments, administration may be by the oral route.

The characteristics of the carrier, excipient or diluent will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

The active compound is included in the pharmaceutically acceptable carrier, excipient or diluent in an amount sufficient to deliver to a patient a therapeutically effective amount without causing serious toxic effects in the patient treated. The effective dosage range of a pharmaceutically acceptable derivative can be calculated based on the weight of the parent compound to be delivered. If the derivative exhibits activity in itself, the effective dosage can be estimated as above using the weight of the derivative, or by other means known to those skilled in the art.

Inhibition of VEGF Receptor Signaling

In some embodiments the invention provides a method of inhibiting VEGF receptor signaling in a cell, comprising contacting a cell in which inhibition of VEGF receptor signaling is desired with an inhibitor of VEGF receptor signaling according to the invention. Because compounds of the invention inhibit VEGF receptor signaling, they are useful research tools for in vitro study of the role of VEGF receptor signaling in biological processes.

In some embodiments, inhibiting VEGF receptor signaling causes an inhibition of cell proliferation of the contacted cells.

ASSAY EXAMPLES

Inhibition of VEGF Activity

The following protocol was used to assay the compounds of the invention.

Assay Example 1

In Vitro Receptor Tyrosine Kinase Assay (VEGF receptor KDR)

This test measures the ability of compounds to inhibit the enzymatic activity of recombinant human VEGF receptor enzymatic activity.

A 1.6-kb cDNA corresponding to the catalytic domain of VEGFR2 (KDR) (Genbank accession number AF035111 amino acid 806 to 1356) is cloned into the Pst I site of the pDEST20 Gateway vector (Invitrogen) for the production of a GST-tagged version of that enzyme. This construct is used to generate recombinant baculovirus using the Bac-to-Bac™ system according to the manufacturer's instructions (Invitrogen).

The GST-VEGFR2806-1356 protein is expressed in Sf9 cells (*Spodoptera frugiperda*) upon infection with recombinant baculovirus construct. Briefly, Sf9 cells grown in suspension and maintained in serum-free medium (Sf900 II supplemented with gentamycin) at a cell density of about $2 \times 10^6$ cells/ml are infected with the above-mentioned viruses at a multiplicity of infection (MOI) of 0.1 during 72 hours at 27° C. with agitation at 120 rpm on a rotary shaker. Infected cells are harvested by centrifugation at 398 g for 15 min. Cell pellets are frozen at −80° C. until purification is performed.

All steps described in cell extraction and purification are performed at 4° C. Frozen. Sf9 cell pellets infected with the GST-VEGFR2806-1356 recombinant baculovirus are thawed and gently resuspended in Buffer A (PBS pH 7.3 supplemented with 1 μg/ml pepstatin, 2 μg/ml Aprotinin and leupeptin, 50 μg/ml PMSF, 50 μg/ml TLCK and 10 μM E64 and 0.5 mM DTT) using 3 ml of buffer per gram of cells. Suspension is Dounce homogenized and 1% Triton X-100 is added to the homogenate after which it is centrifuged at 22500 g, 30 min., 4° C. The supernatant (cell extract) is used as starting material for purification of GST-VEGFR2806-1356.

The supernatant is loaded onto a GST-agarose column (Sigma) equilibrated with PBS pH 7.3. Following a four column volume (CV) wash with PBS pH 7.3+1% Triton X-100 and 4 CV wash with buffer B (50 mM Tris pH 8.0, 20% glycerol and 100 mM NaCl), bound proteins are step eluted with 5 CV of buffer B supplemented with 5 mM DTT and 15 mM glutathion. GST-VEGFR2806-1356 enriched fractions from this chromatography step are pooled based on U.V. trace i.e. fractions with high O.D.280. Final GST-VEGFR2806-1356 protein preparations concentrations are about 0.7 mg/ml with purity approximating 70%. Purified GST-VEGFR2806-1356 protein stocks are aliquoted and frozen at −80° C. prior to use in enzymatic assay.

Inhibition of VEGFR/KDR is measured in a DELFIA™ assay (Perkin Elmer). The substrate poly(Glu4, Tyr) is immobilized onto black high-binding polystyrene 96-well plates. The coated plates are washed and stored at 4° C. During the assay, the enzyme is pre-incubated with inhibitor and Mg-ATP on ice in polypropylene 96-well plates for 4 minutes, and then transferred to the coated plates. The subsequent kinase reaction takes place at 30° C. for 10-30 minutes. ATP concentrations in the assay are 0.6 uM for VEGFR/KDR (2× the Km). Enzyme concentration is 5 nM. After incubation, the kinase reactions are quenched with EDTA and the plates are washed. Phosphorylated product is detected by incubation with Europium-labeled anti-phosphotyrosine MoAb. After washing the plates, bound MoAb is detected by time-resolved fluorescence in a Gemini SpectraMax reader (Molecular Devices). Compounds are evaluated over a range of concentrations, and $IC_{50}$ values (concentration of compounds giving 50% inhibition of enzymatic activity) are determined. The results are shown in Table 60. In the table, "a" indicates an $IC_{50}$ value of less than 50 nanomolar; "b" indicates an $IC_{50}$ value of 50 but <100 nanomolar; "c" indicates an $IC_{50}$ value of ≥100 but <250 nanomolar; and "d" indicates an $IC_{50}$ value of ≥250 nanomolar.

TABLE 60

| Cpd No | VEGFR IC$_{50}$ μM |
|---|---|
| 116 | a |
| 85 | a |
| 88 | a |
| 113 | a |
| 92 | a |
| 3 | a |
| 114 | a |
| 105 | a |
| 115 | a |
| 201 | a |
| 50 | a |
| 25 | a |
| 51 | a |
| 106 | a |
| 8 | b |
| 119 | c |
| 89 | a |
| 86 | a |
| 120 | c |
| 117 | a |
| 14 | d |
| 92-A | a |
| 7 | a |
| 90 | a |
| 123 | a |
| 127 | a |
| 129 | a |
| 130 | a |
| 128 | a |
| 9 | a |
| 93 | a |
| 10 | a |
| 20 | a |
| 19 | a |
| 193 | a |
| 21 | a |
| 194 | a |
| 137 | a |
| 117-A | b |
| 39 | a |
| 4 | a |
| 5 | a |
| 205 | b |
| 43 | a |
| 140 | a |
| 115-A | a |
| 195 | a |
| 49 | a |
| 52 | a |
| 54 | a |
| 53 | a |
| 66 | a |
| 55 | a |
| 108 | a |
| 141 | a |
| 142 | a |
| 67 | a |
| 225 | a |
| 143 | a |
| 72 | a |
| 44 | a |
| 110 | a |
| 259-A | a |
| 217 | a |
| 109 | a |
| 218 | a |
| 45 | a |
| 36 | a |
| 73 | a |
| 35 | a |
| 212 | a |
| 169 | a |
| 70 | a |
| 298 | a |
| 299 | a |
| 111 | a |
| 161-B | a |
| 40 | b |

TABLE 60-continued

| Cpd No | VEGFR IC$_{50}$ μM |
|---|---|
| 161-A | a |
| 222 | a |
| 29 | c |
| 223 | c |
| 253 | a |
| 37 | c |
| 224 | a |
| 254-A | a |
| 235 | a |
| 31 | c |
| 171 | a |
| 227 | a |
| 183 | a |
| 185 | a |
| 34 | a |
| 187 | a |
| 288 | a |
| 38 | a |
| 228 | a |
| 41 | a |
| 229 | a |
| 46 | a |
| 236 | a |
| 168 | a |
| 170 | a |
| 256 | a |
| 50-A | a |
| 258 | a |
| 13 | b |
| 239 | a |
| 237 | a |
| 172 | a |
| 42 | b |
| 154 | a |
| 230 | a |
| 231 | a |
| 58 | a |
| 59 | a |
| 60 | a |
| 232 | a |
| 155 | a |
| 62 | a |
| 63 | a |
| 61 | a |
| 266 | a |
| 48 | a |
| 178 | a |
| 267 | a |
| 283 | a |
| 259 | a |
| 273 | d |
| 76 | a |
| 157 | a |
| 190 | a |
| 238 | a |
| 274 | a |
| 240 | a |
| 275 | a |
| 77 | a |
| 82 | a |
| 241 | a |
| 173 | a |
| 276 | b |
| 79 | a |
| 80 | a |
| 247 | a |
| 254 | a |
| 83 | a |
| 189 | a |
| 255 | b |
| 233 | a |
| 56 | a |
| 257 | a |
| 271-A | b |
| 81 | a |
| 244 | a |
| 180 | a |
| 161 | a |

TABLE 60-continued

| Cpd No | VEGFR IC$_{50}$ μM |
|---|---|
| 57 | a |
| 54-A | a |
| 54-E | a |
| 166 | a |
| 84 | a |
| 54-F | a |
| 54-G | a |
| 277 | c |
| 54-B | a |
| 310 | a |
| 295 | a |
| 311 | a |
| 315 | a |
| 316 | a |
| 54-D | A |
| 68 | a |
| 293 | a |
| 323 | a |
| 324 | a |
| 325 | a |
| 326 | a |
| 327 | a |
| 328 | a |
| 329 | a |
| 330 | a |
| 331 | a |
| 332 | a |
| 333 | a |
| 334 | a |
| 335 | a |
| 339 | a |
| 340 | a |
| 341 | a |
| 343 | a |
| 344 | a |
| 345 | a |
| 346 | a |
| 347 | a |
| 348 | a |
| 349 | a |
| 350 | a |
| 351 | a |
| 352 | a |
| 353 | a |
| 354 | a |
| 355 | a |
| 357 | a |
| 358 | a |
| 363 | a |
| 364 | a |
| 365 | a |
| 367 | b |
| 368 | a |
| 369 | a |
| 372 | a |
| 373 | a |
| 375 | a |
| 376 | a |
| 377 | a |
| 378 | a |
| 379 | a |
| 380 | a |
| 381 | a |
| 382 | a |
| 383 | a |
| 384 | a |
| 385 | a |
| 386 | a |
| 387 | a |
| 388 | a |
| 389 | a |
| 390 | a |
| 391 | a |
| 392 | a |
| 394 | a |
| 395 | a |
| 396 | a |
| 397 | a |
| 399 | a |
| 400 | a |
| 401 | a |
| 402 | a |
| 405 | a |
| 406 | a |
| 407 | a |
| 408 | a |
| 409 | a |
| 410 | a |
| 411 | a |
| 412 | a |
| 413 | a |
| 414 | a |
| 416 | a |
| 417 | a |
| 418 | a |
| 420 | a |
| 421 | a |
| 422 | a |
| 423 | a |
| 424 | a |
| 426 | a |
| 427 | a |
| 428 | a |
| 429 | d |
| 434 | a |
| 440 | d |
| 441 | a |
| 442 | a |
| 443 | d |
| 444 | a |
| 445 | a |
| 446 | a |
| 447 | a |
| 448 | c |
| 449 | a |
| 450 | a |
| 451 | d |
| 452 | a |
| 453 | a |
| 454 | a |
| 455 | c |
| 456 | a |
| 457 | b |
| 458 | b |
| 460 | a |
| 462 | a |
| 465 | b |
| 466 | a |
| 467 | a |
| 468 | a |
| 471 | b |
| 472 | b |
| 473 | a |
| 475 | a |
| 476 | a |
| 477 | a |
| 478 | a |
| 480 | a |
| 481 | a |
| 482 | a |
| 483 | a |
| 484 | a |
| 485 | a |
| 486 | a |
| 487 | a |
| 488 | a |
| 489 | a |
| 490 | a |
| 491 | a |
| 492 | a |
| 493 | a |
| 494 | a |
| 495 | a |
| 496 | a |
| 497 | a |
| 498 | a |

TABLE 60-continued

| Cpd No | VEGFR IC$_{50}$ μM |
|---|---|
| 499 | a |
| 500 | a |
| 502 | a |
| 503 | b |
| 504 | a |
| 505 | b |
| 506 | a |
| 507 | a |
| 508 | a |
| 509 | a |
| 510 | a |
| 511 | a |
| 512 | a |
| 515 | a |
| 516 | a |
| 518 | a |
| 519 | a |
| 520 | a |
| 521 | a |
| 522 | a |
| 524 | a |
| 526 | a |
| 527 | a |
| 528 | a |
| 529 | a |
| 530 | a |
| 531 | a |
| 532 | a |
| 533 | a |
| 535 | a |
| 536 | a |
| 537 | a |
| 538 | a |
| 539 | a |
| 540 | a |
| 543 | a |
| 544 | a |
| 545 | a |
| 546 | a |
| 547 | a |
| 548 | d |
| 549 | a |
| 550 | a |
| 551 | a |
| 552 | a |
| 556 | a |
| 557 | a |
| 558 | a |
| 559 | a |
| 562 | a |
| 570 | a |
| 574 | a |
| 575 | a |
| 576 | a |
| 580 | a |
| 581 | a |
| 582 | a |
| 583 | a |
| 584 | a |
| 588 | a |
| 589 | a |
| 596 | a |
| 599 | a |
| 609 | a |
| 342-A | a |
| 461 | a |
| 462 | a |
| 469 | a |
| 463 | c |

Assay Example 2

VEGF-dependent Erk Phosphorylation

Cells and Growth Factor:

HUVEC cells are purchased from Cambrex Bio Science Walkersville, Inc and cultured according to the vendor's instructions. The full-length coding sequence of VEGF$_{165}$ is cloned using the Gateway Cloning Technology (Invitrogen) for baculovirus expression Sf9 cells. VEGF$_{165}$ is purified from conditioned media using a NaCl gradient elution from a HiTrap heparin column (GE Healthcare Life Sciences) followed by an imidazole gradient elution from a HiTrap chelating column (GE Healthcare Life Sciences), then buffer stored in PBS supplemented with 0.1% BSA and filter sterilized Cell Assays:

Cells are seeded at 8000 cells/well of a 96 wells plate and grown for 48 hours. Cells are then grown overnight in serum and growth factor-free medium and exposed for 1.5 h to compounds dilutions. Following a 15 min incubation in medium, VEGF$_{165}$ (150 ng/ml) cells are lysed in ice-cold lysis buffer (50 mM HEPES, pH 7.4, 150 mM NaCl, 1.5 mM MgCl$_2$, 1% Triton X-100, 10% glycerol) containing 1 mM 4-(2 aminoethyl)benzenesulfonyl fluoride hydrochloride, 200 μM sodium orthovanadate, 1 mM sodium fluoride, 10 μg/mL leupeptin, 10 μg/mL aprotinin, 1 μg/mL pepstatin and 50 μg/mL Na-p-tosyl-L-lysine chloromethyl ketone hydrochloride and processed as Western blots to detect anti-phospho ERK1/2(T202/Y204)(Cell Signaling Technologies).

Western Blot Analysis:

lysates samples from single treatment wells are separated on 5-20% SDS-PAGE gels and immunobloting is performed using Immobilon polyvinylidene difluoride membranes (Amersham) according to the manufacturer's instructions. The blots are washed in Tris-buffered saline with 0.1% Tween 20 detergent (TBST) and probed for antibodies against phospho-Thr202/Tyr204-ERK (Cell signaling technologies. Chemiluminescence detection (Amersham, ECL plus) is performed according to the manufacturer's instructions using a Storm densitometer (GE Healthcare; 800 PMT, 100 nM resolution) for imaging and densitometry analysis. Values of over the range of dilution are used to prepare IC$_{50}$ curves using a 4-parameter fit model. These curves are calculated using GraFit 5.0 software.

Assay Example 3

In Vivo Solid Tumor Disease Model

This test measures the capacity of compounds to inhibit solid tumor growth.

Tumor xenografts are established in the flank of female athymic CD1 mice (Charles River Inc.), by subcutaneous injection of 1×106 U87, A431 or SKLMS cells/mouse. Once established, tumors are then serially passaged s.c. in nude mice hosts. Tumor fragments from these host animals are used in subsequent compound evaluation experiments. For compound evaluation experiments female nude mice weighing approximately 20 g are implanted s.c. by surgical implantation with tumor fragments of ~30 mg from donor tumors. When the tumors are approximately 100 mm3 in size (~7-10 days following implantation), the animals are randomized and separated into treatment and control groups. Each group contains 6-8 tumor-bearing mice, each of which is ear-tagged and followed individually throughout the experiment.

Mice are weighed and tumor measurements are taken by calipers three times weekly, starting on Day 1. These tumor measurements are converted to tumor volume by the well-known formula (L+W/4)3 4/3π. The experiment is terminated when the control tumors reach a size of approximately 1500 mm³. In this model, the change in mean tumor volume for a compound treated group/the change in mean tumor volume of the control group (non-treated or vehicle treated)×100 (ΔT/ΔC) is subtracted from 100 to give the percent tumor growth inhibition (% TGI) for each test compound. In addition to tumor volumes, body weight of animals is monitored twice weekly for up to 3 weeks Assay Example 4

In Vivo Choroidal Neovascularization (CNV) Model

This test measures the capacity of compounds to inhibit CNV progression. CNV is the main cause of severe vision loss in patients suffering from age-related macular degeneration (AMD).

Male Brown-Norway rats (Japan Clea Co., Ltd.) were used in these studies.

Rats were anesthetized by intraperitoneal injection of pentobarbital, and the right pupil was dilated with 0.5% tropicamide and 0.5% phenylephrine hydrochloride. The right eye received 6 laser burns between retinal vessels using a slit lamp delivery system of Green laser Photocoagulator (Nidex Inc., Japan), and microscope slide glass with Healon™ (AMO Inc) used as a contact lens. The laser power was 100 or 200 mW for 0.1 second and spot diameter was 100 μm. At the time of laser burn, bubble production was observed, which is an indication of rupture of Bruch's membrane which is important for CNV generation.

Rats were divided into the groups based on their body weight using SAS software (SAS institute Japan, R8.1) after laser irradiation (Day 0). After animals were anesthetized, and the right pupil dilated (as above mentioned), the right eye of the animal received the compound or vehicle by an injection (10 μL/eye) at doses of 10 or 3 nmol/eye on Day 3. The compounds were dissolved or suspended in CBS, PBS, or other adequate vehicles before injection.

On Day 10, the animals were anesthetized with ether, and high molecular weight fluorescein isothiocyanate (FITC)-dextran (SIGMA, 2×10⁶ MW) was injected via a tail vein (20 mg/rat). About 30 min after FITC-dextran injection, animals were euthanized by ether or carbon dioxide, and the eyes were removed and fixed with 10% formaline neutral buffer solution. After over 1 hour of fixation, RPE-choroid-sclera flat mounts were obtained by removing cornea, lens and retina from the eyeballs. The flat mounts were mounted in 50% glycerol on a microscope slide, and the portion burned by laser was photographed using a fluorescence microscope (Nikon Corporation, excitation filter:465-495 nm, absorption filter:515-555 nm). The CNV area was obtained by measurement of hyper-fluorescence area observed on the photograph using Scion image.

The average CNV area of 6 burns was used as an individual value of CNV area, and the average CNV area of compound treated group was compared with that of the vehicle-treated group. Results with some compounds of the present invention are shown in Table 61 and are indicated as % of inhibition of CNV progression ("A" indicates greater than or equal to 60% inhibition, and "B" indicates ≥40% to <60% inhibition).

TABLE 61

| Cpd. No. | Dose (nmol/eye) | Inhibition of CNV progression |
| --- | --- | --- |
| 2 | 10 | A |
| 3 | 10 | A |
| 5 | 10 | B |
| 6 | 10 | B |
| 7 | 10 | A |
| 9 | 10 | A |
| 25 | 10 | A |
| 26 | 10 | A |
| 36 | 10 | B |
| 41 | 10 | B |
| 43 | 10 | B |
| 45 | 10 | B |
| 49 | 10 | A |
| 51 | 10 | A |
| 55 | 10 | B |
| 74 | 10 | A |
| 83 | 10 | B |
| 89 | 10 | A |
| 90 | 10 | A |
| 137 | 10 | B |
| 142 | 10 | B |
| 154 | 3 | B |
| 230 | 3 | B |
| 232 | 3 | B |
| 234 | 3 | B |
| 288 | 10 | B |

Assay Example 4

VEGF-induced Retinal Vascular Permeability in Rabbits

Materials and Methods

This test measures the capacity of compounds to inhibit VEGF-induced retinal vascular permeability. Vascular permeability is the cause of severe vision loss in patients suffering from age-related macular degeneration (AMD). Female Dutch rabbits (~2 kg; Kitayama LABES CO., LTD, Nagano, Japan) are anesthetized with pentobarbital and topically with 0.4% oxybuprocaine hydrochloride. Test articles or vehicle are injected into vitreous cavity after the dilation of the pupils with 0.5% tropicamide eye drop. Recombinant human $VEGF_{165}$ (500 ng; Sigma-Aldrich Co., St Louis, Mo.) is injected intravitreously 48 hr prior to the measurement of vitreous fluorescein concentration. Rabbits are anesthetized with pentobarbital and sequentially injected sodium fluorescein (2 mg/kg) via the ear vein. Pupils are dilated with 0.5% tropicamide eye drop, and ocular fluorescein levels are measured using the FM-2 Fluorotron Master (Ocumetrics, Mountain View, Calif.) 30 min after fluorescein injection. The fluorescein concentrations in vitreous are obtained at data points that are 0.25 mm apart from posterior-end along an optical axis. Vitreous fluorescence concentration is considered fluorescein leakage from retinal vasculature. The average fluorescence peaks of the test article treated groups are compared with that of the vehicle-treated group.

What is claimed is:

1. A compound having the Formula (I):

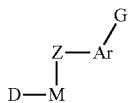

including N-oxides, tautomers, pharmaceutically acceptable salts, and racemic and scalemic mixtures, diastereomers and enantiomers thereof, wherein, D is

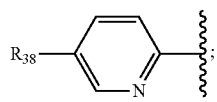

M is

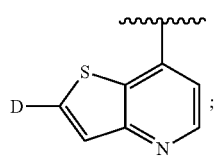 [SMILES: *c1ccnc2cc([2H])sc12]

Z is O;
Ar is phenyl substituted with a halogen; and
G is

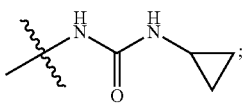

wherein
$R^{38}$ is selected from the group consisting of
$C_2$-$C_6$alkynyl-heterocyclyl,
$R^{37}O$—$C_1$-$C_6$alkyl-C(O)-heterocyclyl-$C_1$-$C_6$alkyl-,
$R^{37}O$—C(O)—$C_0$-$C_6$alkyl-heterocyclyl-$CH_2$—,
$R^{37}$—O—C(O)—$C_1$-$C_6$alkyl-heterocyclyl-C(O)—,
$(R^9)(R^{10})N$—$C_1$-$C_6$alkyl-C(O)-heterocyclyl-$CH_2$—,
$(R^9)(R^{10})N$—C(O)—$C_1$-$C_6$alkyl-heterocyclyl-$CH_2$—,
$(R^9)(R^{10})N$—$C_1$-$C_6$alkyl-C(O)—O—$C_1$-$C_6$alkyl-heterocyclyl-$CH_2$—,
NC—$C_1$-$C_6$alkyl-heterocyclyl-$CH_2$—,
$F_3C$—$C_1$-$C_6$alkyl-heterocyclyl-$CH_2$—,
$C_1$-$C_6$alkyl-C(O)—O—$C_1$-$C_6$alkyl-C(O)-(5 to 10-membered heterocyclyl)-$C_1$-$C_6$alkyl-,
(optionally substituted 8- to 10-membered fused heterocyclyl)-$C_1$-$C_6$alkyl-,
F-heterocyclyl-$C_1$-$C_6$alkyl-,
heteroaryl-$C_1$-$C_6$alkyl-heterocyclyl-$C_1$-$C_6$alkyl-,
$R^{37}$—$C_1$-$C_6$alkyl-O—$C_1$-$C_6$alkyl-heterocyclyl-$C_1$-$C_6$alkyl-,
$R^{37}O$—C(O)—$C_1$-$C_6$alkyl-O-heterocyclyl-$C_1$-$C_6$alkyl-,
$R^{37}O$—C(O)—$C_1$-$C_6$alkyl-heterocyclyl-$C_1$-$C_6$alkyl-,
$(R^6)_2N$-heterocyclyl-$C_1$-$C_6$alkyl-,
$C_1$-$C_6$alkyl-C(O)—$N(R^6)$-heterocyclyl-$C_1$-$C_6$alkyl-,
$C_1$-$C_6$alkylC(O)—O—$C_1$-$C_6$alkyl-C(O)—$N(R^6)$-heterocyclyl-$C_1$-$C_6$alkyl-,
$R^{37})O$—$C_1$-$C_6$alkyl-C(O)—$N(R^6)$-heterocyclyl-$C_1$-$C_6$alkyl-,
heteroaryl-$C_1$-$C_6$alkyl-C(O)—$N(R^6)$-heterocyclyl-$C_1$-$C_6$alkyl-,
$C_1$-$C_6$alkyl-$S(O)_2$—$N(R^6)$-heterocyclyl-$C_1$-$C_6$alkyl-,
$C_1$-$C_6$alkyl-O—C(O)—$N(R^6)$-heterocyclyl-$C_1$-$C_6$alkyl-,
$C_1$-$C_6$alkyl-$N(R^6)$—C(O)—$N(R^6)$-heterocyclyl-$C_1$-$C_6$alkyl-,
$C_1$-$C_6$alkyl-heterocyclyl-C(O)—$N(R^6)$-heterocyclyl-$C_1$-$C_6$alkyl-,
$R^{37}O$—$C_1$-$C_6$alkyl-$N(R^6)$—C(O)—$N(R^6)$-heterocyclyl-$C_1$-$C_6$alkyl-,
$C_1$-$C_6$alkyl-heterocyclyl-C(O)—$C_1$-$C_6$alkyl-,
heterocyclyl-C(O)—$C_1$-$C_6$alkyl-,
$(C_1$-$C_6$alkyl$)_2$N-heterocyclyl-C(O)—$C_1$-$C_6$alkyl-,
(Boc)(H)N-heterocyclyl-C(O)—$C_1$-$C_6$alkyl-,
$C_1$-$C_6$alkyl-O—C(O)-heterocyclyl-C(O)—$C_1$-$C_6$alkyl-,
Boc-heterocyclyl-C(O)—$C_1$-$C_6$alkyl-,
Ac—O—$C_1$-$C_6$alkyl-C(O)-heterocyclyl-C(O)—$C_1$-$C_6$alkyl-,
$R^{37}O$—$C_1$-$C_6$alkyl-C(O)-heterocyclyl-C(O)—$C_1$-$C_6$alkyl-,
(Boc)(H)N—$C_1$-$C_6$alkyl-C(O)-heterocyclyl-C(O)—$C_1$-$C_6$alkyl-,
$NH_2$—$C_1$-$C_6$alkyl-C(O)-heterocyclyl-C(O)—$C_1$-$C_6$alkyl-,
$(C_1$-$C_6$alkyl)(H)N—C(O)-heterocyclyl-C(O)—$C_1$-$C_6$alkyl-,
$NH_2$-heterocyclyl-C(O)—$C_1$-$C_6$alkyl-,
$R^{37}O$—$C_1$-$C_6$alkyl-O—$C_1$-$C_6$alkyl-heterocyclyl-C(O)—,
$C_1$-$C_6$alkyl-O—C(O)—$N(R^6)$-heterocyclyl-C(O)—,
$(R^6)(R^6)N$-heterocyclyl-C(O)—,
$(R^6)(R^6)N$-heterocyclyl-$C_1$-$C_6$alkyl-,
heterocyclyl-O—$C_1$-$C_6$alkyl-,
$C_1$-$C_6$alkyl-$N(R^6)$—C(O)—$N(R^6)$-heterocyclyl-C(O)—,
$(R^6)(R^6)N$—C(O)-heterocyclyl-O—$C_1$-$C_6$alkyl-,
$C_2$-$C_6$alkenyl-C(O)—$N(R^6)$-heterocyclyl-$C_1$-$C_6$alkyl-,
$R^{37}O$—$C_1$-$C_6$alkyl-C(O)-heterocyclyl-O—$C_1$-$C_6$alkyl-,
$R^{37}O$—$C_1$-$C_6$alkyl-$N(R^6)$-heterocycyl-$C_1$-$C_6$alkyl-,
$R^{37}O$—$(CH_2)_j$-$[(CH_2)_iO]_x$-$C_1$-$C_6$alkyl-$N(R^6)$-heterocyclyl-$C_1$-$C_6$alkyl-,
halo-$C_1$-$C_6$alkyl-heterocyclyl-$C_1$-$C_6$alkyl-,
halo-$C_1$-$C_6$alkyl-$N(R^6)$-heterocyclyl-$C_1$-$C_6$alkyl-,
$R^{37}O$—C(O)—$C_1$-$C_6$alkyl-$N(R^6)$-heterocyclyl-$C_1$-$C_6$alkyl-,
$R^{37}$—O—C(O)—$C_1$-$C_6$alkyl-$N(R^6)$—C(O)—$N(R^6)$-heterocyclyl-$C_1$-$C_6$alkyl-,
$(C_1$-$C_6$alkyl)(H)N—C(O)-heterocyclyl-N[$C_1$-$C_6$alkyl-C(O)—OH]—$C_1$-$C_6$alkyl-,
$C_1$-$C_6$alkyl-O—C(O)-heterocycyl-$C_1$-$C_6$alkyl-,
HO—C(O)-heterocyclyl-$C_1$-$C_6$alkyl-,
$C_1$-$C_6$alkyl-heterocyclyl-C(O)-heterocyclyl-$C_1$-$C_6$alkyl-,
$R^{37}O$—$C_1$-$C_6$alkyl-$N(R^6)$—C(O)-heterocyclyl-$C_1$-$C_6$alkyl-,
$(R^6)(R^6)N$—$C_1$-$C_6$alkyl-$N(R^6)$—C(O)-heterocyclyl-$C_1$-$C_6$alkyl-,
$(C_1$-$C_6$alkyl)($C_1$-$C_6$alkyl)N-heterocyclyl-$C_1$-$C_6$alkyl-,
$R^{37}O$—$C_1$-$C_6$alkyl-C(O)—[($C_1$-$C_6$alkyl)($C_1$-$C_6$alkyl)heterocyclyl]-$C_1$-$C_6$alkyl-,
$C_2$-$C_6$alkenyl-C(O)—[($C_1$-$C_6$alkyl)($C_1$-$C_6$alkyl)heterocyclyl]-$C_1$-$C_6$alkyl-,
$R^{37}$—O—$C_1$-$C_6$alkyl-[($C_1$-$C_6$alkyl)($C_1$-$C_6$alkyl)heterocyclyl]-$C_1$-$C_6$alkyl-,
$R^{37}O$—C(O)—$C_1$-$C_6$alkyl-C(O)-heterocyclyl-$C_1$-$C_6$alkyl-,
$R^{37}O$—C(O)—$C_1$-$C_6$alkyl-heterocyclyl-$C_1$-$C_6$alkyl-,
spiro-heterocyclyl-$C_1$-$C_6$alkyl-, R$^{37}$O—C$_1$-C$_6$alkyl-C(O)-spiro-heterocyclyl-C$_1$-C$_6$alkyl-,
R$^{37}$O—C$_1$-C$_6$alkyl-C(O)-heterocyclyl-C$_1$-C$_6$alkyl-,
C$_1$-C$_6$alkyl-heterocyclyl-C$_1$-C$_6$alkyl-,
C$_1$-C$_6$alkyl-C(O)—O—C$_1$-C$_6$alkyl-C(O)-heterocyclyl-C$_1$-C$_6$alkyl-,
heterocyclyl-C$_1$-C$_6$alkyl-C(O)-heterocyclyl-C$_1$-C$_6$alkyl-,
(R$^6$)(R$^6$)N—C$_1$-C$_6$alkyl-C(O)-heterocyclyl-C$_1$-C$_6$alkyl-,
heterocyclyl-C(O)-heterocyclyl-C$_1$-C$_6$alkyl-,
(R$^6$)(R$^6$)N—C$_2$-C$_6$alkenyl-C(O)-heterocyclyl-C$_1$-C$_6$alkyl-,
heterocyclyl-C$_2$-C$_8$alkenyl-C(O)-heterocyclyl-C$_1$-C$_6$alkyl-,
(R$^6$)(R$^6$)N—C$_1$-C$_6$alkyl-N(R$^6$)—C$_1$-C$_6$alkyl-C(O)-heterocyclyl-C$_1$-C$_6$alkyl-,
heterocyclyl-C(O)—,
(R$^6$)(R$^6$)N—C(O)-heterocyclyl-C$_1$-C$_6$alkyl-,
R$^{37}$O—C(O)—C$_1$-C$_6$alkyl-N(R$^6$)—C(O)-heterocyclyl-C$_1$-C$_6$alkyl-,
C$_2$-C$_6$alkenyl-C(O)—O—C$_1$-C$_6$alkyl-N(R$^6$)—C(O)-heterocyclyl-C$_1$-C$_6$alkyl-,
(R$^6$)(R$^6$)N—C(O)-heterocyclyl-C(O)—,
R$^{37}$O—C$_1$-C$_6$alkyl-N(R$^6$)—C(O)-heterocyclyl-C$_1$-C$_6$alkyl-,
R$^{37}$O—C$_1$-C$_6$alkyl-heterocyclyl-C$_1$-C$_6$alkyl-(heterocyclyl)-,
R$^{37}$O—C(O)—C$_1$-C$_6$alkyl-heterocyclyl-C(O)—,
R$^{37}$O—C$_1$-C$_6$alkyl-heterocyclyl-C(O)—,
R$^{37}$O—C$_1$-C$_6$alkyl-C(O)-heterocyclyl-C(O)—,
C$_1$-C$_6$alkyl-O—C(O)—N(R$^6$)—C$_1$-C$_6$alkyl-C(O)—O—C$_1$-C$_6$alkyl-C(O)-heterocyclyl-C$_1$-C$_6$alkyl-
R$^{37}$O—(CH$_2$)$_n$[(CH$_2$)$_i$O]$_x$-C$_1$-C$_6$alkyl-N(R$^6$)—C(O)-heterocyclyl-C$_1$-C$_6$alkyl-,
HO-heterocyclyl-C$_1$-C$_6$alkyl-,
R$^{37}$O-cycloalkyl-C(O)-heterocyclyl-C$_1$-C$_6$alkyl-
and
R$^{37}$O—(CH$_2$)$_n$[(CH$_2$)$_i$O]$_x$-C$_1$-C$_6$alkyl-C(O)—N(R$^6$)-heterocyclyl-C$_1$-C$_6$alkyl-;
each R$^6$ is independently H or C$_1$-C$_6$alkyl;
R$^{37}$ is selected from the group consisting of H, C$_1$-C$_6$alkyl and C$_3$-C$_{10}$cycloalkyl;
j is an integer ranging from 0 to 4
i is 2 or 3;
x is an integer ranging from 0 to 6,
n is an integer ranging from 0 to 4;
R$^9$ is selected from the group consisting of H, —OH, C$_1$-C$_6$ alkyl, C$_3$-C$_{10}$ cycloalkyl, —(CH$_2$)$_{n3}$(C$_6$-C$_{10}$ aryl), —(CH$_2$)$_{n3}$(C$_5$-C$_{10}$ heteroaryl), —(CH$_2$)$_{n3}$(5-10 membered heterocyclyl), —(CH$_2$)$_{n3}$O(CH$_2$)$_{i3}$OR$^{37}$ and —(CH$_2$)$_{n3}$OR$^{37}$, wherein the alkyl, aryl, heteroaryl and heterocyclyl moieties of the foregoing R$^9$ groups are optionally substituted;
R$^{10}$ is selected from the group consisting of H, —OH, C$_1$-C$_6$ alkyl, C$_3$-C$_{10}$ cycloalkyl, —(CH$_2$)$_{n4}$(C$_6$-C$_{10}$ aryl), —(CH$_2$)$_{n4}$(C$_5$-C$_{10}$ heteroaryl), —(CH$_2$)$_{n4}$(5-10 membered heterocyclyl), —(CH$_2$)$_{n4}$O(CH$_2$)$_{i4}$OR$^{37}$ and —(CH$_2$)$_{n4}$OR$^{37}$, wherein the alkyl, aryl, heteroaryl and heterocyclyl moieties of the foregoing R$^{10}$ groups are optionally substituted;
n3 is an integer ranging from 0 to 6;
i3 is an integer ranging from 2 to 6;
n4 is an integer ranging from 0 to 6;
i4 is an integer ranging from 2 to 6.

2. A compound having the Formula (Ia),

(Ia)

including N-oxides, tautomers, pharmaceutically acceptable salts, and racemic and scalemic mixtures, diastereomers and enantiomers thereof, wherein all substituents are as defined in Formula (I) according to claim 1, except that R$^{38}$ is selected from the group consisting of (R$^{23}$)(R$^{24}$)(O)P—C$_1$-C$_6$alkyl-heterocyclyl-C$_1$-C$_6$alkyl-, (optionally substituted 7- or 8-membered heterocyclyl)-C$_1$-C$_6$alkyl-, (optionally substituted 8- to 10-membered fused heterocyclyl)-C$_1$-C$_6$alkyl-, (optionally substituted spiro-heterocyclyl)-C$_1$-C$_6$alkyl-, (optionally substituted bridged bicyclic ring system)-C$_1$-C$_6$alkyl-, (substituted piperazine)-C$_1$-C$_6$alkyl-, (R$^9$)(R$^{10}$)N—C$_1$-C$_6$alkyl-C(O)—O—C$_1$-C$_6$alkyl-C(O)-(5 to 10-membered heterocyclyl)-C$_1$-C$_6$alkyl-, C$_1$-C$_6$alkyl-S(O)$_{0-2}$—C$_1$-C$_6$alkyl-(5 to 10-membered heterocyclyl)-C$_1$-C$_6$alkyl-, (R$^{23}$)(R$^{24}$)P(O)O—C$_1$-C$_6$alkyl-C(O)-(5 to 10-membered heterocyclyl)-C$_1$-C$_6$alkyl-, R$^{37}$S(O)$_{0-2}$-aryl-C(O)—O—C$_1$-C$_6$alkyl-C(O)-(5 to 10-membered heterocyclyl)-C$_1$-C$_6$alkyl-, R$^{37}$O—C$_1$-C$_6$alkyl-piperazine-C$_1$-C$_6$alkyl-, R$^{37}$O—C(O)—C$_1$-C$_6$alkyl-(5 to 10-membered heterocyclyl)-C$_1$-C$_6$alkyl-, (R$^9$)(R$^{10}$)N—C$_1$-C$_6$alkyl-piperazine-C$_1$-C$_6$alkyl-, R$^{37a}$O—C(O)—C$_1$-C$_6$alkyl-N(R$^{37}$)—C(O)—C$_1$-C$_6$alkyl-(5 to 10-membered heterocyclyl)-C$_1$-C$_6$alkyl-, R$^{11}$—C$_1$-C$_6$alkyl-C(O)-piperazine-C$_1$-C$_6$alkyl-, C$_0$-C$_6$alkyl-(5 or 6-membered heterocyclyl)-C$_1$-C$_6$alkyl-piperazine-C$_1$-C$_6$alkyl-, (5-10-membered optionally substituted heterocyclyl)-C$_1$-C$_6$alkyl-O-(oxo substituted 5 to 10-membered heterocyclyl)-C$_1$-C$_6$alkyl-, (5-10-membered optionally substituted heterocyclyl)-C$_1$-C$_6$alkyl-N(R$^1$)-(oxo substituted 5 to 10-membered heterocyclyl)-C$_1$-C$_6$alkyl-, (5-10-membered optionally substituted heterocyclyl)-C$_1$-C$_6$alkyl-S(O)$_{0-2}$-(oxo substituted 5 to 10-membered heterocyclyl)-C$_1$-C$_6$alkyl-, R$^{29}$O—C(O)—C(H)(C(O)—OR$^{29a}$)—O—C$_1$-C$_6$alkyl-(5 to 10-membered heterocyclyl)-C$_1$-C$_6$alkyl-, R$^{29}$O—C(O)—C(H)(C(O)—OR$^{29a}$)—O—C$_1$-C$_6$alkyl-C(O)-(5 to 10-membered heterocyclyl)-C$_1$-C$_6$alkyl- and (substituted piperidine)-C$_1$-C$_6$alkyl-;
wherein
R$^1$ is H or C$_1$-C$_6$alkyl;
R$^{11}$ is —OH, —O—C$_1$-C$_6$alkyl, optionally substituted 5 to 10-membered heterocyclyl, or —O-(amino acid);
R$^{23}$ is selected from the group consisting of H, —OH, C$_1$-C$_6$alkyl, C$_1$-C$_6$alkoxy, aryl, —O-aryl, cycloalkyl, —O-cycloalkyl, heteroaryl, —O-heteroaryl, 5 to 10-membered heterocyclyl, —O-(5 to 10-membered heterocyclyl), —C$_1$-C$_6$alkyl-aryl, —O—C$_1$-C$_6$alkyl-aryl, —C$_1$-C$_6$alkyl-heteroaryl, —O—C$_1$-C$_6$alkyl-heteroaryl, —C$_1$-C$_6$alkyl-cycloalkyl, —O—C$_1$-C$_6$alkyl-cycloalkyl, —C$_1$-C$_6$alkyl-(5 to 10-membered heterocyclyl) and —O—C$_1$-C$_6$alkyl-(5 to 10-membered heterocyclyl);
R$^{24}$ is selected from the group consisting of H, —OH, C$_1$-C$_6$alkyl, C$_1$-C$_6$alkoxy, aryl, —O-aryl, cycloalkyl, —O-cycloalkyl, heteroaryl, —O-heteroaryl, 5 to 10-membered heterocyclyl, —O-(5 to 10-membered heterocyclyl), —C$_1$-C$_6$alkyl-aryl, —O—C$_1$-C$_6$alkyl-aryl, —C$_1$-C$_6$alkyl-heteroaryl, —O—C$_1$-C$_6$alkyl-heteroaryl, —C$_1$-C$_6$alkyl-cycloalkyl, —O—C$_1$-C$_6$alkyl-cycloalkyl, —C$_1$-C$_6$alkyl-(5 to 10-membered heterocyclyl) and —O—C$_1$-C$_6$alkyl-(5 to 10-membered heterocyclyl);

R$^{29}$ is selected from the group consisting of H, C$_1$-C$_6$alkyl and a cation;

R$^{29a}$ is selected from the group consisting of H, C$_1$-C$_6$alkyl and a cation; and R$^{37a}$ is H or C$_1$-C$_6$alkyl.

3. A compound having the Formula (II):

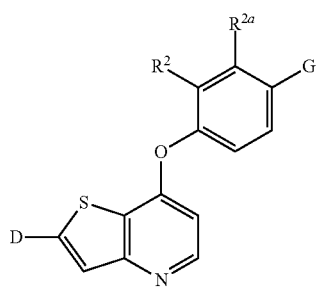

(II)

including N-oxides, tautomers, pharmaceutically acceptable salts, and racemic and scalemic mixtures, diastereomers and enantiomers thereof, wherein, D is

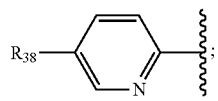

R$^{38}$ is selected from the group consisting of C$_1$-C$_6$alkyl-heterocyclyl-(CH$_2$)$_{1-2}$—, (heterocyclyl)-C(O)— (wherein the heterocyclyl is optionally substituted with C$_1$-C$_6$alkyl), HO-heterocyclyl-CH$_2$—, (R$^9$)(R$^{10}$)N-heterocyclyl-CH$_2$—, (R$^9$)(R$^{10}$)N—C$_0$-C$_6$alkyl-heterocyclyl-C(O)—, (C$_1$-C$_6$alkyl)-C(O)-heterocyclyl-CH$_2$—, R$^{37}$O—C$_1$-C$_6$alkyl-heterocyclyl-CH$_2$—, R$^{37}$O—C$_1$-C$_6$alkyl-C(O)-heterocyclyl-(CH$_2$)$_{1-6}$, R$^{37}$O—C(O)—C$_0$-C$_6$alkyl-heterocyclyl-CH$_2$—, R$^{37}$—O—C(O)—C$_1$-C$_6$alkyl-heterocyclyl-C(O)—, R$^{37}$—O—C(O)-heterocyclyl-C(O)—, C$_0$-C$_6$alkyl-heterocyclyl-C$_0$-C$_6$alkyl-heterocyclyl-C(O)—, (R$^9$)(R$^{10}$)N—C$_1$-C$_6$alkyl-C(O)-heterocyclyl-CH$_2$, (R$^9$)(R$^{10}$)N—C(O)—C$_1$-C$_6$alkyl-heterocyclyl-CH$_2$—, (R$^9$)(R$^{10}$)N—C$_1$-C$_6$alkyl-C(O)—O—C$_1$-C$_6$alkyl-heterocyclyl-CH$_2$—, R$^{37}$O—C$_1$-C$_6$alkyl-heterocyclyl-CH$_2$—, NC—C$_1$-C$_6$alkyl-heterocyclyl-CH$_2$—, heterocyclyl-C$_1$-C$_6$alkyl-heterocyclyl-CH$_2$—, F$_3$C—C$_1$-C$_6$alkyl-heterocyclyl-CH$_2$—, C$_1$-C$_6$alkyl-S(O)$_2$-heterocyclyl-CH$_2$—, heteroaryl-C$_1$-C$_6$alkyl-heterocyclyl-CH$_2$—, (R$^9$)(R$^{10}$)N—C$_1$-C$_6$alkyl-C(O)—O—C$_1$-C$_6$alkyl-C(O)-heterocyclyl-CH$_2$—, C$_1$-C$_6$alkyl-C(O)—O—C$_1$-C$_6$alkyl-C(O)-(5 to 10-membered heterocyclyl)-C$_1$-C$_6$alkyl-, (optionally substituted 8- to 10-membered fused heterocyclyl)-C$_1$-C$_6$alkyl-, (di-fluoro substituted heterocyclyl)-C$_1$-C$_6$alkyl-, C$_0$-C$_6$alkyl-(5 or 6-membered heterocyclyl)-C$_1$-C$_6$alkyl-piperazine-C$_1$-C$_6$alkyl-, R$^{37}$O—C$_1$-C$_6$alkyl-C(O)-heterocyclyl-C$_1$-C$_6$alkyl-;

R$^{37}$ is H, C$_1$-C$_6$alkyl;
R$^9$ is H, C$_1$-C$_6$alkyl;
R$^{10}$ is H, C$_1$-C$_6$alkyl;
R$^2$ is H or F;
R$^{2a}$ is H, F or Cl; and
G is

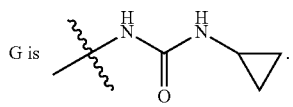 [SMILES: *NC(=O)NC1CC1]

4. The compound according to claim 3, having the Formula (XVIII):

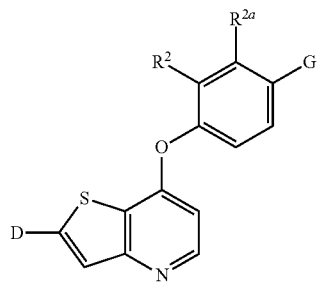

(XVIII)

including N-oxides, tautomers, pharmaceutically acceptable salts, and racemic and scalemic mixtures, diastereomers and enantiomers thereof, wherein, R$^{38}$ is R$^{37}$O—C$_1$-C$_6$alkyl-C(O)-heterocyclyl-CH$_2$—; and
R$^{37}$ is H or C$_1$-C$_6$alkyl.

5. A compound selected from the group consisting of

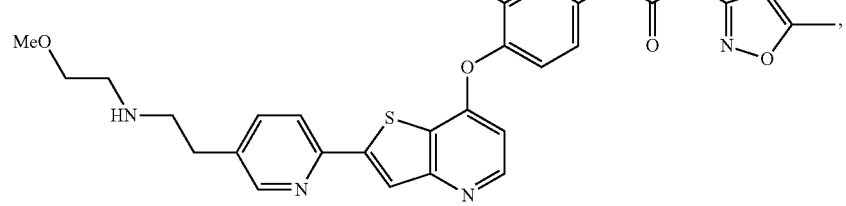

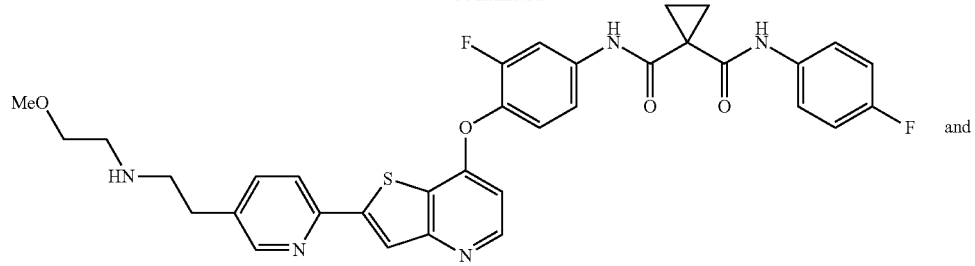

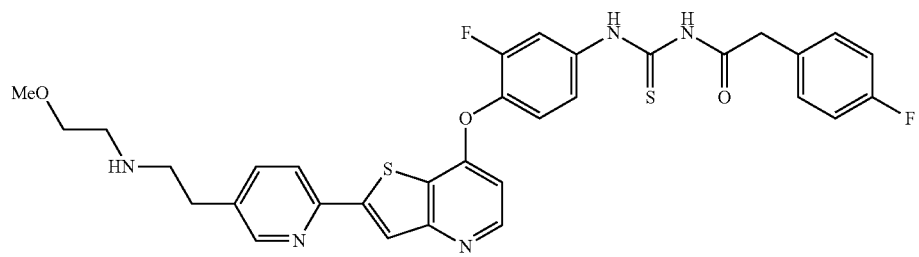

including N-oxides, tautomers, pharmaceutically acceptable salts, and racemic and scalemic mixtures, diastereomers and enantiomers thereof.

6. The compound according to claim 1, wherein $R^{38}$ is selected from the group consisting of $R^{37}O-C(O)-C_1-C_6$alkyl-heterocyclyl-$C_1$-$C_6$alkyl-, $C_1$-$C_6$alkyl-heterocyclyl-C(O)-heterocyclyl-$C_1$-$C_6$alkyl-, $R^{37}O-C_1$-$C_6$alkyl-N($R^6$)—C(O)-heterocyclyl-$C_1$-$C_6$alkyl-, ($R^6$)($R^6$)N—$C_1$-$C_6$alkyl-N($R^6$)—C(O)-heterocyclyl-$C_1$-$C_6$alkyl-, $R^{37}O$—$C_1$-$C_6$alkyl-C(O)-heterocyclyl-$C_1$-$C_6$alkyl-, $R^{37}O$—$C_1$-$C_6$alkyl-heterocyclyl-$C_1$-$C_6$alkyl- and $R^{37}O$—$(CH_2)_j$-$[(CH_2)_iO]_x$—$C_1$-$C_6$alkyl-N($R^6$)—C(O)-heterocyclyl-$C_1$-$C_6$alkyl-, wherein each of said alkyl and heterocyclyl is optionally substituted.

7. The compound according to claim 1, wherein when $R^{38}$ is attached to D by a $C_1$-$C_6$ alkyl, the $C_1$-$C_6$ alkyl is —$CH_2$—.

8. A composition comprising a compound according to claim 1.

9. The compound according to claim 2, wherein $R^{38}$ is selected from the group consisting of $R^{37}O-C(O)-C_1-C_6$alkyl-heterocyclyl-$C_1$-$C_6$alkyl-, $C_1$-$C_6$alkyl-heterocyclyl-C(O)-heterocyclyl-$C_1$-$C_6$alkyl-, $R^{37}O-C_1$-$C_6$alkyl-N($R^6$)—C(O)-heterocyclyl-$C_1$-$C_6$alkyl-, ($R^6$)($R^6$)N—$C_1$-$C_6$alkyl-N($R^6$)—C(O)-heterocyclyl-$C_1$-$C_6$alkyl-, $R^{37}O$—$C_1$-$C_6$alkyl-C(O)-heterocyclyl-$C_1$-$C_6$alkyl-, $R^{37}O$—$C_1$-$C_6$alkyl-heterocyclyl-$C_1$-$C_6$alkyl- and $R^{37}O$—$(CH_2)_j$-$[(CH_2)_iO]_x$—$C_1$-$C_6$alkyl-N($R^6$)—C(O)-heterocyclyl-$C_1$-$C_6$alkyl-, wherein each of said alkyl and heterocyclyl is optionally substituted.

10. The compound according to claim 2, wherein when $R^{38}$ is attached to D by a $C_1$-$C_6$ alkyl, the $C_1$-$C_6$ alkyl is —$CH_2$—.

11. A composition comprising a compound according to claim 2.

12. A composition comprising a compound according to claim 3.

13. A composition comprising a compound according to claim 5.

14. A compound having the formula:

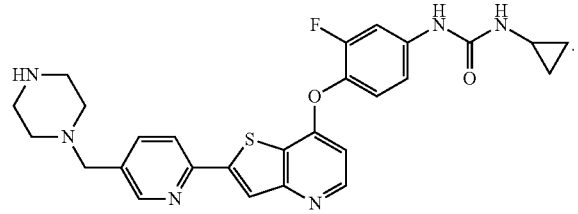 [SMILES: O=C(Nc1ccc(Oc2ccnc3cc(-c4ccc(CN5CCNCC5)cn4)sc23)c(F)c1)NC1CC1]

15. A compound having the formula:

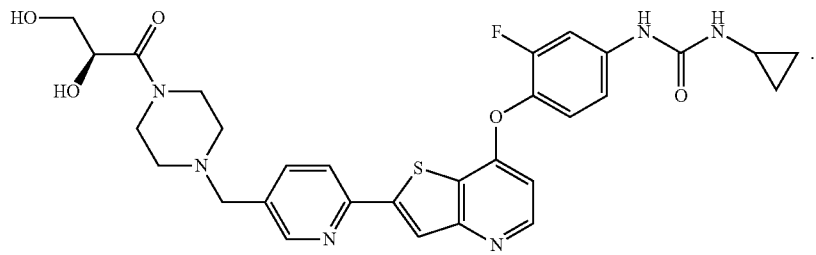 [SMILES: O=C(Nc1ccc(Oc2ccnc3cc(-c4ccc(CN5CCN(C(=O)[C@@H](O)CO)CC5)cn4)sc23)c(F)c1)NC1CC1]

16. A compound having the formula:
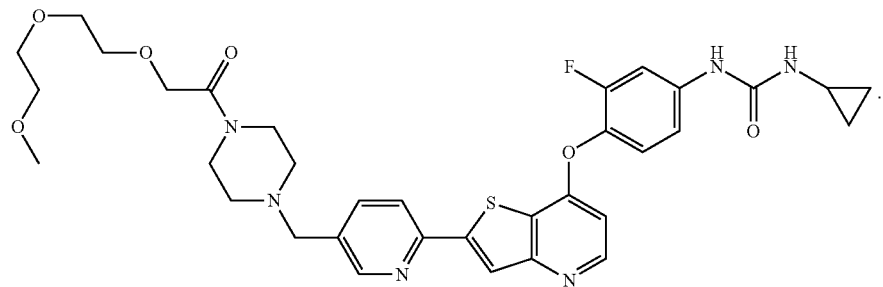 [SMILES: COCCOCCOCC(=O)N1CCN(Cc2ccc(-c3cc4nccc(Oc5ccc(NC(=O)NC6CC6)cc5F)c4s3)nc2)CC1]
17. A compound having the formula:
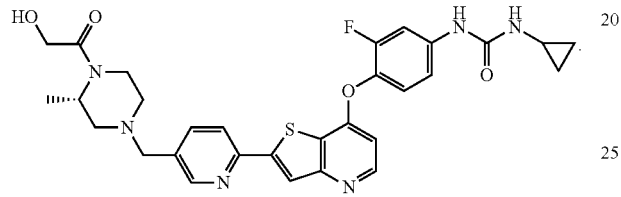
* * * * *